US008124357B2

(12) United States Patent
Fernandez-Salas et al.

(10) Patent No.: US 8,124,357 B2
(45) Date of Patent: Feb. 28, 2012

(54) LIPOPHILIC DYE-BASED FRET ASSAYS FOR CLOSTRIDAL TOXIN ACTIVITY

(75) Inventors: Ester Fernandez-Salas, Fullerton, CA (US); Lance E. Steward, Irvine, CA (US); Kei Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 951 days.

(21) Appl. No.: 11/908,438

(22) PCT Filed: Apr. 4, 2006

(86) PCT No.: PCT/US2006/012426
§ 371 (c)(1), (2), (4) Date: Sep. 12, 2007

(87) PCT Pub. No.: WO2006/107921
PCT Pub. Date: Oct. 12, 2006

(65) Prior Publication Data

US 2008/0160561 A1 Jul. 3, 2008

Related U.S. Application Data

(60) Provisional application No. 60/668,942, filed on Apr. 5, 2005.

(51) Int. Cl.
*C12N 5/07* (2010.01)
*C12N 15/74* (2006.01)
*C12Q 1/37* (2006.01)
*C07H 21/04* (2006.01)

(52) U.S. Cl. ..... 435/7.21; 435/23; 435/69.1; 435/252.3; 435/325; 435/471; 536/23.7; 530/350

(58) Field of Classification Search .................... 435/29, 435/325, 23, 7.21, 69.1, 252.3, 471; 424/236.1, 424/239.1; 530/350; 536/23.7
See application file for complete search history.

(56) References Cited

U.S. PATENT DOCUMENTS

| | | | |
|---|---|---|---|
| 5,965,699 | A | 10/1999 | Schmidt et al. |
| 6,762,280 | B2 | 7/2004 | Schmidt et al. |
| 7,183,066 | B2 | 2/2007 | Fernandez-Salas et al. |
| 7,208,285 | B2 | 4/2007 | Steward et al. |
| 2003/0143651 | A1 | 7/2003 | Steward et al. |
| 2003/0149254 | A1 | 8/2003 | Anderson et al. |
| 2004/0126810 | A1 | 7/2004 | Roques et al. |
| 2005/0100973 | A1 | 5/2005 | Steward et al. |
| 2006/0063221 | A1 | 3/2006 | Williams et al. |
| 2006/0063222 | A1 | 3/2006 | Williams et al. |
| 2006/0134722 | A1 | 6/2006 | Chapman et al. |
| 2007/0122858 | A1 | 5/2007 | Fernandez-Salas et al. |

FOREIGN PATENT DOCUMENTS

| | | |
|---|---|---|
| WO | WO 01/92312 | 12/2001 |
| WO | WO 02/25284 | 3/2002 |
| WO | WO 03/020948 | 3/2003 |
| WO | WO 2004/020748 | 3/2004 |
| WO | WO 2004/029576 | 4/2004 |
| WO | WO 2004/031355 | 4/2004 |
| WO | WO 2004/031773 | 4/2004 |
| WO | WO 2005/076785 | 8/2005 |
| WO | WO 2005/121354 | 12/2005 |
| WO | WO 2006/033843 | 3/2006 |
| WO | WO 2007/001358 | 1/2007 |

OTHER PUBLICATIONS

B. D. Hamman et al., *Binding of a Pleckstrin homology domain protein to phosphoinositide in membranes: a miniaturized FRET-based assay for drug screening*, J. Biomol. Screen. 7(1): 45-55 (2002).
P. Vallotton et al., *Mapping the antagonist binding site of the serotonin type 3 receptor by fluorescence resonance energy transfer*, Biochemistry 40(41): 12237-12242 (2001).
G. M. Jones et al., Analysis of vertical fluorescence resonance energy transfer from the surface of a small-diameter sphere, Biophys. J. 76(1 Pt 1): 517-527 (1999).
Schmidt et al, High-throughput assays for *botulinum* neurotoxin Proteolytic activity: serotypes A, B, D and F, Analytical Biochemistry, vol. 296, pp. 130-137, 2001.
Ekong et al, Recombinant SNAP-25 is an effective substrate for *Clostridium botulinum* type A toxin endopeptidase activity in vitro, Microbiology, vol. 143, No. 10, pp. 3337-3347, 1997.
Hallis et al, Development of novel assays for *botulinum* type A and B neurotoxins based on their endopeptidase activities, Journal of Clinical Microbiology, vol. 34, No. 8, pp. 1934-1938, 1996.
Office Action Date Mailed Jun. 20, 2008 in U.S. Appl. No. 10/598,073.
Keller, James E. et al, FEBS Letters, vol. 456, 1999, pp. 137-142, Persistence of *botulinum* neurotoxin action in cultured spinal cord cells.
U.S. Appl. No. 10/917,844, filed Aug. 13, 2004, Steward et al.
U.S. Appl. No. 11/752,596, filed May 23, 2007, Steward et al.
U.S. Appl. No. 11/753,304, filed May 24, 2007, Steward et al.
U.S. Appl. No. 11/754,046, filed May 25, 2007, Steward et al.
U.S. Appl. No. 11/780,538, filed Jul. 20, 2007, Steward et al.
U.S. Appl. No. 11/780,958, filed Jul. 20, 2007, Steward et al.
U.S. Appl. No. 11/780,925, filed Jul. 20, 2007, Steward et al.
U.S. Appl. No. 11/780,872, filed Jul. 20, 2007, Steward et al.
U.S. Appl. No. 11/780,092, filed Jul. 19, 2007, Steward et al.
U.S. Appl. No. 11/608,912, filed Dec. 11, 2006, Steward et al.
U.S. Appl. No. 11/609,189, filed Dec. 11, 2006, Steward et al.
U.S. Appl. No. 11/609,226, filed Dec. 11, 2006, Steward et al.
Schmidt et al, "High-throughput assays for *botulinum* neurotoxin Proteolytic activity: serotypes A, B, D and F", Analytical Biochemistry, vol. 296, pp. 130-137, 2001.
Ekong et al, "Recombinant SNAP-25 is an effective substrate for *Clostridium botulinum* type A toxin endopeptidase activity in vitro", Microbiology, vol. 143, No. 10, pp. 3337-3347, 1997.
Hallis et al, "Development of novel assays for *botulinum* type A and B neurotoxins based on their endopeptidase activities", Journal of Clinical Microbiology, vol. 34, No. 8, pp. 1934-1938, 1996.

*Primary Examiner* — Chih-Min Kam
(74) *Attorney, Agent, or Firm* — Kenton Abel; Debra Condino

(57) ABSTRACT

Compositions useful for detecting Clostridial toxin activity comprising a cell that comprises a membrane-associated Clostridial toxin substrate comprising a first member of a fluorescence resonance energy transfer pair; and a Clostridial toxin recognition sequence including a cleavage site; and a membrane-associated second member of the FRET pair and methods useful for determining Clostridial toxin activity using such Clostridial toxin substrates.

17 Claims, 19 Drawing Sheets

BoNT/A Exposure (16 hour)

[Bar chart: Percent Fluorescence (%) vs [BoNT/A] (nM); values at 0, 0.05, 0.1, 0.5, 1.0, 5.0, 20]

BoNT/A Exposure (3 day)

[Bar chart: Percent Fluorescence (%) vs [BoNT/A] (nM); values at 0, 0.05, 0.1, 0.5, 1.0, 5.0, 20]

BoNT/A Exposure (3 day)

[Bar chart: Percent Fluorescence (%) vs [BoNT/A] (nM) with values 0, 0.002, 0.005, 0.01, 0.02, 0.05, 0.1, 0.2, 0.5, 1.0]

BoNT/A $EC_{50}$ Curve (3 day)

[Scatter plot: Percent Fluorescence (%) vs $Log_{10}$ [BoNT/A]]

SEQUENCE LISTING

```
<160> NUMBER OF SEQ ID NOS: 184

<210> SEQ ID NO 1
<211> LENGTH: 206
<212> TYPE: PRT
<213> ORGANISM: Homo sapiens SNAP-25A (Human)

<400> SEQUENCE: 1

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
```

```
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 2
<211> LENGTH: 206
<212> TYPE: PRT
<213> ORGANISM: Homo sapiens SNAP-25B (Human)

<400> SEQUENCE: 2

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 3
<211> LENGTH: 211
<212> TYPE: PRT
<213> ORGANISM: Homo sapiens SNAP-23A (Human)

<400> SEQUENCE: 3

Met Asp Asn Leu Ser Ser Glu Glu Ile Gln Gln Arg Ala His Gln Ile
 1               5                  10                  15

Thr Asp Glu Ser Leu Glu Ser Thr Arg Arg Ile Leu Gly Leu Ala Ile
            20                  25                  30

Glu Ser Gln Asp Ala Gly Ile Lys Thr Ile Thr Met Leu Asp Glu Gln
        35                  40                  45

Lys Glu Gln Leu Asn Arg Ile Glu Glu Gly Leu Asp Gln Ile Asn Lys
    50                  55                  60

Asp Met Arg Glu Thr Glu Lys Thr Leu Thr Glu Leu Asn Lys Cys Cys
65                  70                  75                  80

Gly Leu Cys Val Cys Pro Cys Asn Arg Thr Lys Asn Phe Glu Ser Gly
                85                  90                  95
```

Lys Ala Tyr Lys Thr Thr Trp Gly Asp Gly Gly Glu Asn Ser Pro Cys
100 105 110

Asn Val Val Ser Lys Gln Pro Gly Pro Val Thr Asn Gly Gln Leu Gln
115 120 125

Gln Pro Thr Thr Gly Ala Ala Ser Gly Gly Tyr Ile Lys Arg Ile Thr
130 135 140

Asn Asp Ala Arg Glu Asp Glu Met Glu Glu Asn Leu Thr Gln Val Gly
145 150 155 160

Ser Ile Leu Gly Asn Leu Lys Asp Met Ala Leu Asn Ile Gly Asn Glu
165 170 175

Ile Asp Ala Gln Asn Pro Gln Ile Lys Arg Ile Thr Asp Lys Ala Asp
180 185 190

Thr Asn Arg Asp Arg Ile Asp Ile Ala Asn Ala Arg Ala Lys Lys Leu
195 200 205

Ile Asp Ser
210

<210> SEQ ID NO 4
<211> LENGTH: 158
<212> TYPE: PRT
<213> ORGANISM: Homo sapiens SNAP-23B (Human)

<400> SEQUENCE: 4

Met Asp Asn Leu Ser Ser Glu Glu Ile Gln Gln Arg Ala His Gln Ile
1 5 10 15

Thr Asp Glu Ser Leu Glu Ser Thr Arg Arg Ile Leu Gly Leu Ala Ile
20 25 30

Glu Ser Gln Asp Ala Gly Ile Lys Thr Ile Thr Met Leu Asp Glu Gln
35 40 45

Lys Glu Gln Leu Asn Arg Ile Glu Glu Gly Leu Asp Gln Ile Asn Lys
50 55 60

Asp Met Arg Glu Thr Glu Lys Thr Leu Thr Glu Leu Asn Lys Cys Cys
65 70 75 80

Gly Leu Cys Val Cys Pro Cys Asn Ser Ile Thr Asn Asp Ala Arg Glu
85 90 95

Asp Glu Met Glu Glu Asn Leu Thr Gln Val Gly Ser Ile Leu Gly Asn
100 105 110

Leu Lys Asp Met Ala Leu Asn Ile Gly Asn Glu Ile Asp Ala Gln Asn
115 120 125

Pro Gln Ile Lys Arg Ile Thr Asp Lys Ala Asp Thr Asn Arg Asp Arg
130 135 140

Ile Asp Ile Ala Asn Ala Arg Ala Lys Lys Leu Ile Asp Ser
145 150 155

<210> SEQ ID NO 5
<211> LENGTH: 206
<212> TYPE: PRT
<213> ORGANISM: Macaca mulatta SNAP-25B (Rhesus monkey)

<400> SEQUENCE: 5

Met Ala Glu Asp Ala Asp Met Arg Asn Glu Leu Glu Glu Met Gln Arg
1 5 10 15

Arg Ala Asp Gln Leu Ala Asp Glu Ser Leu Glu Ser Thr Arg Arg Met
20 25 30

Leu Gln Leu Val Glu Glu Ser Lys Asp Ala Gly Ile Arg Thr Leu Val
35 40 45

```
Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 6
<211> LENGTH: 206
<212> TYPE: PRT
<213> ORGANISM: Rattus norvegicus SNAP-25A (Rat)

<400> SEQUENCE: 6

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 7
<211> LENGTH: 206
```

<212> TYPE: PRT
<213> ORGANISM: Rattus norvegicus SNAP-25B (Rat)

<400> SEQUENCE: 7

```
Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205
```

<210> SEQ ID NO 8
<211> LENGTH: 206
<212> TYPE: PRT
<213> ORGANISM: Mus musculus SNAP-25B (Mouse)

<400> SEQUENCE: 8

```
Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
```

```
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 9
<211> LENGTH: 210
<212> TYPE: PRT
<213> ORGANISM: Rattus norvegicus SNAP-23 (Rat)

<400> SEQUENCE: 9

Met Asp Asp Leu Ser Pro Glu Glu Ile Gln Leu Arg Ala His Gln Val
 1               5                  10                  15

Thr Asp Glu Ser Leu Glu Ser Thr Arg Arg Ile Leu Gly Leu Ala Ile
            20                  25                  30

Glu Ser Gln Asp Ala Gly Ile Lys Thr Ile Thr Met Leu Asp Glu Gln
        35                  40                  45

Gly Glu Gln Leu Asn Arg Ile Glu Glu Gly Met Asp Gln Ile Asn Lys
    50                  55                  60

Asp Met Arg Glu Ala Glu Lys Thr Leu Thr Glu Leu Asn Lys Cys Cys
65                  70                  75                  80

Gly Leu Cys Val Cys Pro Cys Asn Arg Thr Lys Asn Phe Glu Ser Gly
                85                  90                  95

Lys Asn Tyr Lys Ala Thr Trp Gly Asp Gly Gly Asp Ser Ser Pro Ser
            100                 105                 110

Asn Val Val Ser Lys Gln Pro Ser Arg Ile Thr Asn Gly Gln Pro Gln
        115                 120                 125

Gln Thr Thr Gly Ala Ala Ser Gly Gly Tyr Ile Lys Arg Ile Thr Asn
    130                 135                 140

Asp Ala Arg Glu Asp Glu Met Glu Glu Asn Leu Thr Gln Val Gly Ser
145                 150                 155                 160

Ile Leu Gly Asn Leu Lys Asn Met Ala Leu Asp Met Gly Asn Glu Ile
                165                 170                 175

Asp Ala Gln Asn Gln Gln Ile Gln Lys Ile Thr Glu Lys Ala Asp Thr
            180                 185                 190

Asn Lys Asn Arg Ile Asp Ile Ala Asn Thr Arg Ala Lys Lys Leu Ile
        195                 200                 205

Asp Ser
    210


<210> SEQ ID NO 10
<211> LENGTH: 210
<212> TYPE: PRT
<213> ORGANISM: Mus musculus SNAP-23 (Mouse)

<400> SEQUENCE: 10

Met Asp Asn Leu Ser Pro Glu Glu Val Gln Leu Arg Ala His Gln Val
 1               5                  10                  15

Thr Asp Glu Ser Leu Glu Ser Thr Arg Arg Ile Leu Gly Leu Ala Ile
            20                  25                  30

Glu Ser Gln Asp Ala Gly Ile Lys Thr Ile Thr Met Leu Asp Glu Gln
        35                  40                  45

Gly Glu Gln Leu Asn Arg Ile Glu Glu Gly Met Asp Gln Ile Asn Lys
    50                  55                  60
```

```
Asp Met Arg Glu Ala Glu Lys Thr Leu Thr Glu Leu Asn Lys Cys Cys
65                  70                  75                  80

Gly Leu Cys Ile Cys Pro Cys Asn Arg Thr Lys Asn Phe Glu Ser Gly
                85                  90                  95

Lys Asn Tyr Lys Ala Thr Trp Gly Asp Gly Gly Asp Asn Ser Pro Ser
            100                 105                 110

Asn Val Val Ser Lys Gln Pro Ser Arg Ile Thr Asn Gly Gln Pro Gln
        115                 120                 125

Gln Thr Thr Gly Ala Ala Ser Gly Gly Tyr Ile Lys Arg Ile Thr Asn
    130                 135                 140

Asp Ala Arg Glu Asp Glu Met Glu Glu Asn Leu Thr Gln Val Gly Ser
145                 150                 155                 160

Ile Leu Gly Asn Leu Lys Asn Met Ala Leu Asp Met Gly Asn Glu Ile
                165                 170                 175

Asp Ala Gln Asn Gln Gln Ile Gln Lys Ile Thr Glu Lys Ala Asp Thr
            180                 185                 190

Asn Lys Asn Arg Ile Asp Ile Ala Asn Thr Arg Ala Lys Lys Leu Ile
        195                 200                 205

Asp Ser
    210


<210> SEQ ID NO 11
<211> LENGTH: 206
<212> TYPE: PRT
<213> ORGANISM: Gallus gallus SNAP-25B (Chicken)

<400> SEQUENCE: 11

Met Ala Glu Asp Ala Asp Met Arg Asn Glu Leu Glu Glu Met Gln Arg
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205


<210> SEQ ID NO 12
```

<211> LENGTH: 204
<212> TYPE: PRT
<213> ORGANISM: Carassius auratus SNAP-25A (Goldfish)

<400> SEQUENCE: 12

```
Met Ala Glu Asp Ala Asp Met Arg Asn Glu Leu Ser Asp Met Gln Gln
 1               5                  10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Asp Ala Glu Lys Asn Leu Asn Asp
65                  70                  75                  80

Leu Gly Lys Phe Cys Gly Leu Cys Ser Cys Pro Cys Asn Lys Met Lys
                85                  90                  95

Ser Gly Gly Ser Lys Ala Trp Gly Asn Asn Gln Asp Gly Val Val Ala
            100                 105                 110

Ser Gln Pro Ala Arg Val Val Asp Glu Arg Glu Gln Met Ala Ile Ser
        115                 120                 125

Gly Gly Phe Ile Arg Arg Val Thr Asp Asp Ala Arg Glu Asn Glu Met
    130                 135                 140

Asp Glu Asn Leu Glu Gln Val Gly Gly Ile Ile Gly Asn Leu Arg His
145                 150                 155                 160

Met Ala Leu Asp Met Gly Asn Glu Ile Asp Thr Gln Asn Arg Gln Ile
                165                 170                 175

Asp Arg Ile Met Glu Lys Ala Asp Ser Asn Lys Thr Arg Ile Asp Glu
            180                 185                 190

Ala Asn Gln Arg Ala Thr Lys Met Leu Gly Ser Gly
        195                 200
```

<210> SEQ ID NO 13
<211> LENGTH: 203
<212> TYPE: PRT
<213> ORGANISM: Carassius auratus SNAP-25B (Goldfish)

<400> SEQUENCE: 13

```
Met Ala Asp Glu Ala Asp Met Arg Asn Glu Leu Thr Asp Met Gln Ala
 1               5                  10                  15

Arg Ala Asp Gln Leu Gly Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Asn Leu Cys Gly Leu Cys Pro Cys Pro Cys Asn Lys Leu Lys
                85                  90                  95

Gly Gly Gly Gln Ser Trp Gly Asn Asn Gln Asp Gly Val Val Ser Ser
            100                 105                 110

Gln Pro Ala Arg Val Val Asp Glu Arg Glu Gln Met Ala Ile Ser Gly
        115                 120                 125

Gly Phe Ile Arg Arg Val Thr Asn Asp Ala Arg Glu Asn Glu Met Asp
    130                 135                 140
```

Glu Asn Leu Glu Gln Val Gly Ser Ile Ile Gly Asn Leu Arg His Met
145 150 155 160

Ala Leu Asp Met Gly Asn Glu Ile Asp Thr Gln Asn Arg Gln Ile Asp
165 170 175

Arg Ile Met Asp Met Ala Asp Ser Asn Lys Thr Arg Ile Asp Glu Ala
180 185 190

Asn Gln Arg Ala Thr Lys Met Leu Gly Ser Gly
195 200

<210> SEQ ID NO 14
<211> LENGTH: 204
<212> TYPE: PRT
<213> ORGANISM: Danio rerio SNAP-25A (Zebrafish)

<400> SEQUENCE: 14

Met Ala Glu Asp Ser Asp Met Arg Asn Glu Leu Ala Asp Met Gln Gln
1 5 10 15

Arg Ala Asp Gln Leu Ala Asp Glu Ser Leu Glu Ser Thr Arg Arg Met
20 25 30

Leu Gln Leu Val Glu Glu Ser Lys Asp Ala Gly Ile Arg Thr Leu Val
35 40 45

Met Leu Asp Glu Gln Gly Glu Gln Leu Glu Arg Ile Glu Glu Gly Met
50 55 60

Asp Gln Ile Asn Lys Asp Met Lys Asp Ala Glu Lys Asn Leu Asn Asp
65 70 75 80

Leu Gly Lys Phe Cys Gly Leu Cys Ser Cys Pro Cys Asn Lys Met Lys
85 90 95

Ser Gly Ala Ser Lys Ala Trp Gly Asn Asn Gln Asp Gly Val Val Ala
100 105 110

Ser Gln Pro Ala Arg Val Val Asp Glu Arg Glu Gln Met Ala Ile Ser
115 120 125

Gly Gly Phe Ile Arg Arg Val Thr Asp Asp Ala Arg Glu Asn Glu Met
130 135 140

Asp Glu Asn Leu Glu Gln Val Gly Gly Ile Ile Gly Asn Leu Arg His
145 150 155 160

Met Ala Leu Asp Met Gly Asn Glu Ile Asp Thr Gln Asn Arg Gln Ile
165 170 175

Asp Arg Ile Met Glu Lys Ala Asp Ser Asn Lys Thr Arg Ile Asp Glu
180 185 190

Ala Asn Gln Arg Ala Thr Lys Met Leu Gly Ser Gly
195 200

<210> SEQ ID NO 15
<211> LENGTH: 203
<212> TYPE: PRT
<213> ORGANISM: Danio rerio SNAP-25B (Zebrafish)

<400> SEQUENCE: 15

Met Ala Asp Glu Ser Asp Met Arg Asn Glu Leu Asn Asp Met Gln Ala
1 5 10 15

Arg Ala Asp Gln Leu Gly Asp Glu Ser Leu Glu Ser Thr Arg Arg Met
20 25 30

Leu Gln Leu Val Glu Glu Ser Lys Asp Ala Gly Ile Arg Thr Leu Val
35 40 45

Met Leu Asp Glu Gln Gly Glu Gln Leu Glu Arg Ile Glu Glu Gly Met
50 55 60

Asp Gln Ile Asn Lys Asp Met Lys Glu Ala Glu Lys Asn Leu Thr Asp

```
65                  70                  75                  80

Leu Gly Asn Leu Cys Gly Leu Cys Pro Cys Pro Cys Asn Lys Leu Lys
                85                  90                  95

Gly Gly Gly Gln Ser Trp Gly Asn Asn Gln Asp Gly Val Val Ser Ser
            100                 105                 110

Gln Pro Ala Arg Val Val Asp Glu Arg Glu Gln Met Ala Ile Ser Gly
        115                 120                 125

Gly Phe Ile Arg Arg Val Thr Asn Asp Ala Arg Glu Asn Glu Met Asp
    130                 135                 140

Glu Asn Leu Glu Gln Val Gly Ser Ile Ile Gly Asn Leu Arg His Met
145                 150                 155                 160

Ala Leu Asp Met Gly Asn Glu Ile Asp Thr Gln Asn Arg Gln Ile Asp
                165                 170                 175

Arg Ile Met Asp Met Ala Asp Ser Asn Lys Thr Arg Ile Asp Glu Ala
            180                 185                 190

Asn Gln Arg Ala Thr Lys Met Leu Gly Ser Gly
        195                 200


<210> SEQ ID NO 16
<211> LENGTH: 214
<212> TYPE: PRT
<213> ORGANISM: Danio rerio SNAP-23 (Zebrafish)

<400> SEQUENCE: 16

Met Ala Asp Met Thr Val Glu Asp Ile Thr Met Arg Ala Asn Gln Val
 1               5                  10                  15

Thr Asp Glu Ser Leu Glu Ser Thr Arg Arg Met Leu Gln Met Ala Glu
            20                  25                  30

Glu Ser Arg Glu Thr Gly Val Lys Thr Met Thr Met Leu Asp Glu Gln
        35                  40                  45

Gly Glu Gln Leu Arg Arg Val Asp Gln Gly Met Asp Gln Ile Asn Gln
    50                  55                  60

Asp Met Arg Gln Ala Glu Lys Asn Leu Thr Asp Leu Ser Lys Cys Cys
65                  70                  75                  80

Gly Leu Cys Val Cys Pro Cys Glu Arg Val Thr Ser Ile Glu His Asp
                85                  90                  95

Gly Arg Tyr Lys Arg Thr Trp Gly Thr Gly Ser Asp Asn Ser Ser Thr
            100                 105                 110

Glu Gly Lys Glu Gly Gly Val Val Ser Ser Gln Pro Thr Ala Val Arg
        115                 120                 125

Asn Gly Gln Ala Val Ser Gly Gly Ser Ser Gly Ala Ser Gly Pro Tyr
    130                 135                 140

Ile Lys Arg Ile Thr Asn Asp Ala Arg Glu Asp Glu Met Glu Glu Asn
145                 150                 155                 160

Leu Asp Gln Val Gly Ser Ile Ile Gly Asn Leu Lys Asn Leu Ala Leu
                165                 170                 175

Asp Met Gly Asn Glu Ile Asp Lys Gln Asn Lys Thr Ile Asp Arg Ile
            180                 185                 190

Thr Asp Lys Ala Asp Met Asn Lys Ala Arg Ile Asp Glu Ala Asn Gln
        195                 200                 205

Arg Ala Asn Lys Leu Leu
    210


<210> SEQ ID NO 17
<211> LENGTH: 210
<212> TYPE: PRT
```

<213> ORGANISM: Torpedo marmorata SNAP-25 (Marbled electric ray)

<400> SEQUENCE: 17

Met Glu Asn Ser Val Glu Asn Ser Met Asp Pro Arg Ser Glu Gln Glu
1 5 10 15

Glu Met Gln Arg Cys Ala Asp Gln Ile Thr Asp Glu Ser Leu Glu Ser
20 25 30

Thr Arg Arg Met Leu Gln Leu Val Glu Glu Ser Lys Asp Ala Gly Ile
35 40 45

Arg Thr Leu Val Met Leu Asp Glu Gln Gly Glu Gln Leu Glu Arg Ile
50 55 60

Glu Glu Gly Met Asp Gln Ile Asn Lys Asp Met Lys Glu Ala Glu Lys
65 70 75 80

Asn Leu Ser Asp Leu Gly Lys Cys Cys Gly Leu Cys Ser Cys Pro Cys
85 90 95

Asn Lys Leu Lys Asn Phe Glu Ala Gly Gly Ala Tyr Lys Lys Val Trp
100 105 110

Gly Asn Asn Gln Asp Gly Val Val Ala Ser Gln Pro Ala Arg Val Met
115 120 125

Asp Asp Arg Glu Gln Met Ala Met Ser Gly Gly Tyr Ile Arg Arg Ile
130 135 140

Thr Asp Asp Ala Arg Glu Asn Glu Met Glu Glu Asn Leu Asp Gln Val
145 150 155 160

Gly Ser Ile Ile Gly Asn Leu Arg His Met Ala Leu Asp Met Ser Asn
165 170 175

Glu Ile Gly Ser Gln Asn Ala Gln Ile Asp Arg Ile Val Val Lys Gly
180 185 190

Asp Met Asn Lys Ala Arg Ile Asp Glu Ala Asn Lys His Ala Thr Lys
195 200 205

Met Leu
210

<210> SEQ ID NO 18
<211> LENGTH: 206
<212> TYPE: PRT
<213> ORGANISM: Xenopus laevis SNAP-25A (African clawed frog)

<400> SEQUENCE: 18

Met Ala Asp Asp Ala Asp Met Arg Asn Glu Leu Glu Glu Met Gln Arg
1 5 10 15

Arg Ala Asp Gln Leu Ala Asp Glu Ser Leu Glu Ser Thr Arg Arg Met
20 25 30

Leu Gln Tyr Val Glu Gly Ser Lys Asp Ala Gly Ile Arg Thr Leu Val
35 40 45

Met Leu Asp Glu Gln Gly Glu Gln Leu Asp Arg Val Glu Glu Gly Met
50 55 60

Asn His Ile Asn Gln Asp Met Lys Glu Ala Glu Lys Asn Leu Lys Asp
65 70 75 80

Leu Gly Lys Cys Cys Gly Leu Phe Ile Cys Pro Cys Asn Lys Leu Lys
85 90 95

Ser Ser Gly Ala Tyr Asn Lys Ala Trp Gly Asn Asn Gln Asp Gly Val
100 105 110

Val Ala Ser Gln Pro Ala Arg Val Val Asp Glu Arg Glu Gln Met Ala
115 120 125

Ile Ser Gly Gly Phe Val Arg Arg Val Thr Asn Asp Ala Arg Glu Thr
130 135 140

Glu Met Asp Glu Asn Leu Glu Gln Val Gly Gly Ile Ile Gly Asn Leu
145 150 155 160

Arg His Met Ala Leu Asp Met Gly Asn Glu Ile Asp Thr Gln Asn Arg
165 170 175

Gln Ile Asp Arg Ile Met Glu Lys Ala Asp Ser Asn Lys Ala Arg Ile
180 185 190

Asp Glu Ala Asn Lys His Ala Thr Lys Met Leu Gly Ser Gly
195 200 205

<210> SEQ ID NO 19
<211> LENGTH: 206
<212> TYPE: PRT
<213> ORGANISM: Xenopus laevis SNAP-25B (African clawed frog)

<400> SEQUENCE: 19

Met Ala Asp Asp Ala Asp Met Arg Asn Glu Leu Glu Glu Met Gln Arg
1 5 10 15

Arg Ala Asp Gln Leu Ala Asp Glu Ser Leu Glu Ser Thr Arg Arg Met
20 25 30

Leu Gln Tyr Val Glu Gly Ser Lys Asp Ala Gly Ile Arg Thr Leu Val
35 40 45

Met Leu Asp Glu Gln Gly Glu Gln Leu Glu Arg Ile Glu Glu Gly Met
50 55 60

Glu Gln Ile Asn Lys Asp Met Lys Glu Ala Glu Lys Asn Leu Thr Asp
65 70 75 80

Leu Gly Lys Phe Cys Gly Leu Cys Val Cys Pro Cys Asn Lys Leu Lys
85 90 95

Ser Ser Asp Ala Tyr Lys Lys Ala Trp Gly Asn Asn Gln Asp Gly Val
100 105 110

Val Ala Ser Gln Pro Ala Arg Val Val Asp Glu Arg Glu Gln Met Ala
115 120 125

Ile Ser Gly Gly Phe Val Arg Arg Val Thr Asn Asp Ala Arg Glu Thr
130 135 140

Glu Met Asp Glu Asn Leu Glu Gln Val Gly Gly Ile Ile Gly Asn Leu
145 150 155 160

Arg His Met Ala Leu Asp Met Gly Asn Glu Ile Asp Thr Gln Asn Arg
165 170 175

Gln Ile Asp Arg Ile Met Glu Lys Ala Asp Ser Asn Lys Ala Arg Ile
180 185 190

Asp Glu Ala Asn Lys His Ala Thr Lys Met Leu Gly Ser Gly
195 200 205

<210> SEQ ID NO 20
<211> LENGTH: 204
<212> TYPE: PRT
<213> ORGANISM: Xenopus laevis SNAP-23 (African clawed frog)

<400> SEQUENCE: 20

Met Asp Asp Met Thr Ala Glu Glu Ile Gln Leu Lys Ala Asn Gln Val
1 5 10 15

Ala Asp Glu Ser Leu Glu Ser Thr Arg Arg Met Leu Asn Leu Ala Leu
20 25 30

Glu Ser Gln Asp Ala Gly Ile Lys Thr Ile Thr Met Leu Asp Glu Gln
35 40 45

Gly Glu Gln Leu Asp Arg Ile Glu Glu Gly Met Asp Gln Ile Asn Lys
50 55 60

```
Asp Met Arg Glu Ala Glu Lys Asn Leu Thr Glu Leu Asn Lys Cys Cys
65                  70                  75                  80

Gly Leu Cys Val Cys Pro Gly Lys Arg Ser Lys Asp Phe Glu Thr Gly
                85                  90                  95

Glu Asn Tyr Lys Lys Ala Trp Gly Ser Lys Asp Asn Asp Ser Asp Val
            100                 105                 110

Val Ser Lys Gln Pro Gly Gln Thr Asn Gly Gln Leu Ser Gly Ala Gly
        115                 120                 125

Gln Ser Gly Pro Tyr Ile Lys Arg Ile Thr Asn Asp Asp Arg Glu Asp
    130                 135                 140

Glu Met Asp Glu Asn Leu Val Gln Val Gly Ser Ile Leu Gly Asn Leu
145                 150                 155                 160

Lys Asn Met Ala Ile Asp Met Gly Asn Glu Leu Glu Ser His Asn Gln
                165                 170                 175

Gln Ile Gly Arg Ile Asn Glu Lys Ala Glu Thr Asn Lys Thr Arg Ile
            180                 185                 190

Asp Glu Ala Asn Thr Lys Ala Lys Lys Leu Ile Glu
        195                 200


<210> SEQ ID NO 21
<211> LENGTH: 212
<212> TYPE: PRT
<213> ORGANISM: Strongylocentrotus purpuratus SNAP-25 (Sea urchin)

<400> SEQUENCE: 21

Met Glu Asp Gln Asn Asp Met Asn Met Arg Ser Glu Leu Glu Glu Ile
 1               5                  10                  15

Gln Met Gln Ser Asn Met Gln Thr Asp Glu Ser Leu Glu Ser Thr Arg
            20                  25                  30

Arg Met Leu Gln Met Ala Glu Glu Ser Gln Asp Met Gly Ile Lys Thr
        35                  40                  45

Leu Val Met Leu Asp Glu Gln Gly Glu Gln Leu Asp Arg Ile Glu Glu
    50                  55                  60

Gly Met Asp Gln Ile Asn Thr Asp Met Arg Glu Ala Glu Lys Asn Leu
65                  70                  75                  80

Thr Gly Leu Glu Lys Cys Cys Gly Ile Cys Val Cys Pro Trp Lys Lys
                85                  90                  95

Leu Gly Asn Phe Glu Lys Gly Asp Asp Tyr Lys Lys Thr Trp Lys Gly
            100                 105                 110

Asn Asp Asp Gly Lys Val Asn Ser His Gln Pro Met Arg Met Glu Asp
        115                 120                 125

Asp Arg Asp Gly Cys Gly Gly Asn Ala Ser Met Ile Thr Arg Ile Thr
    130                 135                 140

Asn Asp Ala Arg Glu Asp Glu Met Asp Glu Asn Leu Thr Gln Val Ser
145                 150                 155                 160

Ser Ile Val Gly Asn Leu Arg His Met Ala Ile Asp Met Gln Ser Glu
                165                 170                 175

Ile Gly Ala Gln Asn Ser Gln Val Gly Arg Ile Thr Ser Lys Ala Glu
            180                 185                 190

Ser Asn Glu Gly Arg Ile Asn Ser Ala Asp Lys Arg Ala Lys Asn Ile
        195                 200                 205

Leu Arg Asn Lys
    210


<210> SEQ ID NO 22
<211> LENGTH: 212
```

<212> TYPE: PRT
<213> ORGANISM: Drosophila melanogaster SNAP-25 (Fruit fly)

<400> SEQUENCE: 22

```
Met Pro Ala Asp Pro Ser Glu Glu Val Ala Pro Gln Val Pro Lys Thr
 1               5                  10                  15

Glu Leu Glu Glu Leu Gln Ile Asn Ala Gln Gly Val Ala Asp Glu Ser
            20                  25                  30

Leu Glu Ser Thr Arg Arg Met Leu Ala Leu Cys Glu Glu Ser Lys Glu
        35                  40                  45

Ala Gly Ile Arg Thr Leu Val Ala Leu Asp Asp Gln Gly Glu Gln Leu
    50                  55                  60

Asp Arg Ile Glu Glu Gly Met Asp Gln Ile Asn Ala Asp Met Arg Glu
65                  70                  75                  80

Ala Glu Lys Asn Leu Ser Gly Met Glu Lys Cys Cys Gly Ile Cys Val
                85                  90                  95

Leu Pro Cys Asn Lys Ser Gln Ser Phe Lys Glu Asp Asp Gly Thr Trp
            100                 105                 110

Lys Gly Asn Asp Asp Gly Lys Val Val Asn Asn Gln Pro Gln Arg Val
        115                 120                 125

Met Asp Asp Arg Asn Gly Met Met Ala Gln Ala Gly Tyr Ile Gly Arg
    130                 135                 140

Ile Thr Asn Asp Ala Arg Glu Asp Glu Met Glu Glu Asn Met Gly Gln
145                 150                 155                 160

Val Asn Thr Met Ile Gly Asn Leu Arg Asn Met Ala Leu Asp Met Gly
                165                 170                 175

Ser Glu Leu Glu Asn Gln Asn Arg Gln Ile Asp Arg Ile Asn Arg Lys
            180                 185                 190

Gly Glu Ser Asn Glu Ala Arg Ile Ala Val Ala Asn Gln Arg Ala His
        195                 200                 205

Gln Leu Leu Lys
    210
```

<210> SEQ ID NO 23
<211> LENGTH: 212
<212> TYPE: PRT
<213> ORGANISM: Drosophila melanogaster SNAP-24 (Fruit fly)

<400> SEQUENCE: 23

```
Met Ala Ala Val Glu Asn Ala Glu Pro Arg Thr Glu Leu Gln Glu Leu
 1               5                  10                  15

Gln Phe Lys Ser Gly Gln Val Ala Asp Glu Ser Leu Glu Ser Thr Arg
            20                  25                  30

Arg Met Leu Ala Leu Met Asp Glu Ser Lys Glu Ala Gly Ile Arg Thr
        35                  40                  45

Leu Val Ala Leu Asp Asp Gln Gly Glu Gln Leu Asp Arg Ile Glu Glu
    50                  55                  60

Gly Met Asp Arg Ile Asn Ala Asp Met Arg Glu Ala Glu Lys Asn Leu
65                  70                  75                  80

Ser Gly Met Glu Lys Cys Cys Gly Ile Cys Val Leu Pro Trp Lys Lys
                85                  90                  95

Val Asn Ile Lys Asp Asp Gly Glu Ser Ala Trp Lys Ala Asn Asp Asp
            100                 105                 110

Gly Lys Ile Val Ala Ser Gln Pro Gln Arg Val Ile Asp Glu Arg Glu
        115                 120                 125

Arg Gly Gly Met Gly Ala Pro Pro Gln Ser Gly Tyr Val Ala Arg Ile
```

```
    130                 135                 140

Thr Asn Asp Ala Arg Glu Asp Glu Met Asp Glu Asn Leu Gly Gln Val
145                 150                 155                 160

Asn Ser Met Leu Gly Asn Leu Arg Asn Met Ala Leu Asp Met Gly Ser
                165                 170                 175

Glu Leu Glu Asn Gln Asn Lys Gln Val Asp Arg Ile Asn Ala Lys Gly
            180                 185                 190

Asp Ala Asn Asn Ile Arg Met Asp Gly Val Asn Lys Arg Ala Asn Asn
        195                 200                 205

Leu Leu Lys Ser
    210


<210> SEQ ID NO 24
<211> LENGTH: 212
<212> TYPE: PRT
<213> ORGANISM: Hirudo medicinalis SNAP-25 (Leech)

<400> SEQUENCE: 24

Met Ala Lys Asp Ile Lys Pro Lys Pro Ala Asn Gly Arg Asp Ser Pro
 1               5                  10                  15

Thr Asp Leu Gln Glu Ile Gln Leu Gln Met Asn Ala Ile Thr Asp Asp
            20                  25                  30

Ser Leu Glu Ser Thr Arg Arg Met Leu Ala Met Cys Glu Glu Ser Lys
        35                  40                  45

Asp Ala Gly Ile Arg Thr Leu Val Met Leu Asp Glu Gln Gly Glu Gln
    50                  55                  60

Leu Asp Arg Ile Glu Glu Gly Met Asp Gln Ile Asn Gln Asp Met Arg
65                  70                  75                  80

Asp Ala Glu Lys Asn Leu Glu Gly Met Glu Lys Cys Cys Gly Leu Cys
                85                  90                  95

Ile Leu Pro Trp Lys Arg Thr Lys Asn Phe Asp Lys Gly Ala Glu Trp
            100                 105                 110

Asn Lys Gly Asp Glu Gly Lys Val Asn Thr Asp Gly Pro Arg Leu Val
        115                 120                 125

Val Gly Asp Gly Asn Met Gly Pro Ser Gly Gly Phe Ile Thr Lys Ile
    130                 135                 140

Thr Asn Asp Ala Arg Glu Glu Glu Met Glu Gln Asn Met Gly Glu Val
145                 150                 155                 160

Ser Asn Met Ile Ser Asn Leu Arg Asn Met Ala Val Asp Met Gly Ser
                165                 170                 175

Glu Ile Asp Ser Gln Asn Arg Gln Val Asp Arg Ile Asn Asn Lys Met
            180                 185                 190

Thr Ser Asn Gln Leu Arg Ile Ser Asp Ala Asn Lys Arg Ala Ser Lys
        195                 200                 205

Leu Leu Lys Glu
    210


<210> SEQ ID NO 25
<211> LENGTH: 212
<212> TYPE: PRT
<213> ORGANISM: Loligo pealei SNAP-25 (Longfin squid)

<400> SEQUENCE: 25

Met Ser Ala Asn Gly Glu Val Glu Val Pro Lys Thr Glu Leu Glu Glu
 1               5                  10                  15

Ile Gln Gln Gln Cys Asn Gln Val Thr Asp Asp Ser Leu Glu Ser Thr
            20                  25                  30
```

```
Arg Arg Met Leu Asn Met Cys Glu Glu Ser Lys Glu Ala Gly Ile Arg
        35                  40                  45

Thr Leu Val Met Leu Asp Glu Gln Gly Glu Gln Leu Asp Arg Ile Glu
    50                  55                  60

Glu Gly Leu Asp Gln Ile Asn Gln Asp Met Lys Asp Ala Glu Lys Asn
65                  70                  75                  80

Leu Glu Gly Met Glu Lys Cys Cys Gly Leu Cys Val Leu Pro Trp Lys
                85                  90                  95

Arg Gly Lys Ser Phe Glu Lys Ser Gly Asp Tyr Ala Asn Thr Trp Lys
            100                 105                 110

Lys Asp Asp Asp Gly Pro Thr Asn Thr Asn Gly Pro Arg Val Thr Val
        115                 120                 125

Gly Asp Gln Asn Gly Met Gly Pro Ser Ser Gly Tyr Val Thr Arg Ile
    130                 135                 140

Thr Asn Asp Ala Arg Glu Asp Asp Met Glu Asn Asn Met Lys Glu Val
145                 150                 155                 160

Ser Ser Met Ile Gly Asn Leu Arg Asn Met Ala Ile Asp Met Gly Asn
                165                 170                 175

Glu Ile Gly Ser Gln Asn Arg Gln Val Asp Arg Ile Gln Gln Lys Ala
            180                 185                 190

Glu Ser Asn Glu Ser Arg Ile Asp Glu Ala Asn Lys Lys Ala Thr Lys
        195                 200                 205

Leu Leu Lys Asn
    210


<210> SEQ ID NO 26
<211> LENGTH: 220
<212> TYPE: PRT
<213> ORGANISM: Lymnaea stagnalis SNAP-25 (Great pond snail)

<400> SEQUENCE: 26

Met Thr Thr Asn Gly Glu Ile Leu Pro Val Gly Glu Glu Glu Glu Glu
 1               5                  10                  15

Glu Leu Gly Glu Asp Ala Leu Leu Arg Lys Gln Ile Asp Cys Asn Thr
            20                  25                  30

Asn Glu Ser Leu Glu Ser Thr Arg Arg Met Leu Ser Leu Cys Glu Glu
        35                  40                  45

Ser Lys Glu Ala Gly Ile Lys Thr Leu Val Met Leu Asp Glu Gln Gly
    50                  55                  60

Glu Gln Leu Asp Arg Ile Glu Glu Gly Met Gly Gln Ile Asn Gln Asp
65                  70                  75                  80

Met Arg Asp Ala Glu Lys Asn Leu Glu Gly Leu Glu Lys Cys Cys Gly
                85                  90                  95

Leu Cys Val Leu Pro Trp Lys Arg Ser Lys Asn Phe Glu Lys Gly Ser
            100                 105                 110

Asp Tyr Asn Lys Thr Trp Lys Ala Ser Glu Asp Gly Lys Ile Asn Thr
        115                 120                 125

Asn Gly Pro Arg Leu Val Val Asp Gln Gly Asn Gly Ser Gly Pro Thr
    130                 135                 140

Gly Gly Tyr Ile Thr Arg Ile Thr Asn Asp Ala Arg Glu Asp Glu Met
145                 150                 155                 160

Glu Gln Asn Ile Gly Glu Val Ala Gly Met Val Ser Asn Leu Arg Asn
                165                 170                 175

Met Ala Val Asp Met Gly Asn Glu Ile Glu Ser Gln Asn Lys Gln Leu
            180                 185                 190
```

```
Asp Arg Ile Asn Gln Lys Gly Gly Ser Leu Asn Val Arg Val Asp Glu
        195                 200                 205

Ala Asn Lys Arg Ala Asn Arg Ile Leu Arg Lys Gln
    210                 215                 220


<210> SEQ ID NO 27
<211> LENGTH: 207
<212> TYPE: PRT
<213> ORGANISM: Caenorhabditis elegans SNAP-25 (Round worm)

<400> SEQUENCE: 27

Met Ser Gly Asp Asp Asp Ile Pro Glu Gly Leu Glu Ala Ile Asn Leu
 1               5                  10                  15

Lys Met Asn Ala Thr Thr Asp Asp Ser Leu Glu Ser Thr Arg Arg Met
            20                  25                  30

Leu Ala Leu Cys Glu Glu Ser Lys Glu Ala Gly Ile Lys Thr Leu Val
        35                  40                  45

Met Leu Asp Asp Gln Gly Glu Gln Leu Glu Arg Cys Glu Gly Ala Leu
    50                  55                  60

Asp Thr Ile Asn Gln Asp Met Lys Glu Ala Glu Asp His Leu Lys Gly
65                  70                  75                  80

Met Glu Lys Cys Cys Gly Leu Cys Val Leu Pro Trp Asn Lys Thr Asp
                85                  90                  95

Asp Phe Glu Lys Thr Glu Phe Ala Lys Ala Trp Lys Lys Asp Asp Asp
            100                 105                 110

Gly Gly Val Ile Ser Asp Gln Pro Arg Ile Thr Val Gly Asp Ser Ser
        115                 120                 125

Met Gly Pro Gln Gly Gly Tyr Ile Thr Lys Ile Thr Asn Asp Ala Arg
    130                 135                 140

Glu Asp Glu Met Asp Glu Asn Val Gln Gln Val Ser Thr Met Val Gly
145                 150                 155                 160

Asn Leu Arg Asn Met Ala Ile Asp Met Ser Thr Glu Val Ser Asn Gln
                165                 170                 175

Asn Arg Gln Leu Asp Arg Ile His Asp Lys Ala Gln Ser Asn Glu Val
            180                 185                 190

Arg Val Glu Ser Ala Asn Lys Arg Ala Lys Asn Leu Ile Thr Lys
        195                 200                 205


<210> SEQ ID NO 28
<211> LENGTH: 118
<212> TYPE: PRT
<213> ORGANISM: Homo sapiens VAMP-1-1 (Human)

<400> SEQUENCE: 28

Met Ser Ala Pro Ala Gln Pro Pro Ala Glu Gly Thr Glu Gly Thr Ala
 1               5                  10                  15

Pro Gly Gly Gly Pro Pro Gly Pro Pro Pro Asn Met Thr Ser Asn Arg
            20                  25                  30

Arg Leu Gln Gln Thr Gln Ala Gln Val Glu Glu Val Val Asp Ile Ile
        35                  40                  45

Arg Val Asn Val Asp Lys Val Leu Glu Arg Asp Gln Lys Leu Ser Glu
    50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95
```

-continued

```
Met Met Ile Met Leu Gly Ala Ile Cys Ala Ile Ile Val Val Val Ile
            100                 105                 110

Val Ile Tyr Phe Phe Thr
        115


<210> SEQ ID NO 29
<211> LENGTH: 117
<212> TYPE: PRT
<213> ORGANISM: Homo sapiens VAMP-1-2 (Human)

<400> SEQUENCE: 29

Met Ser Ala Pro Ala Gln Pro Pro Ala Glu Gly Thr Glu Gly Thr Ala
 1               5                  10                  15

Pro Gly Gly Gly Pro Pro Gly Pro Pro Pro Asn Met Thr Ser Asn Arg
            20                  25                  30

Arg Leu Gln Gln Thr Gln Ala Gln Val Glu Glu Val Val Asp Ile Ile
        35                  40                  45

Arg Val Asn Val Asp Lys Val Leu Glu Arg Asp Gln Lys Leu Ser Glu
    50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
            100                 105                 110

Val Ser Lys Tyr Arg
        115


<210> SEQ ID NO 30
<211> LENGTH: 116
<212> TYPE: PRT
<213> ORGANISM: Homo sapiens VAMP-1-3 (Human)

<400> SEQUENCE: 30

Met Ser Ala Pro Ala Gln Pro Pro Ala Glu Gly Thr Glu Gly Thr Ala
 1               5                  10                  15

Pro Gly Gly Gly Pro Pro Gly Pro Pro Pro Asn Met Thr Ser Asn Arg
            20                  25                  30

Arg Leu Gln Gln Thr Gln Ala Gln Val Glu Glu Val Val Asp Ile Ile
        35                  40                  45

Arg Val Asn Val Asp Lys Val Leu Glu Arg Asp Gln Lys Leu Ser Glu
    50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
            100                 105                 110

Val Arg Arg Asp
        115


<210> SEQ ID NO 31
<211> LENGTH: 116
<212> TYPE: PRT
<213> ORGANISM: Homo sapiens VAMP-2 (Human)

<400> SEQUENCE: 31

Met Ser Ala Thr Ala Ala Thr Ala Pro Pro Ala Ala Pro Ala Gly Glu
 1               5                  10                  15
```

Gly Gly Pro Pro Ala Pro Pro Pro Asn Leu Thr Ser Asn Arg Arg Leu
20 25 30

Gln Gln Thr Gln Ala Gln Val Asp Glu Val Val Asp Ile Met Arg Val
35 40 45

Asn Val Asp Lys Val Leu Glu Arg Asp Gln Lys Leu Ser Glu Leu Asp
50 55 60

Asp Arg Ala Asp Ala Leu Gln Ala Gly Ala Ser Gln Phe Glu Thr Ser
65 70 75 80

Ala Ala Lys Leu Lys Arg Lys Tyr Trp Trp Lys Asn Leu Lys Met Met
85 90 95

Ile Ile Leu Gly Val Ile Cys Ala Ile Ile Leu Ile Ile Ile Ile Val
100 105 110

Tyr Phe Ser Thr
115

<210> SEQ ID NO 32
<211> LENGTH: 116
<212> TYPE: PRT
<213> ORGANISM: Macaca mulatta VAMP-2 (Rhesus monkey)

<400> SEQUENCE: 32

Met Ser Ala Thr Ala Ala Thr Ala Pro Pro Ala Ala Pro Ala Gly Glu
1 5 10 15

Gly Gly Pro Pro Ala Pro Pro Pro Asn Leu Thr Ser Asn Arg Arg Leu
20 25 30

Gln Gln Thr Gln Ala Gln Val Asp Glu Val Val Asp Ile Met Arg Val
35 40 45

Asn Val Asp Lys Val Leu Glu Arg Asp Gln Lys Leu Ser Glu Leu Asp
50 55 60

Asp Arg Ala Asp Ala Leu Gln Ala Gly Ala Ser Gln Phe Glu Thr Ser
65 70 75 80

Ala Ala Lys Leu Lys Arg Lys Tyr Trp Trp Lys Asn Leu Lys Met Met
85 90 95

Ile Ile Leu Gly Val Ile Cys Ala Ile Ile Leu Ile Ile Ile Ile Val
100 105 110

Tyr Phe Ser Thr
115

<210> SEQ ID NO 33
<211> LENGTH: 100
<212> TYPE: PRT
<213> ORGANISM: Homo sapiens VAMP-3 (Human)

<400> SEQUENCE: 33

Met Ser Thr Gly Pro Thr Ala Ala Thr Gly Ser Asn Arg Arg Leu Gln
1 5 10 15

Gln Thr Gln Asn Gln Val Asp Glu Val Val Asp Ile Met Arg Val Asn
20 25 30

Val Asp Lys Val Leu Glu Arg Asp Gln Lys Leu Ser Glu Leu Asp Asp
35 40 45

Arg Ala Asp Ala Leu Gln Ala Gly Ala Ser Gln Phe Glu Thr Ser Ala
50 55 60

Ala Lys Leu Lys Arg Lys Tyr Trp Trp Lys Asn Cys Lys Met Trp Ala
65 70 75 80

Ile Gly Ile Thr Val Leu Val Ile Phe Ile Ile Ile Ile Ile Val Trp
85 90 95

```
Val Val Ser Ser
            100


<210> SEQ ID NO 34
<211> LENGTH: 116
<212> TYPE: PRT
<213> ORGANISM: Bos taurus VAMP-2 (Cow)

<400> SEQUENCE: 34

Met Ser Ala Thr Ala Ala Thr Ala Pro Pro Ala Ala Pro Ala Gly Glu
 1               5                  10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Ser
        115


<210> SEQ ID NO 35
<211> LENGTH: 118
<212> TYPE: PRT
<213> ORGANISM: Rattus norvegicus VAMP-1 (Rat)

<400> SEQUENCE: 35

Met Ser Ala Pro Ala Gln Pro Pro Ala Glu Gly Thr Glu Gly Ala Ala
 1               5                  10                  15

Pro Gly Gly Gly Pro Pro Gly Pro Pro Pro Asn Thr Thr Ser Asn Arg
            20                  25                  30

Arg Leu Gln Gln Thr Gln Ala Gln Val Glu Glu Val Val Asp Ile Ile
        35                  40                  45

Arg Val Asn Val Asp Lys Val Leu Glu Arg Asp Gln Lys Leu Ser Glu
    50                  55                  60

Leu Asp Asp Arg Ala Asp Ala Leu Gln Ala Gly Ala Ser Val Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
            100                 105                 110

Val Ile Tyr Ile Phe Thr
        115


<210> SEQ ID NO 36
<211> LENGTH: 117
<212> TYPE: PRT
<213> ORGANISM: Rattus norvegicus VAMP-1b (Rat)

<400> SEQUENCE: 36

Met Ser Ala Pro Ala Gln Pro Pro Ala Glu Gly Thr Glu Gly Ala Ala
 1               5                  10                  15

Pro Gly Gly Gly Pro Pro Gly Pro Pro Pro Asn Thr Thr Ser Asn Arg
            20                  25                  30
```

```
Arg Leu Gln Gln Thr Gln Ala Gln Val Glu Glu Val Val Asp Ile Met
        35                  40                  45

Arg Val Asn Val Asp Lys Val Leu Glu Arg Asp Gln Lys Leu Ser Glu
    50                  55                  60

Leu Asp Asp Arg Ala Asp Ala Leu Gln Ala Gly Ala Ser Val Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
            100                 105                 110

Val Ser Lys Tyr Arg
        115


<210> SEQ ID NO 37
<211> LENGTH: 118
<212> TYPE: PRT
<213> ORGANISM: Mus musculus VAMP-1 (Mouse)

<400> SEQUENCE: 37

Met Ser Ala Pro Ala Gln Pro Pro Ala Glu Gly Thr Glu Gly Ala Ala
 1               5                  10                  15

Pro Gly Gly Gly Pro Pro Gly Pro Pro Pro Asn Met Thr Ser Asn Arg
            20                  25                  30

Arg Leu Gln Gln Thr Gln Ala Gln Val Glu Glu Val Val Asp Ile Met
        35                  40                  45

Arg Val Asn Val Asp Lys Val Leu Glu Arg Asp Gln Lys Leu Ser Glu
    50                  55                  60

Leu Asp Asp Arg Ala Asp Ala Leu Gln Ala Gly Ala Ser Gln Phe Glu
65                  70                  75                  80

Ser Ser Ala Ala Lys Leu Lys Arg Lys Tyr Trp Trp Lys Asn Cys Lys
                85                  90                  95

Met Met Ile Met Leu Gly Ala Ile Cys Ala Ile Ile Val Val Val Ile
            100                 105                 110

Val Ile Tyr Phe Phe Thr
        115


<210> SEQ ID NO 38
<211> LENGTH: 116
<212> TYPE: PRT
<213> ORGANISM: Rattus norvegicus VAMP-2 (Rat)

<400> SEQUENCE: 38

Met Ser Ala Thr Ala Ala Thr Val Pro Pro Ala Ala Pro Ala Gly Glu
 1               5                  10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110
```

```
Tyr Phe Ser Thr
        115


<210> SEQ ID NO 39
<211> LENGTH: 135
<212> TYPE: PRT
<213> ORGANISM: Rattus norvegicus VAMP-2b (Rat)

<400> SEQUENCE: 39

Met Ser Ala Thr Ala Ala Thr Val Pro Pro Ala Ala Pro Ala Gly Glu
 1               5                  10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Gly
            100                 105                 110

Glu Trp Ser Arg Ser Gly Gln Gly Pro Phe Pro Gly Glu Val Glu Gly
        115                 120                 125

Phe Pro Val Gly Ser Gly Leu
    130                 135


<210> SEQ ID NO 40
<211> LENGTH: 116
<212> TYPE: PRT
<213> ORGANISM: Mus musculus VAMP-2 (Mouse)

<400> SEQUENCE: 40

Met Ser Ala Thr Ala Ala Thr Val Pro Pro Ala Ala Pro Ala Gly Glu
 1               5                  10                  15

Gly Gly Pro Pro Ala Pro Pro Pro Asn Leu Thr Ser Asn Arg Arg Leu
            20                  25                  30

Gln Gln Thr Gln Ala Gln Val Asp Glu Val Val Asp Ile Met Arg Val
        35                  40                  45

Asn Val Asp Lys Val Leu Glu Arg Asp Gln Lys Leu Ser Glu Leu Asp
    50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
            100                 105                 110

Tyr Phe Ser Thr
        115


<210> SEQ ID NO 41
<211> LENGTH: 103
<212> TYPE: PRT
<213> ORGANISM: Rattus norvegicus VAMP-3 (Rat)

<400> SEQUENCE: 41

Met Ser Thr Gly Val Pro Ser Gly Ser Ser Ala Ala Thr Gly Ser Asn
 1               5                  10                  15
```

```
Arg Arg Leu Gln Gln Thr Gln Asn Gln Val Asp Glu Val Val Asp Ile
            20                  25                  30

Met Arg Val Asn Val Asp Lys Val Leu Glu Arg Asp Gln Lys Leu Ser
        35                  40                  45

Glu Leu Asp Asp Arg Ala Asp Ala Leu Gln Ala Gly Ala Ser Gln Phe
    50                  55                  60

Glu Thr Ser Ala Ala Lys Leu Lys Arg Lys Tyr Trp Trp Lys Asn Cys
65                  70                  75                  80

Lys Met Trp Ala Ile Gly Ile Ser Val Leu Val Ile Ile Val Ile Ile
                85                  90                  95

Ile Ile Val Trp Cys Val Ser
            100


<210> SEQ ID NO 42
<211> LENGTH: 103
<212> TYPE: PRT
<213> ORGANISM: Mus musculus VAMP-3 (Mouse)

<400> SEQUENCE: 42

Met Ser Thr Gly Val Pro Ser Gly Ser Ser Ala Ala Thr Gly Ser Asn
 1               5                  10                  15

Arg Arg Leu Gln Gln Thr Gln Asn Gln Val Asp Glu Val Val Asp Ile
            20                  25                  30

Met Arg Val Asn Val Asp Lys Val Leu Glu Arg Asp Gln Lys Leu Ser
        35                  40                  45

Glu Leu Asp Asp Arg Ala Asp Ala Leu Gln Ala Gly Ala Ser Gln Phe
    50                  55                  60

Glu Thr Ser Ala Ala Lys Leu Lys Arg Lys Tyr Trp Trp Lys Asn Cys
65                  70                  75                  80

Lys Met Trp Ala Ile Gly Ile Ser Val Leu Val Ile Ile Val Ile Ile
                85                  90                  95

Ile Ile Val Trp Cys Val Ser
            100


<210> SEQ ID NO 43
<211> LENGTH: 259
<212> TYPE: PRT
<213> ORGANISM: Gallus gallus VAMP-1 (Chicken)

<400> SEQUENCE: 43

Met His Gln Glu Asn Gln Thr Lys Gln Val Gln Gln Val Ser Pro Ser
 1               5                  10                  15

Val Asn Ala Ala Trp Lys Leu Leu Val Pro Val Phe Leu Pro Gly Gly
            20                  25                  30

Ser Thr Pro Ala Ala Pro Tyr Pro Asp Cys Cys Ser Thr Arg Ala Gln
        35                  40                  45

Arg Thr Leu Ala Ala Leu Ser Pro Ala Leu Ile Gly Arg Cys Gln Ala
    50                  55                  60

Gly Thr Gly Leu Asn Pro Gly Glu Ser Gly Gly Gln Arg Glu Ala Gly
65                  70                  75                  80

Leu Arg Glu Gly Ala Leu Phe Thr Gly Ala Ser Leu Arg Pro Ser Arg
                85                  90                  95

Gly Ala Leu Ile Gly Phe Gly Glu Gly Glu Gly Gly Ala Asp Ser Arg
            100                 105                 110

Val Ser Ala Arg Pro Ser Cys Asp Tyr Phe Ser Leu Ala Ala Gly Pro
        115                 120                 125
```

```
Cys Gly Ala Gly Leu Phe Val Cys Ala Gly Trp Gly Met Ser Glu Pro
    130                 135                 140

Ala Gln Gln Pro Ala Pro Gly Ala Pro Glu Gly Gly Ala Pro Ala Gly
145                 150                 155                 160

Gly Pro Pro Gly Pro Pro Pro Asn Leu Ser Ser Asn Arg Arg Leu Gln
                165                 170                 175

Gln Thr Gln Ala Gln Val Glu Glu Val Val Asp Ile Met Arg Val Asn
            180                 185                 190

Val Asp Lys Val Leu Glu Arg Asp Gln Lys Leu Ser Glu Leu Asp Asp
        195                 200                 205

Arg Ala Asp Ala Leu Gln Ala Gly Ala Ser Val Phe Glu Ser Ser Ala
    210                 215                 220

Ala Lys Leu Lys Arg Lys Tyr Trp Trp Lys Asn Cys Lys Met Met Ile
225                 230                 235                 240

Met Met Gly Val Ile Cys Ala Ile Val Val Val Val Ile Val Ile Tyr
                245                 250                 255

Phe Phe Thr


<210> SEQ ID NO 44
<211> LENGTH: 114
<212> TYPE: PRT
<213> ORGANISM: Gallus gallus VAMP-2 (Chicken)

<400> SEQUENCE: 44

Met Ser Ala Pro Ala Pro Thr Gln Gly Pro Thr Ser Thr Gly Ala Ala
 1               5                  10                  15

Gly Pro Pro Pro Ala Thr Asn Val Ser Ser Asn Lys Arg Leu Gln Gln
            20                  25                  30

Thr Gln Ala Gln Val Asp Glu Val Val Asp Ile Met Arg Met Asn Val
        35                  40                  45

Asp Lys Val Leu Glu Arg Asp Gln Lys Leu Ser Glu Leu Asp Asn Arg
    50                  55                  60

Ala Asp Ala Leu Gln Ala Gly Ala Ser Gln Phe Glu Thr Ser Ala Ala
65                  70                  75                  80

Lys Leu Lys Arg Lys Tyr Trp Trp Lys Asn Cys Lys Met Met Ile Ile
                85                  90                  95

Leu Gly Val Val Cys Thr Val Ile Leu Ile Ile Ile Ile Ile Tyr Phe
            100                 105                 110

Ser Thr


<210> SEQ ID NO 45
<211> LENGTH: 118
<212> TYPE: PRT
<213> ORGANISM: Gallus gallus VAMP-3 (Chicken)

<400> SEQUENCE: 45

Met Ser Ala Asn Val Pro Gly Asn Thr Asn Val Pro Ala Gly Ser Asn
 1               5                  10                  15

Arg Arg Leu Gln Gln Thr Gln His Gln Val Asp Glu Val Val Asp Ile
            20                  25                  30

Met Arg Val Asn Val Asp Lys Val Leu Glu Arg Asp Gln Lys Leu Ser
        35                  40                  45

Glu Leu Asp Asp Arg Ala Asp Ala Leu Gln Ala Gly Ala Ser Gln Phe
    50                  55                  60

Glu Thr Ser Ala Ala Lys Leu Lys Arg Lys Tyr Trp Trp Lys Asn Cys
65                  70                  75                  80
```

```
Lys Met Trp Ala Ile Leu Ile Ala Val Val Val Ile Ile Ile Ile Ile
                85                  90                  95

Ile Ile Val Val Ser Val Ser Ala Ala Leu Ser Ala Arg Leu Leu Leu
            100                 105                 110

Phe Lys Ala Lys Leu Phe
        115


<210> SEQ ID NO 46
<211> LENGTH: 119
<212> TYPE: PRT
<213> ORGANISM: Danio rerio VAMP-1 (Zebrafish)

<400> SEQUENCE: 46

Met Ser Ala Pro Asp Ala Ala Ala Ser Pro Gly Ala Pro Gly Ala Pro
 1               5                  10                  15

Glu Gly Glu Gly Gly Ala Pro Ala Gln Pro Pro Asn Leu Thr Ser Asn
            20                  25                  30

Arg Arg Leu Gln Gln Thr Gln Ala Gln Val Asp Glu Val Val Asp Ile
        35                  40                  45

Met Arg Val Asn Val Asp Lys Val Leu Glu Arg Asp Gln Lys Leu Ser
    50                  55                  60

Glu Leu Asp Asp Arg Ala Asp Ala Leu Gln Ala Gly Ala Ser Gln Phe
65                  70                  75                  80

Glu Ser Ser Ala Ala Lys Leu Lys Asn Lys Tyr Trp Trp Lys Asn Met
                85                  90                  95

Lys Met Met Ile Ile Met Gly Ile Met Gly Ile Ile Leu Leu Gly Ile
            100                 105                 110

Ala Phe Met Tyr Phe Tyr Tyr
        115


<210> SEQ ID NO 47
<211> LENGTH: 110
<212> TYPE: PRT
<213> ORGANISM: Danio rerio VAMP-2 (Zebrafish)

<400> SEQUENCE: 47

Met Ser Ala Pro Ala Gly Ala Pro Ala Pro Glu Gly Gly Asn Gln Ala
 1               5                  10                  15

Pro Pro Asn Leu Thr Ser Asn Arg Arg Leu Gln Gln Thr Gln Ala Gln
            20                  25                  30

Val Asp Glu Val Val Asp Ile Met Arg Val Asn Val Asp Lys Val Leu
        35                  40                  45

Glu Arg Asp Gln Lys Leu Ser Glu Leu Asp Asp Arg Ala Asp Ala Leu
    50                  55                  60

Gln Ala Gly Ala Ser Gln Phe Glu Thr Ser Ala Ala Lys Leu Lys Asn
65                  70                  75                  80

Lys Tyr Trp Trp Lys Asn Ala Lys Met Met Ile Ile Leu Gly Val Ile
                85                  90                  95

Cys Val Ile Val Leu Ile Ile Ile Ile Val Tyr Phe Ser Thr
            100                 105                 110


<210> SEQ ID NO 48
<211> LENGTH: 102
<212> TYPE: PRT
<213> ORGANISM: Danio rerio VAMP-3 (Zebrafish)

<400> SEQUENCE: 48

Met Ser Ala Pro Gly Ala Asp Ala Ser Gly Ser Ser Gly Ser Asn Arg
 1               5                  10                  15
```

```
Arg Leu Gln Gln Thr Gln Ala Gln Val Asp Glu Val Val Asp Ile Met
            20                  25                  30

Arg Val Asn Val Asp Lys Val Leu Glu Arg Asp Gln Lys Leu Ser Glu
        35                  40                  45

Leu Asp Asp Arg Ala Asp Ala Leu Gln Ala Gly Ala Ser Gln Phe Glu
    50                  55                  60

Thr Ser Ala Ala Lys Leu Lys Arg Lys Phe Trp Trp Lys Asn Val Lys
65                  70                  75                  80

Met Trp Ala Ile Leu Ile Ala Val Val Val Ile Ile Ile Ile Ile Ile
                85                  90                  95

Val Ile Trp Ser Gln Ser
            100


<210> SEQ ID NO 49
<211> LENGTH: 120
<212> TYPE: PRT
<213> ORGANISM: Torpedo marmorata VAMP-1 (Marbled electric ray)

<400> SEQUENCE: 49

Met Ser Ala Pro Pro Ser Gly Pro Ala Pro Asp Ala Gln Gly Gly Ala
 1               5                  10                  15

Pro Gly Gln Pro Thr Gly Pro Pro Gly Ala Pro Pro Asn Thr Thr Ser
            20                  25                  30

Asn Arg Arg Leu Gln Gln Thr Gln Ala Gln Val Glu Glu Val Val Asp
        35                  40                  45

Ile Ile Arg Val Asn Val Asp Lys Val Leu Glu Arg Asp Gln Lys Leu
    50                  55                  60

Ser Glu Leu Asp Asp Arg Ala Asp Ala Leu Gln Ala Gly Ala Ser Gln
65                  70                  75                  80

Phe Glu Ser Ser Ala Ala Lys Leu Lys Arg Lys Tyr Trp Trp Lys Asn
                85                  90                  95

Cys Lys Met Met Ile Met Leu Gly Gly Ile Gly Ala Ile Ile Val Ile
            100                 105                 110

Val Ile Ile Ile Tyr Phe Phe Thr
        115                 120


<210> SEQ ID NO 50
<211> LENGTH: 114
<212> TYPE: PRT
<213> ORGANISM: Xenopus laevis VAMP-2 (African clawed frog)

<400> SEQUENCE: 50

Met Ser Ala Pro Ala Ala Gly Pro Pro Ala Ala Ala Pro Gly Asp Gly
 1               5                  10                  15

Ala Pro Gln Gly Pro Pro Asn Leu Thr Ser Asn Arg Arg Leu Gln Gln
            20                  25                  30

Thr Gln Ala Gln Val Asp Glu Val Val Asp Ile Met Arg Val Asn Val
        35                  40                  45

Asp Lys Val Leu Glu Arg Asp Thr Lys Leu Ser Glu Leu Asp Asp Arg
    50                  55                  60

Ala Asp Ala Leu Gln Ala Gly Ala Ser Gln Phe Glu Thr Ser Ala Ala
65                  70                  75                  80

Lys Leu Lys Arg Lys Tyr Trp Trp Lys Asn Met Lys Met Met Ile Ile
                85                  90                  95

Met Gly Val Ile Cys Ala Ile Ile Leu Ile Ile Ile Ile Val Tyr Phe
            100                 105                 110
```

```
Ser Thr


<210> SEQ ID NO 51
<211> LENGTH: 101
<212> TYPE: PRT
<213> ORGANISM: Xenopus laevis VAMP-3 (African clawed frog)

<400> SEQUENCE: 51

Met Ser Thr Pro Gly Thr Ser Ala Thr Gly Asp Pro Gly Asn Arg Arg
 1               5                   10                  15

Leu Gln Gln Thr Gln Ala Gln Val Asp Glu Val Val Asp Ile Met Arg
            20                  25                  30

Val Asn Val Asp Lys Val Leu Glu Arg Asp Gln Lys Leu Ser Glu Leu
        35                  40                  45

Asp Asp Arg Ala Asp Ala Leu Gln Ala Gly Ala Ser Gln Phe Glu Thr
    50                  55                  60

Ser Ala Ala Lys Leu Lys Arg Lys Tyr Trp Trp Lys Asn Cys Lys Met
65                  70                  75                  80

Trp Ala Ile Leu Ile Ala Val Val Leu Val Ile Ile Ile Ile Ile Ile
                85                  90                  95

Val Trp Ser Val Ser
            100


<210> SEQ ID NO 52
<211> LENGTH: 104
<212> TYPE: PRT
<213> ORGANISM: Strongylocentrotus purpuratus VAMP (Sea urchin)

<400> SEQUENCE: 52

Met Ala Ala Pro Pro Pro Pro Gln Pro Ala Pro Ser Asn Lys Arg Leu
 1               5                   10                  15

Gln Gln Thr Gln Ala Gln Val Asp Glu Val Val Asp Ile Met Arg Val
            20                  25                  30

Asn Val Asp Lys Val Leu Glu Arg Asp Gln Ala Leu Ser Val Leu Asp
        35                  40                  45

Asp Arg Ala Asp Ala Leu Gln Gln Gly Ala Ser Gln Phe Glu Thr Asn
    50                  55                  60

Ala Gly Lys Leu Lys Arg Lys Tyr Trp Trp Lys Asn Cys Lys Met Met
65                  70                  75                  80

Ile Ile Leu Ala Ile Ile Ile Ile Val Ile Leu Ile Ile Ile Ile Val
                85                  90                  95

Ala Ile Val Gln Ser Gln Lys Lys
            100


<210> SEQ ID NO 53
<211> LENGTH: 129
<212> TYPE: PRT
<213> ORGANISM: Drosophila melanogaster SynA1 (Fruit fly)

<400> SEQUENCE: 53

Met Glu Asn Asn Glu Ala Pro Ser Pro Ser Gly Ser Asn Asn Asn Glu
 1               5                   10                  15

Asn Asn Asn Ala Ala Gln Lys Lys Leu Gln Gln Thr Gln Ala Lys Val
            20                  25                  30

Asp Glu Val Val Gly Ile Met Arg Val Asn Val Glu Lys Val Leu Glu
        35                  40                  45

Arg Asp Gln Lys Leu Ser Glu Leu Gly Glu Arg Ala Asp Gln Leu Glu
    50                  55                  60
```

```
Gln Gly Ala Ser Gln Phe Glu Gln Gln Ala Gly Lys Leu Lys Arg Lys
65                  70                  75                  80

Gln Trp Trp Ala Asn Met Lys Met Met Ile Ile Leu Gly Val Ile Ala
                85                  90                  95

Val Val Leu Leu Ile Ile Val Leu Val Ser Val Trp Pro Ser Ser Ser
            100                 105                 110

Asp Ser Gly Ser Gly Gly Gly Asn Lys Ala Ile Thr Gln Ala Pro Pro
        115                 120                 125

His


<210> SEQ ID NO 54
<211> LENGTH: 152
<212> TYPE: PRT
<213> ORGANISM: Drosophila melanogaster SynA2 (Fruit fly)

<400> SEQUENCE: 54

Met Glu Asn Asn Glu Ala Pro Ser Pro Ser Gly Ser Asn Asn Asn Asp
 1               5                  10                  15

Phe Pro Ile Leu Pro Pro Pro Pro Asn Ala Asn Asp Asn Tyr Asn Gln
            20                  25                  30

Phe Gly Asp His Gln Ile Arg Asn Asn Asn Ala Ala Gln Lys Lys Leu
        35                  40                  45

Gln Gln Thr Gln Ala Lys Val Asp Glu Val Val Gly Ile Met Arg Val
    50                  55                  60

Asn Val Glu Lys Val Leu Glu Arg Asp Gln Lys Leu Ser Glu Leu Gly
65                  70                  75                  80

Glu Arg Ala Asp Gln Leu Glu Gln Gly Ala Ser Gln Ser Glu Gln Gln
                85                  90                  95

Ala Gly Lys Leu Lys Arg Lys Gln Trp Trp Ala Asn Met Lys Met Met
            100                 105                 110

Ile Ile Leu Gly Val Ile Ala Val Val Leu Leu Ile Ile Val Leu Val
        115                 120                 125

Ser Val Trp Pro Ser Ser Ser Asp Ser Gly Ser Gly Gly Gly Asn Lys
    130                 135                 140

Ala Ile Thr Gln Ala Pro Pro His
145                 150


<210> SEQ ID NO 55
<211> LENGTH: 132
<212> TYPE: PRT
<213> ORGANISM: Drosophila melanogaster SynB1 (Fruit fly)

<400> SEQUENCE: 55

Met Glu Asn Asn Glu Ala Pro Ser Pro Ser Gly Ser Asn Asn Asn Asp
 1               5                  10                  15

Phe Pro Ile Leu Pro Pro Pro Pro Asn Ala Asn Asp Asn Tyr Asn Gln
            20                  25                  30

Phe Gly Asp His Gln Ile Arg Asn Asn Asn Ala Ala Gln Lys Lys Leu
        35                  40                  45

Gln Gln Thr Gln Ala Lys Val Asp Glu Val Val Gly Ile Met Arg Val
    50                  55                  60

Asn Val Glu Lys Val Leu Glu Arg Asp Gln Lys Leu Ser Glu Leu Gly
65                  70                  75                  80

Glu Arg Ala Asp Gln Leu Glu Gln Gly Ala Ser Gln Phe Glu Gln Gln
                85                  90                  95

Ala Gly Lys Leu Lys Arg Lys Gln Trp Trp Ala Asn Met Lys Met Met
            100                 105                 110
```

```
Ile Ile Leu Gly Val Ile Ala Val Val Leu Leu Ile Ile Val Leu Val
        115                 120                 125

Ser Leu Phe Asn
    130
```

<210> SEQ ID NO 56
<211> LENGTH: 132
<212> TYPE: PRT
<213> ORGANISM: Drosophila melanogaster SynB2 (Fruit fly)

<400> SEQUENCE: 56

```
Met Glu Asn Asn Glu Ala Pro Ser Pro Ser Gly Ser Asn Asn Asn Asp
 1               5                  10                  15

Phe Pro Ile Leu Pro Pro Pro Pro Asn Ala Asn Asp Asn Tyr Asn Gln
            20                  25                  30

Phe Gly Asp His Gln Ile Arg Asn Asn Asn Ala Ala Gln Lys Lys Leu
        35                  40                  45

Gln Gln Thr Gln Ala Lys Val Asp Glu Val Val Gly Ile Met Arg Val
    50                  55                  60

Asn Val Glu Lys Val Leu Glu Arg Asp Gln Lys Leu Ser Glu Leu Gly
65                  70                  75                  80

Glu Arg Ala Asp Gln Leu Glu Gln Gly Ala Ser Gln Ser Glu Gln Gln
                85                  90                  95

Ala Gly Lys Leu Lys Arg Lys Gln Trp Trp Ala Asn Met Lys Met Met
            100                 105                 110

Ile Ile Leu Gly Val Ile Ala Val Val Leu Leu Ile Ile Val Leu Val
        115                 120                 125

Ser Leu Phe Asn
    130
```

<210> SEQ ID NO 57
<211> LENGTH: 183
<212> TYPE: PRT
<213> ORGANISM: Drosophila melanogaster SynC (Fruit fly)

<400> SEQUENCE: 57

```
Met Ala Asp Ala Ala Pro Ala Gly Asp Ala Pro Pro Asn Ala Gly Ala
 1               5                  10                  15

Pro Ala Gly Glu Gly Gly Asp Gly Glu Ile Val Gly Gly Pro His Asn
            20                  25                  30

Pro Gln Gln Ile Ala Ala Gln Lys Arg Leu Gln Gln Thr Gln Ala Gln
        35                  40                  45

Val Asp Glu Val Val Asp Ile Met Arg Thr Asn Val Glu Lys Val Leu
    50                  55                  60

Glu Arg Asp Ser Lys Leu Ser Glu Leu Asp Asp Arg Ala Asp Ala Leu
65                  70                  75                  80

Gln Gln Gly Ala Ser Gln Phe Glu Gln Gln Ala Gly Lys Leu Lys Arg
                85                  90                  95

Lys Phe Trp Leu Gln Asn Leu Lys Met Met Ile Ile Met Gly Val Ile
            100                 105                 110

Gly Leu Val Val Val Gly Ile Ile Ala Asn Lys Leu Gly Leu Ile Gly
        115                 120                 125

Gly Glu Gln Pro Pro Gln Tyr Gln Tyr Pro Pro Gln Tyr Met Gln Pro
    130                 135                 140

Pro Pro Pro Pro Pro Gln Gln Pro Ala Gly Gly Gln Ser Ser Leu Val
145                 150                 155                 160
```

Asp Ala Ala Gly Ala Gly Asp Gly Ala Gly Ala Gly Gly Ser Ala Gly
165 170 175

Ala Gly Asp His Gly Gly Val
180

<210> SEQ ID NO 58
<211> LENGTH: 221
<212> TYPE: PRT
<213> ORGANISM: Drosophila melanogaster SynD (Fruit fly)

<400> SEQUENCE: 58

Met Gly Lys Lys Asp Lys Asn Lys Glu Gln Ala Asp Ala Ala Pro Ala
1 5 10 15

Gly Asp Ala Pro Pro Asn Ala Gly Ala Pro Ala Gly Glu Gly Gly Asp
20 25 30

Gly Glu Ile Val Gly Gly Pro His Asn Pro Gln Gln Ile Ala Ala Gln
35 40 45

Lys Arg Leu Gln Gln Thr Gln Ala Gln Val Asp Glu Val Val Asp Ile
50 55 60

Met Arg Thr Asn Val Glu Lys Val Leu Glu Arg Asp Ser Lys Leu Ser
65 70 75 80

Glu Leu Asp Asp Arg Ala Asp Ala Leu Gln Gln Gly Ala Ser Gln Phe
85 90 95

Glu Gln Gln Ala Gly Lys Leu Lys Arg Lys Phe Trp Leu Gln Asn Leu
100 105 110

Lys Met Met Ile Ile Met Gly Val Ile Gly Leu Val Val Val Gly Ile
115 120 125

Ile Ala Lys Arg Arg Arg Ile Ile Thr Gln Lys Ala Ser Ala Leu Tyr
130 135 140

Asn Phe Ile Asn His Lys Gln Ile Asn Leu Pro Asn Ile Thr Leu Tyr
145 150 155 160

Lys Leu Gly Leu Ile Gly Gly Glu Gln Pro Pro Gln Tyr Gln Tyr Pro
165 170 175

Pro Gln Tyr Met Gln Pro Pro Pro Pro Pro Pro Gln Gln Pro Ala Gly
180 185 190

Gly Gln Ser Ser Leu Val Asp Ala Ala Gly Ala Gly Asp Gly Ala Gly
195 200 205

Ala Gly Gly Ser Ala Gly Ala Gly Asp His Gly Gly Val
210 215 220

<210> SEQ ID NO 59
<211> LENGTH: 192
<212> TYPE: PRT
<213> ORGANISM: Drosophila melanogaster SynE (Fruit fly)

<400> SEQUENCE: 59

Met Gly Lys Lys Asp Lys Asn Lys Glu Gln Ala Asp Ala Ala Pro Ala
1 5 10 15

Gly Asp Ala Pro Pro Asn Ala Gly Ala Pro Ala Gly Glu Gly Gly Asp
20 25 30

Gly Glu Ile Val Gly Gly Pro His Asn Pro Gln Gln Ile Ala Ala Gln
35 40 45

Lys Arg Leu Gln Gln Thr Gln Ala Gln Val Asp Glu Val Val Asp Ile
50 55 60

Met Arg Thr Asn Val Glu Lys Val Leu Glu Arg Asp Ser Lys Leu Ser
65 70 75 80

Glu Leu Asp Asp Arg Ala Asp Ala Leu Gln Gln Gly Ala Ser Gln Phe

```
                85                  90                  95

Glu Gln Gln Ala Gly Lys Leu Lys Arg Lys Phe Trp Leu Gln Asn Leu
            100                 105                 110

Lys Met Met Ile Ile Met Gly Val Ile Gly Leu Val Val Val Gly Ile
        115                 120                 125

Ile Ala Asn Lys Leu Gly Leu Ile Gly Gly Glu Gln Pro Pro Gln Tyr
    130                 135                 140

Gln Tyr Pro Pro Gln Tyr Met Gln Pro Pro Pro Pro Pro Pro Gln Gln
145                 150                 155                 160

Pro Ala Gly Gly Gln Ser Ser Leu Val Asp Ala Ala Gly Ala Gly Asp
                165                 170                 175

Gly Ala Gly Ala Gly Gly Ser Ala Gly Ala Gly Asp His Gly Gly Val
            180                 185                 190


<210> SEQ ID NO 60
<211> LENGTH: 169
<212> TYPE: PRT
<213> ORGANISM: Hirudo medicinalis VAMP (Leech)

<400> SEQUENCE: 60

Met Ala Gln Pro Pro Pro Lys Pro Ser Thr Gly Pro Gly Gly Leu Pro
 1               5                  10                  15

Ala Pro Gly Ala Pro Pro Gln Pro Ala Pro Gln Ser Lys Arg Leu Gln
            20                  25                  30

Gln Ala Gln Ala Gln Val Asp Glu Val Val Asp Met Met Arg Val Asn
        35                  40                  45

Val Asp Lys Val Leu Glu Lys Asp Gln Lys Leu Ala Glu Leu Asp Gly
    50                  55                  60

Arg Ala Asp Ala Leu Gln Ala Gly Ala Ser Gln Phe Glu Ala Ser Ala
65                  70                  75                  80

Gly Lys Leu Lys Arg Lys Phe Trp Trp Lys Asn Met Lys Met Met Leu
                85                  90                  95

Ile Met Gly Ala Val Val Ala Val Val Val Val Ile Phe Gly Ala Trp
            100                 105                 110

Ile Tyr Asn Lys Phe Ser Gly Thr Ser Ser Val Pro Gln Glu Gly Thr
        115                 120                 125

Pro Val Leu Gln Ser Pro Met Ala Gln Gln Pro Gln Ser Leu Pro Glu
    130                 135                 140

Asn Ile Pro Pro Ala Ser Pro Val Gly Gly Gly Gly Gly Gly Lys Lys
145                 150                 155                 160

Gly Lys Asn Lys Gln Pro His Ser Ser
                165


<210> SEQ ID NO 61
<211> LENGTH: 125
<212> TYPE: PRT
<213> ORGANISM: Loligo pealei VAMP (Longfin squid)

<400> SEQUENCE: 61

Met Ser Gly Pro Gln Asn Pro Gln Ala Gly Pro Gly Gly Pro Pro Ser
 1               5                  10                  15

Gly Pro Pro Gln Pro Gly Gly Pro Pro Gly Pro Pro Gln Gly Pro Pro
            20                  25                  30

Gln Pro Val Gln Gln Ser Lys Arg Leu Gln Gln Thr Gln Ala Gln Val
        35                  40                  45

Glu Glu Val Val Asp Ile Met Arg Val Asn Val Asp Lys Val Leu Glu
    50                  55                  60
```

```
Arg Asp Ser Lys Ile Ser Glu Leu Asp Asp Arg Ala Asp Ala Leu Gln
65                  70                  75                  80

Ala Gly Ala Ser Gln Phe Glu Ala Ser Ala Gly Lys Leu Lys Arg Lys
                85                  90                  95

Phe Trp Trp Lys Asn Cys Lys Met Met Ile Ile Leu Gly Gly Ile Val
            100                 105                 110

Ala Val Ile Val Thr Val Ile Ile Val Trp Ala Ala Thr
        115                 120                 125
```

<210> SEQ ID NO 62
<211> LENGTH: 145
<212> TYPE: PRT
<213> ORGANISM: Lymnaea stagnalis VAMp (Great pond snail)

<400> SEQUENCE: 62

```
Met Ala Ala Ser Gln Asn Pro Gln Ala Gly Pro Gly Gly Pro Pro Ser
 1               5                  10                  15

Ala Gly Pro Gly Gly Pro Gly Met Gln Pro Pro Arg Glu Gln Ser Lys
            20                  25                  30

Arg Leu Gln Gln Thr Gln Ala Gln Val Asp Glu Val Val Asp Ile Met
        35                  40                  45

Arg Val Asn Val Glu Lys Val Leu Asp Arg Asp Gln Lys Ile Ser Gln
    50                  55                  60

Leu Asp Asp Arg Ala Glu Ala Leu Gln Ala Gly Ala Ser Gln Phe Glu
65                  70                  75                  80

Ala Ser Ala Gly Lys Leu Lys Arg Lys Tyr Trp Trp Lys Asn Cys Lys
                85                  90                  95

Met Met Leu Ile Leu Gly Ala Ile Ile Gly Ile Ile Cys Ile Ile Ile
            100                 105                 110

Ile Val Trp Val Val Thr Ser Thr Lys Gly Gly Asp Asp Lys Pro Thr
        115                 120                 125

Pro Gln Pro Ala Ile Ser Ser Thr Thr Gly Thr Pro Ser Pro Lys Thr
    130                 135                 140

Thr
145
```

<210> SEQ ID NO 63
<211> LENGTH: 180
<212> TYPE: PRT
<213> ORGANISM: Aplysia californica VAMP (California sea hare)

<400> SEQUENCE: 63

```
Met Ser Ala Gly Pro Gly Gly Pro Gln Gly Gly Met Gln Pro Pro Arg
 1               5                  10                  15

Glu Gln Ser Lys Arg Leu Gln Gln Thr Gln Ala Gln Val Asp Glu Val
            20                  25                  30

Val Asp Ile Met Arg Val Asn Val Glu Lys Val Leu Asp Arg Asp Gln
        35                  40                  45

Lys Ile Ser Gln Leu Asp Asp Arg Ala Glu Ala Leu Gln Ala Gly Ala
    50                  55                  60

Ser Gln Phe Glu Ala Ser Ala Gly Lys Leu Lys Arg Lys Tyr Trp Trp
65                  70                  75                  80

Lys Asn Cys Lys Met Met Leu Ile Leu Gly Ala Ile Ile Gly Val Ile
                85                  90                  95

Val Ile Ile Ile Ile Val Trp Val Val Thr Ser Gln Asp Ser Gly Gly
            100                 105                 110
```

```
Asp Asp Ser Gly Ser Lys Thr Pro Ala Thr Ala Gly Thr Ser Pro Lys
        115                 120                 125

Pro Val Glu Ser Gly Val Gln Gly Gly Gly Gly Arg Gln Gln Arg Pro
    130                 135                 140

His Ser Gln Leu Val Glu Arg Arg Asn Val Leu Arg Arg Thr Glu Asp
145                 150                 155                 160

His Ile Gly Cys Arg Pro His Ile His Ser Phe Ile His Ile Phe Met
                165                 170                 175

Ile Cys Leu Val
            180


<210> SEQ ID NO 64
<211> LENGTH: 109
<212> TYPE: PRT
<213> ORGANISM: Caenorhabditis elegans SNB1 (Round worm)

<400> SEQUENCE: 64

Met Asp Ala Gln Gly Asp Ala Gly Ala Gln Gly Gly Ser Gln Gly Gly
 1               5                  10                  15

Pro Arg Pro Ser Asn Lys Arg Leu Gln Gln Thr Gln Ala Gln Val Asp
            20                  25                  30

Glu Val Val Gly Ile Met Lys Val Asn Val Glu Lys Val Leu Glu Arg
        35                  40                  45

Asp Gln Lys Leu Ser Gln Leu Asp Asp Arg Ala Asp Ala Leu Gln Glu
    50                  55                  60

Gly Ala Ser Gln Phe Glu Lys Ser Ala Ala Thr Leu Lys Arg Lys Tyr
65                  70                  75                  80

Trp Trp Lys Asn Ile Lys Met Met Ile Ile Met Cys Ala Ile Val Val
                85                  90                  95

Ile Leu Ile Ile Ile Ile Val Leu Trp Ala Gly Gly Lys
            100                 105


<210> SEQ ID NO 65
<211> LENGTH: 118
<212> TYPE: PRT
<213> ORGANISM: Caenorhabditis elegans SNB1-like (Round worm)

<400> SEQUENCE: 65

Met Phe Ser Arg Met Ser Ala Asn Asn Glu Ala Asn Lys Asp Leu Glu
 1               5                  10                  15

Ala Gly Asn Gly Glu Ala Gln Pro Pro Thr Gly Thr Tyr Asn Thr Lys
            20                  25                  30

Arg Met Gln Met Ala Gln Ala Gln Val Asn Glu Val Ile Asp Val Met
        35                  40                  45

Arg Asn Asn Val Asn Lys Val Met Glu Arg Asp Val Gln Leu Asn Ser
    50                  55                  60

Leu Asp His Arg Ala Glu Val Leu Gln Asn Gly Ala Ser Gln Phe Gln
65                  70                  75                  80

Gln Ser Ser Arg Thr Leu Arg Gln Lys Tyr Trp Trp Gln Asn Ile Arg
                85                  90                  95

Met Met Ile Ile Ile Gly Leu Ile Ala Phe Leu Val Ile Gly Ile Phe
            100                 105                 110

Leu Ile Trp Ile Phe Asn
        115


<210> SEQ ID NO 66
<211> LENGTH: 288
<212> TYPE: PRT
```

<213> ORGANISM: Homo sapiens Syntaxin-1A (Human)

<400> SEQUENCE: 66

```
Met Lys Asp Arg Thr Gln Glu Leu Arg Thr Ala Lys Asp Ser Asp Asp
 1               5                  10                  15

Asp Asp Asp Val Ala Val Thr Val Asp Arg Asp Arg Phe Met Asp Glu
            20                  25                  30

Phe Phe Glu Gln Val Glu Glu Ile Arg Gly Phe Ile Asp Lys Ile Ala
        35                  40                  45

Glu Asn Val Glu Glu Val Lys Arg Lys His Ser Ala Ile Leu Ala Ser
    50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
    130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
        195                 200                 205

Ile Arg Glu Leu His Asp Met Phe Met Asp Met Ala Met Leu Val Glu
    210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Ile Cys Cys
            260                 265                 270

Val Ile Leu Gly Ile Val Ile Ala Ser Thr Val Gly Gly Ile Phe Ala
        275                 280                 285
```

<210> SEQ ID NO 67
<211> LENGTH: 288
<212> TYPE: PRT
<213> ORGANISM: Homo sapiens Syntaxin-1B1 (Human)

<400> SEQUENCE: 67

```
Met Lys Asp Arg Thr Gln Val Leu Arg Thr Arg Arg Asn Ser Asp Asp
 1               5                  10                  15

Lys Glu Glu Val Val His Val Asp Arg Asp His Phe Met Asp Glu Phe
            20                  25                  30

Phe Glu Gln Glu Glu Glu Ile Arg Gly Cys Ile Glu Lys Leu Ser Glu
        35                  40                  45

Asp Val Glu Gln Val Lys Lys Gln His Ser Ala Ile Leu Ala Ala Pro
    50                  55                  60

Asn Pro Asp Glu Arg Thr Lys Gln Glu Leu Glu Asp Leu Thr Ala Asp
65                  70                  75                  80
```

```
Ile Lys Lys Thr Ala Asn Lys Val Arg Ser Lys Leu Lys Ala Ile Glu
                85                  90                  95

Gln Ser Ile Glu Gln Glu Glu Gly Ser Thr Ala Pro Arg Pro Ile Leu
            100                 105                 110

Arg Ile Arg Lys Thr Gln His Ser Thr Leu Ser Arg Lys Phe Val Glu
        115                 120                 125

Val Met Thr Glu Tyr Asn Ala Thr Gln Ser Lys Tyr Arg Asp Arg Cys
    130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Pro Ile Phe
                165                 170                 175

Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Ile Ile Ile Cys Cys Val
            260                 265                 270

Val Leu Gly Val Val Leu Ala Ser Ser Ile Gly Cys Thr Leu Gly Leu
        275                 280                 285
```

<210> SEQ ID NO 68
<211> LENGTH: 288
<212> TYPE: PRT
<213> ORGANISM: Homo sapiens Syntaxin-1B2 (Human)

<400> SEQUENCE: 68

```
Met Lys Asp Arg Thr Gln Glu Leu Arg Ser Ala Lys Asp Ser Asp Asp
 1               5                  10                  15

Glu Glu Glu Val Val His Val Asp Arg Asp His Phe Met Asp Glu Phe
            20                  25                  30

Phe Glu Gln Val Glu Glu Ile Arg Gly Cys Ile Glu Lys Leu Ser Glu
        35                  40                  45

Asp Val Glu Gln Val Lys Lys Gln His Ser Ala Ile Leu Ala Ala Pro
    50                  55                  60

Asn Pro Asp Glu Lys Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
        115                 120                 125

Val Met Thr Glu Tyr Asn Ala Thr Gln Ser Lys Tyr Arg Asp Arg Cys
    130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175
```

```
Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Ile Cys Cys Val
            260                 265                 270

Val Leu Gly Val Val Leu Ala Ser Ser Ile Gly Gly Thr Leu Gly Leu
        275                 280                 285


<210> SEQ ID NO 69
<211> LENGTH: 287
<212> TYPE: PRT
<213> ORGANISM: Homo sapiens Syntaxin-2-1 (Human)

<400> SEQUENCE: 69

Met Arg Asp Arg Leu Pro Asp Leu Thr Ala Cys Arg Lys Asn Asp Asp
 1               5                  10                  15

Gly Asp Thr Val Val Val Val Glu Lys Asp His Phe Met Asp Asp Phe
            20                  25                  30

Phe His Gln Val Glu Glu Ile Arg Asn Ser Ile Asp Lys Ile Thr Gln
        35                  40                  45

Tyr Val Glu Glu Val Lys Lys Asn His Ser Ile Ile Leu Ser Ala Pro
    50                  55                  60

Asn Pro Glu Gly Lys Ile Lys Glu Glu Leu Glu Asp Leu Asn Lys Glu
65                  70                  75                  80

Ile Lys Lys Thr Ala Asn Lys Ile Arg Ala Lys Leu Lys Ala Ile Glu
                85                  90                  95

Gln Ser Phe Asp Gln Asp Glu Ser Gly Asn Arg Thr Ser Val Asp Leu
            100                 105                 110

Arg Ile Arg Arg Thr Gln His Ser Val Leu Ser Arg Lys Phe Val Glu
        115                 120                 125

Ala Met Ala Glu Tyr Asn Glu Ala Gln Thr Leu Phe Arg Glu Arg Ser
    130                 135                 140

Lys Gly Arg Ile Gln Arg Gln Leu Glu Ile Thr Gly Arg Thr Thr Thr
145                 150                 155                 160

Asp Asp Glu Leu Glu Glu Met Leu Glu Ser Gly Lys Pro Ser Ile Phe
                165                 170                 175

Thr Ser Asp Ile Ile Ser Asp Ser Gln Ile Thr Arg Gln Ala Leu Asn
            180                 185                 190

Glu Ile Glu Ser Arg His Lys Asp Ile Met Lys Leu Glu Thr Ser Ile
        195                 200                 205

Arg Glu Leu His Glu Met Phe Met Asp Met Ala Met Phe Val Glu Thr
    210                 215                 220

Gln Gly Glu Met Ile Asn Asn Ile Glu Arg Asn Val Met Asn Ala Thr
225                 230                 235                 240

Asp Tyr Val Glu His Ala Lys Glu Glu Thr Lys Lys Ala Ile Lys Tyr
                245                 250                 255

Gln Ser Lys Ala Arg Arg Lys Leu Met Phe Ile Ile Ile Cys Val Ile
            260                 265                 270
```

Val Leu Leu Val Ile Leu Gly Ile Ile Leu Ala Thr Thr Leu Ser
275 280 285

<210> SEQ ID NO 70
<211> LENGTH: 288
<212> TYPE: PRT
<213> ORGANISM: Homo sapiens Syntaxin-2-2 (Human)

<400> SEQUENCE: 70

Met Arg Asp Arg Leu Pro Asp Leu Thr Ala Cys Arg Lys Asn Asp Asp
1 5 10 15

Gly Asp Thr Val Val Val Val Glu Lys Asp His Phe Met Asp Asp Phe
20 25 30

Phe His Gln Val Glu Glu Ile Arg Asn Ser Ile Asp Lys Ile Thr Gln
35 40 45

Tyr Val Glu Glu Val Lys Lys Asn His Ser Ile Ile Leu Ser Ala Pro
50 55 60

Asn Pro Glu Gly Lys Ile Lys Glu Glu Leu Glu Asp Leu Asn Lys Glu
65 70 75 80

Ile Lys Lys Thr Ala Asn Lys Ile Arg Ala Lys Leu Lys Ala Ile Glu
85 90 95

Gln Ser Phe Asp Gln Asp Glu Ser Gly Asn Arg Thr Ser Val Asp Leu
100 105 110

Arg Ile Arg Arg Thr Gln His Ser Val Leu Ser Arg Lys Phe Val Glu
115 120 125

Ala Met Ala Glu Tyr Asn Glu Ala Gln Thr Leu Phe Arg Glu Arg Ser
130 135 140

Lys Gly Arg Ile Gln Arg Gln Leu Glu Ile Thr Gly Arg Thr Thr Thr
145 150 155 160

Asp Asp Glu Leu Glu Glu Met Leu Glu Ser Gly Lys Pro Ser Ile Phe
165 170 175

Thr Ser Asp Ile Ile Ser Asp Ser Gln Ile Thr Arg Gln Ala Leu Asn
180 185 190

Glu Ile Glu Ser Arg His Lys Asp Ile Met Lys Leu Glu Thr Ser Ile
195 200 205

Arg Glu Leu His Glu Met Phe Met Asp Met Ala Met Phe Val Glu Thr
210 215 220

Gln Gly Glu Met Ile Asn Asn Ile Glu Arg Asn Val Met Asn Ala Thr
225 230 235 240

Asp Tyr Val Glu His Ala Lys Glu Glu Thr Lys Lys Ala Ile Lys Tyr
245 250 255

Gln Ser Lys Ala Arg Arg Lys Lys Trp Ile Ile Ile Ala Val Ser Val
260 265 270

Val Leu Val Ala Ile Ile Ala Leu Ile Ile Gly Leu Ser Val Gly Lys
275 280 285

<210> SEQ ID NO 71
<211> LENGTH: 299
<212> TYPE: PRT
<213> ORGANISM: Homo sapiens Syntaxin-2-3 (Human)

<400> SEQUENCE: 71

Met Arg Asp Arg Leu Pro Asp Leu Thr Ala Cys Arg Lys Asn Asp Asp
1 5 10 15

Gly Asp Thr Val Val Val Val Glu Lys Asp His Phe Met Asp Asp Phe
20 25 30

-continued

```
Phe His Gln Val Glu Glu Ile Arg Asn Ser Ile Asp Lys Ile Thr Gln
        35                  40                  45

Tyr Val Glu Glu Val Lys Lys Asn His Ser Ile Ile Leu Ser Ala Pro
    50                  55                  60

Asn Pro Glu Gly Lys Ile Lys Glu Glu Leu Glu Asp Leu Asn Lys Glu
65                  70                  75                  80

Ile Lys Lys Thr Ala Asn Lys Ile Ala Ala Lys Leu Lys Ala Ile Glu
                85                  90                  95

Gln Ser Phe Asp Gln Asp Glu Ser Gly Asn Arg Thr Ser Val Asp Leu
            100                 105                 110

Arg Ile Arg Arg Thr Gln His Ser Val Leu Ser Arg Lys Phe Val Glu
        115                 120                 125

Ala Met Ala Glu Tyr Asn Glu Ala Gln Thr Leu Phe Arg Glu Arg Ser
    130                 135                 140

Lys Gly Arg Ile Gln Arg Gln Leu Glu Ile Thr Gly Arg Thr Thr Thr
145                 150                 155                 160

Asp Asp Glu Leu Glu Glu Met Leu Glu Ser Gly Lys Pro Ser Ile Phe
                165                 170                 175

Thr Ser Asp Ile Ile Ser Asp Ser Gln Ile Thr Arg Gln Ala Leu Asn
            180                 185                 190

Glu Ile Glu Ser Arg His Lys Asp Ile Met Lys Leu Glu Thr Ser Ile
        195                 200                 205

Arg Glu Leu His Glu Met Phe Met Asp Met Ala Met Phe Val Glu Thr
    210                 215                 220

Gln Gly Glu Met Ile Asn Asn Ile Glu Arg Asn Val Met Asn Ala Thr
225                 230                 235                 240

Asp Tyr Val Glu His Ala Lys Glu Glu Thr Lys Lys Ala Ile Lys Tyr
                245                 250                 255

Gln Ser Lys Ala Arg Arg Lys Lys Trp Ile Ile Ile Ala Val Ser Val
            260                 265                 270

Val Leu Val Val Tyr Arg Leu Phe Gly Leu Ser Leu Glu Tyr Val Val
        275                 280                 285

Arg Ser Ala Ala Ser Leu Pro Gly Trp Gly Asn
    290                 295


<210> SEQ ID NO 72
<211> LENGTH: 289
<212> TYPE: PRT
<213> ORGANISM: Homo sapiens Syntaxin-3 (Human)

<400> SEQUENCE: 72

Met Lys Asp Arg Leu Glu Gln Leu Lys Ala Lys Gln Leu Thr Gln Asp
 1               5                  10                  15

Asp Asp Thr Asp Ala Val Glu Ile Ala Ile Asp Asn Thr Ala Phe Met
            20                  25                  30

Asp Glu Phe Phe Ser Glu Ile Glu Glu Thr Arg Leu Asn Ile Asp Lys
        35                  40                  45

Ile Ser Glu His Val Glu Glu Ala Lys Lys Leu Tyr Ser Ile Ile Leu
    50                  55                  60

Ser Ala Pro Ile Pro Glu Pro Lys Thr Lys Asp Asp Leu Glu Gln Leu
65                  70                  75                  80

Thr Thr Glu Ile Lys Lys Arg Ala Asn Asn Val Arg Asn Lys Leu Lys
                85                  90                  95

Ser Met Glu Lys His Ile Glu Glu Asp Glu Val Arg Ser Ser Ala Asp
            100                 105                 110
```

-continued

```
Leu Arg Ile Arg Lys Ser Gln His Ser Val Leu Ser Arg Lys Phe Val
        115                 120                 125

Glu Val Met Thr Lys Tyr Asn Glu Ala Gln Val Asp Phe Arg Glu Arg
    130                 135                 140

Ser Lys Gly Arg Ile Gln Arg Gln Leu Glu Ile Thr Gly Lys Lys Thr
145                 150                 155                 160

Thr Asp Glu Glu Leu Glu Glu Met Leu Glu Ser Gly Asn Pro Ala Ile
                165                 170                 175

Phe Thr Ser Gly Ile Ile Asp Ser Gln Ile Ser Lys Gln Ala Leu Ser
            180                 185                 190

Glu Ile Glu Gly Arg His Lys Asp Ile Val Arg Leu Glu Ser Ser Ile
        195                 200                 205

Lys Glu Leu His Asp Met Phe Met Asp Ile Ala Met Leu Val Glu Asn
    210                 215                 220

Gln Gly Glu Met Leu Asp Asn Ile Glu Leu Asn Val Met His Thr Val
225                 230                 235                 240

Asp His Val Glu Lys Ala Arg Asp Glu Ser Lys Lys Ala Val Lys Tyr
                245                 250                 255

Gln Ser Gln Ala Arg Lys Lys Leu Ile Ile Ile Ile Val Leu Val Val
            260                 265                 270

Val Leu Leu Gly Ile Leu Ala Leu Ile Ile Gly Leu Ser Val Gly Leu
        275                 280                 285

Asn


<210> SEQ ID NO 73
<211> LENGTH: 288
<212> TYPE: PRT
<213> ORGANISM: Bos taurus Syntaxin-1A (Cow)

<400> SEQUENCE: 73

Met Lys Asp Arg Thr Gln Glu Leu Arg Thr Ala Lys Asp Ser Asp Asp
 1               5                  10                  15

Asp Asp Asp Val Thr Val Thr Val Asp Arg Asp Arg Phe Met Asp Glu
            20                  25                  30

Phe Phe Glu Gln Val Glu Glu Ile Arg Gly Phe Ile Asp Lys Ile Ser
        35                  40                  45

Glu Asn Val Glu Glu Val Lys Arg Lys His Ser Ala Ile Leu Ala Ser
    50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
    130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
```

```
        195                 200                 205

Ile Arg Glu Leu His Asp Met Phe Met Asp Met Ala Met Leu Val Glu
    210                 215                 220

Ser Gln Gly Glu Met Ile Asp Arg Ile Glu Tyr Asn Val Glu His Ser
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Val Ile Cys Cys
            260                 265                 270

Val Val Leu Gly Ile Val Ile Ala Ser Thr Phe Gly Gly Ile Phe Gly
        275                 280                 285


<210> SEQ ID NO 74
<211> LENGTH: 288
<212> TYPE: PRT
<213> ORGANISM: Bos taurus Syntaxin-1B2 (Cow)

<400> SEQUENCE: 74

Met Lys Asp Arg Thr Gln Glu Leu Arg Ser Ala Lys Asp Ser Asp Asp
 1               5                  10                  15

Glu Glu Glu Val Val His Val Asp Arg Asp His Phe Met Asp Glu Phe
            20                  25                  30

Phe Glu Gln Val Glu Glu Ile Arg Gly Cys Ile Glu Lys Leu Ser Glu
        35                  40                  45

Asp Val Glu Gln Val Lys Lys Gln His Ser Ala Ile Leu Ala Ala Pro
    50                  55                  60

Asn Pro Asp Glu Lys Thr Lys Gln Glu Leu Glu Asp Leu Thr Thr Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
        115                 120                 125

Val Met Thr Glu Tyr Asn Ala Thr Gln Ser Lys Tyr Arg Asp Arg Cys
    130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Ile Cys Cys Val
            260                 265                 270

Val Leu Gly Val Val Leu Ala Ser Ser Ile Gly Gly Thr Leu Gly Leu
        275                 280                 285
```

<210> SEQ ID NO 75
<211> LENGTH: 288
<212> TYPE: PRT
<213> ORGANISM: Rattus norvegicus Syntaxin-1A (Rat)

<400> SEQUENCE: 75

```
Met Lys Asp Arg Thr Gln Glu Leu Arg Thr Ala Lys Asp Ser Asp Asp
 1               5                  10                  15

Asp Asp Asp Val Thr Val Thr Val Asp Arg Asp Arg Phe Met Asp Glu
            20                  25                  30

Phe Phe Glu Gln Val Glu Glu Ile Arg Gly Phe Ile Asp Lys Ile Ala
        35                  40                  45

Glu Asn Val Glu Glu Val Lys Arg Lys His Ser Ala Ile Leu Ala Ser
    50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
    130                 135                 140

Cys Lys Gly Arg Ile Gln Arg Gln Leu Glu Ile Thr Gly Arg Thr Thr
145                 150                 155                 160

Thr Ser Glu Glu Leu Glu Asp Met Leu Glu Ser Gly Asn Pro Ala Ile
                165                 170                 175

Phe Ala Ser Gly Ile Ile Met Asp Ser Ser Ile Ser Lys Gln Ala Leu
            180                 185                 190

Ser Glu Ile Glu Thr Arg His Ser Glu Ile Ile Lys Leu Glu Asn Ser
        195                 200                 205

Ile Arg Glu Leu His Asp Met Phe Met Asp Met Ala Met Leu Val Glu
    210                 215                 220

Ser Gln Gly Glu Met Ile Asp Arg Ile Glu Tyr Asn Val Glu His Ala
225                 230                 235                 240

Val Asp Tyr Val Glu Arg Ala Val Ser Asp Thr Lys Lys Ala Val Lys
                245                 250                 255

Tyr Gln Ser Lys Ala Arg Arg Lys Lys Ile Met Ile Ile Ile Cys Cys
            260                 265                 270

Val Ile Leu Gly Ile Ile Ile Ala Ser Thr Ile Gly Gly Ile Phe Gly
        275                 280                 285
```

<210> SEQ ID NO 76
<211> LENGTH: 288
<212> TYPE: PRT
<213> ORGANISM: Rattus norvegicus Syntaxin-1B2 (Rat)

<400> SEQUENCE: 76

```
Met Lys Asp Arg Thr Gln Glu Leu Arg Ser Ala Lys Asp Ser Asp Asp
 1               5                  10                  15

Glu Glu Glu Val Val His Val Asp Arg Asp His Phe Met Asp Glu Phe
            20                  25                  30

Phe Glu Gln Val Glu Glu Ile Arg Gly Cys Ile Glu Lys Leu Ser Glu
        35                  40                  45

Asp Val Glu Gln Val Lys Lys Gln His Ser Ala Ile Leu Ala Ala Pro
    50                  55                  60
```

-continued

```
Asn Pro Asp Glu Lys Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
        115                 120                 125

Val Met Thr Glu Tyr Asn Ala Thr Gln Ser Lys Tyr Arg Asp Arg Cys
    130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Ile Cys Cys Val
            260                 265                 270

Val Leu Gly Val Val Leu Ala Ser Ser Ile Gly Gly Thr Leu Gly Leu
        275                 280                 285
```

<210> SEQ ID NO 77
<211> LENGTH: 288
<212> TYPE: PRT
<213> ORGANISM: Mus musculus Syntaxin-1A (Mouse)

<400> SEQUENCE: 77

```
Met Lys Asp Arg Thr Gln Glu Leu Arg Thr Ala Lys Asp Ser Asp Asp
 1               5                  10                  15

Asp Asp Asp Val Thr Val Thr Val Asp Arg Asp Arg Phe Met Asp Glu
            20                  25                  30

Phe Phe Glu Gln Val Glu Glu Ile Arg Gly Phe Ile Asp Lys Ile Ala
        35                  40                  45

Glu Asn Val Glu Glu Val Lys Arg Lys His Ser Ala Ile Leu Ala Ser
    50                  55                  60

Pro Asn Pro Asp Glu Lys Thr Lys Glu Glu Leu Glu Glu Leu Met Ser
65                  70                  75                  80

Asp Ile Lys Lys Thr Ala Asn Lys Val Arg Ser Lys Leu Lys Ser Ile
                85                  90                  95

Glu Gln Ser Ile Glu Gln Glu Glu Gly Leu Asn Arg Ser Ser Ala Asp
            100                 105                 110

Leu Arg Ile Arg Lys Thr Gln His Ser Thr Leu Ser Arg Lys Phe Val
        115                 120                 125

Glu Val Met Ser Glu Tyr Asn Ala Thr Gln Ser Asp Tyr Arg Glu Arg
    130                 135                 140

Cys Lys Gly Arg Ile Gln Arg Gln Leu Glu Ile Thr Gly Arg Thr Thr
145                 150                 155                 160
```

Thr Ser Glu Glu Leu Glu Asp Met Leu Glu Ser Gly Asn Pro Ala Ile
165 170 175

Phe Ala Ser Gly Ile Ile Met Asp Ser Ser Ile Ser Lys Gln Ala Leu
180 185 190

Ser Glu Ile Glu Thr Arg His Ser Glu Ile Ile Lys Leu Glu Thr Ser
195 200 205

Ile Arg Glu Leu His Asp Met Phe Met Asp Met Ala Met Leu Val Glu
210 215 220

Ser Gln Gly Glu Met Ile Asp Arg Ile Glu Tyr Asn Val Glu His Ala
225 230 235 240

Val Asp Tyr Val Glu Arg Ala Val Ser Asp Thr Lys Lys Ala Val Lys
245 250 255

Tyr Gln Ser Lys Ala Arg Arg Lys Lys Ile Met Ile Ile Ile Cys Cys
260 265 270

Val Ile Leu Gly Ile Ile Ile Ala Ser Thr Ile Gly Gly Ile Phe Gly
275 280 285

<210> SEQ ID NO 78
<211> LENGTH: 288
<212> TYPE: PRT
<213> ORGANISM: Mus musculus Syntaxin-1B1 (Mouse)

<400> SEQUENCE: 78

Met Lys Glu Trp Thr Gln Glu Arg Arg Ser Ala Lys Asp Ser Asp Asp
1 5 10 15

Glu Glu Glu Val Val His Val Asp Arg Ala His Phe Met Ala Glu Phe
20 25 30

Phe Glu Gln Val Glu Glu Ile Arg Gly Cys Ile Glu Lys Leu Ser Glu
35 40 45

Asp Val Gly Arg Val Gly Gly Gln His Ser Ala Ile Leu Ala Ala Pro
50 55 60

Lys Pro Asp Glu Lys Thr Lys Gln Glu Leu Glu Asp Leu Thr Ala Asp
65 70 75 80

Ile Lys Lys Thr Ala Asn Lys Val Arg Ser Lys Leu Lys Ala Ile Glu
85 90 95

Gln Gly Ile Glu Gln Glu Glu Gly Leu Asn Arg Ser Ser Ala Asp Leu
100 105 110

Arg Tyr Arg Thr Thr Gln His Ser Thr Val Ser Arg Asn Phe Val Glu
115 120 125

Val Met Thr Glu Tyr Asn Ala Thr Lys Ser Lys Tyr Arg Asp Arg Cys
130 135 140

Lys Asp Arg Leu Gln Arg Gln Leu Glu Ile Thr Gly Arg Thr Thr Thr
145 150 155 160

Asn Glu Glu Leu Glu Asp Met Leu Glu Ser Gly Lys Leu Ala Ile Phe
165 170 175

Thr Asp Asp Ile Lys Met Asp Ser Gln Met Thr Lys Gln Ala Arg Asn
180 185 190

Glu Ile Glu Thr Arg His Asn Glu Ile Ile Lys Leu Glu Thr Ser Ile
195 200 205

Arg Glu Leu His Asp Met Phe Val Asp Met Ala Met Leu Val Glu Ser
210 215 220

Gln Gly Glu Met Ile Asp Arg Ile Glu Tyr Asn Val Glu His Ser Val
225 230 235 240

Asp Tyr Val Glu Arg Ala Val Ser Asp Thr Lys Lys Ala Val Lys Tyr
245 250 255

```
Gln Ser Lys Ala Arg Arg Lys Lys Ile Met Ile Ile Ile Cys Cys Val
            260                 265                 270

Val Leu Gly Val Val Leu Ala Ser Ser Ile Gly Gly Thr Leu Gly Leu
        275                 280                 285


<210> SEQ ID NO 79
<211> LENGTH: 288
<212> TYPE: PRT
<213> ORGANISM: Mus musculus Syntaxin-1B2 (Mouse)

<400> SEQUENCE: 79

Met Lys Asp Arg Thr Gln Glu Leu Arg Ser Ala Lys Asp Ser Asp Asp
 1               5                  10                  15

Glu Glu Glu Val Val His Val Asp Arg Asp His Phe Met Asp Glu Phe
            20                  25                  30

Phe Glu Gln Val Glu Glu Ile Arg Gly Cys Ile Glu Lys Leu Ser Glu
        35                  40                  45

Asp Val Glu Gln Val Lys Lys Gln His Ser Ala Ile Leu Ala Ala Pro
    50                  55                  60

Asn Pro Asp Glu Lys Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
        115                 120                 125

Val Met Thr Glu Tyr Asn Ala Thr Gln Ser Lys Tyr Arg Asp Arg Cys
    130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn
            180                 185                 190

Glu Ile Glu Thr Arg His Asn Glu Ile Ile Lys Leu Glu Thr Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Lys Ala Arg Arg Lys Lys Ile Met Ile Ile Ile Cys Cys Val
            260                 265                 270

Val Leu Gly Val Val Leu Ala Ser Ser Ile Gly Gly Thr Leu Gly Leu
        275                 280                 285


<210> SEQ ID NO 80
<211> LENGTH: 290
<212> TYPE: PRT
<213> ORGANISM: Rattus norvegicus Syntaxin-2 (Rat)

<400> SEQUENCE: 80

Met Arg Asp Arg Leu Pro Asp Leu Thr Ala Cys Arg Lys Ser Asp Asp
 1               5                  10                  15
```

Gly Asp Asn Ala Val Ile Ile Thr Val Glu Lys Asp His Phe Met Asp
20 25 30

Ala Phe Phe His Gln Val Glu Glu Ile Arg Ser Ser Ile Ala Arg Ile
35 40 45

Ala Gln His Val Glu Asp Val Lys Lys Asn His Ser Ile Ile Leu Ser
50 55 60

Ala Pro Asn Pro Glu Gly Lys Ile Lys Glu Glu Leu Glu Asp Leu Asn
65 70 75 80

Lys Glu Ile Lys Lys Thr Ala Asn Arg Ile Arg Gly Lys Leu Lys Ala
85 90 95

Ile Glu Gln Ser Cys Asp Gln Asp Glu Asn Gly Asn Arg Thr Ser Val
100 105 110

Asp Leu Arg Ile Arg Arg Thr Gln His Ser Val Leu Ser Arg Lys Phe
115 120 125

Val Asp Val Met Thr Glu Tyr Asn Glu Ala Gln Ile Leu Phe Arg Glu
130 135 140

Arg Ser Lys Gly Arg Ile Gln Arg Gln Leu Glu Ile Thr Gly Arg Thr
145 150 155 160

Thr Thr Asp Glu Glu Leu Glu Glu Met Leu Glu Ser Gly Lys Pro Ser
165 170 175

Ile Phe Ile Ser Asp Ile Ile Ser Asp Ser Gln Ile Thr Arg Gln Ala
180 185 190

Leu Asn Glu Ile Glu Ser Arg His Lys Asp Ile Met Lys Leu Glu Thr
195 200 205

Ser Ile Arg Glu Leu His Glu Met Phe Met Asp Met Ala Met Phe Val
210 215 220

Glu Thr Gln Gly Glu Met Val Asn Asn Ile Glu Arg Asn Val Val Asn
225 230 235 240

Ser Val Asp Tyr Val Glu His Ala Lys Glu Glu Thr Lys Lys Ala Ile
245 250 255

Lys Tyr Gln Ser Lys Ala Arg Arg Lys Lys Trp Ile Ile Ala Ala Val
260 265 270

Val Val Ala Val Ile Ala Val Leu Ala Leu Ile Ile Gly Leu Ser Val
275 280 285

Gly Lys
290

<210> SEQ ID NO 81
<211> LENGTH: 289
<212> TYPE: PRT
<213> ORGANISM: Mus musculus Syntaxin-2 (Mouse)

<400> SEQUENCE: 81

Met Arg Asp Arg Leu Pro Asp Leu Thr Ala Cys Arg Thr Asn Asp Asp
1 5 10 15

Gly Asp Thr Ala Val Val Ile Val Glu Lys Asp His Phe Met Asp Gly
20 25 30

Phe Phe His Gln Val Glu Glu Ile Arg Ser Ser Ile Ala Arg Ile Ala
35 40 45

Gln His Val Glu Asp Val Lys Lys Asn His Ser Ile Ile Leu Ser Ala
50 55 60

Pro Asn Pro Glu Gly Lys Ile Lys Glu Glu Leu Glu Asp Leu Asn Lys
65 70 75 80

Glu Ile Lys Lys Thr Ala Asn Arg Ile Arg Gly Lys Leu Lys Ser Ile
85 90 95

```
Glu Gln Ser Cys Asp Gln Asp Glu Asn Gly Asn Arg Thr Ser Val Asp
            100                 105                 110

Leu Arg Ile Arg Arg Thr Gln His Ser Val Leu Ser Arg Lys Phe Val
        115                 120                 125

Asp Val Met Thr Glu Tyr Asn Glu Ala Gln Ile Leu Phe Arg Glu Arg
    130                 135                 140

Ser Lys Gly Arg Ile Gln Arg Gln Leu Glu Ile Thr Gly Arg Thr Thr
145                 150                 155                 160

Thr Asp Asp Glu Leu Glu Glu Met Leu Glu Ser Gly Lys Pro Ser Ile
                165                 170                 175

Phe Ile Ser Asp Ile Ile Ser Asp Ser Gln Ile Thr Arg Gln Ala Leu
            180                 185                 190

Asn Glu Ile Glu Ser Arg His Lys Asp Ile Met Lys Leu Glu Thr Ser
        195                 200                 205

Ile Arg Glu Leu His Glu Met Phe Met Asp Met Ala Met Phe Val Glu
    210                 215                 220

Thr Gln Gly Glu Met Val Asn Asn Ile Glu Arg Asn Val Val Asn Ser
225                 230                 235                 240

Val Asp Tyr Val Glu His Ala Lys Glu Glu Thr Lys Lys Ala Ile Lys
                245                 250                 255

Tyr Gln Ser Lys Ala Arg Arg Lys Lys Trp Ile Ile Ala Ala Val Ala
            260                 265                 270

Val Ala Val Ile Ala Val Leu Ala Leu Ile Ile Gly Leu Ser Val Gly
        275                 280                 285

Lys


<210> SEQ ID NO 82
<211> LENGTH: 289
<212> TYPE: PRT
<213> ORGANISM: Rattus norvegicus Syntaxin-3A (Rat)

<400> SEQUENCE: 82

Met Lys Asp Arg Leu Glu Gln Leu Lys Ala Lys Gln Leu Thr Gln Asp
 1               5                  10                  15

Asp Asp Thr Asp Glu Val Glu Ile Ala Ile Asp Asn Thr Ala Phe Met
            20                  25                  30

Asp Glu Phe Phe Ser Glu Ile Glu Glu Thr Arg Leu Asn Ile Asp Lys
        35                  40                  45

Ile Ser Glu His Val Glu Glu Ala Lys Lys Leu Tyr Ser Ile Ile Leu
    50                  55                  60

Ser Ala Pro Ile Pro Glu Pro Lys Thr Lys Asp Asp Leu Glu Gln Leu
65                  70                  75                  80

Thr Thr Glu Ile Lys Lys Arg Ala Asn Asn Val Arg Asn Lys Leu Lys
                85                  90                  95

Ser Met Glu Lys His Ile Glu Glu Asp Glu Val Arg Ser Ser Ala Asp
            100                 105                 110

Leu Arg Ile Arg Lys Ser Gln His Ser Val Leu Ser Arg Lys Phe Val
        115                 120                 125

Glu Val Met Thr Lys Tyr Asn Glu Ala Gln Val Asp Phe Arg Glu Arg
    130                 135                 140

Ser Lys Gly Arg Ile Gln Arg Gln Leu Glu Ile Thr Gly Lys Lys Thr
145                 150                 155                 160

Thr Asp Glu Glu Leu Glu Glu Met Leu Glu Ser Gly Asn Pro Ala Ile
                165                 170                 175

Phe Thr Ser Gly Ile Ile Asp Ser Gln Ile Ser Lys Gln Ala Leu Ser
```

```
            180                 185                 190

Glu Ile Glu Gly Arg His Lys Asp Ile Val Arg Leu Glu Ser Ser Ile
        195                 200                 205

Lys Glu Leu His Asp Met Phe Met Asp Ile Ala Met Leu Val Glu Asn
    210                 215                 220

Gln Gly Glu Met Leu Asp Asn Ile Glu Leu Asn Val Met His Thr Val
225                 230                 235                 240

Asp His Val Glu Lys Ala Arg Asp Glu Thr Lys Arg Ala Met Lys Tyr
                245                 250                 255

Gln Gly Gln Ala Arg Lys Lys Leu Ile Ile Ile Ile Val Ile Val Val
            260                 265                 270

Val Leu Leu Gly Ile Leu Ala Leu Ile Ile Gly Leu Ser Val Gly Leu
        275                 280                 285

Lys


<210> SEQ ID NO 83
<211> LENGTH: 289
<212> TYPE: PRT
<213> ORGANISM: Mus musculus Syntaxin-3A (Mouse)

<400> SEQUENCE: 83

Met Lys Asp Arg Leu Glu Gln Leu Lys Ala Lys Gln Leu Thr Gln Asp
 1               5                  10                  15

Asp Asp Thr Asp Glu Val Glu Ile Ala Ile Asp Asn Thr Ala Phe Met
            20                  25                  30

Asp Glu Phe Phe Ser Glu Ile Glu Glu Thr Arg Leu Asn Ile Asp Lys
        35                  40                  45

Ile Ser Glu His Val Glu Glu Ala Lys Lys Leu Tyr Ser Ile Ile Leu
    50                  55                  60

Ser Ala Pro Ile Pro Glu Pro Lys Thr Lys Asp Asp Leu Glu Gln Leu
65                  70                  75                  80

Thr Thr Glu Ile Lys Lys Arg Ala Asn Asn Val Arg Asn Lys Leu Lys
                85                  90                  95

Ser Met Glu Lys His Ile Glu Glu Asp Glu Val Arg Ser Ser Ala Asp
            100                 105                 110

Leu Arg Ile Arg Lys Ser Gln His Ser Val Leu Ser Arg Lys Phe Val
        115                 120                 125

Glu Val Met Thr Lys Tyr Asn Glu Ala Gln Val Asp Phe Arg Glu Arg
    130                 135                 140

Ser Lys Gly Arg Ile Gln Arg Gln Leu Glu Ile Thr Gly Lys Lys Thr
145                 150                 155                 160

Thr Asp Glu Glu Leu Glu Glu Met Leu Glu Ser Gly Asn Pro Ala Ile
                165                 170                 175

Phe Thr Ser Gly Ile Ile Asp Ser Gln Ile Ser Lys Gln Ala Leu Ser
            180                 185                 190

Glu Ile Glu Gly Arg His Lys Asp Ile Val Arg Leu Glu Ser Ser Ile
        195                 200                 205

Lys Glu Leu His Asp Met Phe Met Asp Ile Ala Met Leu Val Glu Asn
    210                 215                 220

Gln Gly Glu Met Leu Asp Asn Ile Glu Leu Asn Val Met His Thr Val
225                 230                 235                 240

Asp His Val Glu Lys Ala Arg Asp Glu Thr Lys Arg Ala Met Lys Tyr
                245                 250                 255

Gln Gly Gln Ala Arg Lys Lys Leu Ile Ile Ile Ile Val Val Val Val
            260                 265                 270
```

Val Leu Leu Gly Ile Leu Ala Leu Ile Ile Gly Leu Ser Val Gly Leu
275 280 285

Lys

<210> SEQ ID NO 84
<211> LENGTH: 283
<212> TYPE: PRT
<213> ORGANISM: Mus musculus Syntaxin-3B (Mouse)

<400> SEQUENCE: 84

Met Lys Asp Arg Leu Glu Gln Leu Lys Ala Lys Gln Leu Thr Gln Asp
1 5 10 15

Asp Asp Thr Asp Glu Val Glu Ile Ala Ile Asp Asn Thr Ala Phe Met
20 25 30

Asp Glu Phe Phe Ser Glu Ile Glu Glu Thr Arg Leu Asn Ile Asp Lys
35 40 45

Ile Ser Glu His Val Glu Glu Ala Lys Lys Leu Tyr Ser Ile Ile Leu
50 55 60

Ser Ala Pro Ile Pro Glu Pro Lys Thr Lys Asp Asp Leu Glu Gln Leu
65 70 75 80

Thr Thr Glu Ile Lys Lys Arg Ala Asn Asn Val Arg Asn Lys Leu Lys
85 90 95

Ser Met Glu Lys His Ile Glu Glu Asp Glu Val Arg Ser Ser Ala Asp
100 105 110

Leu Arg Ile Arg Lys Ser Gln His Ser Val Leu Ser Arg Lys Phe Val
115 120 125

Glu Val Met Thr Lys Tyr Asn Glu Ala Gln Val Asp Phe Arg Glu Arg
130 135 140

Ser Lys Gly Arg Ile Gln Arg Gln Leu Glu Ile Thr Gly Lys Lys Thr
145 150 155 160

Thr Asp Glu Glu Leu Glu Glu Met Leu Glu Ser Gly Asn Pro Ala Ile
165 170 175

Phe Thr Ser Gly Ile Ile Asp Ser Gln Ile Ser Lys Gln Ala Leu Ser
180 185 190

Glu Ile Glu Gly Arg His Lys Asp Ile Val Arg Leu Glu Ser Ser Ile
195 200 205

Lys Glu Leu His Asp Met Phe Met Asp Ile Ala Met Leu Val Glu Asn
210 215 220

Gln Gly Ala Met Ile Asp Arg Ile Glu Asn Asn Met Asp Gln Ser Val
225 230 235 240

Gly Phe Val Glu Arg Ala Val Ala Asp Thr Lys Lys Ala Val Lys Tyr
245 250 255

Gln Ser Glu Ala Arg Arg Lys Lys Ile Met Ile Met Ile Cys Cys Ile
260 265 270

Ile Leu Ala Ile Ile Leu Ala Ser Thr Ile Gly
275 280

<210> SEQ ID NO 85
<211> LENGTH: 269
<212> TYPE: PRT
<213> ORGANISM: Mus musculus Syntaxin-3C (Mouse)

<400> SEQUENCE: 85

Met Lys Asp Arg Leu Glu Gln Leu Lys Ala Lys Gln Leu Thr Gln Asp
1 5 10 15

Asp Asp Thr Asp Glu Val Glu Ile Ala Ile Asp Asn Thr Ala Phe Met

```
            20                  25                  30

Asp Glu Phe Phe Ser Glu Asn Phe His Gly Ile Leu Ser Tyr Leu Leu
        35                  40                  45

Arg Leu Ser Ser His Glu Thr Lys Asp Asp Leu Glu Gln Leu Thr Thr
    50                  55                  60

Glu Ile Lys Lys Arg Ala Asn Asn Val Arg Asn Lys Leu Lys Ser Met
65                  70                  75                  80

Glu Lys His Ile Glu Glu Asp Glu Val Arg Ser Ser Ala Asp Leu Arg
                85                  90                  95

Ile Arg Lys Ser Gln His Ser Val Leu Ser Arg Lys Phe Val Glu Val
            100                 105                 110

Met Thr Lys Tyr Asn Glu Ala Gln Val Asp Phe Arg Glu Arg Ser Lys
        115                 120                 125

Gly Arg Ile Gln Arg Gln Leu Glu Ile Thr Gly Lys Lys Thr Thr Asp
    130                 135                 140

Glu Glu Leu Glu Glu Met Leu Glu Ser Gly Asn Pro Ala Ile Phe Thr
145                 150                 155                 160

Ser Gly Ile Ile Asp Ser Gln Ile Ser Lys Gln Ala Leu Ser Glu Ile
                165                 170                 175

Glu Gly Arg His Lys Asp Ile Val Arg Leu Glu Ser Ser Ile Lys Glu
            180                 185                 190

Leu His Asp Met Phe Met Asp Ile Ala Met Leu Val Glu Asn Gln Gly
        195                 200                 205

Ala Met Ile Asp Arg Ile Glu Asn Asn Met Asp Gln Ser Val Gly Phe
    210                 215                 220

Val Glu Arg Ala Val Ala Asp Thr Lys Lys Ala Val Lys Tyr Gln Ser
225                 230                 235                 240

Glu Ala Arg Arg Lys Lys Ile Met Ile Met Ile Cys Cys Ile Ile Leu
                245                 250                 255

Ala Ile Ile Leu Ala Ser Thr Ile Gly Gly Ile Phe Ala
            260                 265


<210> SEQ ID NO 86
<211> LENGTH: 282
<212> TYPE: PRT
<213> ORGANISM: Gallus gallus Syntaxin-1B (Chicken)

<400> SEQUENCE: 86

Met Lys Asp Arg Thr Gln Glu Leu Arg His Ala Lys Asp Ser Asp Asp
 1               5                  10                  15

Glu Glu Glu Val Val His Val Asp Arg Asn His Phe Met Asp Glu Phe
            20                  25                  30

Phe Glu Gln Val Glu Glu Ile Arg Gly Cys Ile Glu Lys Leu Phe Glu
        35                  40                  45

Asp Val Glu Gln Val Lys Lys Gln His Ser Ala Ile Leu Ala Ala Pro
    50                  55                  60

Asn Pro Asp Glu Arg Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Ala Asp Glu Glu Gly Leu Asn Arg Ser Ser Ala Asp Leu
            100                 105                 110

Arg Ile Arg Lys Thr His Val Arg Glu Val Met Thr Glu Tyr Asn Ala
        115                 120                 125

Thr Gln Ser Lys Tyr Arg Asp Arg Cys Lys Asp Arg Ile Gln Arg Leu
```

130 135 140

Leu Glu Ile Thr Gly Arg Thr Thr Thr Asn Glu Glu Leu Glu Asp Met
145 150 155 160

Leu Glu Ser Gly Lys Leu Ala Val Phe Asn Asp Asp Ile Lys Ile Asp
165 170 175

Ser Gln Met Thr Lys Gln Ala Leu Asn Glu Ile Glu Thr Arg His Asn
180 185 190

Glu Ile Ile Tyr Leu Glu Thr Ser Ile Arg Glu Leu His Asp Met Phe
195 200 205

Val Asp Met Ala Met Leu Val Glu Ser His Gly Glu Ser Ile Arg Pro
210 215 220

Ala Ser Ser Thr Thr Cys Val His Thr Val Asp Tyr Val Glu Pro Val
225 230 235 240

Val Phe Val Thr Lys Ser Ala Val Met Tyr Gln Cys Lys Ser Arg Arg
245 250 255

Lys Lys Ile Met Ile Ile Ile Phe Val Val Val Leu Gly Val Val Leu
260 265 270

Ser Pro Val Ile Cys Gly Thr Leu Gly Leu
275 280

<210> SEQ ID NO 87
<211> LENGTH: 288
<212> TYPE: PRT
<213> ORGANISM: Gallus gallus Syntaxin-2 (Chicken)

<400> SEQUENCE: 87

Met Lys Asp Arg Leu Ala Asp Leu Ala Glu Cys Lys Gly Asn Glu Asp
1 5 10 15

Gly Glu Thr Val Ile Val Glu Lys Asp His Phe Met Asp Asp Phe Phe
20 25 30

Gln Gln Val Glu Glu Ile Arg Asn Asn Ile Thr Lys Ile Ala Gln Asn
35 40 45

Val Glu Glu Val Lys Lys Gln His Ser Ile Ile Leu Ser Ala Pro Asn
50 55 60

Pro Glu Gly Arg Thr Lys Glu Glu Leu Glu Glu Leu Asn Glu Glu Ile
65 70 75 80

Lys Lys Thr Ala Asn Lys Ile Arg Ala Arg Leu Lys Ala Ile Glu Gln
85 90 95

Ser Val Asp Gln Ser Glu Asn Ala Asn Arg Thr Ser Val Asn Val Arg
100 105 110

Ile Arg Lys Thr Gln His Ser Val Leu Ala His Lys Phe Val Glu Val
115 120 125

Met Thr Glu Tyr Asn Glu Thr Gln Thr Leu Phe Arg Glu Arg Ser Lys
130 135 140

Gly Arg Ile Gln Arg Gln Leu Glu Ile Thr Gly Lys Thr Thr Thr Asp
145 150 155 160

Glu Glu Leu Glu Glu Met Leu Glu Ser Gly Asn Pro Ser Ile Phe Thr
165 170 175

Ser Asp Ile Ile Ser Asp Ser Gln Ile Thr Arg Gln Ala Leu Asn Glu
180 185 190

Ile Glu Ser Arg His Lys Asp Ile Met Lys Leu Glu Ser Ser Ile Arg
195 200 205

Glu Leu His Glu Met Phe Met Asp Met Ala Met Phe Val Glu Thr Gln
210 215 220

Gly Glu Met Ile Asn Asn Ile Glu Lys Asn Val Met Asn Ala Thr Asp

```
225                 230                 235                 240

Tyr Val Glu His Ala Lys Glu Glu Thr Lys Lys Ala Val Lys Tyr Gln
                245                 250                 255

Ser Lys Ala Arg Arg Lys Met Trp Ile Ile Ile Ile Val Ser Leu Val
            260                 265                 270

Leu Ile Ala Val Ile Gly Ile Ile Ile Gly Leu Ser Val Gly Ile Arg
        275                 280                 285


<210> SEQ ID NO 88
<211> LENGTH: 288
<212> TYPE: PRT
<213> ORGANISM: Danio rerio Syntaxin-1B (Zebrafish)

<400> SEQUENCE: 88

Met Lys Asp Arg Thr Gln Glu Leu Arg Ser Ala Lys Asp Ser Asp Asp
 1               5                  10                  15

Asp Glu Glu Val Val His Val Asp Arg Asp His Phe Met Asp Glu Phe
            20                  25                  30

Phe Glu Gln Val Glu Glu Ile Arg Gly Cys Ile Glu Lys Leu Ser Glu
        35                  40                  45

Asp Val Glu Gln Val Lys Lys Gln His Ser Ala Ile Leu Ala Ala Pro
    50                  55                  60

Asn Pro Asp Glu Lys Thr Lys Gln Glu Leu Glu Asp Leu Thr Ala Asp
65                  70                  75                  80

Ile Lys Lys Thr Ala Asn Lys Val Arg Ser Lys Leu Lys Ala Ile Glu
                85                  90                  95

Gln Ser Ile Glu Gln Glu Glu Gly Leu Asn Arg Ser Ser Ala Asp Leu
            100                 105                 110

Arg Ile Arg Lys Thr Gln His Ser Thr Leu Ser Arg Lys Phe Val Glu
        115                 120                 125

Val Met Thr Glu Tyr Asn Thr Thr Gln Ser Lys Tyr Arg Asp Arg Cys
    130                 135                 140

Lys Asp Arg Ile Gln Arg Gln Leu Glu Ile Thr Gly Arg Thr Thr Thr
145                 150                 155                 160

Asn Glu Glu Leu Glu Asp Met Leu Glu Ser Gly Lys Leu Ala Ile Phe
                165                 170                 175

Thr Asp Asp Ile Lys Met Asp Ser Gln Met Thr Lys Gln Ala Leu Asn
            180                 185                 190

Glu Ile Glu Thr Arg His Thr Glu Ile Ile Lys Leu Glu Asn Ser Ile
        195                 200                 205

Arg Glu Leu His Asp Met Phe Val Asp Met Ala Met Leu Val Glu Ser
    210                 215                 220

Gln Gly Glu Met Ile Asp Arg Ile Glu Tyr Asn Val Glu His Ser Val
225                 230                 235                 240

Asp Tyr Val Glu Arg Ala Val Ser Asp Thr Lys Lys Ala Val Lys Tyr
                245                 250                 255

Gln Ser Gln Ala Arg Lys Lys Lys Ile Met Ile Ile Ile Cys Cys Val
            260                 265                 270

Ile Leu Gly Val Val Leu Arg Ser Ser Ile Gly Gly Thr Leu Gly Phe
        275                 280                 285


<210> SEQ ID NO 89
<211> LENGTH: 288
<212> TYPE: PRT
<213> ORGANISM: Danio rerio Syntaxin-3 (Zebrafish)

<400> SEQUENCE: 89
```

Met Lys Asp Arg Leu Glu Gln Leu Lys Ala Thr Cys Asp His Asp Asp
1 5 10 15

Glu Asp Val Glu Ile Ala Val Asp Asn Ala Ala Phe Met Asp Glu Phe
20 25 30

Phe Ser Gln Ile Glu Asp Ile Arg Asn Ser Ile Asp Lys Ile Asp Glu
35 40 45

Asn Val Ala Glu Val Lys Lys Leu Tyr Ser Val Ile Leu Ser Ala Pro
50 55 60

Thr Ser Asp Gln Lys Thr Gln Asp Asp Leu Glu Ala Leu Thr Asn Asp
65 70 75 80

Ile Lys Lys Met Ala Asn Asn Ala Arg Asn Lys Leu Lys Thr Ile Glu
85 90 95

Arg Asn Leu Glu Thr Glu Glu Val Glu Arg Val Ser Ala Asp Met Arg
100 105 110

Ile Arg Lys Ser Gln His Ala Val Leu Ser Arg Lys Phe Val Asp Val
115 120 125

Met Thr Lys Tyr Asn Glu Ala Gln Val Asp Phe Arg Glu Lys Ser Lys
130 135 140

Gly Arg Ile Gln Arg Gln Leu Glu Ile Thr Gly Lys Ala Thr Thr Asp
145 150 155 160

Glu Glu Leu Glu Glu Met Leu Glu Gly Gly Asn Ala Ala Val Phe Thr
165 170 175

Ala Gly Ile Val Asp Ser Gly Ile Ser Lys Gln Ala Leu Ser Glu Ile
180 185 190

Glu Ala Arg His Lys Asp Ile Val Arg Leu Glu Ser Ser Ile Lys Glu
195 200 205

Leu His Asp Met Phe Val Asp Ile Ala Met Leu Val Glu Ser Gln Gly
210 215 220

Asn Met Val Asp Asn Ile Glu Val Asn Val Gly Lys Ala Val Asp His
225 230 235 240

Val Glu Ala Ala Arg Asp Glu Thr Lys Lys Ala Val Arg Tyr Gln Ser
245 250 255

Lys Ala Arg Lys Lys Ile Ile Ile Ile Val Ser Val Val Leu Val Ile
260 265 270

Leu Ala Ile Ile Ala Leu Ile Val Gly Leu Ser Val Gly Leu Lys Arg
275 280 285

<210> SEQ ID NO 90
<211> LENGTH: 286
<212> TYPE: PRT
<213> ORGANISM: Strongylocentrotus purpuratus Syntaxin-1B (urchin)

<400> SEQUENCE: 90

Met Arg Asp Arg Leu Gly Ser Leu Lys Arg Asn Glu Glu Asp Asp Val
1 5 10 15

Gly Gln Ser Arg Gly His Val Glu Ser Glu Lys Phe Met Glu Glu Phe
20 25 30

Phe Glu Gln Val Glu Glu Val Arg Asn Asn Ile Asp Lys Ile Ser Lys
35 40 45

Asn Val Asp Glu Val Lys Lys Lys His Ser Asp Ile Leu Ser Ala Pro
50 55 60

Gln Ala Asp Glu Lys Val Lys Asp Glu Leu Glu Glu Leu Met Ser Asp
65 70 75 80

Ile Lys Lys Thr Ala Asn Lys Val Arg Val Lys Leu Lys Met Met Tyr
85 90 95

```
Glu Ser Ile Glu Arg Arg Arg Val Leu Arg Arg Thr Gln Thr Asp Val
            100                 105                 110

Arg Ile Arg Lys Thr Gln His Ser Thr Leu Ser Arg Lys Phe Val Glu
        115                 120                 125

Val Met Thr Asp Tyr Asn Ser Thr Gln Thr Asp Tyr Arg Glu Arg Cys
    130                 135                 140

Lys Gly Arg Ile Gln Arg Gln Leu Glu Ile Thr Gly Lys Ser Thr Thr
145                 150                 155                 160

Asp Ala Glu Leu Glu Asp Met Leu Glu Ser Gly Asn Pro Ala Ile Phe
                165                 170                 175

Thr Ser Gly Ile Ile Met Asp Thr Gln Gln Ala Lys Gln Thr Leu Arg
            180                 185                 190

Asp Ile Glu Ala Arg His Asn Asp Ile Ile Lys Leu Glu Ser Ser Ile
        195                 200                 205

Arg Glu Leu His Asp Met Phe Met Asp Met Ala Met Leu Val Glu Ser
    210                 215                 220

Gln Gly Glu Met Ile Asp Arg Ile Glu Tyr Asn Val Glu Gln Ser Val
225                 230                 235                 240

Asp Tyr Val Arg Arg Gln Asn Asp Thr Lys Lys Ala Val Lys Tyr Gln
                245                 250                 255

Ser Lys Ala Arg Arg Lys Lys Phe Tyr Ile Ala Ile Cys Cys Gly Val
            260                 265                 270

Ala Leu Gly Ile Leu Ile Leu Val Leu Ile Ile Val Leu Ala
        275                 280                 285


<210> SEQ ID NO 91
<211> LENGTH: 291
<212> TYPE: PRT
<213> ORGANISM: Drosophila melanogaster Syntaxin-1A (Fruit fly)

<400> SEQUENCE: 91

Met Thr Lys Asp Arg Leu Ala Ala Leu His Ala Ala Gln Ser Asp Asp
 1               5                  10                  15

Glu Glu Glu Thr Glu Val Ala Val Asn Val Asp Gly His Asp Ser Tyr
            20                  25                  30

Met Asp Asp Phe Phe Ala Gln Val Glu Glu Ile Arg Gly Met Ile Asp
        35                  40                  45

Lys Val Gln Asp Asn Val Glu Glu Val Lys Lys Lys His Ser Ala Ile
    50                  55                  60

Leu Ser Ala Pro Gln Thr Asp Glu Lys Thr Lys Gln Glu Leu Glu Asp
65                  70                  75                  80

Leu Met Ala Asp Ile Lys Lys Asn Ala Asn Arg Val Arg Gly Lys Leu
                85                  90                  95

Lys Gly Ile Glu Gln Asn Ile Glu Gln Glu Glu Gln Gln Asn Lys Ser
            100                 105                 110

Ser Ala Asp Leu Arg Ile Arg Lys Thr Gln His Ser Thr Leu Ser Arg
        115                 120                 125

Lys Phe Val Glu Val Met Thr Glu Tyr Asn Arg Thr Gln Thr Asp Tyr
    130                 135                 140

Arg Glu Arg Cys Lys Gly Arg Ile Gln Arg Gln Leu Glu Ile Thr Gly
145                 150                 155                 160

Arg Pro Thr Asn Asp Asp Glu Leu Glu Lys Met Leu Glu Glu Gly Asn
                165                 170                 175

Ser Ser Val Phe Thr Gln Gly Ile Ile Met Glu Thr Gln Gln Ala Lys
            180                 185                 190
```

```
Gln Thr Leu Ala Asp Ile Glu Ala Arg His Gln Asp Ile Met Lys Leu
        195                 200                 205

Glu Thr Ser Ile Lys Glu Leu His Asp Met Phe Met Asp Met Ala Met
    210                 215                 220

Leu Val Glu Ser Gln Gly Glu Met Ile Asp Arg Ile Glu Tyr His Val
225                 230                 235                 240

Glu His Ala Met Asp Tyr Val Gln Thr Ala Thr Gln Asp Thr Lys Lys
                245                 250                 255

Ala Leu Lys Tyr Gln Ser Lys Ala Arg Arg Lys Lys Ile Met Ile Leu
            260                 265                 270

Ile Cys Leu Thr Val Leu Gly Ile Leu Ala Ala Ser Tyr Val Ser Ser
        275                 280                 285

Tyr Phe Met
    290


<210> SEQ ID NO 92
<211> LENGTH: 295
<212> TYPE: PRT
<213> ORGANISM: Hirudo medicinalis Syntaxin-1A (Leech)

<400> SEQUENCE: 92

Met Thr Lys Asp Arg Leu Ala Ala Leu Lys Ala Ala Gln Ser Asp Asp
 1               5                  10                  15

Asp Asp Glu Pro Gly Glu His Met Pro Met Thr Met Asn Val Asp Gly
            20                  25                  30

Gly Lys Phe Met Glu Glu Phe Phe Glu Gln Val Asn Glu Ile Arg Glu
        35                  40                  45

Met Ile Asp Lys Ile Ala Val Asp Val Asp Glu Val Lys Lys Lys His
    50                  55                  60

Ser Ala Ile Leu Ser Ala Pro Gln Thr Asp Asp Lys Thr Lys Glu Glu
65                  70                  75                  80

Leu Glu Asp Leu Met Ala Glu Ile Lys Lys Thr Ala Asn Lys Val Arg
                85                  90                  95

Gly Lys Leu Lys Val Leu Glu Gln Lys Ile Glu Gln Glu Glu Glu Thr
            100                 105                 110

Asn Lys Ser Ser Ala Asp Leu Arg Ile Arg Lys Thr Gln His Ser Thr
        115                 120                 125

Ile Leu Arg Lys Phe Ile Glu Val Met Asn Gln Tyr Asn Ala Ala Gln
    130                 135                 140

Val Asp Tyr Arg Asp Gly Cys Lys Lys Arg Leu Gln Arg Gln Met Glu
145                 150                 155                 160

Ile Thr Gly Arg Ala Thr Thr Asn Glu Glu Leu Glu Asp Met Leu Glu
                165                 170                 175

Ser Gly Asn Pro Ala Ile Phe Thr Gln Gly Ile Ile Thr Asp Thr Gln
            180                 185                 190

Gln Ala Lys Gln Ser Leu Met Asp Ile Glu Ala Arg His Asn Asp Ile
        195                 200                 205

Met Lys Leu Glu Gln Ser Ile Lys Glu Leu His Asp Met Phe Met Asp
    210                 215                 220

Met Ala Met Leu Val Glu Ser Gln Gly Glu Met Ile Asp Arg Ile Glu
225                 230                 235                 240

His Asn Val Glu Lys Ala Val Asp Tyr Val Glu Thr Ala Ala Ala Asp
                245                 250                 255

Thr Lys Lys Ala Met Lys Tyr Gln Ser Ala Ala Arg Lys Lys Lys Ile
            260                 265                 270
```

Ile Ile Leu Ile Cys Val Ser Val Leu Ile Leu Ile Val Gly Gly Ser
275 280 285

Leu Leu Gly Ile Phe Ile Pro
290 295

<210> SEQ ID NO 93
<211> LENGTH: 292
<212> TYPE: PRT
<213> ORGANISM: Loligo pealei Syntaxin-1A (Longfin squid)

<400> SEQUENCE: 93

Met Thr Lys Asp Arg Leu Ala Ala Leu Lys Ala Ala Val Ser Asp Glu
1 5 10 15

Glu Asp Val Glu Glu Val Ala Val Gln Val Asp Ser Gly Gly Gly Phe
20 25 30

Met Glu Glu Phe Phe Glu Gln Val Glu Glu Ile Arg Ala Met Ile Asp
35 40 45

Lys Ile Ser Asp Asn Val Asp Ala Val Lys Lys Lys His Ser Asp Ile
50 55 60

Leu Ser Ala Pro Gln Thr Asp Asp Gln Met Lys Glu Glu Leu Glu Glu
65 70 75 80

Leu Met Thr Asp Ile Lys Arg Thr Ala Asn Lys Val Arg Gly Lys Leu
85 90 95

Lys Thr Ile Glu Leu Asn Ile Glu Gln Glu Glu His Ser Asn Lys Ser
100 105 110

Ser Ala Asp Leu Arg Ile Arg Lys Thr Gln Tyr Ser Thr Ile Ser Arg
115 120 125

Lys Phe Val Glu Val Met Ser Asp Tyr Asn Thr Thr Gln Ile Asp Tyr
130 135 140

Arg Asp Arg Cys Lys Ala Arg Ile Lys Arg Gln Met Glu Ile Thr Gly
145 150 155 160

Arg Thr Thr Thr Asn Glu Glu Leu Glu Asp Met Leu Glu Ser Gly Asn
165 170 175

Pro Ala Ile Phe Thr Gln Gly Ile Ile Met Glu Thr Gln Gln Ala Lys
180 185 190

Gln Thr Leu Ala Asp Ile Glu Ala Arg His Ala Asp Ile Met Lys Leu
195 200 205

Glu Thr Ser Ile Arg Glu Leu His Asp Met Phe Met Asp Met Ala Met
210 215 220

Leu Val Glu Ser Gln Gly Glu Met Ile Asp Arg Ile Glu Tyr Asn Val
225 230 235 240

Glu Ala Ala Val Asp Tyr Ile Glu Thr Ala Lys Val Asp Thr Lys Lys
245 250 255

Ala Val Lys Tyr Gln Ser Lys Ala Arg Gln Lys Lys Ile Ala Ile Leu
260 265 270

Val Cys Leu Val Ile Leu Val Leu Val Ile Val Ser Thr Val Gly Gly
275 280 285

Val Phe Gly Gly
290

<210> SEQ ID NO 94
<211> LENGTH: 290
<212> TYPE: PRT
<213> ORGANISM: Lymnaea stagnalis Syntaxin-1A (Great pond snail)

<400> SEQUENCE: 94

```
Met Thr Lys Asp Arg Leu Ala Ala Leu Lys Ala Ala Gln Ser Asp Asp
1               5                   10                  15

Asp Glu Asn Asp Asp Val Ala Val Thr Val Asp Ser Ser Gly Phe Met
            20                  25                  30

Glu Glu Phe Phe Glu Gln Val Asp Glu Ile Arg Glu Met Ile Asp Lys
        35                  40                  45

Ile Ala Ser Asn Val Asp Glu Val Lys Lys Lys His Ser Ala Ile Leu
    50                  55                  60

Ser Ala Pro Gln Thr Asp Asp Lys Met Lys Glu Glu Leu Glu Glu Leu
65                  70                  75                  80

Met Ser Glu Ile Lys Lys Asn Ala Asn Lys Val Arg Ala Lys Leu Lys
                85                  90                  95

Val Ile Glu Gln Asn Ile Glu Gln Glu Glu His Thr Asn Lys Ser Ser
            100                 105                 110

Ala Asp Leu Arg Ile Arg Lys Thr Gln His Ala Thr Leu Ser Arg Lys
        115                 120                 125

Phe Val Glu Val Met Asn Asp Tyr Asn Ala Cys Gln Ile Asp Tyr Arg
    130                 135                 140

Glu Arg Cys Lys Gly Arg Ile Lys Arg Gln Leu Ala Ile Thr Gly Lys
145                 150                 155                 160

Thr Thr Thr Asn Glu Glu Leu Glu Asp Met Ile Glu Ser Gly Asn Pro
                165                 170                 175

Ala Ile Phe Thr Gln Gly Ile Ile Met Glu Thr Gln Gln Ala Lys Gln
            180                 185                 190

Thr Leu Ala Asp Ile Glu Ala Arg His Asn Asp Ile Met Lys Leu Glu
        195                 200                 205

Thr Ser Ile Arg Asp Leu His Asp Met Phe Met Asp Met Ala Met Leu
    210                 215                 220

Val Glu Ser Gln Gly Glu Met Ile Asp Arg Ile Glu Tyr Asn Val Glu
225                 230                 235                 240

Gln Ala Val Asp Tyr Ile Glu Thr Ala Lys Met Asp Thr Lys Lys Ala
                245                 250                 255

Val Lys Tyr Gln Ser Lys Ala Arg Arg Lys Lys Ile Met Ile Ile Ile
            260                 265                 270

Cys Val Cys Val Leu Ile Ile Ile Leu Val Gly Ile Leu Gly Gly Thr
        275                 280                 285

Phe Gly
    290


<210> SEQ ID NO 95
<211> LENGTH: 290
<212> TYPE: PRT
<213> ORGANISM: Aplysia californica Syntaxin-1A (sea hare)

<400> SEQUENCE: 95

Met Thr Lys Asp Arg Leu Ala Ala Leu Lys Ala Ala Gln Ser Asp Asp
1               5                   10                  15

Asp Asp Asn Asp Asp Val Ala Val Thr Val Asp Ser Ser Gly Phe Met
            20                  25                  30

Glu Glu Phe Phe Glu Gln Val Asp Glu Ile Arg Glu Met Ile Asp Lys
        35                  40                  45

Ile Ala Ser Asn Val Asp Glu Val Lys Lys Lys His Ser Ala Ile Leu
    50                  55                  60

Ser Ala Pro Gln Thr Asp Asp Lys Met Lys Glu Glu Leu Glu Glu Leu
65                  70                  75                  80
```

```
Met Ser Glu Ile Lys Lys Asn Ala Asn Lys Val Arg Ala Lys Leu Lys
                85                  90                  95

Val Ile Glu Gln Asn Ile Glu Gln Glu Glu His Thr Asn Lys Ser Ser
            100                 105                 110

Ala Asp Leu Arg Ile Arg Lys Thr Gln His Ala Thr Leu Ser Arg Lys
        115                 120                 125

Phe Val Glu Val Met Asn Asp Tyr Asn Ala Cys Gln Ile Asp Tyr Arg
    130                 135                 140

Glu Arg Cys Lys Gly Arg Ile Lys Arg Gln Leu Ala Ile Thr Gly Lys
145                 150                 155                 160

Thr Thr Thr Asn Glu Glu Leu Glu Asp Met Ile Glu Ser Gly Asn Pro
                165                 170                 175

Ala Ile Phe Thr Gln Gly Ile Ile Met Glu Thr Gln Gln Ala Asn Glu
            180                 185                 190

Thr Leu Ala Asp Ile Glu Ala Arg His Asn Asp Ile Met Lys Leu Glu
        195                 200                 205

Thr Ser Ile Arg Asp Leu His Asp Met Phe Met Asp Met Ala Met Leu
    210                 215                 220

Val Glu Ser Gln Gly Glu Met Ile Asp Arg Ile Glu Tyr Asn Val Glu
225                 230                 235                 240

Gln Ala Val Asp Tyr Ile Glu Thr Ala Lys Met Asp Thr Lys Lys Ala
                245                 250                 255

Val Lys Tyr Gln Ser Lys Ala Arg Arg Lys Lys Ile Met Ile Leu Val
            260                 265                 270

Cys Leu Ala Ile Leu Ile Ile Ile Leu Val Gly Val Ile Gly Gly Thr
        275                 280                 285

Leu Gly
    290


<210> SEQ ID NO 96
<211> LENGTH: 8
<212> TYPE: PRT
<213> ORGANISM: Artificial Sequence
<220> FEATURE:
<223> OTHER INFORMATION: BoNT/A SNAP-25 cleavage bond

<400> SEQUENCE: 96

Glu Ala Asn Gln Arg Ala Thr Lys
 1               5


<210> SEQ ID NO 97
<211> LENGTH: 8
<212> TYPE: PRT
<213> ORGANISM: Artificial Sequence
<220> FEATURE:
<223> OTHER INFORMATION: BoNT/B VAMP-2 cleavage bond

<400> SEQUENCE: 97

Gly Ala Ser Gln Phe Glu Thr Ser
 1               5


<210> SEQ ID NO 98
<211> LENGTH: 8
<212> TYPE: PRT
<213> ORGANISM: Artificial Sequence
<220> FEATURE:
<223> OTHER INFORMATION: BoNT/C1 Syntaxin-1 cleavage bond

<400> SEQUENCE: 98

Asp Thr Lys Lys Ala Val Lys Tyr
 1               5
```

<210> SEQ ID NO 99
<211> LENGTH: 8
<212> TYPE: PRT
<213> ORGANISM: Artificial Sequence
<220> FEATURE:
<223> OTHER INFORMATION: BoNT/C1 SNAP-25 cleavage bond

<400> SEQUENCE: 99

Ala Asn Gln Arg Ala Thr Lys Met
1 5

<210> SEQ ID NO 100
<211> LENGTH: 8
<212> TYPE: PRT
<213> ORGANISM: Artificial Sequence
<220> FEATURE:
<223> OTHER INFORMATION: BoNT/D VAMP-2 cleavage bond

<400> SEQUENCE: 100

Arg Asp Gln Lys Leu Ser Glu Leu
1 5

<210> SEQ ID NO 101
<211> LENGTH: 8
<212> TYPE: PRT
<213> ORGANISM: Artificial Sequence
<220> FEATURE:
<223> OTHER INFORMATION: BoNT/E SNAP-25 cleavage bond

<400> SEQUENCE: 101

Gln Ile Asp Arg Ile Met Glu Lys
1 5

<210> SEQ ID NO 102
<211> LENGTH: 8
<212> TYPE: PRT
<213> ORGANISM: Artificial Sequence
<220> FEATURE:
<223> OTHER INFORMATION: BoNT/F VAMP-2 cleavage bond

<400> SEQUENCE: 102

Glu Arg Asp Gln Lys Leu Ser Glu
1 5

<210> SEQ ID NO 103
<211> LENGTH: 8
<212> TYPE: PRT
<213> ORGANISM: Artificial Sequence
<220> FEATURE:
<223> OTHER INFORMATION: BoNT/G VAMP-2 cleavage bond

<400> SEQUENCE: 103

Glu Thr Ser Ala Ala Lys Leu Lys
1 5

<210> SEQ ID NO 104
<211> LENGTH: 8
<212> TYPE: PRT
<213> ORGANISM: Artificial Sequence
<220> FEATURE:
<223> OTHER INFORMATION: TeNT VAMP-2 cleavage bond

<400> SEQUENCE: 104

Gly Ala Ser Gln Phe Glu Thr Ser
1 5

<210> SEQ ID NO 105
<211> LENGTH: 13
<212> TYPE: PRT
<213> ORGANISM: Artificial Sequence
<220> FEATURE:
<223> OTHER INFORMATION: BoNT/A SNAP-25 recognition site

<400> SEQUENCE: 105

Thr Arg Ile Asp Glu Ala Asn Gln Arg Ala Thr Lys Met
1 5 10

<210> SEQ ID NO 106
<211> LENGTH: 15
<212> TYPE: PRT
<213> ORGANISM: Artificial Sequence
<220> FEATURE:
<223> OTHER INFORMATION: BoNT/A SNAP-25 recognition site

<400> SEQUENCE: 106

Ser Asn Lys Thr Arg Ile Asp Glu Ala Asn Gln Arg Ala Thr Lys
1 5 10 15

<210> SEQ ID NO 107
<211> LENGTH: 16
<212> TYPE: PRT
<213> ORGANISM: Artificial Sequence
<220> FEATURE:
<223> OTHER INFORMATION: BoNT/A SNAP-25 recognition site

<400> SEQUENCE: 107

Ser Asn Lys Thr Arg Ile Asp Glu Ala Asn Gln Arg Ala Thr Lys Met
1 5 10 15

<210> SEQ ID NO 108
<211> LENGTH: 17
<212> TYPE: PRT
<213> ORGANISM: Artificial Sequence
<220> FEATURE:
<223> OTHER INFORMATION: BoNT/A SNAP-25 recognition site

<400> SEQUENCE: 108

Ser Asn Lys Thr Arg Ile Asp Glu Ala Asn Gln Arg Ala Thr Lys Met
1 5 10 15

Leu

<210> SEQ ID NO 109
<211> LENGTH: 17
<212> TYPE: PRT
<213> ORGANISM: Artificial Sequence
<220> FEATURE:
<223> OTHER INFORMATION: BoNT/A SNAP-25 recognition site

<400> SEQUENCE: 109

Asp Ser Asn Lys Thr Arg Ile Asp Glu Ala Asn Gln Arg Ala Thr Lys
1 5 10 15

Met

<210> SEQ ID NO 110
<211> LENGTH: 18
<212> TYPE: PRT
<213> ORGANISM: Artificial Sequence
<220> FEATURE:
<223> OTHER INFORMATION: BoNT/A SNAP-25 recognition site

<400> SEQUENCE: 110

Asp Ser Asn Lys Thr Arg Ile Asp Glu Ala Asn Gln Arg Ala Thr Lys
1 5 10 15

Met Leu

<210> SEQ ID NO 111
<211> LENGTH: 17
<212> TYPE: PRT
<213> ORGANISM: Artificial Sequence
<220> FEATURE:
<223> OTHER INFORMATION: BoNT/A SNAP-25 recognition site

<400> SEQUENCE: 111

Ser Asn Lys Thr Arg Ile Asp Glu Ala Asn Gln Arg Ala Thr Lys Ala
1 5 10 15

Leu

<210> SEQ ID NO 112
<211> LENGTH: 17
<212> TYPE: PRT
<213> ORGANISM: Artificial Sequence
<220> FEATURE:
<223> OTHER INFORMATION: BoNT/A SNAP-25 recognition site
<220> FEATURE:
<221> NAME/KEY: VARIANT
<222> LOCATION: (16)...(16)
<223> OTHER INFORMATION: Xaa=2-aminohexanoic acid (norleucine)

<400> SEQUENCE: 112

Ser Asn Lys Thr Arg Ile Asp Glu Ala Asn Gln Arg Ala Thr Lys Xaa
1 5 10 15

Leu

<210> SEQ ID NO 113
<211> LENGTH: 17
<212> TYPE: PRT
<213> ORGANISM: Artificial Sequence
<220> FEATURE:
<223> OTHER INFORMATION: BoNT/A SNAP-25 recognition site

<400> SEQUENCE: 113

Ser Asn Lys Thr Arg Ile Asp Glu Ala Asn Gln Arg Ala Thr Ala Met
1 5 10 15

Leu

<210> SEQ ID NO 114
<211> LENGTH: 17
<212> TYPE: PRT
<213> ORGANISM: Artificial Sequence
<220> FEATURE:
<223> OTHER INFORMATION: BoNT/A SNAP-25 recognition site

<400> SEQUENCE: 114

Ser Asn Lys Thr Arg Ile Asp Glu Ala Asn Gln Arg Ala Ser Lys Met
1 5 10 15

Leu

<210> SEQ ID NO 115
<211> LENGTH: 17
<212> TYPE: PRT
<213> ORGANISM: Artificial Sequence
<220> FEATURE:
<223> OTHER INFORMATION: BoNT/A SNAP-25 recognition site
<220> FEATURE:
<221> NAME/KEY: VARIANT
<222> LOCATION: (14)...(14)
<223> OTHER INFORMATION: Xaa=2-aminobutyric acid

<400> SEQUENCE: 115

Ser Asn Lys Thr Arg Ile Asp Glu Ala Asn Gln Arg Ala Xaa Lys Met
1 5 10 15

Leu

<210> SEQ ID NO 116
<211> LENGTH: 17
<212> TYPE: PRT
<213> ORGANISM: Artificial Sequence
<220> FEATURE:
<223> OTHER INFORMATION: BoNT/A SNAP-25 recognition site
<220> FEATURE:
<221> NAME/KEY: VARIANT
<222> LOCATION: (13)...(13)
<223> OTHER INFORMATION: Xaa=2-aminobutyric acid

<400> SEQUENCE: 116

Ser Asn Lys Thr Arg Ile Asp Glu Ala Asn Gln Arg Xaa Thr Lys Met
1 5 10 15

Leu

<210> SEQ ID NO 117
<211> LENGTH: 17
<212> TYPE: PRT
<213> ORGANISM: Artificial Sequence
<220> FEATURE:
<223> OTHER INFORMATION: BoNT/A SNAP-25 recognition site

<400> SEQUENCE: 117

Ser Asn Lys Thr Arg Ile Asp Glu Ala Asn Ala Arg Ala Thr Lys Met
1 5 10 15

Leu

<210> SEQ ID NO 118
<211> LENGTH: 17
<212> TYPE: PRT
<213> ORGANISM: Artificial Sequence
<220> FEATURE:
<223> OTHER INFORMATION: BoNT/A SNAP-25 recognition site
<220> FEATURE:
<221> NAME/KEY: VARIANT
<222> LOCATION: (11)...(11)
<223> OTHER INFORMATION: Xaa=2-aminobutyric acid

<400> SEQUENCE: 118

Ser Asn Lys Thr Arg Ile Asp Glu Ala Asn Xaa Arg Ala Thr Lys Met
1 5 10 15

Leu

<210> SEQ ID NO 119
<211> LENGTH: 17
<212> TYPE: PRT
<213> ORGANISM: Artificial Sequence
<220> FEATURE:
<223> OTHER INFORMATION: BoNT/A SNAP-25 recognition site

<400> SEQUENCE: 119

Ser Asn Lys Thr Arg Ile Asp Glu Ala Asn Asn Arg Ala Thr Lys Met
1 5 10 15

Leu

<210> SEQ ID NO 120
<211> LENGTH: 17
<212> TYPE: PRT
<213> ORGANISM: Artificial Sequence
<220> FEATURE:

<223> OTHER INFORMATION: BoNT/A SNAP-25 recognition site

<400> SEQUENCE: 120

Ser Asn Lys Thr Arg Ile Asp Glu Ala Ala Gln Arg Ala Thr Lys Met
1 5 10 15

Leu

<210> SEQ ID NO 121
<211> LENGTH: 17
<212> TYPE: PRT
<213> ORGANISM: Artificial Sequence
<220> FEATURE:
<223> OTHER INFORMATION: BoNT/A SNAP-25 recognition site
<220> FEATURE:
<221> NAME/KEY: VARIANT
<222> LOCATION: (9)...(9)
<223> OTHER INFORMATION: Xaa=2-aminobutyric acid

<400> SEQUENCE: 121

Ser Asn Lys Thr Arg Ile Asp Glu Xaa Asn Gln Arg Ala Thr Lys Met
1 5 10 15

Leu

<210> SEQ ID NO 122
<211> LENGTH: 17
<212> TYPE: PRT
<213> ORGANISM: Artificial Sequence
<220> FEATURE:
<223> OTHER INFORMATION: BoNT/A SNAP-25 recognition site

<400> SEQUENCE: 122

Ser Asn Lys Thr Arg Ile Asp Gln Ala Asn Gln Arg Ala Thr Lys Met
1 5 10 15

Leu

<210> SEQ ID NO 123
<211> LENGTH: 17
<212> TYPE: PRT
<213> ORGANISM: Artificial Sequence
<220> FEATURE:
<223> OTHER INFORMATION: BoNT/A SNAP-25 recognition site

<400> SEQUENCE: 123

Ser Asn Lys Thr Arg Ile Asn Glu Ala Asn Gln Arg Ala Thr Lys Met
1 5 10 15

Leu

<210> SEQ ID NO 124
<211> LENGTH: 35
<212> TYPE: PRT
<213> ORGANISM: Artificial Sequence
<220> FEATURE:
<223> OTHER INFORMATION: BoNT/B VAMP-2 recognition site

<400> SEQUENCE: 124

Leu Ser Glu Leu Asp Asp Arg Ala Asp Ala Leu Gln Ala Gly Ala Ser
1 5 10 15

Gln Phe Glu Thr Ser Ala Ala Lys Leu Lys Arg Lys Tyr Trp Trp Lys
20 25 30

Asn Leu Lys
35

<210> SEQ ID NO 125
<211> LENGTH: 35

<212> TYPE: PRT
<213> ORGANISM: Artificial Sequence
<220> FEATURE:
<223> OTHER INFORMATION: BoNT/B VAMP-1 recognition site

<400> SEQUENCE: 125

Leu Ser Glu Leu Asp Asp Arg Ala Asp Ala Leu Gln Ala Gly Ala Ser
1 5 10 15

Gln Phe Glu Ser Ser Ala Ala Lys Leu Lys Arg Lys Tyr Trp Trp Lys
20 25 30

Asn Cys Lys
35

<210> SEQ ID NO 126
<211> LENGTH: 39
<212> TYPE: PRT
<213> ORGANISM: Artificial Sequence
<220> FEATURE:
<223> OTHER INFORMATION: BoNT/D and BoNT/F VAMP-2 recognition site

<400> SEQUENCE: 126

Ala Gln Val Asp Glu Val Val Asp Ile Met Arg Val Asn Val Asp Lys
1 5 10 15

Val Leu Glu Arg Asp Gln Lys Leu Ser Glu Leu Asp Asp Arg Ala Asp
20 25 30

Ala Leu Gln Ala Gly Ala Ser
35

<210> SEQ ID NO 127
<211> LENGTH: 39
<212> TYPE: PRT
<213> ORGANISM: Artificial Sequence
<220> FEATURE:
<223> OTHER INFORMATION: BoNT/D and BoNT/F VAMP-1 recognition site

<400> SEQUENCE: 127

Ala Gln Val Glu Glu Val Val Asp Ile Ile Arg Val Asn Val Asp Lys
1 5 10 15

Val Leu Glu Arg Asp Gln Lys Leu Ser Glu Leu Asp Asp Arg Ala Asp
20 25 30

Ala Leu Gln Ala Gly Ala Ser
35

<210> SEQ ID NO 128
<211> LENGTH: 10
<212> TYPE: PRT
<213> ORGANISM: Artificial Sequence
<220> FEATURE:
<223> OTHER INFORMATION: SNAP-25 membrane targeting domain fragment

<400> SEQUENCE: 128

Cys Gly Leu Cys Val Cys Pro Cys Asn Lys
1 5 10

<210> SEQ ID NO 129
<211> LENGTH: 10
<212> TYPE: PRT
<213> ORGANISM: Artificial Sequence
<220> FEATURE:
<223> OTHER INFORMATION: SNAP-25 Membrane Targeting Domain fragment

<400> SEQUENCE: 129

Cys Gly Leu Phe Ile Cys Pro Cys Asn Lys
1 5 10

<210> SEQ ID NO 130
<211> LENGTH: 10
<212> TYPE: PRT
<213> ORGANISM: Artificial Sequence
<220> FEATURE:
<223> OTHER INFORMATION: SNAP-25 Membrane Targeting Domain fragment

<400> SEQUENCE: 130

Cys Gly Leu Cys Ser Cys Pro Cys Asn Lys
1 5 10

<210> SEQ ID NO 131
<211> LENGTH: 10
<212> TYPE: PRT
<213> ORGANISM: Artificial Sequence
<220> FEATURE:
<223> OTHER INFORMATION: SNAP-25 Membrane Targeting Domain fragment

<400> SEQUENCE: 131

Cys Gly Leu Cys Pro Cys Pro Cys Asn Lys
1 5 10

<210> SEQ ID NO 132
<211> LENGTH: 10
<212> TYPE: PRT
<213> ORGANISM: Artificial Sequence
<220> FEATURE:
<223> OTHER INFORMATION: SNAP-25 Membrane Targeting Domain fragment

<400> SEQUENCE: 132

Cys Gly Ile Cys Val Cys Pro Trp Lys Lys
1 5 10

<210> SEQ ID NO 133
<211> LENGTH: 10
<212> TYPE: PRT
<213> ORGANISM: Artificial Sequence
<220> FEATURE:
<223> OTHER INFORMATION: SNAP-25 Membrane Targeting Domain fragment

<400> SEQUENCE: 133

Cys Gly Ile Cys Val Leu Pro Cys Asn Lys
1 5 10

<210> SEQ ID NO 134
<211> LENGTH: 10
<212> TYPE: PRT
<213> ORGANISM: Artificial Sequence
<220> FEATURE:
<223> OTHER INFORMATION: SNAP-25 Membrane Targeting Domain fragment

<400> SEQUENCE: 134

Cys Gly Leu Cys Val Leu Pro Trp Asn Lys
1 5 10

<210> SEQ ID NO 135
<211> LENGTH: 5
<212> TYPE: PRT
<213> ORGANISM: Artificial Sequence
<220> FEATURE:
<223> OTHER INFORMATION: SNAP-25 Membrane Targeting Domain fragment
<220> FEATURE:
<221> NAME/KEY: VARIANT
<222> LOCATION: (3)...(3)
<223> OTHER INFORMATION: Xaa=any amino acid

<400> SEQUENCE: 135

Gln Pro Xaa Arg Val 1 5

<210> SEQ ID NO 136
<211> LENGTH: 5
<212> TYPE: PRT
<213> ORGANISM: Artificial Sequence
<220> FEATURE:
<223> OTHER INFORMATION: SNAP-25 Membrane Targeting Domain fragment
<220> FEATURE:
<221> NAME/KEY: VARIANT
<222> LOCATION: (3)...(3)
<223> OTHER INFORMATION: Xaa=any amino acid

<400> SEQUENCE: 136

Gln Pro Xaa Arg Ile
1 5

<210> SEQ ID NO 137
<211> LENGTH: 5
<212> TYPE: PRT
<213> ORGANISM: Artificial Sequence
<220> FEATURE:
<223> OTHER INFORMATION: SNAP-25 Membrane Targeting Domain fragment

<400> SEQUENCE: 137

Gln Pro Ala Arg Val
1 5

<210> SEQ ID NO 138
<211> LENGTH: 5
<212> TYPE: PRT
<213> ORGANISM: Artificial Sequence
<220> FEATURE:
<223> OTHER INFORMATION: SNAP-25 Membrane Targeting Domain fragment

<400> SEQUENCE: 138

Gln Pro Gln Arg Val
1 5

<210> SEQ ID NO 139
<211> LENGTH: 5
<212> TYPE: PRT
<213> ORGANISM: Artificial Sequence
<220> FEATURE:
<223> OTHER INFORMATION: SNAP-25 Membrane Targeting Domain fragment

<400> SEQUENCE: 139

Gln Pro Gly Arg Val
1 5

<210> SEQ ID NO 140
<211> LENGTH: 5
<212> TYPE: PRT
<213> ORGANISM: Artificial Sequence
<220> FEATURE:
<223> OTHER INFORMATION: SNAP-25 Membrane Targeting Domain fragment

<400> SEQUENCE: 140

Gln Pro Ser Arg Ile
1 5

<210> SEQ ID NO 141
<211> LENGTH: 5
<212> TYPE: PRT
<213> ORGANISM: Artificial Sequence
<220> FEATURE:
<223> OTHER INFORMATION: SNAP-25 Membrane Targeting Domain fragment

<400> SEQUENCE: 141

```
Gln Pro Met Arg Met
 1              5


<210> SEQ ID NO 142
<211> LENGTH: 4
<212> TYPE: PRT
<213> ORGANISM: Artificial Sequence
<220> FEATURE:
<223> OTHER INFORMATION: SNAP-25 Membrane Targeting Domain fragment

<400> SEQUENCE: 142

Gln Pro Arg Ile
 1


<210> SEQ ID NO 143
<211> LENGTH: 239
<212> TYPE: PRT
<213> ORGANISM: Aequorea coerulescens Green Fluorescent Protein

<400> SEQUENCE: 143

Met Val Ser Lys Gly Ala Glu Leu Phe Thr Gly Ile Val Pro Ile Leu
 1              5                   10                  15

Ile Glu Leu Asn Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
                85                  90                  95

Arg Thr Ile Phe Phe Glu Asp Asp Gly Asn Tyr Lys Ser Arg Ala Glu
            100                 105                 110

Val Lys Phe Glu Gly Asp Thr Leu Val Asn Arg Ile Glu Leu Thr Gly
        115                 120                 125

Thr Asp Phe Lys Glu Asp Gly Asn Ile Leu Gly Asn Lys Met Glu Tyr
    130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Ile Tyr Phe Gly Phe
    210                 215                 220

Val Thr Ala Ala Ala Ile Thr His Gly Met Asp Glu Leu Tyr Lys
225                 230                 235


<210> SEQ ID NO 144
<211> LENGTH: 231
<212> TYPE: PRT
<213> ORGANISM: Zoanthus Green Fluorescent Protein

<400> SEQUENCE: 144

Met Ala Gln Ser Lys His Gly Leu Thr Lys Glu Met Thr Met Lys Tyr
 1              5                   10                  15
```

-continued

```
Arg Met Glu Gly Cys Val Asp Gly His Lys Phe Val Ile Thr Gly Glu
            20                  25                  30

Gly Ile Gly Tyr Pro Phe Lys Gly Lys Gln Ala Ile Asn Leu Cys Val
        35                  40                  45

Val Glu Gly Gly Pro Leu Pro Phe Ala Glu Asp Ile Leu Ser Ala Ala
    50                  55                  60

Phe Met Tyr Gly Asn Arg Val Phe Thr Glu Tyr Pro Gln Asp Ile Ala
65                  70                  75                  80

Asp Tyr Phe Lys Asn Ser Cys Pro Ala Gly Tyr Thr Trp Asp Arg Ser
                85                  90                  95

Phe Leu Phe Glu Asp Gly Ala Val Cys Ile Cys Asn Ala Asp Ile Thr
            100                 105                 110

Val Ser Val Glu Glu Asn Cys Met Tyr His Glu Ser Lys Phe Tyr Gly
        115                 120                 125

Val Asn Phe Pro Ala Asp Gly Pro Val Met Lys Lys Met Thr Asp Asn
    130                 135                 140

Trp Glu Pro Ser Cys Glu Lys Ile Ile Pro Val Pro Lys Gln Gly Ile
145                 150                 155                 160

Leu Lys Gly Asp Val Ser Met Tyr Leu Leu Leu Lys Asp Gly Gly Arg
                165                 170                 175

Leu Arg Cys Gln Phe Asp Thr Val Tyr Lys Ala Lys Ser Val Pro Arg
            180                 185                 190

Lys Met Pro Asp Trp His Phe Ile Gln His Lys Leu Thr Arg Glu Asp
        195                 200                 205

Arg Ser Asp Ala Lys Asn Gln Lys Trp His Leu Thr Glu His Ala Ile
    210                 215                 220

Ala Ser Gly Ser Ala Leu Pro
225                 230
```

<210> SEQ ID NO 145
<211> LENGTH: 239
<212> TYPE: PRT
<213> ORGANISM: Aequorea victoria Green Fluorescent Protein

<400> SEQUENCE: 145

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
```

Gly Ile Lys Val Asn Phe Lys Ile Arg His Asn Ile Glu Asp Gly Ser
165 170 175

Val Gln Leu Ala Asp His Tyr Gln Gln Asn Thr Pro Ile Gly Asp Gly
180 185 190

Pro Val Leu Leu Pro Asp Asn His Tyr Leu Ser Thr Gln Ser Ala Leu
195 200 205

Ser Lys Asp Pro Asn Glu Lys Arg Asp His Met Val Leu Leu Glu Phe
210 215 220

Val Thr Ala Ala Gly Ile Thr Leu Gly Met Asp Glu Leu Tyr Lys
225 230 235

<210> SEQ ID NO 146
<211> LENGTH: 227
<212> TYPE: PRT
<213> ORGANISM: Montastrea cavernosa Monster Green

<400> SEQUENCE: 146

Met Gly Val Ile Lys Pro Asp Met Lys Ile Lys Leu Arg Met Glu Gly
1 5 10 15

Ala Val Asn Gly His Lys Phe Val Ile Glu Gly Asp Gly Lys Gly Lys
20 25 30

Pro Phe Glu Gly Lys Gln Thr Met Asp Leu Thr Val Ile Glu Gly Ala
35 40 45

Pro Leu Pro Phe Ala Tyr Asp Ile Leu Thr Thr Val Phe Asp Tyr Gly
50 55 60

Asn Arg Val Phe Ala Lys Tyr Pro Lys Asp Ile Pro Asp Tyr Phe Lys
65 70 75 80

Gln Thr Phe Pro Glu Gly Tyr Ser Trp Glu Arg Ser Met Thr Tyr Glu
85 90 95

Asp Gln Gly Ile Cys Ile Ala Thr Asn Asp Ile Thr Met Met Lys Gly
100 105 110

Val Asp Asp Cys Phe Val Tyr Lys Ile Arg Phe Asp Gly Val Asn Phe
115 120 125

Pro Ala Asn Gly Pro Val Met Gln Arg Lys Thr Leu Lys Trp Glu Pro
130 135 140

Ser Thr Glu Lys Met Tyr Val Arg Asp Gly Val Leu Lys Gly Asp Val
145 150 155 160

Asn Met Ala Leu Leu Leu Glu Gly Gly Gly His Tyr Arg Cys Asp Phe
165 170 175

Lys Thr Thr Tyr Lys Ala Lys Lys Val Val Gln Leu Pro Asp Tyr His
180 185 190

Phe Val Asp His Arg Ile Glu Ile Val Ser His Asp Lys Asp Tyr Asn
195 200 205

Lys Val Lys Leu Tyr Glu His Ala Glu Ala His Ser Gly Leu Pro Arg
210 215 220

Gln Ala Gly
225

<210> SEQ ID NO 147
<211> LENGTH: 233
<212> TYPE: PRT
<213> ORGANISM: Renilla reniformis green fluorescent protein

<400> SEQUENCE: 147

Met Asp Leu Ala Lys Leu Gly Leu Lys Glu Val Met Pro Thr Lys Ile
1 5 10 15

```
Asn Leu Glu Gly Leu Val Gly Asp His Ala Phe Ser Met Glu Gly Val
            20                  25                  30

Gly Glu Gly Asn Ile Leu Glu Gly Thr Gln Glu Val Lys Ile Ser Val
        35                  40                  45

Thr Lys Gly Ala Pro Leu Pro Phe Ala Phe Asp Ile Val Ser Val Ala
    50                  55                  60

Phe Ser Tyr Gly Asn Arg Ala Tyr Thr Gly Tyr Pro Glu Glu Ile Ser
65                  70                  75                  80

Asp Tyr Phe Leu Gln Ser Phe Pro Glu Gly Phe Thr Tyr Glu Arg Asn
                85                  90                  95

Ile Arg Tyr Gln Asp Gly Gly Thr Ala Ile Val Lys Ser Asp Ile Ser
            100                 105                 110

Leu Glu Asp Gly Lys Phe Ile Val Asn Val Asp Phe Lys Ala Lys Asp
        115                 120                 125

Leu Arg Arg Met Gly Pro Val Met Gln Gln Asp Ile Val Gly Met Gln
    130                 135                 140

Pro Ser Tyr Glu Ser Met Tyr Thr Asn Val Thr Ser Val Ile Gly Glu
145                 150                 155                 160

Cys Ile Ile Ala Phe Lys Leu Gln Thr Gly Lys His Phe Thr Tyr His
                165                 170                 175

Met Arg Thr Val Tyr Lys Ser Lys Lys Pro Val Glu Thr Met Pro Leu
            180                 185                 190

Tyr His Phe Ile Gln His Arg Leu Val Lys Thr Asn Val Asp Thr Ala
        195                 200                 205

Ser Gly Tyr Val Val Gln His Glu Thr Ala Ile Ala Ala His Ser Thr
    210                 215                 220

Ile Lys Lys Ile Glu Gly Ser Leu Pro
225                 230
```

<210> SEQ ID NO 148
<211> LENGTH: 239
<212> TYPE: PRT
<213> ORGANISM: Aequorea victoria Cyan Fluorescent Protein

<400> SEQUENCE: 148

```
Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160
```

```
Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235


<210> SEQ ID NO 149
<211> LENGTH: 229
<212> TYPE: PRT
<213> ORGANISM: Anemonia majano cyan fluorescent protein

<400> SEQUENCE: 149

Met Ala Leu Ser Asn Lys Phe Ile Gly Asp Asp Met Lys Met Thr Tyr
 1               5                  10                  15

His Met Asp Gly Cys Val Asn Gly His Tyr Phe Thr Val Lys Gly Glu
            20                  25                  30

Gly Ser Gly Lys Pro Tyr Glu Gly Thr Gln Thr Ser Thr Phe Lys Val
        35                  40                  45

Thr Met Ala Asn Gly Gly Pro Leu Ala Phe Ser Phe Asp Ile Leu Ser
    50                  55                  60

Thr Val Phe Met Tyr Gly Asn Arg Cys Phe Thr Ala Tyr Pro Thr Ser
65                  70                  75                  80

Met Pro Asp Tyr Phe Lys Gln Ala Phe Pro Asp Gly Met Ser Tyr Glu
                85                  90                  95

Arg Thr Phe Thr Tyr Glu Asp Gly Gly Val Ala Thr Ala Ser Trp Glu
            100                 105                 110

Ile Ser Leu Lys Gly Asn Cys Phe Glu His Lys Ser Thr Phe His Gly
        115                 120                 125

Val Asn Phe Pro Ala Asp Gly Pro Val Met Ala Lys Met Thr Thr Gly
    130                 135                 140

Trp Asp Pro Ser Phe Glu Lys Met Thr Val Cys Asp Gly Ile Leu Lys
145                 150                 155                 160

Gly Asp Val Thr Ala Phe Leu Met Leu Gln Gly Gly Gly Asn Tyr Arg
                165                 170                 175

Cys Gln Phe His Thr Ser Tyr Lys Thr Lys Lys Pro Val Thr Met Pro
            180                 185                 190

Pro Asn His Ala Val Glu His Arg Ile Ala Arg Thr Asp Leu Asp Lys
        195                 200                 205

Gly Gly Asn Ser Val Gln Leu Thr Glu His Ala Val Ala His Ile Thr
    210                 215                 220

Ser Val Val Pro Phe
225


<210> SEQ ID NO 150
<211> LENGTH: 239
<212> TYPE: PRT
<213> ORGANISM: Aequorea  victoria Blue Fluorescent Protein

<400> SEQUENCE: 150

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
```

```
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr His Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Phe Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235


<210> SEQ ID NO 151
<211> LENGTH: 239
<212> TYPE: PRT
<213> ORGANISM: Aequorea  victoria Yellow Fluorescent Protein

<400> SEQUENCE: 151

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
```

```
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235


<210> SEQ ID NO 152
<211> LENGTH: 231
<212> TYPE: PRT
<213> ORGANISM: Zoanthus Yellow Fluorescent Protein

<400> SEQUENCE: 152

Met Ala His Ser Lys His Gly Leu Lys Glu Glu Met Thr Met Lys Tyr
 1               5                  10                  15

His Met Glu Gly Cys Val Asn Gly His Lys Phe Val Ile Thr Gly Glu
            20                  25                  30

Gly Ile Gly Tyr Pro Phe Lys Gly Lys Gln Thr Ile Asn Leu Cys Val
        35                  40                  45

Ile Glu Gly Gly Pro Leu Pro Phe Ser Glu Asp Ile Leu Ser Ala Gly
    50                  55                  60

Phe Lys Tyr Gly Asp Arg Ile Phe Thr Glu Tyr Pro Gln Asp Ile Val
65                  70                  75                  80

Asp Tyr Phe Lys Asn Ser Cys Pro Ala Gly Tyr Thr Trp Gly Arg Ser
                85                  90                  95

Phe Leu Phe Glu Asp Gly Ala Val Cys Ile Cys Asn Val Asp Ile Thr
            100                 105                 110

Val Ser Val Lys Glu Asn Cys Ile Tyr His Lys Ser Ile Phe Asn Gly
        115                 120                 125

Val Asn Phe Pro Ala Asp Gly Pro Val Met Lys Lys Met Thr Thr Asn
    130                 135                 140

Trp Glu Ala Ser Cys Glu Lys Ile Met Pro Val Pro Lys Gln Gly Ile
145                 150                 155                 160

Leu Lys Gly Asp Val Ser Met Tyr Leu Leu Leu Lys Asp Gly Gly Arg
                165                 170                 175

Tyr Arg Cys Gln Phe Asp Thr Val Tyr Lys Ala Lys Ser Val Pro Ser
            180                 185                 190

Lys Met Pro Glu Trp His Phe Ile Gln His Lys Leu Leu Arg Glu Asp
        195                 200                 205

Arg Ser Asp Ala Lys Asn Gln Lys Trp Gln Leu Thr Glu His Ala Ile
    210                 215                 220

Ala Phe Pro Ser Ala Leu Ala
225                 230


<210> SEQ ID NO 153
<211> LENGTH: 225
<212> TYPE: PRT
<213> ORGANISM: Discosoma striata Red Fluorescent Protein

<400> SEQUENCE: 153

Met Arg Ser Ser Lys Asn Val Ile Lys Glu Phe Met Arg Phe Lys Val
 1               5                  10                  15

Arg Met Glu Gly Thr Val Asn Gly His Glu Phe Glu Ile Glu Gly Glu
            20                  25                  30
```

```
Gly Glu Gly Arg Pro Tyr Glu Gly His Asn Thr Val Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225


<210> SEQ ID NO 154
<211> LENGTH: 226
<212> TYPE: PRT
<213> ORGANISM: Discosoma striata Red Fluorescent Protein 1

<400> SEQUENCE: 154

Met Val Arg Ser Ser Lys Asn Val Ile Lys Glu Phe Met Arg Phe Lys
 1               5                  10                  15

Val Arg Met Glu Gly Thr Val Asn Gly His Glu Phe Glu Ile Glu Gly
            20                  25                  30

Glu Gly Glu Gly Arg Pro Tyr Glu Gly His Asn Thr Val Lys Leu Lys
        35                  40                  45

Val Thr Lys Gly Gly Pro Leu Pro Phe Ala Trp Asp Ile Leu Ser Pro
    50                  55                  60

Gln Phe Gln Tyr Gly Ser Lys Val Tyr Val Lys His Pro Ala Asp Ile
65                  70                  75                  80

Pro Asp Tyr Lys Lys Leu Ser Phe Pro Glu Gly Phe Lys Trp Glu Arg
                85                  90                  95

Val Met Asn Phe Glu Asp Gly Gly Val Val Thr Val Thr Gln Asp Ser
            100                 105                 110

Ser Leu Gln Asp Gly Cys Phe Ile Tyr Lys Val Lys Phe Ile Gly Val
        115                 120                 125

Asn Phe Pro Ser Asp Gly Pro Val Met Gln Lys Lys Thr Met Gly Trp
    130                 135                 140

Glu Ala Ser Thr Glu Arg Leu Tyr Pro Arg Asp Gly Val Leu Lys Gly
145                 150                 155                 160

Glu Ile His Lys Ala Leu Lys Leu Lys Asp Gly Gly His Tyr Leu Val
                165                 170                 175
```

Glu Phe Lys Ser Ile Tyr Met Ala Lys Lys Pro Val Gln Leu Pro Gly
180 185 190

Tyr Tyr Tyr Val Asp Ser Lys Leu Asp Ile Thr Ser His Asn Glu Asp
195 200 205

Tyr Thr Ile Val Glu Gln Tyr Glu Arg Thr Glu Gly Arg His His Leu
210 215 220

Phe Leu
225

<210> SEQ ID NO 155
<211> LENGTH: 225
<212> TYPE: PRT
<213> ORGANISM: Discosoma striata Red Fluorescent Protein 2

<400> SEQUENCE: 155

Met Ala Ser Ser Glu Asn Val Ile Thr Glu Phe Met Arg Phe Lys Val
1 5 10 15

Arg Met Glu Gly Thr Val Asn Gly His Glu Phe Glu Ile Glu Gly Glu
20 25 30

Gly Glu Gly Arg Pro Tyr Glu Gly His Asn Thr Val Lys Leu Lys Val
35 40 45

Thr Lys Gly Gly Pro Leu Pro Phe Ala Trp Asp Ile Leu Ser Pro Gln
50 55 60

Phe Gln Tyr Gly Ser Lys Val Tyr Val Lys His Pro Ala Asp Ile Pro
65 70 75 80

Asp Tyr Lys Lys Leu Ser Phe Pro Glu Gly Phe Lys Trp Glu Arg Val
85 90 95

Met Asn Phe Glu Asp Gly Gly Val Ala Thr Val Thr Gln Asp Ser Ser
100 105 110

Leu Gln Asp Gly Cys Phe Ile Tyr Lys Val Lys Phe Ile Gly Val Asn
115 120 125

Phe Pro Ser Asp Gly Pro Val Met Gln Lys Lys Thr Met Gly Trp Glu
130 135 140

Ala Ser Thr Glu Arg Leu Tyr Pro Arg Asp Gly Val Leu Lys Gly Glu
145 150 155 160

Thr His Lys Ala Leu Lys Leu Lys Asp Gly Gly His Tyr Leu Val Glu
165 170 175

Phe Lys Ser Ile Tyr Met Ala Lys Lys Pro Val Gln Leu Pro Gly Tyr
180 185 190

Tyr Tyr Val Asp Ala Lys Leu Asp Ile Thr Ser His Asn Glu Asp Tyr
195 200 205

Thr Ile Val Glu Gln Tyr Glu Arg Thr Glu Gly Arg His His Leu Phe
210 215 220

Leu
225

<210> SEQ ID NO 156
<211> LENGTH: 244
<212> TYPE: PRT
<213> ORGANISM: Discosoma striata Red Fluorescent Protein Express

<400> SEQUENCE: 156

Met Ala Ser Ser Glu Asp Val Ile Lys Glu Phe Met Arg Phe Lys Val
1 5 10 15

Arg Met Glu Gly Ser Val Asn Gly His Glu Phe Glu Ile Glu Gly Glu
20 25 30

```
Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
    50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Ser Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Ala Glu Gly Arg His His Leu Phe
    210                 215                 220

Leu Arg Pro Arg Leu Ile Ile Ile Ser His Thr Thr Phe Val Glu Val
225                 230                 235                 240

Leu Leu Ala Leu


<210> SEQ ID NO 157
<211> LENGTH: 227
<212> TYPE: PRT
<213> ORGANISM: Heteractis crispa Red Fluorescent Protein

<400> SEQUENCE: 157

Met Ala Gly Leu Leu Lys Glu Ser Met Arg Ile Lys Met Tyr Met Glu
 1               5                  10                  15

Gly Thr Val Asn Gly His Tyr Phe Lys Cys Glu Gly Glu Gly Asp Gly
            20                  25                  30

Asn Pro Phe Thr Gly Thr Gln Ser Met Arg Ile His Val Thr Glu Gly
        35                  40                  45

Ala Pro Leu Pro Phe Ala Phe Asp Ile Leu Ala Pro Cys Cys Glu Tyr
    50                  55                  60

Gly Ser Arg Thr Phe Val His His Thr Ala Glu Ile Pro Asp Phe Phe
65                  70                  75                  80

Lys Gln Ser Phe Pro Glu Gly Phe Thr Trp Glu Arg Thr Thr Thr Tyr
                85                  90                  95

Glu Asp Gly Gly Ile Leu Thr Ala His Gln Asp Thr Ser Leu Glu Gly
            100                 105                 110

Asn Cys Leu Ile Tyr Lys Val Lys Val Leu Gly Thr Asn Phe Pro Ala
        115                 120                 125

Asp Gly Pro Val Met Lys Asn Lys Ser Gly Gly Trp Glu Pro Cys Thr
    130                 135                 140

Glu Val Val Tyr Pro Glu Asn Gly Val Leu Cys Gly Arg Asn Val Met
145                 150                 155                 160

Ala Leu Lys Val Gly Asp Arg Arg Leu Ile Cys His Leu Tyr Thr Ser
```

```
                165                 170                 175

Tyr Arg Ser Lys Lys Ala Val Arg Ala Leu Thr Met Pro Gly Phe His
            180                 185                 190

Phe Thr Asp Ile Arg Leu Gln Met Pro Arg Lys Lys Lys Asp Glu Tyr
        195                 200                 205

Phe Glu Leu Tyr Glu Ala Ser Val Ala Arg Tyr Ser Asp Leu Pro Glu
    210                 215                 220

Lys Ala Asn
225


<210> SEQ ID NO 158
<211> LENGTH: 232
<212> TYPE: PRT
<213> ORGANISM: Anemonia sulcata Red Fluorescent Protein

<400> SEQUENCE: 158

Met Ala Ser Leu Leu Lys Lys Thr Met Pro Phe Arg Thr Thr Ile Glu
 1               5                  10                  15

Gly Thr Val Asn Gly His Tyr Phe Lys Cys Thr Gly Lys Gly Glu Gly
            20                  25                  30

Asn Pro Leu Glu Gly Thr Gln Glu Met Lys Ile Glu Val Ile Glu Gly
        35                  40                  45

Gly Pro Leu Pro Phe Ala Phe His Ile Leu Ser Thr Ser Cys Met Tyr
    50                  55                  60

Gly Ser Lys Ala Phe Ile Lys Tyr Val Ser Gly Ile Pro Asp Tyr Phe
65                  70                  75                  80

Lys Gln Ser Leu Pro Glu Gly Phe Thr Trp Glu Arg Thr Thr Thr Tyr
                85                  90                  95

Glu Asp Gly Gly Phe Leu Thr Ala His Gln Asp Thr Ser Leu Asp Gly
            100                 105                 110

Asp Cys Leu Val Tyr Lys Val Lys Ile Leu Gly Asn Asn Phe Pro Ala
        115                 120                 125

Asp Gly Pro Val Met Gln Asn Lys Ala Gly Arg Trp Glu Pro Ser Thr
    130                 135                 140

Glu Ile Val Tyr Glu Val Asp Gly Val Leu Arg Gly Gln Ser Leu Met
145                 150                 155                 160

Ala Leu Glu Cys Pro Gly Gly Arg His Leu Thr Cys His Leu His Thr
                165                 170                 175

Thr Tyr Arg Ser Lys Lys Pro Ala Ser Ala Leu Lys Met Pro Gly Phe
            180                 185                 190

His Phe Glu Asp His Arg Ile Glu Ile Leu Glu Glu Val Glu Lys Gly
        195                 200                 205

Lys Cys Tyr Lys Gln Tyr Glu Ala Ala Val Gly Arg Tyr Cys Asp Ala
    210                 215                 220

Ala Pro Ser Lys Leu Gly His Asn
225                 230


<210> SEQ ID NO 159
<211> LENGTH: 5
<212> TYPE: PRT
<213> ORGANISM: Artificial Sequence
<220> FEATURE:
<223> OTHER INFORMATION: flexible spacer sequence

<400> SEQUENCE: 159

Gly Gly Gly Gly Ser
 1               5
```

<210> SEQ ID NO 160
<211> LENGTH: 16
<212> TYPE: PRT
<213> ORGANISM: Artificial Sequence
<220> FEATURE:
<223> OTHER INFORMATION: Penetratin fragment

<400> SEQUENCE: 160

Arg Gln Ile Lys Ile Trp Phe Gln Asn Arg Arg Met Lys Trp Lys Lys
1 5 10 15

<210> SEQ ID NO 161
<211> LENGTH: 16
<212> TYPE: PRT
<213> ORGANISM: Artificial Sequence
<220> FEATURE:
<223> OTHER INFORMATION: Penetratin fragment

<400> SEQUENCE: 161

Lys Lys Trp Lys Met Arg Arg Asn Gln Phe Trp Ile Lys Ile Gln Arg
1 5 10 15

<210> SEQ ID NO 162
<211> LENGTH: 16
<212> TYPE: PRT
<213> ORGANISM: Artificial Sequence
<220> FEATURE:
<223> OTHER INFORMATION: Penetratin fragment

<400> SEQUENCE: 162

Arg Gln Ile Lys Ile Trp Phe Gln Asn Arg Arg Met Lys Trp Lys Lys
1 5 10 15

<210> SEQ ID NO 163
<211> LENGTH: 16
<212> TYPE: PRT
<213> ORGANISM: Artificial Sequence
<220> FEATURE:
<223> OTHER INFORMATION: Penetratin fragment

<400> SEQUENCE: 163

Arg Gln Ile Lys Ile Trp Phe Pro Asn Arg Arg Met Lys Trp Lys Lys
1 5 10 15

<210> SEQ ID NO 164
<211> LENGTH: 16
<212> TYPE: PRT
<213> ORGANISM: Artificial Sequence
<220> FEATURE:
<223> OTHER INFORMATION: Penetratin fragment

<400> SEQUENCE: 164

Arg Gln Pro Lys Ile Trp Phe Pro Asn Arg Arg Met Pro Trp Lys Lys
1 5 10 15

<210> SEQ ID NO 165
<211> LENGTH: 16
<212> TYPE: PRT
<213> ORGANISM: Artificial Sequence
<220> FEATURE:
<223> OTHER INFORMATION: Penetratin fragment

<400> SEQUENCE: 165

Arg Gln Ile Lys Ile Trp Phe Gln Asn Met Arg Arg Lys Trp Lys Lys
1 5 10 15

<210> SEQ ID NO 166

<211> LENGTH: 16
<212> TYPE: PRT
<213> ORGANISM: Artificial Sequence
<220> FEATURE:
<223> OTHER INFORMATION: Penetratin fragment

<400> SEQUENCE: 166

Arg Gln Ile Arg Ile Trp Phe Gln Asn Arg Arg Met Arg Trp Arg Arg
1 5 10 15

<210> SEQ ID NO 167
<211> LENGTH: 16
<212> TYPE: PRT
<213> ORGANISM: Artificial Sequence
<220> FEATURE:
<223> OTHER INFORMATION: Penetratin fragment

<400> SEQUENCE: 167

Arg Arg Trp Arg Arg Trp Trp Arg Arg Trp Trp Arg Arg Trp Arg Arg
1 5 10 15

<210> SEQ ID NO 168
<211> LENGTH: 11
<212> TYPE: PRT
<213> ORGANISM: Artificial Sequence
<220> FEATURE:
<223> OTHER INFORMATION: HIV TAT fragment

<400> SEQUENCE: 168

Tyr Gly Arg Lys Lys Arg Arg Gln Arg Arg Arg
1 5 10

<210> SEQ ID NO 169
<211> LENGTH: 16
<212> TYPE: PRT
<213> ORGANISM: Artificial Sequence
<220> FEATURE:
<223> OTHER INFORMATION: Kaposi fibroblast growth factor fragment

<400> SEQUENCE: 169

Ala Ala Val Ala Leu Leu Pro Ala Val Leu Leu Ala Leu Leu Ala Pro
1 5 10 15

<210> SEQ ID NO 170
<211> LENGTH: 12
<212> TYPE: PRT
<213> ORGANISM: Artificial Sequence
<220> FEATURE:
<223> OTHER INFORMATION: Nuclear localization signal fragment

<400> SEQUENCE: 170

Thr Pro Pro Lys Lys Lys Arg Lys Val Glu Asp Pro
1 5 10

<210> SEQ ID NO 171
<211> LENGTH: 27
<212> TYPE: PRT
<213> ORGANISM: Artificial Sequence
<220> FEATURE:
<223> OTHER INFORMATION: transportan fragment

<400> SEQUENCE: 171

Gly Trp Thr Leu Asn Ser Ala Gly Tyr Leu Leu Gly Lys Ile Asn Leu
1 5 10 15

Lys Ala Leu Ala Ala Leu Ala Lys Lys Ile Leu
20 25

<210> SEQ ID NO 172
<211> LENGTH: 27
<212> TYPE: PRT
<213> ORGANISM: Artificial Sequence
<220> FEATURE:
<223> OTHER INFORMATION: MPG fragment

<400> SEQUENCE: 172

Gly Ala Leu Phe Leu Gly Phe Leu Gly Ala Ala Gly Ser Thr Met Gly
1 5 10 15

Ala Trp Ser Gln Pro Lys Ser Lys Arg Lys Val
20 25

<210> SEQ ID NO 173
<211> LENGTH: 808
<212> TYPE: PRT
<213> ORGANISM: Homo sapiens

<400> SEQUENCE: 173

Met Gly Ala Pro Ala Cys Ala Leu Ala Leu Cys Val Ala Val Ala Ile
1 5 10 15

Val Ala Gly Ala Ser Ser Glu Ser Leu Gly Thr Glu Gln Arg Val Val
20 25 30

Gly Arg Ala Ala Glu Val Pro Gly Pro Glu Pro Gly Gln Gln Glu Gln
35 40 45

Leu Val Phe Gly Ser Gly Asp Ala Val Glu Leu Ser Cys Pro Pro Pro
50 55 60

Gly Gly Gly Pro Met Gly Pro Thr Val Trp Val Lys Asp Gly Thr Gly
65 70 75 80

Leu Val Pro Ser Glu Arg Val Leu Val Gly Pro Gln Arg Leu Gln Val
85 90 95

Leu Asn Ala Ser His Glu Asp Ser Gly Ala Tyr Ser Cys Arg Gln Arg
100 105 110

Leu Thr Gln Arg Val Leu Cys His Phe Ser Val Arg Val Thr Asp Ala
115 120 125

Pro Ser Ser Gly Asp Asp Glu Asp Gly Glu Asp Glu Ala Glu Asp Thr
130 135 140

Gly Val Asp Thr Gly Ala Pro Tyr Trp Thr Arg Pro Glu Arg Met Asp
145 150 155 160

Lys Lys Leu Leu Ala Val Pro Ala Ala Asn Thr Val Arg Phe Arg Cys
165 170 175

Pro Ala Ala Gly Asn Pro Thr Pro Ser Ile Ser Trp Leu Lys Asn Gly
180 185 190

Arg Glu Phe Arg Gly Glu His Arg Ile Gly Gly Ile Lys Leu Arg His
195 200 205

Gln Gln Trp Ser Leu Val Met Glu Ser Val Val Pro Ser Asp Arg Gly
210 215 220

Asn Tyr Thr Cys Val Val Glu Asn Lys Phe Gly Ser Ile Arg Gln Thr
225 230 235 240

Tyr Thr Leu Asp Val Leu Glu Arg Ser Pro His Arg Pro Ile Leu Gln
245 250 255

Ala Gly Leu Pro Ala Asn Gln Thr Ala Val Leu Gly Ser Asp Val Glu
260 265 270

Phe His Cys Lys Val Tyr Ser Asp Ala Gln Pro His Ile Gln Trp Leu
275 280 285

Lys His Val Glu Val Asn Gly Ser Lys Val Gly Pro Asp Gly Thr Pro
290 295 300

-continued

```
Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
            340                 345                 350

Leu Ser Val His Gly Pro Arg Ala Ala Glu Glu Glu Leu Val Glu Ala
        355                 360                 365

Asp Glu Ala Gly Ser Val Tyr Ala Gly Ile Leu Ser Tyr Gly Val Gly
    370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
            420                 425                 430

Met Ser Ser Asn Thr Pro Leu Val Arg Ile Ala Arg Leu Ser Ser Gly
        435                 440                 445

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
            500                 505                 510

Lys Asp Asp Ala Thr Asp Lys Asp Leu Ser Asp Leu Val Ser Glu Met
        515                 520                 525

Glu Met Met Lys Met Ile Gly Lys His Lys Asn Ile Ile Asn Leu Leu
    530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
            580                 585                 590

Phe Lys Asp Leu Val Ser Cys Ala Tyr Gln Val Ala Arg Gly Met Glu
        595                 600                 605

Tyr Leu Ala Ser Gln Lys Cys Ile His Arg Asp Leu Ala Ala Arg Asn
    610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
            660                 665                 670

Tyr Thr His Gln Ser Asp Val Trp Ser Phe Gly Val Leu Leu Trp Glu
        675                 680                 685

Ile Phe Thr Leu Gly Gly Ser Pro Tyr Pro Gly Ile Pro Val Glu Glu
    690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735
```

```
Pro Ser Gln Arg Pro Thr Phe Lys Gln Leu Val Glu Asp Leu Asp Arg
            740                 745                 750

Val Leu Thr Val Thr Ser Thr Asp Glu Tyr Leu Asp Leu Ser Ala Pro
        755                 760                 765

Phe Glu Gln Tyr Ser Pro Gly Gly Gln Asp Thr Pro Ser Ser Ser Ser
    770                 775                 780

Ser Gly Asp Asp Ser Val Phe Ala His Asp Leu Leu Pro Pro Ala Pro
785                 790                 795                 800

Pro Ser Ser Gly Gly Ser Arg Thr
                805


<210> SEQ ID NO 174
<211> LENGTH: 806
<212> TYPE: PRT
<213> ORGANISM: Homo sapiens

<400> SEQUENCE: 174

Met Gly Ala Pro Ala Cys Ala Leu Ala Leu Cys Val Ala Val Ala Ile
 1               5                  10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
    50                  55                  60

Gly Gly Gly Pro Met Gly Pro Thr Val Trp Val Lys Asp Gly Thr Gly
65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
            100                 105                 110

Leu Thr Gln Arg Val Leu Cys His Phe Ser Val Arg Val Thr Asp Ala
        115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
            180                 185                 190

Arg Glu Phe Arg Gly Glu His Arg Ile Gly Gly Ile Lys Leu Arg His
        195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
            260                 265                 270

Phe His Cys Lys Val Tyr Ser Asp Ala Gln Pro His Ile Gln Trp Leu
        275                 280                 285

Lys His Val Glu Val Asn Gly Ser Lys Val Gly Pro Asp Gly Thr Pro
    290                 295                 300
```

```
Tyr Val Thr Val Leu Lys Thr Ala Gly Ala Asn Thr Thr Asp Lys Glu
305                 310                 315                 320

Leu Glu Val Leu Ser Leu His Asn Val Thr Phe Glu Asp Ala Gly Glu
                325                 330                 335

Tyr Thr Cys Leu Ala Gly Asn Ser Ile Gly Phe Ser His His Ser Ala
            340                 345                 350

Trp Leu Val Val Leu Pro Ala Glu Glu Glu Leu Val Glu Ala Asp Glu
        355                 360                 365

Ala Gly Ser Val Tyr Ala Gly Ile Leu Ser Tyr Gly Val Gly Phe Phe
    370                 375                 380

Leu Phe Ile Leu Val Val Ala Ala Val Thr Leu Cys Arg Leu Arg Ser
385                 390                 395                 400

Pro Pro Lys Lys Gly Leu Gly Ser Pro Thr Val His Lys Ile Ser Arg
                405                 410                 415

Phe Pro Leu Lys Arg Gln Val Ser Leu Glu Ser Asn Ala Ser Met Ser
            420                 425                 430

Ser Asn Thr Pro Leu Val Arg Ile Ala Arg Leu Ser Ser Gly Glu Gly
        435                 440                 445

Pro Thr Leu Ala Asn Val Ser Glu Leu Glu Leu Pro Ala Asp Pro Lys
    450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ala Ile Gly Ile Asp Lys
                485                 490                 495

Asp Arg Ala Ala Lys Pro Val Thr Val Ala Val Lys Met Leu Lys Asp
            500                 505                 510

Asp Ala Thr Asp Lys Asp Leu Ser Asp Leu Val Ser Glu Met Glu Met
        515                 520                 525

Met Lys Met Ile Gly Lys His Lys Asn Ile Ile Asn Leu Leu Gly Ala
    530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                565                 570                 575

Tyr Ser Phe Asp Thr Cys Lys Pro Pro Glu Glu Gln Leu Thr Phe Lys
            580                 585                 590

Asp Leu Val Ser Cys Ala Tyr Gln Val Ala Arg Gly Met Glu Tyr Leu
        595                 600                 605

Ala Ser Gln Lys Cys Ile His Arg Asp Leu Ala Ala Arg Asn Val Leu
    610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                645                 650                 655

Pro Val Lys Trp Met Ala Pro Glu Ala Leu Phe Asp Arg Val Tyr Thr
            660                 665                 670

His Gln Ser Asp Val Trp Ser Phe Gly Val Leu Leu Trp Glu Ile Phe
        675                 680                 685

Thr Leu Gly Gly Ser Pro Tyr Pro Gly Ile Pro Val Glu Glu Leu Phe
    690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
```

725 730 735

Gln Arg Pro Thr Phe Lys Gln Leu Val Glu Asp Leu Asp Arg Val Leu
740 745 750

Thr Val Thr Ser Thr Asp Glu Tyr Leu Asp Leu Ser Ala Pro Phe Glu
755 760 765

Gln Tyr Ser Pro Gly Gly Gln Asp Thr Pro Ser Ser Ser Ser Ser Gly
770 775 780

Asp Asp Ser Val Phe Ala His Asp Leu Leu Pro Pro Ala Pro Pro Ser
785 790 795 800

Ser Gly Gly Ser Arg Thr
805

<210> SEQ ID NO 175
<211> LENGTH: 694
<212> TYPE: PRT
<213> ORGANISM: Homo sapiens

<400> SEQUENCE: 175

Met Gly Ala Pro Ala Cys Ala Leu Ala Leu Cys Val Ala Val Ala Ile
1 5 10 15

Val Ala Gly Ala Ser Ser Glu Ser Leu Gly Thr Glu Gln Arg Val Val
20 25 30

Gly Arg Ala Ala Glu Val Pro Gly Pro Glu Pro Gly Gln Gln Glu Gln
35 40 45

Leu Val Phe Gly Ser Gly Asp Ala Val Glu Leu Ser Cys Pro Pro Pro
50 55 60

Gly Gly Gly Pro Met Gly Pro Thr Val Trp Val Lys Asp Gly Thr Gly
65 70 75 80

Leu Val Pro Ser Glu Arg Val Leu Val Gly Pro Gln Arg Leu Gln Val
85 90 95

Leu Asn Ala Ser His Glu Asp Ser Gly Ala Tyr Ser Cys Arg Gln Arg
100 105 110

Leu Thr Gln Arg Val Leu Cys His Phe Ser Val Arg Val Thr Asp Ala
115 120 125

Pro Ser Ser Gly Asp Asp Glu Asp Gly Glu Asp Glu Ala Glu Asp Thr
130 135 140

Gly Val Asp Thr Gly Ala Pro Tyr Trp Thr Arg Pro Glu Arg Met Asp
145 150 155 160

Lys Lys Leu Leu Ala Val Pro Ala Ala Asn Thr Val Arg Phe Arg Cys
165 170 175

Pro Ala Ala Gly Asn Pro Thr Pro Ser Ile Ser Trp Leu Lys Asn Gly
180 185 190

Arg Glu Phe Arg Gly Glu His Arg Ile Gly Gly Ile Lys Leu Arg His
195 200 205

Gln Gln Trp Ser Leu Val Met Glu Ser Val Val Pro Ser Asp Arg Gly
210 215 220

Asn Tyr Thr Cys Val Val Glu Asn Lys Phe Gly Ser Ile Arg Gln Thr
225 230 235 240

Tyr Thr Leu Asp Val Leu Glu Arg Ser Pro His Arg Pro Ile Leu Gln
245 250 255

Ala Gly Leu Pro Ala Asn Gln Thr Ala Val Leu Gly Ser Asp Val Glu
260 265 270

Phe His Cys Lys Val Tyr Ser Asp Ala Gln Pro His Ile Gln Trp Leu
275 280 285

Lys His Val Glu Val Asn Gly Ser Lys Val Gly Pro Asp Gly Thr Pro

```
    290                 295                 300

Tyr Val Thr Val Leu Lys Val Ser Leu Glu Ser Asn Ala Ser Met Ser
305                 310                 315                 320

Ser Asn Thr Pro Leu Val Arg Ile Ala Arg Leu Ser Ser Gly Glu Gly
                325                 330                 335

Pro Thr Leu Ala Asn Val Ser Glu Leu Glu Leu Pro Ala Asp Pro Lys
            340                 345                 350

Trp Glu Leu Ser Arg Ala Arg Leu Thr Leu Gly Lys Pro Leu Gly Glu
        355                 360                 365

Gly Cys Phe Gly Gln Val Val Met Ala Glu Ala Ile Gly Ile Asp Lys
    370                 375                 380

Asp Arg Ala Ala Lys Pro Val Thr Val Ala Val Lys Met Leu Lys Asp
385                 390                 395                 400

Asp Ala Thr Asp Lys Asp Leu Ser Asp Leu Val Ser Glu Met Glu Met
                405                 410                 415

Met Lys Met Ile Gly Lys His Lys Asn Ile Ile Asn Leu Leu Gly Ala
            420                 425                 430

Cys Thr Gln Gly Gly Pro Leu Tyr Val Leu Val Glu Tyr Ala Ala Lys
        435                 440                 445

Gly Asn Leu Arg Glu Phe Leu Arg Ala Arg Arg Pro Pro Gly Leu Asp
    450                 455                 460

Tyr Ser Phe Asp Thr Cys Lys Pro Pro Glu Glu Gln Leu Thr Phe Lys
465                 470                 475                 480

Asp Leu Val Ser Cys Ala Tyr Gln Val Ala Arg Gly Met Glu Tyr Leu
                485                 490                 495

Ala Ser Gln Lys Cys Ile His Arg Asp Leu Ala Ala Arg Asn Val Leu
            500                 505                 510

Val Thr Glu Asp Asn Val Met Lys Ile Ala Asp Phe Gly Leu Ala Arg
        515                 520                 525

Asp Val His Asn Leu Asp Tyr Tyr Lys Lys Thr Thr Asn Gly Arg Leu
    530                 535                 540

Pro Val Lys Trp Met Ala Pro Glu Ala Leu Phe Asp Arg Val Tyr Thr
545                 550                 555                 560

His Gln Ser Asp Val Trp Ser Phe Gly Val Leu Leu Trp Glu Ile Phe
                565                 570                 575

Thr Leu Gly Gly Ser Pro Tyr Pro Gly Ile Pro Val Glu Glu Leu Phe
            580                 585                 590

Lys Leu Leu Lys Glu Gly His Arg Met Asp Lys Pro Ala Asn Cys Thr
        595                 600                 605

His Asp Leu Tyr Met Ile Met Arg Glu Cys Trp His Ala Ala Pro Ser
    610                 615                 620

Gln Arg Pro Thr Phe Lys Gln Leu Val Glu Asp Leu Asp Arg Val Leu
625                 630                 635                 640

Thr Val Thr Ser Thr Asp Glu Tyr Leu Asp Leu Ser Ala Pro Phe Glu
                645                 650                 655

Gln Tyr Ser Pro Gly Gly Gln Asp Thr Pro Ser Ser Ser Ser Ser Gly
            660                 665                 670

Asp Asp Ser Val Phe Ala His Asp Leu Leu Pro Pro Ala Pro Pro Ser
        675                 680                 685

Ser Gly Gly Ser Arg Thr
    690
```

<210> SEQ ID NO 176
<211> LENGTH: 604

<212> TYPE: PRT
<213> ORGANISM: Homo sapiens

<400> SEQUENCE: 176

```
Ala Gln Arg Arg Lys Glu Arg Glu Glu Leu Ala Gln Gln Tyr Glu Ala
 1               5                  10                  15

Ile Leu Arg Glu Cys Gly His Gly Arg Phe Gln Trp Thr Leu Tyr Phe
            20                  25                  30

Val Leu Gly Leu Ala Leu Met Ala Asp Gly Val Glu Val Phe Val Val
        35                  40                  45

Gly Phe Val Leu Pro Ser Ala Glu Lys Asp Met Cys Leu Ser Asp Ser
    50                  55                  60

Asn Lys Gly Met Leu Gly Leu Ile Val Tyr Leu Gly Met Met Val Gly
65                  70                  75                  80

Ala Phe Leu Trp Gly Gly Leu Ala Asp Arg Leu Gly Arg Arg Gln Cys
                85                  90                  95

Leu Leu Ile Ser Leu Ser Val Asn Ser Val Phe Ala Phe Phe Ser Ser
            100                 105                 110

Phe Val Gln Gly Tyr Gly Thr Phe Leu Phe Cys Arg Leu Leu Ser Gly
        115                 120                 125

Val Gly Ile Gly Gly Ser Ile Pro Ile Val Phe Ser Tyr Phe Ser Glu
    130                 135                 140

Phe Leu Ala Gln Glu Lys Arg Gly Glu His Leu Ser Trp Leu Cys Met
145                 150                 155                 160

Phe Trp Met Ile Gly Gly Val Tyr Ala Ala Ala Met Ala Trp Ala Ile
                165                 170                 175

Ile Pro His Tyr Gly Trp Ser Phe Gln Met Gly Ser Ala Tyr Gln Phe
            180                 185                 190

His Ser Trp Arg Val Phe Val Leu Val Cys Ala Phe Pro Ser Val Phe
        195                 200                 205

Ala Ile Gly Ala Leu Thr Thr Gln Pro Glu Ser Pro Arg Phe Phe Leu
    210                 215                 220

Glu Asn Gly Lys His Asp Glu Ala Trp Met Val Leu Lys Gln Val His
225                 230                 235                 240

Asp Thr Asn Met Arg Ala Lys Gly His Pro Glu Arg Val Phe Ser Val
                245                 250                 255

Thr His Ile Lys Thr Ile His Gln Glu Asp Glu Leu Ile Glu Ile Gln
            260                 265                 270

Ser Asp Thr Gly Thr Trp Tyr Gln Arg Trp Gly Val Arg Ala Leu Ser
        275                 280                 285

Leu Gly Gly Gln Val Trp Gly Asn Phe Leu Ser Cys Phe Gly Pro Glu
    290                 295                 300

Tyr Arg Arg Ile Thr Leu Met Met Met Gly Val Trp Phe Thr Met Ser
305                 310                 315                 320

Phe Ser Tyr Tyr Gly Leu Thr Val Trp Phe Pro Asp Met Ile Arg His
                325                 330                 335

Leu Gln Ala Val Asp Tyr Ala Ser Arg Thr Lys Val Phe Pro Gly Glu
            340                 345                 350

Arg Val Glu His Val Thr Phe Asn Phe Thr Leu Glu Asn Gln Ile His
        355                 360                 365

Arg Gly Gly Gln Tyr Phe Asn Asp Lys Phe Ile Gly Leu Arg Leu Lys
    370                 375                 380

Ser Val Ser Phe Glu Asp Ser Leu Phe Glu Glu Cys Tyr Phe Glu Asp
385                 390                 395                 400
```

Val Thr Ser Ser Asn Thr Phe Phe Arg Asn Cys Thr Phe Ile Asn Thr
405 410 415

Val Phe Tyr Asn Thr Asp Leu Phe Glu Tyr Lys Phe Val Asn Ser Arg
420 425 430

Leu Ile Asn Ser Thr Phe Leu His Asn Lys Glu Gly Cys Pro Leu Asp
435 440 445

Val Thr Gly Thr Gly Glu Gly Ala Tyr Met Val Tyr Phe Val Ser Phe
450 455 460

Leu Gly Thr Leu Ala Val Leu Pro Gly Asn Ile Val Ser Ala Leu Leu
465 470 475 480

Met Asp Lys Ile Gly Arg Leu Arg Met Leu Ala Gly Ser Ser Val Met
485 490 495

Ser Cys Val Ser Cys Phe Phe Leu Ser Phe Gly Asn Ser Glu Ser Ala
500 505 510

Met Ile Ala Leu Leu Cys Leu Phe Gly Gly Val Ser Ile Ala Ser Trp
515 520 525

Asn Ala Leu Asp Val Leu Thr Val Glu Leu Tyr Pro Ser Asp Lys Arg
530 535 540

Thr Thr Ala Phe Gly Phe Leu Asn Ala Leu Cys Lys Leu Ala Ala Val
545 550 555 560

Leu Gly Ile Ser Ile Phe Thr Ser Phe Val Gly Ile Thr Lys Ala Ala
565 570 575

Pro Ile Leu Phe Ala Ser Ala Ala Leu Ala Leu Gly Ser Ser Leu Ala
580 585 590

Leu Lys Leu Pro Glu Thr Arg Gly Gln Val Leu Gln
595 600

<210> SEQ ID NO 177
<211> LENGTH: 683
<212> TYPE: PRT
<213> ORGANISM: Homo sapiens

<400> SEQUENCE: 177

Met Asp Asp Tyr Lys Tyr Gln Asp Asn Tyr Gly Gly Tyr Ala Pro Ser
1 5 10 15

Asp Gly Tyr Tyr Arg Gly Asn Glu Ser Asn Pro Glu Glu Asp Ala Gln
20 25 30

Ser Asp Val Thr Glu Gly His Asp Glu Glu Asp Glu Ile Tyr Glu Gly
35 40 45

Glu Tyr Gln Gly Ile Pro His Pro Asp Asp Val Lys Ala Lys Gln Ala
50 55 60

Lys Met Ala Pro Ser Arg Met Asp Ser Leu Arg Gly Gln Thr Asp Leu
65 70 75 80

Met Ala Glu Arg Leu Glu Asp Glu Glu Gln Leu Ala His Gln Tyr Glu
85 90 95

Thr Ile Met Asp Glu Cys Gly His Gly Arg Phe Gln Trp Ile Leu Phe
100 105 110

Phe Val Leu Gly Leu Ala Leu Met Ala Asp Gly Val Glu Val Phe Val
115 120 125

Val Ser Phe Ala Leu Pro Ser Ala Glu Lys Asp Met Cys Leu Ser Ser
130 135 140

Ser Lys Lys Gly Met Leu Gly Met Ile Val Tyr Leu Gly Met Met Ala
145 150 155 160

Gly Ala Phe Ile Leu Gly Gly Leu Ala Asp Lys Leu Gly Arg Lys Arg
165 170 175

-continued

```
Val Leu Ser Met Ser Leu Ala Val Asn Ala Ser Phe Ala Ser Leu Ser
            180                 185                 190

Ser Phe Val Gln Gly Tyr Gly Ala Phe Leu Phe Cys Arg Leu Ile Ser
        195                 200                 205

Gly Ile Gly Ile Gly Gly Ala Leu Pro Ile Val Phe Ala Tyr Phe Ser
    210                 215                 220

Glu Phe Leu Ser Arg Glu Lys Arg Gly Glu His Leu Ser Trp Leu Gly
225                 230                 235                 240

Ile Phe Trp Met Thr Gly Gly Leu Tyr Ala Ser Ala Met Ala Trp Ser
                245                 250                 255

Ile Ile Pro His Tyr Gly Trp Gly Phe Ser Met Gly Thr Asn Tyr His
            260                 265                 270

Phe His Ser Trp Arg Val Phe Val Ile Val Cys Ala Leu Pro Cys Thr
        275                 280                 285

Val Ser Met Val Ala Leu Lys Phe Met Pro Glu Ser Pro Arg Phe Leu
    290                 295                 300

Leu Glu Met Gly Lys His Asp Glu Ala Trp Met Ile Leu Lys Gln Val
305                 310                 315                 320

His Asp Thr Asn Met Arg Ala Lys Gly Thr Pro Glu Lys Val Phe Thr
                325                 330                 335

Val Ser Asn Ile Lys Thr Pro Lys Gln Met Asp Glu Phe Ile Glu Ile
            340                 345                 350

Gln Ser Ser Thr Gly Thr Trp Tyr Gln Arg Trp Leu Val Arg Phe Lys
        355                 360                 365

Thr Ile Phe Lys Gln Val Trp Asp Asn Ala Leu Tyr Cys Val Met Gly
    370                 375                 380

Pro Tyr Arg Met Asn Thr Leu Ile Leu Ala Val Val Trp Phe Ala Met
385                 390                 395                 400

Ala Phe Ser Tyr Tyr Gly Leu Thr Val Trp Phe Pro Asp Met Ile Arg
                405                 410                 415

Tyr Phe Gln Asp Glu Glu Tyr Lys Ser Lys Met Lys Val Phe Phe Gly
            420                 425                 430

Glu His Val Tyr Gly Ala Thr Ile Asn Phe Thr Met Glu Asn Gln Ile
        435                 440                 445

His Gln His Gly Lys Leu Val Asn Asp Lys Phe Thr Arg Met Tyr Phe
    450                 455                 460

Lys His Val Leu Phe Glu Asp Thr Phe Phe Asp Glu Cys Tyr Phe Glu
465                 470                 475                 480

Asp Val Thr Ser Thr Asp Thr Tyr Phe Lys Asn Cys Thr Ile Glu Ser
                485                 490                 495

Thr Ile Phe Tyr Asn Thr Asp Leu Tyr Glu His Lys Phe Ile Asn Cys
            500                 505                 510

Arg Phe Ile Asn Ser Thr Phe Leu Glu Gln Lys Glu Gly Cys His Met
        515                 520                 525

Asp Leu Glu Gln Asp Asn Asp Phe Leu Ile Tyr Leu Val Ser Phe Leu
    530                 535                 540

Gly Ser Leu Ser Val Leu Pro Gly Asn Ile Ile Ser Ala Leu Leu Met
545                 550                 555                 560

Asp Arg Ile Gly Arg Leu Lys Met Ile Gly Gly Ser Met Leu Ile Ser
                565                 570                 575

Ala Val Cys Cys Phe Phe Leu Phe Phe Gly Asn Ser Glu Ser Ala Met
            580                 585                 590

Ile Gly Trp Gln Cys Leu Phe Cys Gly Thr Ser Ile Ala Ala Trp Asn
        595                 600                 605
```

```
Ala Leu Asp Val Ile Thr Val Glu Leu Tyr Pro Thr Asn Gln Arg Ala
    610                 615                 620

Thr Ala Phe Gly Ile Leu Asn Gly Leu Cys Lys Phe Gly Ala Ile Leu
625                 630                 635                 640

Gly Asn Thr Ile Phe Ala Ser Phe Val Gly Ile Thr Lys Val Val Pro
                645                 650                 655

Ile Leu Leu Ala Ala Ala Ser Leu Val Gly Gly Gly Leu Ile Ala Leu
            660                 665                 670

Arg Leu Pro Glu Thr Arg Glu Gln Val Leu Ile
        675                 680


<210> SEQ ID NO 178
<211> LENGTH: 727
<212> TYPE: PRT
<213> ORGANISM: Homo sapiens

<400> SEQUENCE: 178

Met Glu Asp Ser Tyr Lys Asp Arg Thr Ser Leu Met Lys Gly Ala Lys
 1               5                  10                  15

Asp Ile Ala Arg Glu Val Lys Lys Gln Thr Val Lys Lys Val Asn Gln
            20                  25                  30

Ala Val Asp Arg Ala Gln Asp Glu Tyr Thr Gln Arg Ser Tyr Ser Arg
        35                  40                  45

Phe Gln Asp Glu Glu Asp Asp Asp Asp Tyr Tyr Pro Ala Gly Glu Thr
    50                  55                  60

Tyr Asn Gly Glu Ala Asn Asp Asp Glu Gly Ser Ser Glu Ala Thr Glu
65                  70                  75                  80

Gly His Asp Glu Asp Asp Glu Ile Tyr Glu Gly Glu Tyr Gln Gly Ile
                85                  90                  95

Pro Ser Met Asn Gln Ala Lys Asp Ser Ile Val Ser Val Gly Gln Pro
            100                 105                 110

Lys Gly Asp Glu Tyr Lys Asp Arg Arg Glu Leu Glu Ser Glu Arg Arg
        115                 120                 125

Ala Asp Glu Glu Glu Leu Ala Gln Gln Tyr Glu Leu Ile Ile Gln Glu
    130                 135                 140

Cys Gly His Gly Arg Phe Gln Trp Ala Leu Phe Phe Val Leu Gly Met
145                 150                 155                 160

Ala Leu Met Ala Asp Gly Val Glu Val Phe Val Val Gly Phe Val Leu
                165                 170                 175

Pro Ser Ala Glu Thr Asp Leu Cys Ile Pro Asn Ser Gly Ser Gly Trp
            180                 185                 190

Leu Gly Ser Ile Val Tyr Leu Gly Met Met Val Gly Ala Phe Phe Trp
        195                 200                 205

Gly Gly Leu Ala Asp Lys Val Gly Arg Lys Gln Ser Leu Leu Ile Cys
    210                 215                 220

Met Ser Val Asn Gly Phe Phe Ala Phe Leu Ser Ser Phe Val Gln Gly
225                 230                 235                 240

Tyr Gly Phe Phe Leu Phe Cys Arg Leu Leu Ser Gly Phe Gly Ile Gly
                245                 250                 255

Gly Ala Ile Pro Thr Val Phe Ser Tyr Phe Ala Glu Val Leu Ala Arg
            260                 265                 270

Glu Lys Arg Gly Glu His Leu Ser Trp Leu Cys Met Phe Trp Met Ile
        275                 280                 285

Gly Gly Ile Tyr Ala Ser Ala Met Ala Trp Ala Ile Ile Pro His Tyr
    290                 295                 300
```

```
Gly Trp Ser Phe Ser Met Gly Ser Ala Tyr Gln Phe His Ser Trp Arg
305                 310                 315                 320

Val Phe Val Ile Val Cys Ala Leu Pro Cys Val Ser Ser Val Val Ala
                325                 330                 335

Leu Thr Phe Met Pro Glu Ser Pro Arg Phe Leu Leu Glu Val Gly Lys
            340                 345                 350

His Asp Glu Ala Trp Met Ile Leu Lys Leu Ile His Asp Thr Asn Met
        355                 360                 365

Arg Ala Arg Gly Gln Pro Glu Lys Val Phe Thr Val Asn Lys Ile Lys
    370                 375                 380

Thr Pro Lys Gln Ile Asp Glu Leu Ile Glu Ile Glu Ser Asp Thr Gly
385                 390                 395                 400

Thr Trp Tyr Arg Arg Cys Phe Val Arg Ile Arg Thr Glu Leu Tyr Gly
                405                 410                 415

Ile Trp Leu Thr Phe Met Arg Cys Phe Asn Tyr Pro Val Arg Asp Asn
            420                 425                 430

Thr Ile Lys Leu Thr Ile Val Trp Phe Thr Leu Ser Phe Gly Tyr Tyr
        435                 440                 445

Gly Leu Ser Val Trp Phe Pro Asp Val Ile Lys Pro Leu Gln Ser Asp
    450                 455                 460

Glu Tyr Ala Leu Leu Thr Arg Asn Val Glu Arg Asp Lys Tyr Ala Asn
465                 470                 475                 480

Phe Thr Ile Asn Phe Thr Met Glu Asn Gln Ile His Thr Gly Met Glu
                485                 490                 495

Tyr Asp Asn Gly Arg Phe Ile Gly Val Lys Phe Lys Ser Val Thr Phe
            500                 505                 510

Lys Asp Ser Val Phe Lys Ser Cys Thr Phe Glu Asp Val Thr Ser Val
        515                 520                 525

Asn Thr Tyr Phe Lys Asn Cys Thr Phe Ile Asp Thr Val Phe Asp Asn
    530                 535                 540

Thr Asp Phe Glu Pro Tyr Lys Phe Ile Asp Ser Glu Phe Lys Asn Cys
545                 550                 555                 560

Ser Phe Phe His Asn Lys Thr Gly Cys Gln Ile Thr Phe Asp Asp Asp
                565                 570                 575

Tyr Ser Ala Tyr Trp Ile Tyr Phe Val Asn Phe Leu Gly Thr Leu Ala
            580                 585                 590

Val Leu Pro Gly Asn Ile Val Ser Ala Leu Leu Met Asp Arg Ile Gly
        595                 600                 605

Arg Leu Thr Met Leu Gly Gly Ser Met Val Leu Ser Gly Ile Ser Cys
    610                 615                 620

Phe Phe Leu Trp Phe Gly Thr Ser Glu Ser Met Met Ile Gly Met Leu
625                 630                 635                 640

Cys Leu Tyr Asn Gly Leu Thr Ile Ser Ala Trp Asn Ser Leu Asp Val
                645                 650                 655

Val Thr Val Glu Leu Tyr Pro Thr Asp Arg Arg Ala Thr Gly Phe Gly
            660                 665                 670

Phe Leu Asn Ala Leu Cys Lys Ala Ala Ala Val Leu Gly Asn Leu Ile
        675                 680                 685

Phe Gly Ser Leu Val Ser Ile Thr Lys Ser Ile Pro Ile Leu Leu Ala
    690                 695                 700

Ser Thr Val Leu Val Cys Gly Gly Leu Val Gly Leu Cys Leu Pro Asp
705                 710                 715                 720

Thr Arg Thr Gln Val Leu Met
```

725

<210> SEQ ID NO 179
<211> LENGTH: 742
<212> TYPE: PRT
<213> ORGANISM: Homo sapiens

<400> SEQUENCE: 179

Met Glu Glu Gly Phe Arg Asp Arg Ala Ala Phe Ile Arg Gly Ala Lys
1 5 10 15

Asp Ile Ala Lys Glu Val Lys Lys His Ala Ala Lys Lys Val Val Lys
20 25 30

Gly Leu Asp Arg Val Gln Asp Glu Tyr Ser Arg Arg Ser Tyr Ser Arg
35 40 45

Phe Glu Glu Glu Asp Asp Asp Asp Asp Phe Pro Ala Pro Ser Asp Gly
50 55 60

Tyr Tyr Arg Gly Glu Gly Thr Gln Asp Glu Glu Glu Gly Gly Ala Ser
65 70 75 80

Ser Asp Ala Thr Glu Gly His Asp Glu Asp Asp Glu Ile Tyr Glu Gly
85 90 95

Glu Tyr Gln Asp Ile Pro Arg Ala Glu Ser Gly Gly Lys Gly Glu Arg
100 105 110

Met Ala Asp Gly Ala Pro Leu Ala Gly Val Arg Gly Gly Leu Ser Asp
115 120 125

Gly Glu Gly Pro Pro Gly Gly Arg Gly Glu Ala Gln Arg Arg Lys Glu
130 135 140

Arg Glu Glu Leu Ala Gln Gln Tyr Glu Ala Ile Leu Arg Glu Cys Gly
145 150 155 160

His Gly Arg Phe Gln Trp Thr Leu Tyr Phe Val Leu Gly Leu Ala Leu
165 170 175

Met Ala Asp Gly Val Glu Val Phe Val Val Gly Phe Val Leu Pro Ser
180 185 190

Ala Glu Lys Asp Met Cys Leu Ser Asp Ser Asn Lys Gly Met Leu Gly
195 200 205

Leu Ile Val Tyr Leu Gly Met Met Val Gly Ala Phe Leu Trp Gly Gly
210 215 220

Leu Ala Asp Arg Leu Gly Arg Arg Gln Cys Leu Leu Ile Ser Leu Ser
225 230 235 240

Val Asn Ser Val Phe Ala Phe Phe Ser Ser Phe Val Gln Gly Tyr Gly
245 250 255

Thr Phe Leu Phe Cys Arg Leu Leu Ser Gly Val Gly Ile Gly Gly Ser
260 265 270

Ile Pro Ile Val Phe Ser Tyr Phe Ser Glu Phe Leu Ala Gln Glu Lys
275 280 285

Arg Gly Glu His Leu Ser Trp Leu Cys Met Phe Trp Met Ile Gly Gly
290 295 300

Val Tyr Ala Ala Ala Met Ala Trp Ala Ile Ile Pro His Tyr Gly Trp
305 310 315 320

Ser Phe Gln Met Gly Ser Ala Tyr Gln Phe His Ser Trp Arg Val Phe
325 330 335

Val Leu Val Cys Ala Phe Pro Ser Val Phe Ala Ile Gly Ala Leu Thr
340 345 350

Thr Gln Pro Glu Ser Pro Arg Phe Phe Leu Glu Asn Gly Lys His Asp
355 360 365

Glu Ala Trp Met Val Leu Lys Gln Val His Asp Thr Asn Met Arg Ala

```
    370                 375                 380

Lys Gly His Pro Glu Arg Val Phe Ser Val Thr His Ile Lys Thr Ile
385                 390                 395                 400

His Gln Glu Asp Glu Leu Ile Glu Ile Gln Ser Asp Thr Gly Thr Trp
                405                 410                 415

Tyr Gln Arg Trp Gly Val Arg Ala Leu Ser Leu Gly Gly Gln Val Trp
            420                 425                 430

Gly Asn Phe Leu Ser Cys Phe Gly Pro Glu Tyr Arg Arg Ile Thr Leu
        435                 440                 445

Met Met Met Gly Val Trp Phe Thr Met Ser Phe Ser Tyr Tyr Gly Leu
    450                 455                 460

Thr Val Trp Phe Pro Asp Met Ile Arg His Leu Gln Ala Val Asp Tyr
465                 470                 475                 480

Ala Ser Arg Thr Lys Val Phe Pro Gly Glu Arg Val Gly His Val Thr
                485                 490                 495

Phe Asn Phe Thr Leu Glu Asn Gln Ile His Arg Gly Gly Gln Tyr Phe
            500                 505                 510

Asn Asp Lys Phe Ile Gly Leu Arg Leu Lys Ser Val Ser Phe Glu Asp
        515                 520                 525

Ser Leu Phe Glu Glu Cys Tyr Phe Glu Asp Val Thr Ser Ser Asn Thr
    530                 535                 540

Phe Phe Arg Asn Cys Thr Phe Ile Asn Thr Val Phe Tyr Asn Thr Asp
545                 550                 555                 560

Leu Phe Glu Tyr Lys Phe Val Asn Ser Arg Leu Ile Asn Ser Thr Phe
                565                 570                 575

Leu His Asn Lys Glu Gly Cys Pro Leu Asp Val Thr Gly Thr Gly Glu
            580                 585                 590

Gly Ala Tyr Met Val Tyr Phe Val Ser Phe Leu Gly Thr Leu Ala Val
        595                 600                 605

Leu Pro Gly Asn Ile Val Ser Ala Leu Leu Met Asp Lys Ile Gly Arg
    610                 615                 620

Leu Arg Met Leu Ala Gly Ser Ser Val Met Ser Cys Val Ser Cys Phe
625                 630                 635                 640

Phe Leu Ser Phe Gly Asn Ser Glu Ser Ala Met Ile Ala Leu Leu Cys
                645                 650                 655

Leu Phe Gly Gly Val Ser Ile Ala Ser Trp Asn Ala Leu Asp Val Leu
            660                 665                 670

Thr Val Glu Leu Tyr Pro Ser Asp Lys Arg Thr Thr Ala Phe Gly Phe
        675                 680                 685

Leu Asn Ala Leu Cys Lys Leu Ala Ala Val Leu Gly Ile Ser Ile Phe
    690                 695                 700

Thr Ser Phe Val Gly Ile Thr Lys Ala Ala Pro Ile Leu Phe Ala Ser
705                 710                 715                 720

Ala Ala Leu Ala Leu Gly Ser Ser Leu Ala Leu Lys Leu Pro Glu Thr
                725                 730                 735

Arg Gly Gln Val Leu Gln
            740


<210> SEQ ID NO 180
<211> LENGTH: 422
<212> TYPE: PRT
<213> ORGANISM: Homo sapiens

<400> SEQUENCE: 180

Met Val Ser Glu Ser His His Glu Ala Leu Ala Ala Pro Pro Val Thr
```

-continued

```
1               5                   10                  15

Thr Val Ala Thr Val Leu Pro Ser Asn Ala Thr Glu Pro Ala Ser Pro
            20                  25                  30

Gly Glu Gly Lys Glu Asp Ala Phe Ser Lys Leu Lys Glu Lys Phe Met
        35                  40                  45

Asn Glu Leu His Lys Ile Pro Leu Pro Pro Trp Ala Leu Ile Ala Ile
    50                  55                  60

Ala Ile Val Ala Val Leu Leu Val Leu Thr Cys Cys Phe Cys Ile Cys
65                  70                  75                  80

Lys Lys Cys Leu Phe Lys Lys Lys Asn Lys Lys Lys Gly Lys Glu Lys
                85                  90                  95

Gly Gly Lys Asn Ala Ile Asn Met Lys Asp Val Lys Asp Leu Gly Lys
            100                 105                 110

Thr Met Lys Asp Gln Ala Leu Lys Asp Asp Asp Ala Glu Thr Gly Leu
        115                 120                 125

Thr Asp Gly Glu Glu Lys Glu Glu Pro Lys Glu Glu Glu Lys Leu Gly
    130                 135                 140

Lys Leu Gln Tyr Ser Leu Asp Tyr Asp Phe Gln Asn Asn Gln Leu Leu
145                 150                 155                 160

Val Gly Ile Ile Gln Ala Ala Glu Leu Pro Ala Leu Asp Met Gly Gly
                165                 170                 175

Thr Ser Asp Pro Tyr Val Lys Val Phe Leu Leu Pro Asp Lys Lys Lys
            180                 185                 190

Lys Phe Glu Thr Lys Val His Arg Lys Thr Leu Asn Pro Val Phe Asn
        195                 200                 205

Glu Gln Phe Thr Phe Lys Val Pro Tyr Ser Glu Leu Gly Gly Lys Thr
    210                 215                 220

Leu Val Met Ala Val Tyr Asp Phe Asp Arg Phe Ser Lys His Asp Ile
225                 230                 235                 240

Ile Gly Glu Phe Lys Val Pro Met Asn Thr Val Asp Phe Gly His Val
                245                 250                 255

Thr Glu Glu Trp Arg Asp Leu Gln Ser Ala Glu Lys Glu Glu Gln Glu
            260                 265                 270

Lys Leu Gly Asp Ile Cys Phe Ser Leu Arg Tyr Val Pro Thr Ala Gly
        275                 280                 285

Lys Leu Thr Val Val Ile Leu Glu Ala Lys Asn Leu Lys Lys Met Asp
    290                 295                 300

Val Gly Gly Leu Ser Asp Pro Tyr Val Lys Ile His Leu Met Gln Asn
305                 310                 315                 320

Gly Lys Arg Leu Lys Lys Lys Lys Thr Thr Ile Lys Lys Asn Thr Leu
                325                 330                 335

Asn Pro Tyr Tyr Asn Glu Ser Phe Ser Phe Glu Val Pro Phe Glu Gln
            340                 345                 350

Ile Gln Lys Val Gln Val Val Val Thr Val Leu Asp Tyr Asp Lys Ile
        355                 360                 365

Gly Lys Asn Asp Ala Ile Gly Lys Val Phe Val Gly Tyr Asn Ser Thr
    370                 375                 380

Gly Ala Glu Leu Arg His Trp Ser Asp Met Leu Ala Asn Pro Arg Arg
385                 390                 395                 400

Pro Ile Ala Gln Trp His Thr Leu Gln Val Glu Glu Glu Val Asp Ala
                405                 410                 415

Met Leu Ala Val Lys Lys
            420
```

<210> SEQ ID NO 181
<211> LENGTH: 419
<212> TYPE: PRT
<213> ORGANISM: Homo sapiens

<400> SEQUENCE: 181

```
Met Arg Asn Ile Phe Lys Arg Asn Gln Glu Pro Ile Val Ala Pro Ala
 1               5                  10                  15

Thr Thr Thr Ala Thr Met Pro Ile Gly Pro Val Asp Asn Ser Thr Glu
            20                  25                  30

Ser Gly Gly Ala Gly Glu Ser Gln Glu Asp Met Phe Ala Lys Leu Lys
        35                  40                  45

Glu Lys Leu Phe Asn Glu Ile Asn Lys Ile Pro Leu Pro Pro Trp Ala
    50                  55                  60

Leu Ile Ala Ile Ala Val Val Ala Gly Leu Leu Leu Leu Thr Cys Cys
65                  70                  75                  80

Phe Cys Ile Cys Lys Lys Cys Cys Cys Lys Lys Lys Lys Asn Lys Lys
                85                  90                  95

Glu Lys Gly Lys Gly Met Lys Asn Ala Met Asn Met Lys Asp Met Lys
            100                 105                 110

Gly Gly Gln Asp Asp Asp Asp Ala Glu Thr Gly Leu Thr Glu Gly Glu
        115                 120                 125

Gly Glu Gly Glu Glu Glu Lys Glu Pro Glu Asn Leu Gly Lys Leu Gln
    130                 135                 140

Phe Ser Leu Asp Tyr Asp Phe Gln Ala Asn Gln Leu Thr Val Gly Val
145                 150                 155                 160

Leu Gln Ala Ala Glu Leu Pro Ala Leu Asp Met Gly Gly Thr Ser Asp
                165                 170                 175

Pro Tyr Val Lys Val Phe Leu Leu Pro Asp Lys Lys Lys Lys Tyr Glu
            180                 185                 190

Thr Lys Val His Arg Lys Thr Leu Asn Pro Ala Phe Asn Glu Thr Phe
        195                 200                 205

Thr Phe Lys Val Pro Tyr Gln Glu Leu Gly Gly Lys Thr Leu Val Met
    210                 215                 220

Ala Ile Tyr Asp Phe Asp Arg Phe Ser Lys His Asp Ile Ile Gly Glu
225                 230                 235                 240

Val Lys Val Pro Met Asn Thr Val Asp Leu Gly Gln Pro Ile Glu Glu
                245                 250                 255

Trp Arg Asp Leu Gln Gly Gly Glu Lys Glu Glu Pro Glu Lys Leu Gly
            260                 265                 270

Asp Ile Cys Thr Ser Leu Arg Tyr Val Pro Thr Ala Gly Lys Leu Thr
        275                 280                 285

Val Cys Ile Leu Glu Ala Lys Asn Leu Lys Lys Met Asp Val Gly Gly
    290                 295                 300

Leu Ser Asp Pro Tyr Gly Lys Ile His Leu Met Gln Asn Gly Lys Arg
305                 310                 315                 320

Leu Lys Lys Lys Lys Thr Thr Val Lys Lys Lys Thr Leu Asn Pro Tyr
                325                 330                 335

Phe Asn Glu Ser Phe Ser Phe Glu Ile Pro Phe Glu Gln Ile Gln Lys
            340                 345                 350

Val Gln Val Val Val Thr Val Leu Asp Tyr Asp Lys Leu Gly Lys Asn
        355                 360                 365

Glu Ala Ile Gly Lys Ile Phe Val Gly Ser Asn Ala Thr Gly Thr Glu
    370                 375                 380
```

Leu Arg His Trp Ser Asp Met Leu Ala Asn Pro Arg Arg Pro Ile Ala
385 390 395 400

Gln Trp His Ser Leu Lys Pro Glu Glu Glu Val Asp Ala Leu Leu Gly
405 410 415

Lys Asn Lys

<210> SEQ ID NO 182
<211> LENGTH: 6
<212> TYPE: PRT
<213> ORGANISM: Artificial Sequence
<220> FEATURE:
<221> NAME/KEY: PEPTIDE
<222> LOCATION: (1)...(6)
<223> OTHER INFORMATION: tetracysteine hexapeptide
<220> FEATURE:
<221> NAME/KEY: VARIANT
<222> LOCATION: (4)...(5)
<223> OTHER INFORMATION: Xaa is any amino acid

<400> SEQUENCE: 182

Cys Cys Xaa Xaa Cys Cys
1 5

<210> SEQ ID NO 183
<211> LENGTH: 182
<212> TYPE: PRT
<213> ORGANISM: Homo sapiens

<400> SEQUENCE: 183

Met Asp Lys Asp Cys Glu Met Lys Arg Thr Thr Leu Asp Ser Pro Leu
1 5 10 15

Gly Lys Leu Glu Leu Ser Gly Cys Glu Gln Gly Leu His Glu Ile Lys
20 25 30

Leu Leu Gly Lys Gly Thr Ser Ala Ala Asp Ala Val Glu Val Pro Ala
35 40 45

Pro Ala Ala Val Leu Gly Gly Pro Glu Pro Leu Met Gln Ala Thr Ala
50 55 60

Trp Leu Asn Ala Tyr Phe His Gln Pro Glu Ala Ile Glu Glu Phe Pro
65 70 75 80

Val Pro Ala Leu His His Pro Val Phe Gln Gln Glu Ser Phe Thr Arg
85 90 95

Gln Val Leu Trp Lys Leu Leu Lys Val Val Lys Phe Gly Glu Val Ile
100 105 110

Ser Tyr Gln Gln Leu Ala Ala Leu Ala Gly Asn Pro Ala Ala Thr Ala
115 120 125

Ala Val Lys Thr Ala Leu Ser Gly Asn Pro Val Pro Ile Leu Ile Pro
130 135 140

Cys His Arg Val Val Ser Ser Ser Gly Ala Val Gly Gly Tyr Glu Gly
145 150 155 160

Gly Leu Ala Val Lys Glu Trp Leu Leu Ala His Glu Gly His Arg Leu
165 170 175

Gly Lys Pro Gly Leu Gly
180

<210> SEQ ID NO 184
<211> LENGTH: 296
<212> TYPE: PRT
<213> ORGANISM: Rhodococcus rhodochrous

<400> SEQUENCE: 184

Met Gly Ser Glu Ile Gly Thr Gly Phe Pro Phe Asp Pro His Tyr Val

-continued

```
1               5                   10                  15

Glu Val Leu Gly Glu Arg Met His Tyr Val Asp Val Gly Pro Arg Asp
            20                  25                  30

Gly Thr Pro Val Leu Phe Leu His Gly Asn Pro Thr Ser Ser Tyr Leu
        35                  40                  45

Trp Arg Asn Ile Ile Pro His Val Ala Pro Ser His Arg Cys Ile Ala
    50                  55                  60

Pro Asp Leu Ile Gly Met Gly Lys Ser Asp Lys Pro Asp Leu Asp Tyr
65                  70                  75                  80

Phe Phe Asp Asp His Val Arg Tyr Leu Asp Ala Phe Ile Glu Ala Leu
                85                  90                  95

Gly Leu Glu Glu Val Val Leu Val Ile His Asp Trp Gly Ser Ala Leu
            100                 105                 110

Gly Phe His Trp Ala Lys Arg Asn Pro Glu Arg Val Lys Gly Ile Ala
        115                 120                 125

Cys Met Glu Phe Ile Arg Pro Ile Pro Thr Trp Asp Glu Trp Pro Glu
    130                 135                 140

Phe Ala Arg Glu Thr Phe Gln Ala Phe Arg Thr Ala Asp Val Gly Arg
145                 150                 155                 160

Glu Leu Ile Ile Asp Gln Asn Ala Phe Ile Glu Gly Ala Leu Pro Met
                165                 170                 175

Gly Val Val Arg Pro Leu Thr Glu Val Glu Met Asp His Tyr Arg Glu
            180                 185                 190

Pro Phe Leu Lys Pro Val Asp Arg Glu Pro Leu Trp Arg Phe Pro Asn
        195                 200                 205

Glu Leu Pro Ile Ala Gly Glu Pro Ala Asn Ile Val Ala Leu Val Glu
    210                 215                 220

Ala Tyr Met Asn Trp Leu His Gln Ser Pro Val Pro Lys Leu Leu Phe
225                 230                 235                 240

Trp Gly Thr Pro Gly Val Leu Ile Pro Pro Ala Glu Ala Ala Arg Leu
                245                 250                 255

Ala Glu Ser Leu Pro Asn Cys Lys Thr Val Asp Ile Gly Pro Gly Leu
            260                 265                 270

Phe Leu Leu Gln Glu Asp Asn Pro Asp Leu Ile Gly Ser Glu Ile Ala
        275                 280                 285

Arg Trp Leu Pro Gly Leu Ala Gly
    290                 295
```

LIPOPHILIC DYE-BASED FRET ASSAYS FOR CLOSTRIDAL TOXIN ACTIVITY

This is a national stage application under 35 U.S.C. §371 of PCT patent application PCT/US2006/012426, filed on Apr. 4, 2006 which claims the benefit of priority pursuant to 35 U.S.C. §119(e) to U.S. provisional patent application Ser. No. 60/668,942 filed on Apr. 5, 2005, each of which is hereby incorporated by reference in its entirety.

All of the publications cited in this application are hereby incorporated by reference in their entirety. All GeneBank sequence listings cited this application, as identified by their GenBank accession numbers, are available from the National Center for Biotechnological Information and are all hereby incorporated by reference in their entirety.

The myorelaxant properties of Clostridial toxins (CoNTs) are being exploited in a wide variety of therapeutic and cosmetic applications, see e.g., William J. Lipham, Cosmetic and Clinical Applications of Botulinum Toxin (Slack, Inc., 2004). For example, CoNTs therapies are proposed for treating dystonia, see e.g., Kei Roger Aoki, et al., Method for treating Dystonia with Botulinum Toxin C to G, U.S. Pat. No. 6,319,505 (Nov. 20, 2001); pain, see e.g., Kei Roger Aoki, et al., Method for Treating Pain by Peripheral Administration of a Neurotoxin, U.S. Pat. No. 6,464,986 (Oct. 15, 2002); muscle injuries, see e.g., Gregory F. Brooks, Methods for Treating Muscle Injuries, U.S. Pat. No. 6,423,319 (Jul. 23, 2002); cardiovascular diseases, see e.g., Gregory F. Brooks, Methods for Treating Cardiovascular Diseases with Botulinum Toxins, U.S. Patent Publication No. 2003/0185860 (Oct. 2, 2003); neuropsychiatric disorders, see e.g., Steven Donovan, Therapeutic Treatments for Neuropsychiatric Disorders, U.S. Patent Publication No. 2003/0211121 (Nov. 13, 2003); lower back pain, see e.g., Kei Roger Aoki, et al., Botulinum Toxin Therapy for Lower Back Pain, U.S. Patent Publication No. 2004/0037852 (Feb. 26, 2004); as well as other neuromuscular disorders, see e.g., Kei Roger Aoki, et al., Multiple Botulinum Toxins for Treating Neuromuscular Disorders and Conditions, U.S. Patent Publication No. 2001/0021695 (Sep. 13, 2001); Kei Roger Aoki, et al., Treatment of Neuromuscular Disorders and Conditions with Different Botulinum, U.S. Patent Publication No. 2002/0010138 (Jan. 24, 2002); Kei Roger Aoki, et al., Use of Botulinum Toxins for Treating Various Disorders and Conditions and Associated Pain, U.S. Patent Publication No. 2004/0013692 (Jan. 22, 2004) all of which are hereby incorporated by reference. Additional proposed uses of CoNTs as biopharmaceutical neuromodulators has expanded to cover a wide variety of treatments targeting certain disorders that lack a neuromuscular basis. For example, the effects on the autonomic nervous system has allowed the development of a Botulinum toxin serotype A (BoNT/A) therapy for treating axillary hyperhydrosis or sweating, and reports indicate BoNT/A may be an effective treatment for myofascial pain and tension, stroke, traumatic brain injury, cerebral palsy, gastrointestinal motility disorders, urinary incontinence cancer and migraine headaches. Lastly, cosmetic and other therapeutic applications are widely known. In fact, the expected use of CoNTs in both therapeutic and cosmetic treatments of humans is anticipated to expand to an ever widening range of diseases and aliments that can benefit from the myorelaxant properties of these toxins.

The growing clinical and therapeutic use of Clostridial toxins necessitates the pharmaceutical industry to use accurate assays for Clostridial toxin activity in order to, for example, ensure accurate pharmaceutical formulations and monitor established quality control standards. In addition, given the potential danger associated with small quantities of Clostridial toxins in foodstuffs, the food industry requires Clostridial toxin assays, for example, to validate new food packaging methods and to ensure food safety. The present invention provides novel Clostridial toxin assays for determining the presence or activity of a Clostridial toxin useful for various industries, such as, e.g., the pharmaceutical and food industries, and provides related advantages as well.

BRIEF DESCRIPTION OF THE DRAWINGS

FIG. 1 shows a schematic of a lipophilic dye-based FRET assay which relies on cell lines containing a Clostridial toxin substrate and a lipophilic dye which are incorporated into the cell membrane.

FIG. 3 shows a schematic of SNARE proteins.

FIG. 7 shows Western blot analysis identifying cells with high affinity uptake for a Clostridial toxin.

FIG. 8 shows Western blot analysis identifying cells with high affinity uptake for a Clostridial toxin.

FIG. 9 shows Western blot analysis evaluating the effects of treatments used to increase uptake of a Clostridial toxin.

FIG. 10 shows Western blot analysis evaluating the effects of treatments used to increase uptake of a Clostridial toxin.

FIG. 12 shows the effect of BoNT/A treatment on FRET between SNAP$25_{206}$-GFP and a lipophilic dye localized to the membrane of Neuro-2A cells.

FIG. 15 shows the dose response of differentiated Neuro-2A cells expressing SNAP$25_{206}$-GFP treated with BoNT/A at doses ranging from 0.05 nM to 20 nM and measured in the lipophilic dye-based FRET assay.

FIG. 17 shows the dose response of Neuro-2A cells expressing SNAP$25_{206}$-GFP treated overnight with BoNT/A using black tissue culture plates with clear bottoms.

FIG. 18 shows the dose response of Neuro-2A cells expressing SNAP$25_{206}$-GFP treated overnight with BoNT/A using black tissue culture plates with clear bottoms.

DETAILED DESCRIPTION OF THE INVENTION

The present invention provides novel assays for determining the presence or absence of an active Clostridial toxin in a sample and for determining the activity of a Clostridial toxin, including botulinum toxins of all serotypes and tetanus toxin. The novel cell-based fluorescence resonance energy transfer assays of the invention rely on cells in which a lipophilic dye or other acceptor is membrane-associated, for example, associated with the plasma membrane. The novel cells and cell-based assays of the invention reduce the need for animal toxicity studies, yet serve to analyze multiple toxin functions, namely, binding and cellular uptake of toxin, translocation into the cell cytosol, and protease activity. As discussed further below, the novel cells and methods of the invention can be used to analyze crude and bulk samples as well as highly purified di-chain toxins and formulated toxin products and further are amenable to automated high throughput assay formats.

Figure 1A:
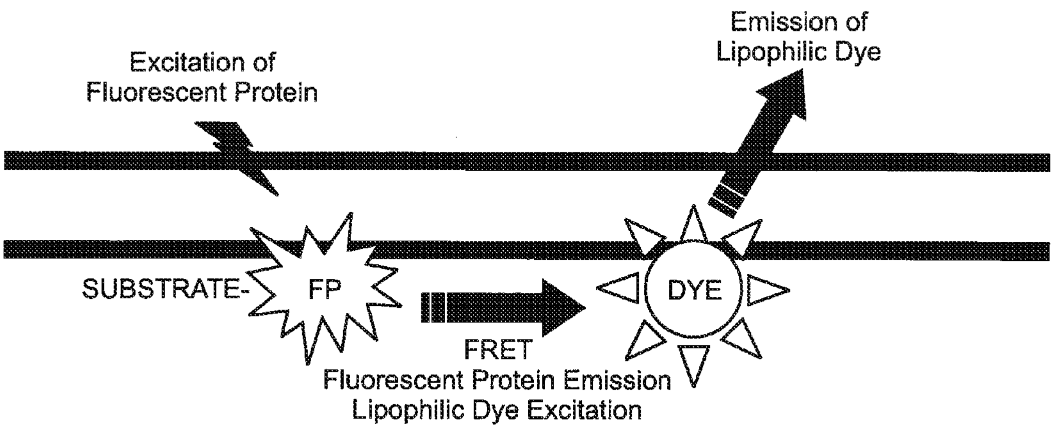
FIG. 1*a* shows an assay scenario where the Clostridial toxin substrate comprises the donor fluorophore and the presence of an uncleaved Clostridial toxin substrate is detected. Upon excitation, the fluorescent protein donor emits fluorescent light at a characteristic wavelength. However, because the uncleaved substrate is localized to the membrane, the close proximity between fluorescent protein donor and the lipophilic dye acceptor allows efficient energy transfer. The emission of the fluorescent protein excites the lipophilic dye which in turn emits fluorescent light at its characteristic wavelength. Detection of the lipophilic dye emissions is indicative of FRET and the presence an uncleaved Clostridial toxin substrate.
Figure 1B:
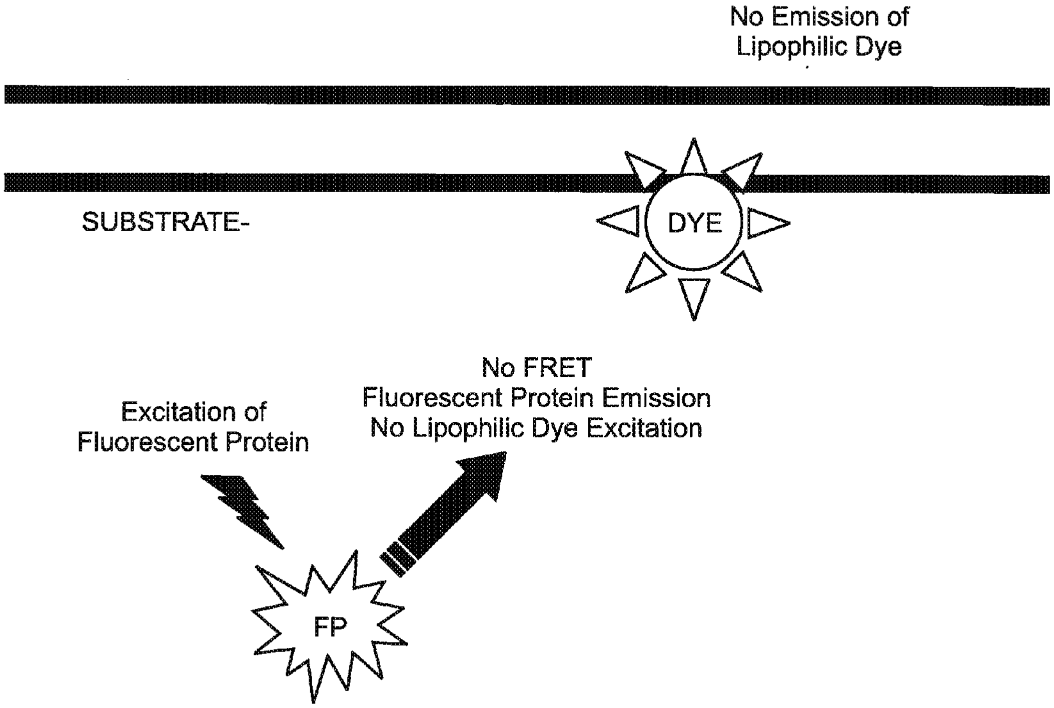
FIG. 1*b* shows an assay scenario where the Clostridial toxin substrate comprises the donor fluorophore and the presence of cleaved Clostridial toxin substrate is detected. Upon excitation, the fluorescent protein donor emits fluorescent light at a characteristic wavelength. However, because the fluorescent protein cleavage product of the Clostridial toxin substrate is released into the cytoplasm, the distance between the fluorescent protein donor and the lipophilic dye acceptor exceeds the maximal distance allowed for efficient energy transfer. Thus, the emissions from the fluorescent protein do not excite the lipophilic dye and FRET does not occur. A decrease in lipophilic dye emissions is indicative of a decrease of FRET, a decrease in uncleaved Clostridial toxin substrate and, conversely, an increase in cleaved Clostridial toxin substrate.
Figure 1C:
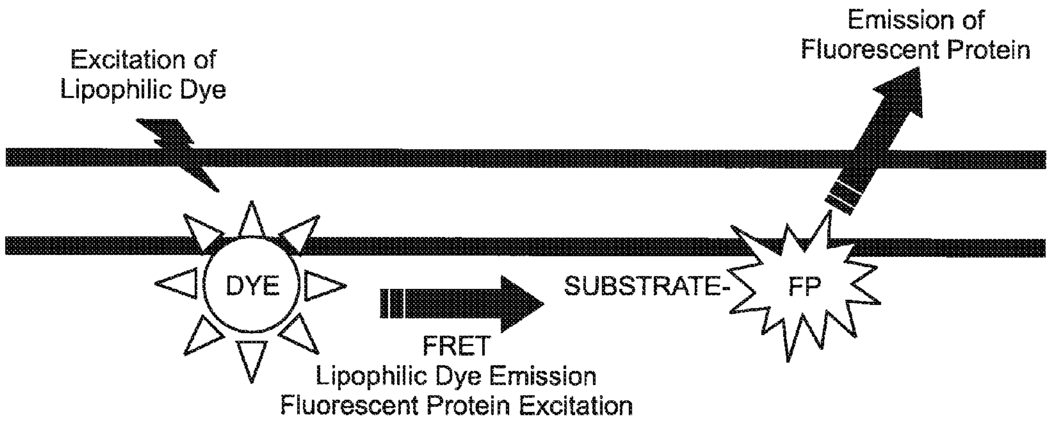
FIG. 1*c* shows an assay scenario where the lipophilic dye comprises the donor fluorophore and the presence of an uncleaved Clostridial toxin substrate is detected. Upon excitation, the lipophilic dye donor emits fluorescent light at a characteristic wavelength. However, because the uncleaved Clostridial toxin substrate is localized to the membrane, the close proximity between the lipophilic dye donor and the fluorescent protein acceptor allows efficient energy transfer. The emission of the lipophilic dye excites the fluorescent protein which in turn emits fluorescent light at its characteristic wavelength. Detection of the fluorescent protein emissions is indicative of FRET and the presence an uncleaved Clostridial toxin substrate.
Figure 1D:
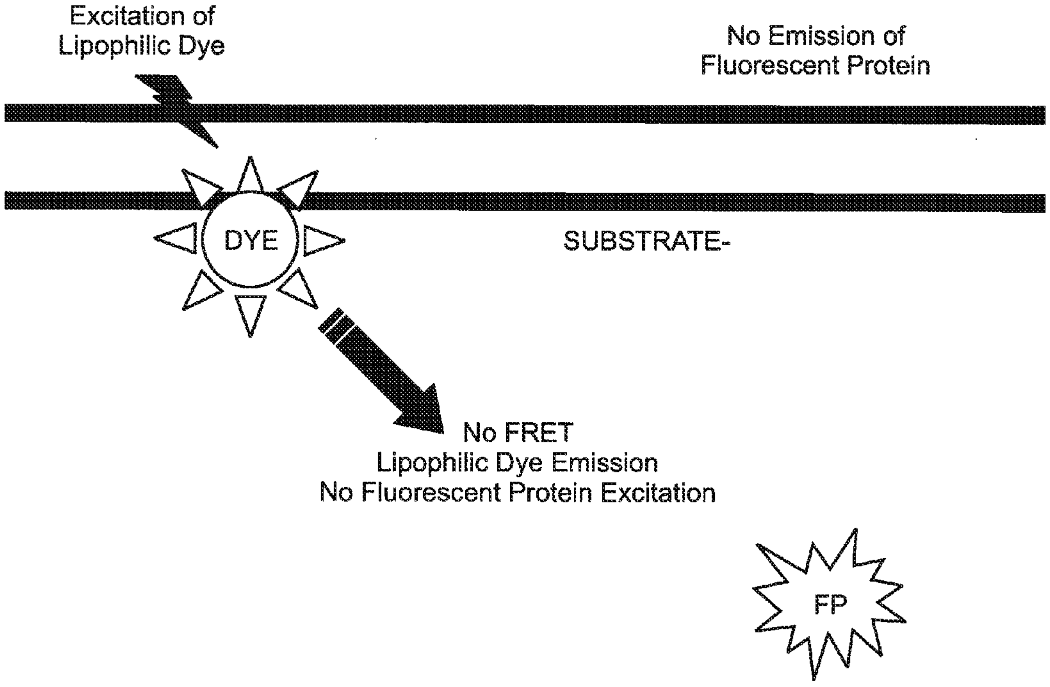
FIG. 1*d* shows an assay scenario where the lipophilic dye comprises the donor fluorophore and the presence of a cleaved Clostridial toxin substrate is detected. Upon excitation, the lipophilic dye donor emits fluorescent light at a characteristic wavelength. However, because the fluorescent protein cleavage product of the Clostridial toxin substrate is released into the cytoplasm, the distance between the lipophilic dye donor and the fluorescent protein acceptor exceeds the maximal distance allowed for efficient energy transfer. Thus, the emissions from the lipophilic dye do not excite the fluorescent protein and FRET does not occur. A decrease in fluorescent protein emissions is indicative of a decrease of FRET, a decrease in uncleaved Clostridial toxin substrate and, conversely, an increase in cleaved Clostridial toxin substrate. Abbreviations: FP, fluorescent protein; DYE, lipophilic dye.

The cell-based fluorescence resonance energy transfer assays of the invention rely on cells such as neuronal cells which are capable of efficient Clostridial toxin uptake and which include a Clostridial toxin substrate containing a FRET donor or acceptor. The second component of the FRET pair, such as a lipophilic dye, is separately membrane-associated. As an example, a cell useful in the invention can express a SNAP$25_{206}$-green fluorescent protein (GFP) fusion protein (absorbance 488 nm, emission 520 nm), which localizes to the plasma membrane. FRET occurs between the donor fluorophore GFP and a lipophilic dye acceptor localized to the plasma membrane and having an absorbance spectrum that overlaps with the emission spectrum of GFP and an emission spectrum which is suitably shifted from that of GFP. Energy transfer between GFP and the lipophilic dye acceptor is observed, for example, as red fluorescence representing emission from the lipophilic dye (see FIG. 1*a*). Upon BoNT/A treatment of cells which express $SNAP25_{206}$-GFP and have been stained with an appropriate lipophilic dye acceptor such as $DiIC_{18}(3)$, red emission at 610 nM is observed. Following cleavage of the $SNAP25_{206}$-GFP substrate, GFP is released into the cell cytoplasm. Upon excitation of the GFP donor fluorophore with a laser, GFP is excited and emits light at 520 nM. However, because energy transfer cannot occur between cytoplasmic GFP and the plasma membrane-localized lipophilic dye, FRET does not occur, and a decrease in red emission at 610 nM is observed (see FIG. 1*b*).

Aspects of the present invention provide a cell comprising (a) a membrane-associated Clostridial toxin substrate comprising (i) a first member of a fluorescence resonance energy transfer (FRET) pair; and (ii) a Clostridial toxin recognition sequence including a cleavage site; and (b) a membrane-associated second member of the FRET pair, wherein the cell is capable of Clostridial toxin intoxication; wherein the FRET pair comprises an acceptor having an absorbance spectrum overlapping the emission spectrum of a donor fluorophore; and wherein, under the appropriate conditions, resonance energy transfer is exhibited between the first and second members of the FRET pair.

Other aspects of the present invention provide a neuronal cell comprising (a) a stably expressed nucleic acid molecule encoding a membrane-associated BoNT/A substrate comprising (i) a fluorescent protein and (ii) a BoNT/A recognition sequence including a cleavage site; and (b) a membrane-associated lipophilic dye which has an absorbance spectrum overlapping the emission spectrum of the fluorescent protein; wherein the cell is capable of BoNT/A intoxication; and wherein, under the appropriate conditions, fluorescence resonance energy transfer is exhibited between the fluorescent protein and the lipophilic dye.

Other aspects of the present invention provide a neuronal cell comprising (a) a stably expressed nucleic acid molecule encoding a membrane-associated BoNT/E substrate comprising (i) a fluorescent protein; and (ii) a BoNT/E recognition sequence including a cleavage site; and (b) a membrane-associated lipophilic dye which has an absorbance spectrum overlapping the emission spectrum of the fluorescent protein; wherein the cell is capable of BoNT/E intoxication; and wherein, under the appropriate conditions, fluorescence resonance energy transfer is exhibited between the fluorescent protein and the lipophilic dye.

Other aspects of the present invention provide a method of determining Clostridial toxin activity comprising (a) contacting with a sample a cell comprising (1) a membrane-associated Clostridial toxin substrate comprising (i) a first member of a fluorescence resonance energy transfer (FRET) pair; and (ii) a Clostridial toxin recognition sequence including a cleavage site; and (2) a membrane-associated second member of the FRET pair; wherein the cell is capable of Clostridial toxin intoxication; wherein the FRET pair comprises an acceptor having an absorbance spectrum overlapping the emission spectrum of a donor fluorophore; and wherein, under the appropriate conditions, fluorescence resonance energy transfer is exhibited between the first and second members of the FRET pair; (b) exciting the donor fluorophore; and (c) determining fluorescence resonance energy transfer of the contacted cell relative to a control cell, wherein a difference in fluorescence resonance energy transfer of the contacted cell as compared to the control cell is indicative of Clostridial toxin activity.

Other aspects of the present invention provide a method of determining BoNT/A activity comprising (a) contacting with a sample a neuronal cell comprising (1) a stably expressed nucleic acid molecule encoding a membrane-associated BoNT/A substrate comprising (i) a fluorescent protein; and (ii) a BoNT/A recognition sequence including a cleavage site; and (2) a membrane-associated lipophilic dye which has an absorbance spectrum overlapping the emission spectrum of the fluorescent protein; wherein the neuronal cell is capable of BoNT/A intoxication; and wherein, under the appropriate conditions, fluorescence resonance energy transfer is exhibited between the fluorescent protein and the lipophilic dye; (b) exciting the fluorescent protein; and (c) determining fluorescence resonance energy transfer of the contacted neuronal cell relative to a control cell, wherein a difference in fluorescence resonance energy transfer of the contacted neuronal cell as compared to the control cell is indicative of BoNT/A activity.

Other aspects of the present invention provide a method of determining BoNT/E activity comprising (a) contacting with a sample a neuronal cell comprising (1) a stably expressed nucleic acid molecule encoding a membrane-associated BoNT/E substrate comprising (i) a fluorescent protein; and (ii) a BoNT/E recognition sequence including a cleavage site; and (2) a membrane-associated lipophilic dye which has an absorbance spectrum overlapping the emission spectrum of the fluorescent protein; wherein the neuronal cell is capable of BoNT/E intoxication; and wherein, under the appropriate conditions, fluorescence resonance energy transfer is exhibited between the fluorescent protein and the lipophilic dye; (b) exciting the fluorescent protein; and (c) determining fluorescence resonance energy transfer of the contacted neuronal cell relative to a control cell, wherein a difference in fluorescence resonance energy transfer of the contacted neuronal cell as compared to the control cell is indicative of BoNT/E activity.

Bacteria of the genus *Clostridia* are strictly anaerobic to aero-tolerant spore-forming bacilli found in soil, freshwater and saltwater sediments, household dust, the surface of foods, feces as well as in the normal intestinal flora of humans and animals. While the majority of isolates are gram-positive, a few gram-negative species exist. Members of this genus produce sophisticated exotoxins that are among the most potent toxins known in the world. Exposure to these toxins during the course of Clostridia infection is the primary cause underlying disease pathogenesis. Clostridia are a major threat to human and animal health, being responsible for many diseases including botulism, tetanus, gas gangrene, pseudomembranous colitis and food poisoning. For example, *Clostridium argentinense, C. bifermentans, C. histolyticum, C. novyi, C. septicum, C. sporogenes* and *C. tertium* are etiological agents for gas gangrene. *C. perfringens* is responsible for foodborne illness, enteritis necroticans where as *C. difficile* is responsible for pseudomembranous enterocolitis. Both *C. baratii* and *C. butyricum* are causative agents for a form of foodborne, intestinal and wound botulism. Interestingly, only a few species of these bacteria are pathogenic for humans, most are saprophytic. Thus, in most cases, Clostridia are opportunistic pathogens that infect a host whose health is compromised.

Of all Clostridia, *Clostridium botulinum* and *Clostridium tetani* produce the most potent biological toxins known and are the causative agents of the neuroparalytic syndromes botulism and tetanus. Seven antigenically-distinct types of Botulinum toxins (BoNTs) have been identified by investigating botulism outbreaks in man (BoNT/A, /B, /E and /F), animals (BoNT/C1 and /D), or isolated from soil (BoNT/G). BoNTs possess approximately 35% amino acid identity with each other and share the same functional domain organization and overall structural architecture. The amino acid sequences of eight Clostridial toxin serotypes have been derived from the corresponding genes (Niemann, "Molecular Biology of Clostridial Neurotoxins" in Sourcebook of Bacterial Protein Toxins Alouf and Freer (Eds.) pp. 303-348 London: Academic Press 1991). It is recognized by those of skill in the art that within each type of Clostridial toxin there can be various strains differing somewhat in their amino acid sequence, and also in the nucleic acids encoding these proteins. While all seven BoNT serotypes have similar structure and pharmacological properties, each also displays heterogeneous bacteriological characteristics. In contrast, tetanus toxin (TeNT) is produced by a uniform group of *C. tetani*. Two other species of clostridia, *C. baratii* and *C. butyricum*, also produce toxins similar to BoNT/F and BoNT/E, respectively.

Clostridia toxins (CoNTs) are each translated as a single chain polypeptide of approximately 150 kDa that is subsequently cleaved by proteolytic scission within a disulphide loop by bacterial or tissue proteases. This posttranslational processing yields a di-chain molecule comprising an approximately 50 kDa light chain (LC) and an approximately 100 kDa heavy chain (HC) held together by a single disulphide bond and noncovalent interactions. Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain contained within the amino-terminal half of the HC($H_N$) that facilitates release of the toxin from intracellular vesicles into the cytoplasm of the target cell; and 3) a binding domain found within the carboxyl-terminal half of the HC ($H_C$) that determines the binding activity and binding specificity of the toxin to the receptor complex located at the surface of the target cell.

Figure 2:
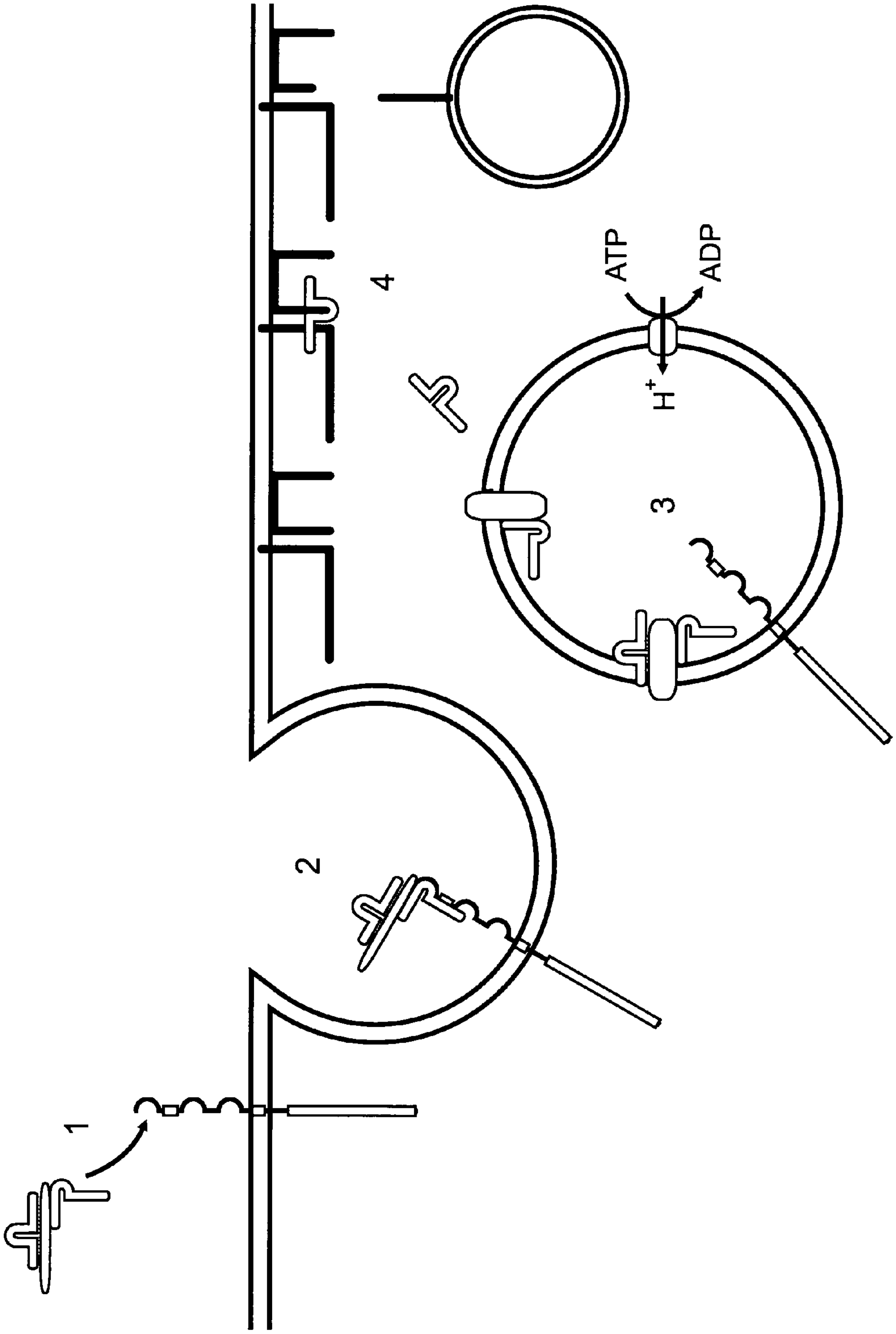
FIG. 2 shows a schematic of the current paradigm of the intoxication mechanism for tetanus and botulinum toxin activity in central and peripheral neuron. This intoxication process can be described as comprising four steps: 1) receptor binding, where Clostridial toxin binds to a Clostridial receptor system initiates the intoxication process; 2) complex internalization, where after toxin binding, a vesicle containing a toxin/receptor system complex is endocytosised into the cell; 3) light chain translocation, where multiple events are thought to occur, including changes in the internal pH of the vesicle, formation of a channel pore comprising the $H_N$ domain of Clostridial toxin heavy chain, separation of the Clostridial toxin light chain from the heavy chain, enzymatic activation of the light chain; and release of the activated light chain and 4) enzymatic target modification, where the activated light chain of Clostridial toxin proteolytically cleaves its target SNARE substrates, such as, e.g., SNAP-25, VAMP or Syntaxin.
Figure 3A:
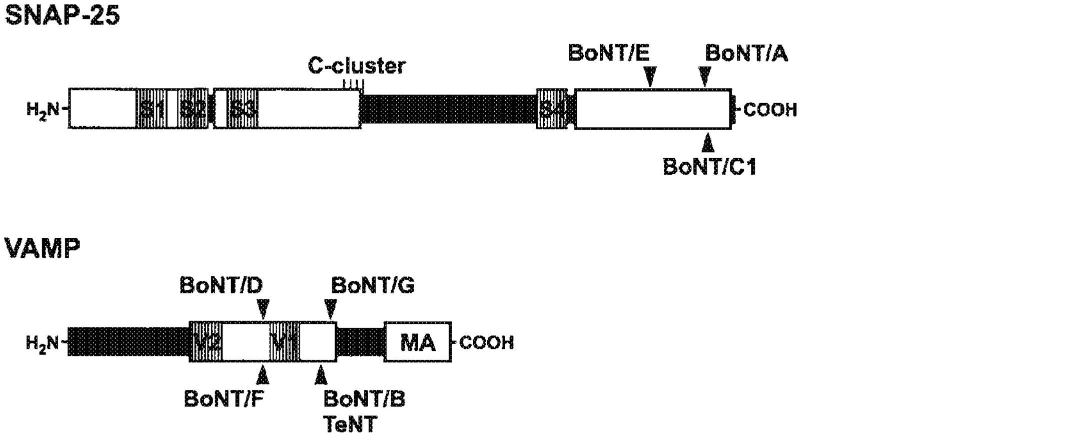
FIG. 3*a* shows the general domain organization of SNAP-25, VAMP and Syntaxin depicting approximate locations of the a-helical regions (white boxes), SNARE motifs (Hatched boxes with S1, S2, S3, S4, V1, V2, X1 or X2 designations) and the membrane anchoring domains (white boxes designated MA).
Figure 3B:
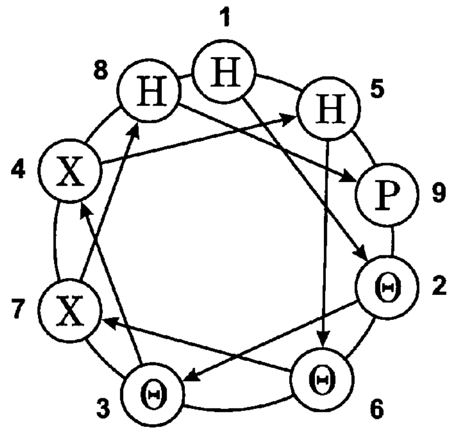
FIG. 3*b* shoes the helical organization of a SNARE motif.

The binding, translocation and enzymatic activity of these three functional domains are all necessary for toxicity. While all details of this process are not yet precisely known, the overall cellular intoxication mechanism whereby CoNTs enter a neuron and inhibit neurotransmitter release is similar, regardless of type. Although the applicants have no wish to be limited by the following description, the intoxication mechanism can be described as comprising four steps: 1) receptor binding, 2) complex internalization, 3) light chain translocation, and 4) enzymatic target modification (see FIG. 2). The process is initiated when the $H_C$ domain of a CoNT binds to CoNT-specific receptor complex located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the CoNT/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote enzymatic activation of the toxin. Once activated, light chain endopeptidase of the toxin is released from the intracellular vesicle into the cytosol where it specifically targets one of three known core components of the neurotransmitter release apparatus. There of these core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family (see FIG. 3). The selective proteolysis of synaptic SNAREs accounts for the total block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release,* 82(5) Biochimie. 427-446 (2000); Kathryn Turton et al., *Botulinum and Tetanus Neurotoxins: Structure, Function and Therapeutic Utility,* 27(11) Trends Biochem. Sci. 552-558. (2002); M. Zouhair Atassi, *Basic and Therapeutic Aspects of Botulinum and Tetanus Toxins*, (Dirk W. Dressler & Joseph J. Jankovic eds., 2003); Giovanna Lalli et al., *The Journey of Tetanus and Botulinum Neurotoxins in Neurons,* 11(9) Trends Microbiol. 431-437, (2003) which are hereby incorporated by reference.

TeNT and BoNT/B, /D, /F, and /G specifically recognize VAMP (also known as synaptobrevin), an integral protein of the synaptic vesicle membrane. VAMP is cleaved at distinct bonds depending on the toxin. BoNT/A and /E recognize and specifically cleave SNAP-25, a protein of the presynaptic membrane, at two different sites in the carboxyl-terminal portion of the protein. BoNT/C1 cleaves Syntaxin, a protein of the nerve plasmalemma, in addition to SNAP-25. The three protein targets of the CoNTs are conserved from yeast to humans although cleavage sites and toxin susceptibility are not necessarily conserved, see below; see, also, e.g., Humeau, supra, (2000); Heiner Niemann et al., Clostridial neurotoxins: new tools for dissecting exocytosis, 4(5) Trends Cell Biol. 179-185 (1994); and Rossella Pellizzari et al., Tetanus and botulinum neurotoxins: mechanism of action and therapeutic uses, 354(1381) Philos. Trans. R. Soc. Lond. B Biol. Sci. 259-268 (1999).

The natural targets of the Clostridial toxins include VAMP, SNAP-25, and Syntaxin. VAMP is associated with the synaptic vesicle membrane, whereas SNAP-25 and Syntaxin are associated with the plasma membrane (see FIG. 4). BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves Syntaxin at a single site near the cytosolic membrane surface. Thus, BoNT/B, BoNT/C1, BoNT/D, BoNT/F, BoNT/G or TeNT proteolysis results in release of a large portion of the cytosolic domain of VAMP or Syntaxin, while only a small portion of SNAP-25 is released by BoNT/A, BoNT/C1 or BoNT/E cleavage, see, e.g., Humeau et al., supra, (2000); Turton et al., supra, (2002); Lalli et al., supra (2003).

Figure 4:
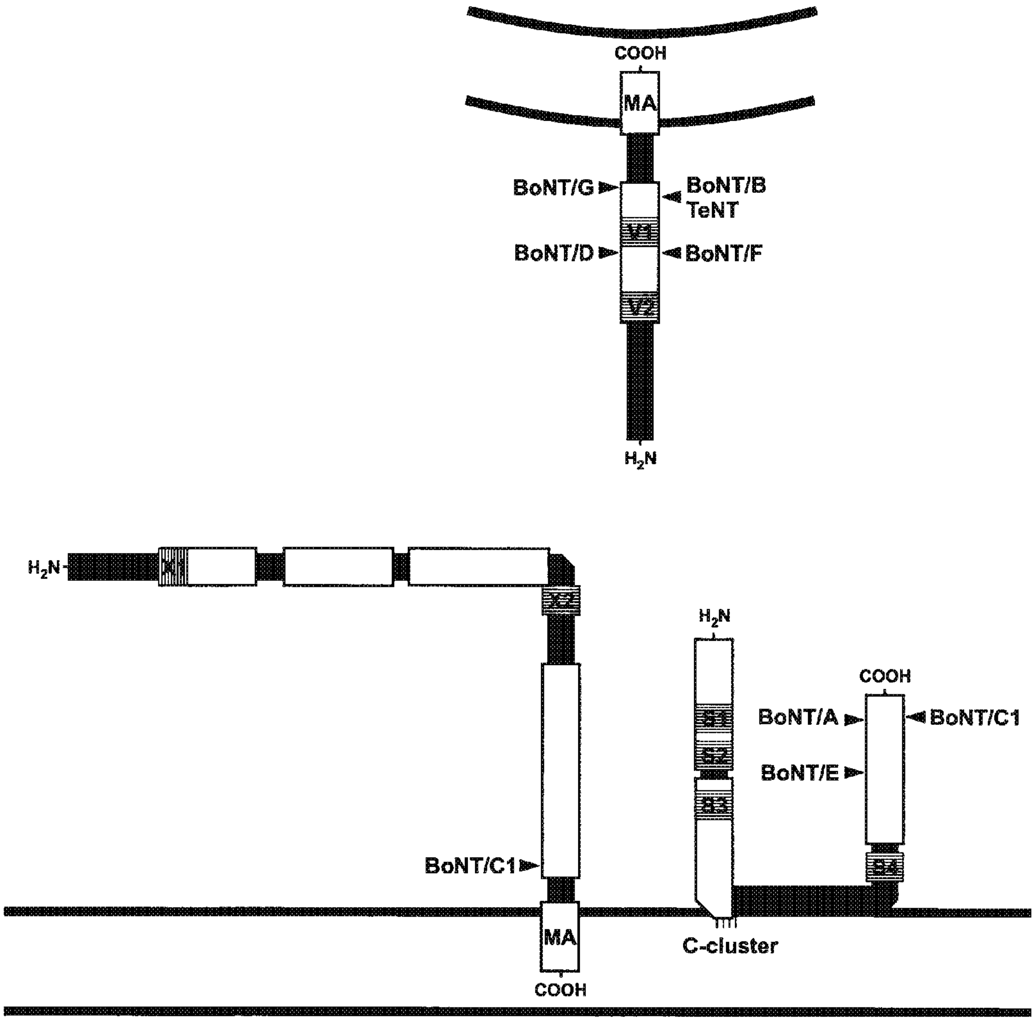
FIG. 4 shows a schematic of the subcellular localization and cleavage sites of SNAP-25, VAMP and Syntaxin. VAMP is localized to synaptic vesicle membrane, whereas SNAP-25 and Syntaxin are localized to the plasma membrane. BoNT/A and BoNT/E cleave SNAP-25 close to the carboxyl-terminus, releasing nine or 26 residues, respectively. BoNT/B, BoNT/D, BoNT/F, BoNT/G and TeNT act on the conserved central portion of VAMP (white box) and release the amino-terminal cytosolic half of VAMP into the cytosol. BoNT/C1 cleaves SNAP-25 close to the carboxyl-terminus as well as cleaving Syntaxin at a single site near the cytosolic membrane surface. The action of BoNT/C1 results in release of a large portion of the cytosolic domain of Syntaxin, while only a small portion of SNAP-25 is released by selective proteolysis of BoNT/C1.

Naturally occurring SNAP-25, a protein of about 206 residues lacking a transmembrane segment, is associated with the cytosolic surface of the nerve plasmalemma (see FIG. 4). SNAP-25 is required for axonal growth during development and may be required for nerve terminal plasticity in the mature nervous system. SNAP-25 has been isolated from a variety of vertebrate and invertebrate species including, e.g., species belonging to the genera *Homo, Macaca, Bos, Rattus, Mus, Gallus, Carassius, Danio, Torpedo, Xenopus, Strongylocentrotus, Drosophila, Hirudo, Loligo, Lymnaea* and *Cae-*

*norhabditis*. In humans, at least two isoforms are differentially expressed during development; isoform a is constitutively expressed during fetal development, while isoform b appears at birth and predominates in adult life. SNAP-25 analogues such as SNAP-23 also are expressed outside the nervous system, for example, in pancreatic cells.

Naturally occurring VAMP is a protein of about 120 residues, with the exact length depending on the species and isoform. As shown in FIG. 4, VAMP contains a short carboxyl-terminal segment inside the vesicle lumen while most of the molecule is exposed to the cytosol. The proline-rich amino-terminal thirty residues are divergent among species and isoforms while the central portion of VAMP (residues 30 to 96), which is rich in charged and hydrophilic residues and includes known cleavage sites, is highly conserved. VAMP colocalizes with synaptophysin on synaptic vesicle membranes. VAMP has been isolated from a variety of vertebrate and invertebrate species including, e.g., species belonging to the genera *Homo, Macaca, Bos, Rattus, Mus, Gallus, Danio, Torpedo, Xenopus, Strongylocentrotus, Drosophila, Hirudo, Loligo, Lymnaea, Aplysia* and *Caenorhabditis*. In addition, multiple isoforms of VAMP have been identified including VAMP-1, VAMP-2 and VAMP-3/cellubrevin, and forms insensitive to toxin cleavage have been identified in non-neuronal cells. VAMP appears to be present in all vertebrate tissues although the distribution of VAMP-1 and VAMP-2 varies in different cell types. Chicken and rat VAMP-1 are not cleaved by TeNT or BoNT/B. These VAMP-1 orthologs have a valine in place of the glutamine present in human and mouse VAMP-1 at the TeNT or BoNT/B cleavage site. The substitution does not affect BoNT/D, /F or /G, which cleave both VAMP-1 and VAMP-2 with similar rates.

Naturally occurring Syntaxin is located on the cytosolic surface of the nerve plasmalemma and is membrane-anchored via a carboxyl-terminal segment, with most of the protein exposed to the cytosol (see FIG. 4). Syntaxin colocalizes with calcium channels at the active zones of the presynaptic membrane, where neurotransmitter release takes place. In addition, Syntaxin interacts with synaptotagmin, a protein of the SSV membrane that forms a functional bridge between the plasmalemma and the vesicles. Syntaxin has been isolated from a variety of vertebrate and invertebrate species including, e.g., species belonging to the genera *Homo, Bos, Rattus, Mus, Gallus, Danio, Strongylocentrotus, Drosophila, Hirudo, Loligo, Lymnaea* and *Aplysia*. Three isoforms of slightly different length (285 and 288 residues) have been identified in nerve cells (isoforms 1A, 1B1 and 1B2), with isoforms 2, 3, 4 and 5 expressed in other tissues. The different isoforms have varying sensitivities to BoNT/C1, with the 1A, 1B1, 1B2, 2 and 3 Syntaxin isoforms cleaved by this toxin.

The compositions and methods of the present specification provide a cell comprising, in part, a Clostridial toxin substrate. By definition, a Clostridial toxin substrate is susceptible to cleavage by at least one Clostridial toxin under conditions suitable for Clostridial toxin protease activity. A variety of Clostridial toxin substrates are discussed herein below. Additional Clostridial toxin substrates are described in, e.g., Lance E. Steward, et al., FRET Protease Assays for Clostridial Toxins, U.S. Patent Publication 2003/0143651 (Jul. 31, 2003); Lance E. Steward, et al., FRET Protease Assays for *Botulinum* Serotype A/E Toxins, U.S. Patent Publication 2003/0143650 (Jul. 31, 2003); and Ester Fernandez-Salas, et al., Cell-based Fluorescence Resonance Energy Transfer (FRET) Assays for Clostridial Toxins, U.S. Patent Publication 2004/0072270 (Apr. 15, 2004).

The Clostridial toxin substrates disclosed in the present specification comprise, in part, a Clostridial toxin recognition sequence including a cleavage site. As used herein, the term "Clostridial toxin recognition sequence" means a scissile bond together with adjacent or non-adjacent recognition elements, or both, sufficient for detectable proteolysis at the scissile bond by a Clostridial toxin under conditions suitable for Clostridial toxin protease activity. A variety of Clostridial toxin recognition sequences are discussed herein below.

Clostridial toxin substrates useful in aspects of the invention include peptides and peptidomimetics as well as derivatized forms thereof. As used herein, the term "peptidomimetic" is used broadly to mean a peptide-like molecule that is cleaved by the same Clostridial toxin as the peptide substrate upon which it is structurally based. Such peptidomimetics include chemically modified peptides, peptide-like molecules containing non-naturally occurring amino acids, and peptoids, which are peptide-like molecules resulting from oligomeric assembly of N-substituted glycines, and are cleaved by the same Clostridial toxin as the peptide substrate upon which the peptidomimetic is derived, see, e.g., Goodman & Ro, Peptidomimetics for Drug Design, pp. 803-861, in "Burger's Medicinal Chemistry and Drug Discovery" Vol. 1 (ed. M. E. Wolff; John Wiley & Sons 1995).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; an α,α-dialkyl-glycine or α-aminocycloalkane carboxylic acid; an $N^{\alpha}$-$C^{\alpha}$ cyclized amino acid; an $N^{\alpha}$-methylated amino acid; β- or γ-amino cycloalkane carboxylic acid; an α,β-unsaturated amino acid; a β, β-dimethyl or β-methyl amino acid; a β-substituted-2,3-methano amino acid; an $NC^{\delta}$ or $C^{\alpha}$-$C^{\delta}$ cyclized amino acid; or a substituted proline or another amino acid mimetic. In addition, a peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

In other embodiments, a Clostridial toxin substrate useful in the invention is a peptide or peptidomimetic having a defined length. A Clostridial toxin substrate can be, for example, a peptide or peptidomimetic having at least 100, at least 150, at least 200, at least 250, at least 300, at least 350 or at least 500 residues. In other embodiments, a Clostridial toxin substrate has at most 20 residues, at most 30 residues, at most 40 residues, at most 50 residues, at most 100 residues, at most 150 residues, at most 200 residues, at most 250 residues, at most 300 residues, at most 350 residues or at most 400 residues.

A wide variety of Clostridial toxin recognition sequences are useful in aspects of the invention. Specific and distinct cleavage sites for different Clostridial toxins are well known in the art. BoNT/A cleaves a Gln-Arg bond; BoNT/B and TeNT cleave a Gln-Phe bond; BoNT/C1 cleaves a Lys-Ala or Arg-Ala bond; BoNT/D cleaves a Lys-Leu bond; BoNT/E cleaves an Arg-Ile bond; BoNT/F cleaves a Gln-Lys bond; and BoNT/G cleaves an Ala-Ala bond (see Table 1). In standard nomenclature, the sequence surrounding a Clostridial toxin cleavage site is denoted $P_5$-$P_4$-$P_3$-$P_2$-$P_1$-$P_1'$-$P_2'$-$P_3'$-$P_4'$-$P_5'$ with $P_1$-$P_1'$ representing the scissile bond. It is understood that a $P_1$ or $P_1'$ site, or both, can be substituted with another amino acid or amino acid mimetic in place of the naturally occurring residue. As an example, BoNT/A substrates have been prepared in which the $P_1$ position (Gln) is modified to be an alanine, 2-aminobutyric acid or asparagine residue; these substrates were hydrolyzed by BoNT/A at the $P_1$-Arg bond, see, e.g., James J. Schmidt & Karen A Bostian, Endoproteinase activity of type A botulinum neurotoxin: substrate requirements and activation by serum albumin, 16(1) J. Protein Chem. 19-26 (1997). While it is recognized that substitutions can be introduced at the $P_1$ position of the scissile bond, for example, a BoNT/A scissile bond, it is further recognized that conservation of the $P_1'$ residue can be advantageous, see, e.g., Vadakkanchery V. Vaidyanathan et al., Proteolysis of SNAP-25 isoforms by botulinum neurotoxin types A, C, and E: domains and amino acid residues controlling the formation of enzyme-substrate complexes and cleavage, 72(1) J. Neurochem. 327-337 (1999).

TABLE 1

Bonds Cleaved in Human VAMP-2, SNAP-25 or Syntaxin-1

| Toxin | Target | $P_4$-$P_3$-$P_2$-$P_1$ -- $P_1'$-$P_2'$-$P_3'$-$P_4'$ | SEQ ID NO: |
|---|---|---|---|
| BoNT/A | SNAP-25 | Glu-Ala-Asn-**Gln-Arg***-Ala-Thr-Lys | 96 |
| BoNT/B | VAMP-2 | Gly-Ala-Ser-**Gln-Phe***-Glu-Thr-Ser | 97 |
| BoNT/C1 | Syntaxin-1 | Asp-Thr-Lys-**Lys-Ala***-Val-Lys-Tyr | 98 |
| BoNT/C1 | SNAP-25 | Ala-Asn-Gln-**Arg-Ala***-Thr-Lys-Met | 99 |
| BoNT/D | VAMP-2 | Arg-Asp-Gln-**Lys-Leu***-Ser-Glu-Leu | 100 |
| BoNT/E | SNAP-25 | Gln-Ile-Asp-**Arg-Ile***-Met-Glu-Lys | 101 |
| BoNT/F | VAMP-2 | Glu-Arg-Asp-**Gln-Lys***-Leu-Ser-Glu | 102 |
| BoNT/G | VAMP-2 | Glu-Thr-Ser-**Ala-Ala***-Lys-Leu-Lys | 103 |
| TeNT | VAMP-2 | Gly-Ala-Ser-**Gln-Phe***-Glu-Thr-Ser | 104 |

*Scissile bond shown in bold

Thus, an embodiment, a membrane-associated Clostridial toxin substrate comprises, in part, a Clostridial toxin recognition sequence comprising a cleavage site. In an aspect of this embodiment, a Clostridial toxin substrate comprises a Clostridial toxin recognition sequence in which the $P_1'$ residue is not modified or substituted relative to the naturally occurring residue in a target protein cleaved by the Clostridial toxin. In another aspect of this embodiment, a Clostridial toxin substrate comprises a Clostridial toxin recognition sequence in which the $P_1$ residue is modified or substituted relative to the naturally occurring residue in a target protein cleaved by the Clostridial toxin; such a Clostridial toxin substrate retains susceptibility to peptide bond cleavage between the $P_1$ and $P_1'$ residues. Any of a variety of Clostridial toxin recognition sequences are useful in the cells of the invention including, without limitation, botulinum toxin recognition sequences such as BoNT/A recognition sequences, BoNT/B recognition sequences, BoNT/C1 recognition sequences, BoNT/D recognition sequences, BoNT/E recognition sequences, BoNT/F recognition sequences, BoNT/G recognition sequences and TeNT recognition sequences.

A variety of BoNT/A recognition sequences are well known in the art and are useful in the invention, see, e.g., Mark A. Breidenbach & Axel T. Brunger, Substrate recognition strategy for botulinum neurotoxin serotype A, 432(7019) Nature 925-929 (2004). A BoNT/A recognition sequence can have, for example, residues 46-206, residues 134 to 206, residues 137 to 206 or 146-206 of human SNAP-25, see, e.g., Teresa A. Ekong et al., Recombinant SNAP-25 is an effective substrate for *Clostridium botulinum* type A toxin endopeptidase activity in vitro, 143 (Pt 10) Microbiology 3337-3347 (1997); Clifford C. Shone et al., Toxin Assays, U.S. Pat. No. 5,962,637 (Oct. 5, 1999); and Vaidyanathan et al., supra, (1999). A BoNT/A recognition sequence also can include, without limitation, the sequence Thr-Arg-Ile-Asp-Glu-Ala-Asn-Gln-Arg-Ala-Thr-Lys-Met (SEQ ID NO: 105) or a peptidomimetic thereof, which corresponds to residues 190 to 202 of human SNAP-25; Ser-Asn-Lys-Thr-Arg-Ile-Asp-Glu-Ala-Asn-Gln-Arg-Ala-Thr-Lys (SEQ ID NO: 106) or a peptidomimetic thereof, which corresponds to residues 187 to 201 of human SNAP-25; Ser-Asn-Lys-Thr-Arg-Ile-Asp-Glu-Ala-Asn-Gln-Arg-Ala-Thr-Lys-Met (SEQ ID NO: 107) or a peptidomimetic thereof, which corresponds to residues 187 to 202 of human SNAP-25; Ser-Asn-Lys-Thr-Arg-Ile-Asp-Glu-Ala-Asn-Gln-Arg-Ala-Thr-Lys-Met-Leu (SEQ ID NO: 108) or a peptidomimetic thereof, which corresponds to residues 187 to 203 of human SNAP-25; Asp-Ser-Asn-Lys-Thr-Arg-Ile-Asp-Glu-Ala-Asn-Gln-Arg-Ala-Thr-Lys-Met (SEQ ID NO: 109) or a peptidomimetic thereof, which corresponds to residues 186 to 202 of human SNAP-25; or Asp-Ser-Asn-Lys-Thr-Arg-Ile-Asp-Glu-Ala-Asn-Gln-Arg-Ala-Thr-Lys-Met-Leu (SEQ ID NO: 110) or a peptidomimetic thereof, which corresponds to residues 186 to 203 of human SNAP-25. See, for example, James J. Schmidt & Karen A Bostian, Proteolysis of synthetic peptides by type A botulinum neurotoxin, 14(8) J. Protein Chem. 703-708 (1995); Schmidt & Bostian, supra, (1997); James J. Schmidt et al., Type A botulinum neurotoxin proteolytic activity: development of competitive inhibitors and implications for substrate specificity at the S1' binding subsite, 435(1) FEBS Lett. 61-64 (1998); and James J. Schmidt & Karen A Bostian, Assay for the proteolytic activity of serotype a from *clostridium botulinum*, U.S. Pat. No. 5,965,699 (Oct. 12, 1999).

A BoNT/A recognition sequence useful in aspects of the invention can correspond to a segment of a protein that is sensitive to cleavage by botulinum toxin serotype A, or can be substantially similar to a segment of a BoNT/A-sensitive protein. As shown in Table 2, a variety of naturally occurring proteins sensitive to cleavage by BoNT/A are known in the art and include, for example, human, rat, mouse, *Danio, Carassius*, SNAP-25A and SNAP-25B; and Torpedo SNAP-25. Thus, a BoNT/A recognition sequence can correspond, for example, to a segment of human SNAP-25A or SNAP-25B; bovine SNAP-25A or SNAP-25B; rat SNAP-25A or SNAP-25B; mouse SNAP-25A or SNAP-25B; *Xenopus* SNAP-25A or SNAP-25B; *Danio* SNAP-25A or SNAP-25B; *Carassius* SNAP-25A or SNAP-25B; Torpedo SNAP-25; *Strongylocentrotus* SNAP-25; *Loligo* SNAP-25; *Lymnaea* SNAP-25; *Aplysia* SNAP-25, isoforms thereof, or another naturally occurring protein sensitive to cleavage by BoNT/A. Furthermore, comparison of native SNAP-25 amino acid sequences cleaved by BoNT/A reveals that such sequences are not absolutely conserved (see Table 2), indicating that a variety of amino acid substitutions and modifications relative to a naturally occurring BoNT/A-sensitive SNAP-25 sequence can be tolerated in a BoNT/A recognition sequence useful in the invention. It is understood that a similar BoNT/A recognition sequence can be prepared, if desired, from a corresponding (homologous) segment of another BoNT/A-sensitive SNAP-25 isoform, paralog or ortholog, such as, the BoNT/A recognition sequence contain in the SNAP-25 proteins identified in the organisms listed above and in Table 2.

TABLE 2

Cleavage of SNAP-25 and Related Proteins[a, b, c]

| Organism | Isoform | Cleavage Sites | BoNT/E ▼ | | BoNT/A ▼ | | BoNT/C1 ▼ | | Cleaved Suscepti-bility |
|---|---|---|---|---|---|---|---|---|---|
| Primate | SNAP-25A SNAP-25B | MALDMGNEIDTQNRQIDR | * | IMEKADSNKTRIDEANQ | * | R | * | ATKMLGSG | BoNT/A; BoNT/C1; BoNT/E |
| Primate | SNAP-23A SNAP-23B | MALNIGNEIDAQNPQIKR | — | ITDKADTNRDRIDIANA | — | R | — | AKKLIDS | None[b] |
| Rodent | SNAP-25A SNAP-25B | MALDMGNEIDTQNRQIDR | * | IMEKADSNKTRIDEANQ | * | R | * | ATKMLGSG | BoNT/A; BoNT/C1; BoNT/E |
| Rodent | SNAP-23 | MALDMFNEIDAQNQQIQK | * | ITEKADTNKNRIDIANT | — | R | — | AKKLIDS | BoNT/E |
| Bird | SNAP-25B | MALDMGNEIDTQNRQIDR | * | IMEKADSNKTRIDEANQ | — | R | — | ATKMLGSG | BoNT/E |
| Am-phibian | SNAP-25A SNAP-25B | MALDMGNEIDTQNRQIDR | ND | IMEKADSNKARIDEANK | ND | H | ND | ATKMLGSG | ND |
| Amp-hibian | SNAP-23 | MAIDMGNELESHNQQIGR | ND | INEKAETNKTRIDEANT | ND | K | ND | AKKLIE | ND |
| Fish | SNAP-25A | MALDMGNEIDTQNRQIDR | * | IMEKADSNKTRIDEANQ | * | R | * | ATKMLGSG | BoNT/A; BoNT/C1; BoNT/E |
| | SNAP-25B | MALDMGNEIDTQNRQIDR | * | IMDMADSNKTRIDEANQ | * | R | * | ATKMLGSG | |
| Fish | SNAP-23 | LALDMGNEIDKQNKTIDR | ND | ITDKADMNKARIDEANQ | ND | R | ND | ANKLL | ND |
| Ray | SNAP-25 | MALDMSNEIGSQNAQIDR | —[c] | IVVKGDMNKARIDEANK | * | H | ND | ATKML | BoNT/A |
| Sea urchin | SNAP-25 | MAIDMQSEIGAQNSQVGR | ND | ITSKAESNEGRINSADK | ND | R | ND | AKNILRNK | ND |
| Insect | SNAP-25 | MALDMGSELENQNRQIDR | — | INRKGESNEARIAVANQ | — | R | * | AHQLLK | BoNT/C1 |
| Insect | SNAP-24 | MALDMGSELENQNKQVDR | ND | INAKGDANNIRMDGVNK | ND | R | ND | ANNLLKS | ND |
| Seg-mented worm | SNAP-25 | MAVDMGSEIDSQNRQVDR | ND | INNKMTSNQLRISDANK | — | R | ND | ASKLLKE | ND |
| Ce-phalopod | SNAP-25 | MAIDMGNEIGSQNRQVDR | ND | IQQKAESNESRIDEANK | ND | K | ND | ATKLLKN | ND |
| Gastropod | SNAP-25 | MAVDMGNEIESQNKQLDR | ND | INQKGGSLNVRVDEANK | ND | R | ND | ANRILRKQ | ND |
| Round worm | SNAP-25 | MAIDMSTEVSNQNRQLDR | * | IHDKAQSNEVRVESANK | — | R | — | AKNLITK | BoNT/E |

Proteolytic cleavage occurs at this site (*);
Proteolytic cleavage not detected at this site (—);
Proteolytic cleavage not determined at this site (ND)
[a]In vitro cleavage of SNAP-25 requires 1000-fold higher BoNT/C concentration than BoNT/A or /E.
[b]Substitution of P182R, or K185DD (boxes) induces susceptibility toward BoNT/E.
[c]Resistance to BoNT/E possibly due to D189 or E189 substitution by V189, see box.

Table 2—Cleavage of SNAP-25 and related proteins. Primate: Human SNAP-25A residues 163-206 of SEQ ID NO: 1; Human SNAP-25B residues 163-206 of SEQ ID NO: 2; Human SNAP-23A residues 169-211 of SEQ ID NO: 3; Human SNAP-23B residues 116-158 of SEQ ID NO: 4; Monkey SNAP-25B residues 163-206 of SEQ ID NO: 5; Rodent: Rat SNAP-25A residues 163-206 of SEQ ID NO: 6; Rat SNAP-25B residues 163-206 of SEQ ID NO: 7; Mouse SNAP-25B residues 163-206 of SEQ ID NO: 8; Rat SNAP-23 residues 168-210 of SEQ ID NO: 9; Mouse SNAP-23 residues 168-210 of SEQ ID NO: 10; Bird: Chicken SNAP-25B residues 163-206 of SEQ ID NO: 11; Fish: Goldfish SNAP- 25A residues 161-204 of SEQ ID NO: 12; Goldfish SNAP-25B residues 160-203 of SEQ ID NO: 13; Zebrafish SNAP-25A residues 161-204 of SEQ ID NO: 14; Zebrafish SNAP-25B residues 160-203 of SEQ ID NO: 15; Zebrafish SNAP-23 residues 174-214 of SEQ ID NO: 16; Ray: marbled electric ray SNAP-25 residues 170-210 of SEQ ID NO: 17; Amphibian: Frog SNAP-25A residues 163-206 of SEQ ID NO: 18; Frog SNAP-25B residues 163-206 of SEQ ID NO: 19; Frog SNAP-23 residues 163-204 of SEQ ID NO: 20; Sea urchin SNAP-25 residues 169-212 of SEQ ID NO: 21; Insect: Fruit fly SNAP-25 residues 171-212 of SEQ ID NO: 22 212; Fruit fly SNAP-24 residues 170-212 of SEQ ID NO: 23; Segmented worm: Leech SNAP-25 residues 170-212 of SEQ ID NO: 24; Cephalopod: squid SNAP-25 residues 245-267 of SEQ ID NO: 25; Gastropod: Pond snail SNAP-25 residues 244-266 of SEQ ID NO: 26; Round worm: Nematode worm SNAP-25 residues 165-207 of SEQ ID NO: 27.

A Clostridial toxin substrate, such as a substrate containing a BoNT/A recognition sequence, can have one or multiple modifications as compared to a naturally occurring sequence that is cleaved by the corresponding Clostridial toxin. As an example, as compared to a 17-mer corresponding to residues 187 to 203 of human SNAP-25, substitution of Asp193 with Asn in the BoNT/A substrate resulted in a relative rate of proteolysis of 0.23; substitution of Glu194 with Gln resulted in a relative rate of 2.08; substitution of Ala195 with 2-aminobutyric acid resulted in a relative rate of 0.38; and substitution of Gln197 with Asn, 2-aminobutyric acid or Ala resulted in a relative rate of 0.66, 0.25, or 0.19, respectively (see Table 3). Furthermore, substitution of Ala199 with 2-aminobutyric acid resulted in a relative rate of 0.79; substitution of Thr200 with Ser or 2-aminobutyric acid resulted in a relative rate of 0.26 or 1.20, respectively; substitution of Lys201 with Ala resulted in a relative rate of 0.12; and substitution of Met202 with Ala or norleucine resulted in a relative rate of 0.38 or 1.20, respectively, see, e.g., Schmidt & Bostian, supra, (1997). These results indicate that a variety of residues can be substituted in a Clostridial toxin substrate as compared to a naturally occurring toxin-sensitive sequence. In the case of BoNT/A, these results indicate that residues including but not limited to Glu194, Ala195, Gln197, Ala199, Thr200 and Met202, Leu203, Gly204, Ser205, and Gly206, as well as residues more distal from the Gln-Arg scissile bond, can be substituted or conjugated to a fluorophore, bulking group, donor fluorophore or acceptor in a BoNT/A substrate useful in the invention. Such a BoNT/A substrate is detectably proteolyzed at the scissile bond by BoNT/A under conditions suitable for Clostridial toxin protease activity. Thus, a BoNT/A substrate can include, if desired, one or several amino acid substitutions, additions or deletions relative to a naturally occurring SNAP-25 sequence.

TABLE 3

Kinetic Parameters of BoNT/A Synthetic Poptide Substrates

| Peptide | Sequence[a] | SEQ ID NO: | Relative Rate[b] |
|---|---|---|---|
| [1-15] | SNKTRIDEANQRATK | 106 | 0.03 |
| [1-16] | SNKTRIDEANQRATKM | 107 | 1.17 |
| [1-17] | SNKTRIDEANQRATKML | 108 | 1.00 |
| M16A | SNKTRIDEANQRATKAL | 111 | 0.38 |
| M16X | SNKTRIDEANQRATKXL | 112 | 1.20 |
| K15A | SNKTRIDEANQRATAML | 113 | 0.12 |
| T14S | SNKTRIDEANQRASKML | 114 | 0.26 |
| T14B | SNKTRIDEANQRABKML | 115 | 1.20 |
| A13B | SNKTRIDEANQRBTKML | 116 | 0.79 |
| Q11A | SNKTRIDEANARATKML | 117 | 0.19 |
| Q11B | SNKTRIDEANBRATKML | 118 | 0.25 |
| Q11N | SNKTRIDEANNRATKML | 119 | 0.66 |
| N10A | SNKTRIDEAAQRATKML | 120 | 0.06 |
| A98 | SNKTRIDEBNQRATKML | 121 | 0.38 |
| E8Q | SNKTRIDQANQRATKML | 122 | 2.08 |
| D7N | SNKTRINEANQRATKML | 123 | 0.23 |

[a] Nonstandard abbreviations: B 2-aminobutyric acid; X 2-aminohexanoic acid (norleucine)

[b] Initial hydrolysis rates relative to peptide [1-17]. Peptide concentrations were 1.0 mM.

Thus, in an embodiment, a cell comprises, in part, a membrane-associated BoNT/A substrate comprising a first member of a FRET pair and a BoNT/A recognition sequence including a cleavage site. As used herein, the term "botulinum toxin serotype A recognition sequence" is synonymous with "BoNT/A recognition sequence" and means a scissile bond together with adjacent or non-adjacent recognition elements, or both, sufficient for detectable proteolysis at the scissile bond by a BoNT/A under conditions suitable for Clostridial toxin protease activity. A scissile bond cleaved by BoNT/A can be, for example, Gln-Arg.

In an aspect of this embodiment, the Clostridial toxin substrate includes, in part, a BoNT/A recognition sequence comprising a BoNT/A recognition sequence containing at least six consecutive residues of SNAP-25 including Gln-Arg. In another aspect of this embodiment, the Clostridial toxin substrate includes, in part, a BoNT/A recognition sequence comprising the BoNT/A recognition sequence Glu-Ala-Asn-Gln-Arg-Ala-Thr-Lys (SEQ ID NO: 96). In other aspects of this embodiment, the Clostridial toxin substrate includes, in part, a BoNT/A recognition sequence comprising a portion of SNAP-25 such as, e.g., residues 1 to 206 of SEQ ID NO: 1; residues 46 to 206 of SEQ ID NO: 1; residues 134 to 206 of SEQ ID NO: 1; residues 137 to 206 of SEQ ID NO: 1; residues 146 to 206 of SEQ ID NO: 1, or a peptidomimetic thereof. In still other aspects of this embodiment, the Clostridial toxin substrate includes, in part, a BoNT/A recognition sequence comprising SEQ ID NO: 105, SEQ ID NO: 106, SEQ ID NO: 107, SEQ ID NO: 108, SEQ ID NO: 109, or SEQ ID NO: 110, or a peptidomimetic thereof.

A variety of BoNT/B recognition sequences are well known in the art or can be defined by routine methods. Such BoNT/B recognition sequences can include, for example, a sequence corresponding to some or all of the hydrophilic core of a VAMP protein such as human VAMP-1 or human VAMP-2. A BoNT/B recognition sequence can include, without limitation, residues 33 to 94, residues 45 to 94, residues 55 to 94, residues 60 to 94, residues 65 to 94, residues 60 to 88 or residues 65 to 88 of human VAMP-2 (SEQ ID NO: 31), or residues 60 to 94 of human VAMP-1-1 (SEQ ID NO: 28), VAMP-1-2 (SEQ ID NO: 29) and VAMP-1-3 (SEQ ID NO: 30) see, e.g., Shone et al., Eur. J. Biochem. 217: 965-971 (1993); and Shone et al., supra, (Oct. 5, 1999). A BoNT/B recognition sequence also can include, without limitation, the sequence Leu-Ser-Glu-Leu-Asp-Asp-Arg-Ala-Asp-Ala-Leu-Gln-Ala-Gly-Ala-Ser-Gln-Phe-Glu-Thr-Ser-Ala-Ala-Lys-Leu-Lys-Arg-Lys-Tyr-Trp-Trp-Lys-Asn-Leu-Lys (SEQ ID NO: 124) or a peptidomimetic thereof, which corresponds to residues 60 to 94 of human VAMP-2, see, e.g., James J. Schmidt & Robert G. Stafford, High Throughput Assays for the Proteolytic Activities of Clostridial Neurotoxins, U.S. Pat. No. 6,762,280 (Jul. 13, 2004) and the BoNT/B recognition sequence Leu-Ser-Glu-Leu-Asp-Asp-Arg-Ala-Asp-Ala-Leu-Gln-Ala-Gly-Ala-Ser-Gln-Phe-Glu-Ser-Ser-Ala-Ala-Lys-Leu-Lys-Arg-Lys-Tyr-Trp-Trp-Lys-Asn-Cys-Lys (SEQ ID NO: 125) or a peptidomimetic thereof, which corresponds to residues 62 to 96 of human VAMP-1.

A BoNT/B recognition sequence useful in aspects of the invention can correspond to a segment of a protein that is sensitive to cleavage by botulinum toxin serotype B, or can be substantially similar to a segment of a BoNT/B-sensitive protein. As shown in Table 4, a variety of naturally occurring proteins sensitive to cleavage by BoNT/B are known in the art and include, for example, human and mouse VAMP-1, VAMP-2 and VAMP-3/cellubrevin; bovine VAMP-2; rat VAMP-2 and VAMP-3; chicken VAMP-2; Torpedo VAMP-1; Strongylocentrotus VAMP; Drosophila sybA, synB, synC, synD and synE; Hirudo VAMP; and Caenorhabditis SNB1-like. Thus, a BoNT/B recognition sequence can correspond, for example, to a segment of human VAMP-1, VAMP-2 or VAMP-3; bovine VAMP-2; rat VAMP-2 or VAMP-3; mouse VAMP-1, VAMP-2 or VAMP-3; chicken VAMP-1, VAMP-2 or VAMP-3; Xenopus VAMP-2 or VAMP-3; Danio VAMP-1 or VAMP-2; Torpedo VAMP-1; Strongylocentrotus VAMP; Drosophila sybA, synB, synC, synD or synE; Hirudo VAMP; Loligo VAMP; Lymnaea VAMP; Aplysia VAMP; Caenorhabditis SNB1, isoforms thereof, or another naturally occurring protein sensitive to cleavage by BoNT/B. Furthermore, as shown in Table 4, comparison of native VAMP amino acid sequences cleaved by BoNT/B reveals that such sequences are not absolutely conserved, indicating that a variety of amino acid substitutions and modifications relative to a naturally occurring VAMP sequence can be tolerated in a BoNT/B substrate of the invention. It is understood that a similar BoNT/B recognition sequence can be prepared, if desired, from a corresponding (homologous) segment of another BoNT/B-sensitive VAMP-1 or VAMP-2 isoform, paralog or ortholog, such as, the BoNT/B recognition sequence contain in the VAMP-1 and VAMP-2 proteins identified in the organisms listed above and in Table 4.

TABLE 4

Cleavage of VAMP and Related Proteins

| Organism | Isoform | | Cleavage Sites | | | | |
|---|---|---|---|---|---|---|---|
| | | | | BoNT/F ▼ | | BoNT/D ▼ | |
| Primate | VAMP1-1<br>VAMP1-2<br>VAMP1-3 | RVNVDKVLERDQ | * | K | * | | LSELDDRADALQAGASQ |
| Primate | VAMP2 | RVNVDKVLERDQ | * | K | * | | LSELDDRADALQAGASQ |
| Primate | VAMP3 | RVNVDKVLERDQ | * | K | * | | LSELDDRADALQAGASQ |
| Bovine | VAMP2 | RVNVDKVLERDQ | * | K | * | | LSELDDRADALQAGASQ |
| Rodent | VAMP1/1b | RVNVDKVLERDQ | * | K | * | | LSELDDRADALQAGAS[V] |
| | VAMP1 | RVNVDKVLERDQ | * | K | * | | LSELDDRADALQAGASQ |
| Rodent | VAMP2<br>VAMP2-b | RVNVDKVLERDQ | * | K | * | | LSELDDRADALQAGASQ |
| Rodent | VAMP3 | RVNVDKVLERDQ | * | K | * | | LSELDDRADALQAGASQ |
| Bird | VAMP1 | RVNVDKVLERDQ | * | K | * | | LSELDDRADALQAGAS[V] |
| Bird | VAMP2 | RMNVDKVLERDQ | * | K | * | | LSELDNRADALQAGASQ |
| Bird | VAMP3 | RVNVDKVLERDQ | ND | K | ND | | LSELDDRADALQAGASQ |
| Amphibian | VAMP2 | RVNVDKVLERDQ[T] | ND | K | ND | | LSELDDRADALQAGASQ |
| Amphibian | VAMP3 | RVNVDKVLERDQ | ND | K | ND | | LSELDDRADALQAGASQ |
| Fish | VAMP1 | RVNVDKVLERDQ | ND | K | ND | | LSELDDRADALQAGASQ |
| Fish | VAMP2 | RVNVDKVLERDQ | ND | K | ND | | LSELDDRADALQAGASQ |
| Fish | VAMP-3 | RVNVDKVLERDQ | ND | K | ND | | LSELDDRADALQAGASQ |
| Ray | VAMP1 | RVNVDKVLERDQ | * | K | * | | LSELDDRADALQAGASQ |
| Sea urchin | VAMP | RVNVDKVLERDQ | — | [A] | — | | LSVLDDRADALQQGASQ |
| Insect | Syn-A1<br>Syn-B1 | RVNVEKVLERDQ | * | K | * | | LSELGERADQLEQGASQ |
| Insect | Syn-A2<br>Syn-B2 | RVNVEKVLERDQ | * | K | * | | LSELGERADQLEQGASQ |
| Insect | Syn-C<br>Syn-D<br>Syn-E | RTNVEKVLERD[S] | — | K | * | | LSELDDRADALQQGASQ |

TABLE 4-continued

Cleavage of VAMP and Related Proteins

| | | | | | | |
|---|---|---|---|---|---|---|
| Segmented worm | VAMP | RVNVDKVLEKDQ | * | K | * | LAELDGRADALQAGASQ |
| Cephalopod | VAMP | RVNVDKVLERDS | ND | K | ND | ISELDDRADALQAGASQ |
| Gastropod | VAMP | RVNVEKVLDRDQ | ND | K | ND | ISQLDDRADALQAGASQ |
| Round worm | SNB1<br>SNB-like | KVNVEKVLERDQ<br>RNNVNKVMERDV | ND<br>— | K<br>Q | ND<br>— | LSQLDDRADALQEGASQ<br>LNSLDHRAEVLQNGASQ |

| | Cleavage Sites | | | | |
|---|---|---|---|---|---|
| Organism | TeNT BoNT/B ▼ | | BoNT/G ▼ | | Cleaved Susceptibility |
| Primate | * | FESSA | * | AKLKRKYWW | BoNT/B; BoNT/D; BoNT/F; BoNT/G; TeNT |
| Primate | * | FETSA | * | AKLKRKYWW | BoNT/B; BoNT/D; BoNT/F; BoNT/G; TeNT |
| Primate | * | FETSA | * | AKLKRKYWW | BoNT/B; BoNT/D; BoNT/F; BoNT/G; TeNT |
| Bovine | * | FETSA | * | AKLKRKYWW | BoNT/B; BoNT/D; BoNT/F; BoNT/G; TeNT |
| Rodent | —[a]<br>* | FESSA<br>FESSA | *<br>* | AKLKRKYWW<br>AKLKRKYWW | BoNT/B; BoNT/D; BoNT/F; BoNT/G; TeNT |
| Rodent | * | FETSA | * | AKLKRKYWW | BoNT/B; BoNT/D; BoNT/F; BoNT/G; TeNT |
| Rodent | * | FETSA | * | AKLKRKYWW | BoNT/B; BoNT/D; BoNT/F; BoNT/G; TeNT |
| Bird | — | FESSA | * | AKLKRKYWW | BoNT/D; BoNT/F; BoNT/G |
| Bird | * | FETSA | * | AKLKRKYWW | BoNT/B; BoNT/D; BoNT/F; BoNT/G; TeNT |
| Bird | ND | FETSA | ND | AKLKRKYWW | ND |
| Amphibian | ND | FETSA | ND | AKLKRKYWW | ND |
| Amphibian | ND | FETSA | ND | AKLKRKYWW | ND |
| Fish | ND | FESSA | ND | AKLKNKYWW | ND |
| Fish | ND | FETSA | ND | AKLKNKYWW | ND |
| Fish | ND | FETSA | ND | AKLKRKYWW | ND |
| Ray | * | FESSA | * | AKLKRKYWW | BoNT/B; BoNT/D; BoNT/F; BoNT/G; TeNT |
| Sea urchin | * | FETNA | — | GKLKRKYWW | BoNT/B; TeNT |
| Insect | * | FEQQA | — | GKLKRKQWW | BoNT/B; BoNT/D; BoNT/F; TeNT |
| Insect | — | SEQQA | — | GKLKRKQWW | BoNT/D; BoNT/F |
| Insect | * | FEQQA | — | GKLKRKFWL | BoNT/B; BoNT/D; TeNT |
| Segmented worm | * | FEASA | — | GKLKRKFWW | BoNT/B; BoNT/D; BoNT/F; TeNT |
| Cephalopod | ND | FEASA | ND | GKLKRKFWW | ND |
| Gastropod | ND | FEASA | ND | GKLKRKFWW | ND |
| Round worm | ND<br>* | FEKSA<br>FQQSS | ND<br>— | ATLKRKYWW<br>RTLRQKYWW | BoNT/B; TeNT |

Proteolytic cleavage occurs at this site (*);
Proteolytic cleavage not detected at this site (—);
Proteolytic cleavage not determined at this site (ND)
[a]Rat VAMP1 resistance to BoNT/B and TeNT possibly due to Q189V substitution, see box.

Table 4—Cleavage of VAMP and related proteins. Primate: Human VAMP-1-1 residues 49-92 of SEQ ID NO: 28; Human VAMP-1-2 residues 49-92 of SEQ ID NO: 29; Human VAMP-1-3 residues 49-92 of SEQ ID NO: 30; Human VAMP-2 residues 47-90 of SEQ ID NO: 31; Monkey VAMP-2 residues 47-90 of SEQ ID NO: 32; Human VAMP-3/cellubrevin residues 30-73 of SEQ ID NO: 33; Bovine: Cow VAMP-2 residues 47-90 of SEQ ID NO: 34; Rodent: Rat VAMP-1 residues 49-92 of SEQ ID NO: 35; Rat VAMP-1-b residues 49-92 of SEQ ID NO: 36; Mouse VAMP-1 residues 49-92 of SEQ ID NO: 37; Rat VAMP-2 residues 47-90 of SEQ ID NO: 38; Rat VAMP-2-b residues 47-90 of SEQ ID NO: 39; Mouse VAMP-2 residues 47-90 of SEQ ID NO: 40; Rat VAMP-3/cellubrevin residues 34-77 of SEQ ID NO: 41; Mouse VAMP-3/cellubrevin residues 34-77 of SEQ ID NO: 42; Bird: Chicken VAMP-1 residues 190-233 of SEQ ID NO: 43; Chicken VAMP-2 residues 47-88 of SEQ ID NO: 44; Chicken VAMP-3/cellubrevin residues 34-77 of SEQ ID NO: 45; Fish: Zebrafish VAMP-1 residues 50-93 of SEQ ID NO: 46; Zebrafish VAMP-2 residues 41-84 of SEQ ID NO: 47; Zebrafish VAMP-3 residues 33-60 of SEQ ID NO: 48; Ray: marbled electric ray VAMP-1 residues 51-94 of SEQ ID NO: 49; Amphibian: Frog VAMP-2 residues 45-88 of SEQ ID NO: 50; Frog VAMP-3 residues 32-75 of SEQ ID NO: 51; Sea urchin VAMP residues 31-74 of SEQ ID NO: 52; Insect: Fruit fly SynA1 residues 40-83 of SEQ ID NO: 53; Fruit fly SynA2 residues 63-106 of SEQ ID NO: 54; Fruit fly SynB1 residues 63-106 of SEQ ID NO: 55; Fruit fly SynB2 residues 63-106 of SEQ ID NO: 56; Fruit fly SynC residues 57-100 of SEQ ID NO: 57; Fruit fly SynD residues 66-109 of SEQ ID NO: 58; Fruit fly SynE residues 57-100 of SEQ ID NO: 59; Segmented worm: Leech VAMP residues 45-88 of SEQ ID NO: 60; Cephalopod: squid VAMP residues 56-99 of SEQ ID NO: 61; Gastropod: Pond snail VAMP residues 49-92 of SEQ ID NO: 62; sea hare VAMP residues 37-80 of SEQ ID NO: 63; Round worm: Nematode worm SNB1 residues 72-115 of SEQ ID NO: 64; Nematode worm SNB-like residues 82-115 of SEQ ID NO: 65.

Thus, in an embodiment, a cell comprises, in part, a membrane-associated BoNT/B substrate comprising a first member of a FRET pair and a BoNT/B recognition sequence including a cleavage site. As used herein, the term "botulinum toxin serotype B recognition sequence" is synonymous with "BoNT/B recognition sequence" and means a scissile bond together with adjacent or non-adjacent recognition elements, or both, sufficient for detectable proteolysis at the scissile bond by a BoNT/B under appropriate conditions. A scissile bond cleaved by BoNT/B can be, for example, Gln-Phe.

In an aspect of this embodiment, the Clostridial toxin substrate includes, in part, a BoNT/B recognition sequence comprising a BoNT/B recognition sequence containing at least six consecutive residues of VAMP including Gln-Phe. In another aspect of this embodiment, the Clostridial toxin substrate includes, in part, a BoNT/B recognition sequence comprising the BoNT/B recognition sequence Gly-Ala-Ser-Gln-Phe-Glu-Thr-Ser (SEQ ID NO: 97). In other aspects of this embodiment, the Clostridial toxin substrate includes, in part, a BoNT/B recognition sequence comprising a portion of VAMP-1-1 such as, e.g., residues 1 to 118 of SEQ ID NO: 28; residues 62 to 96 of SEQ ID NO: 28, or a peptidomimetic thereof. In other aspects of this embodiment, the Clostridial toxin substrate includes, in part, a BoNT/B recognition sequence comprising a portion of VAMP-1-2 such as, e.g., residues 1 to 117 of SEQ ID NO: 29; residues 62 to 96 of SEQ ID NO: 29, or a peptidomimetic thereof. In other aspects of this embodiment, the Clostridial toxin substrate includes, in part, a BoNT/B recognition sequence comprising a portion of VAMP-1-3 such as, e.g., residues 1 to 116 of SEQ ID NO: 30; residues 62 to 96 of SEQ ID NO: 30, or a peptidomimetic thereof. In other aspects of this embodiment, the Clostridial toxin substrate includes, in part, a BoNT/B recognition sequence comprising a portion of VAMP-2 such as, e.g., residues 1 to 116 of SEQ ID NO: 31; residues 33 to 94 of SEQ ID NO: 31; residues 45 to 94 of SEQ ID NO: 31; residues 55 to 94 of SEQ ID NO: 31; residues 60 to 94 of SEQ ID NO: 31; residues 65 to 94 of SEQ ID NO: 31; residues 60 to 88 of SEQ ID NO: 31; residues 65 to 88 of SEQ ID NO: 31, or a peptidomimetic thereof.

It is understood that a BoNT/C1 recognition sequence can correspond to a segment of a protein that is sensitive to cleavage by botulinum toxin serotype C1, or can be substantially similar to a segment of a BoNT/C1-sensitive protein. As further shown in Table 5, a variety of naturally occurring proteins sensitive to cleavage by BoNT/C1 are known in the art and include, for example, human and mouse Syntaxin 1A, Syntaxin 1B1 and Syntaxin 1B2; bovine and rat Syntaxin 1A and Syntaxin 1B2; rat Syntaxin 2 and Rat syntaxin 3; *Strongylocentrotus* Syntaxin; *Drosophila* Syntaxin 1A; *Hirudo* Syntaxin 1A; *Loligo* Syntaxin 1A; *Aplysia* Syntaxin 1A. Thus, a BoNT/C1 recognition sequence can correspond, for example, to a segment of human Syntaxin 1A, Syntaxin 1B1, Syntaxin 1B2, Syntaxin 2-1, Syntaxin 2-2, Syntaxin 2-3 or Syntaxin 3A; bovine Syntaxin 1A, Syntaxin 1B1 or Syntaxin 1B2; rat Syntaxin 1A, Syntaxin 1B1, Syntaxin 1B2, Syntaxin 2 or Syntaxin 3A; mouse Syntaxin 1A, Syntaxin 1B1, Syntaxin 1B2, Syntaxin 2, Syntaxin 3A, Syntaxin 3B or Syntaxin 3C; chicken Syntaxin 1A or Syntaxin 2; *Xenopus* Syntaxin 1A or Syntaxin 1B; *Danio* Syntaxin 1A, Syntaxin 1B or Syntaxin 3; *Torpedo* Syntaxin 1A or Syntaxin 1B; *Strongylocentrotus* Syntaxin 1A or Syntaxin 1B; *Drosophila* Syntaxin 1A or Syntaxin 1B; *Hirudo* Syntaxin 1A or Syntaxin 1B; *Loligo* Syntaxin 1A or Syntaxin 1B; *Lymnaea* Syntaxin 1A or Syntaxin 1B, isoforms thereof, or another naturally occurring protein sensitive to cleavage by BoNT/C1. Furthermore, comparison of native syntaxin amino acid sequences cleaved by BoNT/C1 reveals that such sequences are not absolutely conserved (see Table 5), indicating that a variety of amino acid substitutions and modifications relative to a naturally occurring BoNT/C1-sensitive syntaxin sequence can be tolerated in a BoNT/C1 substrate useful in the invention. It is understood that a similar BoNT/C1 recognition sequence can be prepared, if desired, from a corresponding (homologous) segment of another BoNT/C1-sensitive syntaxin isoform, paralog or ortholog, such as, the BoNT/C1 recognition sequence contain in the syntaxin proteins identified in the organisms listed above and in Table 5.

Table 5—Cleavage of Syntaxin and related proteins. Primate: Human Syntaxin1A residues 242-264 of SEQ ID NO: 66; Human Syntaxin1B1 residues 241-263 of SEQ ID NO: 67; Human Syntaxin1B2 residues 241-263 of SEQ ID NO: 68; Human Syntaxin2-1 residues 241-263 of SEQ ID NO: 69; Human Syntaxin2-2 residues 241-263 of SEQ ID NO: 70; Human Syntaxin2-3 residues 241-263 of SEQ ID NO: 71; Human Syntaxin3 residues 241-263 of SEQ ID NO: 72; Bovine: Cow Syntaxin1A residues 242-264 of SEQ ID NO: 73; Cow Syntaxin1B2 residues 241-263 of SEQ ID NO: 74; Rodent: Rat Syntaxin1A residues 242-264 of SEQ ID NO: 75; Rat Syntaxin1B2 residues 241-263 of SEQ ID NO: 76; Mouse Syntaxin1A residues 242-264 of SEQ ID NO: 77; Mouse Syntaxin1B1 residues 241-263 of SEQ ID NO: 78; Mouse Syntaxin1B2 residues 241-263 of SEQ ID NO: 79; Rat Syntaxin2 residues 243-265 of SEQ ID NO: 80; Mouse Syntaxin2 residues 242-264 of SEQ ID NO: 81; Rat Syntaxin3A residues 241-263 of SEQ ID NO: 82; Mouse Syntaxin3A residues 241-263 of SEQ ID NO: 83; Mouse Syntaxin3B residues 241-263 of SEQ ID NO: 84; Mouse Syntaxin3C residues 223-245 of SEQ ID NO: 85; Bird: Chicken Syntaxin1B residues 235-257 of SEQ ID NO: 86; Chicken Syntaxin2 residues 240-262 of SEQ ID NO: 87; Fish: Zebrafish Syntaxin1B residues 241-263 of SEQ ID NO: 88; Zebrafish Syntaxin3 residues 239-261 of SEQ ID NO: 89; sea urchin Syntaxin1B residues 241-263 of SEQ ID NO: 90; Insect: Fruit fly Syntaxin1A residues 245-267 of SEQ ID NO: 91; Segmented worm: leech Syntaxin1A residues 248-270 of SEQ ID NO: 92; Cephalopod: squid Syntaxin1A residues 245-267 of SEQ ID NO: 93; Gastropod: Pond snail Syntaxin1A residues 244-266 of SEQ ID NO: 94; sea hare Syntaxin1A residues 244-266 of SEQ ID NO: 95.

TABLE 5

Cleavage of Syntaxin and Related Proteins

| | | Cleavage Site | | | |
|---|---|---|---|---|---|
| Organism | Isoform | | BoNT/C1 ▼ | | Cleaved Susceptibility |
| Primate | Syntaxin1A<br>Syntaxin1B1<br>Syntaxin1B2 | DYVERAVSDTKK | * | AVKYQSKARRK | BoNT/C1 |
| Primate | Syntaxin2-1<br>Syntaxin2-2<br>Syntaxin2-3 | DYVEHAKEETKK | ND | AIKYQSKARRK | ND |
| Primate | Syntaxin3A | DHVEKARDESKK | ND | AVKYQSQARKK | ND |
| Bovine | Syntaxin1A<br>Syntaxin1B2 | DYVERAVSDTKK | * | AVKYQSKARRK | BoNT/C1 |
| Rodent | Syntaxin1A<br>Syntaxin1B1<br>Syntaxin1B2 | DYVERAVSDTKK | * | AVKYQSKARRK | BoNT/C1 |
| Rodent | Syntaxin2 | DYVEHAKEETKK | * | AIKYQSKARRK | BoNT/C1 |
| Rodent | Syntaxin3A | DHVEKARDETKR | * | AMKYQGQARKK | BoNT/C1 |
| Rodent | Syntaxin3B<br>Syntaxin3C | GFVERAVADTKK | ND | AVKYQSEARRK | ND |
| Bird | Syntaxin1B | DYVEPVVFVTKS | ND | AVMYQCKSRRK | ND |
| Bird | Syntaxin2 | DYVEHAKEETKK | ND | AVKYQSKARRK | ND |
| Fish | Syntaxin1B | DYVERAVSDTKK | * | AVKYQSQARKK | BoNT/C1 |
| Fish | Syntaxin3 | DHVEAARDETKK | ND | AVRYQSKARKK | ND |
| Sea urchin | Syntaxin1B | DYVRRQNDTKK | * | AVKYQSKARRK | BoNT/C1 |
| Insect | Syntaxin1A | DYVQTATQDTKK | * | ALKYQSKARRK | BoNT/C1 |
| Segmented worm | Syntaxin1A | DYVETAAADTKK | * | AMKYQSAARKK | BoNT/C1 |
| Cephalopod | Syntaxin1A | DYIETAKVDTKK | * | AVKYQSKARQK | BoNT/C1 |
| Gastropod | Syntaxin1A | DYIETAKMDTKK | * | AVKYQSKARRK | BoNT/C1 |

Proteolytic cleavage occurs at this site (*);
Proteolytic cleavage not detected at this site (—);
Proteolytic cleavage not determined at this site (ND)

As further shown in Table 2, a variety of naturally occurring proteins sensitive to cleavage by BoNT/C1 are known in the art and include, for example, human, rat, mouse, *Danio, Carassius* SNAP-25A and SNAP-25B; and *Drosophila* SNAP-25. Thus, a BoNT/C1 recognition sequence can correspond, for example, to a segment of human SNAP-25A or SNAP-25B; bovine SNAP-25A or SNAP-25B; rat SNAP-25A or SNAP-25B; mouse SNAP-25A or SNAP-25B; *Xenopus* SNAP-25A or SNAP-25B; *Danio* SNAP-25A or SNAP-25B; *Carassius* SNAP-25A or SNAP-25B; *Torpedo* SNAP-25; *Strongylocentrotus* SNAP-25; *Drosophila* SNAP-25 or SNAP-24; *Hirudo* SNAP-25; *Loligo* SNAP-25; *Lymnaea* SNAP-25, isoforms thereof, or another naturally occurring protein sensitive to cleavage by BoNT/C1. As discussed above in regard to variants of naturally occurring syntaxin sequences, comparison of native SNAP-25 amino acid sequences cleaved by BoNT/C1 reveals significant sequence variability (Table 2), indicating that a variety of amino acid substitutions and modifications relative to a naturally occurring BoNT/C1-sensitive SNAP-25 sequence can be tolerated in a BoNT/C1 substrate useful in the invention. It is understood that a similar BoNT/C1 recognition sequence can be prepared, if desired, from a corresponding (homologous) segment of another BoNT/C1-sensitive SNAP-25 isoform, paralog or ortholog, such as, the BoNT/A recognition sequence contain in the SNAP-25 proteins identified in the organisms listed above and in Table 2.

Thus, in an embodiment, a cell comprises, in part, a membrane-associated BoNT/C1 substrate comprising a first member of a FRET pair and a BoNT/C1 recognition sequence including a cleavage site. As used herein, the term "botulinum toxin serotype C1 recognition sequence" is synonymous with "BoNT/C1 recognition sequence" and means a scissile bond together with adjacent or non-adjacent recognition elements, or both, sufficient for detectable proteolysis at the scissile bond by a BoNT/C1 under appropriate conditions. A scissile bond cleaved by BoNT/C1 can be, for example, Lys-Ala or Arg-Ala.

In an aspect of this embodiment, the encoded Clostridial toxin substrate includes, in part, a BoNT/C1 recognition sequence comprising a BoNT/C1 recognition sequence containing at least six consecutive residues of Syntaxin including Lys-Ala. In another aspect of this embodiment, the Clostridial toxin substrate includes, in part, a BoNT/C1 recognition sequence comprising the BoNT/C1 recognition sequence Asp-Thr-Lys-Lys-Ala-Val-Lys-Tyr (SEQ ID NO: 98). In another aspect of this embodiment, the Clostridial toxin substrate includes, in part, a BoNT/C1 recognition sequence comprising a BoNT/C1 recognition sequence containing at least six consecutive residues of SNAP-25 including Arg-Ala. In another aspect of this embodiment, the Clostridial toxin substrate includes, in part, a BoNT/C1 recognition sequence comprising the BoNT/C1 recognition sequence Ala-Asn-Gln-Arg-Ala-Thr-Lys-Met (SEQ ID NO: 99). In yet another aspect of this embodiment, the Clostridial toxin substrate includes, in part, a BoNT/C1 recognition sequence comprising a BoNT/C1 recognition sequence containing at least six consecutive residues of Syntaxin including Lys-Ala and a BoNT/C1 recognition sequence comprising a BoNT/C1 recognition sequence containing at least six consecutive residues of SNAP-25 including Arg-Ala.

In other aspects of this embodiment, the Clostridial toxin substrate includes, in part, a BoNT/C1 recognition sequence comprising a portion of Syntaxin-1A such as, e.g., residues 1 to 288 of SEQ ID NO: 66, or a peptidomimetic thereof. In other aspects of this embodiment, the Clostridial toxin substrate includes, in part, a BoNT/C1 recognition sequence comprising a portion of Syntaxin-1B1 such as, e.g., residues 1 to 288 of SEQ ID NO: 67, or a peptidomimetic thereof. In other aspects of this embodiment, the Clostridial toxin substrate includes, in part, a BoNT/C1 recognition sequence comprising a portion of Syntaxin-1B2 such as, e.g., residues 1 to 288 of SEQ ID NO: 68, or a peptidomimetic thereof. In other aspects of this embodiment, the Clostridial toxin substrate includes, in part, a BoNT/C1 recognition sequence comprising a portion of Syntaxin 2-1 such as, e.g., residues 1 to 287 of SEQ ID NO: 69, or a peptidomimetic thereof. In other aspects of this embodiment, the Clostridial toxin substrate includes, in part, a BoNT/C1 recognition sequence comprising a portion of Syntaxin-2-2 such as, e.g., residues 1 to 288 of SEQ ID NO: 70, or a peptidomimetic thereof. In other aspects of this embodiment, the Clostridial toxin substrate includes, in part, a BoNT/C1 recognition sequence comprising a portion of Syntaxin-2-3 such as, e.g., residues 1 to 289 of SEQ ID NO: 71, or a peptidomimetic thereof. In other aspects of this embodiment, the Clostridial toxin substrate includes, in part, a BoNT/C1 recognition sequence comprising a portion of Syntaxin-3A such as, e.g., residues 1 to 289 of SEQ ID NO: 83, or a peptidomimetic thereof. In other aspects of this embodiment, the Clostridial toxin substrate includes, in part, a BoNT/C1 recognition sequence comprising a portion of Syntaxin-3B such as, e.g., residues 1 to 283 of SEQ ID NO: 84, or a peptidomimetic thereof. In other aspects of this embodiment, the Clostridial toxin substrate includes, in part, a BoNT/C1 recognition sequence comprising a portion of Syntaxin-3C such as, e.g., residues 1 to 269 of SEQ ID NO: 85, or a peptidomimetic thereof.

In other aspects of this embodiment, the Clostridial toxin substrate includes, in part, a BoNT/C1 recognition sequence comprising a portion of SNAP-25 such as, e.g., residues 1 to 206 of SEQ ID NO: 1; residues 93 to 206 of SEQ ID NO: 1; residues 134 to 206 of SEQ ID NO: 1; residues 137 to 206 of SEQ ID NO: 1; residues 146 to 206 of SEQ ID NO: 1; residues 137 to 202 of SEQ ID NO: 1, or a peptidomimetic thereof. In still other aspects of this embodiment, the Clostridial toxin substrate includes, in part, a BoNT/C1 recognition sequence comprising SEQ ID NO: 105, SEQ ID NO: 106, SEQ ID NO: 107, SEQ ID NO: 108, SEQ ID NO: 109, or SEQ ID NO: 110, or a peptidomimetic thereof.

A variety of BoNT/D recognition sequences are well known in the art or can be defined by routine methods. A BoNT/D recognition sequence can include, for example, residues 27 to 116; residues 37 to 116; residues 1 to 86; residues 1 to 76; or residues 1 to 69 of rat VAMP-2, see, e.g., Shinji Yamasaki et al., Cleavage of members of the synaptobrevin/VAMP family by types D and F botulinum neurotoxins and tetanus toxin, 269(17) J. Biol. Chem. 12764-12772 (1994). Thus, a BoNT/D recognition sequence can include, for example, residues 27 to 69 or residues 37 to 69 of rat VAMP-2. A BoNT/D recognition sequence also can include, without limitation, the sequence Ala-Gln-Val-Asp-Glu-Val-Val-Asp-Ile-Met-Arg-Val-Asn-Val-Asp-Lys-Val-Leu-Glu-Arg-Asp-Gln-Lys-Leu-Ser-Glu-Leu-Asp-Asp-Arg-Ala-Asp-Ala-Leu-Gln-Ala-Gly-Ala-Ser (SEQ ID NO: 126) or a peptidomimetic thereof, which corresponds to residues 37 to 75 of human VAMP-2, see, e.g., Schmidt & Stafford, supra, (Jul. 13, 2004) and the BoNT/D recognition sequence Ala-Gln-Val-Glu-Glu-Val-Val-Asp-Ile-Ile-Arg-Val-Asn-Val-Asp-Lys-Val-Leu-Glu-Arg-Asp-Gln-Lys-Leu-Ser-Glu-Leu-Asp-Asp-Arg-Ala-Asp-Ala-Leu-Gln-Ala-Gly-Ala-Ser (SEQ ID NO: 127) or a peptidomimetic thereof, which corresponds to residues 39 to 77 of the human VAMP-1 isoforms, VAMP-1-1, VAMP-1-2 and VAMP-1-3.

A BoNT/D recognition sequence can correspond to a segment of a protein that is sensitive to cleavage by botulinum toxin serotype D, or can be substantially similar to a segment of a BoNT/D-sensitive protein. As shown in Table 4, a variety of naturally occurring proteins sensitive to cleavage by BoNT/D are known in the art and include, for example, human, rat and mouse VAMP-1, VAMP-2 and VAMP-3/cellubrevin; bovine VAMP-2; chicken VAMP-1, VAMP-2 and VAMP-3; *Xenopus* VAMP-2 or VAMP-3; *Danio* VAMP-1 or VAMP-2; *Torpedo* VAMP-1; *Strongylocentrotus* VAMP; *Drosophila* sybA, synB, synC, synD, synE; *Hirudo* VAMP; *Loligo* VAMP; *Lymnaea* VAMP; *Aplysia* VAMP; and *Caenorhabditis* SNB1. Thus, a BoNT/D recognition sequence can correspond, for example, to a segment of human VAMP-1, VAMP-2 or VAMP-3; bovine VAMP-2; rat VAMP-1, VAMP-2 or VAMP-3; mouse VAMP-1, VAMP-2 or VAMP-3; chicken VAMP-1, VAMP-2 or VAMP-3; *Xenopus* VAMP-2 or VAMP-3; *Danio* VAMP-1 or VAMP-2; Torpedo VAMP-1; *Strongylocentrotus* VAMP; *Drosophila* sybA, synB, synC, synD, synE; Hirudo VAMP; Loligo VAMP; *Lymnaea* VAMP; Aplysia VAMP; *Caenorhabditis* SNB1, isoforms thereof, or another naturally occurring protein sensitive to cleavage by BoNT/D. Furthermore, as shown in Table 4 above, comparison of native VAMP amino acid sequences cleaved by BoNT/D reveals significant sequence variability, indicating that a variety of amino acid substitutions and modifications relative to a naturally occurring BoNT/D-sensitive VAMP sequence can be tolerated in a BoNT/D substrate useful in the invention. It is understood that a similar BoNT/D recognition sequence can be prepared, if desired, from a corresponding (homologous) segment of another BoNT/D-sensitive VAMP-1 or VAMP-2 isoform, paralog or ortholog, such as, the BoNT/B recognition sequence contain in the VAMP-1 and VAMP-2 proteins identified in the organisms listed above and in Table 4.

Thus, in an embodiment, a cell comprises, in part, a membrane-associated BoNT/D substrate comprising a first member of a FRET pair and a BoNT/D recognition sequence including a cleavage site. The term "botulinum toxin serotype D recognition sequence" is synonymous with "BoNT/D recognition sequence" and means a scissile bond together with adjacent or non-adjacent recognition elements, or both, sufficient for detectable proteolysis at the scissile bond by a BoNT/D under appropriate conditions. A scissile bond cleaved by BoNT/D can be, for example, Lys-Leu.

In an aspect of this embodiment, the Clostridial toxin substrate includes, in part, a BoNT/D recognition sequence comprising a BoNT/D recognition sequence containing at least six consecutive residues of VAMP including Lys-Leu. In another aspect of this embodiment, the Clostridial toxin substrate includes, in part, a BoNT/D recognition sequence comprising the BoNT/D recognition sequence Arg-Asp-Gln-Lys-Leu-Ser-Glu-Leu (SEQ ID NO: 100). In other aspects of this embodiment, the Clostridial toxin substrate includes, in part, a BoNT/D recognition sequence comprising a portion of VAMP-1-1 such as, e.g., residues 1 to 118 of SEQ ID NO: 28; residues 39 to 77 of SEQ ID NO: 28, or a peptidomimetic thereof. In other aspects of this embodiment, the Clostridial toxin substrate includes, in part, a BoNT/D recognition sequence comprising a portion of VAMP-1-2 such as, e.g., residues 1 to 117 of SEQ ID NO: 29; residues 39 to 77 of SEQ ID NO: 29, or a peptidomimetic thereof. In other aspects of this embodiment, the Clostridial toxin substrate includes, in part, a BoNT/D recognition sequence comprising a portion of VAMP-1-3 such as, e.g., residues 1 to 116 of SEQ ID NO: 30; residues 39 to 77 of SEQ ID NO: 30, or a peptidomimetic thereof. In other aspects of this embodiment, the Clostridial toxin substrate includes, in part, a BoNT/D recognition sequence comprising a portion of VAMP-2 such as, e.g., residues 1 to 116 of SEQ ID NO: 31; residues 1 to 86 of SEQ ID NO: 31; residues 1 to 76 of SEQ ID NO: 31; residues 1 to 69 of SEQ ID NO: 31; residues 27 to 116 of SEQ ID NO: 31; residues 37 to 116 of SEQ ID NO: 31; residues 27 to 68 of SEQ ID NO: 31; residues 37 to 69 of SEQ ID NO: 31, or a peptidomimetic thereof.

One skilled in the art appreciates that a BoNT/E recognition sequence can correspond to a segment of a protein that is sensitive to cleavage by botulinum toxin serotype E, or can be substantially similar to a segment of a BoNT/E-sensitive protein. A BoNT/E recognition sequence can have, for example, residues 46-206, residues 92 to 206, residues, residues 134 to 206, residues, 137 to 206; 146-206 or 156-206 of human SNAP-25, see, e.g., Vaidyanathan et al., supra, (1999); and Schmidt & Stafford, supra, (Jul. 13, 2004).

A BoNT/E recognition sequence useful in aspects of the invention can correspond to a segment of a protein that is sensitive to cleavage by botulinum toxin serotype E, or can be substantially similar to a segment of a BoNT/E-sensitive protein. As shown in Table 2, a variety of naturally occurring proteins sensitive to cleavage by BoNT/E are known in the art and include, for example, human, chicken, *Danio, Carassius* SNAP-25A and SNAP-25B; rat and mouse SNAP-25A, SNAP-25B and SNAP-23; and *Caenorhabditis* SNAP-25. Thus, a BoNT/E recognition sequence can correspond, for example, to a segment of human SNAP-25A or SNAP-25B; bovine SNAP-25A or SNAP-25B; rat SNAP-25A, SNAP-25B or SNAP-23; mouse SNAP-25A, SNAP-25B or SNAP-23; *Xenopus* SNAP-25A or SNAP-25B; *Danio* SNAP-25A or SNAP-25B; *Carassius* SNAP-25A or SNAP-25B; *Strongylocentrotus* SNAP-25; *Drosophila* SNAP-24; *Hirudo* SNAP-25; *Loligo* SNAP-25; *Lymnaea* SNAP-25; *Caenorhabditis* SNAP-25, isoforms thereof, or another naturally occurring protein sensitive to cleavage by BoNT/C1. Furthermore, as shown in Table 2, comparison of native SNAP-23 and SNAP-25 amino acid sequences cleaved by BoNT/E reveals that such sequences are not absolutely conserved, indicating that a variety of amino acid substitutions and modifications relative to a naturally occurring BoNT/E-sensitive SNAP-23 or SNAP-25 sequence can be tolerated in a BoNT/E substrate useful in the invention. It is understood that a similar BoNT/E recognition sequence can be prepared, if desired, from a corresponding (homologous) segment of another BoNT/E-sensitive SNAP-25 isoform, paralog or ortholog, such as, the BoNT/E recognition sequence contain in the SNAP-25 proteins identified in the organisms listed above and in Table 2.

Thus, in an embodiment, a cell comprises, in part, a membrane-associated BoNT/E substrate comprising a first member of a FRET pair and a BoNT/E recognition sequence including a cleavage site. As used herein, the term "botulinum toxin serotype E recognition sequence" is synonymous with "BoNT/E recognition sequence" and means a scissile bond together with adjacent or non-adjacent recognition elements, or both, sufficient for detectable proteolysis at the scissile bond by a BoNT/E under appropriate conditions. A scissile bond cleaved by BoNT/E can be, for example, Arg-Ile.

In an aspect of this embodiment, the Clostridial toxin substrate includes, in part, a BoNT/E recognition sequence comprising a BoNT/E recognition sequence containing at least six consecutive residues of SNAP-25 including Arg-Ile. In another aspect of this embodiment, the Clostridial toxin substrate includes, in part, a BoNT/E recognition sequence comprising the BoNT/E recognition sequence Gln-Ile-Asp-Arg-Ile-Met-Glu-Lys (SEQ ID NO: 101). In other aspects of this embodiment, the Clostridial toxin substrate includes, in part, a BoNT/E recognition sequence comprising a portion of SNAP-25 such as, e.g., residues 1 to 206 of SEQ ID NO: 1; residues 46 to 206 of SEQ ID NO: 1; residues 92 to 206 of SEQ ID NO: 1; residues 134 to 206 of SEQ ID NO: 1; residues 137 to 206 of SEQ ID NO: 1, residues 146 to 206 of SEQ ID NO: 1; residues 156 to 206 of SEQ ID NO: 1, or a peptidomimetic thereof.

A variety of BoNT/F recognition sequences are well known in the art or can be defined by routine methods. A BoNT/F recognition sequence can include, for example, residues 27 to 116; residues 37 to 116; residues 1 to 86; residues 1 to 76; or residues 1 to 69 of rat VAMP-2, see, e.g., Yamasaki et al., supra, (1994). A BoNT/F recognition sequence also can include, for example, residues 27 to 69 or residues 37 to 69 of rat VAMP-2. It is understood that a similar BoNT/F recognition sequence can be prepared, if desired, from a corresponding (homologous) segment of another BoNT/F-sensitive VAMP isoform, paralog or ortholog, such as, e.g., human VAMP-1 or human VAMP-2. A BoNT/F recognition sequence also can include, without limitation, the sequence Ala-Gln-Val-Asp-Glu-Val-Val-Asp-Ile-Met-Arg-Val-Asn-Val-Asp-Lys-Val-Leu-Glu-Arg-Asp-Gln-Lys-Leu-Ser-Glu-Leu-Asp-Asp-Arg-Ala-Asp-Ala-Leu-Gln-Ala-Gly-Ala-Ser (SEQ ID NO: 126) or a peptidomimetic thereof, which corresponds to residues 37 to 75 of human VAMP-2, see, e.g., Schmidt & Stafford, supra, (Jul. 13, 2004) and the BoNT/F recognition sequence Ala-Gln-Val-Glu-Glu-Val-Val-Asp-Ile-Ile-Arg-Val-Asn-Val-Asp-Lys-Val-Leu-Glu-Arg-Asp-Gln-Lys-Leu-Ser-Glu-Leu-Asp-Asp-Arg-Ala-Asp-Ala-Leu-Gln-Ala-Gly-Ala-Ser (SEQ ID NO: 127) or a peptidomimetic thereof, which corresponds to residues 39 to 77 of human VAMP-1.

A BoNT/F recognition sequence can correspond to a segment of a protein that is sensitive to cleavage by botulinum toxin serotype F, or can be substantially similar to a segment of a BoNT/F-sensitive protein. As shown in Table 4, a variety of naturally occurring proteins sensitive to cleavage by BoNT/F are known in the art and include, for example, human, rat and mouse VAMP-1, VAMP-2 and VAMP-3/cellubrevin; bovine VAMP-2; chicken VAMP-1 and VAMP-2; Torpedo VAMP-1; and *Drosophila* sybA and synB. Thus, a BoNT/F recognition sequence can correspond, for example, to a segment of human VAMP-1, VAMP-2 or VAMP-3; bovine VAMP-2; rat VAMP-1, VAMP-2 or VAMP-3; mouse VAMP-1, VAMP-2 or VAMP-3; chicken VAMP-1, VAMP-2 or VAMP-3; *Xenopus* VAMP-2 or VAMP-3; *Danio* VAMP-1 or VAMP-2; *Torpedo* VAMP-1; *Drosophila* sybA and synB; *Hirudo* VAMP; *Loligo* VAMP; *Lymnaea* VAMP; *Aplysia* VAMP; *Caenorhabditis* SNB1, isoforms thereof, or another naturally occurring protein sensitive to cleavage by BoNT/F. Thus, a BoNT/F recognition sequence can correspond, for example, to a segment of human VAMP-1 or VAMP-2, mouse VAMP-1 or VAMP-2, bovine VAMP-1 or VAMP-2, rat VAMP-1 or VAMP-2, rat cellubrevin, chicken VAMP-1 or VAMP-2, *Torpedo* VAMP-1, *Aplysia* VAMP, *Drosophila* syb, leech VAMP, or another naturally occurring protein sensitive to cleavage by BoNT/F. Furthermore, as shown in Table 4 above, comparison of native VAMP amino acid sequences cleaved by BoNT/F reveals that such sequences are not absolutely conserved, indicating that a variety of amino acid substitutions and modifications relative to a naturally occurring BoNT/F-sensitive VAMP sequence can be tolerated in a BoNT/F substrate useful in the invention. It is understood that a similar BoNT/F recognition sequence can be prepared, if desired, from a corresponding (homologous) segment of another BoNT/F-sensitive VAMP-1 or VAMP-2 isoform, paralog or ortholog, such as, the BoNT/F recognition sequence contain in the VAMP-1 and VAMP-2 identified in the organisms listed above and in Table 4.

Thus, in an embodiment, a cell comprises, in part, a membrane-associated BoNT/F substrate comprising a first member of a FRET pair and a BoNT/F recognition sequence including a cleavage site. The term "botulinum toxin serotype F recognition sequence," as used herein, is synonymous with "BoNT/F recognition sequence" and means a scissile bond together with adjacent or non-adjacent recognition elements, or both, sufficient for detectable proteolysis at the scissile bond by a BoNT/F under appropriate conditions. A scissile bond cleaved by BoNT/F can be, for example, Gln-Lys.

In an aspect of this embodiment, the Clostridial toxin substrate includes, in part, a BoNT/F recognition sequence comprising a BoNT/F recognition sequence containing at least six consecutive residues of VAMP including Gln-Lys. In another aspect of this embodiment, the Clostridial toxin substrate includes, in part, a BoNT/F recognition sequence comprising the BoNT/F recognition sequence Glu-Arg-Asp-Gln-Lys-Leu-Ser-Glu (SEQ ID NO: 102). In other aspects of this embodiment, the Clostridial toxin substrate includes, in part, a BoNT/F recognition sequence comprising a portion of VAMP-1-1 such as, e.g., residues 1 to 118 of SEQ ID NO: 28; residues 39 to 77 of SEQ ID NO: 28, or a peptidomimetic thereof. In other aspects of this embodiment, the Clostridial toxin substrate includes, in part, a BoNT/F recognition sequence comprising a portion of VAMP-1-2 such as, e.g., residues 1 to 117 of SEQ ID NO: 29; residues 39 to 77 of SEQ ID NO: 29, or a peptidomimetic thereof. In other aspects of this embodiment, the Clostridial toxin substrate includes, in part, a BoNT/F recognition sequence comprising a portion of VAMP-1-3 such as, e.g., residues 1 to 116 of SEQ ID NO: 30; residues 39 to 77 of SEQ ID NO: 30, or a peptidomimetic thereof. In other aspects of this embodiment, the Clostridial toxin substrate includes, in part, a BoNT/F recognition sequence comprising a portion of VAMP-2 such as, e.g., residues 1 to 116 of SEQ ID NO: 31; residues 1 to 86 of SEQ ID NO: 31; residues 1 to 76 of SEQ ID NO: 31; residues 1 to 69 of SEQ ID NO: 31; residues 27 to 116 of SEQ ID NO: 31; residues 37 to 116 of SEQ ID NO: 31; residues 27 to 68 of SEQ ID NO: 31; residues 37 to 75 of SEQ ID NO: 31; residues 37 to 69 of SEQ ID NO: 31, or a peptidomimetic thereof.

A BoNT/G recognition sequence can correspond to a segment of a protein that is sensitive to cleavage by botulinum toxin serotype G. or can be substantially similar to such a BoNT/G-sensitive segment. As shown in Table 4, a variety of naturally occurring proteins sensitive to cleavage by BoNT/G are known in the art and include, for example, human, rat and mouse VAMP-1, VAMP-2 and VAMP-3/cellubrevin; bovine VAMP-2; chicken VAMP-1, and VAMP-2; and Torpedo VAMP-1. Thus, a BoNT/G recognition sequence can correspond, for example, to a segment of human VAMP-1, VAMP-2 or VAMP-3; bovine VAMP-2; rat VAMP-1, VAMP-2 or VAMP-3; mouse VAMP-1, VAMP-2 or VAMP-3; chicken VAMP-1, VAMP-2 or VAMP-3; *Xenopus* VAMP-2 or VAMP-3; *Danio* VAMP-1 or VAMP-2; *Torpedo* VAMP-1; *Caenorhabditis* SNB1, isoforms thereof, or another naturally occurring protein sensitive to cleavage by BoNT/G. Furthermore, as shown in Table 4 above, comparison of native VAMP amino acid sequences cleaved by BoNT/G reveals that such sequences are not absolutely conserved, indicating that a variety of amino acid substitutions and modifications relative to a naturally occurring BoNT/G-sensitive VAMP sequence can be tolerated in a BoNT/G substrate useful in the invention. It is understood that a similar BoNT/G recognition sequence can be prepared, if desired, from a corresponding (homologous) segment of another BoNT/G-sensitive VAMP-1 or VAMP-2 isoform, paralog or ortholog, such as, the BoNT/G recognition sequence contain in the VAMP-1 and VAMP-2 identified in the organisms listed above and in Table 4.

Thus, in an embodiment, a cell comprises, in part, a membrane-associated BoNT/G substrate comprising a first member of a FRET pair and a BoNT/G recognition sequence including a cleavage site. As used herein, the term "botulinum toxin serotype G recognition sequence" is synonymous with "BoNT/G recognition sequence" and means a scissile bond together with adjacent or non-adjacent recognition elements, or both, sufficient for detectable proteolysis at the scissile bond by a BoNT/G under appropriate conditions. A scissile bond cleaved by BoNT/G can be, for example, Ala-Ala.

In an aspect of this embodiment, the Clostridial toxin substrate includes, in part, a BoNT/G recognition sequence comprising a BoNT/G recognition sequence containing at least six consecutive residues of VAMP including Ala-Ala. In another aspect of this embodiment, the Clostridial toxin substrate includes, in part, a BoNT/G recognition sequence comprising the BoNT/G recognition sequence Glu-Thr-Ser-Ala-Ala-Lys-Leu-Lys (SEQ ID NO: 103). In other aspects of this embodiment, the Clostridial toxin substrate includes, in part, a BoNT/G recognition sequence comprising a portion of VAMP-1-1 such as, e.g., residues 1 to 118 of SEQ ID NO: 28, or a peptidomimetic thereof. In other aspects of this embodiment, the Clostridial toxin substrate includes, in part, a BoNT/G recognition sequence comprising a portion of VAMP-1-2 such as, e.g., residues 1 to 117 of SEQ ID NO: 29, or a peptidomimetic thereof. In other aspects of this embodiment, the Clostridial toxin substrate includes, in part, a BoNT/G recognition sequence comprising a portion of VAMP-1-3 such as, e.g., residues 1 to 116 of SEQ ID NO: 30, or a peptidomimetic thereof. In other aspects of this embodiment, the Clostridial toxin substrate includes, in part, a BoNT/G recognition sequence comprising a portion of VAMP-2 such as, e.g., residues 1 to 116 of SEQ ID NO: 31, or a peptidomimetic thereof.

A variety of TeNT recognition sequences are well known in the art or can be defined by routine methods and include sequences corresponding to some or all of the hydrophilic core of a VAMP protein such as human VAMP-1 or human VAMP-2. A TeNT recognition sequence can include, for example, residues 25 to 93 or residues 33 to 94 of human VAMP-2 (SEQ ID NO: 31; F. Cornille et al., Solid-phase synthesis, conformational analysis and in vitro cleavage of synthetic human synaptobrevin II 1-93 by tetanus toxin L chain, 222(1) Eur. J. Biochem. 173-181 (1994); Patrick Foran et al., Differences in the protease activities of tetanus and botulinum B toxins revealed by the cleavage of vesicle-associated membrane protein and various sized fragments, 33(51) Biochemistry 15365-15374 (1994); residues 51 to 93 or residues 1 to 86 of rat VAMP-2, see, e.g., Yamasaki et al., supra, (1994); or residues 33 to 94 of human VAMP-1-1 (SEQ ID NO: 28), residues 33 to 94 of human VAMP-1-2 (SEQ ID NO: 29) and residues 33 to 94 of human VAMP-1-3 (SEQ ID NO: 30). A TeNT recognition sequence also can include, for example, residues 25 to 86, residues 33 to 86 or residues 51 to 86 of human VAMP-2 (SEQ ID NO: 31) or rat VAMP-2 (SEQ ID NO: 38). It is understood that a similar TeNT recognition sequence can be prepared, if desired, from a corresponding (homologous) segment of another TeNT-sensitive VAMP isoform or species homolog such as human VAMP-1 or sea urchin or *Aplysia* VAMP.

Thus, a TeNT recognition sequence can correspond to a segment of a protein that is sensitive to cleavage by tetanus toxin, or can be substantially similar to a segment of a TeNT-sensitive protein. As shown in Table 4, a variety of naturally occurring proteins sensitive to cleavage by TeNT are known in the art and include, for example, human and mouse VAMP-1, VAMP-2 and VAMP-3/cellubrevin; bovine VAMP-2; rat VAMP-2 and VAMP-3; chicken VAMP-2; Torpedo VAMP-1; *Strongylocentrotus* VAMP; *Drosophila* sybA, synB, synC, synD and synE; *Hirudo* VAMP; and *Caenorhabditis* SNB1-like. Thus, a TeNT recognition sequence can correspond, for example, to a segment of human VAMP-1, VAMP-2 or VAMP-3; bovine VAMP-2; rat VAMP-2 or VAMP-3; mouse VAMP-1, VAMP-2 or VAMP-3; chicken VAMP-1, VAMP-2 or VAMP-3; *Xenopus* VAMP-2 or VAMP-3; *Danio* VAMP-1 or VAMP-2; *Torpedo* VAMP-1; *Strongylocentrotus* VAMP; *Drosophila* sybA, synB, synC, synD or synE; *Hirudo* VAMP; *Loligo* VAMP; *Lymnaea* VAMP; *Aplysia* VAMP; *Caenorhabditis* SNB1 and SNB-like, isoforms thereof, or another naturally occurring protein sensitive to cleavage by TeNT. Furthermore, comparison of native VAMP amino acid sequences cleaved by TeNT reveals that such sequences are not absolutely conserved (Table 4). This finding indicates that a variety of amino acid substitutions and modifications relative to a naturally occurring TeNT-sensitive VAMP sequence can be tolerated in a TeNT substrate useful in the invention. It is understood that a similar TeNT recognition sequence can be prepared, if desired, from a corresponding (homologous) segment of another TeNT-sensitive VAMP-1 or VAMP-2 isoform, paralog or ortholog, such as, the TeNT recognition sequence contain in the VAMP-1 and VAMP-2 identified in the organisms listed above and in Table 4.

Thus, in an embodiment, a cell comprises, in part, a membrane-associated TeNT substrate comprising a first member of a FRET pair and a TeNT recognition sequence including a cleavage site. As used herein, the term "tetanus toxin recognition sequence" means a scissile bond together with adjacent or non-adjacent recognition elements, or both, sufficient for detectable proteolysis at the scissile bond by a tetanus toxin under appropriate conditions. A scissile bond cleaved by TeNT can be, for example, Gln-Phe.

In an aspect of this embodiment, the Clostridial toxin substrate includes, in part, a TeNT recognition sequence comprising a TeNT recognition sequence containing at least six consecutive residues of VAMP including Gln-Phe. In another aspect of this embodiment, the Clostridial toxin substrate includes, in part, a TeNT recognition sequence comprising the TeNT recognition sequence Gly-Ala-Ser-Gln-Phe-Glu-Thr-Ser (SEQ ID NO: 104). In other aspects of this embodiment, the Clostridial toxin substrate includes, in part, a TeNT recognition sequence comprising a portion of VAMP-1-1 such as, e.g., residues 1 to 118 of SEQ ID NO: 28 or residues 33 to 94 of SEQ ID NO: 28. In other aspects of this embodiment, the Clostridial toxin substrate includes, in part, a TeNT recognition sequence comprising a portion of VAMP-1-2 such as, e.g., residues 1 to 117 of SEQ ID NO: 29 or residues 33 to 94 of SEQ ID NO: 29. In other aspects of this embodiment, the Clostridial toxin substrate includes, in part, a TeNT recognition sequence comprising a portion of VAMP-1-3 such as, e.g., residues 1 to 116 of SEQ ID NO: 30 or residues 33 to 94 of SEQ ID NO: 30. In other aspects of this embodiment, the Clostridial toxin substrate includes, in part, a TeNT recognition sequence comprising a portion of VAMP-2 such as, e.g., residues 1 to 116 of SEQ ID NO: 31; residues 25 to 94 of SEQ ID NO: 31; residues 33 to 94 of SEQ ID NO: 31; residues 51 to 93 of SEQ ID NO: 31; residues 1 to 86 of SEQ ID NO: 31; residues 25 to 86 of SEQ ID NO: 31; residues 33 to 86 of SEQ ID NO: 31; residues 51 to 86 of SEQ ID NO: 31, or a peptidomimetic thereof.

SNAP-25, VAMP and Syntaxin share a short motif usually located within regions predicted to adopt an α-helical conformation called the SNARE motif. This motif usually comprises a nine amino acid motif with the general formula of H-Θ-Θ-X-H-Θ-X-H-P (see FIG. 3*b*), where H is a aliphatic residue, Θ is a carboxylate residue, P is a polar residue and X is any amino acid, see e.g., Ornella Rossetto et al., SNARE motif and neurotoxins, 372(6505) Nature 415-416 (1994); Rossella Pellizzari et al., Structural determinants of the specificity for synaptic vesicle-associated membrane protein/synaptobrevin of tetanus and botulinum type B and G neurotoxins, 271(34) J. Biol. Chem. 20353-20358 (1996); Rossella Pellizzari et al., The interaction of synaptic vesicle-associated membrane protein/synaptobrevin with botulinum neurotoxins D and F, 409(3) FEBS Lett. 339-342 (1997); and Philip Washbourne et al., Botulinum neurotoxin types A and E require the SNARE motif in SNAP-25 for proteolysis, 418(1-2) FEBS Lett. 1-5 (1997). This motif is present in SNAP-25, VAMP and syntaxin isoforms expressed in animals sensitive to the toxins. In contrast, *Drosophila* and yeast SNAP-25 proteins are resistant to these toxins. In addition, VAMP and syntaxin isoforms not involved in exocytosis contain sequence variations in these α-helical motif regions.

Multiple repetitions of the α-helical motif are present in proteins sensitive to cleavage by Clostridial toxins: Four copies are naturally present in SNAP-25, designated S1-S4; two copies are naturally present in VAMP, designated V1 and V2; and two copies are naturally present in syntaxin, designated X1 and X2, see, e.g., Humeau et al., supra, (2000). Furthermore, peptides corresponding to the specific sequence of the α-helical motifs can inhibit toxin activity in vitro and in vivo, and such peptides can cross-inhibit different toxins. In addition, antibodies raised against such peptides can cross-react among the three target proteins, indicating that this α-helical motif is exposed on the protein surface and adopts a similar configuration in each of the three target proteins. Consistent with these findings, SNAP-25-specific, VAMP-specific and syntaxin-specific toxins cross-inhibit each other by competing for the same binding site, although they do not cleave targets non-specifically. These results indicate that a Clostridial toxin recognition sequence can include, if desired, at least one α-helical motif. It is recognized that an α-helical motif is not required for cleavage by a Clostridial toxin, as evidenced by 16-mer and 17-mer substrates for BoNT/A known in the art, see, e.g., Schmidt & Bostian, supra, (1997);

Schmidt & Bostian, supra, (Oct. 12, 1999); and Schmidt & Stafford, supra, (Jul. 13, 2004).

Although multiple α-helical motifs are found in the naturally occurring SNAP-25, VAMP and syntaxin target proteins, a Clostridial toxin recognition sequence useful in a Clostridial toxin substrate can have a single α-helical motif. In particular embodiments, a method of the invention relies on a Clostridial toxin recognition sequence including two or more α-helical motifs. A BoNT/A or BoNT/E recognition sequence can include, for example, the S4 α-helical motif, alone or combined with one or more additional α-helical motifs; a BoNT/B, BoNT/G or TeNT recognition sequence can include, for example, the V2 α-helical motif, alone or combined with one or more additional α-helical motifs; a BoNT/C1 recognition sequence can include, for example, the S4 α-helical motif, alone or combined with one or more additional α-helical motifs, or the X2 α-helical motif, alone or combined with one or more additional α-helical motifs; and a BoNT/D or BoNT/F recognition sequence can include, for example, the V1 α-helical motif, alone or combined with one or more additional α-helical motifs. Representative SNARE motifs are presented in Tables 6, 7 and 8.

TABLE 5

SNARE motifs of SNAP-25 and Related Proteins

| | | Motif | | | |
|---|---|---|---|---|---|
| Organism | Isoform | S1 | S2 | S3 | S4 |
| Primate | SNAP-25A<br>SNAP-25B | ADESLESTR | VEESKDAGI | LDEQGEQLD<br>LDEQGEQLE | MDENLEQVS |
| Primate | SNAP-23A<br>SNAP-23B | TDESLESTR | AIESQDAGI | LDEQKEQLN | MEENLTQVG |
| Rodent | SNAP-25A<br>SNAP-25B | ADESLESTR | VEESKDAGI | LDEQGEQLD<br>LDEQGEQLE | MDENLEQVS |
| Rodent | SNAP-23 | TDESLESTR | AIESQDAGI | LEDQGEQLN | MEENLTQVG |
| Bird | SNAP-25B | ADESLESTR | VEESKDAGI | LDEQGEQLE | MDENLEQVS |
| Amphibian | SNAP-25A<br>SNAP-25B | ADESLESTR | VEGSKDAGI | LDEQGEQLD<br>LDEQGEQLE | MDENLEQVG |
| Amphibian | SNAP-23 | ADESLESTR | ALESQDAGI | LDEQGEQLD | MDENLVQVG |
| Fish | SNAP-25A<br>SNAP-25B | ADESLESTR<br>GDESLESTR | VEESKDAGI | LDEQGEQLE | MDENLEQVG<br>MDENLEQVG |
| Fish | SNAP-23 | TDESLESTR | AEESRETGV | LDEQGEQLR | MEENLDQVG |
| Ray | SNAP-25 | TDESLESTR | VEESKDAGI | LDEQGEQLE | MEENLDQVG |
| Sea urchin | SNAP-25 | TDESLESTR | AEESKEAGI | LDEQGEQLD | MDENLTQVS |
| Insect | SNAP-25 | ADESLESTR | CEESKEAGI | LDDQGEQLD | MEENMGQVN |
| Insect | SNAP-24 | ADESLESTR | MDESKEAGI | LDDQGEQLD | MDENLGQVN |
| Segmented worm | SNAP-25 | TDDSLESTR | CEESKDAGI | LDEQGEQLD | MEQNMGEVS |
| Cephalopod | SNAP-25 | TDDSLESTR | CEESKEAGI | LDEQGEQLD | MENNMKEVS |
| Gastropod | SNAP-25 | TNESLESTR | CEESKEAGI | LDEQGEQLD | MEQNIGEVA |
| Round worm | SNAP-25 | TDDSLESTR | CEESKEAGI | LDDQGEQLE | MDENVQQVS |

Proteolytic cleavage occurs at this site (*);
Proteolytic cleavage not detected at this site (-);
Proteolytic cleavage not determined at this site (ND)

Table 6—SNARE motifs of SNAP-25 and Related Proteins. Primate: Human SNAP-25A residues 22-30, 36-44, 50-58 and 146-154 of SEQ ID NO: 1; Human SNAP-25B residues 22-30, 36-44, 50-58 and 146-154 of SEQ ID NO: 2; Human SNAP-23A residues 17-25, 31-39, 45-53, and 152-160 of SEQ ID NO: 3; Human SNAP-23B residues 17-25, 31-39, 45-53 and 152-160 of SEQ ID NO: 4; Monkey SNAP-25B residues 22-30, 36-44, 50-58 and 146-154 of SEQ ID NO: 5; Rodent: Rat SNAP-25A residues 22-30, 36-44, 50-58 and 146-154 of SEQ ID NO: 6; Rat SNAP-25B residues 22-30, 36-44, 50-58 and 146-154 of SEQ ID NO: 7; Mouse SNAP-25B residues 22-30, 36-44, 50-58 and 146-154 of SEQ ID NO: 8; Rat SNAP-23 residues 17-25, 31-39, 45-53 and 151-159 of SEQ ID NO: 9; Mouse SNAP-23 residues 17-25, 31-39, 45-53 and 151-159 of SEQ ID NO: 10; Bird: Chicken SNAP-25B residues 22-30, 36-44, 50-58 and 146-154 of SEQ ID NO: 11; Fish: Goldfish SNAP-25A residues 22-30, 36-44, 50-58 and 144-152 of SEQ ID NO: 12; Goldfish SNAP-25B residues 22-30, 36-44, 50-58 and 143-151 of SEQ ID NO: 13; Zebrafish SNAP-25A residues 22-30, 36-44, 50-58 and 144-152 of SEQ ID NO: 14; Zebrafish SNAP-25B residues 22-30, 36-44, 50-58 and 143-151 of SEQ ID NO: 15; Zebrafish SNAP-23 residues 17-25, 31-39, 45-53 and 157-165 of SEQ ID NO: 16; Ray: marbled electric ray SNAP-25 residues 26-34, 40-48, 54-62 and 153-161 of SEQ ID NO: 17; Amphibian: Frog SNAP-25A residues 22-30, 36-44, 50-58 and 146-154 of SEQ ID NO: 18; Frog SNAP-25B residues 22-30, 36-44, 50-58 and 146-154 of SEQ ID NO: 19; Frog SNAP-23 residues 17-25, 31-39, 45-53 and 146-154 of SEQ ID NO: 20; Sea urchin SNAP-25 residues 24-32, 38-46, 52-60 and 152-160 of SEQ ID NO: 21; Insect: Fruit fly SNAP-25 residues 29-37, 43-51, 57-65 and 154-163 of SEQ ID NO: 22 212; Fruit fly SNAP-24 residues 24-32, 38-46, 52-60 and 153-162 of SEQ ID NO: 23; Segmented worm: Leech SNAP-25 residues 30-38, 44-52, 58-66 and 153-161 of SEQ ID NO: 24; Cephalopod: squid SNAP-25 residues 25-33, 39-47, 53-61 and 153-161 of SEQ ID NO: 25; Gastropod: Pond snail SNAP-25 residues 32-40, 46-54, 60-68 and 160-168 of SEQ ID NO: 26; Round worm: Nematode worm SNAP-25 residues 22-30, 36-44, 50-58 and 148-156 of SEQ ID NO: 27.

TABLE 7

SNARE motifs of VAMP and Related Proteins

| Organism | Isoform | Motif V1 | V2 |
|---|---|---|---|
| Primate | VAMP1-1<br>VAMP1-2<br>VAMP1-3 | VEEVVDIIR | LDDRADALQ |
| Primate | VAMP2 | VDEVVDIMR | LDDRADALQ |
| Primate | VAMP3 | VDEVVDIMR | LDDRADALQ |
| Bovine | VAMP2 | VDEVVDIMR | LDDRADALQ |
| Rodent | VAMP1<br>VAMP1/1b | VEEVVDIIR<br>VEEVVDIMR | LDDRADALQ |
| Rodent | VAMP2<br>VAMP2-b | VDEVVDIMR | LDDRADALQ |
| Rodent | VAMP3 | VDEVVDIMR | LDDRADALQ |
| Bird | VAMP1 | VEEVVDIMR | LDDRADALQ |
| Bird | VAMP2 | VDEVVDIMR | LDNRADALQ |
| Bird | VAMP3 | VDEVVDIMR | LDDRADALQ |
| Amphibian | VAMP2 | VDEVVDIMR | LDDRADALQ |
| Amphibian | VAMP3 | VDEVVDIMR | LDDRADALQ |
| Fish | VAMP1 | VDEVVDIMR | LDDRADALQ |
| Fish | VAMP2 | VDEVVDIMR | LDDRADALQ |
| Fish | VAMP-3 | VDEVVDIMR | LDDRADALQ |
| Ray | VAMP1 | VEEVVDIIR | LDDRADALQ |
| Sea urchin | VAMP | VDEVVDIMR | LDDRADALQ |
| Insect | Syn-A1<br>Syn-B1 | VDEVVGIMR | LGERADQLE |
| Insect | Syn-A2<br>Syn-B2 | VDEVVGIMR | LGERADQLE |
| Insect | Syn-C<br>Syn-D<br>Syn-E | VDEVVDIMR | LDDRADALQ |
| Segmented worm | VAMP | VDEVVGMMR | LDGRADALQ |
| Cephalopod | VAMP | VEEVVGIMR | LDDRADALQ |
| Gastropod | VAMP | VDEVVGIMR | LDDRAEALQ |

TABLE 7-continued

SNARE motifs of VAMP and Related Proteins

| Organism | Isoform | Motif V1 | V2 |
|---|---|---|---|
| Round worm | SNB1 | VDEVVGIMK | LDDRADALQ |
| | SNB-like | VNEVIDVMR | LDHRAEVLQ |

Table 7—SNARE motifs of VAMP and Related Proteins. Primate: Human VAMP-1-1 residues 40-48 and 56-64 of SEQ ID NO: 28; Human VAMP-1-2 residues 40-48 and 56-64 of SEQ ID NO: 29; Human VAMP-1-3 residues 40-48 and 56-64 of SEQ ID NO: 30; Human VAMP-2 residues 39-47 and 63-71 of SEQ ID NO: 31; Monkey VAMP-2 residues 39-47 and 63-71 of SEQ ID NO: 32; Human VAMP-3/cellubrevin residues 22-30 and 46-54 of SEQ ID NO: 33; Bovine: Cow VAMP-2 residues 39-47 and 63-71 of SEQ ID NO: 34; Rodent: Rat VAMP-1 residues 40-48 and 56-64 of SEQ ID NO: 35; Rat VAMP-1-b residues 40-48 and 56-64 of SEQ ID NO: 36; Mouse VAMP-1 residues 40-48 and 56-64 of SEQ ID NO: 37; Rat VAMP-2 residues 39-47 and 63-71 of SEQ ID NO: 38; Rat VAMP-2-b residues 39-47 and 63-71 of SEQ ID NO: 39; Mouse VAMP-2 residues 39-47 and 63-71 of SEQ ID NO: 40; Rat VAMP-3/cellubrevin residues 26-34 and 50-58 of SEQ ID NO: 41; Mouse VAMP-3/cellubrevin residues 26-34 and 50-58 of SEQ ID NO: 42; Bird: Chicken VAMP-1 residues 182-190 and 198-206 of SEQ ID NO: 43; Chicken VAMP-2 residues 37-45 and 61-69 of SEQ ID NO: 44; Chicken VAMP-3/cellubrevin residues 26-34 and 50-58 of SEQ ID NO: 45; Fish: Zebrafish VAMP-1 residues 41-49 and 57-65 of SEQ ID NO: 46; Zebrafish VAMP-2 residues 33-41 and 57-65 of SEQ ID NO: 47; Zebrafish VAMP-3 residues 25-33 and 49-57 of SEQ ID NO: 48; Ray: marbled electric ray VAMP-1 residues 42-50 and 58-66 of SEQ ID NO: 49; Amphibian: Frog VAMP-2 residues 37-45 and 61-69 of SEQ ID NO: 50; Frog VAMP-3 residues 24-32 and 48-56 of SEQ ID NO: 51; Sea urchin VAMP residues 23-31 and 39-47 of SEQ ID NO: 52; Insect: Fruit fly SynA1 residues 31-39 and 47-55 of SEQ ID NO: 53; Fruit fly SynA2 residues 54-62 and 70-78 of SEQ ID NO: 54; Fruit fly SynB1 residues 54-62 and 70-78 of SEQ ID NO: 55; Fruit fly SynB2 residues 54-62 and 70-78 of SEQ ID NO: 56; Fruit fly SynC residues 48-56 and 64-72 of SEQ ID NO: 57; Fruit fly SynD residues 67-75 and 83-91 of SEQ ID NO: 58; Fruit fly SynE residues 67-75 and 83-91 of SEQ ID NO: 59; Segmented worm: Leech VAMP residues 37-45 and 53-61 of SEQ ID NO: 60; Cephalopod: squid VAMP residues 47-55 and 63-71 of SEQ ID NO: 61; Gastropod: Pond snail VAMP residues 40-48 and 56-64 of SEQ ID NO: 62; sea hare VAMP residues 30-38 and 46-54 of SEQ ID NO: 63; Round worm: Nematode worm SNB1 residues 34-42 and 50-58 of SEQ ID NO: 64; Nematode worm SNB-like residues 40-48 and 56-64 of SEQ ID NO: 65.

TABLE 8

SNARE motifs of Syntaxin and Related Proteins

| Organism | Isoform | Motif X1 | X2 |
|---|---|---|---|
| Primate | Syntaxin1A | MDEFFEQVE | LEDMLESGN |
| | Syntaxin1B1 | MDEFFEQEE | LEDMLESGK |
| | Syntaxin1B2 | MDEFFEQVE | LEDMLESGK |

TABLE 8-continued

SNARE motifs of Syntaxin and Related Proteins

| Organism | Isoform | Motif X1 | Motif X2 |
|---|---|---|---|
| Primate | Syntaxin2-1<br>Syntaxin2-2<br>Syntaxin2-3 | MDDFFHQVE | LEEMLESGK |
| Primate | Syntaxin3A | MDEFFSEIE | LEEMLESGN |
| Bovine | Syntaxin1A<br>Syntaxin1B2 | MDEFFEQVE | LEDMLESGN<br>LEDMLESGK |
| Rodent | Syntaxin1A<br>Syntaxin1B1<br>Syntaxin1B2 | MDEFFEQVE<br>MAEFFEQVE<br>MDEFFEQVE | LEDMLESGN<br>LEDMLESGK<br>LEDMLESGK |
| Rodent | Syntaxin2 | MDGFFHQVE | LEEMLESGK |
| Rodent | Syntaxin3A<br>Syntaxin3B | MDEFFSEIE | LEEMLESGN |
| Rodent | Syntaxin3C | MDEFFSENF | LEEMLESGN |
| Bird | Syntaxin1B | MDEFFEQVE | LEDMLESGK |
| Bird | Syntaxin2 | MDDFFQQVE | LEEMLESGN |
| Fish | Syntaxin1B | MDEFFEQVE | LEDMLESGK |
| Fish | Syntaxin3 | MDEFFSQIE | LEEMLEGGN |
| Sea urchin | Syntaxin1B | MEEFFEQVE | LEDMLESGN |
| Insect | Syntaxin1A | MDDFFAQVE | LEKMLEEGN |
| Segmented worm | Syntaxin1A | MEEFFEQVN | LEDMLESGN |
| Cephalopod | Syntaxin1A | MEEFFEQVE | LEDMLESGN |
| Gastropod | Syntaxin1A | MEEFFEQVD | LEDMIESGN |

Table 8—SNARE motifs of Syntaxin and Related Proteins. Primate: Human Syntaxin1A residues 30-38 and 165-173 of SEQ ID NO: 66; Human Syntaxin1B1 residues 29-37 and 164-172 of SEQ ID NO: 67; Human Syntaxin1B2 residues 29-37 and 164-172 of SEQ ID NO: 68; Human Syntaxin2-1 residues 29-37 and 168-176 of SEQ ID NO: 69; Human Syntaxin2-2 residues 29-37 and 168-176 of SEQ ID NO: 70; Human Syntaxin2-3 residues 29-37 and 168-176 of SEQ ID NO: 71; Human Syntaxin3 residues 32-40 and 165-173 of SEQ ID NO: 72; Bovine: Cow Syntaxin1A residues 30-38 and 165-173 of SEQ ID NO: 73; Cow Syntaxin1B2 residues 29-37 and 164-172 of SEQ ID NO: 74; Rodent: Rat Syntaxin1A residues 30-38 and 165-173 of SEQ ID NO: 75; Rat Syntaxin1B2 residues 29-37 and 164-172 of SEQ ID NO: 76; Mouse Syntaxin1A residues 30-38 and 165-173 of SEQ ID NO: 77; Mouse Syntaxin1B1 residues 29-37 and 164-172 of SEQ ID NO: 78; Mouse Syntaxin1B2 residues 29-37 and 164-172 of SEQ ID NO: 79; Rat Syntaxin2 residues 31-39 and 170-178 of SEQ ID NO: 80; Mouse Syntaxin2 residues 30-38 and 169-177 of SEQ ID NO: 81; Rat Syntaxin3A residues 32-40 and 165-173 of SEQ ID NO: 82; Mouse Syntaxin3A residues 32-40 and 165-173 of SEQ ID NO: 83; Mouse Syntaxin3B residues 32-40 and 165-173 of SEQ ID NO: 84; Mouse Syntaxin3C residues 32-40 and 147-155 of SEQ ID NO: 85; Bird: Chicken Syntaxin1B residues 29-37 and 157-165 of SEQ ID NO: 86; Chicken Syntaxin2 residues 28-36 and 167-175 of SEQ ID NO: 87; Fish: Zebrafish Syntaxin1B residues 29-37 and 164-172 of SEQ ID NO: 88; Zebrafish Syntaxin3 residues 29-37 and 163-171 of SEQ ID NO: 89; sea urchin Syntaxin1B residues 29-37 and 164-172 of SEQ ID NO: 90; Insect: Fruit fly Syntaxin1A residues 33-41 and 168-176 of SEQ ID NO: 91; Segmented worm: leech Syntaxin1A residues 36-44 and 171-179 of SEQ ID NO: 92; Cephalopod: squid Syntaxin1A residues 33-41 and 168-176 of SEQ ID NO: 93; Gastropod: Pond snail Syntaxin1A residues 32-40 and 167-175 of SEQ ID NO: 94; sea hare Syntaxin1A residues 32-40 and 167-175 of SEQ ID NO: 95.

As discussed above, the SNARE complex is comprised of the t-SNARE SNAP-25 along with another t-SNARE, syntaxin 1 and a v-SNARE VAMP/synaptobrevin. Members of the SNAP-25 family of proteins can be divided into three structural domains and amino-terminal α-helix of approximately 84 residues, an approximately 36 amino acid interhelical loop and a carboxy-terminal α-helix of approximately 86 residues, depending on the individual member. As will be discussed below, all three of these regions may be used to target SNAP-25 to the plasma membrane either alone or in any combination of the three.

The interhelical loop of SNAP-25 appears to be important for conferring targeting specificity of this SNARE protein to the membrane. For example, in one study a membrane-targeting domain comprising residues 85-120 of SNAP-25 was shown to localize to the cell membrane Susana Gonzalo et al., SNAP-25 is targeted to the plasma membrane through a novel membrane-binding domain, 274(30) J. Biol. Chem. 21313-21318 (1999). This region represents two-thirds of the interhelical loop that connects the amino- and carboxy-terminal α-helices of SNAP-25. The function of this targeting domain appears to be independent of SNARE protein-protein interactions since remove of the SNAP-25 regions that associate with either syntaxin or synaptobrevin did not interfere with proper targeting of SNAP-25 to the membrane.

Alignment of SNAP-25 family members revealed two conserved motifs present within the interhelical loop region responsible for membrane targeting. The first is a cysteine-rich region present at the amino-terminal boundary of the membrane-targeting interhelical loop domain. One or more of the cysteines present in this motif is fatty acylated via a thioester linkage of palmitate. Palmitoylation of this cysteine-rich may be important for membrane insertion because elimination of these cysteine residues results in a loss of SNAP-25 membrane-targeting.

The second is a five-amino acid motif located at the carboxy-terminal boundary of the membrane-targeting interhelical loop domain (QPXR(V/I)). This motif is believed to play a role in membrane association, see, e.g., Gonzalo et al., supra, (1999); Philip Washbourne et al., Cysteine residues of SNAP-25 are required for SNARE disassembly and exocytosis, but not for membrane targeting, 357(Pt 3) Biochem. J. 625-634 (2001).

The α-helices of the various SNARE complex members seems to be involved in protein-protein interactions between members. For example, solution of the crystal structure of the SNARE complex reveals that SNAP-25, syntaxin and synaptobrevin appear to favor a heterotrimeric, parallel four-helix bundle association, see, e.g., R. Bryan Sutton et al., Crystal structure of a SNARE complex involved in synaptic exocytosis at 2.4 Å resolution, 395(6700) Nature 347-353 (1998). This analysis indicated an extensive intertwining of the α-helices with the amino-terminal region of the bundle comprising interactions between the amino-terminal α-helix of SNAP-25 with syntaxin, several central associations amongst all three members and an association between syntaxin and synaptobrevin at the carboxyl-terminal portion of the four-helix bundle.

Protein-protein interactions between the α-helices of SNARE complex members appear to be another way of localizing SNAP-25 to the membrane. For example, co-expression of SNAP-25 with syntaxin results in targeting SNAP-25 to the membrane in the absence of a functional interhelical loop suggesting that protein-protein interactions between these two t-SNAREs can target Clostridial toxin substrates to the membrane, see, e.g., Washbourne et al., supra, (2001).

Members of the Syntaxin family of proteins can be divided into several structural domains. In the amino-terminal half of the protein contains an Habc region comprising three α-helix domains located at amino acids 30-60, 69-104 and 110-154. The carboxy-terminal half of Syntaxin-1 contains an α-helix of approximately 52-69 residues, depending on the individual member and an approximately 23 amino acid membrane anchoring domain. As will be discussed below, regions comprising the membrane anchoring domain of Syntaxin may be used to target Clostridial toxin substrates to the plasma membrane.

The Clostridial toxin substrates disclosed in the present specification include, in part, a membrane targeting domain. As used herein, the term "membrane targeting domain" is synonymous with "MTD" and means a SNAP-25 or Syntaxin peptide which directs a Clostridial toxin substrate to the cell membrane. Any and all SNAP-25 or Syntaxin membrane targeting domains can be used in aspects of the present invention, with the proviso that the Clostridial toxin substrate maintains the property to be cleaved by a Clostridial toxin. Examples include, without limitation, naturally occurring membrane targeting domains present in SNAP-25, naturally occurring SNAP-25 MTD variants, and non-naturally occurring SNAP-25 MTD variants, such as, e.g., genetically engineered SNAP-25 MTD variants, produced, e.g., by random mutagenesis or rational designed and SNAP-25 MTD peptidomimetics; and naturally occurring membrane targeting domains present in Syntaxin, naturally occurring Syntaxin MTD variants, and non-naturally occurring Syntaxin MTD variants, such as, e.g., genetically engineered Syntaxin MTD variants, produced, e.g., by random mutagenesis or rational designed and Syntaxin MTD peptidomimetics.

Thus, aspects of the present invention provide a cell comprising (a) a membrane-associated Clostridial toxin substrate comprising (i) a first member of a fluorescence resonance energy transfer (FRET) pair; (ii) a membrane targeting domain; and (iii) a Clostridial toxin recognition sequence including a cleavage site; and (b) a membrane-associated second member of the FRET pair, wherein the cell is capable of Clostridial toxin intoxication; wherein the FRET pair comprises an acceptor having an absorbance spectrum overlapping the emission spectrum of a donor fluorophore; and wherein, under the appropriate conditions, resonance energy transfer is exhibited between the first and second members of the FRET pair.

Other aspects of the present invention provide a neuronal cell comprising (a) a stably expressed nucleic acid molecule encoding a membrane-associated BoNT/A substrate comprising (i) a fluorescent protein; (ii) a membrane targeting domain; and (iii) a BoNT/A recognition sequence including a cleavage site; and (b) a membrane-associated lipophilic dye which has an absorbance spectrum overlapping the emission spectrum of the fluorescent protein; wherein the neural cell is capable of BoNT/A intoxication; and, wherein, under the appropriate conditions, fluorescence resonance energy transfer is exhibited between the fluorescent protein and the lipophilic dye.

Other aspects of the present invention provide a neuronal cell comprising (a) a stably expressed nucleic acid molecule encoding a membrane-associated BoNT/E substrate comprising (i) a fluorescent protein; (ii) a membrane targeting domain; and (iii) a BoNT/E recognition sequence including a cleavage site; and (b) a membrane-associated lipophilic dye which has an absorbance spectrum overlapping the emission spectrum of the fluorescent protein; wherein the neuronal cell is capable of BoNT/E intoxication; and wherein, under the appropriate conditions, fluorescence resonance energy transfer is exhibited between the fluorescent protein and the lipophilic dye.

Other aspects of the present invention provide a method of determining Clostridial toxin activity comprising (a) contacting with a sample a cell comprising (1) a membrane-associated Clostridial toxin substrate comprising (i) a first member of a fluorescence resonance energy transfer (FRET) pair; (ii) a membrane targeting domain; and (iii) a Clostridial toxin recognition sequence including a cleavage site; and (2) a membrane-associated second member of the FRET pair, wherein the cell is capable of Clostridial toxin intoxication; wherein the FRET pair comprises an acceptor having an absorbance spectrum overlapping the emission spectrum of a donor fluorophore; and wherein, under the appropriate conditions, fluorescence resonance energy transfer is exhibited between the first and second members of the FRET pair; (b) exciting the donor fluorophore; and (c) determining fluorescence resonance energy transfer of the contacted cell relative to a control cell, where a difference in fluorescence resonance energy transfer of the contacted cell as compared to the control cell is indicative of Clostridial toxin activity.

Other aspects of the present invention provide a method of determining BoNT/A activity comprising (a) contacting with a sample a neuronal cell comprising (1) a stably expressed nucleic acid molecule encoding a membrane-associated BoNT/A substrate comprising (i) a fluorescent protein; (ii) a membrane targeting domain; and (iii) a BoNT/A recognition sequence including a cleavage site; and (2) a membrane-associated lipophilic dye which has an absorbance spectrum overlapping the emission spectrum of the fluorescent protein; wherein the neuronal cell is capable of BoNT/A intoxication; and wherein, under the appropriate conditions, fluorescence resonance energy transfer is exhibited between the fluorescent protein and the lipophilic dye; (b) exciting the fluorescent protein; and (c) determining fluorescence resonance energy transfer of the contacted neuronal cell relative to a control cell, where a difference in fluorescence resonance energy transfer of the contacted neuronal cell as compared to the control cell is indicative of BoNT/A activity.

Other aspects of the present invention provide a method of determining BoNT/E activity comprising (a) contacting with a sample a neuronal cell comprising (1) a stably expressed nucleic acid molecule encoding a membrane-associated BoNT/E substrate comprising (i) a fluorescent protein; (ii) a membrane targeting domain; and (iii) a BoNT/E recognition sequence including a cleavage site; and (2) a membrane-associated lipophilic dye which has an absorbance spectrum overlapping the emission spectrum of the fluorescent protein; wherein the neuronal cell is capable of BoNT/E intoxication; and wherein, under the appropriate conditions, fluorescence resonance energy transfer is exhibited between the fluorescent protein and the lipophilic dye; (b) exciting the fluorescent protein; and (c) determining fluorescence resonance energy transfer of the contacted neuronal cell relative to a control cell, where a difference in fluorescence resonance energy transfer of the contacted neuronal cell as compared to the control cell is indicative of BoNT/E activity.

Thus, in an embodiment a Clostridial toxin substrate comprises, in part, the membrane targeting domain comprising a region from SNAP-25 sufficient to target a toxin substrate disclosed in the present specification to the membrane. In an aspect of this embodiment, the membrane targeting domain comprising a region from the interhelical region of SNAP-25 sufficient to target a toxin substrate disclosed in the present specification to the membrane. In an aspect of this embodiment the membrane targeting domain comprises the amino acids 85-120 of SEQ ID NO: 1. It is envisioned that an interhelical loop region from SNAP-25 of any and all lengths can comprise the membrane targeting domain with the proviso that the loop region is sufficient to target a toxin substrate disclosed in the present specification to the membrane. Thus, aspects of this embodiment may include an interhelical loop region comprising, e.g., at least 35 residues from amino acids 85-120 of SEQ ID NO: 1, at least 30 residues from amino acids 85-120 of SEQ ID NO: 1, at least 25 residues from amino acids 85-120 of SEQ ID NO: 1, at least 20 residues from amino acids 85-120 of SEQ ID NO: 1, at least 15 residues from amino acids 85-120 of SEQ ID NO: 1, at least 10 residues from amino acids 85-120 of SEQ ID NO: 1 or at least 5 residues from amino acids 85-120 of SEQ ID NO: 1. Further aspects of this embodiment may include an interhelical loop region comprising, e.g., at most 35 residues from amino acids 85-120 of SEQ ID NO: 1, at most 30 residues from amino acids 85-120 of SEQ ID NO: 1, at most 25 residues from amino acids 85-120 of SEQ ID NO: 1, at most 20 residues from amino acids 85-120 of SEQ ID NO: 1, at most 15 residues from amino acids 85-120 of SEQ ID NO: 1, at most 10 residues from amino acids 85-120 of SEQ ID NO: 1 or at most 5 residues from amino acids 85-120 of SEQ ID NO: 1.

In another aspect of this embodiment a Clostridial toxin substrate comprises, in part, the membrane targeting domain comprises amino acids CGLCVCPCNK (SEQ ID NO: 128). In another aspect of this embodiment the membrane targeting domain comprises amino acids CGLFICPCNK (SEQ ID NO: 129). In another aspect of this embodiment the membrane targeting domain comprises amino acids CGLCSCPCNK (SEQ ID NO: 130). In another aspect of this embodiment the membrane targeting domain comprises amino acids CGLCPCPCNK(SEQ ID NO: 131). In another aspect of this embodiment the membrane targeting domain comprises amino acids CGICVCPWKK(SEQ ID NO: 132). In another aspect of this embodiment the membrane targeting domain comprises amino acids CGICVLPCNK (SEQ ID NO: 133). In another aspect of this embodiment the membrane targeting domain comprises amino acids CGLCVLPWNK (SEQ ID NO: 134).

In another embodiment a Clostridial toxin substrate comprises, in part, the membrane targeting domain comprises the amino acids QPXRV (SEQ ID NO: 135), where X is any amino acid. In another aspect of this embodiment the membrane targeting domain comprises amino acids QPXR1 (SEQ ID NO: 136), where X is any amino acid. In another aspect of this embodiment the membrane targeting domain comprises amino acids QPARV (SEQ ID NO: 137). In another aspect of this embodiment the membrane targeting domain comprises amino acids QPQRV (SEQ ID NO: 138). In another aspect of this embodiment the membrane targeting domain comprises amino acids QPGRV (SEQ ID NO: 139). In another aspect of this embodiment the membrane targeting domain comprises amino acids QPSRI (SEQ ID NO: 140). In another aspect of this embodiment the membrane targeting domain comprises amino acids QPMRM (SEQ ID NO: 141). In another aspect of this embodiment the membrane targeting domain comprises amino acids QPRI (SEQ ID NO: 142).

In another embodiment a Clostridial toxin substrate comprises, in part, the membrane targeting domain comprises amino acids from the amino-terminal α-helix of SNAP-25 sufficient to target a toxin substrate disclosed in the present specification to the membrane. In an aspect of this embodiment the membrane targeting domain comprises the amino acids 1-84 of SEQ ID NO: 1. It is envisioned that an amino-terminal α-helix from SNAP-25 of any and all lengths can comprise the membrane targeting domain with the proviso that the loop region is sufficient to target a toxin substrate disclosed in the present specification to the membrane. Thus, aspects of this embodiment may include an amino-terminal α-helix region comprising, e.g., at least 80 residues from amino acids 1-84 of SEQ ID NO: 1, at least 75 residues from amino acids 1-84 of SEQ ID NO: 1, at least 70 residues from amino acids 1-84 of SEQ ID NO: 1, at least 65 residues from amino acids 1-84 of SEQ ID NO: 1, at least 60 residues from amino acids 1-84 of SEQ ID NO: 1, at least 55 residues from amino acids 1-84 of SEQ ID NO: 1, at least 50 residues from amino acids 1-84 of SEQ ID NO: 1, at least 45 residues from amino acids 1-84 of SEQ ID NO: 1, at least 40 residues from amino acids 1-84 of SEQ ID NO: 1, at least 35 residues from amino acids 1-84 of SEQ ID NO: 1, at least 30 residues from amino acids 1-84 of SEQ ID NO: 1, at least 25 residues from amino acids 1-84 of SEQ ID NO: 1, at least 20 residues from amino acids 1-84 of SEQ ID NO: 1, at least 15 residues from amino acids 1-84 of SEQ ID NO: 1, at least 10 residues from amino acids 1-84 of SEQ ID NO: 1 or at least 5 residues from amino acids 1-84 of SEQ ID NO: 1. Further aspects of this embodiment may include an amino-terminal α-helix region comprising, e.g., at most 80 residues from amino acids 1-84 of SEQ ID NO: 1, at most 75 residues from amino acids 1-84 of SEQ ID NO: 1, at most 70 residues from amino acids 1-84 of SEQ ID NO: 1, at most 65 residues from amino acids 1-84 of SEQ ID NO: 1, at most 60 residues from amino acids 1-84 of SEQ ID NO: 1, at most 55 residues from amino acids 1-84 of SEQ ID NO: 1, at most 50 residues from amino acids 1-84 of SEQ ID NO: 1, at most 45 residues from amino acids 1-84 of SEQ ID NO: 1, at most 40 residues from amino acids 1-84 of SEQ ID NO: 1, at most 35 residues from amino acids 1-84 of SEQ ID NO: 1, at most 30 residues from amino acids 1-84 of SEQ ID NO: 1, at most 25 residues from amino acids 1-84 of SEQ ID NO: 1, at most 20 residues from amino acids 1-84 of SEQ ID NO: 1, at most 15 residues from amino acids 1-84 of SEQ ID NO: 1, at most 10 residues from amino acids 1-84 of SEQ ID NO: 1 or at most 5 residues from amino acids 1-84 of SEQ ID NO: 1.

In yet another embodiment a Clostridial toxin substrate comprises, in part, the membrane targeting domain comprises amino acids from the carboxy-terminal α-helix of SNAP-25 sufficient to target a toxin substrate disclosed in the present specification to the membrane. In an aspect of this embodiment the membrane targeting domain comprises the amino acids 121-206 of SEQ ID NO: 1. It is envisioned that an carboxy-terminal α-helix from SNAP-25 of any and all lengths can comprise the membrane targeting domain with the proviso that the loop region is sufficient to target a toxin substrate disclosed in the present specification to the membrane. Thus, aspects of this embodiment may include an carboxy-terminal α-helix region comprising, e.g., at least 80 residues from amino acids 121-206 of SEQ ID NO: 1; at least 75 residues from amino acids 121-206 of SEQ ID NO: 1, at least 70 residues from amino acids 121-206 of SEQ ID NO: 1, at least 65 residues from amino acids 121-206 of SEQ ID NO: 1, at least 60 residues from amino acids 121-206 of SEQ ID NO: 1, at least 55 residues from amino acids 121-206 of SEQ ID NO: 1, at least 50 residues from amino acids 121-206 of SEQ ID NO: 1, at least 45 residues from amino acids 121-206 of SEQ ID NO: 1, at least 40 residues from amino acids 121-206 of SEQ ID NO: 1, at least 35 residues from amino acids 121-206 of SEQ ID NO: 1, at least 30 residues from amino acids 121-206 of SEQ ID NO: 1, at least 25 residues from amino acids 121-206 of SEQ ID NO: 1, at least 20 residues from amino acids 121-206 of SEQ ID NO: 1, at least 15 residues from amino acids 121-206 of SEQ ID NO: 1, at least 10 residues from amino acids 121-206 of SEQ ID NO: 1 or at least 5 residues from amino acids 121-206 of SEQ ID NO: 1. Further aspects of this embodiment may include an carboxy-terminal α-helix region comprising, e.g., at most 85 residues from amino acids 121-206 of SEQ ID NO: 1; at most 80 residues from amino acids 121-206 of SEQ ID NO: 1; at most 75 residues from amino acids 121-206 of SEQ ID NO: 1, at most 70 residues from amino acids 121-206 of SEQ ID NO: 1, at most 65 residues from amino acids 121-206 of SEQ ID NO: 1, at most 60 residues from amino acids 121-206 of SEQ ID NO: 1, at most 55 residues from amino acids 121-206 of SEQ ID NO: 1, at most 50 residues from amino acids 121-206 of SEQ ID NO: 1, at most 45 residues from amino acids 121-206 of SEQ ID NO: 1, at most 40 residues from amino acids 121-206 of SEQ ID NO: 1, at most 35 residues from amino acids 121-206 of SEQ ID NO: 1, at most 30 residues from amino acids 121-206 of SEQ ID NO: 1, at most 25 residues from amino acids 121-206 of SEQ ID NO: 1, at most 20 residues from amino acids 121-206 of SEQ ID NO: 1, at most 15 residues from amino acids 121-206 of SEQ ID NO: 1, at most 10 residues from amino acids 121-206 of SEQ ID NO: 1 or at most 5 residues from amino acids 121-206 of SEQ ID NO: 1.

In another embodiment a Clostridial toxin substrate comprises, in part, the membrane targeting domain comprising a region from Syntaxin sufficient to target a toxin substrate disclosed in the present specification to the membrane. In an aspect of this embodiment, the membrane targeting domain comprising a region from the membrane anchoring domain of Syntaxin sufficient to target a toxin substrate disclosed in the present specification to the membrane. In an aspect of this embodiment the membrane targeting domain comprises the amino acids 266-288 of SEQ ID NO: 66. It is envisioned that an membrane anchoring domain from Syntaxin of any and all lengths can comprise the membrane targeting domain with the proviso that the loop region is sufficient to target a toxin substrate disclosed in the present specification to the membrane. Thus, aspects of this embodiment may include an interhelical loop region comprising, e.g., at least 20 residues from amino acids 266-288 of SEQ ID NO: 66; at least 15 residues from amino acids 266-288 of SEQ ID NO: 66, Or at least 10 residues from amino acids 266-288 of SEQ ID NO: 66. Further aspects of this embodiment may include an membrane anchoring domain comprising, e.g., at most 20 residues from amino acids 266-288 of SEQ ID NO: 66; at most 15 residues from amino acids 266-288 of SEQ ID NO: 66 or at most 10 residues from amino acids 266-288 of SEQ ID NO: 66.

In an aspect of this embodiment, a Clostridial toxin substrate comprises, in part, the membrane targeting domain of human Syntaxin-1A of SEQ ID NO: 66. In another aspect of this embodiment, a Clostridial toxin substrate comprises, in part, the membrane targeting domain comprising amino acids IMIIICCVILGIVIASTVGGIFA, which corresponds to residues 266-288 of SEQ ID NO: 66. In another aspect of this embodiment, a Clostridial toxin substrate comprises, in part, the membrane targeting domain of human Syntaxin-1B1 of SEQ ID NO: 67. In another aspect of this embodiment, a Clostridial toxin substrate comprises, in part, the membrane targeting domain comprising amino acids IIIIICCVVLGVVLASSIGCTLGL, which corresponds to residues 265-288 of SEQ ID NO: 67. In another aspect of this embodiment, a Clostridial toxin substrate comprises, in part, the membrane targeting domain of human Syntaxin-1B2 of SEQ ID NO: 68. In another aspect of this embodiment, a Clostridial toxin substrate comprises, in part, the membrane targeting domain comprising amino acids IMIIICCVVLGVVLASSIGGTLGL, which corresponds to residues 265-288 of SEQ ID NO: 67. In another aspect of this embodiment, a Clostridial toxin substrate comprises, in part, the membrane targeting domain of human Syntaxin-2-1 of SEQ ID NO: 69. In another aspect of this embodiment, a Clostridial toxin substrate comprises, in part, the membrane targeting domain comprising amino acids LMFIIICVIVLLVILGIILATTLS, which corresponds to residues 264-287 of SEQ ID NO: 69. In another aspect of this embodiment, a Clostridial toxin substrate comprises, in part, the membrane targeting domain of human Syntaxin-2-2 of SEQ ID NO: 70. In another aspect of this embodiment, a Clostridial toxin substrate comprises, in part, the membrane targeting domain comprising amino acids WIIIAVSVVLVVIIVLIIGLSVGK, which corresponds to residues 264-288 of SEQ ID NO: 70. In another aspect of this embodiment, a Clostridial toxin substrate comprises, in part, the membrane targeting domain of human Syntaxin-2-3 of SEQ ID NO: 71. In another aspect of this embodiment, a Clostridial toxin substrate comprises, in part, the membrane targeting domain comprising amino acids WIIIAVSVVLVAIIALIIGLSVGK, which corresponds to residues 264-288 of SEQ ID NO: 71. In another aspect of this embodiment, a Clostridial toxin substrate comprises, in part, the membrane targeting domain of human Syntaxin-3 of SEQ ID NO: 72. In another aspect of this embodiment, a Clostridial toxin substrate comprises, in part, the membrane targeting domain comprising amino acids LIIIIVLVVVLLGILALIIGISVGLN, which corresponds to residues 264-289 of SEQ ID NO: 72.

In another aspect of this embodiment, a Clostridial toxin substrate comprises, in part, the membrane targeting domain of cow Syntaxin-1A of SEQ ID NO: 73. In another aspect of this embodiment, a Clostridial toxin substrate comprises, in part, the membrane targeting domain comprising amino acids IMIVICCVVLGIVIASTFGGIFG, which corresponds to residues 266-288 of SEQ ID NO: 67.

In an aspect of this embodiment, a Clostridial toxin substrate comprises, in part, the membrane targeting domain of rat Syntaxin-1A of SEQ ID NO: 75. In another aspect of this embodiment, a Clostridial toxin substrate comprises, in part, the membrane targeting domain comprising amino acids IMIIICCVILGIIIASTIGGIFG, which corresponds to residues 266-288 of SEQ ID NO: 75. In an aspect of this embodiment, a Clostridial toxin substrate comprises, in part, the membrane targeting domain of rat Syntaxin-1B2 of SEQ ID NO: 76. In another aspect of this embodiment, a Clostridial toxin substrate comprises, in part, the membrane targeting domain comprising amino acids IMIIICCVVLGVVLASSIGGTLGL, which corresponds to residues 265-288 of SEQ ID NO: 76. In an aspect of this embodiment, a Clostridial toxin substrate comprises, in part, the membrane targeting domain of rat Syntaxin-2 of SEQ ID NO: 80. In another aspect of this embodiment, a Clostridial toxin substrate comprises, in part, the membrane targeting domain comprising amino acids WIIAAVVVAVIAVLALIIGLSVGK, which corresponds to residues 267-290 of SEQ ID NO: 80. In an aspect of this embodiment, a Clostridial toxin substrate comprises, in part, the membrane targeting domain of mouse Syntaxin-2 of SEQ ID NO: 81. In another aspect of this embodiment, a Clostridial toxin substrate comprises, in part, the membrane targeting domain comprising amino acids WIIAAVAVAVIAVLALIIGLSVGK, which corresponds to residues 266-289 of SEQ ID NO: 81. In an aspect of this embodiment, a Clostridial toxin substrate comprises, in part, the membrane targeting domain of rat Syntaxin-3A of SEQ ID NO: 82. In another aspect of this embodiment, a Clostridial toxin substrate comprises, in part, the membrane targeting domain comprising amino acids LIIIIVIVVVLLGILALIIGISVGLK, which corresponds to residues 264-289 of SEQ ID NO: 82. In an aspect of this embodiment, a Clostridial toxin substrate comprises, in part, the membrane targeting domain of mouse Syntaxin-3A of SEQ ID NO: 83. In another aspect of this embodiment, a Clostridial toxin substrate comprises, in part, the membrane targeting domain comprising amino acids LIIIIVVVVVLLGILALIIGLSVGLK, which corresponds to residues 264-289 of SEQ ID NO: 83. In an aspect of this embodiment, a Clostridial toxin substrate comprises, in part, the membrane targeting domain of mouse Syntaxin-3B of SEQ ID NO: 84. In another aspect of this embodiment, a Clostridial toxin substrate comprises, in part, the membrane targeting domain comprising amino acids IMIMICCIILAIILASTIG, which corresponds to residues 265-283 of SEQ ID NO: 84. In an aspect of this embodiment, a Clostridial toxin substrate comprises, in part, the membrane targeting domain of mouse Syntaxin-3C of SEQ ID NO: 85.

In another aspect of this embodiment, a Clostridial toxin substrate comprises, in part, the membrane targeting domain comprising amino acids IMIMICCIILAIILASTIGGIFA, which corresponds to residues 247-269 of SEQ ID NO: 85.

In an aspect of this embodiment, a Clostridial toxin substrate comprises, in part, the membrane targeting domain of chicken Syntaxin-1A of SEQ ID NO: 86. In another aspect of this embodiment, a Clostridial toxin substrate comprises, in part, the membrane targeting domain comprising amino acids IMIIIFVVVLGVVLSPVICGTLGL, which corresponds to residues 259-282 of SEQ ID NO: 86. In an aspect of this embodiment, a Clostridial toxin substrate comprises, in part, the membrane targeting domain of chicken Syntaxin-2 of SEQ ID NO: 87. In another aspect of this embodiment, a Clostridial toxin substrate comprises, in part, the membrane targeting domain comprising amino acids WIIIIVSLVLIAVIGIIIGLSVGIR, which corresponds to residues 263-288 of SEQ ID NO: 87.

In an aspect of this embodiment, a Clostridial toxin substrate comprises, in part, the membrane targeting domain of zebrafish Syntaxin-1A of SEQ ID NO: 88. In another aspect of this embodiment, a Clostridial toxin substrate comprises, in part, the membrane targeting domain comprising amino acids IMIIICCVILGVVLRSSIGGTLGF, which corresponds to residues 265-288 of SEQ ID NO: 88. In an aspect of this embodiment, a Clostridial toxin substrate comprises, in part, the membrane targeting domain of zebrafish Syntaxin-3 of SEQ ID NO: 89. In another aspect of this embodiment, a Clostridial toxin substrate comprises, in part, the membrane targeting domain comprising amino acids IIIIVSVVLVILAIIALIVGISVGLKR, which corresponds to residues 262-288 of SEQ ID NO: 89.

In an aspect of this embodiment, a Clostridial toxin substrate comprises, in part, the membrane targeting domain of sea urchin Syntaxin-1A of SEQ ID NO: 90. In another aspect of this embodiment, a Clostridial toxin substrate comprises, in part, the membrane targeting domain comprising amino acids YIAICCGVALGILILVLIIVLA, which corresponds to residues 264-286 of SEQ ID NO: 90.

In an aspect of this embodiment, a Clostridial toxin substrate comprises, in part, the membrane targeting domain of fruit fly Syntaxin-1A of SEQ ID NO: 91. In another aspect of this embodiment, a Clostridial toxin substrate comprises, in part, the membrane targeting domain comprising amino acids IMILICLTVLGILAASYVSSYFM, which corresponds to residues 269-291 of SEQ ID NO: 91.

In an aspect of this embodiment, a Clostridial toxin substrate comprises, in part, the membrane targeting domain of leech Syntaxin-1A of SEQ ID NO: 92. In another aspect of this embodiment, a Clostridial toxin substrate comprises, in part, the membrane targeting domain comprising amino acids IIILICVSVLILIVGGSLLGIFIP, which corresponds to residues 272-295 of SEQ ID NO: 92.

In an aspect of this embodiment, a Clostridial toxin substrate comprises, in part, the membrane targeting domain of squid Syntaxin-1A of SEQ ID NO: 93. In another aspect of this embodiment, a Clostridial toxin substrate comprises, in part, the membrane targeting domain comprising amino acids IAILVCLVILVLVIVSTVGGVFGG, which corresponds to residues 269-292 of SEQ ID NO: 93.

In an aspect of this embodiment, a Clostridial toxin substrate comprises, in part, the membrane targeting domain of snail Syntaxin-1A of SEQ ID NO: 94. In another aspect of this embodiment, a Clostridial toxin substrate comprises, in part, the membrane targeting domain comprising amino acids IMIIICVCVLIIILVGILGGTFG, which corresponds to residues 268-290 of SEQ ID NO: 94.

In an aspect of this embodiment, a Clostridial toxin substrate comprises, in part, the membrane targeting domain of sea hare Syntaxin-1A of SEQ ID NO: 95. In another aspect of this embodiment, a Clostridial toxin substrate comprises, in part, the membrane targeting domain comprising amino acids IMILVCLAILIIILVGVIGGTLG, which corresponds to residues 268-290 of SEQ ID NO: 95.

The Clostridial toxin substrates disclosed in the present specification include, in part, a first member of a FRET pair. Such a first member of a FRET pair can be either a donor fluorophore or an acceptor. Thus, the recited clostridial toxin substrate includes, in part, a first member of the FRET pair which is either a donor fluorophore or an acceptor.

A first member of the FRET pair disclosed in the present specification includes fluorescent proteins. As used herein, the term "fluorescent protein" means a peptide which absorbs light energy of a certain wavelength and emits light energy of a different wavelength and encompass those which emit in a variety of spectra, including violet, blue, cyan, green, yellow, orange and red, see Table 9. It is envisioned that fluorescent proteins derived from any of a variety of species can be useful in aspects of the present invention including, but not limited to, *Aequorea* fluorescent proteins, *Anemonia* fluorescent proteins, *Anthozoa* fluorescent proteins, *Discosoma* fluorescent proteins, *Entacmeae* fluorescent proteins, *Heteractis* fluorescent proteins, *Montastrea* fluorescent proteins, *Renilla* fluorescent proteins, *Zoanthus* fluorescent proteins, and fluorescent proteins from other organisms. Fluorescent proteins useful in the invention encompass, without limitation, wild type fluorescent proteins, naturally occurring variants, and genetically engineered variants, produced, e.g., by random mutagenesis or rational designed, and active peptide fragments derived from an organism. Fluorescent proteins useful in aspects of the invention include, e.g., those which have been genetically engineered for superior performance such as, without limitation, altered excitation or emission wavelengths; enhanced brightness, pH resistance, stability or speed of fluorescent protein formation; photoactivation; or reduced oligomerization or photobleaching, see, e.g., Brendan P. Cormack et al., FACS-optimized Mutants of the Green Fluorescent Protein (GFP), U.S. Pat. No. 5,804,387 (Sep. 8, 1998); Roger Y. Tsien & Roger Heim, Modified Green Fluorescent Proteins, U.S. Pat. No. 6,800,733 (Oct. 5, 2004); Roger Y. Tsien et al., Long Wavelength Engineered Fluorescent Proteins, U.S. Pat. No. 6,780,975 (Aug. 24, 2004); and Roger Y. Tsien et al., Fluorescent Protein Sensors For Measuring the pH of a Biological Sample, U.S. Pat. No. 6,627,449 (Sep. 30, 2003). It is understood that a fluorescent protein can be engineered for improved protein expression by converting wild type codons to other codons more efficiently utilized in the cells which serve to express the Clostridial toxin substrate, see, e.g., Brian Seed and Jurgen Haas, High Level Expression of Proteins, U.S. Pat. No. 5,795,737 (Aug. 18, 1998).

It is also envisioned that any of a variety of active protein fragments can be useful in aspects of the present invention with the proviso that these active fragments retain the ability to emit light energy in a range suitable for the proper operation of aspects of the present invention, such as, e.g. 420-460 nm for blue emitting fluorescent proteins, 460-500 nm for cyan emitting fluorescent proteins, 500-520 nm for green emitting fluorescent proteins, 520-550 nm for yellow emitting fluorescent proteins and for 550-740 nm for red emitting fluorescent proteins. Thus, aspects of this embodiment can include active fragments of fluorescent proteins that retain the ability to emit light energy in a range suitable for the proper operation of aspects of the present invention having a length of, e.g., at least 50 amino acids, at least 60 amino acids, at least 70 amino acids, at least 80 amino acids, at least 90 amino acids, at least 100 amino acids, at least 125 amino acids, at least 150 amino acids, at least 175 amino acids and at least 200 amino acids. Other aspects of this embodiment, can include active fragments of fluorescent proteins that retain the ability to emit light energy in a range suitable for the proper operation of aspects of the present invention having a length of, e.g., at most 50 amino acids, at most 60 amino acids, at most 70 amino acids, at most 80 amino acids, at most 90 amino acids, at most 100 amino acids, at most 125 amino acids, at most 150 amino acids, at most 175 amino acids and at most 200 amino acids.

TABLE 9

Excitation and Emission Maxima of Exemplary Fluorescent Proteins

| Fluorescent protein | Excitation maxima (nm) | Emission maxima (nm) |
|---|---|---|
| EBFP | 380 | 440 |
| ECFP | 439 | 476 |
| AmCyan | 458 | 489 |
| AcGFP | 475 | 505 |
| ZsGreen | 493 | 505 |
| Vitality ® hrGFP | 500 | 506 |
| EGFP | 484 | 510 |
| Monster Green ® | 505 | 515 |
| EYFP | 512 | 529 |
| ZsYellow | 529 | 539 |
| DsRed-Express | 557 | 579 |
| DsRed2 | 563 | 582 |
| DsRed | 558 | 583 |
| AsRed2 | 576 | 592 |
| HcRed1 | 588 | 618 |

Non-limiting examples of fluorescent proteins that may be operably-linked to a CoNT substrate disclosed in the specification include, e.g., photoproteins, such as, e.g., aequorin; obelin; *Aequorea* fluorescent proteins, such, e.g., green fluorescent proteins (GFP, EGFP, AcGFP1), cyan fluorescent proteins (CFP, ECFP), blue fluorescent proteins (BFP, EBFP), red fluorescent proteins (RFP), yellow fluorescent proteins (YFP, EYFP), ultraviolet fluorescent protein (GFPuv), their fluorescence-enhancement variants, their peptide destabilization variants, and the like; coral reef fluorescent proteins, such, e.g., Discosoma red fluorescent proteins (DsRed, DsRed1, DsRed2, and DsRed-Express), Anemonia red fluorescent proteins (AsRed and AsRed2), Heteractis far-red fluorescent proteins (HcRed, HcRed1), Anemonia cyan fluorescent proteins (AmCyan, AmCyan1), Zoanthus green fluorescent proteins (ZsGreen, ZsGreen1), Zoanthus yellow fluorescent proteins (ZsYellow, ZsYellow1), their fluorescence-enhancement variants, their peptide destabilization variants, and the like; *Renilla reniformis* green fluorescent protein (Vitality hrGFP), its fluorescence-enhancement variants, its peptide destabilization variants, and the like; and Great Star Coral fluorescent proteins, such, e.g., *Montastrea cavernosa* fluorescent protein (Monster Green® Fluorescent Protein), its fluorescence-enhancement variants, its peptide destabilization variants, and the like. One skilled in the art understands that these and a variety of other fluorescent proteins can be useful as a fluorescent protein in aspects of the invention, see, e.g., Jennifer Lippincott-Schwartz & George H. Patterson, Development and Use of Fluorescent Protein Markers in Living Cells, 300(5616) Science 87-91 (2003); and Jin Zhang et al., 3(12) Nat. Rev. Mol. Cell. Biol. 906-918 (2002). One skilled in the art understands that these and many other fluorescent proteins, including species orthologs and paralogs of the above described naturally occurring fluorescent proteins as well as engineered fluorescent proteins can be useful as a fluorescent protein disclosed in aspects of the present specification. CoNT substrates disclosed in the present specification containing, in part, such fluorescent proteins can be prepared and expressed using standard methods see, e.g., Living Colors® User Manual PT2040-1 (PRI1Y691), BD Biosciences-Clontech, (Nov. 26 2001); BD Living Colors™ User Manual Volume II: Reef Coral Fluorescent Proteins, PT3404-1 (PR37085), BD Biosciences-Clontech, (Jul. 17, 2003); Monster Green Florescent Protein pHMCFP Vector, TB320, Promega Corp., (May, 2004); and Vitality hrGFP Mammalian Expression Vectors, Instruction Manual (rev. 064007g), Stratagene, Inc. Expression vectors suitable for bacterial, mammalian and other expression of fluorescent proteins are available from a variety of commercial sources including BD Biosciences Clontech (Palo Alto, Calif.); Promega Corp. (Madison, Wis.) and Stratagene, Inc. (La Jolla, Calif.).

In an embodiment, the first member of the FRET pair is a green fluorescent protein. As used herein, the term "green fluorescent protein" is synonymous with "GFP" and means a protein which absorbs light of a certain wavelength and emits peak light energy of wavelengths in the range of 500-520 nm. Green fluorescent proteins useful in the invention include, without limitation, the AcGFP1 of SEQ ID NO: 143, genetically engineered AcGFP1 variants and active AcGFP1 fragments thereof that retain the ability to emit peak light energy in the range of 500-520 nm, the ZsGreen of SEQ ID NO: 144, genetically engineered ZsGreen variants and active ZsGreen fragments thereof that retain the ability to emit peak light energy in the range of 500-520 nm, the EGFP of SEQ ID NO: 145, genetically engineered ECFP variants and active ECFP fragments thereof that retain the ability to emit peak light energy in the range of 500-520 nm, the Monster Green Fluorescent Protein (MGFP) of SEQ ID NO: 146, genetically engineered MGFP variants and active MGFP fragments thereof that retain the ability to emit peak light energy in the range of 500-520 nm, the Vitality® hrGFP of SEQ ID NO: 147, genetically engineered hrGFP variants and active hrGFP fragments thereof that retain the ability to emit peak light energy in the range of 500-520 nm, as well as, naturally-occurring GFPs, naturally occurring GFP variants, genetically engineered GFP variants and active GFP fragments thereof that retain the ability to emit peak light energy in the range of 500-520 nm. As non-limiting examples, *Renilla*-derived fluorescent proteins such as, e.g., the dimeric *Renilla mulleri* GFP, which has narrow excitation (498 nm) and emission (509 nm) peaks, see, e.g., Beau Peelle et al., Characterization and use of green fluorescent proteins from *Renilla mulleri* and *Ptilosarcus guernyi* for the human cell display of functional peptides, 20(6) J. Protein Chem. 507-519 (2001); and Aequorea-derived fluorescent proteins as described in, e.g., Roger Y. Tsien & Roger Heim, Modified Green Fluorescent Proteins, U.S. Pat. Nos. 5,625,048 (Apr. 29, 1997), 6,319,669 (Nov. 20, 2001), 6,066,476 (May 23, 2000) and 6,800,733 (Oct. 5, 2004).

Thus, in aspects of this embodiment, the first member of the FRET pair can be a GFP that emits peak s light in the range of 500-520 nm which has, e.g., at least 70% amino acid identity with the AcGFP1 of SEQ ID NO: 143, at least 75% amino acid identity with the AcGFP1 of SEQ ID NO: 143, at least 80% amino acid identity with the AcGFP1 of SEQ ID NO: 143, at least 85% amino acid identity with the AcGFP1 of SEQ ID NO: 143, at least 90% amino acid identity with the AcGFP1 of SEQ ID NO: 143 or at least 95% amino acid identity with the AcGFP1 of SEQ ID NO: 143. In other aspects of this embodiment, the first member of the FRET pair is a GFP that emits light in the range of 500-520 nm which has, e.g., at most one, two, three, four, five, six, seven, eight, nine, or ten amino acid substitutions relative to the AcGFP1 of SEQ ID NO: 143.

In other aspects of this embodiment, the first member of the FRET pair can be a GFP that emits light in the range of 500-520 nm which has, e.g., at least 70% amino acid identity with the ZsGreen of SEQ ID NO: 144, at least 75% amino acid identity with the ZsGreen of SEQ ID NO: 144, at least 80% amino acid identity with the ZsGreen of SEQ ID NO: 144, at least 85% amino acid identity with the ZsGreen of SEQ ID NO: 144, at least 90% amino acid identity with the ZsGreen of SEQ ID NO: 144 or at least 95% amino acid identity with the ZsGreen of SEQ ID NO: 144. In still other aspects of this embodiment, the first member of the FRET pair is a GFP that emits light in the range of 500-520 nm which has, e.g., at most one, two, three, four, five, six, seven, eight, nine, or ten amino acid substitutions relative to the ZsGreen of SEQ ID NO: 144.

In other aspects of this embodiment, the first member of the FRET pair can be a GFP that emits light in the range of 500-520 nm which has, e.g., at least 70% amino acid identity with the EGFP of SEQ ID NO: 145, at least 75% amino acid identity with the EGFP of SEQ ID NO: 145, at least 80% amino acid identity with the EGFP of SEQ ID NO: 145, at least 85% amino acid identity with the EGFP of SEQ ID NO: 145, at least 90% amino acid identity with the EGFP of SEQ ID NO: 145 or at least 95% amino acid identity with the EGFP of SEQ ID NO: 145. In still other aspects of this embodiment, the first member of the FRET pair is a GFP that emits light in the range of 500-520 nm which has, e.g., at most one, two, three, four, five, six, seven, eight, nine, or ten amino acid substitutions relative to the EGFP of SEQ ID NO: 145.

In other aspects of this embodiment, the first member of the FRET pair can be a GFP that emits light in the range of 500-520 nm which has, e.g., at least 70% amino acid identity with the MGFP of SEQ ID NO: 146, at least 75% amino acid identity with the MGFP of SEQ ID NO: 146, at least 80% amino acid identity with the MGFP of SEQ ID NO: 146, at least 85% amino acid identity with the MGFP of SEQ ID NO: 146, at least 90% amino acid identity with the MGFP of SEQ ID NO: 146 or at least 95% amino acid identity with the MGFP of SEQ ID NO: 146. In still other aspects of this embodiment, the first member of the FRET pair is a GFP that emits light in the range of 500-520 nm which has, e.g., at most one, two, three, four, five, six, seven, eight, nine, or ten amino acid substitutions relative to the MGFP of SEQ ID NO: 146.

In other aspects of this embodiment, the first member of the FRET pair can be a GFP that emits light in the range of 500-520 nm which has, e.g., at least 70% amino acid identity with the hrGFP of SEQ ID NO: 147, at least 75% amino acid identity with the hrGFP of SEQ ID NO: 147, at least 80% amino acid identity with the hrGFP of SEQ ID NO: 147, at least 85% amino acid identity with the hrGFP of SEQ ID NO: 147, at least 90% amino acid identity with the hrGFP of SEQ ID NO: 147 or at least 95% amino acid identity with the hrGFP of SEQ ID NO: 147. In still other aspects of this embodiment, the first member of the FRET pair is a GFP that emits light in the range of 500-520 nm which has, e.g., at most one, two, three, four, five, six, seven, eight, nine, or ten amino acid substitutions relative to the hrGFP of SEQ ID NO: 147.

In another embodiment, the first member of the FRET pair is a cyan fluorescent protein. As used herein, the term "cyan fluorescent protein" is synonymous with "CFP" and means a protein which absorbs light of a certain wavelength and emit peak light energy of wavelengths in the range of 460-500 nm. Cyan fluorescent proteins useful in the invention include, without limitation, the ECFP of SEQ ID NO: 148, genetically engineered ECFP variants and active ECFP fragments thereof that retain the ability to emit peak light energy in the range of 460-500 nm, the AmCyan of SEQ ID NO: 149, genetically engineered AmCyan variants and active AmCyan fragments thereof that retain the ability to emit peak light energy in the range of 460-500 nm, as well as, naturally-occurring cyan fluorescent proteins, naturally occurring CFP variants, genetically engineered CFP variants and active CFP fragments thereof that retain the ability to emit peak light energy in the range of 460-500 nm. As a non-limiting example, the CFP variant known as "CGFP" contains a Thr203Tyr substitution that changes the excitation and emission wavelengths of the ECFP of SEQ ID NO: 148 to a range between CFP and EGFP; and Aequorea-derived fluorescent proteins as described in, e.g., Roger Y. Tsien & Roger Heim, Modified Green Fluorescent Proteins, U.S. Pat. Nos. 5,625,048 (Apr. 29, 1997), 6,319,669 (Nov. 20, 2001), 6,066,476 (May 23, 2000) and 6,800,733 (Oct. 5, 2004).

Thus, in aspects of this embodiment, the first member of the FRET pair is a CFP that emits light in the range of 460-500 nm which has, e.g., at least 70% amino acid identity with the ECFP of SEQ ID NO: 148, at least 75% amino acid identity with the ECFP of SEQ ID NO: 148, at least 80% amino acid identity with the ECFP of SEQ ID NO: 148, at least 85% amino acid identity with the ECFP of SEQ ID NO: 148, at least 90% amino acid identity with the ECFP of SEQ ID NO: 148 or at least 95% amino acid identity with the ECFP of SEQ ID NO: 148. In other aspects of this embodiment, the first member of the FRET pair is a CFP that emits light in the range of 460-500 nm which has, e.g., at most one, two, three, four, five, six, seven, eight, nine, or ten amino acid substitutions relative to the ECFP of SEQ ID NO: 148.

In other aspects of this embodiment, the first member of the FRET pair is a CFP that emits light in the range of 460-500 nm which has, e.g., at least 70% amino acid identity with the AmCyan of SEQ ID NO: 149, at least 75% amino acid identity with the AmCyan of SEQ ID NO: 149, at least 80% amino acid identity with the AmCyan of SEQ ID NO: 149, at least 85% amino acid identity with the AmCyan of SEQ ID NO: 149, at least 90% amino acid identity with the AmCyan of SEQ ID NO: 149 or at least 95% amino acid identity with the AmCyan of SEQ ID NO: 149. In still other aspects of this embodiment, the first member of the FRET pair is a CFP that emits light in the range of 460-500 nm which has, e.g., at most one, two, three, four, five, six, seven, eight, nine, or ten amino acid substitutions relative to the AmCyan of SEQ ID NO: 149.

In yet another embodiment, the first member of the FRET pair is a blue fluorescent protein. As used herein, the term "blue fluorescent protein" is synonymous with "BFP" and means a protein which absorbs light of a certain wavelength and emit peak light energy of wavelengths in the range of 420-460 nm. Blue fluorescent proteins useful in the invention include, without limitation, the EBFP of SEQ ID NO: 150, genetically engineered EBFP variants and active EBFP fragments thereof that retain the ability to emit peak light energy in the range of 420-460 nm, as well as, naturally-occurring blue fluorescent proteins, naturally occurring BFP variants, genetically engineered BFP variants and active BFP fragments thereof that retain the ability to emit peak light energy in the range of 420-460 nm. As non-limiting examples, see Aequorea-derived fluorescent proteins as described in, e.g., Roger Y. Tsien & Roger Heim, Modified Green Fluorescent Proteins, U.S. Pat. Nos. 5,625,048 (Apr. 29, 1997), 6,319,669 (Nov. 20, 2001), 6,066,476 (May 23, 2000) and 6,800,733 (Oct. 5, 2004).

Thus, in aspects of this embodiment, the first member of the FRET pair is a BFP that emits light in the range of 420-460 nm which has, e.g., at least 70% amino acid identity with the EBFP of SEQ ID NO: 150, at least 75% amino acid identity with the EBFP of SEQ ID NO: 150, at least 80% amino acid identity with the EBFP of SEQ ID NO: 150, at least 85% amino acid identity with the EBFP of SEQ ID NO: 150, at least 90% amino acid identity with the EBFP of SEQ ID NO: 150 or at least 95% amino acid identity with the EBFP of SEQ ID NO: 150. In other aspects of this embodiment, the first member of the FRET pair is a BFP that emits light in the range of 420-460 nm which has, e.g., at most one, two, three, four, five, six, seven, eight, nine, or ten amino acid substitutions relative to the EBFP of SEQ ID NO: 150.

In yet another embodiment, the first member of the FRET pair is a yellow fluorescent protein. As used herein, the term "yellow fluorescent protein" is synonymous with "YFP" and means a protein which absorbs light of a certain wavelength and emit peak light energy of wavelengths in the range of 520-550 nm. Yellow fluorescent proteins useful in the invention include, without limitation, the EYFP of SEQ ID NO: 151, genetically engineered EYFP variants and active EYFP fragments thereof that retain the ability to emit peak light energy in the range of 520-550 nm, the ZsYellow of SEQ ID NO: 152, genetically engineered ZsYellow variants and active ZsYellow fragments thereof that retain the ability to emit peak light energy in the range of 520-550 nm, as well as, naturally-occurring YFPs, naturally occurring YFP variants, genetically engineered YFP variants and active YFP fragments thereof that retain the ability to emit peak light energy in the range of 520-550 nm. As non-limiting examples, the YFP variants "Citrine," which contain Val68Leu and Gln69Met substitutions in the YFP of SEQ ID NO: 151, and "Venus," which contain Phe46Leu, Met153Thr, Val163Ala and Ser175Gly substitutions in the YFP of SEQ ID NO: 151, are extremely bright and fast-maturing YFPs, see, e.g., Oliver Griesbeck et al., Reducing the environmental sensitivity of yellow fluorescent protein. Mechanism and applications, 276 (31) J. Biol. Chem. 29188-29194 (2001); and Takeharu Nagai et al., A variant of yellow fluorescent protein with fast and efficient maturation for cell-biological applications, 20(1) Nat. Biotechnol. 87-90 (2002); and *Aequorea*-derived fluorescent proteins as described in, e.g., Roger Y. Tsien et al., Long Wavelength Engineered Fluorescent Proteins, U.S. Pat. Nos. 6,124,128 (Sep. 26, 2000), 6,054,321 (Apr. 25, 2000), 6,077,707 (Jun. 20, 2000), 6,403,374 (Jun. 11, 2002) and 6,780,975 (Aug. 24, 2004).

Thus, in aspects of this embodiment, the first member of the FRET pair is a YFP that emits light in the range of 520-550 nm which has, e.g., at least 70% amino acid identity with the YFP of SEQ ID NO: 151, at least 75% amino acid identity with the YFP of SEQ ID NO: 151, at least 80% amino acid identity with the YFP of SEQ ID NO: 151, at least 85% amino acid identity with the YFP of SEQ ID NO: 151, at least 90% amino acid identity with the YFP of SEQ ID NO: 151 or at least 95% amino acid identity with the YFP of SEQ ID NO: 151. In other aspects of this embodiment, the first member of the FRET pair is a YFP that emits light in the range of 520-550 nm which has, e.g., at most one, two, three, four, five, six, seven, eight, nine, or ten amino acid substitutions relative to the YFP of SEQ ID NO: 151.

In other aspects of this embodiment, the first member of the FRET pair is a YFP that emits light in the range of 520-550 nm which has, e.g., at least 70% amino acid identity with the ZsYellow of SEQ ID NO: 152, at least 75% amino acid identity with the ZsYellow of SEQ ID NO: 152, at least 80% amino acid identity with the ZsYellow of SEQ ID NO: 152, at least 85% amino acid identity with the ZsYellow of SEQ ID NO: 152, at least 90% amino acid identity with the ZsYellow of SEQ ID NO: 152 or at least 95% amino acid identity with the ZsYellow of SEQ ID NO: 152. In still other aspects of this embodiment, the first member of the FRET pair is a YFP that emits light in the range of 520-550 nm which has, e.g., at most one, two, three, four, five, six, seven, eight, nine, or ten amino acid substitutions relative to the ZsYellow of SEQ ID NO: 152.

In yet embodiment, the first member of the FRET pair is a red fluorescent protein. As used herein, the term "red fluorescent protein" is synonymous with "RFP" and means a protein which absorbs light of a certain wavelength and emit peak light energy of wavelengths in the range of 550-740 nm. Red fluorescent proteins useful in the invention include, without limitation, the *Discosoma striate* RFP DsRed of SEQ ID NO: 153, DsRed1 of SEQ ID NO: 154, DsRed2 of SEQ ID NO: 155 and DsRed Express of SEQ ID NO: 156, genetically engineered DsRed, DsRed1, DsRed2 and DsRed Express variants and active DsRed, DsRed1, DsRed2 and DsRed Express fragments thereof that retain the ability to emit peak light energy in the range of 550-740 nm; the *Heteractis crispa* RFP HcRed of SEQ ID NO: 157, genetically engineered HcRed variants and active HcRed fragments thereof that retain the ability to emit peak light energy in the range of 550-740 nm; the *Anemonia sulcata* RFP AsRed of SEQ ID NO: 158, genetically engineered AsRed variants and active AsRed fragments thereof that retain the ability to emit peak light energy in the range of 550-740 nm, as well as, naturally-occurring RFPs, naturally occurring RFP variants, genetically engineered RFP variants and active RFP fragments thereof that retain the ability to emit peak light energy in the range of 550-740 nm. As a non-limiting example, *Entacmeae*

*quadricolor* fluorescent proteins including red fluorescent proteins such as, e.g., eqFP611, see, e.g., Jörg Wiedenmann et al., A far-red fluorescent protein with fast maturation and reduced oligomerization tendency from *Entacmaea quadricolor* (Anthozoa, Actinaria), 99(18) Proc. Natl. Acad. Sci. U.S.A. 11646-11651 (2002).

Thus, in aspects of this embodiment, the first member of the FRET pair can be a RFP that emits light in the range of 550-740 nm which has, e.g., at least 70% amino acid identity with the DsRed of SEQ ID NO: 153, at least 75% amino acid identity with the DsRed of SEQ ID NO: 153, at least 80% amino acid identity with the DsRed of SEQ ID NO: 153, at least 85% amino acid identity with the DsRed of SEQ ID NO: 153, at least 90% amino acid identity with the DsRed of SEQ ID NO: 153 or at least 95% amino acid identity with the DsRed of SEQ ID NO: 153. In other aspects of this embodiment, the first member of the FRET pair is a RFP that emits light in the range of 550-740 nm which has, e.g., at most one, two, three, four, five, six, seven, eight, nine, or ten amino acid substitutions relative to the DsRed of SEQ ID NO: 153.

In other aspects of this embodiment, the first member of the FRET pair can be a RFP that emits light in the range of 550-740 nm which has, e.g., at least 70% amino acid identity with the DsRed1 of SEQ ID NO: 154, at least 75% amino acid identity with the DsRed1 of SEQ ID NO: 154, at least 80% amino acid identity with the DsRed1 of SEQ ID NO: 154, at least 85% amino acid identity with the DsRed1 of SEQ ID NO: 154, at least 90% amino acid identity with the DsRed1 of SEQ ID NO: 154 or at least 95% amino acid identity with the DsRed1 of SEQ ID NO: 154. In still other aspects of this embodiment, the first member of the FRET pair is a RFP that emits light in the range of 550-740 nm which has, e.g., at most one, two, three, four, five, six, seven, eight, nine, or ten amino acid substitutions relative to the DsRed1 of SEQ ID NO: 154.

In other aspects of this embodiment, the first member of the FRET pair can be a RFP that emits light in the range of 550-740 nm which has, e.g., at least 70% amino acid identity with the DsRed2 of SEQ ID NO: 155, at least 75% amino acid identity with the DsRed2 of SEQ ID NO: 155, at least 80% amino acid identity with the DsRed2 of SEQ ID NO: 155, at least 85% amino acid identity with the DsRed2 of SEQ ID NO: 155, at least 90% amino acid identity with the DsRed2 of SEQ ID NO: 155 or at least 95% amino acid identity with the DsRed2 of SEQ ID NO: 155. In still other aspects of this embodiment, the first member of the FRET pair is a RFP that emits light in the range of 550-740 nm which has, e.g., at most one, two, three, four, five, six, seven, eight, nine, or ten amino acid substitutions relative to the DsRed2 of SEQ ID NO: 155.

In other aspects of this embodiment, the first member of the FRET pair can be a RFP that emits light in the range of 550-740 nm which has, e.g., at least 70% amino acid identity with the DsRed2 of SEQ ID NO: 156, at least 75% amino acid identity with the DsRed Express of SEQ ID NO: 156, at least 80% amino acid identity with the DsRed Express of SEQ ID NO: 156, at least 85% amino acid identity with the DsRed Express of SEQ ID NO: 156, at least 90% amino acid identity with the DsRed Express of SEQ ID NO: 156 or at least 95% amino acid identity with the DsRed Express of SEQ ID NO: 156. In still other aspects of this embodiment, the first member of the FRET pair is a RFP that emits light in the range of 550-740 nm which has, e.g., at most one, two, three, four, five, six, seven, eight, nine, or ten amino acid substitutions relative to the DsRed Express of SEQ ID NO: 156.

In other aspects of this embodiment, the first member of the FRET pair can be a RFP that emits light in the range of 550-740 nm which has, e.g., at least 70% amino acid identity with the AsRed of SEQ ID NO: 158, at least 75% amino acid identity with the AsRed of SEQ ID NO: 158, at least 80% amino acid identity with the AsRed of SEQ ID NO: 158, at least 85% amino acid identity with the AsRed of SEQ ID NO: 158, at least 90% amino acid identity with the AsRed of SEQ ID NO: 158 or at least 95% amino acid identity with the AsRed of SEQ ID NO: 158. In still other aspects of this embodiment, the first member of the FRET pair is a RFP that emits light in the range of 550-740 nm which has, e.g., at most one, two, three, four, five, six, seven, eight, nine, or ten amino acid substitutions relative to the AsRed of SEQ ID NO: 158.

In other aspects of this embodiment, the first member of the FRET pair can be a RFP that emits light in the range of 550-740 nm which has, e.g., at least 70% amino acid identity with the HcRed of SEQ ID NO: 157, at least 75% amino acid identity with the HcRed of SEQ ID NO: 157, at least 80% amino acid identity with the HcRed of SEQ ID NO: 157, at least 85% amino acid identity with the HcRed of SEQ ID NO: 157, at least 90% amino acid identity with the HcRed of SEQ ID NO: 157 or at least 95% amino acid identity with the HcRed of SEQ ID NO: 157. In still other aspects of this embodiment, the first member of the FRET pair is a RFP that emits light in the range of 550-740 nm which has, e.g., at most one, two, three, four, five, six, seven, eight, nine, or ten amino acid substitutions relative to the HcRed of SEQ ID NO: 157.

A first member of the FRET pair disclosed in the present specification includes fluorophore binding proteins which are subsequently labeled with a fluorophore. A fluorophore binding protein establish a covalent bond, or strong non-covalent interaction, with the fluorophore in a selective chemical or biochemical reaction. Nonlimitng examples of such fluorophore binding proteins and corresponding fluorophores include the bis-arsenical tetracysteine system, see, e.g., B. Albert Griffin et al., Specific covalent labeling of recombinant protein molecules inside live cells, 281(5374) Science 269-272 (1998); and B. Albert Griffin et al., Fluorescent labeling of recombinant proteins in living cells with FlAsH, 327 Methods Enzymol. 565-578 (2000); the alkylguanine-DNA-alkyltransferase (AGT) system, see, e.g., Antje Keppler et al, *A General Method for the Covalant Labeling of Fusion proteins with Small Molecules in vivo,* 21 (1) Nat. Biotech 86-89 (2003); Antje Keppler et al, *Labeling of fusion proteins of O6-alkylguanine-DNA alkyltransferase with small molecules in vivo and in vitro,* 32(4) Methods 437-444 (2004); and Antje Keppler et al, *Labeling of Fusion Proteins with Synthetic Fluorophores in Live Cells,* 101(27) Proc. Natl. Acad. Sci. USA 9955-9959 (2004); and the dehalogenase system. In addition, non-limiting examples of fluorophore binding proteins and corresponding fluorophores, as well as well-characterized reagents, conditions and protocols are readily available from commercial vendors that include, without limitation, TC-FlAsH™ TC-ReAsH™ In-Cell Tetracysteine Tag Detection Kit (Invitrogin Corp., Carlsbad, Calif.); SNAP-tag™ multi-purpose protein tag system (Covalys Biosciences AG, Switzerland); and HaloTag™ Interchangeable Labeling Technology (Promega Corp., Madison Wis.). These protocols are routine procedures well within the scope of one skilled in the art and from the teaching herein.

TABLE 10

| Excitation and Emission Maxima of Exemplary Fluorophores for Fluorophore Binding Proteins | | | |
|---|---|---|---|
| Name | Dye | Excitation maxima (nm) | Emission maxima (nm) |
| bis-Arsenical Tetracysteine System | | | |
| FIAsH | fluorescein arsenical hairpin binding dye | 508 | 528 |
| ReAsH | resorufin arsenical hairpin binding dye | 593 | 608 |
| AGT/SNAP-Tag System | | | |
| BG-430 | para-benzyl guanine diethylaminocoumarin | 421 | 444 and 484 |
| BG-DAF | para-benzyl guanine diacetylfluorescein | 500 | 524 |
| BG-505 | para-benzyl guanine dyomic DY-505-05 | 504 | 532 |
| BG-488 | para-benzyl guanine ATTO 488 | 506 | 526 |
| BG-532 | para-benzyl guanine ATTO 532 | 536 | 554 |
| BG-547 | para-benzyl guanine dyomic DY-547 | 554 | 568 |
| TMR-Star | para-benzyl guanine tetramethylrhodamine | 554 | 580 |
| BG-600 | para-benzyl guanine ATTO 600 | 606 | 626 |
| BG-632 | para-benzyl guanine dyomic DY-632 | 636 | 656 |
| BG-647 | para-benzyl guanine dyomic DY-647 | 660 | 673 |
| BG-732 | para-benzyl guanine dyomic DY-732 | 732 | 747 |
| BG-747 | para-benzyl guanine dyomic DY-747 | 752 | 763 |
| Dehalogenase/HaloTag ™ System | | | |
| HaloTag Coumarian | Coumarian derivative | 353 | 434 |
| HaloTag diAcFAM | nonfluorescent diacetyl fluorescein derivative | 494 | 526 |
| HaloTag TMR | tetramethyl rhodamine derivative | 555 | 585 |

The bis-arsenical tetracysteine system comprises a fusion protein including the protein of interest and a tetracysteine hexapeptide comprising the amino acid sequence C-C-X-X-C-C (SEQ ID NO: 182) and a bis-arsenical fluorophore complexed with two dithiol residues. In the labeling reaction, the tetracysteine peptide displaces the dithiols from the arsenic residues of the fluorophore. This interaction strongly couples the fluorophore with the fluorophore binding protein and significantly increases the signal by reducing the quenching of the fluorophore. Nonlimiting examples of bis-arsenical fluorophores include nonfluorescent biarsenical deriviatives of fluorescein, such as, e.g., FlAsH and nonfluorescent biarsenical deriviatives of resorufin, such as, e.g., ReAsH.

The AGT system comprises a fusion protein including the protein of interest and a modified AGT 22 kDa polypeptide (SEQ ID NO: 183) and a benzyl guanine modified in the para-position by a fluorescent label. In the labeling reaction, the O6-position of the para-substituted benzyl guanine irreversibly binds to a reactive cysteine in the active center of AGT. Nonlimiting examples of modified benzylguanine fluorophores listed in Table 10.

The dehalogenase system comprises a fusion protein including the protein of interest and a modified dehalogenase and a modified fluorophore comprising an alkyl residue. In the labeling reaction, the modified fluorophore strongly interacts with the active site of the modified dehalogenase. The modified dehalogenase is a 33 kDa polypeptide (SEQ ID NO: 184) comprising a mutation in the active center that significantly slows the catalytic activity of the enzyme, effectively creating an irreversible interaction. Nonlimiting examples of modified benzylguanine fluorophores listed in Table 10.

Thus in an embodiment, the first member of the FRET pair is a fluorophore binding protein which strongly interacts with a fluorophore. In another embodiment, the first member of the FRET pair is a tetracysteine peptide which strongly interacts with a fluorophore. In an aspect of this embodiment, the first member of the FRET pair is a tetracysteine peptide comprises SEQ ID NO: 182 which strongly interacts with a fluorophore. In another aspect of this embodiment, the first member of the FRET pair is a tetracysteine peptide that strongly interacts with a nonfluorescent biarsenical deriviatives of fluorescein. In another aspect of this embodiment, the first member of the FRET pair is a tetracysteine peptide that strongly interacts with a nonfluorescent biarsenical deriviatives of resorufin.

Thus, in an embodiment, the first member of the FRET pair is an AGT polypeptide which strongly interacts with a fluorophore. In an aspect of this embodiment, the first member of the FRET pair is an AGT which strongly interacts with a fluorophore comprises SEQ ID NO: 183. In other aspects of this embodiment, the first member of the FRET pair can be a AGT which strongly interacts with a fluorophore that has, e.g., at least 70% amino acid identity with the AGT of SEQ ID NO: 183, at least 75% amino acid identity with the AGT of SEQ ID NO: 183, at least 80% amino acid identity with the AGT of SEQ ID NO: 183, at least 85% amino acid identity with the AGT of SEQ ID NO: 183, at least 90% amino acid identity with the AGT of SEQ ID NO: 183 or at least 95% amino acid identity with the AGT of SEQ ID NO: 183. In still other aspects of this embodiment, the first member of the FRET pair is a AGT which strongly interacts with a fluorophore that has, e.g., at most one, two, three, four, five, six, seven, eight, nine, or ten amino acid substitutions relative to the AGT of SEQ ID NO: 183. In other aspects of this embodiment, the first member of the FRET pair is an AGT that strongly interacts with a para-substituted benzyl guanine derivative comprising a diethylaminocoumarin, a diacetylfluorescein, a dyomic DY-505-05, an ATTO 488, an ATTO 532, a DY-547, a tetramethylrhodamine, an ATTO 600, a dyomic DY-632, a dyomic DY-647, a dyomic DY-732 or a dyomic DY-747.

Thus, in an embodiment, the first member of the FRET pair is a dehalogenase polypeptide which strongly interacts with a fluorophore. In an aspect of this embodiment, the first member of the FRET pair is a dehalogenase which strongly interacts with a fluorophore comprises SEQ ID NO: 184. In other aspects of this embodiment, the first member of the FRET pair can be a dehalogenase which strongly interacts with a fluorophore that has, e.g., at least 70% amino acid identity with the dehalogenase of SEQ ID NO: 184, at least 75% amino acid identity with the dehalogenase of SEQ ID NO: 184, at least 80% amino acid identity with the dehalogenase of SEQ ID NO: 184, at least 85% amino acid identity with the dehalogenase of SEQ ID NO: 184, at least 90% amino acid identity with the dehalogenase of SEQ ID NO: 184 or at least 95% amino acid identity with the dehalogenase of SEQ ID NO: 184. In still other aspects of this embodiment, the first member of the FRET pair is a dehalogenase which strongly interacts with a fluorophore that has, e.g., at most one, two, three, four, five, six, seven, eight, nine, or ten amino acid substitutions relative to the dehalogenase of SEQ ID NO: 184. In other aspects of this embodiment, the first member of the FRET pair is an dehalogenase that strongly interacts with a coumarin derivative such as HaloTag Coumarian, a fluorescein derivative such as HaloTag diAcFAM or a tetramethyl rhodamine derivative such as HaloTag TMR.

The compositions and methods of the present specification provide a cell comprising, in part, a membrane-associated second member of the FRET pair. Such a second member of a FRET pair can be either a donor fluorophore or an acceptor. Thus, the recited FRET pair comprises, in part, a second member of the FRET pair which is either a donor fluorophore or an acceptor.

A membrane-associated second member of the FRET pair disclosed in the present specification includes lipophilic dyes. Lipophilic dyes useful in the invention include, without limitation, amphiphilic probes which are molecules containing a charged fluorophore that localizes the probe at the membrane's surface and a lipophilic aliphatic "tail" that inserts into the membrane and thereby anchors the probe to the membrane's surface. Characteristics of representative lipophilic dyes are summarized in Table 11. Methods for cellular labeling with lipophilic dyes are well known in the art as described, e.g., in Wouterlood (Ed.), Neuroscience Protocols pages 1-20 Elsevier Science Publishers (1993); and Haugland, *Handbook of Fluorescent Probes and Research Chemicals* 6th Edition, Molecular Probes, Inc., Eugene, Oreg., 1996.

Lipophilic dyes useful in the invention include, but are not limited to, carbocyanine lipophilic dyes including short-chain carbocyanines with short alkyl tails of less than 7 carbon atoms, the long-chain dialkylcarbocyanines, which have at least 12 carbons in their alkyl tail, and dialkylaminostyryl dyes. Carbocyanine lipophilic dyes are very strongly light-absorbing dyes which diffuse laterally to stain entire cells and are well-retained in cell membranes. Furthermore, these dyes fluoresce weakly in water yet possess very bright signals with high extinction coefficients. Widely useful carbocyanine membrane probes include the octadecyl ($C_{18}$) indocarbocyanines, DiI and DiD, thiacarbocyanines (DiS) oxacarbocyanines DiO. DiO emits green fluorescence; DiI, orange-red fluorescence; and DiD, far-red fluorescence.

TABLE 11

Excitation and Emission Maxima of Exemplary Lipophilic Dyes

| Cat No. | Dye | Excitation maxima (nm) | Emission maxima (nm) |
|---|---|---|---|
| | DiO and analogs | | |
| D3898 | FAST DiO | 484 | 499 |
| D275 | $DiOC_{18}(3)$ "DiO" | 484 | 501 |
| D1125 | $DiOC_{16}(3)$ | 484 | 501 |
| D7778 | SP-$DiOC_{18}(3)$ | 497 | 513 |
| | DiA and analogs | | |
| D3883 | 4-Di-16-ASP "DiA" | 491 | 613 |
| D3897 | FAST DiA oil | 492 | 612 |
| D7758 | FAST DiA | 492 | 612 |
| D291 | 4-Di-10-ASP | 492 | 612 |
| | DiS and DiI and analogs | | |
| B413 | $DiSBAC_2(3)$ | 535 | 560 |
| D282/D3911 | $DiIC_{18}(3)$ "DiI" | 549 | 565 |
| D384 | $DiICi_6(3)$ | 549 | 565 |
| D383 | $DiICi_2(3)$ | 549 | 565 |
| D3899 | FAST DiI oil | 549 | 564 |
| D7756 | FAST DiI | 549 | 564 |
| D3886 | $\Delta^9$-DiI oil | 549 | 564 |
| F6999 | FM ®DiI | 553 | 570 |
| C7000/C7001 | CellTracker CM-DiI | 553 | 570 |
| D7776 | $DiIC_{18}(3)$-DS | 555 | 570 |
| D7777 | SP-$DiIC_{18}(3)$ | 556 | 573 |
| D7766 | $Br_2$-$DiIC_{18}(3)$ | 558 | 575 |
| D7779 | 5,5'-$Ph_2$-$DiIC_{18}(3)$ | 576 | 599 |
| | DiD and analogs | | |
| D307 | $DiIC_{18}(5)$ oil "DiD" | 644 | 665 |
| D7757 | $DiIC_{18}(5)$ "DiD" | 644 | 663 |
| D12730 | $DiIC_{18}(5)$-DS | 650 | 670 |
| | DiR and analogs | | |
| D12731 | $DiIC_{18}(7)$ "DiR" | 748 | 780 |
| | Miscellaneous Molecules | | |
| D202 | DPH | 300 | 452 |
| T204 | TMA-DPH | 355 | 430 |
| T53 | 2,6-TNS | 318 | 443 |
| D250 | laurdan | 364 | 497 |
| B153 | bis-ANS | 395 | 500 |
| | FM ® and analogs | | |
| T3163 | FM ® 1-43 | 479 | 598 |
| T3164 | FM ® 1-84 | 510 | 625 |
| T7508 | FM ® 2-10 | 506 | 620 |
| T3166 | FM ® 4-64 | 506 | 750 |
| T23360 | FM ® 5-95 | 560 | 734 |
| T1111 | RH 414 | 500 | 635 |

Carbocyanine lipophilic dyes useful in the invention include, without limitation, octadecyl indocarbocyanines such as, e.g., $DiIC_{18}$ (3) and oxacarbocyanines such as, e.g., $DiOC_{18}$ (3) (Molecular Probes, Inc., Eugene, Oreg.). The octadecyl indocarbocyanines and oxacarbocyanines are respectively designated $DiIC_{18}$ (3) and $DiOC_{18}$ (3), where the subscript is the number of carbon atoms in each alkyl tail and the parenthetical numeral is the number of carbon atoms in the bridge between the indoline or benzoxazole ring systems. Indocarbocyanines and oxacarbocyanines useful in the invention include, without limitation DiI and DiO analogs with unsaturated alkyl tails such as $\Delta^9$-DiI, FAST DiO and FAST DiI (Molecular Probes, Inc., Eugene, Oreg.); DiI and DiO analogs with shorter alkyl tails such as $DiIC_{12}(3)$, $DiIC_{16}(3)$ and $DiOC_{16}(3)$ (Molecular Probes, Inc., Eugene, Oreg.); long wavelength light-excitable carbocyanines such as, e.g., $DiIC_{18}(5)$ (Molecular Probes, Inc., Eugene, Oreg.); infrared light-excitable carbocyanines such as, e.g., $DiIC_{18}(7)$ (Molecular Probes, Inc., Eugene, Oreg.); and phenyl-substituted and sulfonated derivatives of DiI and DiO. Useful substitutions include those made on the indoline or benzoxazole ring systems; such derivatives made retain the octadecyl tails identical to those of DiI or DiO and include, without limitation, chloromethylbenzamido DiI derivatives such as CellTracker CM-DiI (Molecular Probes, Inc., Eugene, Oreg.); diphenyl DiI derivatives such as 5,5'-$Ph_2$-$DiIC_{18}(3)$ (Molecular Probes, Inc., Eugene, Oreg.); and anionic sulfophenyl derivatives such as SP-$DiIC_{18}(3)$ and SP-$DiOC_{18}(3)$; or sulfonate derivatives such as $DiIC_{18}(3)$-DS and $DiIC_{18}(5)$-DS (Molecular Probes, Inc., Eugene, Oreg.). Thiacarbocyanines useful in the invention include, without limitation $DiSBAC_2(3)$ (Molecular Probes, Inc., Eugene, Oreg.). Other carbocyanines useful in the invention include, without limitation 5,5',6,6'-tetrachloro-1,1',3,3'-tetraethylbenzimidazolylcarbocyanine iodide (JC-1), 3,3'-dimethylnaphthoxacarbocyanine iodide (JC-9) and carbonyl cyanide 3-chlorophenylhydrazone (CCCP) (Molecular Probes, Inc., Eugene, Oreg.).

The features of a variety of lipophilic carbocyanine dyes are summarized in Table 11. Lipophilic carbocyanines are well known in the art as reviewed in, e.g., Wolf, "Probing the Lateral Organization and Dynamics of Membranes," *Spectroscopic Membrane Probes*, Vol. I, Loew, Ed. pp. 193-220 (1988). As is well known, the spectral properties of dialkylcarbocyanines are largely independent of the lengths of the alkyl chains, being determined instead by the heteroatoms in the terminal ring systems and the length of the connecting bridge.

Lipophilic dyes useful in the invention further encompass, without limitation, lipophilic aminostyryl dyes and amphiphilic styryl dyes. Aminostyryl dyes include, without limitation, dialkylaminostyryl dyes, which insert into membranes with their two alkyl tails and their fluorophore generally oriented parallel to the phospholipids acyl chains. Exemplary lipophilic aminostyryl dyes include 4-Di-10-ASP (D291); DiA, D3883 and FAST DiA (Molecular Probes, Inc., Eugene, Oreg.).

Lipophilic dyes useful in the invention further encompass, without limitation, an amphiphilic probe comprising derivatives of a rhodamine, a fluorescein or a coumarin with a lipophilic "tail." Non-limiting examples of such amphiphilic probes include octadecyl rhodamine B; fluoresceins, such as, e.g., 5-Dodecanoylaminofluorescein, 5-hexadecanoyl-aminofluorescein, 5-octadecanoyl-aminofluorescein and the octadecyl ester of fluorescein; and 4-heptadecyl-7-hydroxycoumarin.

Lipophilic dyes useful in the invention further encompass, without limitation, an amphiphilic probe comprising 1,6-Diphenyl-1,3,5-hexatriene (DPH) or DPH derivatives with a lipophilic "tail." Non-limiting examples of such amphiphilic probes include 1,6-Diphenyl-1,3,5-hexatriene (DPH), 1-(4-trimethylammoniumphenyl)-6-phenyl-1,3,5-hexatriene p-toluenesulfonate (TMA-DPH), N-((4-(6-phenyl-1,3,5-hexatrienyl)phenyl)propyl)trimethylammonium p-toluenesulfonate (TMAP-DPH), Dapoxyl sulfonic acid and 3-(4-(6-phenyl)-1,3,5-hexatrienyl)phenylpropionic acid (DPH propionic acid).

Additional lipophilic dyes useful in the invention further encompass, without limitation, an nonpolar probe comprising a BODIPY molecule with a lipophilic "tail." Non-limiting examples of such nonpolar probes include BODIPY 493/503, BODIPY 505/515, BODIPY 665/676, BODIPY FL C5-ceramide and CellTrace BODIPY TR methyl ester. Other lipophilic dyes useful in the invention further encompass, without limitation, an nonpolar probe comprising a phenoxazine dye nile red, a 1,3-Bis-(1-pyrene)propane or bimane azide molecule with a lipophilic "tail."

Additional lipophilic dyes useful in the invention further encompass, without limitation, a membrane probe with environment-sensitive spectral shifts with a lipophilic "tail." Non-limiting examples of such membrane probes include dapoxyl derivatives, such as, e.g., dapoxyl sulfonic acid; 6-propionyl-2-dimethylaminonaphthalene (prodan), 6-dodecanoyl-2-dimethylaminonaphthalene (laurdan), 6-acryloyl-2-dimethylaminonaphthalene (acrylodan), 6-bromoacetyl-2-dimethylaminonaphthalene (badan); anilinonaphthalenesulfonate (ANS) and derivatives thereof, such as, e.g., 1-anilinonaphthalene-8-sulfonic acid (1,8-ANS), 2-anilinonaphthalene-6-sulfonic acid (2,6-ANS), 2-(p-toluidinyl)naphthalene-6-sulfonic acid (2,6-TNS), 4,4'-dianilino-1,1'-binaphthyl-5,5'-disulfonic acid (bis-ANS); 4-(dicyanovinyl)julolidine (DCVJ); and 4-amino-4'-benzamidostilbene-2,2'-disulfonic acid (MBDS or BADS).

Additional lipophilic dyes useful in the invention include, yet are not limited to, lipophilic cations such as octadecyl rhodamine, and FM dyes such as N-(3-triethylammoniumpropyl)-4-(4-(dibutylamino)styryl)pyridinium di bromide (FM® 1-43), N-(3-triethylammoniumpropyl)-4-(4-(dipentylamino)styryl)pyridinium dibromide (FM® 1-84), N-(3-triethylammoniumpropyl)-4-(4-(diethylamino)styryl)pyridinium dibromide (FM® 2-10) N-(3-triethylammoniumpropyl)-4-(6-(4-(diethylamino)phenyl) hexatrienyl) pyridinium dibromide (FM® 4-64), N-(3-trimethylammoniumpropyl)-4-(6-(4-(diethylamino)phenyl) hexatrienyl) pyridinium dibromide (FM® 5-95), N-(3-triethylammoniumpropyl)-4-(4-(4-(diethylamino)phenyl) butadienyl) pyridinium dibromide (RH 414) and derivatives thereof (Molecular Probes, Inc., Eugene, Oreg.); fluorescent phospholipid conjugates such as NBD-PE (Molecular Probes, Inc., Eugene, Oreg.), which can be paired with rhodamine acceptors such as rhodamine DHPE and Texas Red DHPE; lipid raft probes, which are detergent-insoluble, sphingolipid- and cholesterol membrane microdomains that form lateral assemblies in the plasma membrane and are available from Molecular Probes as Vybrant Lipid Raft Labeling Kits; fast response and slow response dyes for membrane potential and environmentally sensitive membrane probes. One skilled in the art understands that these and other well known lipophilic dyes also can be useful in the invention.

In an embodiment, the second member of the FRET pair can be a DiO. As used herein, the term "DiO" means a lipophilic dye which absorbs peak light energy of wavelengths in the range of 425-500 nm and emits peak light energy in the range of 500-520 nm. DiO dyes useful in the invention include, without limitation, FAST DiO and analogs thereof that absorb peak light energy of wavelengths in the range of 425-500 nm and emit peak light energy in the range of 500-520 nm; $DiOC_{18}(3)$ and analogs thereof that absorb peak light energy of wavelengths in the range of 425-500 nm and emit peak light energy in the range of 500-520 nm; $DiOC_{16}(3)$ and analogs thereof that absorb peak light energy of wavelengths in the range of 425-500 nm and emit peak light energy in the range of 500-520 nm; and SP-$DiOC_{18}(3)$ and analogs thereof that absorb peak light energy of wavelengths in the range of 425-500 nm and emit peak light energy in the range of 500-520 nm.

In another embodiment, the second member of the FRET pair can be a DiA. As used herein, the term "DiA" means a lipophilic dye which absorbs peak light energy of wavelengths in the range of 400-500 nm and emits peak light energy in the range of 600-620 nm. DiA dyes useful in the invention include, without limitation, 4-Di-16-ASP and analogs thereof that absorb peak light energy of wavelengths in the range of 400-500 nm and emit peak light energy in the range of 600-620 nm; FAST DiA and analogs thereof that absorb peak light energy of wavelengths in the range of 400-500 nm and emit peak light energy in the range of 600-620 nm; and 4-Di-10-ASP and analogs thereof that absorb peak light energy of wavelengths in the range of 400-500 nm and emit peak light energy in the range of 600-620 nm.

In another embodiment, the second member of the FRET pair can be a DiS. As used herein, the term "DiS" means a lipophilic dye which absorbs peak light energy of wavelengths in the range of 510-550 nm and emits peak light energy in the range of 540-580 nm. DiS dyes useful in the invention include, without limitation, $DiSBAC_2(3)$ and analogs thereof that absorb peak light energy of wavelengths in the range of 525-545 nm and emit peak light energy in the range of 550-570 nm.

In another embodiment, the second member of the FRET pair can be a DiI. As used herein, the term "DiI" means a lipophilic dye which absorbs peak light energy of wavelengths in the range of 500-560 nm and emits peak light energy in the range of 560-580 nm. DiI dyes useful in the invention include, without limitation, $DiIC_{18}(3)$ and analogs thereof that absorb peak light energy of wavelengths in the range of 500-560 nm and emit peak light energy in the range of 560-580 nm; $DiIC_{16}(3)$ and analogs thereof that absorb peak light energy of wavelengths in the range of 500-560 nm and emit peak light energy in the range of 560-580 nm; $DiIC_{12}(3)$ and analogs thereof that absorb peak light energy of wavelengths in the range of 500-560 nm and emit peak light energy in the range of 560-580 nm; FAST DiI and analogs thereof that absorb peak light energy of wavelengths in the range of 500-560 nm and emit peak light energy in the range of 560-580 nm; $\Delta^9$-DiI and analogs thereof that absorb peak light energy of wavelengths in the range of 500-560 nm and emit peak light energy in the range of 560-580 nm; FM® DiI and analogs thereof that absorb peak light energy of wavelengths in the range of 500-560 nm and emit peak light energy in the range of 560-580 nm; CellTracker CM-DiI and analogs thereof that absorb peak light energy of wavelengths in the range of 500-560 nm and emit peak light energy in the range of 560-580 nm; $DiIC_{18}(3)$-DS and analogs thereof that absorb peak light energy of wavelengths in the range of 500-560 nm and emit peak light energy in the range of 560-580 nm; SP-$DiIC_{18}(3)$ and analogs thereof that absorb peak light energy of wavelengths in the range of 500-560 nm and emit peak light energy in the range of 560-580 nm; and $Br_2$-$DiIC_{18}(3)$ and analogs thereof that absorb peak light energy of wavelengths in the range of 500-560 nm and emit peak light energy in the range of 560-580 nm.

In another embodiment, the second member of the FRET pair can be a 5,5'-$Ph_2$-$DiIC_{18}(3)$. As used herein, the term "5,5'-$Ph_2$-$DiIC_{18}(3)$" means a DiI analog lipophilic dye which absorbs peak light energy of wavelengths in the range of 520-590 nm and emits peak light energy in the range of 590-620 nm. 5,5'-$Ph_2$-$DiIC_{18}(3)$ dyes useful in the invention include, without limitation, 5,5'-$Ph_2$-$DiIC_{18}(3)$ and analogs thereof that absorb peak light energy of wavelengths in the range of 520-590 nm and emit peak light energy in the range of 590-620 nm.

In another embodiment, the second member of the FRET pair can be a DiD. As used herein, the term "DiD" means a lipophilic dye which absorbs peak light energy of wavelengths in the range of 575-660 nm and emits peak light energy in the range of 660-680 nm. DiD dyes useful in the invention include, without limitation, $DiIC_{18}(5)$ and analogs thereof that absorb peak light energy of wavelengths in the range of 575-660 nm and emit peak light energy in the range of 660-680 nm; and $DiIC_{18}(5)$-DS and analogs thereof that absorb peak light energy of wavelengths in the range of 575-660 nm and emit peak light energy in the range of 660-680 nm.

In another embodiment, the second member of the FRET pair can be a DiR. As used herein, the term "DiR" means a lipophilic dye which absorbs peak light energy of wavelengths in the range of 725-770 nm and emits peak light energy in the range of 770-790 nm. DiR dyes useful in the invention include, without limitation, $DiIC_{18}(7)$ and analogs thereof that absorb peak light energy of wavelengths in the range of 725-770 nm and emit peak light energy in the range of 770-790 nm.

In another embodiment, the second member of the FRET pair can be a derivative of a rhodamine, fluorescein or coumarin. Such dyes useful in the invention include, without limitation, 4-heptadecyl-7-hydroxycoumarin which absorbs peak light energy of wavelengths in the range of 360-380 nm and emits peak light energy in the range of 440-460 nm.

In another embodiment, the second member of the FRET pair can be a DPH or a derivative of DPH. As used herein, the term "DPH" means a lipophilic dye which absorbs peak light energy of wavelengths in the range of 340-370 nm and emits peak light energy in the range of 420-460 nm. DPH dyes useful in the invention include, without limitation, DPH which absorbs peak light energy of wavelengths in the range of 340-360 nm and emits peak light energy in the range of 440-460 nm; and TMA-DPH which absorb peak light energy of wavelengths in the range of 350-370 nm and emit peak light energy in the range of 420-440 nm.

In another embodiment, the second member of the FRET pair can be a dapoxyl derivative. As used herein, the term "dapoxyl derivative" means a lipophilic dye which absorbs peak light energy of wavelengths in the range of 350-400 nm and emits peak light energy in the range of 490-530 nm. Dapoxyl derivative dyes useful in the invention include, without limitation, 6-propionyl-2-dimethylaminonaphthalene (prodan) which absorbs peak light energy of wavelengths in the range of 350-370 nm and emits peak light energy in the range of 490-510 nm; 6-dodecanoyl-2-dimethylaminonaphthalene (laurdan) which absorbs peak light energy of wavelengths in the range of 355-375 nm and emits peak light energy in the range of 490-510 nm; 6-acryloyl-2-dimethylaminonaphthalene (acrylodan) which absorbs peak light energy of wavelengths in the range of 380-400 nm and emits peak light energy in the range of 490-510 nm; 6-bromoacetyl-2-dimethylaminonaphthalene (badan) which absorbs peak light energy of wavelengths in the range of 380-400 nm and emits peak light energy in the range of 510-530 nm; and dapoxyl sulfonic acid which absorbs peak light energy of wavelengths in the range of 350-370 nm and emits peak light energy in the range of 510-530 nm.

In another embodiment, the second member of the FRET pair can be an anilinonaphthalene sulfonate (ANS) and ANS derivatives. As used herein, the term "ANS" means a lipophilic dye which absorbs peak light energy of wavelengths in the range of 310-405 nm and emits peak light energy in the range of 410-510 nm. ANS dyes useful in the invention include, without limitation, 1-anilinonaphthalene-8-sulfonic acid (1,8-ANS) which absorbs peak light energy of wavelengths in the range of 360-380 nm and emits peak light energy in the range of 470-490 nm, 2-anilinonaphthalene-6-sulfonic acid (2,6-ANS) which absorbs peak light energy of wavelengths in the range of 310-330 nm and emits peak light energy in the range of 410-430 nm; 2-(p-toluidinyl)naphthalene-6-sulfonic acid (2,6-TNS) which absorbs peak light energy of wavelengths in the range of 310-330 nm and emits peak light energy in the range of 430-450 nm; and 4,4'-dianilino-1,1'-binaphthyl-5,5'-disulfonic acid (bis-ANS) which absorbs peak light energy of wavelengths in the range of 385-405 nm and emits peak light energy in the range of 490-510 nm.

In yet another embodiment, the second member of the FRET pair can be 4-(dicyanovinyl)julolidine (DCVJ) which absorbs peak light energy of wavelengths in the range of 445-465 nm and emits peak light energy in the range of 480-500 nm.

In another embodiment, the second member of the FRET pair can be a FM dye. FM dyes useful in the invention include, without limitation, FM® 1-43 and analogs thereof that absorb peak light energy of wavelengths in the range of 400-525 nm and emit peak light energy in the range of 590-610 nm; FM® 1-84 and analogs thereof that absorb peak light energy of wavelengths in the range of 400-525 nm and emit peak light energy in the range of 610-640 nm; FM® 2-10 and analogs thereof that absorb peak light energy of wavelengths in the range of 400-525 nm and emit peak light energy in the range of 610-640 nm; RH 414 and analogs thereof that absorb peak light energy of wavelengths in the range of 400-525 nm and emit peak light energy in the range of 610-640 nm; FM® 4-64 and analogs thereof that absorb peak light energy of wavelengths in the range of 425-575 nm and emit peak light energy in the range of 730-770 nm; and FM® 5-95 and analogs thereof that absorb peak light energy of wavelengths in the range of 425-575 nm and emit peak light energy in the range of 720-740 nm.

The Clostridial toxin substrates disclosed in the present specification include, in part, a first member of a fluorescence resonance energy transfer (FRET) pair. As used herein, the term "fluorescence resonance energy transfer pair," is synonymous with "FRET pair" and means a donor fluorophore and an acceptor that has an absorbance spectrum overlapping the emission spectrum of the donor fluorophore. It is understood that, where the first member of the FRET pair is a donor fluorophore, the second member of the pair will be an acceptor. Similarly, where the first member of the FRET pair is an acceptor, the second member of the pair will be a donor fluorophore.

As used herein, the term "donor fluorophore" means a molecule that, when irradiated with light of a certain wavelength, emits light, also denoted fluorescence, of a different wavelength. The term fluorophore is synonymous in the art with the term "fluorochrome." As used herein, the term "acceptor" means a molecule that can absorb energy from a donor fluorophore and is a term that encompasses fluorophores as well as non-fluorescent molecules. As used herein, the term "absorb" is synonymous with the term "excite" and the term "absorbance" is synonymous with the term "excitation." An acceptor useful in the invention has an absorbance spectrum which overlaps the emission spectrum of the donor fluorophore. An acceptor useful in the invention generally has rather low absorption at a wavelength suitable for excitation of the donor fluorophore. As set forth above, an acceptor has an absorbance spectrum that overlaps the emission spectrum of the donor fluorophore. The term "overlapping," as used herein in reference to the absorbance spectrum of an acceptor and the emission spectrum of a donor fluorophore, means an absorbance spectrum and emission spectrum that are partly or entirely shared. Thus, in such overlapping spectra, the high end of the range of the emission spectrum of the donor fluorophore is higher than the low end of the range of the absorbance spectrum of the acceptor.

In a clostridial toxin substrate useful in the invention, the donor fluorophore and acceptor are selected so that the donor fluorophore and acceptor exhibit resonance energy transfer when the donor fluorophore is excited. A fluorescence resonance energy transfer (FRET) pair comprises a donor fluorophore and an acceptor where the overlap between the emissions spectrum of the donor fluorophore and the absorbance spectrum of the acceptor is sufficient to enable FRET.

The present invention relies, in part, on FRET, which is a physical process whereby energy is transferred non-radiatively from an excited donor fluorophore to an acceptor, which may be another fluorophore, through intramolecular long-range dipole-dipole coupling. FRET is dependent on the inverse sixth power of the intramolecular separation of the donor fluorophore and acceptor, and for effective transfer, the donor fluorophore and acceptor are in close proximity, separated, for example, by about 10 A to about 100 A. Effective energy transfer is dependent on the spectral characteristics of the donor fluorophore and acceptor as well as their relative orientation. For effective transfer over 10 to 100 A, the quantum yield of the donor fluorophore generally is at least 0.1, and the absorption coefficient of the acceptor generally is at least 1000, see, e.g., Clegg, 6 Curr. Opin. Biotech. 103-110 (1995); and Selvin, 7 Nat. Struct. Biol. 730-734 (2000). One factor to be considered in choosing the donor fluorophore/acceptor pair is the efficiency of FRET between the donor fluorophore and acceptor.

As is well known in the art, the efficiency of FRET is dependent on the separation distance and the orientation of the donor fluorophore and acceptor as described by the Förster equation, as well as the fluorescent quantum yield of the donor fluorophore and the energetic overlap with the acceptor. In particular, the efficiency (E) of FRET can be determined as follows: $E=1-F_{DA}/F_D=1/(1+(R/R_0)^6)$, where $F_{DA}$ and $F_D$ are the fluorescence intensities of the donor fluorophore in the presence and absence of the acceptor, respectively, and R is the distance between the donor fluorophore and the acceptor.

The Förster radius ($R_o$) is the distance at which resonance energy transfer is 50% efficient, that is, 50% of excited donor fluorophores are deactivated by FRET, see, e.g. Förster, 2 Ann. Physik 55-75 (1948). The magnitude of the Förster radius depends on the quantum yield of the donor fluorophore; the extinction coefficient of the acceptor; and the overlap between the donor fluorophore's emission spectrum and the acceptor's excitation spectrum.

$$R_O=[8.8\times10^{23}\cdot\kappa^2\cdot n^{-4}QY_D*J(\lambda)]^{1/6}A,\text{ where}$$

$\kappa^2$=dipole orientation factor (range 0 to 4; $\kappa^2$=2/3 for randomly oriented donors and acceptors)

$QY_D$=fluorescence quantum yield of the donor in the absence of the acceptor n=refractive index $J(\lambda)$=spectral overlap integral=$\int\epsilon_A(\lambda)\cdot F_D(\lambda)\cdot\lambda^4 d\lambda$ $cm^3M^{-1}$, where $\epsilon_A$=extinction coefficient of acceptor $F_D$=fluorescence emission intensity of donor as a fraction of the total integrated intensity Any of a number of donor fluorophores and acceptors in various combinations can be included in a clostridial toxin substrate useful in the invention. A donor fluorophore generally is selected such that there is substantial spectral overlap between the emission spectrum of the donor fluorophore and the excitation spectrum of the acceptor. In addition, a donor fluorophore can be selected, for example, to have an excitation maximum near a convenient laser frequency such as Helium-Cadmium 442 nm or argon 488 nm, since laser light serves as a convenient and effective means to excite the donor fluorophore.

Thus, in an embodiment, the distance between the center of the donor fluorophore and the center of the acceptor is approximately 10 Å. In another embodiment, the distance between the center of the donor fluorophore and the center of the acceptor is approximately 50 Å. In another embodiment, the distance between the center of the donor fluorophore and the center of the acceptor is approximately 100 Å. In aspects of this embodiment, the distance between the center of the donor fluorophore and the center of the acceptor can be, e.g., at least 10 Å, at least 20 Å, at least 30 Å, at least 40 Å, at least 50 Å, at least 60 Å, at least 70 Å, at least 80 Å, at least 90 Å or at least 100 Å. In other aspects of this embodiment, the distance between the center of the donor fluorophore and the center of the acceptor can be, e.g., at most 10 Å, at most 20 Å, at most 30 Å, at most 40 Å, at most 50 Å, at most 60 Å, at most 70 Å, at most 80 Å, at most 90 Å or at most 100 Å.

In another embodiment, the efficiency of FRET between the donor fluorophore and acceptor is approximately 10%. In another embodiment, the efficiency of FRET between the donor fluorophore and acceptor is approximately 50%. In another embodiment, the efficiency of FRET between the donor fluorophore and acceptor is approximately 100%. In aspects of this embodiment, the efficiency of FRET between the donor fluorophore and acceptor can be, e.g., at least 10%, at least 20%, at least 30%, at least 40%, at least 50%, at least 60%, at least 70%, at least 80%, at least 90% or at least 100%. In other aspects of this embodiment, the efficiency of FRET between the donor fluorophore and acceptor can be, e.g., at most 10%, at most 20%, at most 30%, at most 40%, at most 50%, at most 60%, at most 70%, at most 80%, at most 90% or at most 100%.

In another embodiment, the wavelength maximum of the emission spectrum of the acceptor is approximately 10 nm greater than the wavelength maximum of the excitation spectrum of the donor fluorophore. In another embodiment, the wavelength maximum of the emission spectrum of the acceptor is approximately 50 nm greater than the wavelength maximum of the excitation spectrum of the donor fluorophore. In another embodiment, the wavelength maximum of the emission spectrum of the acceptor is approximately 100 nm greater than the wavelength maximum of the excitation spectrum of the donor fluorophore. In aspects of this embodiment, the wavelength maximum of the emission spectrum of the acceptor is greater than the wavelength maximum of the excitation spectrum of the donor fluorophore by, e.g., at least 10 nm, at least 20 nm, at least 30 nm, at least 40 nm, at least 50 nm, at least 60 nm, at least 70 nm, at least 80 nm, at least 90 nm or at least 100 nm. In other aspects of this embodiment, the wavelength maximum of the emission spectrum of the acceptor is greater than the wavelength maximum of the excitation spectrum of the donor fluorophore by, e.g., at most 10 nm, at most 20 nm, at most 30 nm, at most 40 nm, at most 50 nm, at most 60 nm, at most 70 nm, at most 80 nm, at most 90 nm or at most 100 nm.

In another embodiment, the spectral overlap between the donor fluorophore and acceptor is approximately 10%. In another embodiment, the spectral overlap between the donor fluorophore and acceptor is approximately 50%. In another embodiment, the spectral overlap between the donor fluorophore and acceptor is approximately 80%. In aspects of this embodiment, the spectral overlap between the donor fluorophore and acceptor can be, e.g., at least 10%, at least 20%, at least 30%, at least 40%, at least 50%, at least 60%, at least 70% or at least 80%. In other aspects of this embodiment, the spectral overlap between the donor fluorophore and acceptor can be, e.g., at most 10%, at most 20%, at most 30%, at most 40%, at most 50%, at most 60%, at most 70% or at most 80%.

In another embodiment, the difference between the peak light energy emitted by the donor fluorophore and the peak light energy absorbed by the acceptor can be, e.g., at least 25 nm, at least 50 nm, at least 75 nm or at least 100 nm. In another embodiment, the difference between the peak light energy emitted by the donor fluorophore and the peak light energy absorbed by the acceptor can be, e.g., at most 25 nm, at most 50 nm, at most 75 nm or at most 100 nm.

Nonlimiting examples of FRET pairs include, EBFP, ECFP, AmCyan or HaloTag Coumarian as donor fluorophore and $DiOC_{18}(3)$, $DiOC_{16}(3)$, SP-$DiOC_{18}$ (3), 4-Di-16-ASP, FAST DiA or 4-Di-10-ASP as acceptor; DPH, TMA-DPH or 2,6-TNA as donor fluorophore and ECFP, AmCyan, AcGFP or AGT/BG-430 as acceptor; AcGFP, ZsGreen, Vitality hrGFP, EGFP or Monster Green as donor fluorophore and $DiSBAC_2(3)$, $DiIC_{18}$ (3), FM 1-84, FM 2-10 or RH 414 as acceptor; DPH, laurdan or bis-ANS as donor fluorophore and AmCyan, AcGFP, ZsGreen, Vitality hrGFP, EGFP, Monster Green, tetracysteine/FlAsH, AGT/BG-DAF, AGT/BG-505, AGT/BG-488 or HaloTag diAcFAM as acceptor; Monster Green, EYFP, ZsYellow, tetracysteine/FlAsH, AGT/BG-DAF, AGT/BG-505, AGT/BG-488 or HaloTag diAcFAM as donor fluorophore and FM 1-84, $DiSBAC_2(3)$, $DiIC_{18}$ (3), $DiIC_{16}$ (3), $DiIC_{12}$ (3), FAST DiI, $DiIC_{18}$ (3)-DS or SP-$DiIC_{18}$ (3) as acceptor; FAST DiO, $DiOC_{18}$ (3), $DiOC_{16}$ (3), SP-$DiOC_{18}$ (3), laurdan or bis-ANS as donor fluorophore and Monster Green, EYFP, ZsYellow, tetracysteine/FlAsH, AGT/BG-DAF, AGT/BG-505, AGT/BG-488 or HaloTag diAcFAM as acceptor; DsRed, Ds-Red2, Ds-Red Express, AGT/BG-547, AGT/TMR-Star or HaloTag TMR as donor fluorophore and FM DiI, $DiIC_{18}$ (3)-DS, SP-$DiIC_{18}$ (3) or $Br_2$-$DiIC_{18}$ (3) as acceptor; $DiSBAC_2(3)$, $DiIC_{18}$ (3), $DiIC_{16}$ (3), $DiIC_{12}$ (3) or FAST DiI as donor fluorophore and DsRed, Ds-Red2 or Ds-Red Express as acceptor; and $DiSBAC_2(3)$, $DiIC_{18}$ (3), $DiIC_{16}$ (3), $DiIC_{12}$ (3), FAST DiI, FM DiI, $DiIC_{18}$ (3)-DS, SP-$DiIC_{18}$ (3) or $Br_2$-$DiIC_{18}$ (3) as donor fluorophore and AsRed2 or HcRed1 as acceptor. Other FRET pairs combinations are indicated in Table 14.

Aspects of the present invention can rely on a Clostridial toxin substrate which contains a non-fluorescent acceptor. As used herein, the term "non-fluorescent acceptor" is synonymous with "quencher" and means a molecule which absorbs light energy of a certain wavelength, including, e.g., violet, blue, cyan, green, yellow, orange and red, but has reduced ability to emit or cannot emit light energy. A non-fluorescent acceptor can be useful, for example, in eliminating background fluorescence resulting from direct (nonsensitized) acceptor excitation. A variety of non-fluorescent acceptors are known in the art and include without limitation Dabcyl, Dabsyl, Malachite green, QSY 7, QSY 9, QSY 21, QSY 35, BHQ-0, BHQ-1, BHQ-2, BHQ-3 and BHQ-10. These quenchers can be attached to a Clostridial toxin substrate using standard conjugation chemistry methods known in the art. Dabcyl and Dabsyl absorb peak light energy in the range of 400-525 nm and can be useful in FRET applications as an energy transfer acceptor for donor fluorophores that emit light energy within this wavelength range, such as, e.g., BFP, CFP, GFP and YFP. QSY 35 absorbs peak light energy in the range of 425-525 nm and can be useful in FRET applications as an energy transfer acceptor for donor fluorophores that emit light energy within this wavelength range, such as, e.g., BFP, CFP, GFP and YFP. BHQ-0 absorbs peak light energy in the range of 430-520 nm and can be useful in FRET applications as an energy transfer acceptor for donor fluorophores that emit light energy within this wavelength range, such as, e.g., BFP, CFP, GFP and YFP. BHQ-1 absorbs peak light energy in the range of 480-580 nm and can be useful in FRET applications as an energy transfer acceptor for donor fluorophores that emit light energy within this wavelength range, such as, e.g., CFP, GFP, YFP and RFP. QSY 7 and QSY 9 absorb peak light energy in the range of 500-600 nm and can be useful in FRET applications as an energy transfer acceptor for donor fluorophores that emit light energy within this wavelength range, such as, e.g., GFP, YFP and RFP. BHQ-2 absorbs peak light energy in the range of 559-650 nm and can be useful in FRET applications as an energy transfer acceptor for donor fluorophores that emit light energy within this wavelength range, such as, e.g., YFP and RFP. Malachite green absorbs peak light energy in the range of 575-675 nm and can be useful in FRET applications as an energy transfer acceptor for donor fluorophores that emit light energy within this wavelength range, such as, e.g., YFP and RFP. QSY 21 absorbs peak light energy in the range of 575-725 nm and can be useful in FRET applications as an energy transfer acceptor for donor fluorophores that emit light energy within this wavelength range, such as, e.g., YFP and RFP. BHQ-3 absorbs peak light energy in the range of 620-730 nm and can be useful in FRET applications as an energy transfer acceptor for donor fluorophores that emit light energy within this wavelength range, such as, e.g., RFP.

Thus, an embodiment, a non-fluorescent acceptor can be a molecule that absorbs peak light energy in the range of 400-525 nm. In an aspect of this embodiment, the non-fluorescent acceptor is Dabcyl. In another aspect of this embodiment, the non-fluorescent acceptor is Dabsyl. In another embodiment, a non-fluorescent acceptor can be a molecule that absorbs peak light energy in the range of 425-525 nm. In an aspect of this embodiment, the non-fluorescent acceptor is QSY 35. In another embodiment, a non-fluorescent acceptor can be a molecule that absorbs peak light energy in the range of 430-520 nm. In an aspect of this embodiment, the non-fluorescent acceptor is BHQ-0.

In yet another embodiment, a non-fluorescent acceptor can be a molecule that absorbs peak light energy in the range of 480-580 nm. In an aspect of this embodiment, the non-fluorescent acceptor is BHQ-1. In yet another embodiment, a non-fluorescent acceptor can be a molecule that absorbs peak light energy in the range of 500-600 nm. In an aspect of this embodiment, the non-fluorescent acceptor is QSY 7. In another aspect of this embodiment, the non-fluorescent acceptor is QSY 9.

In still another embodiment, a non-fluorescent acceptor can be a molecule that absorbs peak light energy in the range of 559-650 nm. In an aspect of this embodiment, the non-fluorescent acceptor is BHQ-2. In still another embodiment, a non-fluorescent acceptor can be a molecule that absorbs peak light energy in the range of 575-675 nm. In an aspect of this embodiment, the non-fluorescent acceptor is Malachite green. In still another embodiment, a non-fluorescent acceptor can be a molecule that absorbs peak light energy in the range of 575-725 nm. In an aspect of this embodiment, the non-fluorescent acceptor is QSY 21. In still another embodiment, a non-fluorescent acceptor can be a molecule that absorbs peak light energy in the range of 620-730 nm. In an aspect of this embodiment, the non-fluorescent acceptor is BHQ-3.

It is understood that a Clostridial toxin substrate useful in the invention optionally can include one or more additional components. As a non-limiting example, a flexible spacer sequence such as GGGGS (SEQ ID NO: 159) can be included in a Clostridial toxin substrate useful in the invention. A useful Clostridial toxin substrate further can include, without limitation, one or more of the following: epitope-binding tags, such as, e.g., FLAG, Express™, human Influenza virus hemagluttinin (HA), human p62$^{c\text{-}Myc}$ protein (c-MYC), Vesicular Stomatitis Virus Glycoprotein (VSV-G), glycoprotein-D precursor of Herpes simplex virus (HSV), V5, and AU1; affinity-binding, such as, e.g., polyhistidine (HIS), streptavidin binding peptide (strep), and biotin or a biotinylation sequence; peptide-binding regions, such as, e.g., the glutathione binding domain of glutathione-S-transferase, the calmodulin binding domain of the calmodulin binding protein, and the maltose binding domain of the maltose binding protein; immunoglobulin hinge region; an N-hydroxysuccinimide linker; a peptide or peptidomimetic hairpin turn; or a hydrophilic sequence or another component or sequence that, for example, promotes the solubility or stability of the Clostridial toxin substrate. Non-limiting examples of specific protocols for selecting, making and using an appropriate binding peptide are described in, e.g., Epitope Tagging, pp. 17.90-17.93 (Sambrook and Russell, eds., Molecular Cloning A Laboratory Manual, Vol. 3, 3$^{rd}$ ed. 2001); Antibodies: A Laboratory Manual (Edward Harlow & David Lane, eds., Cold Spring Harbor Laboratory Press, 2$^{nd}$ ed. 1998); and Using Antibodies: A Laboratory Manual: Portable Protocol No. I (Edward Harlow & David Lane, Cold Spring Harbor Laboratory Press, 1998), which are hereby incorporated by reference. In addition, non-limiting examples of binding peptides as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. These protocols are routine procedures well within the scope of one skilled in the art and from the teaching herein.

The compositions and methods of the present specification provide a cell, in part, capable of Clostridial toxin intoxication. As used herein, the term "cell," means any eukaryotic cell that expresses, or can be engineered to express, at least one receptor that binds a Clostridial toxin. The term cell encompasses cells from a variety of organisms, such as, e.g., murine, rat, porcine, bovine, equine, primate and human cells; from a variety of cell types such as, e.g., neural and non-neural; and can be isolated from or part of a heterogeneous cell population, tissue or organism. It is understood that cells useful in aspects of the invention can included, without limitation, primary cells; cultured cells; established cells; normal cells; transformed cells; tumor cells; infected cells; proliferating and terminally differentiated cells; and stably or transiently transfected cells, including stably and transiently transfected cells. It is further understood that cells useful in aspects of the invention can be in any state such as proliferating or quiescent; intact or permeabilized such as through chemical-mediated transfection such as, e.g., calcium phosphate-mediated, diethyl-laminoethyl (DEAE) dextran-mediated, lipid-mediated, polyethyleneimine (PEI)-mediated and polybrene-mediated; physical-mediated transfection, such as, e.g., biolistic particle delivery, microinjection and electroporation; and viral-mediated transfection, such as, e.g., retroviral-mediated transfection. It is further understood that cells useful in aspects of the invention may include those which express a Clostridial toxin substrate under control of a constitutive, tissue-specific, cell-specific or inducible promoter element, enhancer element or both. It further is understood that cells useful in aspects of the invention may or may not express one or more endogenous Clostridial toxin target proteins such as, e.g., SNAP-25, VAMP and syntaxin.

The cell compositions disclosed in the present specification are capable of Clostridial toxin intoxication. As used herein, the term "cell capable of Clostridial toxin intoxication" means a cell that can enable the overall cellular mechanism whereby a Clostridial toxin proteolytically cleaves a substrate and encompasses the binding of a Clostridial toxin to a low or high affinity receptor, the internalization of the toxin/receptor complex, the translocation of the Clostridial toxin light chain into the cytoplasm and the enzymatic target modification of a Clostridial toxin substrate. By definition, a cell capable of Clostridial toxin intoxication must express one or more endogenous low or high affinity Clostridial toxin receptors for one or more Clostridial toxin serotypes; express one or more exogenous low or high affinity Clostridial toxin receptors for one or more Clostridial toxin serotypes; or express a combination of endogenous low or high affinity Clostridial toxin receptors and exogenous low or high affinity Clostridial toxin receptors for one or more Clostridial toxin serotypes.

Thus, in an embodiment, a cell capable of Clostridial toxin intoxication can be a cell expressing a Clostridial toxin receptor. In aspects of this embodiment, the Clostridial toxin receptor can be a low affinity Clostridial toxin receptor, a high affinity Clostridial toxin receptor, an endogenous Clostridial toxin receptor, an exogenous Clostridial toxin receptor, or any combination thereof. In other aspects of this embodiment, the Clostridial toxin receptor can be a BoNT/A receptor, a BoNT/B receptor, a BoNT/C1 receptor, a BoNT/D receptor, a BoNT/E receptor, a BoNT/F receptor, a BoNT/G receptor or a TeNT receptor.

In another embodiment, a cell capable of Clostridial toxin intoxication can be a cell expressing a plurality of Clostridial toxin receptors. In aspects of this embodiment, a plurality of Clostridial toxin receptor can comprise low affinity Clostridial toxin receptors, high affinity Clostridial toxin receptors, endogenous Clostridial toxin receptors, exogenous Clostridial toxin receptors, or any combination thereof. In aspects of this embodiment, a plurality of Clostridial toxin receptor can comprise, e.g., two or more Clostridial toxin receptors, three or more Clostridial toxin receptors, four or more Clostridial toxin receptors, five or more Clostridial toxin receptors, six or more Clostridial toxin receptors, seven or more Clostridial toxin receptors and eight or more Clostridial toxin receptors. In other aspects of this embodiment, cell capable of Clostridial toxin intoxication can express two or more of the following receptors a BoNT/A receptor, a BoNT/B receptor, a BoNT/C1 receptor, a BoNT/D receptor, a BoNT/E receptor, a BoNT/F receptor, a BoNT/G receptor or a TeNT receptor. In other aspects of this embodiment, cell capable of Clostridial toxin intoxication can express three or more of the following receptors a BoNT/A receptor, a BoNT/B receptor, a BoNT/C1 receptor, a BoNT/D receptor, a BoNT/E receptor, a BoNT/F receptor, a BoNT/G receptor or a TeNT receptor. In other aspects of this embodiment, cell capable of Clostridial toxin intoxication can express four or more of the following receptors a BoNT/A receptor, a BoNT/B receptor, a BoNT/C1 receptor, a BoNT/D receptor, a BoNT/E receptor, a BoNT/F receptor, a BoNT/G receptor or a TeNT receptor. In other aspects of this embodiment, cell capable of Clostridial toxin intoxication can express five or more of the following receptors a BoNT/A receptor, a BoNT/B receptor, a BoNT/C1 receptor, a BoNT/D receptor, a BoNT/E receptor, a BoNT/F receptor, a BoNT/G receptor or a TeNT receptor. In other aspects of this embodiment, cell capable of Clostridial toxin intoxication can express six or more of the following receptors a BoNT/A receptor, a BoNT/B receptor, a BoNT/C1 receptor, a BoNT/D receptor, a BoNT/E receptor, a BoNT/F receptor, a BoNT/G receptor or a TeNT receptor. In other aspects of this embodiment, cell capable of Clostridial toxin intoxication can express seven or more of the following receptors a BoNT/A receptor, a BoNT/B receptor, a BoNT/C1 receptor, a BoNT/D receptor, a BoNT/E receptor, a BoNT/F receptor, a BoNT/G receptor or a TeNT receptor.

Cells that express one or more endogenous or exogenous Clostridial toxin receptors can be identified by routine methods including direct and indirect assays for toxin uptake. Assays that determine Clostridial toxin binding or uptake properties can be used to assess whether a cell is expressing a Clostridial toxin receptor. Such assays include, without limitation, cross-linking assays using labeled Clostridial toxins, such as, e.g., [$^{125}$I] BoNT/A, [$^{125}$I] BoNT/B, [$^{125}$I] BoNT/C1, [$^{125}$I] BoNT/D, [$^{125}$I] BoNT/E, BoNT/F, [$^{125}$I] BoNT/G and [$^{125}$I] TeNT, see, e.g., Noriko Yokosawa et al., Binding of *Clostridium botulinum* type C neurotoxin to different neuroblastoma cell lines, 57(1) Infect. Immun. 272-277 (1989); Noriko Yokosawa et al., Binding of botulinum type C1, D and E neurotoxins to neuronal cell lines and synaptosomes, 29(2) Toxicon 261-264 (1991); and Tei-ichi Nishiki et al., Identification of protein receptor for *Clostridium botulinum* type B neurotoxin in rat brain synaptosomes, 269(14) J. Biol. Chem. 10498-10503 (1994). Other non-limiting assays include immunocytochemical assays that detect toxin binding using labeled or unlabeled antibodies, see, e.g., Atsushi Nishikawa et al., The receptor and transporter for internalization of *Clostridium botulinum* type C progenitor toxin into HT-29 cells, 319(2) Biochem. Biophys. Res. Commun. 327-333 (2004) and immunoprecipitation assays, see, e.g., Yukako Fujinaga et al., Molecular characterization of binding subcomponents of *Clostridium botulinum* type C progenitor toxin for intestinal epithelial cells and erythrocytes, 150(Pt 5) Microbiology 1529-1538 (2004), that detect bound toxin using labeled or unlabeled antibodies. Antibodies useful for these assays include, without limitation, antibodies selected against a Clostridial toxin, such as, e.g., BoNT/A, BoNT/B, BoNT/C1, BoNT/D, BoNT/E, BoNT/F, BoNT/G or TeNT, antibodies selected against a CoNT receptor, such as, e.g., FGFR3 or synaptotagmin, and/or antibodies selected against a ganglioside, such as, e.g., GD1a, GD1b, GD3, GQ1b, or GT1b. If the antibody is labeled, the binding of the molecule can be detected by various means, including Western blotting, direct microscopic observation of the cellular location of the antibody, measurement of cell or substrate-bound antibody following a wash step, or electrophoresis, employing techniques well-known to those of skill in the art. If the antibody is unlabeled, one may employ a labeled secondary antibody for indirect detection of the bound molecule, and detection can proceed as for a labeled antibody. It is understood that these and similar assays that determine Clostridial toxin uptake properties or characteristics can be useful in selecting a neuron or other cells useful in aspects of the invention.

Assays that monitor the release of a molecule after exposure to a Clostridial toxin can also be used to assess whether a cell is expressing a Clostridial toxin receptor. In these assays, inhibition of the molecule's release would occur in cells expressing a Clostridial toxin receptor after Clostridial toxin treatment. Well known assays include methods that measure inhibition of radio-labeled catecholamine release from neurons, such as, e.g., [$^3$H] noradrenaline or [$^3$H] dopamine release, see e.g., A Fassio et al., Evidence for calcium-dependent vesicular transmitter release insensitive to tetanus toxin and botulinum toxin type F, 90(3) Neuroscience 893-902 (1999); and Sara Stigliani et al., The sensitivity of catecholamine release to botulinum toxin C1 and E suggests selective targeting of vesicles set into the readily releasable pool, 85(2) J. Neurochem. 409-421 (2003), or measures catecholamine release using a fluorometric procedure, see, e.g., Anton de Paiva et al., A role for the interchain disulfide or its participating thiols in the internalization of botulinum neurotoxin A revealed by a toxin derivative that binds to ecto-acceptors and inhibits transmitter release intracellularly, 268(28) J. Biol. Chem. 20838-20844 (1993); Gary W. Lawrence et al., Distinct exocytotic responses of intact and permeabilised chromaffin cells after cleavage of the 25-kDa synaptosomal-associated protein (SNAP-25) or synaptobrevin by botulinum toxin A or B, 236(3) Eur. J. Biochem. 877-886 (1996); and Patrick Foran et al., Botulinum neurotoxin C1 cleaves both syntaxin and SNAP-25 in intact and permeabilized chromaffin cells: correlation with its blockade of catecholamine release, 35(8) Biochemistry 2630-2636 (1996). Other non-limiting examples include assays that measure inhibition of hormone release from endocrine cells, such as, e.g., anterior pituitary cells or ovarian cells. It is understood that these and similar assays for molecule release can be useful in selecting a neuron or other cells useful in aspects of the invention.

Assays that detect the cleavage of a Clostridial toxin substrate after exposure to a Clostridial toxin can also be used to assess whether a cell is expressing a Clostridial toxin receptor. In these assays, generation of a Clostridial toxin substrate cleavage-product would be detected in cells expressing a Clostridial toxin receptor after Clostridial toxin treatment. Non-limiting examples of specific Western blotting procedures, as well as well-characterized reagents, conditions and protocols are readily available from commercial vendors that include, without limitation, Amersham Biosciences, Piscataway, N.J.; Bio-Rad Laboratories, Hercules, Calif.; Pierce Biotechnology, Inc., Rockford, Ill.; Promega Corporation, Madison, Wis., and Stratagene, Inc., La Jolla, Calif. It is understood that these and similar assays for Clostridial toxin substrate cleavage can be useful in selecting a neuron or other cells useful in aspects of the invention.

As non-limiting examples, western blot analysis using an antibody that specifically recognizes BoNT/A SNAP-25-cleaved product can be used to assay for uptake of BoNT/A; western blot analysis using an antibody that specifically recognizes BoNT/C1 SNAP-25-cleaved product can be used to assay for uptake of BoNT/C1; and western blot analysis using an antibody that specifically recognizes a BoNT/E SNAP-25-cleaved product can be used to assay for uptake of BoNT/E. Examples of anti-SNAP-25 antibodies useful for these assays include, without limitation, rabbit polyclonal anti-$SNAP25_{197}$ antiserum pAb anti-SNAP25197 #1 (Allergan, Inc., Irvine, Calif.), mouse monoclonal anti-SNAP-25 antibody SMI-81 (Sternberger Monoclonals, Lutherville, Md.), mouse monoclonal anti-SNAP-25 antibody CI 71.1 (Synaptic Systems, Goettingen, Germany), mouse monoclonal anti-SNAP-25 antibody CI 71.2 (Synaptic Systems, Goettingen, Germany), mouse monoclonal anti-SNAP-25 antibody SP12 (Abcam, Cambridge, Mass.), rabbit polyclonal anti-SNAP-25 antiserum (Synaptic Systems, Goettingen, Germany), and rabbit polyclonal anti-SNAP-25 antiserum (Abcam, Cambridge, Mass.).

As additional non-limiting examples, western blot analysis using an antibody that specifically recognizes a BoNT/B VAMP-cleaved product can be used to assay for uptake of BoNT/B; western blot analysis using an antibody that specifically recognizes BoNT/D VAMP-cleaved product can be used to assay for uptake of BoNT/D; western blot analysis using an antibody that specifically recognizes BoNT/F VAMP-cleaved product can be used to assay for uptake of BoNT/F; western blot analysis using an antibody that specifically recognizes BoNT/G VAMP-cleaved product can be used to assay for uptake of BoNT/G; and western blot analysis using an antibody that specifically recognizes TeNT. Examples of anti-VAMP antibodies useful for these assays include, without limitation, mouse monoclonal anti-VAMP-1 antibody CI 10.1 (Synaptic Systems, Goettingen, Germany), mouse monoclonal anti-VAMP-1 antibody SP10 (Abcam, Cambridge, Mass.), mouse monoclonal anti-VAMP-1 antibody SP11 (Abcam, Cambridge, Mass.), rabbit polyclonal anti-VAMP-1 antiserum (Synaptic Systems, Goettingen, Germany), rabbit polyclonal anti-VAMP-1 antiserum (Abcam, Cambridge, Mass.), mouse monoclonal anti-VAMP-2 antibody CI 69.1 (Synaptic Systems, Goettingen, Germany), rabbit polyclonal anti-VAMP-2 antiserum (Synaptic Systems, Goettingen, Germany), rabbit polyclonal anti-VAMP-2 antiserum (Abcam, Cambridge, Mass.), mouse monoclonal anti-VAMP-3 antibody CI 10.1 (Synaptic Systems, Goettingen, Germany), rabbit polyclonal anti-VAMP-3 antiserum (Synaptic Systems, Goettingen, Germany) and rabbit polyclonal anti-VAMP-3 antiserum (Abcam, Cambridge, Mass.), As another non-limiting example, western blot analysis using an antibody that specifically recognizes BoNT/C1 Syntaxin-cleaved product can be used to assay for uptake of BoNT/C1. Examples of anti-Syntaxin antibodies useful for these assays include, without limitation, mouse monoclonal anti-Syntaxin-1 antibody CI 78.2 (Synaptic Systems, Goettingen, Germany), mouse monoclonal anti-Syntaxin-1A antibody CI 78.3 (Synaptic Systems, Goettingen, Germany), rabbit polyclonal anti-Syntaxin-1A antiserum (Synaptic Systems, Goettingen, Germany), rabbit polyclonal anti-Syntaxin-1B antiserum (Synaptic Systems, Goettingen, Germany), rabbit polyclonal anti-Syntaxin antiserum (Abcam, Cambridge, Mass.), rabbit polyclonal anti-Syntaxin-2 antiserum (Abcam, Cambridge, Mass.) and rabbit polyclonal anti-Syntaxin-3 antiserum (Abcam, Cambridge, Mass.), It is envisioned that an exogenous Clostridial toxin receptor can include, without limitation, a nucleic acid molecule, such as, e.g., DNA and RNA, that encodes a Clostridial toxin receptor disclosed in the present specification and peptide molecule or peptidomimetic comprising a Clostridial toxin receptor disclosed in the present specification. In is also envisioned that an exogenous Clostridial toxin receptor can be transiently or stably expressed in a cell useful in aspects of the invention. Thus, aspects of this embodiment include a cell that transiently contains a nucleic acid molecule, such as, e.g., DNA and RNA, that encode a Clostridial toxin receptor disclosed in the present specification and a cell that transiently contains a peptide molecule or peptidomimetic comprising Clostridial toxin receptor disclosed in the present specification. Other aspects of this embodiment include a cell that stably contains a nucleic acid molecule, such as, e.g., DNA and RNA, that encode a Clostridial toxin substrate disclosed in the present specification and a cell that stably contains a peptide molecule or peptidomimetic comprising Clostridial toxin substrate disclosed in the present specification. Stably-maintained nucleic acid molecules may be extra-chromosomal and replicate autonomously, or they may be integrated into the chromosomal material of the cell and replicate non-autonomously.

It is understood that the selection of a cell depends, in part, on which Clostridial toxin is to be assayed. As a non-limiting example, to assay for BoNT/A activity, one selects a cell that expresses or can be engineered to express a low or high affinity receptor for BoNT/A. As a further example, to assay for BoNT/B activity, one selects a cell that expresses or can be engineered to express a low or high affinity receptor for BoNT/B. As a still further example, to assay for BoNT/C1 activity, one selects a cell that expresses or can be engineered to express a low or high affinity receptor for BoNT/C1. As a still further example, to assay for BoNT/D activity, one selects a cell that expresses or can be engineered to express a low or high affinity receptor for BoNT/D. As a still further example, to assay for BoNT/E activity, one selects a cell that expresses or can be engineered to express a low or high affinity receptor for BoNT/E. As a still further example, to assay for BoNT/F activity, one selects a cell that expresses or can be engineered to express a low or high affinity receptor for BoNT/F. As a still further example, to assay for BoNT/G activity, one selects a cell that expresses or can be engineered to express a low or high affinity receptor for BoNT/G. As a still further example, to assay for TeNT activity, one selects a cell that expresses or can be engineered to express a low or high affinity receptor for TeNT.

As discussed above, it is understood that a cell useful in the invention expresses endogenous or exogenous low or high affinity Clostridial toxin receptors for one or more Clostridial toxins. Such a cell also generally exhibits inhibition of exocytosis upon exposure to Clostridial toxin with, for example, an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM. In particular embodiments, the invention provides a neuron containing a BoNT/A substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to BoNT/A. In further embodiments, the invention provides a neuron containing a BoNT/B substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to BoNT/B. In other embodiments, the invention provides a neuron containing a BoNT/C1 substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to BoNT/C1. In still further embodiments, the invention provides a neuron containing a BoNT/D substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to BoNT/D. In additional embodiments, the invention provides a neuron containing a BoNT/E substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to BoNT/E. In yet further embodiments, the invention provides a neuron containing a BoNT/F substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to BoNT/F. In further embodiments, the invention provides a neuron containing a BoNT/G substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to BoNT/G. In still further embodiments, the invention provides a neuron containing a TeNT substrate which exhibits inhibition of exocytosis with an $IC_{50}$ of less than 500 nM, less than 100 mM, less than 50 nM, less than 5 nM, less than 0.5 nM, less than 0.05 nM, less than 0.005 nM, less than 0.0005 nM, less than 0.00005 nM or less than 0.000005 nM upon exposure to TeNT. It is understood that the same neuron can express two or more receptors for different Clostridial toxin serotypes, with the same or a different $IC_{50}$ for each individual toxin serotype.

Cells useful in aspects of the invention include both neuronal and non-neuronal cells. Neuronal cells useful in aspects of the invention include, without limitation, primary neuronal cells; immortalized or established neuronal cells; transformed neuronal cells; neuronal tumor cells; stably and transiently transfected neuronal cells and further include, yet are not limited to, mammalian, murine, rat, primate and human neuronal cells. Non-limiting examples of neuronal cells useful in aspects of the invention include, e.g., peripheral neuronal cells, such as, e.g., motor neurons and sensory neurons; and CNS neuronal cells, such as, e.g., spinal cord neurons like embryonic spinal cord neurons, dorsal root ganglia (DRG) neurons, cerebral cortex neurons, cerebellar neurons, hippocampal neurons and motor neurons. Neuronal cells useful in the invention include, without limitation, those described herein below or tabulated in Table 13. Such neuronal cells can be, for example, central nervous system (CNS) neurons; neuroblastoma cells; motor neurons, hippocampal neurons or cerebellar neurons and further can be, without limitation, Neuro-2A, SH-SY5Y, NG108-15, N1E-115 or SK-N-DZ cells. The skilled person understands that these and additional primary and established neurons can be useful in the cells and methods of the invention.

Neurons useful in aspects of the invention include, without limitation, primary cultures such as primary cultures of embryonic dorsal root ganglion (DRG) neurons. As one example, primary cultures of embryonic rat DRG neurons are described in Mary J. Welch et al., Sensitivity of embryonic rat dorsal root ganglia neurons to *Clostridium botulinum* neurotoxins, 38(2) Toxicon 245 258 (2000); and primary cultures of fetal spinal cord neurons, for example, primary cultures of murine fetal spinal cord neurons are described in Elaine A. Neale et al., Botulinum neurotoxin A blocks synaptic vesicle exocytosis but not endocytosis at the nerve terminal, 147(6) J. Cell Biol. 1249-1260 (1999), and John A. Chaddock et al., Inhibition of vesicular secretion in both neuronal and non-neuronal cells by a retargeted endopeptidase derivative of *Clostridium botulinum* neurotoxin type A, 68(5) Infect. Immun. 2587-2593 (2000). Thus, in an embodiment, a cell capable of Clostridial toxin intoxication can be a neuron. In aspects of this embodiment, a neuron can be a neuron from, e.g., a primary culture, an embryonic dorsal root ganglion primary culture or a fetal spinal cord primary culture. As non-limiting examples, cells useful for determining Clostridial toxin activity according to a method disclosed in the present specification can include, a primary neuronal cell, such as, e.g., rat embryonic dorsal root ganglion (DRG) neurons or murine fetal spinal cord neurons, that include a Clostridial toxin substrate comprising a SNAP-25 recognition sequence; such as, e.g., a BoNT/A recognition sequence or a BoNT/E recognition sequence; a primary neuronal cell, such as, e.g., rat embryonic dorsal root ganglion (DRG) neurons or murine fetal spinal cord neurons, that include a Clostridial toxin substrate comprising a VAMP recognition sequence; such as, e.g., a BoNT/B recognition sequence or a TeNT recognition sequence; and a primary neuronal cell, such as, e.g., rat embryonic dorsal root ganglion (DRG) neurons or murine fetal spinal cord neurons, that include a Clostridial toxin substrate comprising a Syntaxin recognition sequence; such as, e.g., a BoNT/C1 recognition sequence.

Neuronal cell lines useful in aspects of the invention include, without limitation, neuroblastoma cell lines, neuronal hybrid cell lines, spinal cord cell lines, central nervous system cell lines, cerebral cortex cell lines, dorsal root ganglion cell lines, hippocampal cell lines and pheochromocytoma cell lines.

Neuroblastoma cell lines, such as, e.g., murine, rat, primate or human neuroblastoma cell lines can be useful in aspects of the invention. Neuroblastoma cell lines useful in aspects of the invention include, without limitation, BE(2)-C (ATCC CRL-2268; ECACC 95011817), BE(2)-M17 (ATCC CRL-2267; ECACC 95011816), C1300 (ECACC 93120817), CHP-212 (ATCC CRL-2273), CHP-126 (DSMZ ACC 304), IMR 32 (ATCC CRL-127; ECACC 86041809; DSMZ ACC 165), KELLY (ECACC 92110411; DSMZ ACC 355), LA-N2, see, e.g., Robert C. Seeger et al., Morphology, growth, chromosomal pattern and fibrinolytic activity of two new human neuroblastoma cell lines, 37(5) Cancer Res. 1364-1371 (1977); and G. J. West et al., Adrenergic, cholinergic, and inactive human neuroblastoma cell lines with the action-potential Na+ ionophore, 37(5) Cancer Res. 1372-1376 (1977), MC-IXC (ATCC CRL-2270), MHH-NB-11 (DSMZ ACC 157), N18Tg2 (DSMZ ACC 103), N1E-115 (ATCC CCL-2263; ECACC 88112303), N4TG3 (DSMZ ACC 101), Neuro-2A (ATCC CCL-131; ECACC 89121404; DSMZ ACC 148), NB41A3 (ATCC CCL-147; ECACC 89121405), NS20Y (DSMZ ACC 94), SH-SY5Y (ATCC CRL-2266; ECACC 94030304; DSMZ ACC 209), SIMA (DSMZ ACC 164), SK-N-DZ (ATCC CRL-2149; ECACC 94092305), SK-N-F1 (ATCC CRL-2142, ECACC 94092304), SK-N-MC (ATCC HTB-10, DSMZ ACC 203) and SK-N-SH (ATCC HTB-11, ECACC 86012802). Thus, in an embodiment, a cell capable of Clostridial toxin intoxication can be a neuroblastoma cell. In aspects of this embodiment, a neuroblastoma cell can be, e.g., BE(2)-C, BE(2)-M17, C1300, CHP-212, CHP-126, IMR 32, KELLY, LA-N2, MC-IXC, MHH-NB-11, N18Tg2, N1E-115, N4TG3, Neuro-2A, NB41A3, NS20Y, SH-SY5Y, SIMA, SK-N-DZ, SK-N-F1, SK-N-MC and SK-N-SH. As non-limiting examples, cells useful for determining Clostridial toxin activity according to a method disclosed in the present specification can include, a neuroblastoma cell, such as, e.g., SH-SY5Y cells, that include a Clostridial toxin substrate comprising a SNAP-25 recognition sequence; such as, e.g., a BoNT/A recognition sequence or a BoNT/E recognition sequence; Neuro-2a cells, that include a Clostridial toxin substrate comprising a SNAP-25 recognition sequence; such as, e.g., a BoNT/A recognition sequence; and N1E-115 cells or SK-N-DZ cells, that include a Clostridial toxin substrate comprising a SNAP-25 recognition sequence; such as, e.g., a BoNT/E recognition sequence.

Neuronal hybrid cell lines, such as, e.g., murine, rat, primate and human hybrid neuronal cell lines can be useful in aspects of the invention. Such hybrid cell lines include neuroblastoma/glioma hybrids, such as, e.g., N18 (ECACC 88112301), NG108-15 (ATCC HB-12317, ECACC 88112302) and NG115-401L (ECACC 87032003); neuroblastoma/motor neuron hybrids, such as, e.g., NSC-19 and NSC-34, which express motor neuron characteristics, display a multipolar neuron-like phenotype, express high levels of choline acetyltransferase (CHAT), generate action potentials, express neurofilament triplet proteins and synthesize, store and release acetylcholine., see, e.g., N. R. Cashman et al., Neuroblastoma x spinal cord (NSC) hybrid cell lines resemble developing motor neurons, 194(3) Dev. Dyn. 209-221 (1992); and Christopher J. Eggett et al., Development and characterisation of a glutamate-sensitive motor neuronal cell line, 74(5) J. Neurochem. 1895-1902 (2000); neuroblastoma/dorsal root ganglion neuron hybrids, such as, e.g., F11, see, e.g., Doros Platika et al., Neuronal traits of clonal cell lines derived by fusion of dorsal root ganglia neurons with neuroblastoma cells, 82(10) Proc. Natl. Acad. Sci. U.S.A. 3499-3503 (1985), ND-C (ECACC 92090913), ND-E (ECACC 92090915), ND-U1 (ECACC 92090916), ND3 (ECACC 92090901), ND7/23 (ECACC 92090903), ND8/34 (ECACC 92090904), ND8/47, ND15 (ECACC 92090907), ND27 (ECACC 92090912); neuroblastoma/hippocampal neuron hybrids, such as, e.g., HN-33, see, e.g., Henry J. Lee et al., Neuronal properties and trophic activities of immortalized hippocampal cells from embryonic and young adult mice. 10(6) J. Neurosci. 1779-1787 (1990). Thus, in an embodiment, a cell capable of Clostridial toxin intoxication can be a hybrid neuron. In aspects of this embodiment, a hybrid neuron can be, e.g., a neuroblastoma/glioma hybrid, a neuroblastoma/motor neuron hybrid, a neuroblastoma/root ganglion neuron hybrid and a neuroblastoma/hippocampal neuron hybrid. In further aspects of this embodiment, a neuroblastoma/glioma hybrid can be, e.g., N18, NG108-15 and NG115-401 L. In further aspects of this embodiment, a neuroblastoma/motor neuron hybrid can be, e.g., NSC-19 and NSC-32. In further aspects of this embodiment, a neuroblastoma/dorsal root ganglion neuron hybrid can be, e.g., ND8-47. In further aspects of this embodiment, a neuroblastoma/root ganglion neuron hybrid can be, e.g., F11, ND-C, ND-E, ND-U1, ND3, ND7/23, ND8/34, ND8/47, ND15 and ND27. In further aspects of this embodiment, a neuroblastoma/hippocampal neuron hybrid can be, e.g., HN-33.

The NG108-15 cell line is a hybrid of mouse neuroblastoma and rat glioma cells that binds BoNT/C1 at subnanomolar concentrations with an $IC_{50}$ of 0.2 nM (0.18 ng of complex per microliter), reaching saturation at 6 nM, see, e.g., Noriko Yokosawa et al., Binding of *Clostridium botulinum* type C neurotoxin to different neuroblastoma cell lines, 57(1) Infect. Immun. 272-277 (1989); and Noriko Yokosawa et al., Binding of botulinum type Cl, D and E neurotoxins to neuronal cell lines and synaptosomes, 29(2) Toxicon 261-264 (1991). Based on binding data, the NG108-15 cell line may contain both low and high affinity receptors for BoNT/C1. As non-limiting examples, cells useful for determining Clostridial toxin activity according to a method disclosed in the present specification can include, a neuronal hybrid cell, such as, e.g., NG108-15 cells, that include a Clostridial toxin substrate comprising a SNAP-25 recognition sequence; such as, e.g., a BoNT/A recognition sequence, a BoNT/C1 recognition sequence or a BoNT/E recognition sequence; and NG108-15 cells, that include a Clostridial toxin substrate comprising a Syntaxin recognition sequence; such as, e.g., a BoNT/C1 recognition sequence.

Spinal cord cell lines, such as, e.g., murine, rat, primate or human spinal cord cell lines can be useful in aspects of the invention and include, without limitation, TE 189.T (ATCC CRL-7947) and M4b, see, e.g., Ana M. Cardenas et al., Establishment and characterization of immortalized neuronal cell lines derived from the spinal cord of normal and trisomy 16 fetal mice, an animal model of Down syndrome, 68(1) J. Neurosci. Res. 46-58 (2002). As an example, a human spinal cord cell line can be generated from precursors of human embryonic spinal cord cells (first trimester embryos) that are immortalized with a tetracycline repressible v-myc oncogene as described in Ronghao Li et al., Motoneuron differentiation of immortalized human spinal cord cell lines, 59(3) J. Neurosci. Res. 342-352 (2000). Such cells can be expanded indefinitely in proliferative growth conditions before rapid differentiation (4-7 days) into functional neurons that express neuronal phenotypic markers such as choline acetyltransferase. As another example, a murine spinal cord cell line can be prepared by immortalizing an embryonic spinal cord culture using transforming media. Such a spinal cord cell line can be, for example, the murine M4b line and can express neuronal markers such as NSE, synaptophysin, MAP 2 and choline acetyltransferase, and can release acetylcholine upon appropriate stimulation, see, e.g., Cardenas et al., supra, (2002). Thus, in an embodiment, a cell capable of Clostridial toxin intoxication can be a spinal cord cell. In aspects of this embodiment, a spinal cord cell can be, e.g., TE 189.T and M4b.

Central nervous system (CNS) cell lines, such as, e.g., murine, rat, primate and human CNS cell lines, can be useful in aspects of the invention. A useful CNS cell line can be, for example, a human CNS cell line immortalized with a tetracycline repressible v-myc oncogene as described in Dinah W. Sah et al., Bipotent progenitor cell lines from the human CNS, 15(6) Nat. Biotechnol. 574-580 (1997). Upon repression of the oncogene, the cells differentiate into neurons. Thus, in an embodiment, a cell capable of Clostridial toxin intoxication can be a CNS cell.

Cerebral cortex cell lines, such as, e.g., murine, rat, primate and human cerebral cortex cell lines, can be useful in aspects of the invention and include, without limitation, CNh, see, e.g., Ana M. Cardenas et al., Calcium signals in cell lines derived from the cerebral cortex of normal and trisomy 16 mice, 10(2) Neuroreport 363-369 (1999), HCN-1a (ATCC CRL-10442) and HCN-2 (ATCC CRL-10742). As an example, murine cortex primary cultures from 12-16 days embryos can be immortalized, for example, by culturing the cells in conditioned media from a rat thyroid cell line that induces transformation in vitro. The immortalized cells can be differentiated into neurons expressing neuronal markers using the appropriate media; these differentiated cells express choline acetyltransferase and secrete acetylcholine and glutamate in response to depolarization and nicotine stimulation, see, e.g., David D. Allen et al., Impaired cholinergic function in cell lines derived from the cerebral cortex of normal and trisomy 16 mice, 12(9) Eur. J. Neurosci. 3259-3264 (2000). Thus, in an embodiment, a cell capable of Clostridial toxin intoxication can be a cerebral cortex cell. In aspects of this embodiment, a cerebral cortex cell can be, e.g., CNh, HCN-1a and HCN-2.

Dorsal root ganglia cell lines, such as, e.g., murine, rat, primate and human dorsal root ganglia cell lines, can be useful in aspects of the invention and include, without limitation, G4b, see, e.g., David D. Allen et al., A dorsal root ganglia cell line derived from trisomy 16 fetal mice, a model for Down syndrome, 13(4) Neuroreport 491-496 (2002). Embryonic dorsal root ganglia primary cultures can be immortalized with transforming conditioned media as described above. Upon differentiation, the cell line exhibits neuronal traits and lacks glial markers by immunohistochemistry. Release of neurotransmitters such as acetylcholine can be induced in response to potassium and nicotine, see, e.g., Allen et al., supra, (2002). Thus, in an embodiment, a cell capable of Clostridial toxin intoxication can be a dorsal root ganglia cell. In aspects of this embodiment, a dorsal root ganglia cell can be, e.g., G4b.

Hippocampal cell lines, such as, e.g., murine, rat, primate and human hippocampal lines can be useful in aspects of the invention and include, without limitation, HT-4, see, e.g., K. Frederiksen et al., Immortalization of precursor cells from the mammalian CNS, 1(6) Neuron 439-448 (1988) and HT-22, see, e.g., John B. Davis and Pamela Maher, Protein kinase C activation inhibits glutamate-induced cytotoxicity in a neuronal cell line, 652(1) Brain Res. 169-173 (1994). As a non-limiting example, the murine hippocampal cell line HT-22 can be useful in the invention. As a further non-limiting example, the immortalized HN33 hippocampal cell line can be useful in the invention. This hippocampal cell line was derived from the fusion of primary neurons from the hippocampus of postnatal day 21 mice with the N18TG2 neuroblastoma cell line, and, when differentiated, shares membrane properties with adult hippocampal neurons in primary culture, see, e.g., Henry J. Lee et al., Neuronal Properties and Trophic Activities of Immortalized Hippocampal Cells from Embryonic and Young Adult Mice, 19(6) J. Neurosci. 1779-1787 (1990); and Henry J. Lee et al., Immortalized young adult neurons from the septal region: generation and characterization, 52(1-2) Brain Res. Dev Brain Res. 219-228 (1990). Thus, in an embodiment, a cell capable of Clostridial toxin intoxication can be a hippocampal cell. In aspects of this embodiment, a hippocampal cell can be, e.g., HT-4, HT-22 and HN33.

A variety of non-neuronal cells are useful in aspects of the invention. Non-neuronal cells useful in aspects of the invention include, without limitation, primary non-neuronal cells; immortalized or established non-neuronal cells; transformed non-neuronal cells; non-neuronal tumor cells; stably and transiently transfected non-neuronal cells and further include, yet are not limited to, mammalian, murine, rat, primate and human non-neuronal cells. Non-neuronal cells useful in aspects of the invention further include, without limitation, any of the following primary or established cells: anterior pituitary cells; adrenal cells, such as, e.g., chromaffin cells of the adrenal medulla; pancreatic cells, such as, e.g., pancreatic acinar cells, pancreatic islet β cells and insulinoma HIT or INS-1 cells; ovarian cells, such as, e.g., steroid-producing ovarian cells; kidney cells, such as, e.g., HEK-293 cells (ATCC CRL 1573) and inner medullary collecting duct (IMCD) cells; stomach cells, such as, e.g., enterochromaffin cells; blood cells, such as, e.g., eurythrocytes, leucocytes, platelets, neutrophils, eosinophils, mast cells; epithelial cells, such as, e.g., those of the apical plasma membrane; fibroblasts; thyroid cells; chondrocytes; muscle cells; hepatocytes; glandular cells such as, e.g., pituitary cells, adrenal cells, chromaffin cells; and cells involved in glucose transporter (GLUT4) translocation. Thus, in an embodiment, a cell capable of Clostridial toxin intoxication can be a non-neuronal cell. In aspects of this embodiment, a non-neuronal cell can be from a primary or established non-neuronal cell line from the, e.g., anterior pituitary cells, adrenal cells, pancreatic cells, ovarian cells, kidney cells, stomach cells, blood cells, epithelial cells, fibroblasts, thyroid cells, chondrocytes, muscle cells, hepatocytes and glandular cells. In an aspects of this embodiment, a kidney cell line can be, e.g., HEK-293.

As non-limiting examples, cells useful for determining Clostridial toxin activity according to a method disclosed in the present specification can include, a primary or established non-neuronal cell, such as, e.g., chromaffin cells or pancreatic acinar cells, that include a Clostridial toxin substrate comprising a SNAP-25 recognition sequence; such as, e.g., a BoNT/A recognition sequence or a BoNT/E recognition sequence; a primary neuronal cell, such as, e.g., chromaffin cells or pancreatic acinar cells, that include a Clostridial toxin substrate comprising a VAMP recognition sequence; such as, e.g., a BoNT/B recognition sequence or a TeNT recognition sequence; and a primary neuronal cell, such as, e.g., chromaffin cells or pancreatic acinar cells, that include a Clostridial toxin substrate comprising a Syntaxin recognition sequence; such as, e.g., a BoNT/C1 recognition sequence.

As discussed above, cells useful in the invention include neuronal and non-neuronal cells that express low or undetectable levels of endogenous receptor but which have been transfected with, or otherwise engineered to express, one or more exogenous nucleic acid molecules encoding one or more Clostridial toxin receptors. The selection of the Clostridial toxin receptor depends on which Clostridial toxin is to be assayed. As a non-limiting example, a neuronal or non-neuronal cell can be transiently or stably engineered to express an exogenous nucleic acid molecule encoding the fibroblast growth factor 3 receptor (FGFR3), which serves as a BoNT/A receptor, see, e.g., PCT Patent Application No. 2005/006421. As another non-limiting example, a neuronal or non-neuronal cell can be transiently or stably engineered to express an exogenous nucleic acid molecule encoding a synaptic vesicle glycoprotein 2 (SV2) isoform, which serves as a BoNT/A receptor, see, e.g., Min Dong et al., SV2 *Is the Protein Receptor for Botulinum Neurotoxin A*, Science (2006); S. Mahrhold et al, *The Synaptic Vesicle Protein 2C Mediates the Uptake of Botulinum Neurotoxin A into Phrenic Nerves,* 580(8) FEBS Lett. 2011-2014 (2006). Additionally, a neuronal or non-neuronal cell can be transiently or stably engineered to express multiple exogenous nucleic acid molecules encoding FGFR3 and an SV2 isoform. As another non-limiting example, a neuronal or non-neuronal cell can be transiently or stably engineered to express an exogenous nucleic acid molecule encoding the synaptotagmin 1, which serves as a BoNT/B receptor and as a BoNT/G receptor, see, e.g., Min Dong et al., Synaptotagmins I and II mediate entry of botulinum neurotoxin B into cells, 162(7) J. Cell Biol. 1293-1303 (2003); and Andreas Rummel et al., Synaptotagmins I and II act as nerve cell receptors for botulinum neurotoxin G, 279 (29) J. Biol. Chem. 30865-30870 (2004). As another non-limiting example, a neuronal or non-neuronal cell can be transiently or stably engineered to express an exogenous nucleic acid molecule encoding the synaptotagmin II, which serves as a BoNT/B receptor and as a BoNT/G receptor, see, e.g., Min Dong et al., supra, (2003); and Andreas Rummel et al., supra, (2004).

Thus in an embodiment, a neuronal or non-neuronal cell is transiently or stably engineered to express an exogenous nucleic acid molecule encoding a FGFR3. In aspects of this embodiment, a neuronal or non-neuronal cell is transiently or stably engineered to express an exogenous nucleic acid molecule encoding the FGFR3 of SEQ ID NO: 173, the FGFR3 of SEQ ID NO: 174 or the FGFR3 of SEQ ID NO: 175.

In another embodiment, a neuronal or non-neuronal cell is transiently or stably engineered to express an exogenous nucleic acid molecule encoding a SV2. In aspects of this embodiment, a neuronal or non-neuronal cell is transiently or stably engineered to express an exogenous nucleic acid molecule encoding the SV2 of SEQ ID NO: 176, the SV2 of SEQ ID NO: 177, the SV2 of SEQ ID NO: 178 or the SV2 of SEQ ID NO: 179.

In another embodiment, a neuronal or non-neuronal cell is transiently or stably engineered to express an exogenous nucleic acid molecule encoding a FGFR3 and an exogenous nucleic acid molecule encoding a SV2. In aspects of this embodiment, a neuronal or non-neuronal cell is transiently or stably engineered to express an exogenous nucleic acid molecule encoding the FGFR3 of SEQ ID NO: 173, the FGFR3 of SEQ ID NO: 174 or the FGFR3 of SEQ ID NO: 175 and an exogenous nucleic acid molecule encoding the SV2 of SEQ ID NO: 176, the SV2 of SEQ ID NO: 177, the SV2 of SEQ ID NO: 178 or the SV2 of SEQ ID NO: 179.

In another embodiment, a neuronal or non-neuronal cell is transiently or stably engineered to express an exogenous nucleic acid molecule encoding a Synaptotagmin I. In aspects of this embodiment, a neuronal or non-neuronal cell is transiently or stably engineered to express an exogenous nucleic acid molecule encoding the Synaptotagmin of SEQ ID NO: 180.

In another embodiment, a neuronal or non-neuronal cell is transiently or stably engineered to express an exogenous nucleic acid molecule encoding a Synaptotagmin II. In aspects of this embodiment, a neuronal or non-neuronal cell is transiently or stably engineered to express an exogenous nucleic acid molecule encoding the Synaptotagmin of SEQ ID NO: 181.

Cells useful in aspects of the present invention further include, without limitation, transformed, tumor or other cells which over-express one or more endogenous Clostridial toxin receptors or which express one or more endogenous Clostridial toxin receptors. It is understood that the over-expressed receptor can be a wild type form of the receptor or can include one or more amino acid modifications as compared to the wild type receptor, with the proviso that the process of Clostridial toxin intoxication can still occur. As a non-limiting example, cells useful for determining BoNT/A activity encompass those which express or over-express a form of the fibroblast growth factor 3 receptor (FGFR3). As another non-limiting example, cells useful for determining BoNT/B activity encompass those which express or over-express a form of synaptotagmin I. As another non-limiting example, cells useful for determining BoNT/B activity encompass those which express or over-express a form of synaptotagmin II. As another non-limiting example, cells useful for determining BoNT/G activity encompass those which express or over-express a form of synaptotagmin 1. As another non-limiting example, cells useful for determining BoNT/G activity encompass those which express or over-express a form of synaptotagmin II.

Cells which express or over-express a form of the fibroblast growth factor 3 receptor include, yet are not limited to, naturally occurring and genetically modified as well as primary and established myeloma cells, bladder carcinoma cells, prostate carcinoma cells, thyroid carcinoma cells and cervical carcinoma cells. Such cells useful in aspects of the invention further encompass, without limitation, human myeloma cell lines including H929 (ATCC CRL-9068; ECACC 95050415; DSMZ ACC 163), JIM-3, see, e.g., H. Barker et al., pp. 155-158 (J. Radl & B. van Camp eds., EURAGE Monoclonal Gammopathies III: Clinical Significance and Basic Mechanisms, 1991), KMS-11, see, e.g., Masayoshi Namba et al., Establishment of five human myeloma cell lines, 25(8) In Vitro Cell Dev. Biol. 723-729 (1989), KMS-18, see, e.g., Naozo Nakazawa et al., Interphase detection of t(4;14) (p16.3;q32.3) by in situ hybridization and FGFR3 over-expression in plasma cell malignancies, 117(2) Cancer Genet. Cytogenet. 89-96 (2000), LB278, see, e.g., D. Ronchetti et al., Characterization of the t(4;14) (p16.3;q32) in the KMS-18 multiple myeloma cell line, 15(5) Leukemia 864-865 (2001), LB375, see, e.g., Ronchetti et al., supra, (2001), LB1017, see, e.g., Ronchetti et al., supra, (2001), LB2100, see, e.g., Ronchetti et al., supra, (2001), LP-1 (DSMZ ACC 41), OPM-2 (DSMZ ACC 50), PCL1, see, e.g., Ronchetti et al., supra, (2001), UTMC-2, see, e.g., Shuji Ozaki et al., Characterization of a novel interleukin-6 autocrine-dependent human plasma cell line, 8(12) Leukemia 2207-2213 (1994), which over-express FGFR3 due to chromosomal translocation t(4;14)(q16.3;q32.3) and other multiple myeloma cells with a t(4:14) translocation; leukemia cells including chronic myeloid leukemia (CML) cells such as CD34+BCR-ABL+ cells; and bladder carcinoma cells including primary and other urothelial carcinoma cells. One skilled in the art understands that these and other cells which over-express or express a form of the fibroblast growth factor 3 receptor can be useful in determining BoNT/A activity according to a method of the invention.

Thus, in an embodiment, a cell capable of Clostridial toxin intoxication can be a cell expressing an endogenous Clostridial toxin receptor. In aspects of this embodiment, an endogenous Clostridial toxin receptor expressed by a cell is a receptor for, e.g., BoNT/A, BoNT/B, BoNT/C1, BoNT/D, BoNT/E, BoNT/F, BoNT/G and TeNT. In further aspects of this embodiment, an endogenous Clostridial toxin receptor is, e.g., FGFR3, synaptotagmin I or synaptotagmin II. In another aspect of this embodiment, a cell expressing an endogenous Clostridial toxin receptor can be from, e.g., a primary myeloma cell line, an established myeloma cell line, a primary bladder carcinoma cell line, an established bladder carcinoma cell line, a primary cervical carcinoma cell line and an established cervical carcinoma cell line. In another embodiment, an FGFR3 expressing cell can be, e.g., a cell containing a t(4;14)(q16.3;q32.3) chromosomal translocation. In further aspects of this embodiment, an FGFR3 expressing cell can be, e.g., H929, JIM-3, KMS-11, KMS-18, LB278, LB375, LB1017, LB2100, LP-1, OPM-2, PCL1 and UTMC-2. In further aspects of this embodiment, an FGFR3 expressing cell can be, e.g., H929, JIM-3, KMS-11, KMS-18, LB278, LB375, LB1017, LB2100, LP-1, OPM-2, PCL1 and UTMC-2. As non-limiting examples, cells useful for determining Clostridial toxin activity according to a method disclosed in the present specification can include, an established myeloma cell, such as, e.g., KMS-11 or H929, that include a Clostridial toxin substrate comprising a SNAP-25 recognition sequence; such as, e.g., a BoNT/A recognition sequence; a primary or established bladder carcinoma cell that includes a Clostridial toxin substrate comprising a SNAP-25 recognition sequence; such as, e.g., a BoNT/A recognition sequence; and a primary or established cervical carcinoma cell that includes a Clostridial toxin substrate comprising a SNAP-25 recognition sequence; such as, e.g., a BoNT/A recognition sequence.

Further such cells useful in aspects of the invention further encompass, without limitation, stably transfected cell lines expressing a Clostridial toxin receptor. including, e.g., B9, see, e.g., Elizabeth E. Plowright et al., Ectopic expression of fibroblast growth factor receptor 3 promotes myeloma cell proliferation and prevents apoptosis, 95(3) Blood 992-998 (2000); TC, see, e.g., Hiroyuki Onose et al., Over-expression of fibroblast growth factor receptor 3 in a human thyroid carcinoma cell line results in overgrowth of the confluent cultures, 140(2) Eur. J. Endocrinol. 169-173 (1999); L6, see, e.g., M. Kana et al., Signal transduction pathway of human fibroblast growth factor receptor 3. Identification of a novel 66-kDa phosphoprotein, 272(10) J. Biol. Chem. 6621-6628 (1997); and CFK2, see, e.g., Janet E. Henderson et al., Expression of FGFR3 with the G380R achondroplasia mutation inhibits proliferation and maturation of CFK2 chondrocytic cells, 15(1) J. Bone Miner. Res. 155-165 (2000). One skilled in the art understands that these and other cells which over-express or express an activated form of the fibroblast growth factor 3 receptor can be useful in determining BoNT/A activity according to a method of the invention. Thus, in an embodiment, a cell capable of Clostridial toxin intoxication can be a cell stably expressing an exogenous Clostridial toxin receptor. In aspects of this embodiment, an exogenous Clostridial toxin receptor stably expressed by a cell is a receptor for, e.g., BoNT/A, BoNT/B, BoNT/C1, BoNT/D, BoNT/E, BoNT/F, BoNT/G and TeNT. In further aspects of this embodiment, an exogenous Clostridial toxin receptor is, e.g., FGFR3. In further aspects of this embodiment, an FGFR3 expressing cell can be, e.g., B9, TC, L6 and CFK2. As non-limiting examples, cells useful for determining Clostridial toxin activity according to a method disclosed in the present specification can include a B9 cell which stably express a nucleic acid molecule encoding a Clostridial toxin substrate, such as, e.g., a BoNT/A substrate; a B9 cell which stably contains a Clostridial toxin substrate, such as, e.g., a BoNT/A substrate; a TC cell which stably express a nucleic acid molecule encoding a Clostridial toxin substrate, such as, e.g., a BoNT/A substrate; a TC cell which stably contains a Clostridial toxin substrate, such as, e.g., a BoNT/A substrate; a L6 cell which stably express a nucleic acid molecule encoding a Clostridial toxin substrate, such as, e.g., a BoNT/A substrate; a L6 cell which stably contains a Clostridial toxin substrate, such as, e.g., a BoNT/A substrate; a CFK2 cell which stably express a nucleic acid molecule encoding a Clostridial toxin substrate, such as, e.g., a BoNT/A substrate; and a CFK2 cell which stably contains a Clostridial toxin substrate, such as, e.g., a BoNT/A substrate.

The cell compositions disclosed in the present specification include, in part, a Clostridial toxin substrate. In is envisioned that any and all Clostridial toxin substrate disclosed in the present specification can be used. Thus, aspects of this embodiment include nucleic acid molecules, such as, e.g., DNA and RNA, that encode a Clostridial toxin substrate disclosed in the present specification and peptide molecule or peptidomimetic comprising a Clostridial toxin substrate disclosed in the present specification. Other aspects of this embodiment include, in part, a Clostridial toxin recognition sequence including, without limitation, a BoNT/A toxin recognition sequence, a BoNT/B toxin recognition sequence, a BoNT/C1 toxin recognition sequence, a BoNT/D toxin recognition sequence, a BoNT/E toxin recognition sequence, a BoNT/F toxin recognition sequence, a BoNT/G toxin recognition sequence and a TeNT toxin recognition sequence. Other aspects of this embodiment include, in part, a membrane targeting domain including, without limitation, naturally occurring membrane targeting domains present in SNAP-25, naturally occurring SNAP-25 MTD variants, and non-naturally occurring SNAP-25 MTD variants, and SNAP-25 MTD peptidomimetics; and naturally occurring membrane targeting domains present in syntaxin, naturally occurring syntaxin MTD variants, and non-naturally occurring syntaxin MTD variants and syntaxin MTD peptidomimetics. Other aspects of this embodiment include, in part, a first member of a FRET pair including, without limitation, wild-type fluorescent proteins, naturally occurring variants, genetically engineered variants, and active peptide fragments derived from *Aequorea* fluorescent proteins, *Anemonia* fluorescent proteins, *Anthozoa* fluorescent proteins, *Discosoma* fluorescent proteins, *Entacmeae* fluorescent proteins, *Heteractis* fluorescent proteins, *Montastrea* fluorescent proteins, *Renilla* fluorescent proteins, *Zoanthus* fluorescent proteins. Non-limiting examples of fluorescent proteins include, e.g., EBFP, ECFP, AmCyan, AcGFP, ZsGreen, Vitalitye hrGFP, EGFP, Monster Greene hMGFP, EYFP, ZsYellow, DsRed-Express, DsRed2, DsRed, AsRed2 and HcRed1. Other aspects of this embodiment include, in part, a second member of a FRET pair including, without limitation, a long-chain carbocyanine dye, an aminostyryl dye, an amphiphilic styryl dye, a lipophilic cation, a membrane probe with environment-sensitive spectral shifts or FM dye. Non-limiting examples of lipophilic dyes include long-chain dialkylcarbocyanine dyes such as, e.g., DiI Vibrant, $DiIC_{18}(3)$, $DiIC_{18}(3)$-DS, SP-$DiIC_{18}(3)$, 5-5'-Ph2-$DiIC_{18}(3)$ and DiD.

octadecyl rhodamine B, 5-Dodecanoylaminofluorescein, 5-hexadecanoyl-aminofluorescein, 5-octadecanoyl-aminofluorescein, 4-heptadecyl-7-hydroxycoumarin, DPH, TMA-DPH, TMAP-DPH, DPH propionic acid, BODIPY 493/503, BODIPY 505/515, BODIPY 665/676, BODIPY FL C5-ceramide, CellTrace BODIPY TR methyl ester, a phenoxazine dye nile red, a 1,3-Bis-(1-pyrene)propane, bimane azide, prodan, laurdan, acrylodan, badan, 1,8-ANS, 2,6-ANS, 2,6-TNS, bis-ANS, DCVJ, MBDS The cell compositions disclosed in the present specification include, in part, a cell that transiently contains a Clostridial toxin substrate. As used herein, the term "transiently containing" means a Clostridial toxin substrate that is temporarily introduced into a cell in order to perform the assays disclosed in the present specification. By definition, in order to perform the assays disclosed in the present specification at least 50% of the cells comprising a cell population must contain a Clostridial toxin substrate. As used herein, the term "cell population" means the total number of cells used in a method that transiently introduces a Clostridial toxin substrate for a given assay. As a non-limiting example, given a cell population comprising $1.5\times10^5$ cells, at least $7.5\times10^4$ cells must contain a non-naturally occurring Clostridial toxin substrate after transduction using, e.g., an adenoviral method or a lentiviral method. As another non-limiting example, given a cell population comprising $1.5\times10^5$ cells, at least $7.5\times10^4$ cells must contain a Clostridal toxin substrate after transfection using, e.g., a protein transfection method. Thus, aspects of a cell transiently containing a Clostridial toxin substrate disclosed in the specification may include a cell that contains a substrate for, e.g., at most about one day, at most about two days, at most about three days, at most about four days, at most about five days, and at most about six days, at most about seven days, at most about eight days, at most about nine days and at most about ten days and wherein the cell population containing a Clostridial toxin substrate comprises, e.g., at least 50% of the cells within the cell population, at least 60% of the cells within the cell population, at least 70% of the cells within the cell population, at least 80% of the cells within the cell population, and at least 90% of the cells within the cell population.

Thus, in an embodiment, a cell transiently contains a nucleic acid molecule that encodes a membrane-associated Clostridial toxin substrate. In aspects of this embodiment, the membrane-associated Clostridial toxin substrate encoded by the nucleic acid molecule can be, e.g., a BoNT/A substrate, a BoNT/B substrate, a BoNT/C1 substrate, a BoNT/D substrate, a BoNT/E substrate, a BoNT/F substrate, a BoNT/G substrate or a TeNT substrate. As non-limiting examples, cells useful for determining Clostridial toxin activity according to a method disclosed in the present specification can include SH-SY5Y cells such as, e.g., differentiated SH-SY5Y cells and SH-SY5Y cells which transiently express a nucleic acid molecule encoding a Clostridial toxin substrate, such as, e.g., a BoNT/A substrate or a BoNT/E substrate; NG108-15 cells such as, e.g., differentiated NG108-15 cells and NG108-15 cells which transiently express a nucleic acid molecule encoding a Clostridial toxin substrate, such as, e.g., a BoNT/A substrate or a BoNT/E substrate; Neuro-2A cells such as, e.g., differentiated Neuro-2A cells and Neuro-2A cells which transiently express a nucleic acid molecule encoding a Clostridial toxin substrate, such as, e.g., a BoNT/A substrate; N1E-115 cells such as, e.g., differentiated N1E-115 cells and N1E-115 cells which transiently express a nucleic acid molecule encoding a Clostridial toxin substrate, such as, e.g., a BoNT/E substrate; and SK-N-DZ cells such as, e.g., differentiated SK-N-DZ cells and SK-N-DZ cells which transiently express a nucleic acid molecule encoding a Clostridial toxin substrate, such as, e.g., a BoNT/E substrate.

In another embodiment, a cell transiently contains an membrane-associated Clostridial toxin substrate. In aspects of this embodiment, the Clostridial toxin substrate capable of being localized to the plasma membrane can be, e.g., a BoNT/A substrate, a BoNT/B substrate, a BoNT/C1 substrate, a BoNT/D substrate, a BoNT/E substrate, a BoNT/F substrate, a BoNT/G substrate or a TeNT substrate. As non-limiting examples, cells useful for determining Clostridial toxin activity according to a method disclosed in the present specification can include SH-SY5Y cells such as, e.g., differentiated SH-SY5Y cells and SH-SY5Y cells which transiently contain a Clostridial toxin substrate, such as, e.g., a BoNT/A substrate or a BoNT/E substrate; NG108-15 cells such as, e.g., differentiated NG108-15 cells and NG108-15 cells which transiently contain a Clostridial toxin substrate, such as, e.g., a BoNT/A substrate or a BoNT/E substrate; Neuro-2A cells such as, e.g., differentiated Neuro-2A cells and Neuro-2A cells which transiently contain a Clostridial toxin substrate, such as, e.g., a BoNT/A substrate; N1E-115 cells such as, e.g., differentiated N1E-115 cells and N1E-115 cells which transiently contain a Clostridial toxin substrate, such as, e.g., a BoNT/E substrate; and SK-N-DZ cells such as, e.g., differentiated SK-N-DZ cells and SK-N-DZ cells which transiently contain a Clostridial toxin substrate, such as, e.g., a BoNT/E substrate.

The cell compositions disclosed in the present specification include, in part, a cell that stably contains a Clostridial toxin substrate. As used herein, the term "stably containing" means a Clostridial toxin substrate that is introduced into a cell and maintained for long periods of time in order to perform the fluorescence assays of the present invention. Stably-maintained nucleic acid molecules encompass stably-maintained nucleic acid molecules that are extra-chromosomal and replicate autonomously and stably-maintained nucleic acid molecules that are integrated into the chromosomal material of the cell and replicate non-autonomously. Thus aspects of a cell stably containing a Clostridial toxin substrate disclosed in the specification may include a cell that contains a substrate for, e.g., at least ten days, at least 20 two days, at least 30 days, at least forty days, at least 50 days, and at least 60 days, at least 70 days, at least 80 days, at least 90 days and at least 100 days. Other aspects of a cell stably containing a Clostridial toxin substrate disclosed in the specification may include a cell that contains a substrate for, e.g., at least 100 days, at least 200 days, at least 300 days, at least 400 days, and at least 500 days. Still other aspects of a cell stably containing a Clostridial toxin substrate disclosed in the specification may include a cell that permanently contains a Clostridial toxin substrate.

Thus, in an embodiment, a cell stably contains a nucleic acid molecule that encodes a membrane-associated Clostridial toxin substrate. In aspects of this embodiment, the membrane-associated Clostridial toxin substrate encoded by the nucleic acid molecule can be, e.g., a BoNT/A substrate, a BoNT/B substrate, a BoNT/C1 substrate, a BoNT/D substrate, a BoNT/E substrate, a BoNT/F substrate, a BoNT/G substrate or a TeNT substrate. As non-limiting examples, cells useful for determining Clostridial toxin activity according to a method disclosed in the present specification can include SH-SY5Y cells such as, e.g., differentiated SH-SY5Y cells and SH-SY5Y cells which stably express a nucleic acid molecule encoding a Clostridial toxin substrate, such as, e.g., a BoNT/A substrate or a BoNT/E substrate; NG108-15 cells such as, e.g., differentiated NG108-15 cells and NG108-15 cells which stably express a nucleic acid molecule encoding a Clostridial toxin substrate, such as, e.g., a BoNT/A substrate or a BoNT/E substrate; Neuro-2A cells such as, e.g., differentiated Neuro-2A cells and Neuro-2A cells which stably express a nucleic acid molecule encoding a Clostridial toxin substrate, such as, e.g., a BoNT/A substrate; KMS-11 cells such as, e.g., differentiated KMS-11 cells and KMS-11 cells which stably express a nucleic acid molecule encoding a Clostridial toxin substrate, such as, e.g., a BoNT/A substrate; N1E-115 cells such as, e.g., differentiated N1E-115 cells and N1E-115 cells which stably express a nucleic acid molecule encoding a Clostridial toxin substrate, such as, e.g., a BoNT/E substrate; and SK-N-DZ cells such as, e.g., differentiated SK-N-DZ cells and SK-N-DZ cells which stably express a nucleic acid molecule encoding a Clostridial toxin substrate, such as, e.g., a BoNT/E substrate.

In another embodiment, a cell stably contains a membrane-associated Clostridial toxin substrate. In aspects of this embodiment, the membrane-associated Clostridial toxin substrate can be, e.g., a BoNT/A substrate, a BoNT/B substrate, a BoNT/C1 substrate, a BoNT/D substrate, a BoNT/E substrate, a BoNT/F substrate, a BoNT/G substrate or a TeNT substrate. As non-limiting examples, cells useful for determining Clostridial toxin activity according to a method disclosed in the present specification can include SH-SY5Y cells such as, e.g., differentiated SH-SY5Y cells and SH-SY5Y cells which stably contain a Clostridial toxin substrate, such as, e.g., a BoNT/A substrate or a BoNT/E substrate; NG108-15 cells such as, e.g., differentiated NG108-15 cells and NG108-15 cells which stably contain a Clostridial toxin substrate, such as, e.g., a BoNT/A substrate or a BoNT/E substrate; Neuro-2A cells such as, e.g., differentiated Neuro-2A cells and Neuro-2A cells which stably contain a Clostridial toxin substrate, such as, e.g., a BoNT/A substrate; KMS-11 cells such as, e.g., differentiated KMS-11 cells and KMS-11 cells which stably contain a Clostridial toxin substrate, such as, e.g., a BoNT/A substrate; N1E-115 cells such as, e.g., differentiated N1E-115 cells and N1E-115 cells which stably contain a Clostridial toxin substrate, such as, e.g., a BoNT/E substrate; and SK-N-DZ cells such as, e.g., differentiated SK-N-DZ cells and SK-N-DZ cells which stably contain a Clostridial toxin substrate, such as, e.g., a BoNT/E substrate.

As mentioned above, a nucleic acid molecule can be used to express a Clostridial toxin substrate disclosed in the present specification. It is envisioned that any and all methods for introducing a nucleic acid molecule into a cell can be used. Methods useful for introducing a nucleic acid molecule into a cell including, without limitation, calcium phosphate-mediated, DEAE dextran-mediated, lipid-mediated, polybrene-mediated, polylysine-mediated, viral-mediated, microinjection, protoplast fusion, biolistic, electroporation and conjugation to an antibody, gramacidin S, artificial viral envelope or other intracellular carrier such as TAT., see, e.g., Introducing Cloned Genes into Cultured Mammalian Cells, pp. 16.1-16.62 (Sambrook & Russell, eds., Molecular Cloning A Laboratory Manual, Vol. 3, 3rd ed. 2001); Alessia Colosimo et al., Transfer and expression of foreign genes in mammalian cells, 29(2) Biotechniques 314-318, 320-322, 324 (2000); Philip Washbourne & A. Kimberley McAllister, Techniques for gene transfer into neurons, 12(5) Curr. Opin. Neurobiol. 566-573 (2002); and Current Protocols in Molecular Biology, John Wiley and Sons, pp 9.16.4-9.16.11 (2000). One skilled in the art understands that selection of a specific method to introduce a nucleic acid molecule into a cell will depend, in part, on whether the cell will transiently contain the Clostridial toxin substrate or whether the cell will stably contain the Clostridial toxin substrate.

In an aspect of this embodiment, a chemical-mediated method, termed transfection, is used to introduce a nucleic acid molecule encoding a Clostridial toxin substrate into a cell. In chemical-mediated methods of transfection the chemical reagent forms a complex with the nucleic acid that facilitates its uptake into the cells. Such chemical reagents include, without limitation, calcium phosphate-mediated, see, e.g., Martin Jordan & Florian Worm, Transfection of adherent and suspended cells by calcium phosphate, 33(2) Methods 136-143 (2004); diethyl-laminoethyl (DEAE) dextran-mediated, lipid-mediated, cationic polymer-mediated like polyethyleneimine (PEI)-mediated and polylysine-mediated and polybrene-mediated, see, e.g., Chun Zhang et al., Polyethylenimine strategies for plasmid delivery to brain-derived cells, 33(2) Methods 144-150 (2004). Such chemical-mediated delivery systems can be prepared by standard methods and are commercially available, see, e.g., CellPhect Transfection Kit (Amersham Biosciences, Piscataway, N.J.); Mammalian Transfection Kit, Calcium phosphate and DEAE Dextran, (Stratagene, Inc., La Jolla, Calif.); Lipofectamine™ Transfection Reagent (Invitrogen, Inc., Carlsbad, Calif.); ExGen 500 Transfection kit (Fermentas, Inc., Hanover, Md.), and SuperFect and Effectene Transfection Kits (Qiagen, Inc., Valencia, Calif.).

In another aspect of this embodiment, a physical-mediated method is used to introduce a nucleic acid molecule encoding a Clostridial toxin substrate into a cell. Physical reagents include, without limitation, electroporation, biolistic and microinjection. Biolistics and microinjection techniques perforate the cell wall in order to introduce the nucleic acid molecule into the cell, see, e.g., Jeike E. Biewenga et al., Plasmid-mediated gene transfer in neurons using the biolistics technique, 71 (1) J. Neurosci. Methods. 67-75 (1997); and John O'Brien & Sarah C. R. Lummis, Biolistic and diolistic transfection: using the gene gun to deliver DNA and lipophilic dyes into mammalian cells, 33(2) Methods 121-125 (2004). Electroporation, also termed electropermeabilization, uses brief, high-voltage, electrical pulses to create transient pores in the membrane through which the nucleic acid molecules enter and be used effectively for stable and transient transfections of all cell types, see, e.g., M. Golzio et al., In vitro and in vivo electric field-mediated permeabilization, gene transfer, and expression, 33(2) Methods 126-135 (2004); and Oliver Gresch et al., New non-viral method for gene transfer into primary cells, 33(2) Methods 151-163 (2004).

In another aspect of this embodiment, a viral-mediated method, termed transduction, is used to introduce a nucleic acid molecule encoding a Clostridial toxin substrate into a cell. In viral-mediated methods of transient transduction, the process by which viral particles infect and replicate in a host cell has been manipulated in order to use this mechanism to introduce a nucleic acid molecule into the cell. Viral-mediated methods have been developed from a wide variety of viruses including, without limitation, retroviruses, adenoviruses, adeno-associated viruses, herpes simplex viruses, picornaviruses, alphaviruses and baculoviruses, see, e.g., Armin Blesch, Lentiviral and MLV based retroviral vectors for ex vivo and in vivo gene transfer, 33(2) Methods 164-172 (2004); and Maurizio Federico, From lentiviruses to lentivirus vectors, 229 Methods Mol. Biol. 3-15 (2003); E. M. Poeschla, Non-primate lentiviral vectors, 5(5) Curr. Opin. Mol. Ther. 529-540 (2003); Karim Benihoud et al, Adenovirus vectors for gene delivery, 10(5) Curr. Opin. Biotechnol. 440-447 (1999); H. Bueler, Adeno-associated viral vectors for gene transfer and gene therapy, 380(6) Biol. Chem. 613-622 (1999); Chooi M. Lai et al., Adenovirus and adeno-associated virus vectors, 21(12) DNA Cell Biol. 895-913 (2002); Edward A. Burton et al., Gene delivery using herpes simplex virus vectors, 21(12) DNA Cell Biol. 915-936 (2002); Paola Grandi et al., Targeting HSV amplicon vectors, 33(2) Methods 179-186 (2004); Ilya Frolov et al., Alphavirus-based expression vectors: strategies and applications, 93(21) Proc. Natl. Acad. Sci. U.S.A. 11371-11377 (1996); Markus U. Ehrengruber, Alphaviral gene transfer in neurobiology, 59(1) Brain Res. Bull. 13-22 (2002); Thomas A. Kost & J. Patrick Condreay, Recombinant baculoviruses as mammalian cell gene-delivery vectors, 20(4) Trends Biotechnol. 173-180 (2002); and A. Huser & C. Hofmann, Baculovirus vectors: novel mammalian cell gene-delivery vehicles and their applications, 3(1) Am. J. Pharmacogenomics 53-63 (2003).

Adenoviruses, which are non-enveloped, double-stranded DNA viruses, are often selected for mammalian cell transduction because adenoviruses handle relatively large nucleic acid molecules of about 36 kd, are produced at high titer, and can efficiently infect a wide variety of both dividing and non-dividing cells, see, e.g., Wim T. J. M. C. Hermens et al., Transient gene transfer to neurons and glia: analysis of adenoviral vector performance in the CNS and PNS, 71 (1) J. Neurosci. Methods 85-98 (1997); and Hiroyuki Mizuguchi et al., Approaches for generating recombinant adenovirus vectors, 52(3) Adv. Drug Deliv. Rev. 165-176 (2001). Transduction using adenoviral-based system do not support prolonged protein expression because the nucleic acid molecule is carried from an episome in the cell nucleus, rather than being integrated into the host cell chromosome. Adenovirual vector systems and specific protocols for how to use such vectors are disclosed in, e.g., ViraPower™ Adenoviral Expression System (Invitrogen, Inc., Carlsbad, Calif.) and ViraPower™ Adenoviral Expression System Instruction Manual 25-0543 version A, Invitrogen, Inc., (Jul. 15, 2002); and AdEaSy™ Adenoviral Vector System (Stratagene, Inc., La Jolla, Calif.) and AdEaSy™ Adenoviral Vector System Instruction Manual 064004f, Stratagene, Inc.

Nucleic acid molecule delivery can also use single-stranded RNA retroviruses viruses, such as, e.g., oncoretroviruses and lentiviruses. Retroviral-mediated transduction often produce transduction efficiencies close to 100%, can easily control the proviral copy number by varying the multiplicity of infection (MOI), and can be used to either transiently or stably transduce cells, see, e.g., Tiziana Tonini et al., Transient production of retroviral- and lentiviral-based vectors for the transduction of Mammalian cells, 285 Methods Mol. Biol. 141-148 (2004); Armin Blesch, Lentiviral and MLV based retroviral vectors for ex vivo and in vivo gene transfer, 33(2) Methods 164-172 (2004); Felix Recillas-Targa, Gene transfer and expression in mammalian cell lines and transgenic animals, 267 Methods Mol. Biol. 417-433 (2004); and Roland Wolkowicz et al., Lentiviral vectors for the delivery of DNA into mammalian cells, 246 Methods Mol. Biol. 391-411 (2004). Retroviral particles consist of an RNA genome packaged in a protein capsid, surrounded by a lipid envelope. The retrovirus infects a host cell by injecting its RNA into the cytoplasm along with the reverse transcriptase enzyme. The RNA template is then reverse transcribed into a linear, double stranded cDNA that replicates itself by integrating into the host cell genome. Viral particles are spread both vertically (from parent cell to daughter cells via the provirus) as well as horizontally (from cell to cell via virions). This replication strategy enables long-term persist expression since the nucleic acid molecules of interest are stably integrated into a chromosome of the host cell, thereby enabling long-term expression of the protein. For instance, animal studies have shown that lentiviral vectors injected into a variety of tissues produced sustained protein expression for more than 1 year, see, e.g., Luigi Naldini et al., In vivo gene delivery and stable transduction of non-dividing cells by a lentiviral vector, 272(5259) Science 263-267 (1996). The Oncoretroviruses-derived vector systems, such as, e.g., Moloney murine leukemia virus (MoMLV), are widely used and infect many different non-dividing cells. Lentiviruses can also infect many different cell types, including dividing and non-dividing cells and possess complex envelope proteins, which allows for highly specific cellular targeting.

Retroviral vector systems and specific protocols for how to use such vectors are disclosed in, e.g., U.S. patent Nos. Manfred Gossen & Hermann Bujard, Tight control of gene expression in eukaryotic cells by tetracycline-responsive promoters, U.S. Pat. No. 5,464,758 (Nov. 7, 1995) and Hermann Bujard & Manfred Gossen, Methods for regulating gene expression, U.S. Pat. No. 5,814,618 (Sep. 29, 1998) David S. Hogness, Polynucleotides encoding insect steroid hormone receptor polypeptides and cells transformed with same, U.S. Pat. No. 5,514,578 (May 7, 1996) and David S. Hogness, Polynucleotide encoding insect ecdysone receptor, U.S. Pat. No. 6,245,531 (Jun. 12, 2001); Elisabetta Vegeto et al., Progesterone receptor having C. terminal hormone binding domain truncations, U.S. Pat. No. 5,364,791 (Nov. 15, 1994), Elisabetta Vegeto et al., Mutated steroid hormone receptors, methods for their use and molecular switch for gene therapy, U.S. Pat. No. 5,874,534 (Feb. 23, 1999) and Elisabetta Vegeto et al., Mutated steroid hormone receptors, methods for their use and molecular switch for gene therapy, U.S. Pat. No. 5,935,934 (Aug. 10, 1999). Furthermore, such viral delivery systems can be prepared by standard methods and are commercially available, see, e.g., BD™ Tet-Off and Tet-On Gene Expression Systems (BD Biosciences-Clonetech, Palo Alto, Calif.) and BD™ Tet-Off and Tet-On Gene Expression Systems User Manual, PT3001-1, BD Biosciences Clonetech, (Mar. 14, 2003), GeneSwitch™ System (Invitrogen, Inc., Carlsbad, Calif.) and GeneSwitch™ System A Mifepristone-Regulated Expression System for Mammalian Cells version D, 25-0313, Invitrogen, Inc., (Nov. 4, 2002); ViraPower™ Lentiviral Expression System (Invitrogen, Inc., Carlsbad, Calif.) and ViraPower™ Lentiviral Expression System Instruction Manual 25-0501 version E, Invitrogen, Inc., (Dec. 8, 2003); and Complete Control® Retroviral Inducible Mammalian Expression System (Stratagene, La Jolla, Calif.) and Complete Control® Retroviral Inducible Mammalian Expression System Instruction Manual, 064005e.

As mentioned above, a Clostridial toxin substrate disclosed in the present specification can be introduced into a cell. It is envisioned that any and all methods using a delivery agent to introduce a Clostridial toxin substrate into a cell population can be used. As used herein, the term "delivery agent" means any molecule that enables or enhances internalization of a covalently-linked, non-covalently-linked or in any other manner associated with a Clostridial toxin substrate into a cell. Thus, the term "delivery agent" encompasses, without limitation, proteins, peptides, peptidomimetics, small molecules, nucleic acid molecules, liposomes, lipids, viruses, retroviruses and cells that, without limitation, transport a covalently or non-covalently linked substrate to the cell membrane, cell cytoplasm or nucleus. It further is understood that the term "delivery agent" encompasses molecules that are internalized by any mechanism, including delivery agents which function via receptor mediated endocytosis and those which are independent of receptor mediated endocytosis.

It is also envisioned that any and all methods useful for introducing a Clostridial toxin substrate with a delivery agent into a cell population can be useful with the proviso that this method introduce a Clostridial toxin substrate disclosed in the present specification in at least 50% of the cells within a given cell population. Thus, aspects of this embodiment can include a cell population in which, e.g., at least 90% of the given cell population contains a Clostridial toxin substrate, at least 80% of the given cell population contains a Clostridial toxin substrate, at least 70% of the given cell population contains a Clostridial toxin substrate, at least 60% of the given cell population contains a Clostridial toxin substrate, at least 50% of the given cell population contains a Clostridial toxin substrate.

It is also envisioned that any and all methods useful for introducing a Clostridial toxin substrate disclosed in the present specification linked to a delivery agent can be useful, including methods that covalently link the delivery agent to the substrate and methods that non-covalently link the delivery agent to the substrate. Covalent linking methods that attach a delivery agent to a Clostridial toxin substrate can include chemical conjugation and genetically produced fusion proteins. In one non-limiting method, a polynucleotide, such as, e.g., a plasmid or oligonucleotide, is attached to a Clostridial toxin substrate by conjugation chemistry and introduced into the cell using a method useful for introducing a nucleic acid molecule into a cell population as described in the present specification. In another non-limiting method, a lipid, such as, e.g., a cationic liposome, is attached to a Clostridial toxin substrate by conjugation chemistry and introduced into the cell using a method useful for introducing a nucleic acid molecule into a cell population as described in the present specification. In yet another non-limiting method, a peptide, is attached to a Clostridial toxin substrate by conjugation chemistry and introduced into the cell using a protein delivery method described below. In yet another non-limiting method, a peptide is attached to a Clostridial toxin substrate by producing a nucleic acid molecule that encodes the peptide delivery agent and substrate as an operationally linked fusion protein and this fusion protein is introduced into the cell using a protein delivery method described below.

In an aspect of the present invention, a Clostridial toxin substrate disclosed in the present specification can be introduced into a cell using a peptide delivery agent to produce a cell transiently containing a Clostridial toxin substrate capable of being localized to the plasma. It is envisioned that a variety of peptide delivery agents can be covalently linked to a Clostridial toxin substrate, including, without limitation, the active fragment of protein transduction peptides; the active fragment of cell permeant peptides; phosphopeptides; the active fragment of membrane-translocating peptides; the active fragment of secreted proteins; the active fragment of nuclear localization signal peptides; predominantly hydrophobic peptides; predominantly α-helical peptides, such as, e.g., amphipathic-helical peptide; predominantly basic peptides, such as, e.g., basic amphipathic peptides; peptides containing D-amino acids; short peptides, such as, e.g., KDEL; denatured peptides linked to a denatured or folded Clostridial toxin substrate as described in, e.g., Steven F. Dowdy, Methods for Transducing Fusion Molecules, PCT Publication No. WO99/55899 (Nov. 11, 1999); and Steven F. Dowdy, Novel Transduction Molecules and Methods for Using the Same, PCT Publication No. WO00/62067 (Oct. 19, 2000); and, and any other denatured or folded, modified or unmodified, naturally occurring or synthetic peptide, peptidomimetics or analogs thereof.

It is envisioned that any and all peptide lengths of a delivery agent can be useful in aspects of the present invention. In aspects of this embodiment, therefore, a delivery agent useful for introducing a Clostridial toxin substrate disclosed in the present specification in a cell can be a peptide or peptidomimetic having a length of less than 10 residues, a length of less than 20 residues, a length of less than 30 residues, a length of less than 40 residues, or a length of less than 50 residues.

As non-limiting examples, delivery agents suitable for introducing a Clostridial toxin substrate disclosed in the present specification into a cell include polylysine; ciliary neurotrophic factor (CNTF) or an active fragment thereof; caveolin or an active fragment thereof; interleukin-1 (IL-1) or an active fragment thereof; thioredoxin or an active fragment thereof; homeodomain-derived peptides or an active fragment thereof, such as, e.g., Antennapedia (Antp) or an active fragment thereof, like penetratin-1 (SEQ ID NO: 160), Engrailed 1 (En1) or an active fragment thereof, Engrailed 2 (En2) or an active fragment thereof, Hoxb-4 or an active fragment thereof, Hoxa-5 or an active fragment thereof, Hoxc-8 or an active fragment thereof, and Knotted-1 (KN1) or an active fragment thereof; fibroblast growth factor-1 (FGF-1) or an active fragment thereof; Kaposi fibroblast growth factor (kFGF) or an active fragment thereof, such as, e.g., AAVALLPAVLLALLAP (SEQ ID NO: 169); human 3 integrin or an active fragment thereof such as, e.g., a hydrophobic signal sequence; a nuclear localization sequence (NLS) or an active fragment thereof, such as, e.g., TPPKKKRKVEDP (SEQ ID NO: 170); FGF-2 or an active fragment thereof; transportan or an active fragment thereof, such as, e.g., GWTLNSAGYLLGKINLKALAALAKKIL (SEQ ID NO: 171); lactoferrin or an active fragment thereof; VP22 or an active fragment thereof; HIV type I transactivator (HIV TAT) or an active fragment thereof, such as, e.g., (YGRKKRRQRRR; SEQ ID NO: 168); or a heat shock protein such as HSP70 or an active fragment thereof. These and additional delivery agents are well known in the art as described in, e.g., Steven R. Schwarze and Steven F. Dowdy, In vivo protein transduction: intracellular delivery of biologically active proteins, compounds and DNA, 21(2) Trends Pharmacol. Sci. 45-48 (2000); Dara J. Dunican and Patrick Doherty, Designing cell-permeant phosphopeptides to modulate intracellular signaling pathways, 60(1) Biopolymers 45-60 (2001); K. G. Ford et al., Protein transduction: an alternative to genetic intervention? 8(1) Gene Ther. 1-4 (2001); Alain Prochiantz, Messenger proteins: homeoproteins, TAT and others, 12(4) Curr. Opin. Cell Biol. 400-406 (2000); J. J. Schwartz and S. Zhang, Peptide-mediated cellular delivery, 2(2) Curr. Opin. Mol. Ther. 162-167 (2000); and Steven F. Dowdy, Protein Transduction System and Methods of Use Thereof, PCT Publication No. WO00/34308 (Jun. 15, 2000).

In an embodiment, a delivery agent can be a homeoprotein or an active fragment thereof, such as, e.g., a homeodomain or an active fragment thereof. Homeoproteins are helix-turn-helix proteins that contain a DNA-binding domain of about 60 residues, denoted the homeodomain. A variety of homeoproteins, homeodomains and active fragments thereof can be delivery agents useful in the invention including, without limitation, Antennapedia, Engrailed1 (En1), Engrailed2 (En2), Hoxa-5, Hoxc-8, Hoxb-4 and Knotted-1 (KN1). As an example, En1 and En1 have been expressed in COS-7 cells, where they are first secreted and then internalized by other cells, see, e.g., Prochiantz, supra, (2000). Delivery agents using peptides derived from homeodomains and methods of using such agents are described in, e.g., Gerard Chassaing & Alain Prochiantz, Peptides which can be Used as Vectors for the Intracellular Addressing of Active Molecules, U.S. Pat. No. 6,080,724 (Jun. 27, 2000).

TABLE 12

Penetratin-Derived Peptides Useful As Delivery Agents

| Peptide | Sequence | SEQ ID NO: |
|---|---|---|
| 43-58 | RQIKIWFQNRRMKWKK | 160 |
| 58-43 | KKWKMRRNQFWIKIQR | 161 |
| 43-58 | RQIKIWFQNRRMKWKK | 162 |
| Pro50 | RQIKIWFPNRRMKWKK | 163 |
| 3Pro | RQPKIWFPNRRMPWKK | 164 |
| Met-Arg | RQIKIWFQNMRRKWKK | 165 |
| 7Arg | RQIRIWFQNRRMRWRR | 166 |
| W/R | RRWRRWWRRWWRRWRR | 167 |

In an aspect of this embodiment, a substrate composition of the invention includes a delivery agent which is the homeodomain protein, Antennapedia, or an active fragment thereof. Antennapedia is a member of a family of developmentally important *Drosophila* homeoproteins which translocate across neuronal membranes. The third helix of the Antennapedia homeodomain, the 16 residue peptide "penetratin-1" (SEQ ID NO: 160), is internalized into live cells. The internalization occurs both at 37° C. and 4° C., indicating that delivery is neither receptor-mediated nor energy-dependent. Additional delivery agents include peptides and peptidomimetics related in sequence to Penetratin-1 such as, without limitation, one of the peptides shown below in Table 12 or another penetratin-derived peptide or peptidomimetic, including a retroinverse or all D-amino acid peptide or peptidomimetic, or a related but non-α-helical peptide or peptidomimetic, see, e.g., Chassaing & Prochiantz, supra, (2000). In one embodiment, such a penetratin-derived peptide retains the tryptophan, phenylalanine and glutamine residues of penetratin-1 (SEQ ID NO: 160).

In another embodiment, a substrate composition of the invention includes a delivery agent which is a HIV trans-activator (TAT) protein or an active fragment thereof. Such a delivery agent can include, for example, a sequence identical or similar to residues 47-57 or 47-59 of HIV TAT, see, e.g., Alan Frankel et al., Fusion Protein Comprising TAT-derived Transport Moiert, U.S. Pat. No. 5,674,980 (Oct. 7, 1995); Alan Frankel et al., TAT-derived Transport Polypeptide Conjugates, U.S. Pat. No. 5,747,641 (May 5, 1998); and Alan Frankel et al., TAT-derived Transport Polypeptides and Fusion Proteins, U.S. Pat. No. 5,804,604 (Sep. 8, 1998). As an example, fusion proteins including residues 47-57 of HIV TAT (YGRKKRRQRRR; SEQ ID NO: 168) cross the plasma membrane of, for example, human and murine cells in vitro and in vivo, see, e.g., Schwartz and Zhang, supra, (2000); a variety of proteins from 15 to 120 KDa have been shown to retain biological activity when fused to a HIV TAT delivery agent. An HIV TAT delivery agent can be positively charged and can function, for example, in an energy-, receptor-, transporter- and endocytosis-independent manner to deliver a covalently linked Clostridial toxin substrate to, for example, 90-100% of target cells. Delivery agents using peptides derived from TAT and methods of using such agents are described in, e.g., Frankel et al., supra, (1995); Frankel et al., supra, (1998); and Frankel et al., supra, (1998).

In another embodiment, a substrate composition of the invention also can include as a delivery agent a herpes simplex virus VP22 protein or active fragment thereof. In an aspect of this embodiment, a substrate composition of the invention includes an HSV type 1 (HSV-1) VP22 protein or active fragment thereof. HSV VP22, a nuclear transcription factor, can cross the plasma membrane through non-classical endocytosis and can enter cells independent of GAP junctions and physical contacts. As a fusion with a variety of different proteins, HSV VP22 results in uptake into cells of different types including terminally differentiated cells and can function to deliver a linked Clostridial toxin substrate to, for example, 90-100% of cultured cells. Delivery agents using peptides derived from TAT and methods of using such agents are described in, e.g., Peter F. J. O'Hare & Gillian D. Elliott, Transport Proteins and Their Uses, PCT Patent Publication No. WO97/05265 (Feb. 13, 1997); Peter F. J. O'Hare & Gillian D. Elliott, Fusion Proteins for Intracellular and Intercellular Transport and Their Uses, PCT Patent Publication No. WO98/32866 (Jul. 30, 1998); Peter F. J. O'Hare et al., Use of Transport Proteins, U.S. Pat. No. 6,734,167 (May 11, 2004).

In another embodiment, a delivery agent useful in the invention corresponds to or is derived from a hydrophobic signal sequence. Such a delivery agent can be, for example, the Kaposi fibroblast growth factor (kFGF) or an active fragment thereof such as AAVALLPAVLLALLAP (SEQ ID NO: 169); human P3 integrin or an active fragment thereof; or another hydrophobic delivery agent such as one of those described in, e.g., Dunican & Doherty, supra, (2001). Delivery agents using peptides derived from hydrophobic signal sequences and methods of using such agents are described in, e.g., Yao-Zhong Lin & Jack J. Hawiger, Method for importing biologically active molecules into cells, U.S. Pat. No. 5,807,746 (Sep. 15, 1998); Yao-Zhong Lin & Jack J. Hawiger, Method for importing biologically active molecules into cells, U.S. Pat. No. 6,043,339 (Mar. 28, 2000); Yao-Zhong Lin et al., Sequence and Method for Genetic Engineering of Proteins with Cell Membrane Translocating Activity, U.S. Pat. No. 6,248,558 (Jun. 19, 2001); Yao-Zhong Lin et al., Sequence and Method for Genetic Engineering of Proteins with Cell Membrane Translocating Activity, U.S. Pat. No. 6,432,680 (Aug. 13, 2002); Jack J. Hawiger et al., Method for importing biologically active molecules into cells, U.S. Pat. No. 6,495,518 (Dec. 17, 2002); and Yao-Zhong Lin et al., Sequence and Method for Genetic Engineering of Proteins with Cell Membrane Translocating Activity, U.S. Pat. No. 6,780,843 (Aug. 24, 2004).

In another embodiment, a delivery agent useful in the invention also can be a synthetic sequence that shares one or more characteristics of a naturally occurring delivery agent such as, e.g., a protein transduction domain (PTD). Such delivery agents include, but are not limited to, L- and D-arginine oligomers, for example, 9-mers of L- or D-arginine and related peptoids, see, e.g., Jonathan B. Rothbard & Paul A Wender, Method and Composition for Enhancing Transport Across Biological Membranes, U.S. Pat. No. 6,306,993 (Oct. 23, 2001); and Jonathan B. Rothbard & Paul A Wender, Method and Composition for Enhancing Transport Across Biological Membranes, U.S. Pat. No. 6,495,663 (Dec. 17, 2002). Such delivery agents further include basic peptides and peptidomimetics; basic α-helical peptides and peptidomimetics; and peptides and peptidomimetics with optimized arginine alignment or optimized α-helical character as compared to a naturally occurring protein transduction domain such as residues 47-57 of HIV TAT, see, e.g., Rothbard & Wender, supra, (2001); and Rothbard & Wender, supra, (2002). The skilled person understands that these and other naturally occurring and synthetic delivery agents can be useful in the substrate compositions of the invention.

In another embodiment, a protein conjugate consisting of antibody directed at a receptor on the plasma membrane and a Clostridial toxin substrate disclosed in the present specification can be introduced into a cell. Delivery agents using antibodies and methods of using such agents are described in, e.g., Pamela B. Davis et al., Fusion proteins for protein delivery, U.S. Pat. No. 6,287,817 (Sep. 11, 2001).

A delivery agent useful in the invention also can be an agent that enables or enhances cellular uptake of a non-covalently associated Clostridial toxin substrate. In one embodiment, such a delivery agent is peptide containing two independent domains: a hydrophobic domain and a hydrophilic domain. In another embodiment, such a delivery agent is an MPG peptide, which is a peptide derived from both the nuclear localization sequence (NLS) of SV40 large T antigen and the fusion peptide domain of HIV-1 gp41, see, e.g., Virginie Escriou et al., NLS bioconjugates for targeting therapeutic genes to the nucleus, 55(2) Adv. Drug Deliv. Rev. 295-306 (2003). In a further embodiment, such a delivery agent is an MPG peptide having the amino acid sequence GALFLGFLGAAGSTMGAWSQPKSKRKV (SEQ ID NO: 172). In yet a further embodiment, such a delivery agent is an amphipathic peptide such as Pep-1. These and related delivery agents that function in the absence of covalent linkage and methods of using such agents are described in, e.g., Gilles Divita et al, Peptide-mediated Transfection Agents and Methods of Use, U.S. Pat. No. 6,841,535 (Jan. 11, 2005); Philip L Felgner and Olivier Zelphati, Intracellular Protein Delivery Compositions and Methods of Use, U.S. Patent Publication No. 2003/0008813); and Michael Karas Intracellular Delivery of Small Molecules, Proteins and Nucleic Acids, U.S. Patent Publication 2004/0209797 (Oct. 21, 2004). Such peptide delivery agents can be prepared and used by standard methods and are commercially available, see, e.g. the Chariot™ Reagent (Active Motif, Carlsbad, Calif.); BioPORTER® Reagent (Gene Therapy Systems, Inc., San Diego, Calif.), BioTrek™ Protein Delivery Reagent (Stratagene, La Jolla, Calif.), and Pro-Ject™ Protein Transfection Reagent (Pierce Biotechnology Inc., Rockford, Ill.).

Another aspect of the present invention provides expression constructs that allow for expression of a nucleic acid molecule encoding a Clostridial toxin substrate disclosed in the present specification. These expression constructs comprise an open reading frame encoding a Clostridial toxin substrate disclosed in the present specification, operably-linked to control sequences from an expression vector useful for expressing the Clostridial toxin substrate in a cell. The term "operably linked" as used herein, refers to any of a variety of cloning methods that can ligate a nucleic acid molecule disclosed in the present specification into an expression vector such that a peptide encoded by the composition is expressed when introduced into a cell. Well-established molecular biology techniques that may be necessary to make an expression construct disclosed in the present specification including, but not limited to, procedures involving polymerase chain reaction (PCR) amplification restriction enzyme reactions, agarose gel electrophoresis, nucleic acid ligation, bacterial transformation, nucleic acid purification, nucleic acid sequencing are routine procedures well within the scope of one skilled in the art and from the teaching herein. Non-limiting examples of specific protocols necessary to make an expression construct are described in e.g., Molecular Cloning A Laboratory Manual, supra, (2001); and Current Protocols in Molecular Biology (Frederick M. Ausubel et al., eds. John Wiley & Sons, 2004), which are hereby incorporated by reference. These protocols are routine procedures well within the scope of one skilled in the art and from the teaching herein.

A wide variety of expression vectors can be employed for expressing an open reading frame encoding an Clostridial toxin substrate and include without limitation, viral expression vectors, prokaryotic expression vectors and eukaryotic expression vectors including yeast, insect and mammalian expression vectors and generally are equivalent to the expression vectors disclosed herein in Examples 4-6 and 8-14. Non-limiting examples of expression vectors, along with well-established reagents and conditions for making and using an expression construct from such expression vectors are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; EMD Biosciences-Novagen, Madison, Wis.; QIAGEN, Inc., Valencia, Calif.; and Stratagene, La Jolla, Calif. The selection, making and use of an appropriate expression vector are routine procedures well within the scope of one skilled in the art and from the teachings herein.

It is envisioned that any of a variety of expression systems may be useful for expressing construct compositions disclosed in the present specification. An expression system encompasses both cell-based systems and cell-free expression systems. Cell-based systems include, without limited, viral expression systems, prokaryotic expression systems, yeast expression systems, baculoviral expression systems, insect expression systems and mammalian expression systems. Cell-free systems include, without limitation, wheat germ extracts, rabbit reticulocyte extracts and *E. coli* extracts. Expression using an expression system can include any of a variety of characteristics including, without limitation, inducible expression, non-inducible expression, constitutive expression, viral-mediated expression, stably-integrated expression, and transient expression. Expression systems that include well-characterized vectors, reagents, conditions and cells are well-established and are readily available from commercial vendors that include, without limitation, Ambion, Inc. Austin, Tex.; BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; Roche Applied Science, Indianapolis, Ind.; and Stratagene, La Jolla, Calif. Non-limiting examples on the selection and use of appropriate heterologous expression systems are described in e.g., Protein Expression. A Practical Approach (S. J. Higgins and B. David Hames eds., Oxford University Press, 1999); Joseph M. Fernandez & James P. Hoeffler, Gene Expression Systems. Using Nature for the Art of Expression (Academic Press, 1999); and Meena Rai & Harish Padh, *Expression Systems for Production of Heterologous Proteins,* 80(9) Current Science 1121-1128, (2001), which are hereby incorporated by reference. These protocols are routine procedures well within the scope of one skilled in the art and from the teaching herein.

An expression construct comprising a nucleic acid molecule encoding a Clostridial toxin substrate disclosed in the present specification can be operationally-linked to a variety of regulatory elements that can positively or negatively modulate, either directly or indirectly, the expression of a nucleic acid molecule, such as, e.g., constitutive, tissue-specific, inducible or synthetic promoters and enhancers. Non-limiting examples of constitutive regulatory elements include, e.g., the cytomegalovirus (CMV), herpes simplex virus thymidine kinase (HSV TK), simian virus 40 (SV40) early, 5' long terminal repeat (LTR), elongation factor-1a (EF-1a) and polyubiquitin (UbC) regulatory elements. Non-limiting examples of inducible regulatory elements useful in aspects of the present invention include, e.g., chemical-inducible regulatory elements such as, without limitation, alcohol-regulated, tetracycline-regulated, steroid-regulated, metal-regulated and pathogenesis-related; and physical-inducible regulatory elements such as, without limitation, temperature-regulated and light-regulated. Such inducible regulatory elements can be prepared and used by standard methods and are commercially available, including, without limitation, tetracycline-inducible and tetracycline-repressible elements such as, e.g., Tet-On™ and Tet-Off™ (BD Biosciences-Clontech, Palo Alto, Calif.) and the T-REx™ (Tetracycline-Regulated Expression) and Flp-In™ T-REx™ systems (Invitrogen, Inc., Carlsbad, Calif.); ecdysone-inducible regulatory elements such as, e.g., the Complete Control® Inducible Mammalian Expression System (Stratagene, Inc., La Jolla, Calif.); isopropyl β-D-galactopyranoside (IPTG)-inducible regulatory elements such as, e.g., the LacSwitch® II Inducible Mammalian Expression System (Stratagene, Inc., La Jolla, Calif.); and steroid-inducible regulatory elements such as, e.g., the chimeric progesterone receptor inducible system, GeneSwitch (Invitrogen, Inc., Carlsbad, Calif.). The skilled person understands that these and a variety of other constitutive and inducible regulatory systems are commercially available or well known in the art and can be useful in the invention for controlling expression of a nucleic acid molecule which encodes a Clostridial toxin substrate.

In an embodiment, a nucleic acid molecule encoding the Clostridial toxin substrate can optionally be linked to a regulatory element such as a constitutive regulatory element.

In another embodiment, a nucleic acid molecule encoding the Clostridial toxin substrate can optionally be linked to a regulatory element such as an inducible regulatory element. In an aspect of this embodiment, expression of the nucleic acid molecule is induced using, e.g., tetracycline-inducible, ecdysone-inducible or steroid-inducible.

Aspects of the present invention provide methods of determining Clostridial toxin activity comprising (a) contacting with a sample a cell comprising (1) a membrane-associated Clostridial toxin substrate comprising (i) a first member of a fluorescence resonance energy transfer (FRET) pair; and (ii) a clostridial toxin recognition sequence including a cleavage site; and (2) a membrane-associated second member of the FRET pair, wherein the cell is capable of Clostridial toxin intoxication; wherein the FRET pair contains an acceptor having an absorbance spectrum overlapping the emission spectrum of a donor fluorophore; and wherein, under the appropriate conditions, fluorescence resonance energy transfer is exhibited between the first and second members of the FRET pair; (b) exciting the donor fluorophore; and (c) determining fluorescence resonance energy transfer of the contacted cell relative to a control cell, where a difference in fluorescence resonance energy transfer of the contacted cell as compared to the control cell is indicative of clostridial toxin activity.

Further provided herein is a method of determining BoNT/A activity comprising (a) contacting with a sample a neuronal cell comprising (1) a stably expressed nucleic acid molecule encoding a membrane-associated BoNT/A substrate comprising (i) a fluorescent protein; and (ii) a BoNT/A recognition sequence including a cleavage site; and (2) a membrane-associated lipophilic dye which has an absorbance spectrum overlapping the emission spectrum of the fluorescent protein; wherein the neuronal cell is capable of BoNT/A intoxication; and wherein, under the appropriate conditions, fluorescence resonance energy transfer is exhibited between the fluorescent protein and the lipophilic dye; (b) exciting the fluorescent protein; and (c) determining fluorescence resonance energy transfer of the contacted neuronal cell relative to a control cell, where a difference in fluorescence resonance energy transfer of the contacted neuronal cell as compared to the control cell is indicative of BoNT/A activity. In one embodiment, a method of the invention for determining BoNT/A activity is practiced using a neuronal cell which is a Neuro-2A cell. In another embodiment, a method of the invention for determining BoNT/A activity is practiced using a BoNT/A substrate containing, in part, a green fluorescent protein. In a further embodiment, a method of the invention for determining BoNT/A activity is practiced using a BoNT/A substrate comprising, in part, a BoNT/A recognition sequence which includes residues 1 to 206 of SEQ ID NO: 90. In a further embodiment, a method of the invention for determining BoNT/A activity is practiced using $DiIC_{18}(3)$ as the lipophilic dye.

The present invention additionally provides a method of determining BoNT/E activity comprising (a) contacting with a sample a neuronal cell comprising (1) a stably expressed nucleic acid molecule encoding a membrane-associated BoNT/E substrate comprising (i) a fluorescent protein; and (ii) a BoNT/E recognition sequence including a cleavage site; and (2) a membrane-associated lipophilic dye which has an absorbance spectrum overlapping the emission spectrum of the fluorescent protein; wherein the neuronal cell is capable of BoNT/E intoxication; and wherein, under the appropriate conditions, fluorescence resonance energy transfer is exhibited between the fluorescent protein and the lipophilic dye; (b) exciting the fluorescent protein; and (c) determining fluorescence resonance energy transfer of the contacted neuronal cell relative to a control cell, where a difference in fluorescence resonance energy transfer of the contacted neuronal cell as compared to the control cell is indicative of BoNT/E activity. In one embodiment, a method of the invention for determining BoNT/E activity is practiced using a neuronal cell which is a SK-N-DZ cell. In another embodiment, a method of the invention for determining BoNT/E activity is practiced using a neuronal cell which is a SH-SY5Y cell. In another embodiment, a method of the invention for determining BoNT/E activity is practiced using a BoNT/E substrate containing, in part, a green fluorescent protein. In a further embodiment, a method of the invention for determining BoNT/E activity is practiced using a BoNT/E substrate containing, in part, a BoNT/E recognition sequence which includes residues 1 to 206 of SEQ ID NO: 90. In a further embodiment, a method of the invention for determining BoNT/E activity is practiced using $DiIC_{18}(3)$ as the lipophilic dye.

The methods disclosed in the present specification include, in part, a Clostridial toxin substrate. In is envisioned that any and all Clostridial toxin substrate disclosed in the present specification can be used to practice the present methods. Thus, aspects of this embodiment include nucleic acid molecules, such as, e.g., DNA and RNA, that encode a Clostridial toxin substrate disclosed in the present specification and peptide molecule or peptidomimetic comprising a Clostridial toxin substrate disclosed in the present specification. Other aspects of this embodiment include, in part, a Clostridial toxin recognition sequence including, without limitation, a BoNT/A toxin recognition sequence, a BoNT/B toxin recognition sequence, a BoNT/C1 toxin recognition sequence, a BoNT/D toxin recognition sequence, a BoNT/E toxin recognition sequence, a BoNT/F toxin recognition sequence, a BoNT/G toxin recognition sequence and a TeNT toxin recognition sequence. Other aspects of this embodiment include, in part, a membrane targeting domain including, without limitation, naturally occurring membrane targeting domains present in SNAP-25, naturally occurring SNAP-25 MTD variants, and non-naturally occurring SNAP-25 MTD variants, and SNAP-25 MTD peptidomimetics; and naturally occurring membrane targeting domains present in syntaxin, naturally occurring syntaxin MTD variants, and non-naturally occurring syntaxin MTD variants and syntaxin MTD peptidomimetics.

The methods disclosed in the present specification include, in part, a first member of a FRET pair including, without limitation, wild type fluorescent proteins, naturally occurring variants, genetically engineered variants, active peptide fragments derived from *Aequorea* fluorescent proteins, *Anemonia* fluorescent proteins, *Anthozoa* fluorescent proteins, *Discosoma* fluorescent proteins, *Entacmeae* fluorescent proteins, *Heteractis* fluorescent proteins, *Montastrea* fluorescent proteins, *Renilla* fluorescent proteins, *Zoanthus* fluorescent proteins and fluorophore binding proteins. Non-limiting examples of fluorescent proteins include, e.g., EBFP, ECFP, AmCyan, AcGFP, ZsGreen, Vitality® hrGFP, EGFP, Monster Greene hMGFP, EYFP, ZsYellow, DsRed-Express, DsRed2, DsRed, AsRed2 and HcRed1. Non-limiting examples of fluorescent proteins include, e.g., a tetracysteine peptide, an AGT and a dehalogenase.

The methods disclosed in the present specification include, in part, a second member of a FRET pair including, without limitation, a long-chain carbocyanine dye, aminostyryl dye, amphiphilic styryl dye, lipophilic cation or FM dye. A variety of lipophilic dyes are useful in methods of the present invention include, without limitation, FAST DiO, $DiOC_{18}(3)$, $DiOC_{16}(3)$, SP-$DiOC_{18}(3)$, 4-Di-16-ASP, 4-Di-10-ASP, FAST DiA, $DiIC_{18}(3)$, $DiIC_{16}(3)$, $DiIC_{12}(3)$, FAST DiI, $\Delta^9$-DiI, FM®DiI, CellTracker CM-DiI, $DiIC_{18}(3)$-DS, SP-$DiIC_{18}(3)$, $Br_2$-$DiIC_{18}(3)$, 5,5'-$Ph_2$-$DiIC_{18}(3)$, $DiIC_{18}(5)$, $DiIC_{18}(5)$-DS, $DiIC_{18}(7)$, FM® 1-43, FM® 1-84, FM® 2-10, FM® 4-64, FM® 5-95, RH 414. $DiSBAC_2(3)$, JC-1, CCCP, octadecyl rhodamine B; 5-Dodecanoylaminofluorescein, 5-hexadecanoyl-aminofluorescein, 5-octadecanoyl-aminofluorescein and the octadecyl ester of fluorescein, 4-heptadecyl-7-hydroxycoumarin, DPH, TMA-DPH, TMAP-DPH, DPH propionic acid, BODIPY 493/503, BODIPY 505/515, BODIPY 665/676, BODIPY FL C5-ceramide, CellTrace BODIPY TR methyl ester, phenoxazine dye nile red, 1,3-Bis-(1-pyrene)propane, dapoxyl sulfonic acid, prodan, laurdan, acrylodan, badan, 1,8-ANS, 2,6-ANS, 2,6-TNS, bis-ANS, DCVJ and MBDS.

The methods disclosed in the present specification include, in part, a cell capable of Clostridial toxin intoxication. In is envisioned that any and all cells disclosed in the present specification can be used to practice the present methods. Thus, aspects of this embodiment include cells, such as, e.g., cells expressing one or more Clostridial toxin receptors including, without limitation, a low affinity Clostridial toxin receptor, a high affinity Clostridial toxin receptor, an endogenous Clostridial toxin receptor, an exogenous Clostridial toxin receptors, a BoNT/A receptor, a BoNT/B receptor, a BoNT/C1 receptor, a BoNT/D receptor, a BoNT/E receptor, a BoNT/F receptor, a BoNT/G receptor and a TeNT receptor. Other aspects of this embodiment include cells, such as, e.g., neuronal cells including, without limitation, primary neuronal cells; immortalized or established neuronal cells; transformed neuronal cells; neuronal tumor cells; stably and transiently transfected neuronal cells expressing a Clostridial toxin receptor, and further include, yet are not limited to, mammalian, murine, rat, primate and human neuronal cells. Other aspects of this embodiment include cells from, such as, e.g., neuronal cell lines including, without limitation, neuroblastoma cell lines, neuronal hybrid cell lines, spinal cord cell lines, central nervous system cell lines, cerebral cortex cell lines, dorsal root ganglion cell lines, hippocampal cell lines and pheochromocytoma cell lines. Non-limiting examples of neuronal cell lines include, e.g., neuroblastoma cell lines BE(2)-C, BE(2)-M17, C1300, CHP-212, CHP-126, IMR 32, KELLY, LA-N-2, MC-IXC, MHH-NB-11, N18Tg2, N1E-115, N4TG3, Neuro-2A, NB41A3, NS20Y, SH-SY5Y, SIMA, SK-N-DZ, SK-N-F1, SK-N-MC and SK-N-SH; neuroblastoma/glioma hybrid cell lines N18, NG108-15 and NG115-401L; neuroblastoma/motor neuron hybrid cell lines NSC-19 and NSC-32; neuroblastoma/root ganglion neuron hybrid cell lines F11, ND-C, ND-E, ND-U1, ND3, ND7/23, ND8/34, ND8/47, ND15 and ND27; the neuroblastoma/hippocampal neuron hybrid cell line HN-33; spinal cord cell lines TE 189.T and M4b; cerebral cortex cell lines CNh, HCN-1a and HCN-2; dorsal root ganglia cell line G4b; hippocampal cell lines HT-4, HT-22 and HN33; FGFR3 expressing cell lines H929, JIM-3, KMS-11, KMS-18, LB278, LB375, LB1017, LB2100, LP-1, OPM-2, PCL1 and UTMC-2. In further aspects of this embodiment, an FGFR3 expressing cell can be, e.g., H929, JIM-3, KMS-11, KMS-18, LB278, LB375, LB1017, LB2100, LP-1, OPM-2, PCL1 UTMC-2, B9, TC, L6 and CFK2. Other aspects of this embodiment include cells, such as, e.g., non-neuronal cells including, without limitation, primary non-neuronal cells; immortalized or established non-neuronal cells; transformed non-neuronal cells; non-neuronal tumor cells; stably and transiently transfected non-neuronal cells expressing a Clostridial toxin receptor, and further include, yet are not limited to, mammalian, murine, rat, primate and human non-neuronal cells. Other aspects of this embodiment include cells, such as, e.g., non-neuronal cells useful in aspects of the invention further include, without limitation, anterior pituitary cells; adrenal cells, pancreatic cells, ovarian cells, kidney cells, such as, e.g., HEK293, stomach cell, blood cells, epithelial cells, fibroblasts, thyroid cells, chondrocytes, muscle cells, hepatocytes, glandular cells and cells involved in glucose transporter (GLUT4) translocation.

The methods disclosed in the present specification include, in part, a sample. As used herein, the term "sample" means any biological matter that contains or potentially contains an active Clostridial toxin. A variety of samples can be assayed according to a method disclosed in the present specification including, without limitation, purified, partially purified, or unpurified Clostridial toxin; recombinant single chain or di-chain toxin with a naturally or non-naturally occurring sequence; recombinant Clostridial toxin with a modified protease specificity; recombinant Clostridial toxin with an altered cell specificity; chimeric toxin containing structural elements from multiple Clostridial toxin species or subtypes; bulk Clostridial toxin; formulated Clostridial toxin product, including, e.g., formulated BoNT/A and BoNT/E products; and foods; cells or crude, fractionated or partially purified cell lysates, for example, engineered to include a recombinant nucleic acid encoding a Clostridial toxin; bacterial, baculoviral and yeast lysates; raw, cooked, partially cooked or processed foods; beverages; animal feed; soil samples; water samples; pond sediments; lotions; cosmetics; and clinical formulations. It is understood that the term sample encompasses tissue samples, including, without limitation, mammalian tissue samples, livestock tissue samples such as sheep, cow and pig tissue samples; primate tissue samples; and human tissue samples. Such samples encompass, without limitation, intestinal samples such as infant intestinal samples, and tissue samples obtained from a wound. As non-limiting examples, a method of the invention can be useful for determining the presence or activity of a Clostridial toxin in a food or beverage sample; to assay a sample from a human or animal, for example, exposed to a Clostridial toxin or having one or more symptoms of a Clostridial toxin; to follow activity during production and purification of Clostridial toxin; or to assay formulated Clostridial toxin products such as pharmaceuticals or cosmetics.

In several methods of the invention, resonance energy transfer of the contacted cell is determined relative to a control cell. As used herein, the term "control cell" means a cell of the same or similar type as the contacted cell and grown under the same conditions but which is not contacted with any sample or is contacted with a defined negative sample or a defined positive sample. One skilled in the art understands that a variety of control cells are useful in the methods of the invention and that a control cell can be a positive control cell or a negative control cell. A control cell can be, for example, a negative control cell such as a similar or identical cell containing the same or similar Clostridial toxin substrate that is contacted with a similar, defined negative sample, which is known to lack active Clostridial toxin, or that is not contacted with any sample. A control cell also can be, for example, a positive control cell such as a cell containing one or both cleavage products that result from proteolysis of the Clostridial toxin substrate at the cleavage site or a cell containing the same or similar substrate contacted with a defined positive sample, which is known to include active Clostridial toxin.

The methods disclosed in the present specification include, in part, determining the Clostridial toxin activity from a sample by determining the fluorescence resonance energy transfer of a cell contacted with sample relative to a control cell. A variety of means can be useful in the methods of the invention for determining fluorescence resonance energy transfer of a cell contacted with sample relative to a control cell. In one embodiment, fluorescence resonance energy transfer is determined by detecting acceptor fluorescence intensity of the contacted cell, where decreased acceptor fluorescence intensity of the contacted cell as compared to the control cell is indicative of clostridial toxin activity. In another embodiment, fluorescence resonance energy transfer is determined by detecting donor fluorescence intensity of the contacted cell, where increased donor fluorescence intensity of the contacted cell as compared to the control cell is indicative of clostridial toxin activity. In still another embodiment, fluorescence resonance energy transfer is determined by detecting an acceptor emission maximum and a donor fluorophore emission maximum of the contacted cell, where a shift in emission maxima from near the acceptor emission maximum to near the donor fluorophore emission maximum is indicative of clostridial toxin activity. In yet another embodiment, fluorescence resonance energy transfer is determined by detecting the ratio of fluorescence amplitudes near an acceptor emission maximum to the fluorescence amplitudes near a donor fluorophore emission maximum, where a decreased ratio in the contacted cell as compared to the control cell is indicative of clostridial toxin activity. In a further embodiment, fluorescence resonance energy transfer is determined by detecting the excited state lifetime of the donor fluorophore in the contacted cell, where an increased donor fluorophore excited state lifetime in the contacted cell as compared to the control cell is indicative of clostridial toxin activity.

Fluorescence resonance energy transfer and, hence, clostridial toxin activity, can be detected by a variety of means, for example, by detecting increased donor fluorescence intensity; decreased acceptor fluorescence intensity; a shift in emission maxima from near the acceptor emission maximum to near the donor fluorophore emission maximum; a increased ratio of fluorescence amplitudes near the donor emission maximum to the fluorescence amplitudes near the acceptor fluorophore emission maximum; a decreased ratio of fluorescence amplitudes near the acceptor emission maximum to the fluorescence amplitudes near the donor fluorophore emission maximum; an increased donor fluorophore excited state lifetime; or a decrease acceptor fluorophore excited state lifetime. In aspects of this embodiment, an increased donor fluorescence intensity can be, e.g., at least two-fold, at least three-fold, at least four-fold, at least five-fold, at least ten-fold, at least twenty-fold or more relative to fluorescence intensity at the same wavelength of the same cell detected at a different time point, or relative to fluorescence intensity at the same wavelength of a similar cell not contacted with a sample, such as, e.g., a control cell. In other aspects of this embodiment, an increased donor fluorescence intensity can be, e.g., at most two-fold, at most three-fold, at most four-fold, at most five-fold, at most ten-fold, at most twenty-fold relative to fluorescence intensity at the same wavelength of the same cell detected at a different time point, or relative to fluorescence intensity at the same wavelength of a similar cell not contacted with a sample, such as, e.g., a control cell. In yet other aspects of this embodiment, a decreased acceptor fluorescence intensity can be, e.g., at least two-fold, at least three-fold, at least four-fold, at least five-fold, at least ten-fold, at least twenty-fold or more relative to fluorescence intensity at the same wavelength of the same cell detected at a different time point, or relative to fluorescence intensity at the same wavelength of a similar cell not contacted with a sample, such as, e.g., a control cell. In yet other aspects of this embodiment, a decreased acceptor fluorescence intensity can be, e.g., at most two-fold, at most three-fold, at most four-fold, at most five-fold, at most ten-fold, at most twenty-fold relative to fluorescence intensity at the same wavelength of the same cell detected at a different time point, or relative to fluorescence intensity at the same wavelength of a similar cell not contacted with a sample, such as, e.g., a control cell.

In additional aspects of this embodiment, a shift in emission maxima from near the acceptor emission maximum to near the donor fluorophore emission maximum can be, e.g., at least two-fold, at least three-fold, at least four-fold, at least five-fold, at least ten-fold, at least twenty-fold or more relative to fluorescence intensity at the same wavelength of the same cell detected at a different time point, or relative to fluorescence intensity at the same wavelength of a similar cell not contacted with a sample, such as, e.g., a control cell. In yet additional aspects of this embodiment, a shift in emission maxima from near the acceptor emission maximum to near the donor fluorophore emission maximum can be, e.g., at most two-fold, at most three-fold, at most four-fold, at most five-fold, at most ten-fold, at most twenty-fold relative to fluorescence intensity at the same wavelength of the same cell detected at a different time point, or relative to fluorescence intensity at the same wavelength of a similar cell not contacted with a sample, such as, e.g., a control cell.

In still other aspects of this embodiment, a decreased ratio of fluorescence amplitudes near the acceptor emission maximum to the fluorescence amplitudes near the donor fluorophore emission maximum can be, e.g., at least two-fold, at least three-fold, at least four-fold, at least five-fold, at least ten-fold, at least twenty-fold or more relative to fluorescence intensity at the same wavelength of the same cell detected at a different time point, or relative to fluorescence intensity at the same wavelength of a similar cell not contacted with a sample, such as, e.g., a control cell. In still other aspects of this embodiment, a decreased ratio of fluorescence amplitudes near the acceptor emission maximum to the fluorescence amplitudes near the donor fluorophore emission maximum can be, e.g., at most two-fold, at most three-fold, at most four-fold, at most five-fold, at most ten-fold, at most twenty-fold relative to fluorescence intensity at the same wavelength of the same cell detected at a different time point, or relative to fluorescence intensity at the same wavelength of a similar cell not contacted with a sample, such as, e.g., a control cell. In still other aspects of this embodiment, an increased ratio of fluorescence amplitudes near the donor emission maximum to the fluorescence amplitudes near the acceptor fluorophore emission maximum can be, e.g., at least two-fold, at least three-fold, at least four-fold, at least five-fold, at least ten-fold, at least twenty-fold or more relative to fluorescence intensity at the same wavelength of the same cell detected at a different time point, or relative to fluorescence intensity at the same wavelength of a similar cell not contacted with a sample, such as, e.g., a control cell. In still other aspects of this embodiment, an increased ratio of fluorescence amplitudes near the donor emission maximum to the fluorescence amplitudes near the acceptor fluorophore emission maximum can be, e.g., at most two-fold, at most three-fold, at most four-fold, at most five-fold, at most ten-fold, at most twenty-fold relative to fluorescence intensity at the same wavelength of the same cell detected at a different time point, or relative to fluorescence intensity at the same wavelength of a similar cell not contacted with a sample, such as, e.g., a control cell.

In further aspects of this embodiment, an increased donor fluorophore excited state lifetime can be, e.g., at least two-fold, at least three-fold, at least four-fold, at least five-fold, at least ten-fold, at least twenty-fold or more relative to fluorescence intensity at the same wavelength of the same cell detected at a different time point, or relative to fluorescence intensity at the same wavelength of a similar cell not contacted with a sample, such as, e.g., a control cell. In still further aspects of this embodiment, an increased donor fluorophore excited state lifetime can be, e.g., at most two-fold, at most three-fold, at most four-fold, at most five-fold, at most ten-fold, at most twenty-fold relative to fluorescence intensity at the same wavelength of the same cell detected at a different time point, or relative to fluorescence intensity at the same wavelength of a similar cell not contacted with a sample, such as, e.g., a control cell. In still further aspects of this embodiment, a decrease acceptor fluorophore excited state lifetime can be, e.g., at least two-fold, at least three-fold, at least four-fold, at least five-fold, at least ten-fold, at least twenty-fold or more relative to fluorescence intensity at the same wavelength of the same cell detected at a different time point, or relative to fluorescence intensity at the same wavelength of a similar cell not contacted with a sample, such as, e.g., a control cell. In still further aspects of this embodiment, a decrease acceptor fluorophore excited state lifetime can be, e.g., at most two-fold, at most three-fold, at most four-fold, at most five-fold, at most ten-fold, at most twenty-fold relative to fluorescence intensity at the same wavelength of the same cell detected at a different time point, or relative to fluorescence intensity at the same wavelength of a similar cell not contacted with a sample, such as, e.g., a control cell.

It is recognized that changes in the absolute amount of clostridial toxin substrate in the cell, excitation intensity, and turbidity or other background absorbance at the excitation wavelength effects the fluorescence intensities of donor and acceptor fluorophores roughly in parallel. Thus, it is understood that a ratio of emission intensities is independent of the absolute amount of substrate, excitation intensity, and turbidity or other background absorbance, and can be a useful indicator of clostridial toxin activity. Similarly, one skilled in the art understands that the excitation state lifetime of a donor fluorophore is independent of the absolute amount of substrate, excitation intensity, and turbidity or other background absorbance and can be useful in a method of the invention. It is understood that the relevant fluorescence intensities or excited state lifetimes are detected at the appropriate wavelength or range of wavelengths. As an example, where donor fluorescence intensity is detected, the appropriate wavelength is at or near the emission maxima of the donor fluorophore, or is a range of wavelengths encompassing or near to the emission maxima of the donor fluorophore.

In one embodiment, Clostridial toxin activity from a sample is determined by detecting the fluorescence intensity. Detection of fluorescence intensity can be practiced as "fixed-time" assays or as continuous-time assays and comparisons can be made using different time points taken from the same contacted cell or relative to a control cell. Thus, aspect of this embodiment include detecting the fluorescence intensity in, e.g., at least two different time points, at least three different time points, at least four different time points, at least five different time points, at least ten different time points and at least 20 different time points. Other aspects of this embodiment include detecting the fluorescence intensity over time intervals that are, e.g., no more than 1 minute apart, no more than 5 minutes apart, no more than 10 minutes apart, no more than 15 minutes apart, no more than 30 minutes apart and no more than 30 minutes apart. Other aspects of this embodiment include detecting the fluorescence intensity over time intervals that are, e.g., no less than 15 minutes apart, no less than 30 minutes apart, no less than 45 minutes apart, no less than 60 minutes apart, no less than 90 minutes apart and no less than 120 minutes apart. Still other aspects of this embodiment include detecting the fluorescence intensity continuously over time for, e.g., at most about 5 minutes, at most about 10 minutes, at most about 15 minutes, at most about 30 minutes, at most about 45 minutes, at most about 60 minutes, at most about 90 minutes and at most about 120 minutes. Still other aspects of this embodiment include detecting the fluorescence intensity continuously over time for, e.g., at least about 15 minutes, at least about 30 minutes, at least about 45 minutes, at least about 60 minutes, at least about 90 minutes and at least about 120 minutes.

It is understood that fluorescence intensity can be detected from a single time point or a plurality of time points. It is envisioned that comparison of the fluorescence intensity detected from the contacted cell to the fluorescence intensity detected from the control cell can be made using the values obtained from the same, or similar time point or from different time points. Thus, aspect of this embodiment include detecting the fluorescence intensity from the contacted cell and control cell in, e.g., at least one different time point, at least two different time points, at least three different time points, at least four different time points, at least five different time points, at least ten different time points and at least 20 different time points. Other aspects of this embodiment can include comparison of the fluorescence intensity detected from the contacted cell obtained from a single time point to the fluorescence intensity detected from the control cell obtained, e.g., at the same time point, at a similar time point, at a time point later than the time point obtained from the contact cell, at a time point earlier than the time point obtained from the contact cell, at a plurality time points later than the time point obtained from the contact cell, at a plurality time points earlier than the time point obtained from the contact cell and at a plurality time point both later than and earlier than the time point obtained from the contact cell, Other aspects of this embodiment can include comparison of the fluorescence intensity detected from the contacted cell obtained from a plurality of time points to the fluorescence intensity detected from the control cell obtained, e.g., from a single time point, at the same time points, at a similar time points, at a time point later than the time points obtained from the contact cell, at a time point earlier than the time points obtained from the contact cell, at a plurality time points later than the time points obtained from the contact cell, at a plurality time points earlier than the time points obtained from the contact cell and at a plurality time point both later than and earlier than the time points obtained from the contact cell.

In another embodiment, Clostridial toxin activity from a sample is determined by detecting the shift in emission maxima. Detection the shift in emission maxima can be practiced as a "fixed-time" assay or as a continuous-time assay and comparisons can be made using different time points taken from the same contacted cell or relative to a control cell. Thus, aspect of this embodiment include detecting the shift in emission maxima in, e.g., at least two different time points, at least three different time points, at least four different time points, at least five different time points, at least ten different time points and at least 20 different time points. Other aspects of this embodiment include detecting the shift in emission maxima over time intervals that are, e.g., no more than 1 minute apart, no more than 5 minutes apart, no more than 10 minutes apart, no more than 15 minutes apart, no more than 30 minutes apart and no more than 30 minutes apart. Other aspects of this embodiment include detecting the shift in emission maxima over time intervals that are, e.g., no less than 15 minutes apart, no less than 30 minutes apart, no less than 45 minutes apart, no less than 60 minutes apart, no less than 90 minutes apart and no less than 120 minutes apart. Still other aspects of this embodiment include detecting the shift in emission maxima continuously over time for, e.g., at most about 5 minutes, at most about 10 minutes, at most about 15 minutes, at most about 30 minutes, at most about 45 minutes, at most about 60 minutes, at most about 90 minutes and at most about 120 minutes. Still other aspects of this embodiment include detecting the shift in emission maxima continuously over time for, e.g., at least about 15 minutes, at least about 30 minutes, at least about 45 minutes, at least about 60 minutes, at least about 90 minutes and at least about 120 minutes. It is understood that the observed shift in emission maxima generally will not be a complete shift but that only part of the emission intensity will be shifted to near the donor fluorophore emission maximum.

It is understood that the shift in emission maxima can be detected from a single time point or a plurality of time points. It is envisioned that comparison of the shift in emission maxima detected from the contacted cell to the shift in emission maxima detected from the control cell can be made using the values obtained from the same, or similar time point or from different time points. Thus, aspect of this embodiment include detecting the shift in emission maxima from the contacted cell and control cell in, e.g., at least one different time point, at least two different time points, at least three different time points, at least four different time points, at least five different time points, at least ten different time points and at least 20 different time points. Other aspects of this embodiment can include comparison of the shift in emission maxima detected from the contacted cell obtained from a single time point to the shift in emission maxima detected from the control cell obtained, e.g., at the same time point, at a similar time point, at a time point later than the time point obtained from the contact cell, at a time point earlier than the time point obtained from the contact cell, at a plurality time points later than the time point obtained from the contact cell, at a plurality time points earlier than the time point obtained from the contact cell and at a plurality time point both later than and earlier than the time point obtained from the contact cell, Other aspects of this embodiment can include comparison of the shift in emission maxima detected from the contacted cell obtained from a plurality of time points to the shift in emission maxima detected from the control cell obtained, e.g., from a single time point, at the same time points, at a similar time points, at a time point later than the time points obtained from the contact cell, at a time point earlier than the time points obtained from the contact cell, at a plurality time points later than the time points obtained from the contact cell, at a plurality time points earlier than the time points obtained from the contact cell and at a plurality time point both later than and earlier than the time points obtained from the contact cell.

In another embodiment, Clostridial toxin activity from a sample is determined by detecting the ratio of fluorescent amplitudes. Detection the ratio of fluorescent amplitudes can be practiced as a "fixed-time" assay or as a continuous-time assay and comparisons can be made using different time points taken from the same contacted cell or relative to a control cell. Thus, aspect of this embodiment include detecting the ratio of fluorescent amplitudes in, e.g., at least two different time points, at least three different time points, at least four different time points, at least five different time points, at least ten different time points and at least 20 different time points. Other aspects of this embodiment include detecting the ratio of fluorescent amplitudes over time intervals that are, e.g., no more than 1 minute apart, no more than 5 minutes apart, no more than 10 minutes apart, no more than 15 minutes apart, no more than 30 minutes apart and no more than 30 minutes apart. Other aspects of this embodiment include detecting the ratio of fluorescent amplitudes over time intervals that are, e.g., no less than 15 minutes apart, no less than 30 minutes apart, no less than 45 minutes apart, no less than 60 minutes apart, no less than 90 minutes apart and no less than 120 minutes apart. Still other aspects of this embodiment include detecting the ratio of fluorescent amplitudes continuously over time for, e.g., at most about 5 minutes, at most about 10 minutes, at most about 15 minutes, at most about 30 minutes, at most about 45 minutes, at most about 60 minutes, at most about 90 minutes and at most about 120 minutes. Still other aspects of this embodiment include detecting the ratio of fluorescent amplitudes continuously over time for, e.g., at least about 15 minutes, at least about 30 minutes, at least about 45 minutes, at least about 60 minutes, at least about 90 minutes and at least about 120 minutes.

It is understood that the ratio of fluorescent amplitudes can be detected from a single time point or a plurality of time points. It is envisioned that comparison of the ratio of fluorescent amplitudes detected from the contacted cell to the ratio of fluorescent amplitudes detected from the control cell can be made using the values obtained from the same, or similar time point or from different time points. Thus, aspect of this embodiment include detecting the ratio of fluorescent amplitudes from the contacted cell and control cell in, e.g., at least one different time point, at least two different time points, at least three different time points, at least four different time points, at least five different time points, at least ten different time points and at least 20 different time points. Other aspects of this embodiment can include comparison of the ratio of fluorescent amplitudes detected from the contacted cell obtained from a single time point to the ratio of fluorescent amplitudes detected from the control cell obtained, e.g., at the same time point, at a similar time point, at a time point later than the time point obtained from the contact cell, at a time point earlier than the time point obtained from the contact cell, at a plurality time points later than the time point obtained from the contact cell, at a plurality time points earlier than the time point obtained from the contact cell and at a plurality time point both later than and earlier than the time point obtained from the contact cell, Other aspects of this embodiment can include comparison of the ratio of fluorescent amplitudes detected from the contacted cell obtained from a plurality of time points to the ratio of fluorescent amplitudes detected from the control cell obtained, e.g., from a single time point, at the same time points, at a similar time points, at a time point later than the time points obtained from the contact cell, at a time point earlier than the time points obtained from the contact cell, at a plurality time points later than the time points obtained from the contact cell, at a plurality time points earlier than the time points obtained from the contact cell and at a plurality time point both later than and earlier than the time points obtained from the contact cell.

In another embodiment, Clostridial toxin activity from a sample is determined by detecting the fluorophore excited state lifetime. Detection the fluorophore excited state lifetime can be practiced as a “fixed-time” assay or as a continuous-time assay and comparisons can be made using different time points taken from the same contacted cell or relative to a control cell. Thus, aspect of this embodiment include detecting the fluorophore excited state lifetime in, e.g., at least two different time points, at least three different time points, at least four different time points, at least five different time points, at least ten different time points and at least 20 different time points. Other aspects of this embodiment include detecting the fluorophore excited state lifetime over time intervals that are, e.g., no more than 1 minute apart, no more than 5 minutes apart, no more than 10 minutes apart, no more than 15 minutes apart, no more than 30 minutes apart and no more than 30 minutes apart. Other aspects of this embodiment include detecting the fluorophore excited state lifetime over time intervals that are, e.g., no less than 15 minutes apart, no less than 30 minutes apart, no less than 45 minutes apart, no less than 60 minutes apart, no less than 90 minutes apart and no less than 120 minutes apart. Still other aspects of this embodiment include detecting the fluorophore excited state lifetime continuously over time for, e.g., at most about 5 minutes, at most about 10 minutes, at most about 15 minutes, at most about 30 minutes, at most about 45 minutes, at most about 60 minutes, at most about 90 minutes and at most about 120 minutes. Still other aspects of this embodiment include detecting the fluorophore excited state lifetime continuously over time for, e.g., at least about 15 minutes, at least about 30 minutes, at least about 45 minutes, at least about 60 minutes, at least about 90 minutes and at least about 120 minutes.

It is understood that the fluorophore excited state lifetime can be detected from a single time point or a plurality of time points. It is envisioned that comparison of the fluorophore excited state lifetime detected from the contacted cell to the fluorophore excited state lifetime detected from the control cell can be made using the values obtained from the same, or similar time point or from different time points. Thus, aspect of this embodiment include detecting the fluorophore excited state lifetime from the contacted cell and control cell in, e.g., at least one different time point, at least two different time points, at least three different time points, at least four different time points, at least five different time points, at least ten different time points and at least 20 different time points. Other aspects of this embodiment can include comparison of the fluorophore excited state lifetime detected from the contacted cell obtained from a single time point to the fluorophore excited state lifetime detected from the control cell obtained, e.g., at the same time point, at a similar time point, at a time point later than the time point obtained from the contact cell, at a time point earlier than the time point obtained from the contact cell, at a plurality time points later than the time point obtained from the contact cell, at a plurality time points earlier than the time point obtained from the contact cell and at a plurality time point both later than and earlier than the time point obtained from the contact cell, Other aspects of this embodiment can include comparison of the fluorophore excited state lifetime detected from the contacted cell obtained from a plurality of time points to the fluorophore excited state lifetime detected from the control cell obtained, e.g., from a single time point, at the same time points, at a similar time points, at a time point later than the time points obtained from the contact cell, at a time point earlier than the time points obtained from the contact cell, at a plurality time points later than the time points obtained from the contact cell, at a plurality time points earlier than the time points obtained from the contact cell and at a plurality time point both later than and earlier than the time points obtained from the contact cell.

Fluorescence of a contacted cell typically is determined using a fluorimeter. In general, excitation radiation from an excitation source having a first wavelength passes through excitation optics. The excitation optics cause the excitation radiation to excite the substrate in the cell. In response, fluorescent protein in the substrate emit radiation which has a wavelength that is different from the excitation wavelength. Collection optics then collect the emission; if desired, the device includes a temperature controller to maintain the cell at a specific temperature while being scanned. If desired, a multi axis translation stage moves a microtiter plate containing a plurality of samples in order to position different wells to be exposed. It is understood that the multi-axis translation stage, temperature controller, auto-focusing feature, and electronics associated with imaging and data collection can be managed by the appropriate digital computer. The aspects of the invention involve exciting a donor fluorophore within a cell. One skilled in the art understands that a donor fluorophore generally is excited at or near the optimal absorption wavelength (excitation wavelength) of the donor fluorophore. As an example, where the donor fluorophore is fluorescein, the donor can be excited, for example, at or near the optimal absorption wavelength of 488 nm.

For detection of donor fluorescence intensity, excitation is set at the wavelength of donor fluorophore absorption, and the emission of the donor fluorophore is monitored. The emission wavelength of the donor fluorophore generally is selected such that little or no contribution from acceptor fluorescence is observed. The presence of acceptor quenches donor fluorescence. Energy transfer efficiency, E, is calculated from $E=1-I_{DA}/I_D$, where $I_{DA}$ and $I_D$ are donor intensities in the presence and absence of acceptor. Both are normalized to the same donor fluorophore concentration. If desired, time resolved measurements, for which donor fluorophore concentration is not required, can be performed using $E=1-\{\tau_{DA}\}/\tau_D$, where $\{\tau_{DA}\}$ and $\{\tau_D\}$ are amplitude averaged lifetimes of donor fluorophore in the presence and absence of acceptor.

For detection of acceptor fluorescence intensity, excitation is set at the wavelength of donor fluorophore absorption, and the emission of the acceptor fluorophore is monitored. The emission wavelength of the acceptor fluorophore generally is selected such that little or no contribution from donor fluorescence is observed. The presence of acceptor quenches donor fluorescence. Energy transfer efficiency, E, is calculated from $E=1-I_{AD}/I_A$, where $I_{AD}$ and $I_A$ are acceptor intensities in the presence and absence of donor. Both are normalized to the same acceptor fluorophore concentration. If desired, time resolved measurements, for which acceptor fluorophore concentration is not required, can be performed using $E=1-\{\tau_{AD}\}/\tau_A$, where $\{\tau_{AD}\}$ and $\{\tau_A\}$ are amplitude averaged lifetimes of acceptor fluorophore in the presence and absence of acceptor.

It is further understood that the methods of the invention can be automated and can be configured in a high throughput or ultra high-throughput format using, without limitation, 96-well, 384-well or 1536-well plates. As one non-limiting example, fluorescence emission can be detected using the SpectraMax M5 microplate reader (Molecular Devices, Sunnyvale, Calif.), a dual-monochromator, multi-detection microplate reader with a wavelength range of 250-850 nm and a 6-384 microplate reading capability. As another non-limiting example, fluorescence emission can be detected using the Typhoon™ 9410 system (Amersham Biosciences, Piscataway, N.J.). Designd for microplate assays, this system utilizes is capable of excitation fluorescence at 488 nm, 532 nm or 633 nm and has a semiconfocal optimal system with a charge coupled device (CCD) camera to illuminate and image the entire plate. The FPM-2 96-well plate reader (Folley Consulting and Research, Round Lake, Ill.) also can be useful in detecting fluorescence emission in the methods of the invention. One skilled in the art understands that these and other automated systems with the appropriate spectroscopic compatibility such as the ECLIPSE cuvette reader (Varian-Cary; Walnut Creek, Calif.) and the FLIPR® and Gemini XPS spectrofluorometer systems (Molecular Devices, Sunnyvale, Calif.).

It is envisioned that a variety of conditions suitable for determining Clostridial toxin activity in a sample can be useful according to the methods disclosed in the present specification. In aspects of this embodiment, conditions suitable for determining Clostridial toxin activity can be provided such that, e.g., at least 10% of the substrate is cleaved, at least 20% of the substrate is cleaved, at least 30% of the substrate is cleaved, at least 40% of the substrate is cleaved, at least 50% of the substrate is cleaved, at least 60% of the substrate is cleaved, at least 70% of the substrate is cleaved, at least 80% of the substrate is cleaved or at least 90% of the substrate is cleaved. In other aspects of this embodiment, conditions suitable for determining Clostridial toxin activity can be provided such that, e.g., at most 10% of the substrate is cleaved, at most 20% of the substrate is cleaved, at most 30% of the substrate is cleaved, at most 40% of the substrate is cleaved, at most 50% of the substrate is cleaved, at most 60% of the substrate is cleaved, at most 70% of the substrate is cleaved, at most 80% of the substrate is cleaved or at most 90% of the substrate is cleaved. In another aspect of this embodiment, conditions suitable for determining Clostridial toxin activity can be provided such that 100% of the substrate is cleaved. In another aspect of this embodiment, the conditions suitable for determining Clostridial toxin activity are provided such that the assay is linear. In another aspect of this embodiment, the conditions suitable for determining Clostridial toxin activity are provided such that the assay is non-linear.

Clostridial toxins are zinc metalloproteases, and a source of zinc, such as zinc chloride or zinc acetate, typically in the range of 1 to 500 μM, for example, 5 to 10 μM can be included, if desired, as part of the conditions suitable for determining Clostridial toxin activity. One skilled in the art understands that zinc chelators such as EDTA generally are excluded from a buffer for determining the presence or activity of a Clostridial toxin.

The concentration of purified or partially purified Clostridial toxin to be assayed in a method of the invention generally is in the range of about 0.0001 ng/ml to 500 μg/ml toxin, for example, about 0.0001 ng/ml to 50 μg/ml toxin, 0.001 ng/ml to 500 μg/ml toxin, 0.001 ng/ml to 50 μg/ml toxin, 0.0001 to 5000 ng/ml toxin, 0.001 ng/ml to 5000 ng/ml, 0.01 ng/ml to 5000 ng/ml, 0.1 ng/ml to 5000 ng/ml, 0.1 ng/ml to 500 ng/ml, 0.1 ng/ml to 50 ng/ml, 1 ng/ml to 5000 ng/ml, 1 ng/ml to 500 ng/ml, 1 ng/ml to 50 ng/ml, 10 ng/ml to 5000 ng/ml, 10 ng/ml to 500 ng/ml, 50 ng/ml to 5000 ng/ml, 50 ng/ml to 500 ng/ml or 100 ng/ml to 5000 ng/ml toxin, which can be, for example, purified recombinant di-chain or single chain toxin or formulated Clostridial toxin product containing human serum albumin and excipients. In aspects of this embodiment, the concentration of purified or partially purified Clostridial toxin assayed results in cleavage of, e.g., at least 10% of the total substrate present, at least 20% of the total substrate present, at least 30% of the total substrate present, at least 40% of the total substrate present, at least 50% of the total substrate present, at least 60% of the total substrate present, at least 70% of the total substrate present, at least 80% of the total substrate present or at least 90% of the total substrate present. In further aspects of this embodiment, the concentration of purified or partially purified Clostridial toxin assayed results in cleavage of, e.g., at most 10% of the total substrate present, at most 20% of the total substrate present, at most 30% of the total substrate present, at most 40% of the total substrate present, at most 50% of the total substrate present, at most 60% of the total substrate present, at most 70% of the total substrate present, at most 80% of the total substrate present or at most 90% of the total substrate present. In another aspect of this embodiment, the concentration of purified or partially purified Clostridial toxin assayed results in cleavage of 100% of the total substrate present.

The concentration of purified or partially purified Clostridial toxin assayed in a method of the invention can be, for example, in the range of about 0.1 pM to 500 μM, 0.1 pM to 100 μM, 0.1 pM to 10 μM, 0.1 pM to 1 μM, 0.1 pM to 500 nM, 0.1 pM to 100 nM, 0.1 pM to 10 nM, 0.1 pM to 1 nM, 0.1 pM to 500 pM, 0.1 pM to 100 pM, 0.1 pM to 50 pM, 0.1 pM to 10 pM, 1 M to 500 μM, 1 pM to 100 μM, 1 pM to 10 μM, 1 pM to 1 μM, 1 pM to 500 nM, 1 pM to 100 nM, 1 pM to 10 nM, 1 pM to 1 nM, 1 pM to 500 pM, 1 pM to 100 pM, 1 pM to 50 pM, 1 pM to 10 pM, 10 pM to 500 μM, 10 pM to 100 μM, 10 pM to 10 μM, 10 pM to 10 pM, 10 pM to 500 nM, 10 pM to 100 nM, 10 pM to 10 nM, 10 pM to 1 nM, 10 pM to 500 pM, 10 pM to 100 pM, 10 pM to 50 pM, 100 pM to 500 μM, 100 pM to 100 μM, 100 pM to 10 μpM, 100 pM to 1 μM, 100 pM to 500 nM, 100 pM to 100 nM, 100 pM to 10 nM, 100 pM to 1 nM, 100 pM to 500 pM 1 nM to 500 μM, 1 nM to 100 μM, 1 nM to 10 μM, 1 nM to 1 μM, 1 nM to 500 nM, 1 nM to 100 nM, 1 nM to 50 nM, 1 nM to 10 nM, 3 nM to 100 nM toxin, which can be, for example, purified native or recombinant light chain or di-chain toxin or formulated Clostridial toxin product containing human serum albumin and excipients. One skilled in the art understands that the concentration of purified or partially purified Clostridial toxin will depend on the serotype of the toxin assayed, as well as the purity or recombinant sequence of the toxin, the presence of inhibitory components, and the assay conditions. It is additionally understood that purified, partially purified or crude samples can be diluted to within a convenient range for assaying for Clostridial toxin activity against a standard curve. Similarly, it is understood that a sample can be diluted, if desired, such that the assay is linear. In aspects of this embodiment, the concentration of purified or partially purified Clostridial toxin assayed results in cleavage of, e.g., at least 10% of the total substrate present, at least 20% of the total substrate present, at least 30% of the total substrate present, at least 40% of the total substrate present, at least 50% of the total substrate present, at least 60% of the total substrate present, at least 70% of the total substrate present, at least 80% of the total substrate present at least 90% of the total substrate present. In further aspects of this embodiment, the concentration of purified or partially purified Clostridial toxin assayed results in cleavage of, e.g., at most 10% of the total substrate present, at most 20% of the total substrate present, at most 30% of the total substrate present, at most 40% of the total substrate present, at most 50% of the total substrate present, at most 60% of the total substrate present, at most 70% of the total substrate present, at most 80% of the total substrate present at most 90% of the total substrate present. In another aspect of this embodiment, the concentration of purified or partially purified Clostridial toxin assayed results in cleavage of 100% of the total substrate present.

In still another embodiment, it is envisioned that any and all temperatures that allow the function of a Clostridial activity assay can be used in methods disclosed in the present specification. Assay temperatures can be varied as appropriate by one skilled in the art and generally depend, in part, on the concentration, purity and activity of the Clostridial toxin, the sample to be assayed, the assay time or the convenience of the artisan. Thus, an assay temperature should not be as low as to cause the solution to freeze and should not be as high as to denature the Clostridial toxin, the Clostridial toxin substrate disclosed in the present specification. In an aspect of this embodiment, the assay is performed within a temperature range above 0° C., but below 40° C. In another aspect of this embodiment, the assay is performed within a temperature range of about 4° C. to about 37° C. In yet another aspect of this embodiment, the assay is performed within a temperature range of about 2° C. to 10° C. In yet another aspect of this embodiment, the assay is performed at about 4° C. In still another aspect of this embodiment, the assay is performed within a temperature range of about 10° C. to about 18° C. In still another aspect of this embodiment, the assay is performed at about 16° C. In yet another aspect of this embodiment, the assay is performed within a temperature range of about 18° C. to about 32° C. In yet another aspect of this embodiment, the assay is performed at about 20° C. In another aspect of this embodiment, the assay is performed within a temperature range of about 32° C. to about 40° C. In another aspect of this embodiment, the assay is performed at about 37° C. In aspects of this embodiment, the amount of Clostridial toxin substrate cleaved within a temperature range is, e.g., at least 10% of the total substrate present, at least 20% of the total substrate present, at least 30% of the total substrate present, at least 40% of the total substrate present, at least 50% of the total substrate present, at least 60% of the total substrate present, at least 70% of the total substrate present, at least 80% of the total substrate present or at least 90% of the total substrate present. In further aspects of this embodiment, the amount of Clostridial toxin substrate cleaved within a temperature range is, e.g., at most 10% of the total substrate present, at most 20% of the total substrate present, at most 30% of the total substrate present, at most 40% of the total substrate present, at most 50% of the total substrate present, at most 60% of the total substrate present, at most 70% of the total substrate present, at most 80% of the total substrate present or at most 90% of the total substrate present. In another aspect of this embodiment, the amount of Clostridial toxin substrate cleaved within a temperature range is 100%.

In still another embodiment, it is foreseen that any and all times sufficient for the detection of the presence of Clostridial toxin substrate cleavage products can be used in methods disclosed in the present specification. Assay times can be varied as appropriate by the skilled artisan and generally depend, in part, on the concentration, purity and activity of the Clostridial toxin, the sample to be assayed, incubation temperature or the convenience of the artisan. Assay times generally vary, without limitation, in the range of about 15 minutes to about 4 hours, 30 minutes to 8 hours, 1 hour to 12 hours, 2 hours to 24 hours, 4 hours to 48 hours, 6 hours to 72 hours. In aspects of this embodiment, the amount of Clostridial toxin substrate cleaved during an assay time is, e.g., at least 10% of the total substrate present, at least 20% of the total substrate present, at least 30% of the total substrate present, at least 40% of the total substrate present, at least 50% of the total substrate present, at least 60% of the total substrate present, at least 70% of the total substrate present, at least 80% of the total substrate present or at least 90% of the total substrate present. In further aspects of this embodiment, the amount of Clostridial toxin substrate cleaved during an assay time is, e.g., at most 10% of the total substrate present, at most 20% of the total substrate present, at most 30% of the total substrate present, at most 40% of the total substrate present, at most 50% of the total substrate present, at most 60% of the total substrate present, at most 70% of the total substrate present, at most 80% of the total substrate present or at most 90% of the total substrate present. In another aspect of this embodiment, the amount of Clostridial toxin substrate cleaved during an assay time is 100%. It is understood that assays can be terminated, if desired, prior to exciting the fluorescent protein.

Aspects of the present invention can also be described as follows:

1. A cell composition, comprising a) a membrane-associated Clostridial toxin substrate comprising i) a first member of a fluorescence resonance energy transfer (FRET) pair; and ii) a Clostridial toxin recognition sequence including a cleavage site; and b) a membrane-associated second member of said FRET pair, wherein said cell is capable of Clostridial toxin intoxication; wherein said FRET pair comprises an acceptor having an absorbance spectrum overlapping the emission spectrum of a donor fluorophore; and wherein under the appropriate conditions, resonance energy transfer is exhibited between said first and said second members of said FRET pair.
2. The composition of 1, wherein said cell transiently contains said Clostridial toxin substrate.
3. The composition of 1, wherein said cell stably contains said Clostridial toxin substrate.
4. The composition of 1, wherein said substrate is expressed from a nucleic acid molecule.
5. The composition of 4, wherein said substrate comprises a viral expression construct encoding a Clostridial toxin substrate.
6. The composition of 1, wherein said cell is a neuronal cell.
7. The composition of 6, wherein said neuronal cell is selected from the group consisting of a primary neuronal cell, an immortalized neuronal cell and a transformed neuronal cell.

8. The composition of 6, wherein said neuronal cell is selected from the group consisting of a neuroblastoma cell, a neuronal hybrid cell, a spinal cord cell, a central nervous system cell, a cerebral cortex cell, a dorsal root ganglion cell, a hippocampal cell and a pheochromocytoma cell.

9. The composition of 6, wherein said neuronal cell is selected from the group consisting of Neuro-2a, SH-SY5Y, NG108-C15, N1E-115, ND8/34 and SK-N-DZ.

10. The composition of 1, wherein said cell is a non-neuronal cell.

11. The composition of 10, wherein said non-neuronal cell is selected from the group consisting of a primary non-neuronal cell, an immortalized non-neuronal cell and a transformed non-neuronal cell.

12. The composition of 10, wherein said non-neuronal cell is selected from the group consisting of an anterior pituitary cell, an adrenal cell, a pancreatic cell, an ovarian cell, a kidney cell, a stomach cell, a blood cell, an epithelial cell, a fibroblast, a thyroid cell, a chondrocyte, a muscle cell, a hepatocyte, a glandular cell.

13. The composition of 12, wherein said kidney cell is HEK-293.

14. The composition of 1, wherein said cell is sensitive to said intoxication at Clostridial toxin concentrations of 2 nM and below.

15. The composition of 1, wherein said cell is sensitive to said intoxication at Clostridial toxin concentrations of 0.1 nM and below.

16. The composition of 1, wherein said cell is sensitive to said intoxication at Clostridial toxin concentrations of 0.02 nM and below.

17. The composition of 1, wherein said first member of said FRET pair is a fluorescent protein.

18. The composition of 17, wherein said fluorescent protein is selected from the group consisting of a green fluorescent protein, a blue fluorescent protein, a cyan fluorescent protein, a yellow fluorescent protein and a red fluorescent protein.

19. The composition of 1, wherein said first member of said FRET pair is a fluorophore binding protein.

20. The composition of 19, wherein said fluorophore binding protein is selected from the group consisting of a tetracysteine peptide, an AGT and a dehalogenase.

21. The composition of 20, wherein said tetracysteine peptide binds to a fluorophore selected from the group consisting of a nonfluorescent biarsenical derivitive of fluorescein and a nonfluorescent biarsenical derivitive of resorufin.

22. The composition of 20, wherein said AGT binds to a fluorophore selected from the group consisting of a para-benzyl guanine diethylaminocoumarin, a para-benzyl guanine diacetylfluorescein, a para-benzyl guanine dyomic DY-505-05, a para-benzyl guanine ATTO 488, a para-benzyl guanine ATTO 532, a para-benzyl guanine dyomic DY-547, a para-benzyl guanine tetramethylrhodamine, a para-benzyl guanine ATTO 600, a para-benzyl guanine dyomic DY-632, a para-benzyl guanine dyomic DY-647, a para-benzyl guanine dyomic DY-732 and a para-benzyl guanine dyomic DY-747.

23. The composition of 20, wherein said dehalogenase binds to a fluorophore selected from the group consisting of a HaloTag Coumarian, a HaloTag diAcFAM and a HaloTag TMR.

24. The composition of 1, wherein said substrate comprises a Clostridial toxin recognition sequence selected from the group consisting of a BoNT/A recognition sequence including a cleavage site, a BoNT/B recognition sequence including a cleavage site, a BoNT/C1 recognition sequence including a cleavage site, a BoNT/D recognition sequence including a cleavage site, a BoNT/E recognition sequence including a cleavage site, a BoNT/F recognition sequence including a cleavage site, a BoNT/G recognition sequence including a cleavage site and a TeNT recognition sequence including a cleavage site.

25. The composition of 1, wherein said Clostridial toxin recognition sequence comprises at least six consecutive residues of SNAP-25, said six consecutive residues comprising Gln-Arg.

26. The composition of 1, wherein said Clostridial toxin recognition sequence comprises at least six consecutive residues of VAMP, said six consecutive residues comprising Gln-Phe.

27. The composition of 1, wherein said Clostridial toxin recognition sequence comprises at least six consecutive residues of SNAP-25, said six consecutive residues comprising Arg-Ala.

28. The composition of 1, wherein said Clostridial toxin recognition sequence comprises at least six consecutive residues of Syntaxin, said six consecutive residues comprising Lys-Ala.

29. The composition of 1, wherein said Clostridial toxin recognition sequence comprises at least six consecutive residues of VAMP, said six consecutive residues comprising Lys-Leu.

30. The composition of 1, wherein said Clostridial toxin recognition sequence comprises at least six consecutive residues of SNAP-25, said six consecutive residues comprising Arg-Ile.

31. The composition of 1, wherein said Clostridial toxin recognition sequence comprises at least six consecutive residues of VAMP, said six consecutive residues comprising Gln-Lys.

32. The composition of 1, wherein said Clostridial toxin recognition sequence comprises at least six consecutive residues of VAMP, said six consecutive residues comprising Ala-Ala.

33. The composition of 1, wherein said second member of said FRET pair is a lipophilic dye.

34. The composition of 33, wherein said lipophilic dye is selected from the group consisting of a DiO, a DiA, a DiS, a DiI, a DiD and a DiR.

35. The composition of 47, wherein said lipophilic dye is selected from the group consisting of a DPH, a Dapoxyl, an ANS, a BODIPY and a FM dye 36. The composition of 1, wherein said donor fluorophore is selected from the group consisting of EBFP, ECFP, AmCyan and HaloTag Coumarian; and said acceptor is selected from the group consisting of $DiOC_{18}(3)$, $DiOC_{16}$ (3), SP-$DiOC_{18}$ (3), 4Di-16-ASP, FAST DiA and 4-Di-10-ASP.

37. The composition of 1, wherein said donor fluorophore is selected from the group consisting of DPH, TMA-DPH and 2,6-TNA; and said acceptor is selected from the group consisting of ECFP, AmCyan, AcGFP and AGT/BG-430.

38. The composition of 1, wherein said donor fluorophore is selected from the group consisting of AcGFP, ZsGreen, Vitality hrGFP, EGFP and Monster Green; and said acceptor is selected from the group consisting of $DiSBAC_2(3)$, $DilC_{18}$ (3), FM 1-84, FM 2-10 and RH 414.

39. The composition of 1, wherein said donor fluorophore is selected from the group consisting of DPH, laurdan and bis-ANS; and said acceptor is selected from the group consisting of AmCyan, AcGFP, ZsGreen, Vitality hrGFP, EGFP, Monster Green, tetracysteine/FlAsH, AGT/BG-DAF, AGT/BG-505, AGT/BG-488 and HaloTag diAcFAM.

40. The composition of 1, wherein said donor fluorophore is selected from the group consisting of Monster Green, EYFP, ZsYellow, tetracysteine/FlAsH, AGT/BG-DAF, AGT/BG-505, AGT/BG-488 and HaloTag diAcFAM; and said acceptor is selected from the group consisting of FM 1-84, $DiSBAC_2(3)$, $DilC_{18}$ (3), $DilC_{16}$ (3), $DilC_{12}$ (3), FAST Dil, $DilC_{18}$ (3)-DS and SP-$DilC_{18}$ (3).

41. The composition of 1, wherein said donor fluorophore is selected from the group consisting of FAST DiO, $DiOC_{18}$ (3), $DiOC_{16}$ (3), SP-$DiOC_{18}$ (3), laurdan and bis-ANS; and said acceptor is selected from the group consisting of Monster Green, EYFP, ZsYellow, tetracysteine/FlAsH, AGT/BG-DAF, AGT/BG-505, AGT/BG-488 and HaloTag diAcFAM.

42. A neuronal cell composition, comprising a) a stably expressed nucleic acid molecule which encodes a membrane-associated BoNT/A substrate comprising i) a first member of a fluorescence resonance energy transfer (FRET) pair; and ii) a BoNT/A recognition sequence including a cleavage site; and b) a membrane-associated second member of said FRET pair comprising a membrane-associated lipophilic dye which has an absorbance spectrum overlapping the emission spectrum of said fluorescent protein; wherein said neuronal cell is capable of BoNT/A intoxication; and wherein said FRET pair comprises an acceptor having an absorbance spectrum overlapping the emission spectrum of a donor fluorophore; and wherein under the appropriate conditions, resonance energy transfer is exhibited between said first and said second members of said FRET pair.

43. The composition of 42, wherein said neuronal cell is selected from the group consisting of a primary neuronal cell, an immortalized neuronal cell and a transformed neuronal cell.

44. The composition of 42, wherein said neuronal cell is selected from the group consisting of a neuroblastoma cell, a neuronal hybrid cell, a spinal cord cell, a central nervous system cell, a cerebral cortex cell, a dorsal root ganglion cell, a hippocampal cell and a pheochromocytoma cell.

45. The composition of 42, wherein said neuronal cell is selected from the group consisting of Neuro-2a, SH-SY5Y, NG108-C15, N1E-115, ND8/34 and SK-N-DZ.

46. The composition of 42, wherein said first member of said FRET pair is a fluorescent protein.

47. The composition of 46, wherein said fluorescent protein is selected from the group consisting of a green fluorescent protein, a blue fluorescent protein, a cyan fluorescent protein, a yellow fluorescent protein and a red fluorescent protein.

48. The composition of 42, wherein said first member of said FRET pair is a fluorophore binding protein.

49. The composition of 48, wherein said fluorophore binding protein is selected from the group consisting of a tetracysteine peptide, an AGT and a dehalogenase.

50. The composition of 49, wherein said tetracysteine peptide binds to a fluorophore selected from the group consisting of a nonfluorescent biarsenical derivitive of fluorescein and a nonfluorescent biarsenical derivitive of resorufin.

51. The composition of 49, wherein said AGT binds to a fluorophore selected from the group consisting of a para-benzyl guanine diethylaminocoumarin, a para-benzyl guanine diacetylfluorescein, a para-benzyl guanine dyomic DY-505-05, a para-benzyl guanine ATTO 488, a para-benzyl guanine ATTO 532, a para-benzyl guanine dyomic DY-547, a para-benzyl guanine tetramethylrhodamine, a para-benzyl guanine ATTO 600, a para-benzyl guanine dyomic DY-632, a para-benzyl guanine dyomic DY-647, a para-benzyl guanine dyomic DY-732 and a para-benzyl guanine dyomic DY-747.

52. The composition of 49, wherein said dehalogenase binds to a fluorophore selected from the group consisting of a HaloTag Coumarian, a HaloTag diAcFAM and a HaloTag TMR.

53. The composition of 42, wherein said BoNT/A toxin recognition sequence comprises at least six consecutive residues of SNAP-25, said six consecutive residues comprising Gln-Arg.

54. The composition of 42, wherein said BoNT/A toxin recognition sequence is selected from the group consisting of SEQ ID NO: 1, SEQ ID NO: 2, SEQ ID NO: 5, SEQ ID NO: 6, SEQ ID NO: 7, SEQ ID NO: 8, , SEQ ID NO: 12, SEQ ID NO: 13, SEQ ID NO: 14, SEQ ID NO: 15, , SEQ ID NO: 17, SEQ ID NO: 18, and SEQ ID NO: 19.

55. The composition of 42, wherein said second member of said FRET pair is a lipophilic dye.

56. The composition of 55, wherein said lipophilic dye is selected from the group consisting of a DiO, a DiA, a DiS, a Dil, a DiD and a DiR.

57. The composition of 55, wherein said lipophilic dye is selected from the group consisting of a DPH, a Dapoxyl, an ANS, a BODIPY and a FM dye 58. The composition of 42, wherein said donor fluorophore is selected from the group consisting of EBFP, ECFP, AmCyan and HaloTag Coumarian; and said acceptor is selected from the group consisting of $DiOC_{18}(3)$, $DiOC_{16}$ (3), SP-$DiOC_{18}$ (3), 4Di-16-ASP, FAST DiA and 4-Di-10-ASP.

59. The composition of 42, wherein said donor fluorophore is selected from the group consisting of DPH, TMA-DPH and 2,6-TNA; and said acceptor is selected from the group consisting of ECFP, AmCyan, AcGFP and AGT/BG-430.

60. The composition of 42, wherein said donor fluorophore is selected from the group consisting of AcGFP, ZsGreen, Vitality hrGFP, EGFP and Monster Green; and said acceptor is selected from the group consisting of $DiSBAC_2(3)$, $DilC_{18}$ (3), FM 1-84, FM 2-10 and RH 414.

61. The composition of 42, wherein said donor fluorophore is selected from the group consisting of DPH, laurdan and bis-ANS; and said acceptor is selected from the group consisting of AmCyan, AcGFP, ZsGreen, Vitality hrGFP, EGFP, Monster Green, tetracysteine/FlAsH, AGT/BG-DAF, AGT/BG-505, AGT/BG-488 and HaloTag diAcFAM.

62. The composition of 42, wherein said donor fluorophore is selected from the group consisting of Monster Green, EYFP, ZsYellow, tetracysteine/FlAsH, AGT/BG-DAF, AGT/BG-505, AGT/BG-488 and HaloTag diAcFAM; and said acceptor is selected from the group consisting of FM 1-84, $DiSBAC_2(3)$, $DilC_{18}$ (3), $DilC_{16}$ (3), $DilC_{12}$ (3), FAST Dil, $DilC_{18}$ (3)-DS and SP-$DilC_{18}$ (3).

63. The composition of 42, wherein said donor fluorophore is selected from the group consisting of FAST DiO, $DiOC_{18}$ (3), $DiOC_{16}$ (3), SP-$DiOC_{18}$ (3), laurdan and bis-ANS; and said acceptor is selected from the group consisting of Monster Green, EYFP, ZsYellow, tetracysteine/FlAsH, AGT/BG-DAF, AGT/BG-505, AGT/BG-488 and HaloTag diAcFAM.

64. A neuronal cell, comprising a) a stably expressed nucleic acid molecule which encodes a membrane-associated BoNT/E substrate comprising i) a fluorescent protein and ii) a BoNT/E recognition sequence including a cleavage site; and b) a membrane-associated lipophilic dye which has an absorbance spectrum overlapping the emission spectrum of said fluorescent protein; wherein said neuronal cell is capable of BoNT/E intoxication; and wherein under the appropriate conditions, fluorescence resonance energy transfer is exhibited between said fluorescent protein and said lipophilic dye.

65. The composition of 64, wherein said neuronal cell is selected from the group consisting of a primary neuronal cell, an immortalized neuronal cell and a transformed neuronal cell.

66. The composition of 64, wherein said neuronal cell is selected from the group consisting of a neuroblastoma cell, a neuronal hybrid cell, a spinal cord cell, a central nervous system cell, a cerebral cortex cell, a dorsal root ganglion cell, a hippocampal cell and a pheochromocytoma cell.

67. The composition of 64, wherein said neuronal cell is selected from the group consisting of Neuro-2a, SH-SY5Y, NG108-C15, N1E-115and SK-N-DZ.

68. The composition of 64, wherein said first member of said FRET pair is a fluorescent protein.

69. The composition of 68, wherein said fluorescent protein is selected from the group consisting of a green fluorescent protein, a blue fluorescent protein, a cyan fluorescent protein, a yellow fluorescent protein and a red fluorescent protein.

70. The composition of 64, wherein said first member of said FRET pair is a fluorophore binding protein.

71. The composition of 70, wherein said fluorophore binding protein is selcted from the group consisting of a tetracysteine peptide, a AGT and a dehalogenase.

72. The composition of 71, wherein said tetracysteine peptide binds to a fluorophore selected from the group consisting of a nonfluorescent biarsenical derivitive of fluorescein and a nonfluorescent biarsenical derivitive of resorufin.

73. The composition of 71, wherein said AGT binds to a fluorophore selected from the group consisting of a para-benzyl guanine diethylaminocoumarin, a para-benzyl guanine diacetylfluorescein, a para-benzyl guanine dyomic DY-505-05, a para-benzyl guanine ATTO 488, a para-benzyl guanine ATTO 532, a para-benzyl guanine dyomic DY-547, a para-benzyl guanine tetramethylrhodamine, a para-benzyl guanine ATTO 600, a para-benzyl guanine dyomic DY-632, a para-benzyl guanine dyomic DY-647, a para-benzyl guanine dyomic DY-732 and a para-benzyl guanine dyomic DY-747.

74. The composition of 71, wherein said dehalogenase binds to a fluorophore selected from the group consisting of a HaloTag Coumarian, a HaloTag diAcFAM and a HaloTag TMR.

75. The composition of 64, wherein said BoNT/E recognition sequence comprises at least six consecutive residues of SNAP-25, said six consecutive residues comprising Arg-Ile.

76. The composition of 64, wherein said BoNT/E toxin recognition sequence is selected from the group consisting of SEQ ID NO: 1, SEQ ID NO: 2, SEQ ID NO: 5, SEQ ID NO: 6, SEQ ID NO: 7, SEQ ID NO: 8,, SEQ ID NO: 12, SEQ ID NO: 13, SEQ ID NO: 14, SEQ ID NO: 15,, SEQ ID NO: 17, SEQ ID NO: 18, and SEQ ID NO: 19.

77. The composition of 64, wherein said second member of said FRET pair is a lipophilic dye.

78. The composition of 77, wherein said lipophilic dye is selected from the group consisting of a DiO, a DiA, a DiS, a Dil, a DiD and a DiR.

79. The composition of 77, wherein said lipophilic dye is selected from the group consisting of a DPH, a Dapoxyl, an ANS, a BODIPY and a FM dye 80. The composition of 64, wherein said donor fluorophore is selected from the group consisting of EBFP, ECFP, AmCyan and HaloTag Coumarian; and said acceptor is selected from the group consisting of $DiOC_{18}(3)$, $DiOC_{16}$ (3), SP-$DiOC_{18}$ (3), 4Di-16-ASP, FAST DiA and 4-Di-10-ASP.

81. The composition of 64, wherein said donor fluorophore is selected from the group consisting of DPH, TMA-DPH and 2,6-TNA; and said acceptor is selected from the group consisting of ECFP, AmCyan, AcGFP and AGT/BG-430.

82. The composition of claim 64, wherein said donor fluorophore is selected from the group consisting of AcGFP, ZsGreen, Vitality hrGFP, EGFP and Monster Green; and said acceptor is selected from the group consisting of $DiSBAC_2(3)$, $DilC_{18}$ (3), FM 1-84, FM 2-10 and RH 414.

83. The composition of 64, wherein said donor fluorophore is selected from the group consisting of DPH, laurdan and bis-ANS; and said acceptor is selected from the group consisting of AmCyan, AcGFP, ZsGreen, Vitality hrGFP, EGFP, Monster Green, tetracysteine/FlAsH, AGT/BG-DAF, AGT/BG-505, AGT/BG-488 and HaloTag diAcFAM.

84. The composition of 64, wherein said donor fluorophore is selected from the group consisting of Monster Green, EYFP, ZsYellow, tetracysteine/FlAsH, AGT/BG-DAF, AGT/BG-505, AGT/BG-488 and HaloTag diAcFAM; and said acceptor is selected from the group consisting of FM 1-84, $DiSBAC_2(3)$, $DilC_{18}$ (3), $DilC_{16}$ (3), $DilC_{12}$ (3), FAST Dil, $DilC_{18}$ (3)-DS and SP-$DilC_{18}$ (3).

85. The composition of 64, wherein said donor fluorophore is selected from the group consisting of FAST DiO, $DiOC_{18}$ (3), $DiOC_{16}$ (3), SP-$DiOC_{18}$ (3), laurdan and bis-ANS; and said acceptor is selected from the group consisting of Monster Green, EYFP, ZsYellow, tetracysteine/FIAsH, AGT/BG-DAF, AGT/BG-505, AGT/BG-488 and HaloTag diAcFAM.

86. A method of determining Clostridial toxin activity, comprising a) contacting with a sample a cell comprising 1) a membrane-associated Clostridial toxin substrate comprising i) a first member of a fluorescence resonance energy transfer (FRET) pair; and ii) a Clostridial toxin recognition sequence including a cleavage site; and 2) a membrane-associated second member of said FRET pair; wherein said cell is capable of Clostridial toxin intoxication; wherein said FRET pair comprises an acceptor having an absorbance spectrum overlapping the emission spectrum of a donor fluorophore; and wherein under the appropriate conditions, resonance energy transfer is exhibited between said first and said second members of said FRET pair; b) exciting said donor fluorophore; and c) determining fluorescence resonance energy transfer of said contacted cell relative to a control cell; wherein a difference in fluorescence resonance energy transfer of said contacted cell as compared to said control cell is indicative of Clostridial toxin activity.

87. The method of 86, wherein said sample is selected from the group consisting of a purified Clostridial toxin, a partially purified Clostridial toxin or unpurified Clostridial toxin.

88. The method of 86, wherein said sample is selected from the group consisting of a purified Clostridial toxin light chain, a partially purified Clostridial toxin light chain or unpurified Clostridial toxin light chain.

89. The method of 86, wherein said sample is selected from the group consisting of a bulk Clostridial toxin, a formulated Clostridial toxin, a cosmetics Clostridial toxin formulation or a clinical Clostridial toxin formulation.

90. The method of 86, wherein said sample is a recombinant Clostridial toxin.

91. The method of 86, wherein said sample is a recombinant Clostridial toxin light chain.

92. The method of 86, wherein said sample is selected from the group consisting of a raw food, a cooked food, a partially cooked food or a processed food.

93. The method of 86, wherein said sample is a sample taken from a mammal.

94. The method of 93, wherein said mammalian sample is selected from the group consisting of a tissue, a saliva, an excretion or a feces.

95. The method of 86, wherein said cell transiently contains said Clostridial toxin substrate.

96. The method of 86, wherein said cell stably contains said Clostridial toxin substrate.

97. The method of 86, wherein said cell is a neuronal cell.

98. The method of 97, wherein said neuronal cell is selected from teh group consisting of a primary neuronal cell, an immortalized neuronal cell and a transformed neuronal cell.

99. The method of 97, wherein said neuronal cell is selected from the group consisting of a neuroblastoma cell, a neuronal hybrid cell, a spinal cord cell, a central nervous system cell, a cerebral cortex cell, a dorsal root ganglion cell, a hippocampal cell and a pheochromocytoma cell.

100. The method of 86, wherein said cell is a non-neuronal cell.

101. The method of 100, wherein said non-neuronal cell is selected from the group consisting of a primary neuronal cell, an immortalized neuronal cell and a transformed neuronal cell.

102. The method of 100, wherein said non-neuronal cell is selected from the group consisting of an anterior pituitary cell, an adrenal cell, a pancreatic cell, an ovarian cell, a kidney cell, a stomach cell, a blood cell, an epithelial cell, a fibroblast, a thyroid cell, a chondrocyte, a muscle cell, a hepatocyte, a glandular cell.

103. The method of 86, wherein said cell is sensitive to said intoxication at Clostridial toxin concentrations of 2 nM and below.

104. The method of 86, wherein said cell is sensitive to said intoxication at Clostridial toxin concentrations of 0.1 nM and below.

105. The method of 86, wherein said cell is sensitive to said intoxication at Clostridial toxin concentrations of 0.02 nM and below.

106. The composition of 86, wherein said first member of said FRET pair is a fluorescent protein.

107. The composition of 106, wherein said fluorescent protein is selected from the group consisting of a green fluorescent protein, a blue fluorescent protein, a cyan fluorescent protein, a yellow fluorescent protein and a red fluorescent protein.

108. The composition of 86, wherein said first member of said FRET pair is a fluorophore binding protein.

109. The composition of 108, wherein said fluorophore binding protein is selcted from the group consisting of a tetracysteine peptide, a AGT and a dehalogenase.

110. The composition of 109, wherein said tetracysteine peptide binds to a fluorophore selected from the group consisting of a nonfluorescent biarsenical derivitive of fluorescein and a nonfluorescent biarsenical derivitive of resorufin.

111. The composition of 109, wherein said AGT binds to a fluorophore selected from the group consisting of a para-benzyl guanine diethylaminocoumarin, a para-benzyl guanine diacetylfluorescein, a para-benzyl guanine dyomic DY-505-05, a para-benzyl guanine ATTO 488, a para-benzyl guanine ATTO 532, a para-benzyl guanine dyomic DY-547, a para-benzyl guanine tetramethylrhodamine, a para-benzyl guanine ATTO 600, a para-benzyl guanine dyomic DY-632, a para-benzyl guanine dyomic DY-647, a para-benzyl guanine dyomic DY-732 and a para-benzyl guanine dyomic DY-747.

112. The composition of 109, wherein said dehalogenase binds to a fluorophore selected from the group consisting of a HaloTag Coumarian, a HaloTag diAcFAM and a HaloTag TMR.

113. The method of 86, wherein said substrate comprises a Clostridial toxin recognition sequence selected from the group consisting of a BoNT/A recognition sequence including a cleavage site, a BoNT/B recognition sequence including a cleavage site, a BoNT/C1 recognition sequence including a cleavage site, a BoNT/D recognition sequence including a cleavage site, a BoNT/E recognition sequence including a cleavage site, a BoNT/F recognition sequence including a cleavage site, a BoNT/G recognition sequence including a cleavage site and a TeNT recognition sequence including a cleavage site.

114. The method of 86, wherein said second member of said FRET pair is a lipophilic dye.

115. The method of 86, wherein said second member of said FRET pair is a lipophilic dye.

116. The method of 115, wherein said lipophilic dye is selected from the group consisting of a DiO, a DiA, a DiS, a Dil, a DiD and a DiR.

117. The method of 115, wherein said lipophilic dye is selected from the group consisting of a DPH, a Dapoxyl, an ANS, a BODIPY and a FM dye 118. The method of 86, wherein said donor fluorophore is selected from the group consisting of EBFP, ECFP, AmCyan and HaloTag Coumarian; and said acceptor is selected from the group consisting of $DiOC_{18}(3)$, $DiOC_{16}$ (3), SP-$DiOC_{18}$ (3), 4Di-16-ASP, FAST DiA and 4-Di-10-ASP.

119. The method of 86, wherein said donor fluorophore is selected from the group consisting of DPH, TMA-DPH and 2,6-TNA; and said acceptor is selected from the group consisting of ECFP, AmCyan, AcGFP and AGT/BG-430.

120. The method of 86, wherein said donor fluorophore is selected from the group consisting of AcGFP, ZsGreen, Vitality hrGFP, EGFP and Monster Green; and said acceptor is selected from the group consisting of $DiSBAC_2(3)$, $DilC_{18}$ (3), FM 1-84, FM 2-10 and RH 414.

121. The method of 86, wherein said donor fluorophore is selected from the group consisting of DPH, laurdan and bis-ANS; and said acceptor is selected from the group consisting of AmCyan, AcGFP, ZsGreen, Vitality hrGFP, EGFP, Monster Green, tetracysteine/FlAsH, AGT/BG-DAF, AGT/BG-505, AGT/BG-488 and HaloTag diAcFAM.

122. The method of 86, wherein said donor fluorophore is selected from the group consisting of Monster Green, EYFP, ZsYellow, tetracysteine/FlAsH, AGT/BG-DAF, AGT/BG-505, AGT/BG-488 and HaloTag diAcFAM; and said acceptor is selected from the group consisting of FM 1-84, $DiSBAC_2(3)$, $DilC_{18}$ (3), $DilC_{16}$ (3), $DilC_{12}$ (3), FAST Dil, $DilC_{18}$ (3)-DS and SP-$DilC_{18}$ (3).

123. The method of 86, wherein said donor fluorophore is selected from the group consisting of FAST DiO, $DiOC_{18}$ (3), $DiOC_{16}$ (3), SP-$DiOC_{18}$ (3), laurdan and bis-ANS; and said acceptor is selected from the group consisting of Monster Green, EYFP, ZsYellow, tetracysteine/FlAsH, AGT/BG-DAF, AGT/BG-505, AGT/BG-488 and HaloTag diAcFAM.

124. The method of 86, step (c) comprising detecting acceptor fluorescence intensity of said contacted cell, wherein decreased acceptor fluorescence intensity of said contacted cell as compared to said control cell is indicative of Clostridial toxin activity.

125. The method of 86, step (c) comprising detecting donor fluorescence intensity of said contacted cell, wherein increased donor fluorescence intensity of said contacted cell as compared to said control cell is indicative of Clostridial toxin activity.

126. The method of 86, step (c) comprising detecting an acceptor emission maximum and a donor fluorophore emission maximum of said contacted cell, wherein a shift in emission maxima from near said acceptor emission maximum to near said donor fluorophore emission maximum is indicative of Clostridial toxin activity.

127. The method of 86, step (c) comprising detecting the ratio of fluorescence amplitudes near an acceptor emission maximum to the fluorescence amplitudes near a donor fluorophore emission maximum, wherein a decreased ratio in said contacted cell as compared to the control cell is indicative of Clostridial toxin activity.

128. The method of 86, step (c) comprising detecting the excited state lifetime of the donor fluorophore in said contacted cell, wherein an increased donor fluorophore excited state lifetime in said contacted cell as compared to said control cell is indicative of Clostridial toxin activity.

129. A method of determining BoNT/A activity, comprising a) contacting with a sample a neuronal cell comprising 1) a stably expressed nucleic acid molecule encoding a membrane-associated BoNT/A substrate comprising i) a first member of a fluorescence resonance energy transfer (FRET) pair; and ii) a BoNT/A recognition sequence including a cleavage site; and 2) a second member of a fluorescence resonance energy transfer (FRET) pair comprising a membrane-associated lipophilic dye which has an absorbance spectrum overlapping the emission spectrum of said fluorescent protein; wherein said cell is capable of Clostridial toxin intoxication; wherein said FRET pair comprises an acceptor having an absorbance spectrum overlapping the emission spectrum of a donor fluorophore; and wherein under the appropriate conditions, resonance energy transfer is exhibited between said first and said second members of said FRET pair; b) exciting said donor fluorophore; and c) determining fluorescence resonance energy transfer of said contacted neuronal cell relative to a control cell; wherein a difference in fluorescence resonance energy transfer of said contacted neuronal cell as compared to said control cell is indicative of BoNT/A activity.

130. The method of 129, wherein said sample is selected from the group consisting of a purified BoNT/A, a partially purified BoNT/A or unpurified BoNT/A.

131. The method of 129, wherein said sample is selected from the group consisting of a purified BoNT/A light chain, a partially purified BoNT/A light chain or unpurified BoNT/A light chain.

132. The method of 129, wherein said sample is selected from the group consisting of a bulk BoNT/A, a formulated BoNT/A, a cosmetic BoNT/A formulation or a clinical BoNT/A formulation.

133. The method of 129, wherein said sample is a recombinant BoNT/A.

134. The method of 129, wherein said sample is a recombinant BoNT/A light chain.

135. The method of 129, wherein said sample is selected from the group consisting of a raw food, a cooked food, a partially cooked food or a processed food.

136. The method of 129, wherein said sample is a sample taken from a mammal.

137. The method of 136, wherein said mammalian sample is selected from the group consisting of a tissue, a saliva, an excretion or a feces.

138. The method of 129, wherein said neuronal cell is selected from the group consisting of a primary neuronal cell, an immortalized neuronal cell and a transformed neuronal cell.

139. The method of 129, wherein said neuronal cell is selected from the group consisting of a neuroblastoma cell, a neuronal hybrid cell, a spinal cord cell, a central nervous system cell, a cerebral cortex cell, a dorsal root ganglion cell, a hippocampal cell and a pheochromocytoma cell.

140. The method of 129, wherein said neuronal cell is selected from the group consisting of Neuro-2a, SH-SY5Y, NG108-C15, N1E-115, ND8/34, and SK-N-DZ.

141. The composition of 129, wherein said first member of said FRET pair is a fluorescent protein.

142. The composition of 141, wherein said fluorescent protein is selected from the group consisting of a green fluorescent protein, a blue fluorescent protein, a cyan fluorescent protein, a yellow fluorescent protein and a red fluorescent protein.

143. The composition of 129, wherein said first member of said FRET pair is a fluorophore binding protein.

144. The composition of 143, wherein said fluorophore binding protein is selcted from the group consisting of a tetracysteine peptide, an AGT and a dehalogenase.

145. The composition of 144, wherein said tetracysteine peptide binds to a fluorophore selected from the group consisting of a nonfluorescent biarsenical derivitive of fluorescein and a nonfluorescent biarsenical derivitive of resorufin.

146. The composition of 144, wherein said AGT binds to a fluorophore selected from the group consisting of a para-benzyl guanine diethylaminocoumarin, a para-benzyl guanine diacetylfluorescein, a para-benzyl guanine dyomic DY-505-05, a para-benzyl guanine ATTO 488, a para-benzyl guanine ATTO 532, a para-benzyl guanine dyomic DY-547, a para-benzyl guanine tetramethylrhodamine, a para-benzyl guanine ATTO 600, a para-benzyl guanine dyomic DY-632, a para-benzyl guanine dyomic DY-647, a para-benzyl guanine dyomic DY-732 and a para-benzyl guanine dyomic DY-747.

147. The composition of 144, wherein said dehalogenase binds to a fluorophore selected from the group consisting of a HaloTag Coumarian, a HaloTag diAcFAM and a HaloTag TMR.

148. The method of 129, wherein said BoNT/A toxin recognition sequence comprises at least six consecutive residues of SNAP-25, said six consecutive residues comprising Gln-Arg.

149. The method of 129, wherein said BoNT/A toxin recognition sequence is selected from the group consisting of SEQ ID NO: 1, SEQ ID NO: 2, SEQ ID NO: 5, SEQ ID NO: 6, SEQ ID NO: 7, SEQ ID NO: 8,, SEQ ID NO: 12, SEQ ID NO: 13, SEQ ID NO: 14, SEQ ID NO: 15, SEQ ID NO: 17, SEQ ID NO: 18, and SEQ ID NO: 19.

150. The method of 129, wherein said second member of said FRET pair is a lipophilic dye.

151. The method of 150, wherein said lipophilic dye is selected from the group consisting of a DiO, a DiA, a DiS, a DiI, a DiD and a DiR.

152. The method of 150, wherein said lipophilic dye is selected from the group consisting of a DPH, a Dapoxyl, an ANS, a BODIPY and a FM dye 153. The method of 129, wherein said donor fluorophore is selected from the group consisting of EBFP, ECFP, AmCyan and HaloTag Coumarian; and said acceptor is selected from the group consisting of $DiOC_{18}(3)$, $DiOC_{16}$ (3), SP-$DiOC_{18}$ (3), 4Di-16-ASP, FAST DiA and 4-Di-10-ASP.

154. The method of 129, wherein said donor fluorophore is selected from the group consisting of DPH, TMA-DPH and 2,6-TNA; and said acceptor is selected from the group consisting of ECFP, AmCyan, AcGFP and AGT/BG-430.

155. The method of 129, wherein said donor fluorophore is selected from the group consisting of AcGFP, ZsGreen, Vitality hrGFP, EGFP and Monster Green; and said acceptor is selected from the group consisting of $DiSBAC_2(3)$, $DiIC_{18}$ (3), FM 1-84, FM 2-10 and RH 414.

156. The method of 129, wherein said donor fluorophore is selected from the group consisting of DPH, laurdan and bis-ANS; and said acceptor is selected from the group consisting of AmCyan, AcGFP, ZsGreen, Vitality hrGFP, EGFP, Monster Green, tetracysteine/FlAsH, AGT/BG-DAF, AGT/BG-505, AGT/BG-488 and HaloTag diAcFAM.

157. The method of 129, wherein said donor fluorophore is selected from the group consisting of Monster Green, EYFP, ZsYellow, tetracysteine/FlAsH, AGT/BG-DAF, AGT/BG-505, AGT/BG-488 and HaloTag diAcFAM; and said acceptor is selected from the group consisting of FM 1-84, $DiSBAC_2(3)$, $DiIC_{18}$ (3), $DiIC_{16}$ (3), $DiIC_{12}$ (3), FAST DiI, $DiIC_{18}$ (3)-DS and SP-$DiIC_{18}$ (3).

158. The method of 129, wherein said donor fluorophore is selected from the group consisting of FAST DiO, $DiOC_{18}$ (3), $DiOC_{16}$ (3), SP-$DiOC_{18}$ (3), laurdan and bis-ANS; and said acceptor is selected from the group consisting of Monster Green, EYFP, ZsYellow, tetracysteine/FlAsH, AGT/BG-DAF, AGT/BG-505, AGT/BG-488 and HaloTag diAcFAM.

159. The method of 129, step (c) comprising detecting acceptor fluorescence intensity of said contacted cell, wherein decreased acceptor fluorescence intensity of said contacted cell as compared to said control cell is indicative of BoNT/A activity.

160. The method of 129, step (c) comprising detecting donor fluorescence intensity of said contacted neuronal cell, wherein increased donor fluorescence intensity of said contacted neuronal cell as compared to said control cell is indicative of BoNT/A activity.

161. The method of 129, step (c) comprising detecting an acceptor emission maximum and a donor fluorophore emission maximum of said contacted neuronal cell, wherein a shift in emission maxima from near said acceptor emission maximum to near said donor fluorophore emission maximum is indicative of BoNT/A activity.

162. The method of 129, step (c) comprising detecting the ratio of fluorescence amplitudes near an acceptor emission maximum to the fluorescence amplitudes near a donor fluorophore emission maximum, wherein a decreased ratio in said contacted neuronal cell as compared to the control cell is indicative of BoNT/A activity.

163. The method of 159, step (c) comprising detecting the excited state lifetime of the donor fluorophore in said contacted neuronal cell, wherein an increased donor fluorophore excited state lifetime in said contacted neuronal cell as compared to said control cell is indicative of BoNT/A activity.

164. A method of determining BoNT/E activity, comprising a) contacting with a sample a neuronal cell comprising 1) a stably expressed nucleic acid molecule encoding a membrane-associated BoNT/E substrate comprising i) a first member of a fluorescence resonance energy transfer (FRET) pair; and ii) a BoNT/E recognition sequence including a cleavage site; and 2) a second member of a fluorescence resonance energy transfer (FRET) pair comprising a membrane-associated lipophilic dye which has an absorbance spectrum overlapping the emission spectrum of said fluorescent protein; wherein said cell is capable of Clostridial toxin intoxication; wherein said FRET pair comprises an acceptor having an absorbance spectrum overlapping the emission spectrum of a donor fluorophore; and wherein under the appropriate conditions, resonance energy transfer is exhibited between said first and said second members of said FRET pair; b) exciting said donor fluorophore; and c) determining fluorescence resonance energy transfer of said contacted neuronal cell relative to a control cell; wherein a difference in fluorescence resonance energy transfer of said contacted neuronal cell as compared to said control cell is indicative of BoNT/E activity.

165. The method of 164, wherein said sample is selected from the group consisting of a purified BoNT/E, a partially purified BoNT/E or unpurified BoNT/E.

166. The method of 164, wherein said sample is selected from the group consisting of a purified BoNT/E light chain, a partially purified BoNT/E light chain or unpurified BoNT/E light chain.

167. The method of 164, wherein said sample is selected from the group consisting of a bulk BoNT/E, a formulated BoNT/E, a cosmetic BoNT/E formulation or a clinical BoNT/E formulation.

168. The method of 164, wherein said sample is a recombinant BoNT/E. 169. The method of 164, wherein said sample is a recombinant BoNT/E light chain.

170. The method of 164, wherein said sample is selected from the group consisting of a raw food, a cooked food, a partially cooked food or a processed food.

171. The method of 164, wherein said sample is a sample taken from a mammal.

172. The method of 171, wherein said mammalian sample is selected from the group consisting of a tissue, a saliva, an excretion or a feces.

173. The composition of 164, wherein said neuronal cell is selected from the group consisting of a primary neuronal cell, an immortalized neuronal cell and a transformed neuronal cell.

174. The composition of 164, wherein said neuronal cell is selected from the group consisting of a neuroblastoma cell, a neuronal hybrid cell, a spinal cord cell, a central nervous system cell, a cerebral cortex cell, a dorsal root ganglion cell, a hippocampal cell and a pheochromocytoma cell.

175. The composition of claim 164, wherein said neuronal cell is selected from the group consisting of Neuro-2a, SH-SY5Y, NG108-C15, N1E-115and SK-N-DZ.

176. The composition of 164, wherein said first member of said FRET pair is a fluorescent protein.

177. The composition of 176, wherein said fluorescent protein is selected from the group consisting of a green fluorescent protein, a blue fluorescent protein, a cyan fluorescent protein, a yellow fluorescent protein and a red fluorescent protein.

178. The composition of 164, wherein said first member of said FRET pair is a fluorophore binding protein.
179. The composition of 178, wherein said fluorophore binding protein is selcted from the group consisting of a tetracysteine peptide, a AGT and a dehalogenase.
180. The composition of 179, wherein said tetracysteine peptide binds to a fluorophore selected from the group consisting of a nonfluorescent biarsenical derivitive of fluorescein and a nonfluorescent biarsenical derivitive of resorufin.
181. The composition of 179, wherein said AGT binds to a fluorophore selected from the group consisting of a para-benzyl guanine diethylaminocoumarin, a para-benzyl guanine diacetylfluorescein, a para-benzyl guanine dyomic DY-505-05, a para-benzyl guanine ATTO 488, a para-benzyl guanine ATTO 532, a para-benzyl guanine dyomic DY-547, a para-benzyl guanine tetramethylrhodamine, a para-benzyl guanine ATTO 600, a para-benzyl guanine dyomic DY-632, a para-benzyl guanine dyomic DY-647, a para-benzyl guanine dyomic DY-732and a para-benzyl guanine dyomic DY-747.
182. The composition of 179, wherein said dehalogenase binds to a fluorophore selected from the group consisting of a HaloTag Coumarian, a HaloTag diAcFAM and a HaloTag TMR.
183. The composition of 164, wherein said BoNT/E recognition sequence comprises at least six consecutive residues of SNAP-25, said six consecutive residues comprising Arg-Ile.
184. The composition of 164, wherein said BoNT/E toxin recognition sequence is selected from the group consisting of SEQ ID NO: 1, SEQ ID NO: 2, SEQ ID NO: 5, SEQ ID NO: 6, SEQ ID NO: 7, SEQ ID NO: 8,, SEQ ID NO: 12, SEQ ID NO: 13, SEQ ID NO: 14, SEQ ID NO: 15, SEQ ID NO: 17, SEQ ID NO: 18, and SEQ ID NO: 19.
185. The method of 164, wherein said second member of said FRET pair is a lipophilic dye.
186. The method of 185, wherein said lipophilic dye is selected from the group consisting of a DiO, a DiA, a DiS, a Dil, a DiD and a DiR.
187. The method of 185, wherein said lipophilic dye is selected from the group consisting of a DPH, a Dapoxyl, an ANS, a BODIPY and a FM dye.
188. The method of 164, wherein said donor fluorophore is selected from the group consisting of EBFP, ECFP, AmCyan and HaloTag Coumarian; and said acceptor is selected from the group consisting of $DiOC_{18}$(3), $DiOC_{16}$ (3), SP-$DiOC_{18}$ (3), 4Di-16-ASP, FAST DiA and 4-Di-10-ASP.
189. The method of 164, wherein said donor fluorophore is selected from the group consisting of DPH, TMA-DPH and 2,6-TNA; and said acceptor is selected from the group consisting of ECFP, AmCyan, AcGFP and AGT/BG-430.
190. The method of 164, wherein said donor fluorophore is selected from the group consisting of AcGFP, ZsGreen, Vitality hrGFP, EGFP and Monster Green; and said acceptor is selected from the group consisting of $DiSBAC_2$(3), $DilC_{18}$ (3), FM 1-84, FM 2-10and RH 414.
191. The method of 164, wherein said donor fluorophore is selected from the group consisting of DPH, laurdan and bis-ANS; and said acceptor is selected from the group consisting of AmCyan, AcGFP, ZsGreen, Vitality hrGFP, EGFP, Monster Green, tetracysteine/FlAsH, AGT/BG-DAF, AGT/BG-505, AGT/BG-488 and HaloTag diAcFAM.
192. The method of 164, wherein said donor fluorophore is selected from the group consisting of Monster Green, EYFP, ZsYellow, tetracysteine/FlAsH, AGT/BG-DAF, AGT/BG-505, AGT/BG-488 and HaloTag diAcFAM; and said acceptor is selected from the group consisting of FM 1-84, $DiSBAC_2$(3), $DilC_{18}$ (3), $DilC_{16}$ (3), $DilC_{12}$ (3), FAST Dil, $DilC_{18}$ (3)-DS and SP-$DilC_{18}$ (3).
193. The method of 164, wherein said donor fluorophore is selected from the group consisting of FAST DiO, $DiOC_{18}$ (3), $DiOC_{16}$ (3), SP-$DiOC_{18}$ (3), laurdan and bis-ANS; and said acceptor is selected from the group consisting of Monster Green, EYFP, ZsYellow, tetracysteine/FlAsH, AGT/BG-DAF, AGT/BG-505, AGT/BG-488 and HaloTag diAcFAM.
194. The method of 164, step (c) comprising detecting acceptor fluorescence intensity of said contacted cell, wherein decreased acceptor fluorescence intensity of said contacted cell as compared to said control cell is indicative of BoNT/E activity.
195. The method of 164, step (c) comprising detecting donor fluorescence intensity of said contacted neuronal cell, wherein increased donor fluorescence intensity of said contacted neuronal cell as compared to said control cell is indicative of BoNT/E activity.
196. The method of 164, step (c) comprising detecting an acceptor emission maximum and a donor fluorophore emission maximum of said contacted neuronal cell, wherein a shift in emission maxima from near said acceptor emission maximum to near said donor fluorophore emission maximum is indicative of BoNT/E activity.
197. The method of 164, step (c) comprising detecting the ratio of fluorescence amplitudes near an acceptor emission maximum to the fluorescence amplitudes near a donor fluorophore emission maximum, wherein a decreased ratio in said contacted neuronal cell as compared to the control cell is indicative of BoNT/E activity.
198. The method of 164, step (c) comprising detecting the excited state lifetime of the donor fluorophore in said contacted neuronal cell, wherein an increased donor fluorophore excited state lifetime in said contacted neuronal cell as compared to said control cell is indicative of BoNT/E activity.

The following examples are intended to illustrate but not limit aspects of the present invention.

EXAMPLES

The following non-limiting examples are provided for illustrative purposes only in order to facilitate a more complete understanding of disclosed embodiments and are in no way intended to limit any of the embodiments disclosed in the present invention.

Example I

Construction of Clostridial Toxin Substrates

1. Construction of BoNT/A, BoNT/C1 and BoNT/E SNAP-25 substrates

1a. Construction of pQBI25/SNAP-$25_{206}$-GFP

To construct pQBI-25/GFP-SNAP-$25_{206}$, a pGEX/SNAP-$25_{206}$ construct was digested with BamHI and EcoRI to excise a fragment containing the entire open reading frame of SNAP-$25_{206}$. The resulting restriction fragment was purified by the QIAquick Gel Extraction Kit (QIAGEN, Inc., Valencia, Calif.), and subcloned using a T4 DNA ligase procedure into a pQBI-25C3 vector (Qbiogene, Inc., Irvine, Calif.), digested BamHI and EcoRI, to yield pQBI-25/GFP-SNAP-$25_{206}$. The ligation mixture was transformed into chemically competent *E. coli* TOP10 cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Ampicillin-resistant colonies were analyzed using an alkaline lysis plasmid mini-preparation procedure and candidate expression constructs were screened by restriction endonuclease mapping to determine the presence and orientation of the correct insert fragment. Cultures containing the desired expression construct were used to inoculate 1 L baffled flasks containing 200 mL of Luria-Bertani media containing 100 μg/mL of Ampicillin and placed in a 37° C. incubator, shaking at 250 rpm, for overnight growth. Purified plasmid DNA corresponding to an expression construct was isolated using the QIAGEN Maxi-prep method (QIAGEN, Inc., Valencia, Calif.) and sequenced to verify that the correct expression construct was made (service contract with Sequetech Corp., Mountain View, Calif.). This cloning strategy yielded a pQBI-25 expression construct encoding a GFP-SNAP-$25_{206}$.

To construct pQBI-25/SNAP-$25_{206}$-GFP, a nucleic acid fragment encoding the amino acid region comprising SNAP-$25_{206}$ is amplified from pQBI-25/GFP-SNAP$25_{206}$ DNA using a polymerase chain reaction method and subcloned into a pCR2.1 vector using the TOPO® TA cloning method (Invitrogen, Inc, Carlsbad, Calif.). The resulting pCR2.1/SNAP-$25_{206}$ construct is digested with BamHI and EcoRI to excise a fragment containing the entire open reading frame of SNAP-$25_{206}$. The resulting restriction fragment was purified by the QIAquick Gel Extraction Kit (QIAGEN, Inc., Valencia, Calif.), and subcloned using a T4 DNA ligase procedure into a pQBI-25A2 vector (Qbiogene, Inc., Irvine, Calif.), digested BamHI and EcoRI, to yield pQBI-25/SNAP-$25_{206}$-GFP. The ligation mixture was transformed into chemically competent *E. coli* TOP10 cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Ampicillin-resistant colonies were analyzed using an alkaline lysis plasmid mini-preparation procedure and candidate expression constructs were screened by restriction endonuclease mapping to determine the presence and orientation of the correct insert fragment. Cultures containing the desired expression construct were used to inoculate 1 L baffled flasks containing 200 mL of Luria-Bertani media containing 100 μg/mL of Ampicillin and placed in a 37° C. incubator, shaking at 250 rpm, for overnight growth. Purified plasmid DNA corresponding to an expression construct was isolated using the QIAGEN Maxi-prep method (QIAGEN, Inc., Valencia, Calif.) and sequenced to verify that the correct expression construct was made (service contract with Sequetech Corp., Mountain View, Calif.). This cloning strategy yielded a pQBI-25 expression construct encoding a SNAP-$25_{206}$-GFP (see FIG. 5).

1b. Construction of pQBI25/SNAP-$25_{134}$-GFP

To construct pQBI-25/SNAP-$25_{206}$-GFP, a nucleic acid fragment encoding the amino acid region comprising SNAP-$25_{206}$ is amplified from pQBI-25/GFP-SNAP$25_{206}$ DNA using a polymerase chain reaction method and subcloned into a pCR2.1 vector using the TOPO® TA cloning method (Invitrogen, Inc, Carlsbad, Calif.). The resulting pCR2.1/SNAP-$25_{206}$ construct is digested with BamHI and EcoRI to excise a fragment containing the entire open reading frame of SNAP-$25_{206}$. The resulting restriction fragment was purified by the QIAquick Gel Extraction Kit (QIAGEN, Inc., Valencia, Calif.), and subcloned using a T4 DNA ligase procedure into a pQBI-25A2 vector (Qbiogene, Inc., Irvine, Calif.), digested BamHI and EcoRI, to yield pQBI-25/SNAP-$25_{206}$-GFP. The ligation mixture was transformed into chemically competent *E. coli* TOP10 cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Ampicillin-resistant colonies were analyzed using an alkaline lysis plasmid mini-preparation procedure and candidate expression constructs were screened by restriction endonuclease mapping to determine the presence and orientation of the correct insert fragment. Cultures containing the desired expression construct were used to inoculate 1 L baffled flasks containing 200 mL of Luria-Bertani media containing 100 μg/mL of Ampicillin and placed in a 37° C. incubator, shaking at 250 rpm, for overnight growth. Purified plasmid DNA corresponding to an expression construct was isolated using the QIAGEN Maxi-prep method (QIAGEN, Inc., Valencia, Calif.) and sequenced to verify that the correct expression construct was made (service contract with Sequetech Corp., Mountain View, Calif.). This cloning strategy yielded a pQBI-25 expression construct encoding a SNAP-$25_{206}$-GFP.

1c. Subcellular Localization of SNAP-25-GFP Substrate and Cleavage Products

Figure 6:
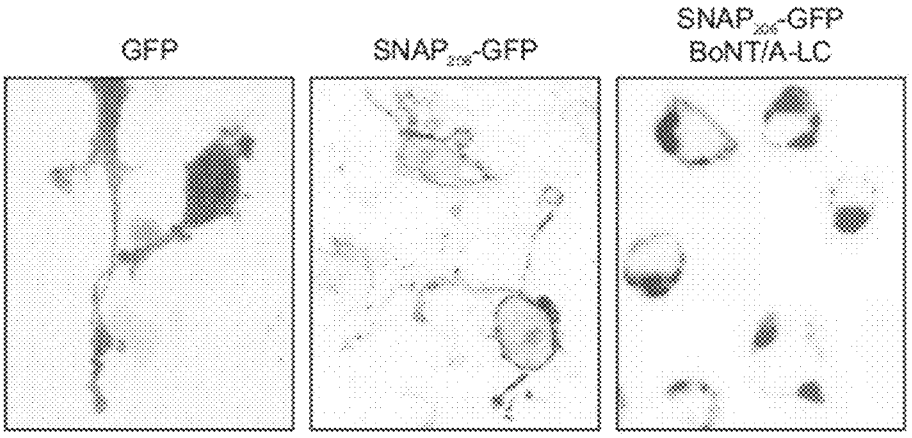
FIG. 6 shows PC12 cells transfected with a plasmid encoding a green fluorescent protein alone (GFP, transfected with a plasmid encoding a Clostridial toxin substrate alone (GFP-$SNAP25_{206}$), or co-transfected a plasmid encoding a Clostridial toxin substrate alone (GFP-$SNAP25_{206}$) and a plasmid encoding the light chain of BoNT/A (BoNT/A-LC). Cells expressing green fluorescent protein alone (GFP) had fluorescence dispersed throughout the cell including the nuclei. Confocal pictures were taken with the plane in the middle of the cell. Cells expressing the Clostridial toxin substrate alone (GFP-$SNAP25_{206}$) demonstrated fluorescence in the plasma membrane of the cell body and neurites. Cells co-expressing the Clostridial toxin substrate and the BoNT/A light chain (GFP-$SNAP25_{206}$, BoNT/A-LC) exhibit a loss of plasma membrane localization of the GFP fluorescence. The GFP fluorescence instead accumulates in some areas of the cytoplasm.

In order to determine whether a BoNT/A substrate can associate with the cell membrane, we assessed whether a cell expressing a plasmid encoding a SNAP-25-GFP substrate was able to localize the substrate to the cell membrane. To transiently express a SNAP-25-GFP substrate in a cell line, a suitable density of PC12 cells was plated into the wells of 6-well, poly-D-lysine/Laminin coated, tissue culture plates containing 3 mL of a suitable medium (see Table 13), and grown in a 37° C. incubator under 5% carbon dioxide until cells reach the desired density (see Table 13). A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 10 μg of a pQBI-25/GFP-SNAP-$25_{206}$ construct or 10 μg of a QBI-25/SNAP-$25_{206}$-GFP construct. This transfection was incubated at room temperature for approximately 20 minutes. The media was replaced with fresh unsupplemented media and the 500 μL transfection solution was added to the cells. The cells were then incubated in a 37° C. incubator under 5% carbon dioxide for approximately 6 to 18 hours. Transfection media was replaced with 3 mL of fresh media and incubate cells in a 37° C. incubator under 5% carbon dioxide. After 48 hours, cells were fixed with paraformaldehyde and imaged in a confocal microscope as described in, e.g., Ester Fernandez-Salas et al., Plasma membrane localization signals in the light chain of botulinum neurotoxin, 101(9) Proc. Natl. Acad. Sci. U.S.A. 3208-3213 (2004). Both the GFP-SNAP$25_{206}$ and SNAP$25_{206}$-GFP substrates localized to the plasma membrane (see FIG. 6).

In order to determine whether a cell membrane-localized BoNT/A substrate can be susceptible to BoNT/A cleavage, we assessed whether BoNT/A exposure to a cell containing a membrane-localized SNAP-25-GFP substrate resulted in the cleavage of the substrate. PC12 cells were transiently transfected with pQBI-25-SNAP$25_{206}$-GFP a plasmid construct that encodes a SNAP$25_{206}$-GFP substrate, and pcDNA3.1-LC/A, a plasmid construct that encodes the light chain of BoNT/A as described above in Example I, 1b. Observation of living cells 24 to 48 hours post-transfection using a fluorescence inverted microscope indicated that PC12 cells co-expressing SNAP$25_{206}$-GFP and the light chain of BoNT/A resulted in a change in fluorescent intensity relative to control cells expressing only the SNAP$25_{206}$-GFP substrate. The change in fluorescent intensity resulted from a reduced level of fluorescence emitted from the cells, as well as a change in subcellular localization of the GFP fluorescence; fluorescence in the cells co-expressing both substrate and enzyme was observed in the cytoplasm with accumulation in some areas or cytoplasmic structures (see FIG. 6). This cytoplasmic accumulation appears to represent the cleavage product containing the 9 amino acid cleavage fragment from SNAP-25 fused to GFP. These results indicate that there is a distinct fluorescence pattern as well as a different degree of fluorescence in cells containing the uncleaved $SNAP25_{206}$-GFP substrate as compared to cells containing the cleavage products of this substrate ($SNAP25_{197}$ and the remaining 9 residue fragment of SNAP-25 fused to GFP).

1d. Construction of pQBI67/SNAP-$25_{206}$-GFP

To construct pQBI-67/SNAP-$25_{206}$-GFP, a nucleic acid fragment encoding the amino acid region comprising SNAP-$25_{206}$-GFP substrate is amplified from pQBI-25/$SNAP25_{206}$-GFP DNA using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/SNAP-$25_{206}$-GFP construct is digested with restriction enzymes that 1) excise the insert containing the entire open reading frame encoding the SNAP-$25_{206}$-GFP peptide; and 2) enable this insert to be operably-linked to a pQBI-67 vector (Qbiogene, Inc., Irvine, Calif.). This insert is subcloned using a T4 DNA ligase procedure into a pQBI-67 vector that is digested with appropriate restriction endonucleases to yield pQBI-67/SNAP-$25_{206}$-GFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. This cloning strategy yields a mammalian expression construct encoding the SNAP-$25_{206}$-GFP operably-linked to the expression elements of the pQBI-67 vector.

2. Construction of BoNT/B, BoNT/D, BoNT/F, BoNT/G and TeNT VAMP Substrates

2a. Construction of pQBI25/VAMP-1-GFP

To make a VAMP-1 substrate suitable for methods disclosed in the present specification, a pQBI-25/VAMP-1-GFP construct will be made using a Splicing by Overlapping ends polymerase chain reaction (SOE-PCR) procedure, see, e.g., R. M. Horton et al., Engineering hybrid genes without the use of restriction enzymes: gene splicing by overlapping extension, 77(1) Gene 61-68 (1989); and R. M. Horton, PCR-mediated recombination and mutagenesis. SOEing together tailor-made genes, 3(2) Mol. Biotechnol. 93-99 (1995). A nucleic acid fragment comprising a region encoding amino acids 85 to 120 of SNAP-25 (SEQ ID NO: 1) will be operably-linked by SOE-PCR to a VAMP-1 sequence comprising a region encoding amino acids 49-92 of SEQ ID NO: 28 and subcloned into a pCR2.1 vector using the TOPO® TA cloning method (Invitrogen, Inc, Carlsbad, Calif.). The forward and reverse oligonucleotide primers used for these reaction are designed to include unique restriction enzyme sites useful for subsequent subcloning steps. The resulting pCR2./VAMP-1 construct is digested with restriction enzymes that 1) excise the insert containing the entire open reading frame encoding amino acids 85-120 of SNAP-25 (SEQ ID NO: 1) and amino acids 49-92 of VAMP-1 (SEQ ID NO: 28); and 2) enable this insert to be operably-linked to a pQBI-25A vector (Qbiogene, Inc., Carlsbad, Calif.). The resulting restriction fragment will be purified by the QIAquick Gel Extraction Kit (QIAGEN, Inc., Valencia, Calif.), and will be subcloned using a T4 DNA ligase procedure into a pQBI-25A vector (Qbiogene, Inc., Irvine, Calif.) to yield pQBI-25/VAMP-1-GFP. This cloning strategy yielded a pQBI-25 expression construct encoding a SNAP-25 membrane targeting domain comprising amino acids 85-120 of SNAP-25 (SEQ ID NO: 1), a Clostridial toxin recognition sequence comprising amino acids 49-92 of VAMP-1 (SEQ ID NO: 28) and a GFP all operably-linked and suitable to detect activity from BoNT/B, BoNT/D, BoNT/F, BoNT/G or TeNT The subcellular localization of VAMP-1-GFP substrates and their cleavage products will be analyzed using the procedures essentially as described above in Example I, 1c, with the exception that the pQBI-25/VAMP-1-GFP construct described above in Example I, 2a will be used instead of expression constructs encoding SNAP-$25_{206}$-GFP. In addition, a suitable expression construct encoding the light chain of an appropriate Clostridial toxin, such as, e.g., the light chain BoNT/B, BoNT/D, BoNT/F, BoNT/G or TeNT will be used instead of the pcDNA3.1-LC/A construct.

2b. Construction of pQBI25/VAMP-2-GFP

To make a VAMP-2 substrate suitable for methods disclosed in the present specification, a pQBI-25/VAMP-2-GFP construct will be made using a SOE-PCR procedure. A nucleic acid fragment comprising a region encoding amino acids 85 to 120 of SNAP-25 (SEQ ID NO: 1) will be operably-linked by SOE-PCR to a VAMP-2 sequence comprising a region encoding amino acids 47-90 of SEQ ID NO: 31 and subcloned into a pCR2.1 vector using the TOPO® TA cloning method (Invitrogen, Inc, Carlsbad, Calif.). The forward and reverse oligonucleotide primers used for these reaction are designed to include unique restriction enzyme sites useful for subsequent subcloning steps. The resulting pCR2.1/VAMP-2 construct is digested with restriction enzymes that 1) excise the insert containing the entire open reading frame encoding amino acids 85-120 of SNAP-25 (SEQ ID NO: 1) and amino acids 47-90 of VAMP-2 (SEQ ID NO: 31); and 2) enable this insert to be operably-linked to a pQBI-25A vector (Qbiogene, Inc., Carlsbad, Calif.). The resulting restriction fragment will be purified by the QIAquick Gel Extraction Kit (QIAGEN, Inc., Valencia, Calif.), and will be subcloned using a T4 DNA ligase procedure into a pQBI-25A vector (Qbiogene, Inc., Irvine, Calif.) to yield pQBI-25/VAMP-2-GFP. This cloning strategy yielded a pQBI-25 expression construct encoding a SNAP-25 membrane targeting domain comprising amino acids 85-120 of SNAP-25 (SEQ ID NO: 1), a Clostridial toxin recognition sequence comprising amino acids 47-90 of VAMP-2 (SEQ ID NO: 31) and a GFP all operably-linked and suitable to detect activity from BoNT/B, BoNT/D, BoNT/F, BoNT/G or TeNT The subcellular localization of VAMP-2-GFP substrates and their cleavage products will be analyzed using the procedures essentially as described above in Example I, 1c, with the exception that the pQBI-25/VAMP-2-GFP construct described above in Example I, 2b will be used instead of expression constructs encoding SNAP-$25_{206}$-GFP. In addition, a suitable expression construct encoding the light chain of an appropriate Clostridial toxin, such as, e.g., the light chain BoNT/B, BoNT/D, BoNT/F, BoNT/G or TeNT will be used instead of the pcDNA3.1-LC/A construct.

2c. Construction of pQBI25/VAMP-3-GFP

To make a VAMP-3 substrate suitable for methods disclosed in the present specification, a pQBI-25/VAMP-3-GFP construct will be made using a SOE-PCR procedure. A nucleic acid fragment comprising a region encoding amino acids 85 to 120 of SNAP-25 (SEQ ID NO: 1) will be operably-linked by SOE-PCR to a VAMP-3 sequence comprising a region encoding amino acids 34-77 of SEQ ID NO: 33 and subcloned into a pCR2.1 vector using the TOPO® TA cloning method (Invitrogen, Inc, Carlsbad, Calif.). The forward and reverse oligonucleotide primers used for these reaction are designed to include unique restriction enzyme sites useful for subsequent subcloning steps. The resulting pCR2.1/VAMP-3 construct is digested with restriction enzymes that 1) excise the insert containing the entire open reading frame encoding amino acids 85-120 of SNAP-25 (SEQ ID NO: 1) and amino acids 34-77 of VAMP-3 (SEQ ID NO: 33); and 2) enable this insert to be operably-linked to a pQBI-25A vector (Qbiogene, Inc., Carlsbad, Calif.). The resulting restriction fragment will be purified by the QIAquick Gel Extraction Kit (QIAGEN, Inc., Valencia, Calif.), and will be subcloned using a T4 DNA ligase procedure into a pQBI-25A vector (Qbiogene, Inc., Irvine, Calif.) to yield pQBI-25/VAMP-3-GFP. This cloning strategy yielded a pQBI-25 expression construct encoding a SNAP-25 membrane targeting domain comprising amino acids 85-120 of SNAP-25 (SEQ ID NO: 1), a Clostridial toxin recognition sequence comprising amino acids 34-77 of VAMP-3 (SEQ ID NO: 33) and a GFP all operably-linked and suitable to detect activity from BoNT/B, BoNT/D, BoNT/F, BoNT/G or TeNT The subcellular localization of VAMP-3-GFP substrates and their cleavage products will be analyzed using the procedures essentially as described above in Example I, 1c, with the exception that the pQBI-25/VAMP-3-GFP construct described above in Example I, 2c will be used instead of expression constructs encoding SNAP-$25_{206}$-GFP. In addition, a suitable expression construct encoding the light chain of an appropriate Clostridial toxin, such as, e.g., the light chain BoNT/B, BoNT/D, BoNT/F, BoNT/G or TeNT will be used instead of the pcDNA3.1-LC/A construct.

2d. Construction of pQBI67/VAMP-1-GFP

To construct pQBI-67/VAMP-1-GFP, a nucleic acid fragment encoding the amino acid region comprising the VAMP-1-GFP substrate as described above in Example I, 2a, is amplified from pQBI-25/VAMP-1-GFP DNA using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/VAMP-1-GFP construct is digested with restriction enzymes that 1) excise the insert containing the entire open reading frame encoding the VAMP-1-GFP peptide; and 2) enable this insert to be operably-linked to a pQBI-67 vector (Qbiogene, Inc., Irvine, Calif.). This insert is subcloned using a T4 DNA ligase procedure into a pQBI-67 vector that is digested with appropriate restriction endonucleases to yield pQBI-67/VAMP-1-GFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. This cloning strategy yields a mammalian expression construct encoding the VAMP-1-GFP operably-linked to the expression elements of the pQBI-67 vector.

2e. Construction of pQBI67/VAMP-2-GFP

To construct pQBI-67/VAMP-2-GFP, a nucleic acid fragment encoding the amino acid region comprising the VAMP-2-GFP substrate as described above in Example I, 2b, is amplified from pQBI-25/VAMP-2-GFP DNA using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/VAMP-2-GFP construct is digested with restriction enzymes that 1) excise the insert containing the entire open reading frame encoding the VAMP-2-GFP peptide; and 2) enable this insert to be operably-linked to a pQBI-67 vector (Qbiogene, Inc., Irvine, Calif.). This insert is subcloned using a T4 DNA ligase procedure into a pQBI-67 vector that is digested with appropriate restriction endonucleases to yield pQBI-67/VAMP-2-GFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. This cloning strategy yields a mammalian expression construct encoding the VAMP-2-GFP operably-linked to the expression elements of the pQBI-67 vector.

2f. Construction of pQBI67/VAMP-3-GFP

To construct pQBI-67/VAMP-3-GFP, a nucleic acid fragment encoding the amino acid region comprising the VAMP-3-GFP substrate as described above in Example I, 2c, is amplified from pQBI-25/VAMP-3-GFP DNA using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/VAMP-3-GFP construct is digested with restriction enzymes that 1) excise the insert containing the entire open reading frame encoding the VAMP-3-GFP peptide; and 2) enable this insert to be operably-linked to a pQBI-67 vector (Qbiogene, Inc., Irvine, Calif.). This insert is subcloned using a T4 DNA ligase procedure into a pQBI-67 vector that is digested with appropriate restriction endonucleases to yield pQBI-67/VAMP-3-GFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. This cloning strategy yields a mammalian expression construct encoding the VAMP-3-GFP operably-linked to the expression elements of the pQBI-67 vector.

3. Construction of BoNT/C1 Syntaxin Substrates

3a. Construction of pQBI25/Syntaxin-1-GFP

To make a Syntaxin-1 substrate suitable for methods disclosed in the present specification, a pQBI-25/Syntaxin-1-GFP construct will be made using a SOE-PCR procedure. A nucleic acid fragment comprising a region encoding amino acids 85 to 120 of SNAP-25 (SEQ ID NO: 1) will be operably-linked by SOE-PCR to a Syntaxin-1 sequence comprising a region encoding amino acids 242-264 of SEQ ID NO: 66 and subcloned into a pCR2.1 vector using the TOPO® TA cloning method (Invitrogen, Inc, Carlsbad, Calif.). The forward and reverse oligonucleotide primers used for these reaction are designed to include unique restriction enzyme sites useful for subsequent subcloning steps. The resulting pCR2.1/Syntaxin-1 construct is digested with restriction enzymes that 1) excise the insert containing the entire open reading frame encoding amino acids 85-120 of SNAP-25 (SEQ ID NO: 1) and amino acids 242-264 of Syntaxin-1 (SEQ ID NO: 66); and 2) enable this insert to be operably-linked to a pQBI-25A vector (Qbiogene, Inc., Carlsbad, Calif.). The resulting restriction fragment will be purified by the QIAquick Gel Extraction Kit (QIAGEN, Inc., Valencia, Calif.), and will be subcloned using a T4 DNA ligase procedure into a pQBI-25A vector (Qbiogene, Inc., Irvine, Calif.) to yield pQBI-25/Syntaxin-1-GFP. This cloning strategy yielded a pQBI-25 expression construct encoding a SNAP-25 membrane targeting domain comprising amino acids 85-120 of SNAP-25 (SEQ ID NO: 1), a Clostridial toxin recognition sequence comprising amino acids 242-264 of Syntaxin-1 (SEQ ID NO: 66) and a GFP all operably-linked and suitable to detect activity from BoNT/C1

The subcellular localization of Syntaxin-1-GFP substrates and their cleavage products will be analyzed using the procedures essentially as described above in Example I, 1c, with the exception that the pQBI-25/Syntaxin-1-GFP construct described above in Example I, 2c will be used instead of expression constructs encoding SNAP-$25_{206}$-GFP. In addition, a suitable expression construct encoding the light chain of an appropriate Clostridial toxin, such as, e.g., the light chain BoNT/C1 will be used instead of the pcDNA3.1-LC/A construct.

3b. Construction of pQBI67/Syntaxin-1-GFP

To construct pQBI-67/Syntaxin-1-GFP, a nucleic acid fragment encoding the amino acid region comprising the Syntaxin-1-GFP substrate as described above in Example I, 3a, is amplified from pQBI-25/Syntaxin-1-GFP DNA using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/Syntaxin-1-GFP construct is digested with restriction enzymes that 1) excise the insert containing the entire open reading frame encoding the Syntaxin-1-GFP peptide; and 2) enable this insert to be operably-linked to a pQBI-67 vector (Qbiogene, Inc., Irvine, Calif.). This insert is subcloned using a T4 DNA ligase procedure into a pQBI-67 vector that is digested with appropriate restriction endonucleases to yield pQBI-67/Syntaxin-1-GFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. This cloning strategy yields a mammalian expression construct encoding the Syntaxin-1-GFP operably-linked to the expression elements of the pQBI-67 vector.

Example II

Identification of Cell Lines with High Affinity Uptake for CoNTs

Distinct sensitivities to each of the CoNT serotypes might be expected based on the individual receptor systems for each different toxin and toxin serotype and their differing expression in different cell lines. The presence of a high affinity receptor system in a cell for CoNT can be characterized by two attributes: a rapid uptake of the neurotoxin by the cell, and a low neurotoxin concentration needed for cell intoxication. To identify a cell line having a high affinity receptor system for a CoNT, we tested cell lines using one of two different in vitro cleavage assay, one to determine the amount of toxin required for intoxication, the other to determine the length of time necessary for the cell to uptake the neurotoxin.

1. Identification of Cell Lines with High Affinity Uptake for BoNT/A

1a. Assay to Determine the BoNT/A Concentration Necessary for Cell Intoxication

In order to assess the amount of BoNT/A needed to intoxicate a cell, a panel of mammalian cell lines of neuronal origin was screened to determine the concentration of toxin necessary to cleave endogenously expressed SNAP-25 (see Table 13). A suitable seed density of cells from each line was plated into individual wells of 6-well, poly-D-lysine/Laminin coated, tissue culture plates containing 3 mL of a suitable medium (see Table 13), and grown in a 37° C. incubator under 5% carbon dioxide for approximately 24 hours. BoNT/A (Metabiologics, Inc., Madison, Wis.) was added at different concentrations (0 nM, 1 nM, 5 nM, 12.5 nM, 25 nM, 50 nM) in the culture medium containing the cells for approximately 8 or approximately 16 hours. Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl) piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol and 1% (v/v) Triton-X® 100 (4-octylphenol polyethoxylate), with rotation for 1 hour at 4° C. Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/ml or higher concentration.

TABLE 13

| Culture Conditions for Cell Lines | | | |
|---|---|---|---|
| Cell Line | Complete Culture Media | Passage Conditions | Seed Density (cells/mm$^2$) |
| SK-N-DZ | 90% DMEM, A | Trypsin/EDTA treatment, 1:4 dilution split every 2-3 day | $4.25 \times 10^3$ |
| SK-N-F1 | 90% DMEM, A | Trypsin/EDTA treatment, 1:4 dilution spilt twice a week | $4.25 \times 10^3$ |
| SK-N-SH | Ham's F12, DMEM or EMEM, B | Trypsin/EDTA treatment, 1:20 dilution split every 4-7 day | $4.25 \times 10^3$ |
| SH-SY5Y | EMEM and Ham's F12 1:1, C | Trypsin/EDTA treatment, 1:6 dilution split every 2-3 day | $4.25 \times 10^3$ |
| SK-N-BE(2) | EMEM and Ham's F12 1:1, D | Trypsin/EDTA treatment, 1:6 dilution split every 3 day | $4.25 \times 10^3$ |
| BE(2)-C | EMEM and Ham's F12 1:1, D | Trypsin/EDTA treatment, 1:4 dilution split every 2-3 day | $4.25 \times 10^3$ |
| BE(2)-M17 | EMEM and Ham's F12 1:1, D | Trypsin/EDTA treatment, 1:20 dilution split every 4-7 day | $4.25 \times 10^3$ |
| Neuro 2a | EMEM, E | Trypsin/EDTA treatment, 1:3 dilution split every 3 day | $4.25 \times 10^3$ |
| C1300 | RPMI 1640, B | Trypsin/EDTA treatment, 1:3 dilution split every 3 day | $4.25 \times 10^3$ |
| NB4 1A3 | Ham's F10, F | Trypsin/EDTA treatment, 1:3 dilution split every 3 day | $4.25 \times 10^3$ |
| N1E-115 | DMEM, G | Trypsin/EDTA treatment, 1:3 dilution split every 3 day | $4.25 \times 10^3$ |
| NG108-15 | DMEM, B | 1:4 dilution split every 1-2 days | $4.25 \times 10^3$ |
| HCN-1A | DMEM, H | Trypsin/EDTA treatment, 1:3 dilution split every 3 day | $4.25 \times 10^3$ |
| HCN-2 | DMEM, H | Trypsin/EDTA treatment, 1:3 dilution split every 3 day | $4.25 \times 10^3$ |
| TE 189.T | DMEM, H | Trypsin/EDTA treatment, 1:3 dilution split every 3 day | $4.25 \times 10^3$ |
| ND8/34 | DMEM, B | Trypsin/EDTA treatment, 1:3 dilution split every 3 day | $4.25 \times 10^3$ |

Figure 7A:
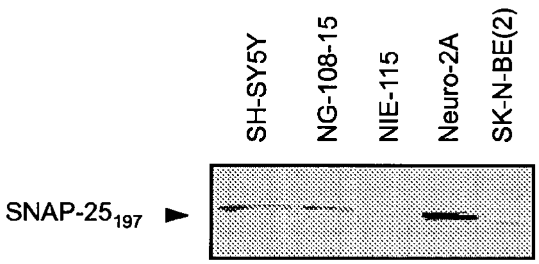
FIG. 7*a* shows a Western blot analysis used to identify cells capable of BoNT/A uptake. The blot shows five cell lines treated with 1 nM of Pure BoNT/A overnight, with equal amounts of protein loaded per lane and probed with an antibody that detects the BoNT/A SNAP-$25_{197}$ cleavage product.

A contains 1.5 g/L sodium bicarbonate, 0.1 mM Non-essential amino acids (NEAA), 4 mM Glutamine & 10% Fetal Calf serum (FCS)
B contains 2 mM Glutamine & 10% FCS
C contains 1.5 g/L sodium bicarbonate, 0.1 mM NEAA, 4 mM Glutamine, 1% sodium pyruvate, 1% penicillin/streptomycin (P/S) & 10% FCS
D contains 0.1 mM NEAA, 4 mM Glutamine, & 10% FCS
E contains 1.5 g/L sodium bicarbonate, 0.1 mM NEAA, 2 mM Glutamine, 1 mM sodium pyruvate & 10% FCS
F contains 2 mM Glutamine, 15% Horse Serum & 2.5% FCS
G contains 4.5 g/L glucose & 10% FCS
H contains 4 mM glucose & 10% FCS
Freeze medium comprises 95% culture medium and 5% DMSO To detect for the presence of a cleaved BoNT/A substrate, samples were boiled for 5 min, and 40 μl aliquots were separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Separated peptides were transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes were blocked by incubating at room temperature for 2 hours in a solution containing 25 mM Tris-Buffered Saline (25 mM 2-amino-2-hydroxymethyl-1,3-propanediol hydrochloric acid (Tris-HCl)(pH 7.4), 137 mM sodium chloride, 2.7 mM potassium chloride), 0.1% TWEEN-20®, polyoxyethylene (20) sorbitan monolaureate, 2% bovine serum albumin, 5% nonfat dry milk. Blocked membranes were incubated at 4° C. for overnight in Tris-Buffered Saline TWEEN-20® (25 mM Tris-Buffered Saline, 0.1% TWEEN-20®, polyoxyethylene (20) sorbitan monolaureate) containing a 1:5,000 dilution of rabbit polyclonal anti-SNAP25 antiserum pAb anti-SNAP25197 #1, a polyclonal antibody which is specific for the $SNAP25_{197}$-cleavage product and does not cross-react with full-length $SNAP25_{206}$, (Allergan, Inc., generated under contract with Zymed Laboratories Inc., South San Francisco, Calif.). Primary antibody probed blots were washed three times for 15 minutes each time in Tris-Buffered Saline TWEEN-20®. Washed membranes were incubated at room temperature for 2 hours in Tris-Buffered Saline TWEEN-20®, containing a 1:20,000 dilution of goat polyclonal anti-rabbit immunoglobulin G, heavy and light chains (IgG, H+L) antibody conjugated to horseradish peroxidase (HRP; Pierce Biotechnology, Inc., Rockford, Ill.) as a secondary antibody. Secondary antibody-probed blots were washed three times for 15 minutes each time in Tris-Buffered Saline TWEEN-200. Signal detection of the labeled BoNT/A $SNAP25_{197}$-cleavage product was visualized using the ECL Plus™ Western Blot Detection System (Amersham Biosciences, Piscataway, N.J.) and the membrane was imaged and cleavage product quantitated with a Typhoon 9410 Variable Mode Imager and Imager Analysis software (Amersham Biosciences, Piscataway, N.J.). The choice of pixel size (100 to 200 pixels) and PMT voltage settings (350 to 600, normally 400) depended on the individual blot. A BoNT/A $SNAP25_{197}$-cleavage product was detected in the cell lines SH-SY5Y, NG108-15, N1E-115, Neuro-2A and SK-N-BE(2) after at least an 8 hour incubation with at least 5 nM BoNT/A, thereby indicating the ability of BoNT/A to intoxicate these cell lines (see FIG. 7*a*).

Figure 7B:
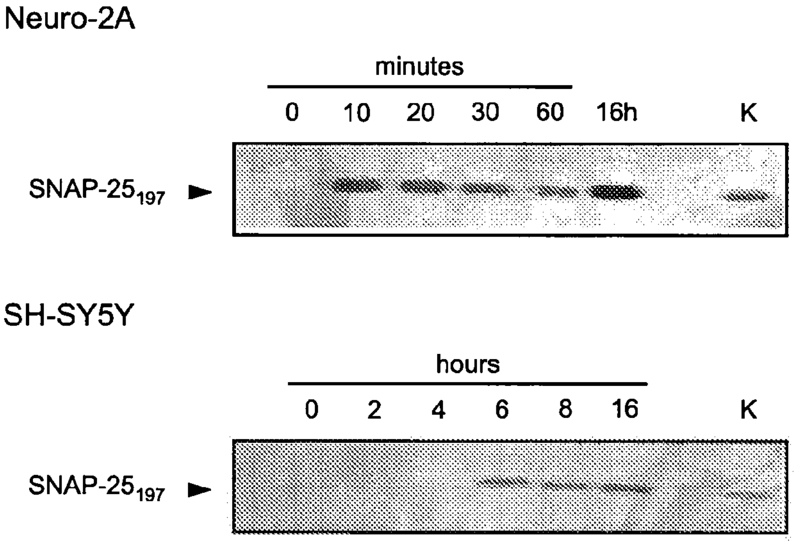
FIG. 7*b* shows Western blot analysis used to evaluate the time necessary for BoNT/A uptake. The blots show either Neuro-2A cells or SH-SY5Y cells treated with 1 nM of Pure BoNT/A for various lengths of time, with equal amounts of protein loaded per lane and probed with an antibody that detects the BoNT/A SNAP-$25_{197}$ cleavage product.
Figure 7C:
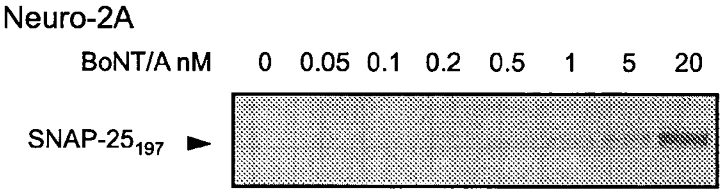
FIG. 7*c* shows a Western blot analysis used to evaluate the concentration range necessary of BoNT/A uptake. The blots show Neuro-2A cells treated with a range of Pure BoNT/A concentrations overnight, with equal amounts of protein loaded per lane and probed with an antibody that detects the BoNT/A SNAP-$25_{197}$ cleavage product.

The mouse neuroblastoma cell line Neuro-2A was further analyzed with lower concentrations of BoNT/A to determine the concentration of neurotoxin necessary to cleave endogenously expressed SNAP-25. Cells were grown in poly-D-lysine/Laminin coated 6-well plates as described above in Example II, 1a. BoNT/A (Metabiologics, Inc., Madison, Wis.) was added at different concentrations (0 nM, 0.05 nM, 0.1 nM, 0.2 nM, 0.5 nM, 1 nM, 5 nM and 20 nM) in the culture medium containing cells for either approximately 8 or approximately 16 hours. Toxin treated cells were harvested and lysed as described above in Example II, 1a. The presence of a BoNT/A $SNAP25_{197}$-cleavage product was determined by Western blot analysis as described above in Example II, 1a. A BoNT/A $SNAP25_{197}$-cleavage product was detected in the cell line Neuro-2A after at least a 8 hour incubation with at least 0.5 nM BoNT/A, thereby indicating the ability of BoNT/A to intoxicate these cell lines (see FIG. 7*c*).

1b. Assay to Determine the Time Required by a Cell to Uptake BoNT/A

In order to assess the amount of time needed by a cell line to uptake BoNT/A, a panel of mammalian cell lines of neuronal origin was screened to determine the length of toxin exposure necessary to cleave endogenously expressed SNAP-25. Cells from each line were grown in poly-D-lysine/Laminin coated 6-well plates as described above in Example II, 1a. Approximately 1 nM BoNT/A (Metabiologics, Inc., Madison, Wis.) was added to the culture medium for 10 min, 20 min, 30 min, 60 min 2 hours, 4 hours, 6 hours, 8 hours or 16 hours. Toxin treated cells were collected and lysed as described above in Example II, 1a. The presence of a BoNT/A $SNAP25_{197}$-cleavage product was determined by Western blot analysis as described above in Example II, 1a. A BoNT/A $SNAP25_{197}$-cleavage product was detected in the cell lines Neuro-2A, SH-SY5Y, and NG108-15 after at least an 8 hour incubation with 1 nM BoNT/A, thereby indicating the ability of these cell lines to rapidly uptake BoNT/A (see FIG. 7*b*).

2. Identification of Cell Lines with High Affinity Uptake for BoNT/B

2a. Assay to Determine the BoNT/B Concentration Necessary for Cell Intoxication

In order to assess the amount of BoNT/B needed to intoxicate a cell line, a panel of mammalian cell lines of neuronal origin will be screened to determine the concentration of neurotoxin necessary to cleave endogenously expressed VAMP (see Table 13). Cells will be grown in poly-D-lysine/Laminin coated 6-well plates as described above in Example II, 1a. BoNT/B (Metabiologics, Inc., Madison, Wis.) will be added at different concentrations (0 nM, 1 nM, 2 nM, 5 nM, 10 nM, 20 nM and 100 nM) in the culture medium containing cells for either approximately 8 or approximately 16 hours. Cells will be harvested and lysed as described above in Example II, 1a.

To detect for the presence of a cleaved BoNT/B substrate, western blot analysis will be conducted as described above in Example II, 1a, with the exception that blocked PVDF membranes will be incubated in a primary antibody solution containing one of the following antibodies in order to detect a BoNT/B VAMP-cleavage product rather than the rabbit polyclonal anti-SNAP25 antiserum pAb anti-SNAP25197 #1:1) 1:1000 dilution of mouse monoclonal anti-VAMP-1 antibody clone CI 10.1 (Synaptic Systems, Goettingen, Germany); 2) 1:20,000 dilution of mouse monoclonal anti-VAMP-2 antibody clone CI 69.1 (Synaptic Systems, Goettingen, Germany); or 3) 1:1000 dilution of mouse monoclonal anti-VAMP-3 antibody clone CI 10.1 (Synaptic Systems, Goettingen, Germany). In addition, a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) will be used rather than the goat polyclonal anti-rabbit IgG-HRP antibody. Detection of a BoNT/B VAMP-cleavage product in a cell line after at least an 8 hours incubation with at least 20 nM BoNT/B will indicate the ability of BoNT/B to intoxicate these cell lines.

2b. Assay to Determine the Time Required by a Cell to Uptake BoNT/B

In order to assess the amount of time needed by a cell line to uptake BoNT/B, a panel of mammalian cell lines of neuronal origin will be screened to determine the length of toxin exposure necessary to cleave endogenously expressed VAMP. Cells will be grown in poly-D-lysine/Laminin coated 6-well plates as described above in Example II, 2a. Approximately 1 nM BoNT/B (Metabiologics, Inc., Madison, Wis.) will be added to the culture medium for 10 min, 20 min, 30 min, 60 min 2 hours, 4 hours, 6 hours, 8 hours or 16 hours. Toxin treated cells will be harvested and lysed as described above in Example II, 2a. The presence of a BoNT/B VAMP-cleavage product will be determined by Western blot analysis as described above in Example II, 2a. Detection of a BoNT/B VAMP-cleavage product in a cell line after at least an 8 hour incubation with 1 nM BoNT/B will indicate a cell line that can rapidly uptake BoNT/B.

3. Identification of Cell Lines with High Affinity Uptake for BoNT/C1

3a. Assay to Determine the BoNT/C1 Concentration Necessary for Cell Intoxication In order to assess the amount of BoNT/C1 needed to intoxicate a cell line, a panel of mammalian cell lines of neuronal origin will be screened to determine the concentration of neurotoxin necessary to cleave endogenously expressed SNAP-25 or endogenously expressed Syntaxin (see Table 13). Cells will be grown in poly-D-lysine/Laminin coated 6-well plates as described above in Example II, 1a. BoNT/C1 (Metabiologics, Inc., Madison, Wis.) will be added at different concentrations (0 nM, 1 nM, 2 nM, 5 nM, 10 nM, 20 nM and 100 nM) in the culture medium containing cells for either approximately 8 or approximately 16 hours. Cells will be harvested and lysed as described above in Example II, 1a.

To detect for the presence of a cleaved BoNT/C1 substrate, western blot analysis will be conducted as described above in Example II, 1a, with the exception: 1) blocked PVDF membranes will be incubated in a primary antibody solution containing a 1:50,000 dilution of mouse monoclonal anti-SNAP-25 antibody (SMI-81; Sternberger Monoclonals, Lutherville, Md.) rather than the rabbit polyclonal anti-SNAP25 antiserum pAb anti-SNAP25197 #1 and a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) rather than the goat polyclonal anti-rabbit IgG-HRP antibody in order to detect a BoNT/C1 $SNAP25_{198}$-cleavage product; 2) blocked PVDF membranes will be incubated in a primary antibody solution containing a 1:5000 dilution of mouse monoclonal anti-Syntaxin-1 antibody clone CI 78.2 (Synaptic Systems, Goettingen, Germany) rather than the rabbit polyclonal anti-SNAP25 antiserum pAb anti-SNAP25197 #1 and a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) rather than the goat polyclonal anti-rabbit IgG-HRP antibody in order to detect a BoNT/C1 Syntaxin-cleavage product. Detection of a $SNAP25_{198}$-cleavage product in a cell line after at least an 8 hours incubation with at least 20 nM BoNT/C1 will indicate the ability of BoNT/C1 to intoxicate these cell lines. Detection of a Syntaxin-cleavage product in a cell line after at least an 8 hours incubation with at least 20 nM BoNT/C1 will indicate the ability of BoNT/C1 to intoxicate these cell lines.

3b. Assay to Determine the Time Required by a Cell to Uptake BoNT/C1

In order to assess the amount of time needed by a cell line to uptake BoNT/C1, a panel of mammalian cell lines of neuronal origin will be screened to determine the length of toxin exposure necessary to cleave endogenously expressed SNAP-25 or endogenously expressed Syntaxin. Cells will be grown in poly-D-lysine/Laminin coated 6-well plates as described above in Example II, 3a. Approximately 1 nM BoNT/C1 (Metabiologics, Inc., Madison, Wis.) will be added to the culture medium for 10 min, 20 min, 30 min, 60 min 2 hours, 4 hours, 6 hours, 8 hours or 16 hours. Toxin treated cells will be harvested and lysed as described above in Example II, 3a. The presence of a BoNT/C1 $SNAP25_{198}$-cleavage product and BoNT/C1 Syntaxin-cleavage product will be determined by Western blot analysis as described above in Example II, 3a. Detection of a BoNT/C1 $SNAP25_{198}$-cleavage product in a cell line after at least an 8 hour incubation with 1 nM BoNT/C1 will indicate a cell line that can rapidly uptake BoNT/C1. Detection of a BoNT/C1

Syntaxin-cleavage product in a cell line after at least an 8 hour incubation with 1 nM BoNT/C1 will indicate a cell line that can rapidly uptake BoNT/C1.

4. Identification of Cell Lines with High Affinity Uptake for BoNT/D

4a. Assay to Determine the BoNT/D Concentration Necessary for Cell Intoxication

In order to assess the amount of BoNT/D needed to intoxicate a cell line, a panel of mammalian cell lines of neuronal origin will be screened to determine the concentration of neurotoxin necessary to cleave endogenously expressed VAMP (see Table 13). Cells will be grown in poly-D-lysine/Laminin coated 6-well plates as described above in Example II, 1a. BoNT/D (Metabiologics, Inc., Madison, Wis.) will be added at different concentrations (0 nM, 1 nM, 2 nM, 5 nM, 10 nM, 20 nM and 100 nM) in the culture medium containing cells for either approximately 8 or approximately 16 hours. Cells will be harvested and lysed as described above in Example II, 1a.

To detect for the presence of a cleaved BoNT/D substrate, western blot analysis will be conducted as described above in Example II, 1a, with the exception that blocked PVDF membranes will be incubated in a primary antibody solution containing one of the following antibodies in order to detect a BoNT/D VAMP-cleavage product rather than the rabbit polyclonal anti-SNAP25 antiserum pAb anti-SNAP25197 #1:1) 1:1000 dilution of mouse monoclonal anti-VAMP-1 antibody clone CI 10.1 (Synaptic Systems, Goettingen, Germany); 2) 1:20,000 dilution of mouse monoclonal anti-VAMP-2 antibody clone CI 69.1 (Synaptic Systems, Goettingen, Germany); or 3) 1:1000 dilution of mouse monoclonal anti-VAMP-3 antibody clone CI 10.1 (Synaptic Systems, Goettingen, Germany). In addition, a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) will be used rather than the goat polyclonal anti-rabbit IgG-HRP antibody. Detection of a BoNT/D VAMP-cleavage product in a cell line after at least an 8 hours incubation with at least 20 nM BoNT/D will indicate the ability of BoNT/D to intoxicate these cell lines.

4b. Assay to Determine the Time Required by a Cell to Uptake BoNT/D

In order to assess the amount of time needed by a cell line to uptake BoNT/D, a panel of mammalian cell lines of neuronal origin will be screened to determine the length of toxin exposure necessary to cleave endogenously expressed VAMP. Cells will be grown in poly-D-lysine/Laminin coated 6-well plates as described above in Example II, 4a. Approximately 1 nM BoNT/D (Metabiologics, Inc., Madison, Wis.) will be added to the culture medium for 10 min, 20 min, 30 min, 60 min 2 hours, 4 hours, 6 hours, 8 hours or 16 hours. Toxin treated cells will be harvested and lysed as described above in Example II, 4a. The presence of a BoNT/D VAMP-cleavage product will be determined by Western blot analysis as described above in Example II, 4a. Detection of a BoNT/D VAMP-cleavage product in a cell line after at least an 8 hour incubation with 1 nM BoNT/D will indicate a cell line that can rapidly uptake BoNT/D.

5. Identification of Cell Lines with High Affinity Uptake for BoNT/E

5a. Assay to Determine the BoNT/E Concentration Necessary for Cell Intoxication

In order to assess the amount of BoNT/E needed to intoxicate a cell line, a panel of mammalian cell lines of neuronal origin was screened to determine the concentration of neurotoxin necessary to cleave endogenously expressed SNAP-25 (see Table 13). A suitable density of cells from each line was plated into individual wells of 6-well, poly-D-lysine/Laminin coated, tissue culture plates containing 3 mL of a suitable medium (see Table 13), and grown in a 37° C. incubator under 5% carbon dioxide for approximately 24 hours. BoNT/E (Metabiologics, Inc., Madison, Wis.) was added at different concentrations (0 nM, 2 nM or 20 nM) in the culture medium containing cells for either approximately 6 or approximately 16 hours. Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl) piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol and 1% (v/v) Triton-X® 100 (4-octylphenol polyethoxylate), with rotation for 1 hour at 4° C. Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/ml or higher concentration.

Figure 8A:
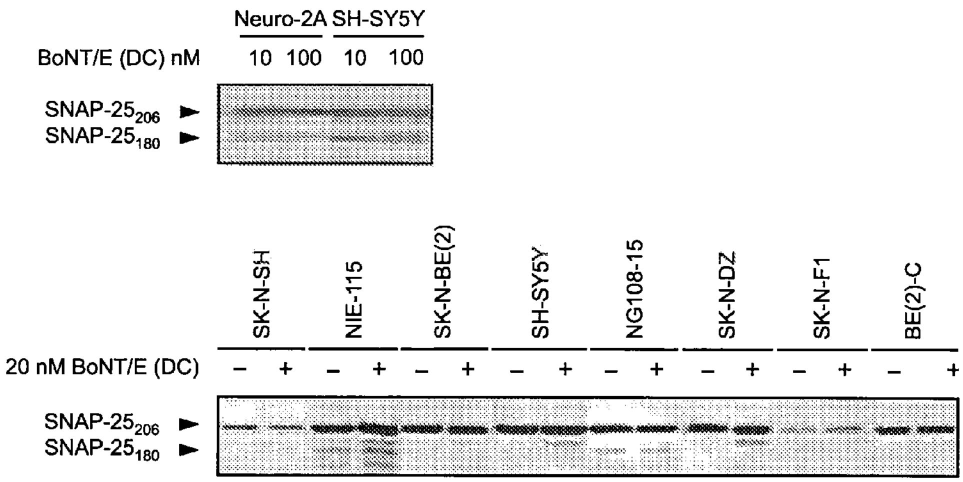
FIG. 8*a* shows a Western blot analysis used to identify cells capable of BoNT/E uptake. The top blot show Neuro-2A cells and SH-SY5Y cells treated with either 10 nM or 100 nM of BoNT/E di-chain overnight, with equal amounts of protein loaded per lane and probed with an antibody (SMI-81; Sternberger Monoclonals, Lutherville, Md.) that detects the uncleaved SNAP-$25_{206}$ substrate and the BoNT/E SNAP-$25_{180}$ cleavage product. The bottom blot show various cells treated with 20 nM of BoNT/E di-chain, with equal amounts of protein loaded per lane and probed with an antibody for the uncleaved SNAP-$25_{206}$ substrate and the BoNT/E SNAP-$25_{180}$ cleavage product.

To detect for the presence of a cleaved BoNT/E substrate, western blot analysis was conducted as described above in Example II, 1a, with the exception that blocked PVDF membranes were incubated in a primary antibody solution containing a 1:50,000 dilution of mouse monoclonal anti-SNAP-25 antibody (SMI-81; Sternberger Monoclonals, Lutherville, Md.) rather than the rabbit polyclonal anti-SNAP25 antiserum pAb anti-SNAP25197 #1 and a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) rather than the goat polyclonal anti-rabbit IgG-HRP antibody in order to detect a BoNT/E $SNAP25_{180}$-cleavage product. A BoNT/E $SNAP25_{180}$-cleavage product was detected in the cell lines Neuro-2A, SH-SY5Y, N1E-115, SK-N-BE(2), NG108-15, SK-N-DZ and BE(2)-C after at least a 6 hour incubation with at least 20 nM BoNT/E, thereby indicating the ability of BoNT/E to intoxicate these cell lines (see FIG. 8*a*).

Figure 8B:
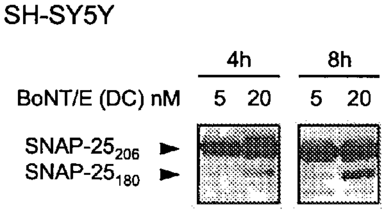
FIG. 8*b* shows Western blot analysis used to determine a time course for BoNT/E uptake. The blots show SH-SY5Y cells treated with either 5 nM or 20 nM of BoNT/E di-chain for either 4 hours or 8 hours, with equal amounts of protein loaded per lane or probed with an antibody (SMI-81; Sternberger Monoclonals, Lutherville, Md.) that detects the uncleaved SNAP-$25_{206}$ substrate and the BoNT/E SNAP-$25_{180}$ cleavage product.
Figure 8C:
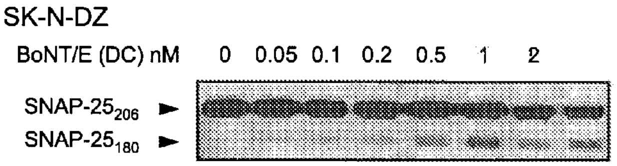
FIG. 8*c* shows a Western blot analysis used to evaluate the concentration range necessary of BoNT/E uptake. The blots show SK-N-DZ cells treated with a range of BoNT/E di-chain concentrations for approximately 6 hours, with equal amounts of protein loaded per lane and probed with an antibody (SMI-81; Sternberger Monoclonals, Lutherville, Md.) that detects the uncleaved SNAP-$25_{206}$ substrate and the BoNT/E SNAP-$25_{180}$ cleavage product.

The human neuroblastoma cell line SK-N-DZ was further analyzed with lower concentrations of BoNT/E to determine the concentration of neurotoxin necessary to cleave endogenously expressed SNAP-25. Cells were grown in poly-D-lysine/Laminin coated 6-well plates as described above in Example II, 5a. BoNT/E (Metabiologics, Inc., Madison, Wis.) was added at different concentrations (0 nM, 0.05 nM, 0.1 nM, 0.2 nM, 0.5 nM, 1 nM, 2 nM and 5 nM) in the culture medium containing cells for approximately 6 hours. Toxin treated cells were harvested and lysed as described above in Example II, 5a. The presence of a BoNT/E $SNAP25_{180}$-cleavage product was determined by Western blot analysis as described above in Example II, 5a. A BoNT/E $SNAP25_{180}$-cleavage product was detected in the cell line SK-N-DZ after at least a 6 hour incubation with at least 0.1 nM BoNT/E, thereby indicating the ability of BoNT/E to intoxicate these cell lines (see FIG. 8*c*).

5b. Assay to Determine the Time Required by a Cell to Uptake BoNT/E

In order to assess the amount of time needed by a cell line to uptake BoNT/E, a panel of mammalian cell lines of neuronal origin was screened to determine the length of toxin exposure necessary to cleave endogenously expressed SNAP-25 (see Table 13). Cells were grown in poly-D-lysine/Laminin coated 6-well plates as described above in Example II, 5a. Approximately 1 nM BoNT/E (Metabiologics, Inc., Madison, Wis.) was added to the culture medium for 10 min, 20 min, 30 min, 60 min 2 hours, 4 hours, 6 hours, 8 hours or 16 hours. Toxin treated cells were harvested and lysed as described above in Example II, 5a. The presence of a BoNT/E $SNAP25_{180}$-cleavage product was determined by Western blot analysis as described above in Example II, 5a. A BoNT/E $SNAP25_{180}$-cleavage product was detected in the cell lines Neuro-2A, SH-SY5Y, and NG108-15 after at least an 6 hour incubation with 1 nM BoNT/E, thereby indicating the ability of these cell lines to rapidly uptake BoNT/E (see FIG. 8*b*).

6. Identification of Cell Lines with High Affinity Uptake for BoNT/F

6a. Assay to Determine the BoNT/F Concentration Necessary for Cell Intoxication

In order to assess the amount of BoNT/F needed to intoxicate a cell line, a panel of mammalian cell lines of neuronal origin will be screened to determine the concentration of neurotoxin necessary to cleave endogenously expressed VAMP (see Table 13). Cells will be grown in poly-D-lysine/Laminin coated 6-well plates as described above in Example II, 1a. BoNT/F (Metabiologics, Inc., Madison, Wis.) will be added at different concentrations (0 nM, 1 nM, 2 nM, 5 nM, 10 nM, 20 nM and 100 nM) in the culture medium containing cells for either approximately 8 or approximately 16 hours. Cells will be harvested and lysed as described above in Example II, 1a.

To detect for the presence of a cleaved BoNT/F substrate, western blot analysis will be conducted as described above in Example II, 1a, with the exception that blocked PVDF membranes will be incubated in a primary antibody solution containing one of the following antibodies in order to detect a BoNT/F VAMP-cleavage product rather than the rabbit polyclonal anti-SNAP25 antiserum pAb anti-SNAP25197 #1:1) 1:1000 dilution of mouse monoclonal anti-VAMP-1 antibody clone CI 10.1 (Synaptic Systems, Goettingen, Germany); 2) 1:20,000 dilution of mouse monoclonal anti-VAMP-2 antibody clone CI 69.1 (Synaptic Systems, Goettingen, Germany); or 3) 1:1000 dilution of mouse monoclonal anti-VAMP-3 antibody clone CI 10.1 (Synaptic Systems, Goettingen, Germany). In addition, a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) will be used rather than the goat polyclonal anti-rabbit IgG-HRP antibody. Detection of a BoNT/F VAMP-cleavage product in a cell line after at least an 8 hours incubation with at least 20 nM BoNT/F will indicate the ability of BoNT/F to intoxicate these cell lines.

6b. Assay to Determine the Time Required by a Cell to Uptake BoNT/F

In order to assess the amount of time needed by a cell line to uptake BoNT/F, a panel of mammalian cell lines of neuronal origin will be screened to determine the length of toxin exposure necessary to cleave endogenously expressed VAMP. Cells will be grown in poly-D-lysine/Laminin coated 6-well plates as described above in Example II, 6a. Approximately 1 nM BoNT/F (Metabiologics, Inc., Madison, Wis.) will be added to the culture medium for 10 min, 20 min, 30 min, 60 min 2 hours, 4 hours, 6 hours, 8 hours or 16 hours. Toxin treated cells will be harvested and lysed as described above in Example II, 6a. The presence of a BoNT/F VAMP-cleavage product will be determined by Western blot analysis as described above in Example II, 6a. Detection of a BoNT/F VAMP-cleavage product in a cell line after at least an 8 hour incubation with 1 nM BoNT/F will indicate a cell line that can rapidly uptake BoNT/F.

7. Identification of Cell Lines with High Affinity Uptake for BoNT/G

7a. Assay to Determine the BoNT/G Concentration Necessary for Cell Intoxication

In order to assess the amount of BoNT/G needed to intoxicate a cell line, a panel of mammalian cell lines of neuronal origin will be screened to determine the concentration of neurotoxin necessary to cleave endogenously expressed VAMP (see Table 13). Cells will be grown in poly-D-lysine/Laminin coated 6-well plates as described above in Example II, 1a. BoNT/G (Metabiologics, Inc., Madison, Wis.) will be added at different concentrations (0 nM, 1 nM, 2 nM, 5 nM, 10 nM, 20 nM and 100 nM) in the culture medium containing cells for either approximately 8 or approximately 16 hours. Cells will be harvested and lysed as described above in Example II, 1a.

To detect for the presence of a cleaved BoNT/G substrate, western blot analysis will be conducted as described above in Example II, 1a, with the exception that blocked PVDF membranes will be incubated in a primary antibody solution containing one of the following antibodies in order to detect a BoNT/G VAMP-cleavage product rather than the rabbit polyclonal anti-SNAP25 antiserum pAb anti-SNAP25197 #1:1) 1:1000 dilution of mouse monoclonal anti-VAMP-1 antibody clone CI 10.1 (Synaptic Systems, Goettingen, Germany); 2) 1:20,000 dilution of mouse monoclonal anti-VAMP-2 antibody clone CI 69.1 (Synaptic Systems, Goettingen, Germany); or 3) 1:1000 dilution of mouse monoclonal anti-VAMP-3 antibody clone CI 10.1 (Synaptic Systems, Goettingen, Germany). In addition, a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) will be used rather than the goat polyclonal anti-rabbit IgG-HRP antibody. Detection of a BoNT/G VAMP-cleavage product in a cell line after at least an 8 hours incubation with at least 20 nM BoNT/G will indicate the ability of BoNT/G to intoxicate these cell lines.

7b. Assay to Determine the Time Required by a Cell to Uptake BoNT/G

In order to assess the amount of time needed by a cell line to uptake BoNT/G, a panel of mammalian cell lines of neuronal origin will be screened to determine the length of toxin exposure necessary to cleave endogenously expressed VAMP. Cells will be grown in poly-D-lysine/Laminin coated 6-well plates as described above in Example II, 7a. Approximately 1 nM BoNT/G (Metabiologics, Inc., Madison, Wis.) will be added to the culture medium for 10 min, 20 min, 30 min, 60 min 2 hours, 4 hours, 6 hours, 8 hours or 16 hours. Toxin treated cells will be harvested and lysed as described above in Example II, 7a. The presence of a BoNT/G VAMP-cleavage product will be determined by Western blot analysis as described above in Example II, 7a. Detection of a BoNT/G VAMP-cleavage product in a cell line after at least an 8 hour incubation with 1 nM BoNT/G will indicate a cell line that can rapidly uptake BoNT/G.

8. Identification of Cell Lines with High Affinity Uptake for TeNT

8a. Assay to Determine the TeNT Concentration Necessary for Cell Intoxication

In order to assess the amount of TeNT needed to intoxicate a cell line, a panel of mammalian cell lines of neuronal origin will be screened to determine the concentration of neurotoxin necessary to cleave endogenously expressed VAMP (see Table 13). Cells will be grown in poly-D-lysine/Laminin coated 6-well plates as described above in Example II, 1a. TeNT (Metabiologics, Inc., Madison, Wis.) will be added at different concentrations (0 nM, 1 nM, 2 nM, 5 nM, 10 nM, 20 nM and 100 nM) in the culture medium containing cells for either approximately 8 or approximately 16 hours. Cells will be harvested and lysed as described above in Example II, 1a.

To detect for the presence of a cleaved TeNT substrate, western blot analysis will be conducted as described above in Example II, 1a, with the exception that blocked PVDF membranes will be incubated in a primary antibody solution containing one of the following antibodies in order to detect a TeNT VAMP-cleavage product rather than the rabbit polyclonal anti-SNAP25 antiserum pAb anti-SNAP25197 #1:1) 1:1000 dilution of mouse monoclonal anti-VAMP-1 antibody clone CI 10.1 (Synaptic Systems, Goettingen, Germany); 2) 1:20,000 dilution of mouse monoclonal anti-VAMP-2 antibody clone CI 69.1 (Synaptic Systems, Goettingen, Germany); or 3) 1:1000 dilution of mouse monoclonal anti-VAMP-3 antibody clone CI 10.1 (Synaptic Systems, Goettingen, Germany). In addition, a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) will be used rather than the goat polyclonal anti-rabbit IgG-HRP antibody. Detection of a TeNT VAMP-cleavage product in a cell line after at least an 8 hours incubation with at least 20 nM TeNT will indicate the ability of TeNT to intoxicate these cell lines.

8b. Assay to Determine the Time Required by a Cell to Uptake TeNT

In order to assess the amount of time needed by a cell line to uptake TeNT, a panel of mammalian cell lines of neuronal origin will be screened to determine the length of toxin exposure necessary to cleave endogenously expressed VAMP. Cells will be grown in poly-D-lysine/Laminin coated 6-well plates as described above in Example II, 8a. Approximately 1 nM TeNT (Metabiologics, Inc., Madison, Wis.) will be added to the culture medium for 10 min, 20 min, 30 min, 60 min 2 hours, 4 hours, 6 hours, 8 hours or 16 hours. Toxin treated cells will be harvested and lysed as described above in Example II, 8a. The presence of a TeNT VAMP-cleavage product will be determined by Western blot analysis as described above in Example II, 8a. Detection of a TeNT VAMP-cleavage product in a cell line after at least an 8 hour incubation with 1 nM TeNT will indicate a cell line that can rapidly uptake TeNT.

Example III

Treatments to Increase Uptake of a Cell for a Clostridial Toxin

Cell surface gangliosides are part of the receptor system for Clostridial toxins and appear to participate in binding of a toxin to its receptor system. Although toxin binding is not strictly dependent on the presence of gangliosides, the presence of specific gangliosides appears to be required for high affinity binding. In particular, CoNTs have been observed to interact in vitro and in vivo with polysialogangliosides, especially those of the G1b series (GD1a, GD1b, GD3, GQ1b, or GT1b), see, e.g., Jane L. Halpern & Elaine A. Neale, Neurospecific binding, internalization, and retrograde axonal transport, 195 Curr. Top. Microbiol. Immunol. 221-241 (1995). Likewise, the differentiated state of a cell could influence the expression, or level of expression of important components of a Clostridial toxin receptor system, such as, e.g., a cell-surface receptor. For example, Neuro-2A and SH-SY5Y cells can be differentiated to acquire a neuronal-like phenotype that may facilitate toxin uptake. To determine whether we could increase the uptake of a Clostridial toxin by a particular cell, we tested 1) whether a treatment that increased the ganglioside content of the cell membrane increased uptake of a Clostridial toxin by a cell; and 2) whether changing the state of differentiation of a cell could increase uptake of a Clostridial toxin by a cell.

1. Identification of Treatments that Increased Uptake of BoNT/A by a Cell

1a. Ganglioside Treatment to Increase High Affinity Uptake of BoNT/A by a Cell

Figure 9A:
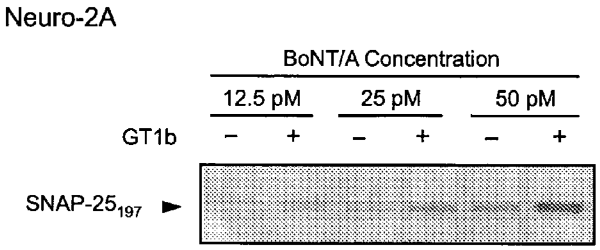
FIG. 9*a* shows a Western blot analysis evaluating the effects of ganglioside treatment on the uptake of BoNT/A. The blot shows Neuro-2A cells treated without or with 25 μg/mL of GT1b (− or +) and exposed overnight to three different concentrations of BoNT/A (12.5 μM, 25 μM or 50 μM), with equal amounts of protein loaded per lane and probed with an antibody that detects the BoNT/A SNAP-$25_{197}$ cleavage product.

In order to assess the effect of ganglioside treatment on the ability of BoNT/A to intoxicate a cell, a Neuro-2A cell line was pre-treated with different gangliosides to determine whether these sugar moieties could increase the uptake of BoNT/A by these cells. Neuro-2A cells were plated at a suitable density into individual wells of 6-well, poly-D-lysine/Laminin coated, tissue culture plates containing 3 mL of a suitable medium (see Table 13), and grown in a 37° C. incubator under 5% carbon dioxide. After approximately 24 hours, the medium was replaced by a serum-free media and 25 μg/mL of one of the following gangliosides was added to individual wells: GD1a, GD1b, GD3, GQ1b, or GT1b (AXXORA, LLC, San Diego, Calif.). After an overnight 37° C. incubation period, the ganglioside-treated cells were washed three times with 1 ml of phosphate-buffered saline, pH 7.4 and then incubated at 37° C. with 1% serum media containing different concentrations (0 nM, 12.5 nM, 25 nM, 50 nM) of BoNT/A (Metabiologics, Inc., Madison, Wis.) for approximately 8 or approximately 16 hours. Cells were collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl) piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol and 1% (v/v) Triton-X® 100 (4-octylphenol polyethoxylate), with rotation for 1 hour at 4° C. Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/ml or higher concentration. The presence of a BoNT/A $SNAP25_{197}$-cleavage product was determined by Western blot analysis as described above in Example II, 1a. An increase in BoNT/A $SNAP25_{197}$-cleavage product was detected in the Neuro-2A cell line treated with the ganglioside GT1b, thereby indicating that GT1b-treatment can increase the uptake of BoNT/A by Neuro-2A cells (see FIG. 9*a*).

Figure 9B:
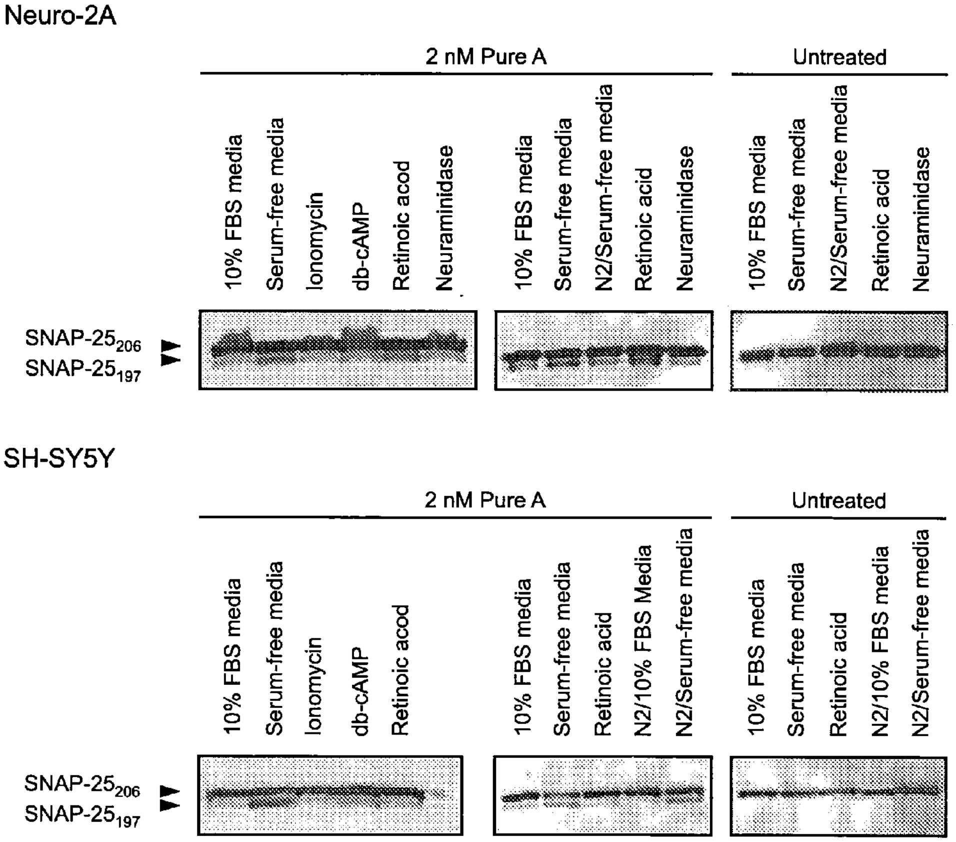
FIG. 9*b* shows Western blot analysis evaluating the effects of cell differentiation on the uptake of BoNT/A. The blots show either Neuro-2A cells or SH-SY5Y cells treated 2 nM of Pure BoNT/A overnight that where either grown in serum-free media or with various differentiation reagents (Ionomycin, db-cAMP, Retinoic acid, Neuraminidase or N2), with equal amounts of protein loaded per lane and probed with an antibody (SMI-81; Sternberger Monoclonals, Lutherville, Md.) that detects the uncleaved SNAP-$25_{206}$ substrate and the BoNT/A SNAP-$25_{197}$ cleavage product.

1b. Differentiation Reagent Treatment to Increase High Affinity Uptake of BoNT/A by a Cell In order to assess the effect of cellular differentiation on the ability of BoNT/A to intoxicate a cell, Neuro-2A and SH-SY5Y cells were treated with different growth conditions or differentiation reagents to determine whether differentiation of these cells could result in an increased uptake of BoNT/A by these cells. Cells were plated at a suitable density into individual wells of 6-well, poly-D-lysine/Laminin coated, tissue culture plates containing 3 mL of a suitable medium (see Table 13), and grown in a 37° C. incubator under 5% carbon dioxide. After approximately 24 hours, the medium was replaced with either a serum-free culture media or a 10% serum media and one of the following differentiating reagents was added to individual wells: 0.2 units Neuraminidase Type V (Sigma-Aldrich, St. Louis, Mo.), in water containing 0.2% ALBUMAX II (Invitrogen, Inc., Carlsbad, Calif.); 20 μM All Trans-Retinoic acid (Sigma-Aldrich, St. Louis, Mo.) in DMSO (Sigma-Aldrich, St. Louis, Mo.); 1 mM N6,2'-O-Dibutyryladenosine 3':5'-cyclic monophosphate sodium salt (db-cAMP) (Sigma-Aldrich, St. Louis, Mo.); 1 μM Ionomycin, calcium salt (Molecular Probes, Eugene, Oreg.) in DMSO (Sigma-Aldrich, St. Louis, Mo.); or 1×N-2 Supplement (Invitrogen, Inc., 17502-048, Carlsbad, Calif.). After a three day 37° C. incubation period, the serum-free media cells and the reagent-treated cells were washed three times with 1 ml of phosphate-buffered saline, pH 7.4 and then incubated at 37° C. with either serum-free media containing 2 nM Pure A (BTX-540) toxin (Metabiologics, Inc., Madison, Wis.) for approximately 18 hours (the growth condition experiments), or 10% serum media containing 2 nM Pure A (BTX-540) toxin (Metabiologics, Inc., Madison, Wis.) for approximately 18 hours (the differentiation reagent experiments). Cells were harvested by trypsin treatment, collected in 15 ml tubes, washed once with 1 ml of phosphate-buffered saline, pH 7.4, and then transferred to 1.5 ml microcentrifuge tubes. Cells were lysed in 0.5 ml of lysis buffer containing 50 mM N-(2-hydroxyethyl) piperazine-N'-(2-ethanesulfonic acid) (HEPES), pH 6.8, 150 mM sodium chloride, 1.5 mM magnesium chloride, 1 mM ethylene glycol bis(β-aminoethyl ether) N,N,N',N'-tetraacetic acid (EGTA), 10% glycerol and 1% (v/v) Triton-X® 100 (4-octylphenol polyethoxylate), with rotation for 1 to 2 hours at 4° C. Lysed cells were centrifuged at 5000 rpm for 10 min at 4° C. to eliminate debris and the supernatants were transferred to fresh 1.5 mL siliconized tubes. Protein concentrations were measured by Bradford's method and resuspended in 1×SDS sample buffer at 1 mg/ml or higher concentration. The presence of a BoNT/A $SNAP25_{197}$-cleavage product was determined by Western blot analysis as described above in Example II, 1a, with the exception that blocked PVDF membranes were incubated in a primary antibody solution containing a 1:50,000 dilution of mouse monoclonal anti-SNAP-25 antibody (SMI-81; Sternberger Monoclonals, Lutherville, Md.) rather than the rabbit polyclonal anti-SNAP25 antiserum pAb anti-SNAP25197 #1 and a secondary antibody solution containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) rather than the goat polyclonal anti-rabbit IgG-HRP antibody in order to detect both the uncleaved SNAP-25 and the BoNT/A $SNAP25_{197}$-cleavage product. An increase in BoNT/A $SNAP25_{197}$-cleavage product was detected in Neuro-2A and SH-SY5Y cells differentiated in serum-free conditions as compared to 10% serum media, thereby indicating that serum-free media conditions can increase the uptake of BoNT/A by Neuro-2A and SH-SY5Y cells (see FIG. 9*b*). Likewise, an increase in BoNT/A $SNAP25_{197}$-cleavage product was detected in Neuro-2A cells treated with all trans retinoic acid, thereby indicating that retinoic-induced differentiation of Neuro-2A can increase the uptake of BoNT/A by these cells (see FIG. 9*b*).

2. Identification of Treatments that Increased Uptake of BoNT/B by a Cell

2a. Ganglioside Treatment to Increase High Affinity Uptake of BoNT/B by a Cell

In order to assess the effect of ganglioside treatment on the ability of BoNT/B to intoxicate a cell, suitable mammalian cells will be pre-treated with different gangliosides to determine whether these sugar moieties can increase the uptake of BoNT/B by these cells. Cells will be grown in poly-D-lysine/Laminin coated 6-well plates and treated with gangliosides as described above in Example III, 1a. The ganglioside-treated cells will be incubated with BoNT/B (Metabiologics, Inc., Madison, Wis.) at different concentrations (0 nM, 12.5 nM, 25 nM, 50 nM) in 1% serum media for either approximately 8 or approximately 16 hours. Toxin treated cells will be harvested and lysed as described above in Example III, 1a. The presence of a BoNT/B VAMP-cleavage product will be determined by Western blot analysis as described above in Example II, 2a. An increase in BoNT/B VAMP-cleavage product detected in the cell line treated with a ganglioside will indicate that treatment with that ganglioside can increase the uptake of BoNT/B by these cells.

2b. Differentiation Reagent Treatment to Increase High Affinity Uptake of BoNT/B by a Cell In order to assess the effect of cellular differentiation on the ability of BoNT/B to intoxicate a cell, suitable mammalian cells will be treated with different growth conditions or differentiation reagents to determine whether differentiation of these cells can result in an increased uptake of BoNT/B by these cells. Cells will be grown in poly-D-lysine/Laminin coated 6-well plates using either serum-free or 10% serum media treated with differentiation reagents as described above in Example III, 1b. After a three day 37° C. incubation period, the serum-free media cells and the reagent-treated cells will be washed three times with 1 ml of phosphate-buffered saline, pH 7.4 and then will be incubated at 37° C. with either serum-free media containing BoNT/B (Metabiologics, Inc., Madison, Wis.) for approximately 18 hours (the growth condition experiments), or 10% serum media containing BoNT/B (Metabiologics, Inc., Madison, Wis.) for approximately 18 hours (the differentiation reagent experiments). Cells were harvested, collected and lysed as described above in Example III, 1a. The presence of a BoNT/B VAMP-cleavage product will be determined by Western blot analysis as described above in Example II, 2a. An increase in a BoNT/B VAMP-cleavage product detected in cells grown in serum-free media will indicate that treatment with that reagent can increase the uptake of BoNT/B by these cells. An increase in a BoNT/B VAMP-cleavage product detected in cells treated with a differentiation reagent will indicate that treatment with that reagent can increase the uptake of BoNT/B by these cells.

3. Identification of Treatments that Increased Uptake of BoNT/C1 by a Cell

3a. Ganglioside Treatment to Increase High Affinity Uptake of BoNT/C1 by a Cell

In order to assess the effect of ganglioside treatment on the ability of BoNT/C1 to intoxicate a cell, suitable mammalian cells will be pre-treated with different gangliosides to determine whether these sugar moieties can increase the uptake of BoNT/C1 by these cells. Cells will be grown in poly-D-lysine/Laminin coated 6-well plates and treated with gangliosides as described above in Example III, 1a. The ganglioside-treated cells will be incubated with BoNT/C1 (Metabiologics, Inc., Madison, Wis.) at different concentrations (0 nM, 12.5 nM, 25 nM, 50 nM) in 1% serum media for either approximately 8 or approximately 16 hours. Toxin treated cells will be harvested and lysed as described above in Example III, 1a. The presence of a BoNT/C1 $SNAP25_{180}$-cleavage product will be determined by Western blot analysis as described above in Example II, 3a. The presence of a BoNT/C1 Syntaxin-cleavage product will be determined by Western blot analysis as described above in Example II, 3a. An increase in BoNT/C1 $SNAP25_{180}$-cleavage product detected in the cell line treated with a ganglioside will indicate that treatment with that ganglioside can increase the uptake of BoNT/C1 by these cells. An increase in BoNT/C1 Syntaxin-cleavage product detected in the cell line treated with a ganglioside will indicate that treatment with that ganglioside can increase the uptake of BoNT/C1 by these cells.

3b. Differentiation Reagent Treatment to Increase High Affinity Uptake of BoNT/C1 by a Cell In order to assess the effect of cellular differentiation on the ability of BoNT/C1 to intoxicate a cell, suitable mammalian cells will be treated with different growth conditions or differentiation reagents to determine whether differentiation of these cells can result in an increased uptake of BoNT/C1 by these cells. Cells will be grown in poly-D-lysine/Laminin coated 6-well plates using either serum-free or 10% serum media treated with differentiation reagents as described above in Example III, 1b. After a three day 37° C. incubation period, the serum-free media cells and the reagent-treated cells will be washed three times with 1 ml of phosphate-buffered saline, pH 7.4 and then will be incubated at 37° C. with either serum-free media containing BoNT/C1 (Metabiologics, Inc., Madison, Wis.) for approximately 18 hours (the growth condition experiments), or 10% serum media containing BoNT/C1 (Metabiologics, Inc., Madison, Wis.) for approximately 18 hours (the differentiation reagent experiments). Cells were harvested, collected and lysed as described above in Example III, 1a. The presence of a BoNT/C1 $SNAP25_{180}$-cleavage product will be determined by Western blot analysis as described above in Example II, 3a. The presence of a BoNT/C1 Syntaxin-cleavage product will be determined by Western blot analysis as described above in Example II, 3a. An increase in a BoNT/C1 $SNAP25_{180}$-cleavage product detected in cells grown in serum-free media will indicate that treatment with that reagent can increase the uptake of BoNT/C1 by these cells. An increase in a BoNT/C1 $SNAP25_{180}$-cleavage product detected in cells treated with a differentiation reagent will indicate that treatment with that reagent can increase the uptake of BoNT/C1 by these cells. An increase in a BoNT/C1 Syntaxin-cleavage product detected in cells grown in serum-free media will indicate that treatment with that reagent can increase the uptake of BoNT/C1 by these cells. An increase in a BoNT/C1 Syntaxin-cleavage product detected in cells treated with a differentiation reagent will indicate that treatment with that reagent can increase the uptake of BoNT/C1 by these cells.

4. Identification of Treatments that Increased Uptake of BoNT/D by a Cell

4a. Ganglioside Treatment to Increase High Affinity Uptake of BoNT/D by a Cell

In order to assess the effect of ganglioside treatment on the ability of BoNT/D to intoxicate a cell, suitable mammalian cells will be pre-treated with different gangliosides to determine whether these sugar moieties can increase the uptake of BoNT/D by these cells. Cells will be grown in poly-D-lysine/Laminin coated 6-well plates and treated with gangliosides as described above in Example III, 1a. The ganglioside-treated cells will be incubated with BoNT/D (Metabiologics, Inc., Madison, Wis.) at different concentrations (0 nM, 12.5 nM, 25 nM, 50 nM) in 1% serum media for either approximately 8 or approximately 16 hours. Toxin treated cells will be harvested and lysed as described above in Example III, 1a. The presence of a BoNT/D VAMP-cleavage product will be determined by Western blot analysis as described above in Example II, 4a. An increase in BoNT/D VAMP-cleavage product detected in the cell line treated with a ganglioside will indicate that treatment with that ganglioside can increase the uptake of BoNT/D by these cells.

4b. Differentiation Reagent Treatment to Increase High Affinity Uptake of BoNT/D by a Cell In order to assess the effect of cellular differentiation on the ability of BoNT/D to intoxicate a cell, suitable mammalian cells will be treated with different growth conditions or differentiation reagents to determine whether differentiation of these cells can result in an increased uptake of BoNT/D by these cells. Cells will be grown in poly-D-lysine/Laminin coated 6-well plates using either serum-free or 10% serum media treated with differentiation reagents as described above in Example III, 1b. After a three day 37° C. incubation period, the serum-free media cells and the reagent-treated cells will be washed three times with 1 ml of phosphate-buffered saline, pH 7.4 and then will be incubated at 37° C. with either serum-free media containing BoNT/D (Metabiologics, Inc., Madison, Wis.) for approximately 18 hours (the growth condition experiments), or 10% serum media containing BoNT/D (Metabiologics, Inc., Madison, Wis.) for approximately 18 hours (the differentiation reagent experiments). Cells were harvested, collected and lysed as described above in Example III, 1a. The presence of a BoNT/D VAMP-cleavage product will be determined by Western blot analysis as described above in Example II, 4a. An increase in a BoNT/D VAMP-cleavage product detected in cells grown in serum-free media will indicate that treatment with that reagent can increase the uptake of BoNT/D by these cells. An increase in a BoNT/D VAMP-cleavage product detected in cells treated with a differentiation reagent will indicate that treatment with that reagent can increase the uptake of BoNT/D by these cells.

5. Identification of Treatments that Increased Uptake of BoNT/E by a Cell

5a. Ganglioside Treatment to Increase High Affinity Uptake of BoNT/E by a Cell

Figure 10A:
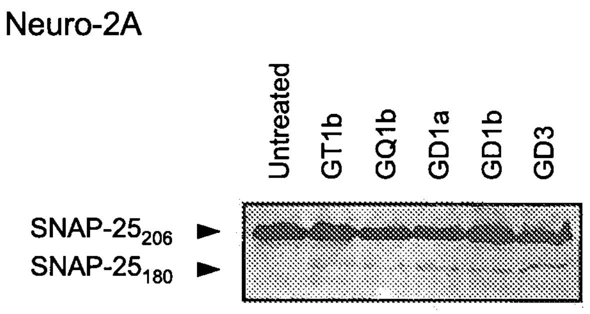
FIG. 10*a* shows a Western blot analysis evaluating the effects of ganglioside treatment on the uptake of BoNT/E. The blot shows Neuro-2A cells treated with either 25 μg/mL of GT1b, GQ1b, GD1a, GD1b or GD3 and exposed for approximately 5 hours to 14 nM of BoNT/E di-chain, with equal amounts of protein loaded per lane and probed with an antibody (SMI-81; Sternberger Monoclonals, Lutherville, Md.) that detects the uncleaved SNAP-$25_{206}$ substrate and the BoNT/E SNAP-$25_{180}$ cleavage product.

In order to assess the effect of ganglioside treatment on the ability of BoNT/E to intoxicate a cell, a Neuro-2A cell line was pre-treated with different gangliosides to determine whether these sugar moieties could increase the uptake of BoNT/E by these cells. Neuro-2A cells were grown in poly-D-lysine/Laminin coated 6-well plates and treated with gangliosides as described above in Example III, 1a. The ganglioside-treated cells were incubated with BoNT/E (Metabiologics, Inc., Madison, Wis.) at different concentrations (0 nM, 12.5 nM, 25 nM, 50 nM) in 1% serum media for either approximately 6 or approximately 16 hours. Toxin treated cells were harvested and lysed as described above in Example II, 5a. The presence of a BoNT/E $SNAP25_{180}$-cleavage product was determined by Western blot analysis as described above in Example II, 5a. An increase in BoNT/E $SNAP25_{180}$-cleavage product was detected in the Neuro-2A cell lines treated with the gangliosides GD3, GD1b and GD1a, thereby indicating that GD3-treatment, GD1b-treatment or GD1a-treatment can increase the uptake of BoNT/E by Neuro-2A cells (see FIG. 10*a*).

Figure 10B:
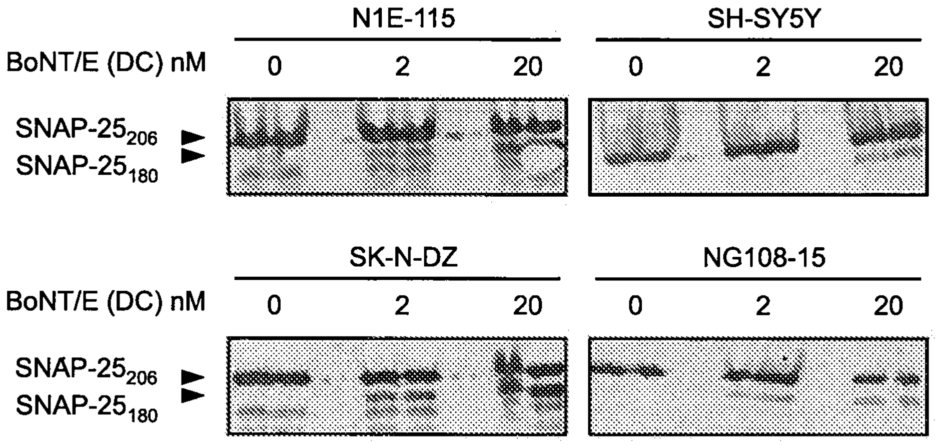
FIG. 10*b* shows Western blot analysis evaluating the effects of cell differentiation on the uptake of BoNT/E. The blots show either N1E-115 cells, SH-SY5Y cells, SK-N-DZ cells or NG108-15 cells treated with either 0 nM, 2 nM or 20 nM of BoNT/E di-chain for approximately 6 hours that where grown in serum-free media, with equal amounts of protein loaded per lane and probed with an antibody (SMI-81; Sternberger Monoclonals, Lutherville, Md.) that detects the uncleaved SNAP-$25_{206}$ substrate and the BoNT/E SNAP-$25_{180}$ cleavage product.

5b. Differentiation Reagent Treatment to Increase High Affinity Uptake of BoNT/E by a Cell In order to assess the effect of cellular differentiation on the ability of BoNT/E to intoxicate a cell, SH-SY5Y cells were treated with different growth conditions to determine whether differentiation of these cells could result in an increased uptake of BoNT/E by these cells. SH-SY5Y cells were grown in poly-D-lysine/Laminin coated 6-well plates using serum-free as described above in Example III, 1b. The serum-free media cells were incubated with BoNT/E (Metabiologics, Inc., Madison, Wis.) at concentrations of 5 nM and 20 nM for approximately 30 minutes, approximately 1 hour, approximately 2 hours, approximately 4 hours, approximately 8 hours and approximately 16 hours. Toxin treated cells were harvested, collected and lysed as described above in Example III, 1b. The presence of a BoNT/E $SNAP25_{180}$-cleavage product was determined by Western blot analysis as described above in Example II, 5a. An increase in BoNT/E $SNAP25_{180}$-cleavage product was detected in SH-SY5Y cells differentiated in serum-free conditions as early as 4 hours following exposure to toxin, with a maximal signal evident at least at 8 hours after BoNT/E-treatment, as compared to 10% serum media, thereby indicating that serum-free media conditions can increase the uptake of BoNT/E by SH-SY5Y cells (see FIG. 10*b*).

6. Identification of Treatments that Increased Uptake of BoNT/F by a Cell

6a. Ganglioside Treatment to Increase High Affinity Uptake of BoNT/F by a Cell

In order to assess the effect of ganglioside treatment on the ability of BoNT/F to intoxicate a cell, suitable mammalian cells will be pre-treated with different gangliosides to determine whether these sugar moieties can increase the uptake of BoNT/F by these cells. Cells will be grown in poly-D-lysine/Laminin coated 6-well plates and treated with gangliosides as described above in Example III, 1a. The ganglioside-treated cells will be incubated with BoNT/F (Metabiologics, Inc., Madison, Wis.) at different concentrations (0 nM, 12.5 nM, 25 nM, 50 nM) in 1% serum media for either approximately 8 or approximately 16 hours. Toxin treated cells will be harvested and lysed as described above in Example III, 1a. The presence of a BoNT/F VAMP-cleavage product will be determined by Western blot analysis as described above in Example II, 6a. An increase in BoNT/F VAMP-cleavage product detected in the cell line treated with a ganglioside will indicate that treatment with that ganglioside can increase the uptake of BoNT/F by these cells.

6b. Differentiation Reagent Treatment to Increase High Affinity Uptake of BoNT/F by a Cell In order to assess the effect of cellular differentiation on the ability of BoNT/F to intoxicate a cell, suitable mammalian cells will be treated with different growth conditions or differentiation reagents to determine whether differentiation of these cells can result in an increased uptake of BoNT/F by these cells. Cells will be grown in poly-D-lysine/Laminin coated 6-well plates using either serum-free or 10% serum media treated with differentiation reagents as described above in Example III, 1b. After a three day 37° C. incubation period, the serum-free media cells and the reagent-treated cells will be washed three times with 1 ml of phosphate-buffered saline, pH 7.4 and then will be incubated at 37° C. with either serum-free media containing BoNT/F (Metabiologics, Inc., Madison, Wis.) for approximately 18 hours (the growth condition experiments), or 10% serum media containing BoNT/F (Metabiologics, Inc., Madison, Wis.) for approximately 18 hours (the differentiation reagent experiments). Cells were harvested, collected and lysed as described above in Example III, 1a. The presence of a BoNT/F VAMP-cleavage product will be determined by Western blot analysis as described above in Example II, 6a. An increase in a BoNT/F VAMP-cleavage product detected in cells grown in serum-free media will indicate that treatment with that reagent can increase the uptake of BoNT/F by these cells. An increase in a BoNT/F VAMP-cleavage product detected in cells treated with a differentiation reagent will indicate that treatment with that reagent can increase the uptake of BoNT/F by these cells.

7. Identification of Treatments that Increased Uptake of BoNT/G by a Cell

7a. Ganglioside Treatment to Increase High Affinity Uptake of BoNT/G by a Cell

In order to assess the effect of ganglioside treatment on the ability of BoNT/G to intoxicate a cell, suitable mammalian cells will be pre-treated with different gangliosides to determine whether these sugar moieties can increase the uptake of BoNT/G by these cells. Cells will be grown in poly-D-lysine/Laminin coated 6-well plates and treated with gangliosides as described above in Example III, 1a. The ganglioside-treated cells will be incubated with BoNT/G (Metabiologics, Inc., Madison, Wis.) at different concentrations (0 nM, 12.5 nM, 25 nM, 50 nM) in 1% serum media for either approximately 8 or approximately 16 hours. Toxin treated cells will be harvested and lysed as described above in Example III, 1a. The presence of a BoNT/G VAMP-cleavage product will be determined by Western blot analysis as described above in Example II, 7a. An increase in BoNT/G VAMP-cleavage product detected in the cell line treated with a ganglioside will indicate that treatment with that ganglioside can increase the uptake of BoNT/G by these cells.

7b. Differentiation Reagent Treatment to Increase High Affinity Uptake of BoNT/G by a Cell In order to assess the effect of cellular differentiation on the ability of BoNT/G to intoxicate a cell, suitable mammalian cells will be treated with different growth conditions or differentiation reagents to determine whether differentiation of these cells can result in an increased uptake of BoNT/G by these cells. Cells will be grown in poly-D-lysine/Laminin coated 6-well plates using either serum-free or 10% serum media treated with differentiation reagents as described above in Example III, 1b. After a three day 37° C. incubation period, the serum-free media cells and the reagent-treated cells will be washed three times with 1 ml of phosphate-buffered saline, pH 7.4 and then will be incubated at 37° C. with either serum-free media containing BoNT/G (Metabiologics, Inc., Madison, Wis.) for approximately 18 hours (the growth condition experiments), or 10% serum media containing BoNT/G (Metabiologics, Inc., Madison, Wis.) for approximately 18 hours (the differentiation reagent experiments). Cells were harvested, collected and lysed as described above in Example III, 1a. The presence of a BoNT/G VAMP-cleavage product will be determined by Western blot analysis as described above in Example II, 7a. An increase in a BoNT/G VAMP-cleavage product detected in cells grown in serum-free media will indicate that treatment with that reagent can increase the uptake of BoNT/G by these cells. An increase in a BoNT/G VAMP-cleavage product detected in cells treated with a differentiation reagent will indicate that treatment with that reagent can increase the uptake of BoNT/G by these cells.

8. Identification of Treatments that Increased Uptake of TeNT by a Cell

8a. Ganglioside Treatment to Increase High Affinity Uptake of TeNT by a Cell

In order to assess the effect of ganglioside treatment on the ability of TeNT to intoxicate a cell, suitable mammalian cells will be pre-treated with different gangliosides to determine whether these sugar moieties can increase the uptake of TeNT by these cells. Cells will be grown in poly-D-lysine/Laminin coated 6-well plates and treated with gangliosides as described above in Example III, 1a. The ganglioside-treated cells will be incubated with TeNT (Metabiologics, Inc., Madison, Wis.) at different concentrations (0 nM, 12.5 nM, 25 nM, 50 nM) in 1% serum media for either approximately 8 or approximately 16 hours. Toxin treated cells will be harvested and lysed as described above in Example III, 1a. The presence of a TeNT VAMP-cleavage product will be determined by Western blot analysis as described above in Example II, 8a. An increase in TeNT VAMP-cleavage product detected in the cell line treated with a ganglioside will indicate that treatment with that ganglioside can increase the uptake of TeNT by these cells.

8b. Differentiation Reagent Treatment to Increase High Affinity Uptake of TeNT by a Cell In order to assess the effect of cellular differentiation on the ability of TeNT to intoxicate a cell, suitable mammalian cells will be treated with different growth conditions or differentiation reagents to determine whether differentiation of these cells can result in an increased uptake of TeNT by these cells. Cells will be grown in poly-D-lysine/Laminin coated 6-well plates using either serum-free or 10% serum media treated with differentiation reagents as described above in Example III, 1b. After a three day 37° C. incubation period, the serum-free media cells and the reagent-treated cells will be washed three times with 1 ml of phosphate-buffered saline, pH 7.4 and then will be incubated at 37° C. with either serum-free media containing TeNT (Metabiologics, Inc., Madison, Wis.) for approximately 18 hours (the growth condition experiments), or 10% serum media containing TeNT (Metabiologics, Inc., Madison, Wis.) for approximately 18 hours (the differentiation reagent experiments). Cells were harvested, collected and lysed as described above in Example III, 1a. The presence of a TeNT VAMP-cleavage product will be determined by Western blot analysis as described above in Example II, 8a. An increase in a TeNT VAMP-cleavage product detected in cells grown in serum-free media will indicate that treatment with that reagent can increase the uptake of TeNT by these cells. An increase in a TeNT VAMP-cleavage product detected in cells treated with a differentiation reagent will indicate that treatment with that reagent can increase the uptake of TeNT by these cells.

Example IV

Generation of Cells Transiently Containing a CLOSTRIDIAL TOXIN SUBSTRATE

1. Generation of Cells Containing a BoNT/A, BoNT/C1 or BoNT/E SNAP-25 Substrate by Adenoviral Transduction 1a. Construction of pAd-DEST/SNAP-$25_{206}$-GFP To make a pAd-DEST/SNAP-$25_{206}$-GFP construct, a nucleic acid fragment encoding the amino acid region comprising SNAP-$25_{206}$-GFP of is amplified from pQBI-25/SNAP$25_{206}$-GFP DNA (see Example I, 1a) using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/SNAP-$25_{206}$-GFP construct is digested with restriction enzymes that 1) excise the insert containing the entire open reading frame encoding the SNAP-$25_{206}$-GFP peptide; and 2) enable this insert to be operably-linked to a pAd-DEST vector (Invitrogen, Inc., Carlsbad, Calif.). This insert is subcloned using a T4 DNA ligase procedure into a pAd-DEST vector that is digested with appropriate restriction endonucleases to yield pAd-DEST/SNAP-$25_{206}$-GFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. This cloning strategy yields a mammalian expression construct encoding the SNAP-$25_{206}$-GFP operably-linked to the expression elements of the pAd-DEST vector.

1b. Production of an Adenoviral Stock Containing pAd-DEST/SNAP-25-GFP

To produce an adenoviral stock containing an expression construct encoding a BoNT/A, BoNT/C1 or BoNT/E SNAP-25-GFP substrate, such as, e.g., pAd-DEST/SNAP-$25_{206}$-GFP, about $5\times10^5$ 293A cells are plated in a 35 mm tissue culture dish containing 3 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about $5\times10^5$ cells/ml (6-16 hours). One the day of transfection, replace complete, supplemented DMEM media with 2 mL of OPTI-MEM Reduced Serum Medium. A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of the linearized expression construct encoding a BoNT/A, BoNT/C1 or BoNT/E SNAP-25-GFP substrate, such as, e.g., pAd-DEST/SNAP-$25_{206}$-GFP. To linearize a pAd-DEST/SNAP-25-GFP construct, 5 μg of a pAd-DEST/SNAP-25-GFP construct is digested with PacI (New England Biolabs, Beverly, Mass.). The linearized plasmid is purified using QIAquick kit procedure (QIAGEN, Inc., Valencia, Calif.) and is resuspended in TE Buffer. This transfection is incubated at room temperature for approximately 20 minutes. The 500 μL transfection solution is then added to the 293A cells and the cells are incubated in a 37° C. incubator under 5% carbon dioxide for approximately 16 hours. Transfection media is replaced with 3 mL of fresh complete, supplemented DMEM and cells are incubated in a 37° C. incubator under 5% carbon dioxide for approximately 24 hours. The cells are trypsinized and the contents of each well are transferred to a sterile 10 cm tissue culture plate containing 10 mL of complete, supplemented DMEM. Replace the old media with fresh complete, supplemented DMEM every 2 or 3 days until visible regions of cytopathic effect are observed (typically 7-10 days). Replenish the old culture media with fresh complete, supplemented DMEM and allow the infections to proceed until approximately 80% cytopathic effect is observed (typically 10-13 days post transfection). The adenovirus-containing cells are harvested by detaching the cells using the culture media and scraping cells from the culture plate. Detached cells and media are transferred to a 15 mL tube. The harvested cells are lysed using one freeze-thaw round consisting of −80° C. for 30 minutes then 37° C. for 15 minutes. The cell lysate is centrifuged (5,000×g at 20° C. for 15 minutes) to pellet the cellular debris. The clarified supernatant containing the adenoviral particles is transferred to 2 mL cryovials in 1 mL aliquots and should contain approximately $1\times10^7$ to $10^8$ pfu of adenoviral particles. Aliquots can be stored at −80° C. until needed.

1c. Amplification of an Adenoviral Stock Containing pAd-DEST/SNAP-25-GFP

To amplified to the adenoviral stock containing an expression construct encoding a BoNT/A, BoNT/C1 or BoNT/E SNAP-25-GFP substrate, such as, e.g., pAd-DEST/SNAP-$25_{206}$-GFP, about $3\times10^6$ 293A cells are plated in a 100 mm culture dish containing in 10 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about 80-90% confluency (6-16 hours). The cells are inoculated cells with 100 μL of adenoviral stock and incubated for approximately 48-72 hours in a 37° C. incubator under 5% carbon dioxide until the cells round up and are floating or lightly attached to the culture plate. The adenovirus-containing cells are harvested by detaching the cells using the culture media and scraping cells from the culture plate. Detached cells and media are transferred to a 15 mL tube. The harvested cells are lysed using three freeze-thaw round consisting of −80° C. for 30 minutes then 37° C. for 15 minutes. The cell lysate is centrifuged (5,000×g at 20° C. for 15 minutes) to pellet the cellular debris. The clarified supernatant containing the adenoviral particles is transferred to 2 mL cryovials in 1 mL aliquots and should contain approximately $1\times10^8$ to $10^9$ pfu of adenoviral particles. Aliquots can be stored at −80° C. until needed.

1d. Transduction of Cells with an Adenoviral Stock Containing pAd-DEST/SNAP-25-GFP To transduce cells with the adenoviral stock containing an expression construct encoding a BoNT/A, BoNT/C1 or BoNT/E SNAP-25-GFP substrate, such as, e.g., pAd-DEST/SNAP-$25_{206}$-GFP, about $1.5\times10^5$ SH-SY5Y cells are plated in a 6-well tissue culture dish containing 3 mL of complete 1:1 EMEM and Ham's F12 Media (EMEM:F12), supplemented with 10% fetal bovine serum (FBS), 4 mM glutamine (Invitrogen, Inc, Carlsbad, Calif.), 1% sodium pyruvate (Invitrogen, Inc, Carlsbad, Calif.), 1.5 g/L sodium bicarbonate, 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about $5\times10^5$ cells/ml (6-16 hours). Cells are inoculated with approximately 4 μL of the adenoviral stock (approximately $5\times10^8$ pfu/ml) and are incubated for approximately 24 hours in a 37° C. incubator under 5% carbon dioxide. The transduction media is replaced with 3 mL of fresh complete, supplemented EMEM:F12 and cells are incubated in a 37° C. incubator under 5% carbon dioxide for approximately 24 hours. The transduced cells can be used to conduct a BoNT/A, BoNT/C1 or BoNT/E activity assay using a SNAP-25-GFP substrate.

2. Generation of Cells Containing a BoNT/A, BoNT/C1 or BoNT/E Substrate by Lentiviral Transduction 2a. Construction of pLenti6Ubc/V5-SNAP-$25_{206}$-GFP To make a pLenti6Ubc/V5-SNAP-$25_{206}$-GFP construct, a nucleic acid fragment encoding the amino acid region comprising a BoNT/A, BoNT/C1 or BoNT/E SNAP-25-GFP substrate is amplified from, e.g., pQBI-25/SNAP$25_{206}$-GFP DNA (see Example I, 1a) using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/SNAP-$25_{206}$-GFP construct is digested with restriction enzymes that 1) excise the insert containing the entire open reading frame encoding the SNAP-$25_{206}$-GFP peptide; and 2) enable this insert to be operably-linked to a pLenti6Ubc/V5 vector (Invitrogen, Inc., Carlsbad, Calif.). This insert is subcloned using a T4 DNA ligase procedure into a pLenti6Ubc/V5 vector that is digested with appropriate restriction endonucleases to yield pLenti6Ubc/V5-SNAP-$25_{206}$-GFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. This cloning strategy yields a mammalian expression construct encoding the SNAP-$25_{206}$-GFP operably-linked to the expression elements of the pLenti6Ubc/V5 vector an amino-terminal V5 peptide.

2b. Production of a Lentiviral Stock Containing pLenti6Ubc/v5-SNAP-25-GFP

To produce a lentiviral stock containing pLenti6Ubc/V5-SNAP-25-GFP, a 3.0 mL transfection solution is prepared by adding 1.5 mL of OPTI-MEM Reduced Serum Medium containing 36 μL of LipofectAmine 2000 (Invitrogen, Carlsbad, Calif.) incubated at room temperature for 5 minutes to 1.5 mL of OPTI-MEM Reduced Serum Medium containing 3 μg of an expression construct encoding a BoNT/A, BoNT/C1 or BoNT/E SNAP-25 substrate, such as, e.g., pLenti6Ubc/V5-SNAP-$25_{206}$-GFP and 9 μg of ViraPower™ Packaging Mix. After an approximately 20 minute incubation at room temperature, the DNA-lipid complexes are added to a 10 cm tissue culture plate containing 5 mL OPTI-MEM Reduced Serum Medium. A 5 mL cell suspension containing approximately $6\times10^6$ 293A cells are then added to DNA-lipid complex media and grown in a 37° C. incubator under 5% carbon dioxide overnight. Transfection media is replaced with 10 mL of complete Dulbecco's Modified Eagle Media (DMEM), supplemented with 10% fetal bovine serum (FBS), 2 mM glutamine (Invitrogen, Inc, Carlsbad, Calif.), 1 mM sodium pyruvate (Invitrogen, Inc, Carlsbad, Calif.), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide for approximately 24-48 hours. The lentivirus-containing cells are harvested by detaching the cells using the culture media and scraping cells from the culture plate. Detached cells and media are transferred to a 15 mL tube and centrifuged (5,000×g at 20° C. for 15 minutes) to pellet the cellular debris. The clarified supernatant containing the lentiviral particles is transferred to 2 mL cryovials in 1 mL aliquots and should contain approximately $5\times10^5$ to $2\times10^7$ pfu/mL of lentiviral particles. Aliquots can be stored at −80° C. until needed.

2c. Transduction of Cells with an Lentiviral Stock Containing a pLenti6Ubc/V5-SNAP-25-GFP To transduce cells with the lentiviral stock containing pLenti6Ubc/V5-SNAP-25-GFP, about $1.5\times10^5$ SH-SY5Y cells are plated in a 6-well tissue culture dish containing 3 mL of complete 1:1 EMEM and Ham's F12 Media (EMEM:F12), supplemented with 10% fetal bovine serum (FBS), 4 mM glutamine (Invitrogen, Inc, Carlsbad, Calif.), 1% sodium pyruvate (Invitrogen, Inc, Carlsbad, Calif.), 1.5 g/L sodium bicarbonate, 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about $5\times10^5$ cells/ml (6-16 hours). Cells are inoculated with the lentiviral stock containing an expression construct encoding a BoNT/A, BoNT/C1 or BoNT/E SNAP-25 substrate, such as, e.g., pLenti6Ubc/V5-SNAP-$25_{206}$-GFP (see Example I, 1), using a suitable multiplicity of infection and are incubated for approximately 16-24 hours in a 37° C. incubator under 5% carbon dioxide. The transduction media is replaced with 3 mL of fresh complete, supplemented EMEM:F12 and cells are incubated in a 37° C. incubator under 5% carbon dioxide for approximately 24-48 hours. The transduced cells can be used to conduct a BoNT/A, BoNT/C1 or BoNT/E activity assay using a SNAP-25-GFP substrate.

3. Generation of Cells Containing a BoNT/A, BoNT/C1 or BoNT/E Substrate by Protein Transformation 3a. Expression of a SNAP-25-GFP Substrate Using a Bacterial Cell Line To express a BoNT/A, BoNT/C1 or BoNT/E SNAP-25-GFP substrate using bacteria, an expression construct encoding a BoNT/A, BoNT/C1 or BoNT/E SNAP-25-GFP substrate, such as, e.g., pQBI-67/SNAP-$25_{206}$-GFP as described above in Example I, 1d, is introduced into chemically competent *E. coli* BL21 (DE3) cells (Invitrogen, Inc, Carlsbad, Calif.) using a heat-shock transformation protocol. The heat-shock reaction is then plated onto 1.5% Luria-Bertani agar plates (pH 7.0) containing 100 μg/mL of Ampicillin and placed in a 37° C. incubator for overnight growth. A single Ampicillin-resistant colony of transformed *E. coli* containing pQBI-67/SNAP-$25_{206}$-GFP is used to inoculate a 15 mL test tube containing 3.0 mL Luria-Bertani media, (pH 7.0) containing 100 μg/mL of Ampicillin which is then placed in a 37° C. incubator, shaking at 250 rpm, for overnight growth. The resulting overnight starter culture is used to inoculate a 1.0 L baffled flask containing 100 mL Luria-Bertani media, (pH 7.0) containing 100 μg/mL of Ampicillin at a dilution of 1:1000. This culture is grown in a 32° C. incubator shaking at 250 rpm for approximately 6.5 hours until mid-log phase is reached ($OD_{600}$ of about 0.6-0.8). Protein expression is then induced by adding 1 mM isopropyl-β-D-thiogalactopyranoside (IPTG) and the culture is placed in a 32° C. incubator shaking at 250 rpm for overnight expression. Cells are harvested by centrifugation (4,000 rpm at 4° C. for 20-30 minutes) to pellet the cells. The supernatant is discarded and the cell pellet is used immediately for subsequent steps, or the pellet is stored at −80° C. until needed.

3b. Expression of a SNAP-25-GFP Substrate Using a Mammalian Cell Line

To express a BoNT/A, BoNT/C1 or BoNT/E SNAP-25-GFP substrate using a mammalian cell line, about $1.5\times10^5$ SH-SY5Y cells are plated in a 35 mm tissue culture dish containing 3 mL of complete 1:1 EMEM and Ham's F12 Media (EMEM:F12), supplemented with 10% fetal bovine serum (FBS), 4 mM glutamine (Invitrogen, Inc, Carlsbad, Calif.), 1% sodium pyruvate (Invitrogen, Inc, Carlsbad, Calif.), 1.5 g/L sodium bicarbonate, 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about $5\times10^5$ cells/ml (6-16 hours). A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of an expression construct encoding a BoNT/A, BoNT/C1 or BoNT/E SNAP-25-GFP substrate, such as, e.g., pQBI-25/$SNAP25_{206}$-GFP (see Example I, 1a). This transfection is incubated at room temperature for approximately 20 minutes. The complete, supplemented EMEM:F12 media is replaced with 2 mL of OPTI-MEM Reduced Serum Medium and the 500 μL transfection solution is added to the SH-SY5Y cells and the cells are incubated in a 37° C. incubator under 5% carbon dioxide for approximately 16 hours. Transfection media is replaced with 3 mL of fresh complete, supplemented EMEM:F12 and cells are incubated in a 37° C. incubator under 5% carbon dioxide for approximately 48 hours. Cells are harvest by rinsing cells once with 3.0 mL of 100 mM phosphate-buffered saline, pH 7.4 and detaching rinsed cells by adding 500 μl of 100 mM phosphate-buffered saline, pH 7.4 and scraping cells from the culture plate. Detached cells are transferred to a 1.5 mL test tube and are pelleted by microcentrifugation (10,000×g at 4° C. for 5 minutes). The supernatant is discarded and the cell pellet is used immediately for subsequent steps, or the pellet is stored at −80° C. until needed.

3c. Purification of a SNAP-25-GFP Substrate

To purify a SNAP-25-GFP substrate, a cell pellet expressing an expression construct encoding a BoNT/A, BoNT/C1 or BoNT/E SNAP-25 substrate, such as, e.g., either a pQBI-67/SNAP-$25_{206}$-GFP or a pQBI-25/SNAP-$25_{206}$-GFP construct, is resuspended in 10 mL of Tris-EDTA Buffer (10 mM Tris-HCl, pH 8.0; 1 mM EDTA, pH 8.0), containing 1 mg/mL of lysozyme and the cells are lysed using three freeze-thaw rounds consisting of −80° C. for 5 minutes then 37° C. for 5 minutes. The cell lysate is centrifuged (5,000×g at 4° C. for 15 minutes) to pellet the cellular debris and the supernatant is transferred to a new tube containing an equal volume of Column Binding Buffer (4 M ammonium sulfate). A hydrophobic interaction chromatography (HIC) column is prepared using a 20 mL Econo-Pac column support (Bio-Rad Laboratories, Hercules, Calif.) that is packed with 2.5-5.0 mL of methyl HIC resin (Bio-Rad Laboratories, Hercules, Calif.), which is then equilibrated by rinsing with 5 column volumes of Column Equilibration Buffer (2 M ammonium sulfate). The clarified lysate is applied slowly to the equilibrated column by gravity flow (approximately 0.25-0.3 mL/minute). The column is then washed with 5 column volumes of Column Wash Buffer (1.3 M ammonium sulfate). The SNAP-$25_{206}$-GFP substrate is eluted with 20-30 mL of Column Elution Buffer (10 mM TE Buffer) and is collected in approximately twelve 1 mL fractions. The progress of the SNAP-$25_{206}$-GFP substrate sample through the column as well as which elution fractions contain the sample is monitored using an ultraviolet light from a hand-held transilluminator. The amount of SNAP-$25_{206}$-GFP substrate contained in each elution fraction is determined by a Bradford dye assay. In this procedure, 20 μL aliquot from each 1.0 mL fraction is combined with 200 μL of Bio-Rad Protein Reagent (Bio-Rad Laboratories, Hercules, Calif.), diluted 1 to 4 with deionized, distilled water, and then the intensity of the colorimetric signal is measured using a spectrophotometer. The five fractions with the strongest signal are considered to comprise the elution peak and are pooled. Total protein yield are determined by estimating the total protein concentration of the pooled peak elution fractions using bovine gamma globulin as a standard (Bio-Rad Laboratories, Hercules, Calif.). The amount of SNAP-$25_{206}$-GFP substrate is adjusted to a protein concentration of approximately 100 ng/mL.

3d. Protein Transformation of a SNAP-25-GFP Substrate

To transform a SNAP-25-GFP substrate into a mammalian cell line, about $1.5\times10^5$ SH-SY5Y cells are plated in a 35 mm tissue culture dish containing 3 mL of complete 1:1 EMEM and Ham's F12 Media (EMEM:F12), supplemented with 10% fetal bovine serum (FBS), 4 mM glutamine (Invitrogen, Inc, Carlsbad, Calif.), 1% sodium pyruvate (Invitrogen, Inc, Carlsbad, Calif.), 1.5 g/L sodium bicarbonate, 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about $5\times10^5$ cells/ml (6-16 hours). A 200 μL protein transfection solution is prepared by adding 100 μL of distilled water containing 6 μL of Chariot™ protein delivery agent (Active Motif, Carlsbad, Calif.) to 100 μL of 100 mM phosphate-buffered saline, pH 7.4 containing 1 μg of a SNAP25-GFP substrate, such as, e.g., $SNAP25_{206}$-GFP, and this solution is incubated at room temperature for approximately 30 minutes. After incubation, the cells are washed once by rinsing cells with 3.0 mL of 100 mM phosphate-buffered saline, pH 7.4. The 200 μL protein transfection solution is added to the washed cells, followed by 400 μL of OPTI-MEM Reduced Serum Medium and the cells are incubated in a 37° C. incubator under 5% carbon dioxide for approximately 1 hour. Add 1 mL of fresh complete, supplemented EMEM:F12 to the cells and incubate in a 37° C. incubator under 5% carbon dioxide. After 1-2 hours, the transformed cells can be used to conduct a BoNT/A, BoNT/C1 or BoNT/E activity assay.

4. Generation of Cells Containing a BoNT/B, BoNT/D, BoNT/F, BoNT/G or TeNT VAMP Substrate by Adenoviral Transduction 4a. Construction of pAd-DEST/VAMP-GFP To make a pAd-DEST/VAMP-GFP construct encoding a BoNT/B, BoNT/D, BoNT/F, BoNT/G or TeNT VAMP-GFP substrate, a nucleic acid fragment encoding the amino acid region comprising VAMP-GFP of is amplified from, e.g., pQBI-25/VAMP-1-GFP DNA, pQBI-25/VAMP-2-GFP DNA or pQBI-25/VAMP-3-GFP DNA (see Examples I, 2a; I, 2b; or I, 2c) using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/VAMP-GFP construct is digested with restriction enzymes that 1) excise the insert containing the entire open reading frame encoding the VAMP-GFP peptide; and 2) enable this insert to be operably-linked to a pAd-DEST vector (Invitrogen, Inc., Carlsbad, Calif.). This insert is subcloned using a T4 DNA ligase procedure into a pAd-DEST vector that is digested with appropriate restriction endonucleases to yield pAd-DEST/VAMP-GFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. This cloning strategy yields a mammalian expression construct encoding the VAMP-GFP operably-linked to the expression elements of the pAd-DEST vector.

4b. Production of an Adenoviral Stock Containing pAd-DEST/VAMP-GFP

To produce an adenoviral stock containing an expression construct encoding a BoNT/B, BoNT/D, BoNT/F, BoNT/G or TeNT VAMP-GFP substrate, such as, e.g., pAd-DEST/VAMP-GFP, about $5\times10^5$ 293A cells are plated in a 35 mm tissue culture dish containing 3 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about $5\times10^5$ cells/ml (6-16 hours). One the day of transfection, replace complete, supplemented DMEM media with 2 mL of OPTI-MEM Reduced Serum Medium. A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of the linearized expression construct encoding a BoNT/B, BoNT/D, BoNT/F, BoNT/G or TeNT VAMP-GFP substrate, such as, e.g., pAd-DEST/VAMP-GFP. To linearize a pAd-DEST/VAMP-GFP construct, 5 μg of a pAd-DEST/VAMP-GFP construct is digested with PacI (New England Biolabs, Beverly, Mass.). The linearized plasmid is purified using QIAquick kit procedure (QIAGEN, Inc., Valencia, Calif.) and is resuspended in TE Buffer. This transfection is incubated at room temperature for approximately 20 minutes. The 500 μL transfection solution is then added to the 293A cells and the cells are incubated in a 37° C. incubator under 5% carbon dioxide for approximately 16 hours. Transfection media is replaced with 3 mL of fresh complete, supplemented DMEM and cells are incubated in a 37° C. incubator under 5% carbon dioxide for approximately 24 hours. The cells are trypsinized and the contents of each well are transferred to a sterile 10 cm tissue culture plate containing 10 mL of complete, supplemented DMEM. Replace the old media with fresh complete, supplemented DMEM every 2 or 3 days until visible regions of cytopathic effect are observed (typically 7-10 days). Replenish the old culture media with fresh complete, supplemented DMEM and allow the infections to proceed until approximately 80% cytopathic effect is observed (typically 10-13 days post transfection). The adenovirus-containing cells are harvested by detaching the cells using the culture media and scraping cells from the culture plate. Detached cells and media are transferred to a 15 mL tube. The harvested cells are lysed using one freeze-thaw round consisting of −80° C. for 30 minutes then 37° C. for 15 minutes. The cell lysate is centrifuged (5,000×g at 20° C. for 15 minutes) to pellet the cellular debris. The clarified supernatant containing the adenoviral particles is transferred to 2 mL cryovials in 1 mL aliquots and should contain approximately $1\times10^7$ to $10^8$ pfu of adenoviral particles. Aliquots can be stored at −80° C. until needed.

4c. Amplification of an Adenoviral Stock Containing pAd-DEST/VAMP-GFP

To amplified to the adenoviral stock containing an expression construct encoding a BoNT/B, BoNT/D, BoNT/F, BoNT/G or TeNT VAMP-GFP substrate, such as, e.g., pAd-DEST/VAMP-GFP, about $3\times10^6$ 293A cells are plated in a 100 mm culture dish containing in 10 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about 80-90% confluency (6-16 hours). The cells are inoculated cells with 100 μL of adenoviral stock and incubated for approximately 48-72 hours in a 37° C. incubator under 5% carbon dioxide until the cells round up and are floating or lightly attached to the culture plate. The adenovirus-containing cells are harvested by detaching the cells using the culture media and scraping cells from the culture plate. Detached cells and media are transferred to a 15 mL tube. The harvested cells are lysed using three freeze-thaw round consisting of −80° C. for 30 minutes then 37° C. for 15 minutes. The cell lysate is centrifuged (5,000×g at 20° C. for 15 minutes) to pellet the cellular debris. The clarified supernatant containing the adenoviral particles is transferred to 2 mL cryovials in 1 mL aliquots and should contain approximately $1\times10^8$ to $10^9$ pfu of adenoviral particles. Aliquots can be stored at −80° C. until needed.

4d. Transduction of Cells with an Adenoviral Stock Containing pAd-DEST/VAMP-GFP

To transduce cells with the adenoviral stock containing an expression construct encoding a BoNT/B, BoNT/D, BoNT/F, BoNT/G or TeNT VAMP-GFP substrate, such as, e.g., pAd-DEST/VAMP-GFP, a suitable density ($1\times10^5$ to $1\times10^6$) of appropriate cells are plated in a 6-well tissue culture dish containing 3 mL of complete, supplemented culture media and are grown in a 37° C. incubator under 5% carbon dioxide until the cells reach a density appropriate for transduction. Cells are inoculated with approximately 4 µL of the adenoviral stock (approximately $5\times10^8$ pfu/ml) and are incubated for approximately 24 hours in a 37° C. incubator under 5% carbon dioxide. The transduction media is replaced with 3 mL of fresh complete, supplemented media and cells are incubated in a 37° C. incubator under 5% carbon dioxide for approximately 24 hours. The transduced cells can be used to conduct a BoNT/B, BoNT/D, BoNT/F, BoNT/G or TeNT activity assay using a VAMP-GFP substrate.

5. Generation of Cells Containing a BoNT/B, BoNT/D, BoNT/F, BoNT/G or TeNT Substrate by Lentiviral Transduction 5a. Construction of pLenti6Ubc/V5-VAMP-GFP To make a pLenti6Ubc/V5-VAMP-GFP construct encoding a BoNT/B, BoNT/D, BoNT/F, BoNT/G or TeNT VAMP-GFP substrate, a nucleic acid fragment encoding the amino acid region comprising a BoNT/B, BoNT/D, BoNT/F, BoNT/G or TeNT VAMP-GFP substrate is amplified from, e.g., e.g., pQBI-25/VAMP-1-GFP DNA, pQBI-25/VAMP-2-GFP DNA or pQBI-25/VAMP-3-GFP DNA (see Examples I, 2a; I, 2b; or I, 2c), using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/VAMP-GFP construct is digested with restriction enzymes that 1) excise the insert containing the entire open reading frame encoding the VAMP-GFP peptide; and 2) enable this insert to be operably-linked to a pLenti6Ubc/V5 vector (Invitrogen, Inc., Carlsbad, Calif.). This insert is subcloned using a T4 DNA ligase procedure into a pLenti6Ubc/V5 vector that is digested with appropriate restriction endonucleases to yield pLenti6Ubc/V5-VAMP-GFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 µg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. This cloning strategy yields a mammalian expression construct encoding the VAMP-GFP operably-linked to the expression elements of the pLenti6Ubc/V5 vector an amino-terminal V5 peptide.

5b. Production of a Lentiviral Stock Containing pLenti6Ubc/V5-VAMP-GFP

To produce a lentiviral stock containing an expression construct encoding a BoNT/B, BoNT/D, BoNT/F, BoNT/G or TeNT VAMP-GFP substrate, a 3.0 mL transfection solution is prepared by adding 1.5 mL of OPTI-MEM Reduced Serum Medium containing 36 µL of LipofectAmine 2000 (Invitrogen, Carlsbad, Calif.) incubated at room temperature for 5 minutes to 1.5 mL of OPTI-MEM Reduced Serum Medium containing 3 µg of an expression construct encoding a BoNT/B, BoNT/D, BoNT/F, BoNT/G or TeNT VAMP-GFP substrate, such as, e.g., pLenti6Ubc/V5-VAMP-GFP and 9 µg of ViraPower™ Packaging Mix. After an approximately 20 minute incubation at room temperature, the DNA-lipid complexes are added to a 10 cm tissue culture plate containing 5 mL OPTI-MEM Reduced Serum Medium. A 5 mL cell suspension containing approximately $6\times10^6$ 293A cells are then added to DNA-lipid complex media and grown in a 37° C. incubator under 5% carbon dioxide overnight. Transfection media is replaced with 10 mL of complete Dulbecco's Modified Eagle Media (DMEM), supplemented with 10% fetal bovine serum (FBS), 2 mM glutamine (Invitrogen, Inc, Carlsbad, Calif.), 1 mM sodium pyruvate (Invitrogen, Inc, Carlsbad, Calif.), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide for approximately 24-48 hours. The lentiovirus-containing cells are harvested by detaching the cells using the culture media and scraping cells from the culture plate. Detached cells and media are transferred to a 15 mL tube and centrifuged (5,000×g at 20° C. for 15 minutes) to pellet the cellular debris. The clarified supernatant containing the lentiviral particles is transferred to 2 mL cryovials in 1 mL aliquots and should contain approximately $5\times10^5$ to $2\times10^7$ pfu/mL of lentiviral particles. Aliquots can be stored at −80° C. until needed.

5c. Transduction of Cells with an Lentiviral Stock Containing a pLenti6Ubc/V5-VAMP-GFP To transduce cells with the lentiviral stock containing an expression construct encoding a BoNT/B, BoNT/D, BoNT/F, BoNT/G or TeNT VAMP-GFP substrate, a suitable density ($1.5\times10^5$ to $1.5\times10^6$) of appropriate cells is plated in a 6-well tissue culture dish containing 3 mL of complete, supplemented culture media and the cells are grown in a 37° C. incubator under 5% carbon dioxide until the cells reach a density of about $5\times10^5$ cells/ml (6-16 hours). Cells are inoculated with the lentiviral stock containing an expression construct encoding a BoNT/B, BoNT/D, BoNT/F, BoNT/G or TeNT VAMP-GFP substrate, such as, e.g., pLenti6Ubc/V5-VAMP-GFP, using a suitable multiplicity of infection and are incubated for approximately 16-24 hours in a 37° C. incubator under 5% carbon dioxide. The transduction media is replaced with 3 mL of fresh complete, supplemented media and cells are incubated in a 37° C. incubator under 5% carbon dioxide for approximately 24-48 hours. The transduced cells can be used to conduct a BoNT/B, BoNT/D, BoNT/F, BoNT/G or TeNT activity assay using a VAMP-GFP substrate.

6. Generation of Cells Containing a BoNT/B, BoNT/D, BoNT/F, BoNT/G or TeNT Substrate by Protein Transformation 6a. Expression of a VAMP-GFP Substrate Using a Bacterial Cell Line To express a BoNT/B, BoNT/D, BoNT/F, BoNT/G or TeNT VAMP-GFP substrate using bacteria, an expression construct encoding a BoNT/B, BoNT/D, BoNT/F, BoNT/G or TeNT VAMP-GFP substrate, such as, e.g., pQBI-67/VAMP-1-GFP, pQBI-67/VAMP-2-GFP or pQBI-67/VAMP-3-GFP as described above in Examples I, 2d; I, 2e; or I, 2f, is introduced into chemically competent *E. coli* BL21 (DE3) cells (Invitrogen, Inc, Carlsbad, Calif.) using a heat-shock transformation protocol. The heat-shock reaction is then plated onto 1.5% Luria-Bertani agar plates (pH 7.0) containing 100 μg/mL of Ampicillin and placed in a 37° C. incubator for overnight growth. A single Ampicillin-resistant colony of transformed *E. coli* containing pQBI-67/VAMP-GFP is used to inoculate a 15 mL test tube containing 3.0 mL Luria-Bertani media, (pH 7.0) containing 100 μg/mL of Ampicillin which is then placed in a 37° C. incubator, shaking at 250 rpm, for overnight growth. The resulting overnight starter culture is used to inoculate a 1.0 L baffled flask containing 100 mL Luria-Bertani media, (pH 7.0) containing 100 μg/mL of Ampicillin at a dilution of 1:1000. This culture is grown in a 32° C. incubator shaking at 250 rpm for approximately 6.5 hours until mid-log phase is reached ($OD_{600}$ of about 0.6-0.8). Protein expression is then induced by adding 1 mM isopropyl-β-D-thiogalactopyranoside (IPTG) and the culture is placed in a 32° C. incubator shaking at 250 rpm for overnight expression. Cells are harvested by centrifugation (4,000 rpm at 4° C. for 20-30 minutes) to pellet the cells. The supernatant is discarded and the cell pellet is used immediately for subsequent steps, or the pellet is stored at −80° C. until needed.

6b. Expression of a VAMP-GFP Substrate Using a Mammalian Cell Line

To express a BoNT/B, BoNT/D, BoNT/F, BoNT/G or TeNT VAMP-GFP substrate using a mammalian cell line, a suitable density ($1.0\times10^5$ to $1.0\times10^6$) of appropriate cells is plated in a 35 mm tissue culture dish containing 3 mL of complete, supplemented culture media and the cells are grown in a 37° C. incubator under 5% carbon dioxide until the cells reach a density of about $5\times10^5$ cells/ml (6-16 hours). A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of an expression construct encoding a BoNT/B, BoNT/D, BoNT/F, BoNT/G or TeNT VAMP-GFP substrate, such as, e.g., pQBI-25/VAMP-1-GFP, pQBI-25/VAMP-2-GFP or pQBI-25/VAMP-3-GFP (see Examples I, 2a; I, 2b; or I, 2c). This transfection is incubated at room temperature for approximately 20 minutes. The complete, supplemented culture media is replaced with 2 mL of OPTI-MEM Reduced Serum Medium and the 500 μL transfection solution is added to the cells and the cells are incubated in a 37° C. incubator under 5% carbon dioxide for approximately 16 hours. Transfection media is replaced with 3 mL of fresh complete, supplemented EMEM:F12 and cells are incubated in a 37° C. incubator under 5% carbon dioxide for approximately 48 hours. Cells are harvest by rinsing cells once with 3.0 mL of 100 mM phosphate-buffered saline, pH 7.4 and detaching rinsed cells by adding 500 μl of 100 mM phosphate-buffered saline, pH 7.4 and scraping cells from the culture plate. Detached cells are transferred to a 1.5 mL test tube and are pelleted by microcentrifugation (10,000×g at 4° C. for 5 minutes). The supernatant is discarded and the cell pellet is used immediately for subsequent steps, or the pellet is stored at −80° C. until needed.

6c. Purification of a VAMP-GFP Substrate

To purify a VAMP-GFP substrate, a cell pellet expressing an expression construct encoding a BoNT/B, BoNT/D, BoNT/F, BoNT/G or TeNT VAMP-GFP substrate, such as, e.g., either a pQBI-67/VAMP-1-GFP or a pQBI-25/VAMP-1-GFP construct, is resuspended in 10 mL of Tris-EDTA Buffer (10 mM Tris-HCl, pH 8.0; 1 mM EDTA, pH 8.0), containing 1 mg/mL of lysozyme and the cells are lysed using three freeze-thaw rounds consisting of −80° C. for 5 minutes then 37° C. for 5 minutes. The cell lysate is centrifuged (5,000×g at 4° C. for 15 minutes) to pellet the cellular debris and the supernatant is transferred to a new tube containing an equal volume of Column Binding Buffer (4 M ammonium sulfate). A hydrophobic interaction chromatography (HIC) column is prepared using a 20 mL Econo-Pac column support (Bio-Rad Laboratories, Hercules, Calif.) that is packed with 2.5-5.0 mL of methyl HIC resin (Bio-Rad Laboratories, Hercules, Calif.), which is then equilibrated by rinsing with 5 column volumes of Column Equilibration Buffer (2 M ammonium sulfate). The clarified lysate is applied slowly to the equilibrated column by gravity flow (approximately 0.25-0.3 mL/minute). The column is then washed with 5 column volumes of Column Wash Buffer (1.3 M ammonium sulfate). The VAMP-GFP substrate is eluted with 20-30 mL of Column Elution Buffer (10 mM TE Buffer) and is collected in approximately twelve 1 mL fractions. The progress of the VAMP-GFP substrate sample through the column as well as which elution fractions contain the sample is monitored using an ultraviolet light from a hand-held transilluminator. The amount of VAMP-GFP substrate contained in each elution fraction is determined by a Bradford dye assay. In this procedure, 20 μL aliquot from each 1.0 mL fraction is combined with 200 μL of Bio-Rad Protein Reagent (Bio-Rad Laboratories, Hercules, Calif.), diluted 1 to 4 with deionized, distilled water, and then the intensity of the colorimetric signal is measured using a spectrophotometer. The five fractions with the strongest signal are considered to comprise the elution peak and are pooled. Total protein yield are determined by estimating the total protein concentration of the pooled peak elution fractions using bovine gamma globulin as a standard (Bio-Rad Laboratories, Hercules, Calif.). The amount of VAMP-GFP substrate is adjusted to a protein concentration of approximately 100 ng/mL.

6d. Protein Transformation of a VAMP-GFP Substrate

To transform a VAMP-GFP substrate into a mammalian cell line, a suitable density ($1.0\times10^5$ to $1.0\times10^6$) of appropriate cells is plated in a 35 mm tissue culture dish containing 3 mL of complete, supplemented culture media and the cells are grown in a 37° C. incubator under 5% carbon dioxide until the cells reach a density of about $5\times10^5$ cells/ml (6-16 hours). A 200 μL protein transfection solution is prepared by adding 100 μL of distilled water containing 6 μL of Chariot™ protein delivery agent (Active Motif, Carlsbad, Calif.) to 100 μL of 100 mM phosphate-buffered saline, pH 7.4 containing 1 μg of a VAMP-GFP substrate and this solution is incubated at room temperature for approximately 30 minutes. After incubation, the cells are washed once by rinsing cells with 3.0 mL of 100 mM phosphate-buffered saline, pH 7.4. The 200 μL protein transfection solution is added to the washed cells, followed by 400 μL of OPTI-MEM Reduced Serum Medium and the cells are incubated in a 37° C. incubator under 5% carbon dioxide for approximately 1 hour. Add 1 mL of fresh complete, supplemented culture media to the cells and incubate in a 37° C. incubator under 5% carbon dioxide. After 1-2 hours, the transformed cells can be used to conduct a BoNT/B, BoNT/D, BoNT/F, BoNT/G or TeNT activity assay using a VAMP-GFP substrate.

7. Generation of Cells Containing a BoNT/C1 Syntaxin Substrate by Adenoviral Transduction 7a. Construction of pAd-DEST/Syntaxin-GFP To make a pAd-DEST/Syntaxin-GFP construct encoding a BoNT/C1 Syntaxin-GFP substrate, a nucleic acid fragment encoding the amino acid region comprising Syntaxin-GFP of is amplified an expression construct encoding a BoNT/C1-GFP substrate, such as, e.g., pQBI-25/Syntaxin-1-GFP DNA (see Example I, 3a) using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/Syntaxin-GFP construct is digested with restriction enzymes that 1) excise the insert containing the entire open reading frame encoding the Syntaxin-GFP peptide; and 2) enable this insert to be operably-linked to a pAd-DEST vector (Invitrogen, Inc., Carlsbad, Calif.). This insert is subcloned using a T4 DNA ligase procedure into a pAd-DEST vector that is digested with appropriate restriction endonucleases to yield pAd-DEST/Syntaxin-GFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. This cloning strategy yields a mammalian expression construct encoding the Syntaxin-GFP operably-linked to the expression elements of the pAd-DEST vector.

7b. Production of an Adenoviral Stock Containing pAd-DEST/Syntaxin-GFP

To produce an adenoviral stock containing an expression construct encoding a BoNT/C1 Syntaxin-GFP substrate, about $5\times10^5$ 293A cells are plated in a 35 mm tissue culture dish containing 3 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about $5\times10^5$ cells/ml (6-16 hours). One the day of transfection, replace complete, supplemented DMEM media with 2 mL of OPTI-MEM Reduced Serum Medium. A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of the linearized expression construct encoding a BoNT/C1 Syntaxin-GFP substrate, such as, e.g., pAd-DEST/Syntaxin-GFP. To linearize a pAd-DEST/Syntaxin-GFP construct, 5 μg of a pAd-DEST/Syntaxin-GFP construct is digested with PacI (New England Biolabs, Beverly, Mass.). The linearized plasmid is purified using QIAquick kit procedure (QIAGEN, Inc., Valencia, Calif.) and is resuspended in TE Buffer. This transfection is incubated at room temperature for approximately 20 minutes. The 500 μL transfection solution is then added to the 293A cells and the cells are incubated in a 37° C. incubator under 5% carbon dioxide for approximately 16 hours. Transfection media is replaced with 3 mL of fresh complete, supplemented DMEM and cells are incubated in a 37° C. incubator under 5% carbon dioxide for approximately 24 hours. The cells are trypsinized and the contents of each well are transferred to a sterile 10 cm tissue culture plate containing 10 mL of complete, supplemented DMEM. Replace the old media with fresh complete, supplemented DMEM every 2 or 3 days until visible regions of cytopathic effect are observed (typically 7-10 days). Replenish the old culture media with fresh complete, supplemented DMEM and allow the infections to proceed until approximately 80% cytopathic effect is observed (typically 10-13 days post transfection). The adenovirus-containing cells are harvested by detaching the cells using the culture media and scraping cells from the culture plate. Detached cells and media are transferred to a 15 mL tube. The harvested cells are lysed using one freeze-thaw round consisting of −80° C. for 30 minutes then 37° C. for 15 minutes. The cell lysate is centrifuged (5,000×g at 20° C. for 15 minutes) to pellet the cellular debris. The clarified supernatant containing the adenoviral particles is transferred to 2 mL cryovials in 1 mL aliquots and should contain approximately $1\times10^7$ to $10^8$ pfu of adenoviral particles. Aliquots can be stored at −80° C. until needed.

7c. Amplification of an Adenoviral Stock Containing pAd-DEST/Syntaxin-GFP

To amplified to the adenoviral stock containing an expression construct encoding a BoNT/C1 Syntaxin-GFP substrate, such as, e.g., pAd-DEST/Syntaxin-GFP, about $3\times10^6$ 293A cells are plated in a 100 mm culture dish containing in 10 mL of complete Dulbecco's Modified Eagle Media (DMEM), supplemented with 10% fetal bovine serum (FBS), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about 80-90% confluency (6-16 hours). The cells are inoculated cells with 100 μL of adenoviral stock and incubated for approximately 48-72 hours in a 37° C. incubator under 5% carbon dioxide until the cells round up and are floating or lightly attached to the culture plate. The adenovirus-containing cells are harvested by detaching the cells using the culture media and scraping cells from the culture plate. Detached cells and media are transferred to a 15 mL tube. The harvested cells are lysed using three freeze-thaw round consisting of −80° C. for 30 minutes then 37° C. for 15 minutes. The cell lysate is centrifuged (5,000×g at 20° C. for 15 minutes) to pellet the cellular debris. The clarified supernatant containing the adenoviral particles is transferred to 2 mL cryovials in 1 mL aliquots and should contain approximately $1\times10^8$ to $10^9$ pfu of adenoviral particles. Aliquots can be stored at −80° C. until needed.

7d. Transduction of Cells with an Adenoviral Stock Containing pAd-DEST/Syntaxin-GFP To transduce cells with the adenoviral stock containing an expression construct encoding a BoNT/C1 Syntaxin-GFP substrate, such as, e.g., pAd-DEST/Syntaxin-GFP, a suitable density ($1\times10^5$ to $1\times10^6$) of appropriate cells are plated in a 6-well tissue culture dish containing 3 mL of complete, supplemented culture media and are grown in a 37° C. incubator under 5% carbon dioxide until the cells reach a density appropriate for transduction. Cells are inoculated with approximately 4 μL of the adenoviral stock (approximately $5\times10^8$ pfu/ml) and are incubated for approximately 24 hours in a 37° C. incubator under 5% carbon dioxide. The transduction media is replaced with 3 mL of fresh complete, supplemented media and cells are incubated in a 37° C. incubator under 5% carbon dioxide for approximately 24 hours. The transduced cells can be used to conduct a BoNT/C1 activity assay using a Syntaxin-GFP substrate.

8. Generation of Cells Containing a BoNT/C1 Substrate by Lentiviral Transduction 8a. Construction of pLenti6Ubc/V5-Syntaxin-GFP To make a pLenti6Ubc/V5-Syntaxin-GFP construct encoding a BoNT/C1 Syntaxin-GFP substrate, a nucleic acid fragment encoding the amino acid region comprising a BoNT/C1 Syntaxin-GFP substrate is amplified from, e.g., pQBI-25/Syntaxin-1-GFP DNA (see Example I, 3a) using a polymerase chain reaction method and subcloned into a pCR2.1 vector using the TOPO® TA cloning method (Invitrogen, Inc, Carlsbad, Calif.). The forward and reverse oligonucleotide primers used for this reaction are designed to include unique restriction enzyme sites useful for subsequent subcloning steps. The resulting pCR2.1/Syntaxin-GFP construct is digested with restriction enzymes that 1) excise the insert containing the entire open reading frame encoding the Syntaxin-GFP peptide; and 2) enable this insert to be operably-linked to a pLenti6Ubc/V5 vector (Invitrogen, Inc., Carlsbad, Calif.). This insert is subcloned using a T4 DNA ligase procedure into a pLenti6Ubc/V5 vector that is digested with appropriate restriction endonucleases to yield pLenti6Ubc/V5-Syntaxin-GFP. The ligation mixture is transformed into chemically competent *E. coli* BL21 (DE3) cells (Invitrogen, Inc, Carlsbad, Calif.) using a heat shock method, plated on 1.5% Luria-Bertani agar plates (pH 7.0) containing 100 μg/mL of Ampicillin, and placed in a 37° C. incubator for overnight growth. Bacteria containing expression constructs are identified as Ampicillin resistant colonies. Candidate constructs are isolated using an alkaline lysis plasmid mini-preparation procedure and analyzed by restriction endonuclease digest mapping to determine the presence and orientation of the inset. This cloning strategy yields a mammalian expression construct encoding the Syntaxin-GFP operably-linked to the expression elements of the pLenti6Ubc/V5 vector an amino-terminal V5 peptide.

8b. Production of a Lentiviral Stock Containing pLenti6Ubc/V5-Syntaxin-GFP

To produce a lentiviral stock containing an expression construct encoding a BoNT/C1 Syntaxin-GFP substrate, a 3.0 mL transfection solution is prepared by adding 1.5 mL of OPTI-MEM Reduced Serum Medium containing 36 μL of LipofectAmine 2000 (Invitrogen, Carlsbad, Calif.) incubated at room temperature for 5 minutes to 1.5 mL of OPTI-MEM Reduced Serum Medium containing 3 μg of an expression construct encoding a BoNT/C1 Syntaxin-GFP substrate, such as, e.g., pLenti6Ubc/V5-Syntaxin-GFP and 9 μg of ViraPower™ Packaging Mix. After an approximately 20 minute incubation at room temperature, the DNA-lipid complexes are added to a 10 cm tissue culture plate containing 5 mL OPTI-MEM Reduced Serum Medium. A 5 mL cell suspension containing approximately $6\times10^6$ 293A cells are then added to DNA-lipid complex media and grown in a 37° C. incubator under 5% carbon dioxide overnight. Transfection media is replaced with 10 mL of complete Dulbecco's Modified Eagle Media (DMEM), supplemented with 10% fetal bovine serum (FBS), 2 mM glutamine (Invitrogen, Inc, Carlsbad, Calif.), 1 mM sodium pyruvate (Invitrogen, Inc, Carlsbad, Calif.), 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide for approximately 24-48 hours. The lentiovirus-containing cells are harvested by detaching the cells using the culture media and scraping cells from the culture plate. Detached cells and media are transferred to a 15 mL tube and centrifuged (5,000×g at 20° C. for 15 minutes) to pellet the cellular debris. The clarified supernatant containing the lentiviral particles is transferred to 2 mL cryovials in 1 mL aliquots and should contain approximately $5\times10^5$ to $2\times10^7$ pfu/mL of lentiviral particles. Aliquots can be stored at −80° C. until needed.

8c. Transduction of Cells with an Lentiviral Stock Containing a pLenti6Ubc/V5-Syntaxin-GFP To transduce cells with the lentiviral stock containing an expression construct encoding a BoNT/C1 Syntaxin-GFP substrate, a suitable density ($1.5\times10^5$ to $1.5\times10^6$) of appropriate cells is plated in a 6-well tissue culture dish containing 3 mL of complete, supplemented culture media and the cells are grown in a 37° C. incubator under 5% carbon dioxide until the cells reach a density of about $5\times10^5$ cells/ml (6-16 hours). Cells are inoculated with the lentiviral stock containing an expression construct encoding a BoNT/C1 Syntaxin-GFP substrate, such as, e.g., pLenti6Ubc/V5-Syntaxin-GFP, using a suitable multiplicity of infection and are incubated for approximately 16-24 hours in a 37° C. incubator under 5% carbon dioxide. The transduction media is replaced with 3 mL of fresh complete, supplemented media and cells are incubated in a 37° C. incubator under 5% carbon dioxide for approximately 24-48 hours. The transduced cells can be used to conduct a BoNT/C1 activity assay using a Syntaxin-GFP substrate.

9. Generation of Cells Containing a BoNT/C1 Substrate by Protein Transformation

9a. Expression of a Syntaxin-GFP Substrate Using a Bacterial Cell Line

To express a BoNT/C1 Syntaxin-GFP substrate using bacteria, an expression construct encoding a BoNT/C1 Syntaxin-GFP substrate, such as, e.g., pQBI-67/Syntaxin-1-GFP as described above in Example I, 3b, is introduced into chemically competent *E. coli* BL21 (DE3) cells (Invitrogen, Inc, Carlsbad, Calif.) using a heat-shock transformation protocol. The heat-shock reaction is then plated onto 1.5% Luria-Bertani agar plates (pH 7.0) containing 100 μg/mL of Ampicillin and placed in a 37° C. incubator for overnight growth. A single Ampicillin-resistant colony of transformed *E. coli* containing pQBI-67/Syntaxin-GFP is used to inoculate a 15 mL test tube containing 3.0 mL Luria-Bertani media, (pH 7.0) containing 100 μg/mL of Ampicillin which is then placed in a 37° C. incubator, shaking at 250 rpm, for overnight growth. The resulting overnight starter culture is used to inoculate a 1.0 L baffled flask containing 100 mL Luria-Bertani media, (pH 7.0) containing 100 μg/mL of Ampicillin at a dilution of 1:1000. This culture is grown in a 32° C. incubator shaking at 250 rpm for approximately 6.5 hours until mid-log phase is reached ($OD_{600}$ of about 0.6-0.8). Protein expression is then induced by adding 1 mM isopropyl-β-D-thiogalactopyranoside (IPTG) and the culture is placed in a 32° C. incubator shaking at 250 rpm for overnight expression. Cells are harvested by centrifugation (4,000 rpm at 4° C. for 20-30 minutes) to pellet the cells. The supernatant is discarded and the cell pellet is used immediately for subsequent steps, or the pellet is stored at −80° C. until needed.

9b. Expression of a Syntaxin-GFP Substrate Using a Mammalian Cell Line

To express a BoNT/C1 Syntaxin-GFP substrate using a mammalian cell line, a suitable density ($1.0\times10^5$ to $1.0\times10^6$) of appropriate cells is plated in a 35 mm tissue culture dish containing 3 mL of complete, supplemented culture media and the cells are grown in a 37° C. incubator under 5% carbon dioxide until the cells reach a density of about $5\times10^5$ cells/ml (6-16 hours). A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of an expression construct encoding a BoNT/C1 Syntaxin-GFP substrate, such as, e.g., pQBI-25/Syntaxin-1-GFP (see Example I, 3a). This transfection is incubated at room temperature for approximately 20 minutes. The complete, supplemented culture media is replaced with 2 mL of OPTI-MEM Reduced Serum Medium and the 500 μL transfection solution is added to the cells and the cells are incubated in a 37° C. incubator under 5% carbon dioxide for approximately 16 hours. Transfection media is replaced with 3 mL of fresh complete, supplemented culture media and cells are incubated in a 37° C. incubator under 5% carbon dioxide for approximately 48 hours. Cells are harvest by rinsing cells once with 3.0 mL of 100 mM phosphate-buffered saline, pH 7.4 and detaching rinsed cells by adding 500 μl of 100 mM phosphate-buffered saline, pH 7.4 and scraping cells from the culture plate. Detached cells are transferred to a 1.5 mL test tube and are pelleted by microcentrifugation (10,000×g at 4° C. for 5 minutes). The supernatant is discarded and the cell pellet is used immediately for subsequent steps, or the pellet is stored at −80° C. until needed.

9c. Purification of a Syntaxin-GFP Substrate

To purify a Syntaxin-GFP substrate, a cell pellet expressing an expression construct encoding a BoNT/C1 Syntaxin-GFP substrate, such as, e.g., either a pQBI-67/Syntaxin-1-GFP or a pQBI-25/Syntaxin-1-GFP construct, is resuspended in 10 mL of Tris-EDTA Buffer (10 mM Tris-HCl, pH 8.0; 1 mM EDTA, pH 8.0), containing 1 mg/mL of lysozyme and the cells are lysed using three freeze-thaw rounds consisting of −80° C. for 5 minutes then 37° C. for 5 minutes. The cell lysate is centrifuged (5,000×g at 4° C. for 15 minutes) to pellet the cellular debris and the supernatant is transferred to a new tube containing an equal volume of Column Binding Buffer (4 M ammonium sulfate). A hydrophobic interaction chromatography (HIC) column is prepared using a 20 mL Econo-Pac column support (Bio-Rad Laboratories, Hercules, Calif.) that is packed with 2.5-5.0 mL of methyl HIC resin (Bio-Rad Laboratories, Hercules, Calif.), which is then equilibrated by rinsing with 5 column volumes of Column Equilibration Buffer (2 M ammonium sulfate). The clarified lysate is applied slowly to the equilibrated column by gravity flow (approximately 0.25-0.3 mL/minute). The column is then washed with 5 column volumes of Column Wash Buffer (1.3 M ammonium sulfate). The Syntaxin-GFP substrate is eluted with 20-30 mL of Column Elution Buffer (10 mM TE Buffer) and is collected in approximately twelve 1 mL fractions. The progress of the Syntaxin-GFP substrate sample through the column as well as which elution fractions contain the sample is monitored using an ultraviolet light from a hand-held transilluminator. The amount of Syntaxin-GFP substrate contained in each elution fraction is determined by a Bradford dye assay. In this procedure, 20 μL aliquot from each 1.0 mL fraction is combined with 200 μL of Bio-Rad Protein Reagent (Bio-Rad Laboratories, Hercules, Calif.), diluted 1 to 4 with deionized, distilled water, and then the intensity of the colorimetric signal is measured using a spectrophotometer. The five fractions with the strongest signal are considered to comprise the elution peak and are pooled. Total protein yield are determined by estimating the total protein concentration of the pooled peak elution fractions using bovine gamma globulin as a standard (Bio-Rad Laboratories, Hercules, Calif.). The amount of Syntaxin-GFP substrate is adjusted to a protein concentration of approximately 100 ng/mL.

9d. Protein Transformation of a Syntaxin-GFP Substrate

To transform a Syntaxin-GFP substrate into a mammalian cell line, a suitable density ($1.0\times10^5$ to $1.0\times10^6$) of appropriate cells is plated in a 35 mm tissue culture dish containing 3 mL of complete, supplemented culture media and the cells are grown in a 37° C. incubator under 5% carbon dioxide until the cells reach a density of about $5\times10^5$ cells/ml (6-16 hours). A 200 μL protein transfection solution is prepared by adding 100 μL of distilled water containing 6 μL of Chariot™ protein delivery agent (Active Motif, Carlsbad, Calif.) to 100 μL of 100 mM phosphate-buffered saline, pH 7.4 containing 1 μg of a Syntaxin-GFP substrate and this solution is incubated at room temperature for approximately 30 minutes. After incubation, the cells are washed once by rinsing cells with 3.0 mL of 100 mM phosphate-buffered saline, pH 7.4. The 200 μL protein transfection solution is added to the washed cells, followed by 400 μL of OPTI-MEM Reduced Serum Medium and the cells are incubated in a 37° C. incubator under 5% carbon dioxide for approximately 1 hour. Add 1 mL of fresh complete, supplemented culture media to the cells and incubate in a 37° C. incubator under 5% carbon dioxide. After 1-2 hours, the transformed cells can be used to conduct a BoNT/C1 activity assay using a Syntaxin-GFP substrate.

Example V

Generation of Cells Stably Containing a Clostridial Toxin Substrate

1. Generation of Cells Stably Containing a BoNT/A, BoNT/C1 or BoNT/E Substrate

1a. Stably Transformed Neuro-2A Cells Using a Recombinant Crossing-Over Procedure To generate a stably-integrated cell line expressing a BoNT/A, BoNT/C1 or BoNT/E SNAP-25 substrate using a crossing over procedure, approximately $1.5\times10^5$ Neuro-2A cells were plated in a 35 mm tissue culture dish containing 3 mL of complete EMEM, supplemented with 10% FBS, 2 mM glutamine (Invitrogen, Inc, Carlsbad, Calif.), 1 mM sodium pyruvate (Invitrogen, Inc, Carlsbad, Calif.), 1.5 g/L sodium bicarbonate and 1×MEM non-essential amino acids solution (Invitrogen, Inc, Carlsbad, Calif.), and grown in a 37° C. incubator under 5% carbon dioxide until the cells reached a density of about $5\times10^5$ cells/ml. A 500 μL transfection solution was prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of an expression construct encoding a BoNT/A, BoNT/C1 or BoNT/E, substrate, such as, e.g., pQBI-25/$SNAP25_{206}$-GFP (see EXAMPLE I, 1). This transfection was incubated at room temperature for approximately 20 minutes. The complete, supplemented EMEM media was replaced with 2 mL of OPTI-MEM Reduced Serum Medium and the 500 μL transfection solution was added to the Neuro-2A cells and the cells incubated in a 37° C. incubator under 5% carbon dioxide for approximately 16 hours. Transfection media was replaced with 3 mL of fresh complete, supplemented EMEM and cells were incubated in a 37° C. incubator under 5% carbon dioxide for approximately 48 hours. Media was replaced with 3 mL of fresh complete EMEM, containing approximately 5 μg/mL of G418, 10% FBS, 2 mM glutamine (Invitrogen, Inc, Carlsbad, Calif.), 1 mM sodium pyruvate (Invitrogen, Inc, Carlsbad, Calif.). 1.5 g/L sodium bicarbonate and 1×MEM non-essential amino acids solution (Invitrogen, Inc, Carlsbad, Calif.). Cells were incubated in a 37° C. incubator under 5% carbon dioxide for approximately 4 weeks, with old media being replaced with fresh G418-selective, complete, supplemented EMEM every 4 to 5 days. Once G418-resistant Neuro-2A colonies were established, resistant clones were replated to new 35 mm culture plates containing fresh G418-selective, complete, supplemented EMEM, until these cells reached a density of 6 to $20\times10^5$ cells/mL.

To test for expression of SNAP-$25_{206}$-GFP from isolated Neuro-2A cell lines that stably-integrated expression construct encoding a BoNT/A, BoNT/C1 or BoNT/E, substrate, such as, e.g., pQBI-25/SNAP$25_{206}$-GFP (see Example I, 1a), approximately $1.5\times10^5$ Neuro-2A cells from each cell line were plated in a 35 mm tissue culture dish containing 3 mL of G418-selective, complete, supplemented EMEM and grown in a 37° C. incubator under 5% carbon dioxide until cells reached a density of about $5\times10^5$ cells/ml (6-16 hours). Media was replaced with 3 mL of fresh G418-selective, complete, supplemented EMEM and cells were incubated in a 37° C. incubator under 5% carbon dioxide. After 48 hours, the cells were harvested by rinsing the cells once with 3.0 mL of 100 mM phosphate-buffered saline, pH 7.4 and lysed with a buffer containing 62.6 mM 2-amino-2-hydroxymethyl-1,3-propanediol hydrochloric acid (Tris-HCl), pH 6.8 and 2% sodium lauryl sulfate (SDS). Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/ml or higher concentration.

To detect for the presence of the SNAP-25-GFP substrate, samples were boiled for 5 min, and 40 μl aliquots were separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Separated peptides were transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes were blocked by incubating at room temperature for 2 hours in a solution containing 25 mM Tris-Buffered Saline (25 mM 2-amino-2-hydroxymethyl-1,3-propanediol hydrochloric acid (Tris-HCl)(pH 7.4), 137 mM sodium chloride, 2.7 mM potassium chloride), 0.1% TWEEN-200, polyoxyethylene (20) sorbitan monolaureate, 2% bovine serum albumin, 5% nonfat dry milk. Blocked membranes were incubated at 4° C. for overnight in Tris-Buffered Saline TWEEN-200 (25 mM Tris-Buffered Saline, 0.1% TWEEN-200, polyoxyethylene (20) sorbitan monolaureate) containing a 1:50,000 dilution of mouse monoclonal anti-SNAP-25 antibody (SMI-81; Sternberger Monoclonals, Lutherville, Md.). Primary antibody probed blots were washed three times for 15 minutes each time in Tris-Buffered Saline TWEEN-200. Washed membranes were incubated at room temperature for 2 hours in Tris-Buffered Saline TWEEN-20® containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) as a secondary antibody. Secondary antibody-probed blots were washed three times for 15 minutes each time in Tris-Buffered Saline TWEEN-200. Signal detection of the labeled SNAP-$25_{206}$-GFP substrate was visualized using the ECL Plus™ Western Blot Detection System (Amersham Biosciences, Piscataway, N.J.) and the membrane was imaged and substrate quantitated with a Typhoon 9410 Variable Mode Imager and Imager Analysis software (Amersham Biosciences, Piscataway, N.J.). The choice of pixel size (100 to 200 pixels) and PMT voltage settings (350 to 600, normally 400) depended on the individual blot. X isolated Neuro-2A cell lines were identified that stably integrated and expressed the SNAP-$25_{206}$-GFP substrate of SEQ ID NO: 1.

To determine the subcellular localization of the SNAP-25-GFP substrate from isolated Neuro-2A cell lines that stably-integrated an expression construct encoding a BoNT/A, BoNT/C1 or BoNT/E, substrate, such as, e.g., pQBI-25/SNAP$25_{206}$-GFP (see Example I, 1a), approximately $1.5\times10^5$ Neuro-2A cells from each cell line were plated in a 35 mm tissue culture dish containing 3 mL of G418-selective, complete, supplemented EMEM and grown in a 37° C. incubator under 5% carbon dioxide until cells reached a density of about $5\times10^5$ cells/ml (6-16 hours). Media was replaced with 3 mL of fresh G418-selective, complete, supplemented EMEM and cells were incubated in a 37° C. incubator under 5% carbon dioxide. After 24-48 hours, living cells were observation using a fluorescence inverted microscope. X isolated Neuro-2A cell lines were detected to have the localization of the GFP fluorescence in the cell membrane indicating that the expressed SNAP$25_{206}$-GFP in these isolated Neuro-2A cell lines was correctly targeted to the cell membrane. Stably transduced cells can be used to conduct a BoNT/A, BoNT/C1 or BoNT/E activity assay.

1b. Stably Transduced SH-SY5Y Cells Using a Lentiviral Procedure

To generate a stably-integrated cell line expressing a BoNT/A, BoNT/C1 or BoNT/E SNAP-25 substrate using a lentiviral procedure, about $1.5\times10^5$ SH-SY5Y cells are plated in a 6-well tissue culture dish containing 3 mL of complete 1:1 EMEM and Ham's F12 Media (EMEM:F12), supplemented with 10% fetal bovine serum (FBS), 4 mM glutamine (Invitrogen, Inc, Carlsbad, Calif.), 1% sodium pyruvate (Invitrogen, Inc, Carlsbad, Calif.), 1.5 g/L sodium bicarbonate, 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about $5\times10^5$ cells/ml (6-16 hours). Cells are inoculated with the lentiviral stock containing an expression construct encoding a BoNT/A, BoNT/C1 or BoNT/E, substrate, such as, e.g., pLenti6Ubc/V5-SNAP-$25_{206}$-GFP, as described above in Example IV, 2b, using a suitable multiplicity of infection and are incubated for approximately 16-24 hours in a 37° C. incubator under 5% carbon dioxide. The transduction media is replaced with 3 mL of fresh complete, supplemented EMEM:F12 containing an appropriate amount of Blasticidin. Cells are incubated in a 37° C. incubator under 5% carbon dioxide for approximately 2 weeks, with old media being replaced with fresh Blasticidin-selective, complete, supplemented EMEM:F12 every 3 to 4 days. Once Blasticidin-resistant SH-SY5Y colonies are established, resistant clones are replated to new 35 mm culture plates containing fresh Blasticidin-selective, complete, supplemented EMEM:F12, until these cells reached a density of 6 to $20\times10^5$ cells/mL.

The presence of the SNAP-25-GFP substrate in isolated cell lines will be determined by Western blot analysis as describes above in Example V, 1a. The subcellular localization of the SNAP-$25_{206}$-GFP substrate in isolated cell lines will be determined by fluorescence microscopy as describes above in Example V, 1a. Stably transduced cells can be used to conduct a BoNT/A, BoNT/C1 or BoNT/E activity assay.

1c. Stably Transduced SK-N-DZ Cells Using a Recombinant Crossing-Over Procedure

To generate a stably-integrated cell line expressing a BoNT/A, BoNT/C1 or BoNT/E SNAP-25 substrate using a crossing over procedure, approximately $1.5\times10^5$ SK-N-DZ cells were plated in a 35 mm tissue culture dish containing 3 mL of complete DMEM, supplemented with 10% FBS, 4 mM glutamine (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reached a density of about $5\times10^5$ cells/ml. A 500 μL transfection solution was prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of an expression construct encoding a BoNT/A, BoNT/C1 or BoNT/E, substrate, such as, e.g., pQBI-25/SNAP25$_{206}$-GFP (see Example I, 1a). This transfection was incubated at room temperature for approximately 20 minutes. The complete, supplemented DMEM media was replaced with 2 mL of OPTI-MEM Reduced Serum Medium and the 500 μL transfection solution was added to the SK-N-DZ cells and the cells incubated in a 37° C. incubator under 5% carbon dioxide for approximately 16 hours. Transfection media was replaced with 3 mL of fresh complete, supplemented DMEM and cells were incubated in a 37° C. incubator under 5% carbon dioxide for approximately 48 hours. Media was replaced with 3 mL of fresh complete DMEM, containing approximately 5 μg/mL of G418, 10% FBS, 1× penicillin/streptomycin solution (Invitrogen, Inc, Carlsbad, Calif.) and 1×MEM non-essential amino acids solution (Invitrogen, Inc, Carlsbad, Calif.). Cells were incubated in a 37° C. incubator under 5% carbon dioxide for approximately 4 weeks, with old media being replaced with fresh G418 selective, complete, supplemented DMEM every 4 to 5 days. Once G418-resistant SK-N-DZ colonies were established, resistant clones were replated to new 35 mm culture plates containing fresh complete DMEM, supplemented with approximately 5 μg/mL of G418, 10% FBS, 1× penicillin/streptomycin solution (Invitrogen, Inc, Carlsbad, Calif.) and 1×MEM non-essential amino acids solution (Invitrogen, Inc, Carlsbad, Calif.), until these cells reached a density of 6 to $20\times10^5$ cells/mL.

To test for expression of SNAP-25-GFP from isolated SK-N-DZ cell lines that stably-integrated an expression construct encoding a BoNT/A, BoNT/C1 or BoNT/E, substrate, such as, e.g., pQBI-25/SNAP25$_{206}$-GFP (see Example I, 1a), approximately $1.5\times10^5$ SK-N-DZ cells from each cell line were plated in a 35 mm tissue culture dish containing 3 mL of G418-selective, complete, supplemented DMEM and grown in a 37° C. incubator under 5% carbon dioxide until cells reached a density of about $5\times10^5$ cells/ml (6-16 hours). Media was replaced with 3 mL of fresh G418-selective, complete, supplemented DMEM and cells were incubated in a 37° C. incubator under 5% carbon dioxide. After 48 hours, the cells were harvested by rinsing the cells once with 3.0 mL of 100 mM phosphate-buffered saline, pH 7.4 and lysed with a buffer containing 62.6 mM 2-amino-2-hydroxymethyl-1,3-propanediol hydrochloric acid (Tris-HCl), pH 6.8 and 2% sodium lauryl sulfate (SDS). Lysed cells were centrifuged at 5000 rpm for 10 min at 4° C. to eliminate debris and the supernatants were transferred to fresh siliconized tubes. Protein concentrations were measured by Bradford's method and resuspended in 1×SDS sample buffer at 1 mg/ml or higher concentration.

To detect for the presence of the SNAP-25$_{206}$-GFP substrate, samples were boiled for 5 min, and 40 μl aliquots were separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Separated peptides were transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes were blocked by incubating at room temperature for 2 hours in a solution containing 25 mM Tris-Buffered Saline (25 mM 2-amino-2-hydroxymethyl-1,3-propanediol hydrochloric acid (Tris-HCl)(pH 7.4), 137 mM sodium chloride, 2.7 mM potassium chloride), 0.1% TWEEN-20®, polyoxyethylene (20) sorbitan monolaureate, 2% bovine serum albumin, 5% nonfat dry milk. Blocked membranes were incubated at 4° C. for overnight in Tris-Buffered Saline TWEEN-200 (25 mM Tris-Buffered Saline, 0.1% TWEEN-200, polyoxyethylene (20) sorbitan monolaureate) containing a 1:50,000 dilution of mouse monoclonal anti-SNAP-25 antibody (SMI-81; Sternberger Monoclonals, Lutherville, Md.). Primary antibody probed blots were washed three times for 15 minutes each time in Tris-Buffered Saline TWEEN-200. Washed membranes were incubated at room temperature for 2 hours in Tris-Buffered Saline TWEEN-200 containing a 1:20,000 dilution of goat polyclonal anti-mouse immunoglobulin G, heavy and light chains (IgG, H+L) antibody conjugated to horseradish peroxidase (HRP; Pierce Biotechnology, Inc., Rockford, Ill.) as a secondary antibody. Secondary antibody-probed blots were washed three times for 15 minutes each time in Tris-Buffered Saline TWEEN-200. Signal detection of the labeled SNAP-25$_{206}$-GFP substrate was visualized using the ECL Plus™ Western Blot Detection System (Amersham Biosciences, Piscataway, N.J.) and the membrane was imaged and substrate quantitated with a Typhoon 9410 Variable Mode Imager and Imager Analysis software (Amersham Biosciences, Piscataway, N.J.). The choice of pixel size (100 to 200 pixels) and PMT voltage settings (350 to 600, normally 400) depended on the individual blot. X isolated SK-N-DZ cell lines were identified that stably integrated and expressed the SNAP-25$_{206}$-GFP substrate of SEQ ID NO: 1.

To determine the subcellular localization of the SNAP-25$_{206}$-GFP substrate from isolated SK-N-DZ cell lines that stably-integrated an expression construct encoding a BoNT/A, BoNT/C1 or BoNT/E, substrate, such as, e.g., pQBI-25/SNAP25$_{206}$-GFP (see Example I, 1a), approximately $1.5\times10^5$ SK-N-DZ cells from each cell line were plated in a 35 mm tissue culture dish containing 3 mL of G418-selective, complete, supplemented DMEM and grown in a 37° C. incubator under 5% carbon dioxide until cells reached a density of about $5\times10^5$ cells/ml (6-16 hours). Media was replaced with 3 mL of fresh G418-selective, complete, supplemented DMEM and cells were incubated in a 37° C. incubator under 5% carbon dioxide. After 24-48 hours, living cells were observation using a fluorescence inverted microscope. X isolated SK-N-DZ cell lines were detected to have the localization of the GFP fluorescence in the cell membrane indicating that the expressed SNAP25$_{206}$-GFP in these isolated SK-N-DZ cell lines was correctly targeted to the cell membrane. Stably transduced cells can be used to conduct a BoNT/A, BoNT/C1 or BoNT/E activity assay using a SNAP-25-GFP substrate.

1d. Stably Transduced SK-N-DZ Cells Using a Lentiviral Procedure

To generate a stably-integrated cell line expressing a BoNT/A, BoNT/C1 or BoNT/E SNAP-25 substrate using a lentiviral procedure, approximately $1.5\times10^5$ SK-N-DZ cells are plated in a 6-well tissue culture dish containing 3 mL of complete DMEM, supplemented with 10% FBS, 4 mM glutamine (Invitrogen, Inc, Carlsbad, Calif.) and 1×MEM non-essential amino acids solution (Invitrogen, Inc, Carlsbad, Calif.), and grown in a 37° C. incubator under 5% carbon dioxide until the cells reach a density of about $5\times10^5$ cells/ml (6-16 hours). Cells are inoculated with the lentiviral stock containing an expression construct encoding a BoNT/A, BoNT/C1 or BoNT/E substrate, such as, e.g., pLenti6Ubc/V5-SNAP-25$_{206}$-GFP, as described above in Example IV, 2b, using a suitable multiplicity of infection and are incubated for approximately 16-24 hours in a 37° C. incubator under 5% carbon dioxide. The transduction media is replaced with 3 mL of fresh complete, supplemented EMEM:F12 containing an appropriate amount of Blasticidin. Cells are incubated in a 37° C. incubator under 5% carbon dioxide for approximately 2 weeks, with old media being replaced with fresh Blasticidin-selective, complete, supplemented EMEM:F12 every 3 to 4 days. Once Blasticidin-resistant SH-SY5Y colonies are established, resistant clones are replated to new 35 mm culture plates containing fresh Blasticidin-selective, complete, supplemented EMEM:F12, until these cells reached a density of 6 to $20\times10^5$ cells/mL.

The presence of the SNAP-$25_{206}$-GFP substrate in isolated cell lines will be determined by Western blot analysis as describes above in Example V, 1a. The subcellular localization of the SNAP-$25_{206}$-GFP substrate in isolated cell lines will be determined by fluorescence microscopy as describes above in Example V, 1a. Stably transduced cells can be used to conduct a BoNT/A, BoNT/C1 or BoNT/E activity assay using a SNAP-25-GFP substrate.

2. Generation of Cells Stably Containing a BoNT/B, BoNT/D, BoNT/F, BoNT/G or TeNT Substrate 2a. Stably Transformed Cells Using a Recombinant Crossing-Over Procedure To generate a stably-integrated cell line expressing a BoNT/B, BoNT/D, BoNT/F, BoNT/G or TeNT VAMP substrate using a crossing over procedure, a suitable density ($1\times10^5$ to $1\times106^6$ cells) of appropriate cells are plated in a 35 mm tissue culture dish containing 3 mL of complete, supplemented culture media and grown in a 37° C. incubator under 5% carbon dioxide until the cells reached a density appropriate for transfection. A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of expression construct encoding a BoNT/B, BoNT/D, BoNT/F, BoNT/G or TeNT VAMP substrate, such as, e.g., pQBI-25/VAMP-1-GFP, pQBI-25/VAMP-2-GFP or pQBI-25/VAMP-3-GFP (see Examples I, 2a; I, 2b; or I, 2c). This transfection was incubated at room temperature for approximately 20 minutes. The complete, supplemented media is replaced with 2 mL of OPTI-MEM Reduced Serum Medium and the 500 μL transfection solution is added to the cells and the cells are incubated in a 37° C. incubator under 5% carbon dioxide for approximately 16 hours. Transfection media is replaced with 3 mL of fresh complete, supplemented culture media and the cells are incubated in a 37° C. incubator under 5% carbon dioxide for approximately 48 hours. Media is replaced with 3 mL of fresh complete, supplemented culture media, containing approximately 5 μg/mL of G418. Cells are incubated in a 37° C. incubator under 5% carbon dioxide for approximately 4 weeks, with old media being replaced with fresh G418 selective, complete, supplemented media every 4 to 5 days. Once G418-resistant colonies are established, resistant clones are replated to new 35 mm culture plates containing fresh complete culture media, supplemented with approximately 5 μg/mL of G418 until these cells reached a density of 6 to $20\times10^5$ cells/mL.

To test for expression of a BoNT/B, BoNT/D, BoNT/F, BoNT/G or TeNT VAMP-GFP from isolated cell lines that stably-integrated an expression construct encoding a BoNT/B, BoNT/D, BoNT/F, BoNT/G or TeNT VAMP-GFP substrate, such as, e.g., pQBI-25/VAMP-1-GFP, pQBI-25/VAMP-2-GFP or pQBI-25/VAMP-3-GFP (see Examples I, 2a; I, 2b; or I, 2c), approximately $1.5\times10^5$ cells from each cell line are plated in a 35 mm tissue culture dish containing 3 mL of G418-selective, complete, supplemented DMEM and are grown in a 37° C. incubator under 5% carbon dioxide until cells reached a density of about $5\times10^5$ cells/ml (6-16 hours). Media is replaced with 3 mL of fresh G418-selective, complete, supplemented culture media and cells are incubated in a 37° C. incubator under 5% carbon dioxide. After 48 hours, the cells are harvested by rinsing the cells once with 3.0 mL of 100 mM phosphate-buffered saline, pH 7.4 and are lysed with a buffer containing 62.6 mM 2-amino-2-hydroxymethyl-1,3-propanediol hydrochloric acid (Tris-HCl), pH 6.8 and 2% sodium lauryl sulfate (SDS). Lysed cells are centrifuged at 5000 rpm for 10 min at 4° C. to eliminate debris and the supernatants are transferred to fresh siliconized tubes. Protein concentrations are measured by Bradford's method and are resuspended in 1×SDS sample buffer at 1 mg/ml or higher concentration.

To detect for the presence of the VAMP-GFP substrate, samples are separated by MOPS polyacrylamide gel electrophoresis and analyzed by Western blotting procedures as described above in Examples II, 2a; II, 4a; II, 6a; II, 7a; and II, 8a, in order to identify cell lines that have stably integrated and express the VAMP-GFP substrate.

To determine the subcellular localization of the VAMP-GFP substrate from isolated cell lines that stably-integrated an expression construct encoding a BoNT/B, BoNT/D, BoNT/F, BoNT/G or TeNT VAMP-GFP substrate, such as, e.g., pQBI-25/VAMP-1-GFP, pQBI-25/VAMP-2-GFP or pQBI-25/VAMP-3-GFP (see Examples I, 2a; I, 2b; or I, 2c), approximately $1.5\times10^5$ cells from each cell line are plated in a 35 mm tissue culture dish containing 3 mL of G418-selective, complete, supplemented culture media and are grown in a 37° C. incubator under 5% carbon dioxide until cells reached a density of about $5\times10^5$ cells/ml (6-16 hours). Media is replaced with 3 mL of fresh G418-selective, complete, supplemented culture media and cells are incubated in a 37° C. incubator under 5% carbon dioxide. After 24-48 hours, living cells are observation using a fluorescence inverted microscope in order to identify isolated cell lines that exhibit GFP fluorescence localized to the cell membrane, thereby indicating that the expressed VAMP-GFP in these isolated cell lines is correctly targeted to the cell membrane. Stably transduced cells can be used to conduct a BoNT/B, BoNT/D, BoNT/F, BoNT/G or TeNT activity assay using a VAMP-GFP substrate.

2b. Stably Transduced Cells Using a Lentiviral Procedure

To generate a stably-integrated cell line expressing a BoNT/B, BoNT/D, BoNT/F, BoNT/G or TeNT VAMP substrate using a lentiviral procedure, a suitable density ($1\times10^5$ to $1\times106^6$ cells) of appropriate cells are plated in a 6-well tissue culture dish containing 3 mL of complete, supplemented culture media and are grown in a 37° C. incubator under 5% carbon dioxide until the cells reach a density appropriate for transduction. Cells are inoculated with the lentiviral stock, as described above in Example IV, 5b, using a suitable multiplicity of infection and are incubated for approximately 16-24 hours in a 37° C. incubator under 5% carbon dioxide. The transduction media is replaced with 3 mL of fresh complete, supplemented media containing an appropriate amount of Blasticidin. Cells are incubated in a 37° C. incubator under 5% carbon dioxide for approximately 2 weeks, with old media being replaced with fresh Blasticidin-selective, complete, supplemented media every 3 to 4 days. Once Blasticidin-resistant colonies are established, resistant clones are replated to new 35 mm culture plates containing fresh Blasticidin-selective, complete, supplemented media, until these cells reached a density of 6 to $20\times10^5$ cells/mL.

The presence of the VAMP-GFP substrate in isolated cell lines will be determined by Western blot analysis as describes above in Example V, 2a. The subcellular localization of the VAMP-GFP substrate in isolated cell lines will be determined by fluorescence microscopy as describes above in Example V, 2a. Stably transduced cells can be used to conduct a BoNT/B, BoNT/D, BoNT/F, BoNT/G or TeNT activity assay using a VAMP-GFP substrate.

3. Generation of Cells Stably Containing a BoNT/C1 Syntaxin Substrate

3a. Stably Transformed Cells Using a Recombinant Crossing-Over Procedure

To generate a stably-integrated cell line expressing a BoNT/C1 Syntaxin substrate using a crossing over procedure, a suitable density ($1\times10^5$ to $1\times106^6$ cells) of appropriate cells are plated in a 35 mm tissue culture dish containing 3 mL of complete, supplemented culture media and grown in a 37° C. incubator under 5% carbon dioxide until the cells reached a density appropriate for transfection. A 500 μL transfection solution is prepared by adding 250 μL of OPTI-MEM Reduced Serum Medium containing 15 μL of LipofectAmine 2000 (Invitrogen, Carlsbad, Calif.) incubated at room temperature for 5 minutes to 250 μL of OPTI-MEM Reduced Serum Medium containing 5 μg of expression construct encoding a BoNT/C1 Syntaxin substrate, such as, e.g., pQBI-25/Syntaxin-1-GFP (see Example I, 3a). This transfection was incubated at room temperature for approximately 20 minutes. The complete, supplemented media is replaced with 2 mL of OPTI-MEM Reduced Serum Medium and the 500 μL transfection solution is added to the cells and the cells are incubated in a 37° C. incubator under 5% carbon dioxide for approximately 16 hours. Transfection media is replaced with 3 mL of fresh complete, supplemented culture media and the cells are incubated in a 37° C. incubator under 5% carbon dioxide for approximately 48 hours. Media is replaced with 3 mL of fresh complete, supplemented culture media, containing approximately 5 μg/mL of G418. Cells are incubated in a 37° C. incubator under 5% carbon dioxide for approximately 4 weeks, with old media being replaced with fresh G418 selective, complete, supplemented media every 4 to 5 days. Once G418-resistant colonies are established, resistant clones are replated to new 35 mm culture plates containing fresh complete culture media, supplemented with approximately 5 μg/mL of G418 until these cells reached a density of 6 to $20\times10^5$ cells/mL.

To test for expression of a BoNT/C1 Syntaxin-GFP from isolated cell lines that stably-integrated an expression construct encoding a BoNT/C1 Syntaxin-GFP substrate, such as, e.g., pQBI-25/Syntaxin-1-GFP (see Example I, 3a), approximately $1.5\times10^5$ cells from each cell line are plated in a 35 mm tissue culture dish containing 3 mL of G418-selective, complete, supplemented culture media and are grown in a 37° C. incubator under 5% carbon dioxide until cells reached a density of about $5\times10^5$ cells/ml (6-16 hours). Media is replaced with 3 mL of fresh G418-selective, complete, supplemented culture media and cells are incubated in a 37° C. incubator under 5% carbon dioxide. After 48 hours, the cells are harvested by rinsing the cells once with 3.0 mL of 100 mM phosphate-buffered saline, pH 7.4 and are lysed with a buffer containing 62.6 mM 2-amino-2-hydroxymethyl-1,3-propanediol hydrochloric acid (Tris-HCl), pH 6.8 and 2% sodium lauryl sulfate (SDS). Lysed cells are centrifuged at 5000 rpm for 10 min at 4° C. to eliminate debris and the supernatants are transferred to fresh siliconized tubes. Protein concentrations are measured by Bradford's method and are resuspended in 1×SDS sample buffer at 1 mg/ml or higher concentration.

To detect for the presence of the Syntaxin-GFP substrate, samples are separated by MOPS polyacrylamide gel electrophoresis and analyzed by Western blotting procedures as described above in Examples II, 3a, in order to identify cell lines that have stably integrated and express the Syntaxin-GFP substrate.

To determine the subcellular localization of the Syntaxin-GFP substrate from isolated cell lines that stably-integrated an expression construct encoding a BoNT/C1 Syntaxin-GFP substrate, such as, e.g., pQBI-25/Syntaxin-1-GFP (see Example I, 3a), approximately $1.5\times10^5$ cells from each cell line are plated in a 35 mm tissue culture dish containing 3 mL of G418-selective, complete, supplemented culture media and are grown in a 37° C. incubator under 5% carbon dioxide until cells reached a density of about $5\times10^5$ cells/ml (6-16 hours). Media is replaced with 3 mL of fresh G418-selective, complete, supplemented culture media and cells are incubated in a 37° C. incubator under 5% carbon dioxide. After 24-48 hours, living cells are observation using a fluorescence inverted microscope in order to identify isolated cell lines that exhibit GFP fluorescence localized to the cell membrane, thereby indicating that the expressed Syntaxin-GFP in these isolated cell lines is correctly targeted to the cell membrane. Stably transduced cells can be used to conduct a BoNT/C1 activity assay using a Syntaxin-GFP substrate.

3b. Stably Transduced Cells Using a Lentiviral Procedure

To generate a stably-integrated cell line expressing a BoNT/C1 Syntaxin substrate using a lentiviral procedure, a suitable density ($1\times10^5$ to $1\times106^6$ cells) of appropriate cells are plated in a 6-well tissue culture dish containing 3 mL of complete, supplemented culture media and are grown in a 37° C. incubator under 5% carbon dioxide until the cells reach a density appropriate for transduction. Cells are inoculated with the lentiviral stock, as described above in Example IV, 8b, using a suitable multiplicity of infection and are incubated for approximately 16-24 hours in a 37° C. incubator under 5% carbon dioxide. The transduction media is replaced with 3 mL of fresh complete, supplemented media containing an appropriate amount of Blasticidin. Cells are incubated in a 37° C. incubator under 5% carbon dioxide for approximately 2 weeks, with old media being replaced with fresh Blasticidin-selective, complete, supplemented media every 3 to 4 days. Once Blasticidin-resistant colonies are established, resistant clones are replated to new 35 mm culture plates containing fresh Blasticidin-selective, complete, supplemented media, until these cells reached a density of 6 to $20\times10^5$ cells/mL.

The presence of the Syntaxin-GFP substrate in isolated cell lines will be determined by Western blot analysis as describes above in Example V, 3a. The subcellular localization of the Syntaxin-GFP substrate in isolated cell lines will be determined by fluorescence microscopy as describes above in Example V, 3a. Stably transduced cells can be used to conduct a BoNT/C1 activity assay using a Syntaxin-GFP substrate.

Example VI

Optimizing Conditions for Lipophilic Dye-Based FRET Assays

1. Identification of Suitable Lipophilic Dyes for Lipophilic Dye-Based FRET Assays To determine the suitability of a lipophilic dye as a second member of a FRET pair, the absorbance spectrum of various lipophilic dyes were first examined for spectral overlap of the emissions spectrum of the first member of a FRET pair. Candidate dyes were selected based on suitable spectral overlap (see Table 14).

Figure 11:
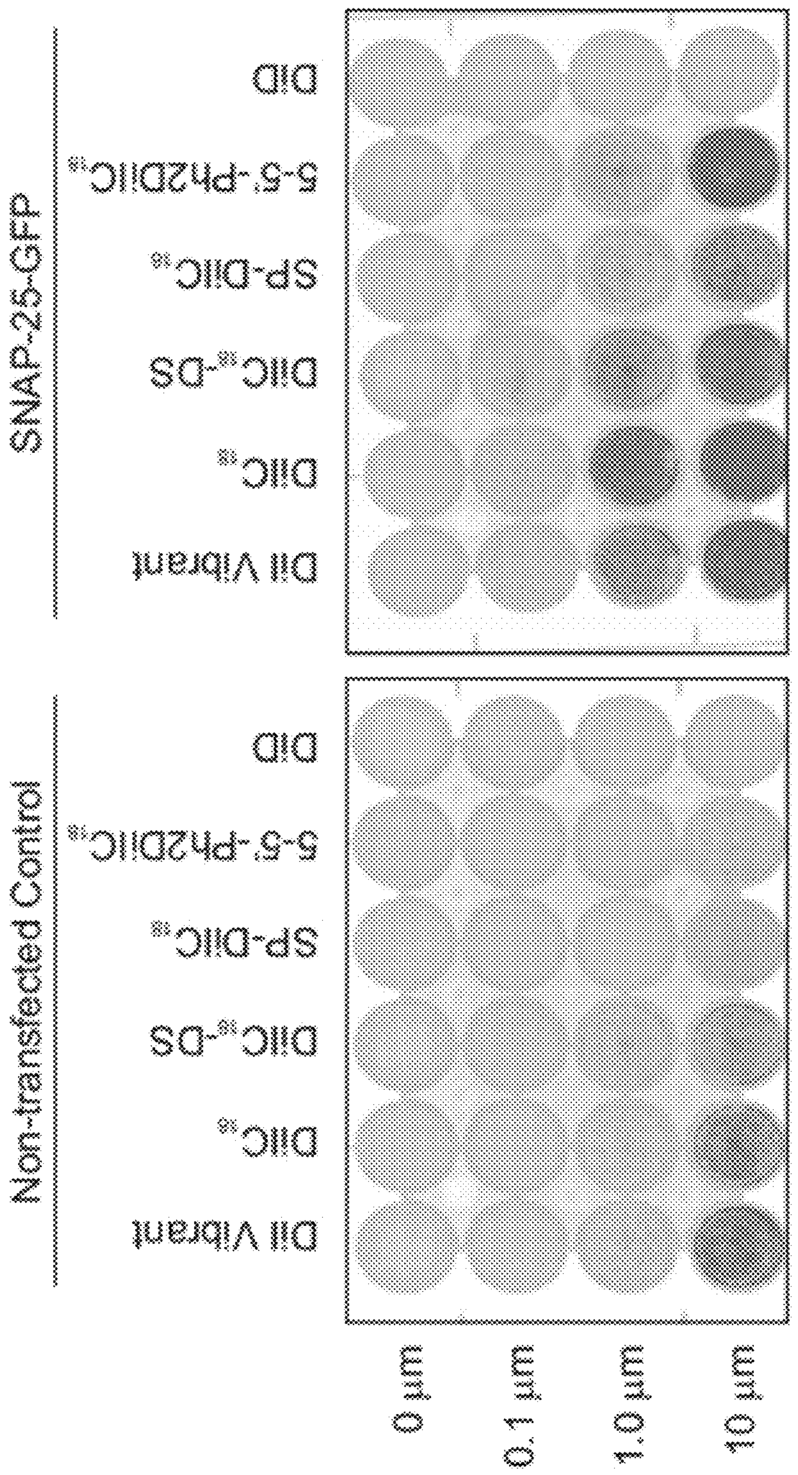
FIG. 11 shows the detection of FRET in a Neuro-2A cell line expressing SNAP$25_{206}$-GFP and stained with one of the following lipophilic dye: DiI Vibrant, DiI$C_{18}$(3), DiI$C_{18}$-DS, SP-DiI$C_{18}$, 5-5'-Ph2-DiI$C_{18}$ or DiD. Plates were exposed to a 488 nm laser for excitation of the donor fluorophore GFP. Emission was collected with a filter set at 610 nm±30 nm to detect the red fluorescence of the various lipophilic dye acceptors. The increased fluorescence in cells expressing SNAP$25_{206}$-GFP in comparison to the untransfected controls was due to energy transfer from GFP to the lipophilic dye acceptor.

In order to assess the suitability of selected lipophilic dyes as a second member of a FRET pair, candidate FRET pairs are tested for FRET. As a non-limiting example, a Neuro-2A cell line stably containing a SNAP-$25_{206}$-GFP substrate was pre-treated with different lipophilic dyes to determine whether FRET could occur. Approximately $2.5\times10^5$ Neuro-2A cells were plated into each well of a 24-well tissue culture dish containing 2 mL of G418-selective, complete, supplemented EMEM and grown in a 37° C. incubator under 5% carbon dioxide overnight to allow for cell attachment. Media was replaced with 3 mL of fresh G418-selective, serum-free EMEM and cells were incubated in a 37° C. incubator under 5% carbon dioxide for approximately three day to induce differentiation. The cells were incubated for 2 hours in serum-free media containing 0.1 μM, 1.0 μM and 10 μM of each of the following lipophilic dyes: DiI Vibrant, $DiIC_{18}(3)$, $DiIC_{18}(3)$-DS, SP-$DiIC_{18}$, 5-5'-$Ph_2$-$DiIC_{18}$ and DiD (see Table 14). The various dyes were selected such that they would not be excited by the 488 nm laser (absorption spectra ~550-590 nm) and would require energy transfer from SNAP$25_{206}$-GFP for fluorescence. The cells were scanned using a Typhoon 9140 (Amersham Biosciences, Piscataway, N.J.) set at the following parameters: excitation laser was set at 488 nm and the emissions were detected using a collection filter set at 610 nm±30 nm with the focal plane of the laser 3 mm above the glass. Neuro-2A cells expressing SNAP$25_{206}$-GFP display an increase of red fluorescence in cells exposed to various dyes at concentrations ranging from 1 μM to 10 μM. for two hours. For example, there was fluorescence in the cells expressing SNAP$25_{206}$-GFP stained containing 1.0 μM of DiI Vibrant, 1.0 μM $DiIC_{18}(3)$ or 1.0 μM $DiIC_{18}(3)$-DS (FIG. 11). However, there was no fluorescence at this wavelength detected in the control cells lacking SNAP$25_{206}$-GFP (untransfected) treated with 1.0 μM of DiI Vibrant, 1.0 μM $DiIC_{18}(3)$ or 1.0 μM $DiIC_{18}(3)$-DS (FIG. 11). These results indicate that the increase of red fluorescence in the cells expressing SNAP$25_{206}$-GFP was due to the transfer of energy from the excited GFP to the membrane dye and subsequent emission by the dye.

In order to assess the suitability of a selected fluorescent protein as a second member of a FRET pair, candidate FRET pairs are tested for FRET. As a non-limiting example, a Neuro-2A cell line stably containing a SNAP-$25_{206}$-HcRed1 substrate will be pre-treated with different lipophilic dyes to determine whether FRET could occur. Approximately $2.5\times10^5$ Neuro-2a cells will be plated into each well of a 24-well tissue culture dish containing 2 mL of G418-selective, complete, supplemented EMEM and will be grown in a 37° C. incubator under 5% carbon dioxide overnight to allow for cell attachment. Media will be replaced with 3 mL of fresh G418-selective, serum-free EMEM and cells will be incubated in a 37° C. incubator under 5% carbon dioxide for approximately three day to induce differentiation. The cells will be incubated for 2 hours in serum-free media containing 0.1 μM, 1.0 μM and 10 μM of each of the following lipophilic dyes: 4-Di-16-ASP, 4-Di-10-ASP, FAST DiA (see Table 14). The fluorescent protein is selected such that it would not be excited by a 492 nm laser (absorption spectra ~500-600 nm) and would require energy transfer from the lipophilic dyes for fluorescence. The cells are scanned using a Typhoon 9140 (Amersham Biosciences, Piscataway, N.J.) set at the following parameters: excitation laser is set at 492 nm and the emissions are detected using a collection filter set at 618 nm±30 nm with the focal plane of the laser 3 mm above the glass. Neuro-2A cells containing a suitable lipophilic dye-SNAP$25_{206}$-HcRed1 FRET pair will display an increased red fluorescence due to the transfer of energy from the excited lipophilic dye to the SNAP$25_{206}$-HcRed1.

Figure 12A:
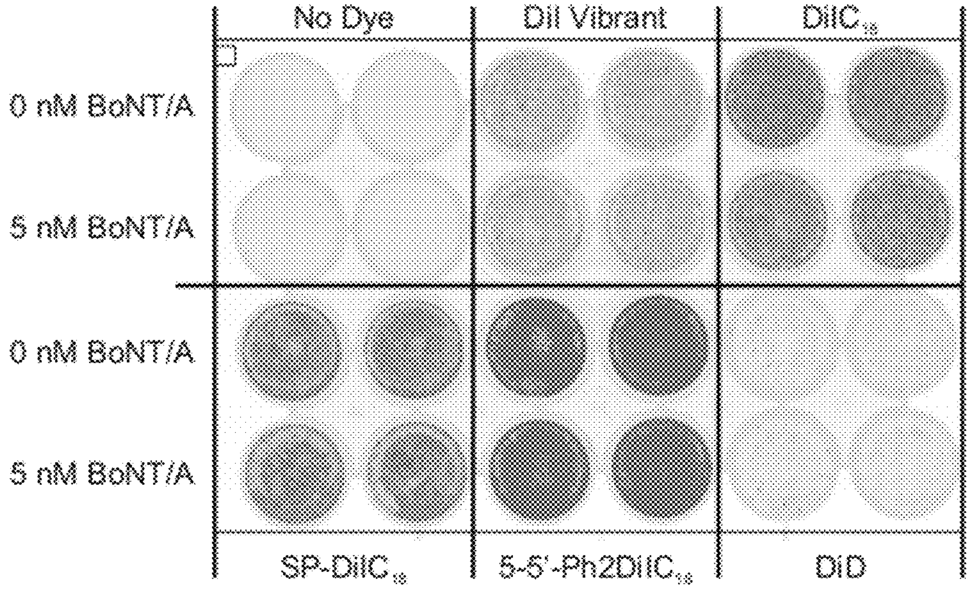
FIG. 12*a* shows plates where cells were exposed overnight to 0 nM BoNT/A (control, no toxin) or 5 nM of BoNT/A, and loaded for two hours with the indicated lipophilic dye: no dye control, DiI Vibrant, DiI$C_{18}$(3), SP-DiI$C_{18}$, 5-5'-Ph2-DiI$C_{18}$ or DiD. Plates were exposed to a 488 nm laser in the Amersham Typhoon 9140 Imager to excite the GFP donor fluorophore. Emission was collected with a filter set at 610 nm±30 nm such that red fluorescence of the various lipophilic dyes is detected.
Figure 12B:
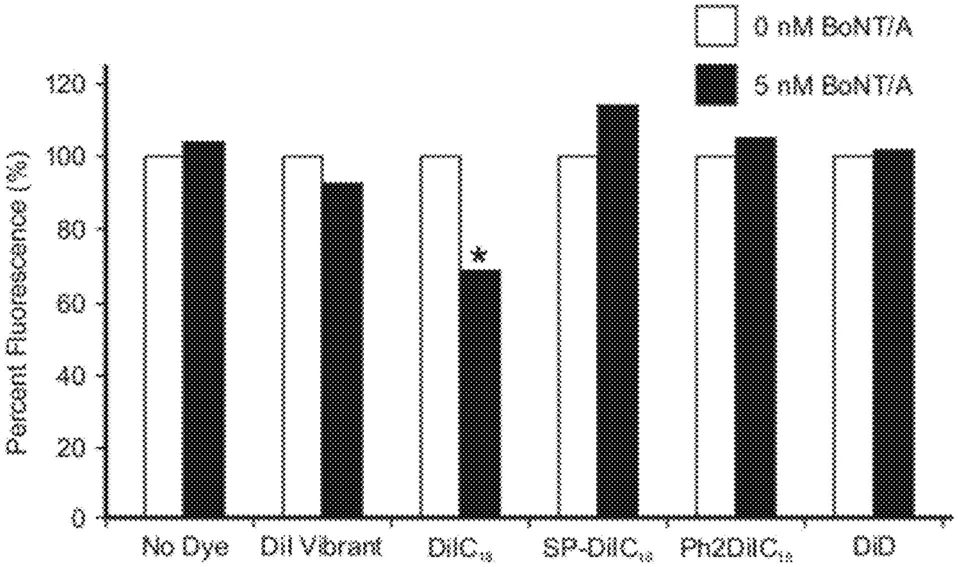
FIG. 12*b* shows the fluorescence detected in each well quantitated using the Typhoon 9140 software. The amount of fluorescence emission at 610 nm following excitation at 488 nm was measured as volume. In order to normalize the data in each dye combination, raw fluorescence numbers at 610 nm were represented as a percentage of the fluorescence emission from control cells which contained lipophilic dye but were not treated with toxin and read at 610 nm to normalize the data in each dye combination.

To determine whether the activity of a Clostridial toxin could be measured using a lipophilic dye-based FRET assay where the first FRET member is a fluorescent protein and the second member is a lipophilic dye, Neuro-2a cells stably containing a SNAP-$25_{206}$-GFP substrate were grown in 24-well tissue culture dishes and differentiated as described above in Example VI, 1. Differentiated cells were then exposed to 5 nM of BoNT/A for 16 hours. BoNT/A treated cells were then incubated for two hours with one of the following lipophilic dyes: DiI Vibrant, $DiIC_{18}(3)$, SP-$DiIC_{18}$, 5-5'-$Ph_2$-$DiIC_{18}$ and DiD. The cells were excited with a 488 nm laser and emissions collected at 610 nm+/−30 nm. In the cells stained with $DiIC_{18}(3)$, there was a decrease in the fluorescent signal at 610 nm following treatment with BoNT/A as compared with the untreated control (see FIG. 12*a*). This data indicates that the BoNT/A activity can be detected using the FRET assay. The fluorescence detected in each assay was quantified with the TYPHOON 9140 IMAGE QUANT TL A software (Amersham Biosciences, Piscataway, N.J.). The software assigns a numerical value to each well containing cells based on the amount (volume) of fluorescence emitted. The amount of fluorescence was then expressed as a percent of the untreated control to normalize for the background fluorescence of the dyes (FIG. 12*b*). There was a 30% decrease in FRET in cells treated with BoNT/A as compared to the untreated control cells using the lipophilic marker $DiIC_{18}(3)$.

To determine whether the activity of a Clostridial toxin could be measured using a lipophilic dye-based FRET assay where the first FRET member is a lipophilic dye and the second member is a fluorescent protein, Neuro-2a cells stably containing a SNAP-$25_{206}$-HcRed1 substrate are grown in 24-well tissue culture dishes and are differentiated as described above in Example VI, 1. Differentiated cells are then exposed to 5 nM of BoNT/A for 16 hours. BoNT/A treated cells are then incubated for two hours with one of the following lipophilic dyes: 4-Di-16-ASP, 4-Di-10-ASP, FAST DiA. The cells are excited with a 492 nm laser and emissions are collected at 618 nm+/−30 nm. The fluorescence detected in each assay will be quantified with the TYPHOON 9140 IMAGE QUANT TL A software (Amersham Biosciences, Piscataway, N.J.). The software assigns a numerical value to each well containing cells based on the amount (volume) of fluorescence emitted. The amount of fluorescence will then be expressed as a percent of the untreated control to normalize for the background fluorescence of the fluorescent protein. Cells showing a decrease in the fluorescent signal at 618 nm following treatment with BoNT/A as compared with the untreated control will indicate that the BoNT/A activity can be detected using the FRET assay.

TABLE 14

Excitation ad Emission Maxima Overlap of Exemplary FRET pairs

| Donor | | Acceptor | |
|---|---|---|---|
| Emission Spectrum (nm) | Examples | Absorbance Spectrum (nm) | Examples |
| BFP (420-460)<br>Tag (425-495) | EBFP, BGA30, HaloTag Coumarian | DiO (425-500)<br>DiA (400-500)<br>Tag (410-430) | FAST DiO, $DiOC_{18}(3)$, $DiOC_{16}(3)$, SP-$DiOC_{18}(3)$, 4-Di-16-ASP, 4-Di-10-ASP, FAST DiA, FM ® 1-43, BG-430 |
| CFP (460-500)<br>Tag (425-495) | ECFP, AmCyan, BG-430 | DiO (425-500)<br>DiA (400-500)<br>FM (400-525)/(425-575)<br>Tag (485-520) | FAST DiO, $DiOC_{18}(3)$, $DiOC_{16}(3)$, SP-$DiOC_{18}(3)$, 4-Di-16-ASP, 4-Di-10-ASP, FAST DiA, FM ® 1-43, FM ® 1-84, FM ® 2-10, FM ® 4-64, FM ® 5-95, RH 414, FIAsH, BG-505, BG-488, BG-432, HaloTag diAcFAM |
| GFP (500-520)<br>Tag (515-540) | AcGFP, ZsGreen, Vitality ® hfGFP, EGFP, Monster Green, FIAsH, BG-DAF, BG-488, HaloTag diAcFAM | DiI (500-560)<br>FM (400-525)/(425-575)<br>Tag (525-565) | $DiIC_{18}(3)$, $DiIC_{16}(3)$, $DiIC_{12}(3)$, FAST DiI, $\Delta^9$-DiI, FM ®DiI, CellTracker CM-DiI, $DiIC_{18}(3)$-DS, SP-$DMC_{18}(3)$, $Br_2$-$DiIC_{18}(3)$, FM ® 1-43, FM ® 1-84, FM ® 2-10, FM ® 4-64, FM ® 5-95, RH 414, BG-532, BG-547, TMR-Star |
| YFP (520-550)<br>Tag (515-540)<br>Tag (520-565) | EYFP, ZsYellow, FIAsH, BG-DAF, BG-488, HaloTag diAcFAM, BG-505, BG-532 | DiI (500-560)<br>FM (400-525)/(425-575)<br>Tag (525-565) | $DiIC_{18}(3)$, $DiIC_{16}(3)$, $DiIC_{12}(3)$, FAST DiI, $\Delta^9$-DiI, FM ®DiI, CellTracker CM-DiI, $DiIC_{18}(3)$-DS, SP-$DMC_{18}(3)$, $Br_2$-$DiIC_{18}(3)$, FM ® 1-43, FM ® 1-84, FM ® 2-10, FM ® 4-64, FM ® 5-95, RH 414, BG-532, BG-547, TMR-Star, HaloTag TMR |
| RFP (550-740)<br>Tag (560-770) | DsRed, DsRed2, DsRed-Express, AsRed2, HcRed1, ReAsH, BG-547, TMR-Star, BG-600, BG-632, BG-647, BG-732, BG-747, HaloTag TMR | DiD (575-660)<br>DiR (625-770)<br>Tag (580-760) | 5,5'-$Ph_2$-$DiIC_{18}(3)$, $DiIC_{18}(5)$, $DiIC_{18}(5)$-DS, $DiIC_{18}(7)$, ReAsH, BG-600, BG-632, BG-647, BG-732, BG-747 |
| DPH (420-460)<br>ANS (410-510)<br>DCVJ (480-500) | DPH, TMA-DPH, 1,8-ANS, 2,6-ANS, 2,6-TNS, bis-ANS, DCVJ | GFP (425-505)<br>YFP (450-525)<br>RFP (475-575)<br>Quenchers* | AcGFP, ZsGreen, Vitality ® hfGFP, EGFP, Monster Green, EYFP, ZsYellow, DsRed, DsRed2, DsRed-Express, AsRed2, HcRed1 Dabcyl, Dabsyl, BHQ-0, BHQ-1, QSY 7/QSY 9 |
| DiO (500-520)<br>Dapoxyl (490-530) | FAST DiO, $DiOC_{18}(3)$, $DiOC_{16}(3)$, SP-$DiOC_{18}(3)$, Prodan, Laurdan, Acrylodan, Badan, dapoxyl sulfonic acid | GFP (425-505)<br>YFP (450-525)<br>RFP (475-575)<br>Quenchers* | AcGFP, ZsGreen, Vitality ® hfGFP, EGFP, Monster Green, EYFP, ZsYellow, DsRed, DsRed2, DsRed-Express, AsRed2, HcRed1 Dabcyl, Dabsyl, BHQ-0, BHQ-1, QSY 7/QSY 9 |
| DiI (560-580) | $DiIC_{18}(3)$, $DiIC_{16}(3)$, $DiIC_{12}(3)$, FAST DiI, $\Delta^9$-DiI, FM ®DiI, CellTracker CM-DiI, $DiIC_{18}(3)$-DS, SP-$DiIC_{18}(3)$, $Br_2$-$DiIC_{18}(3)$ | RFP (475-575)<br>RFP (500-600)<br>Quenchers* | DsRed, DsRed2, DsRed-Express, AsRed2, HcRed1 BHQ-1, QSY 7/QSY 9, BHQ-2, QSY 21, BHQ-3 |
| DiA (590-620)<br>FM (590-610) | 5,5'-$Ph_2$-$DiIC_{18}(3)$, 4-Di-16-ASP, 4-Di-10-ASP, FAST DiA, FM ® 1-43 | RFP (475-575)<br>RFP (500-600)<br>Quenchers* | DsRed, DsRed2, DsRed-Express, AsRed2, HcRed1 BHQ-1, QSY 7/QSY 9, BHQ-2, QSY 21, BHQ-3 |

*The absorbance spectrum of quenchers vary: Dabcyl (400-525), Dabsyl (400-525), BHQ-0 (430-520), BHQ-1 (480-580), QSY 7/QSY 9 (500-600), BHQ-2 (559-650), QSY 21 (575-725), BHQ-3 (620-730).

Using the procedures outlined above, cell lines stably containing a VAMP-GFP substrate or a Syntaxin-GFP substrate disclosed in the present specification can be tested with different lipophilic dyes to identify dyes that elicit a suitable FRET response useful to practice aspects of the present invention. Likewise, Clostridial toxin substrates operationally linked to a different fluorescent protein, such as, e.g., a BFP, a CFP, a YFP or a RFP can be tested with different lipophilic dyes to identify dyes that elicit a FRET response useful to practice aspects of the present invention. (see Table 14). In addition, the procedures outlined above can test various lipophilic dyes as suitable donor fluorophores in conjunction with fluorescent proteins as acceptors (see Table 14).

2. Optimizing Lipophilic Dye Conditions for Lipophilic Dye-Based FRET Assays

Different lipophilic dye concentrations and different dye loading times are evaluated in order to determine more optimal FRET conditions for a lipophilic dye-based FRET assay.

Figure 13:
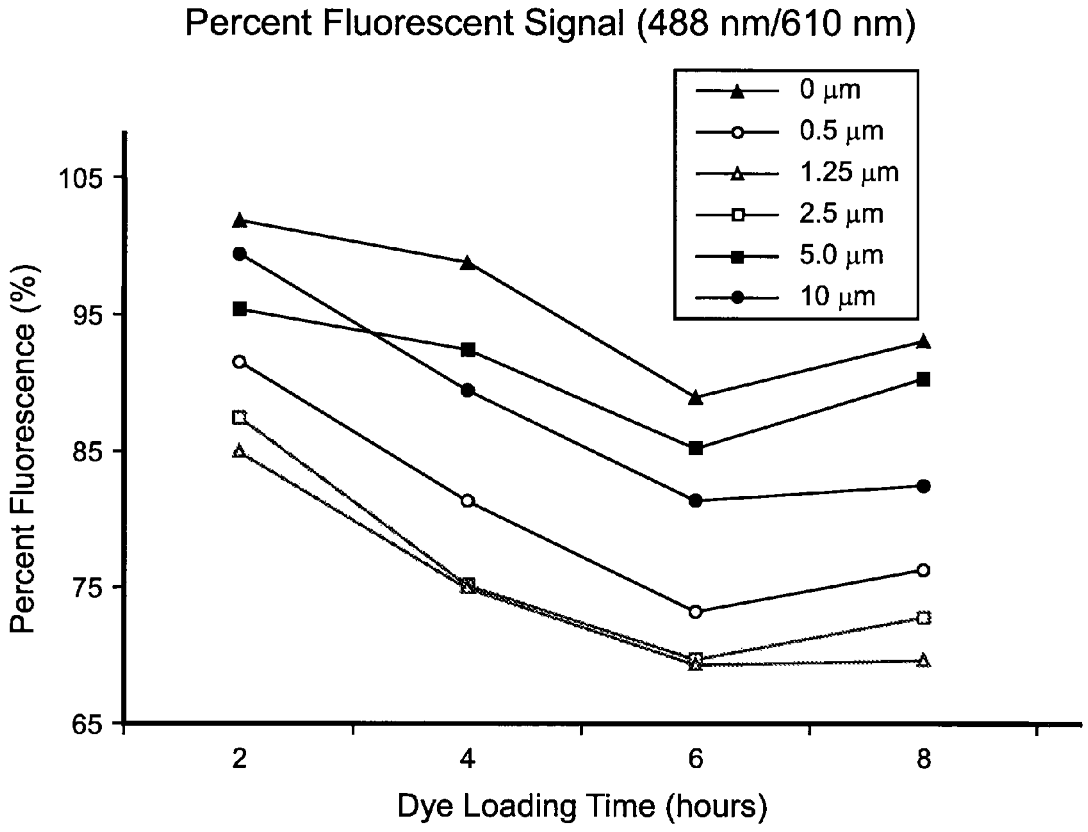
FIG. 13 shows the dose response of Neuro-2A cells expressing SNAP$25_{206}$-GFP to the lipophilic dye DiI$C_{18}$(3) treated with 1 nM BoNT/A. Cells were exposed for 6 hours to different concentration of DiI$C_{18}$(3) ranging from 0.5 μM to 10 μM as indicated. Fluorescence was quantitated using Typhoon 9140 software with excitation at 488 nm and emission at 610 nm. The greatest differences between control and treated cells were observed with 1.25 μM and 2.5 μM dye loaded for 6 hours.

To determine more optimal lipophilic dye conditions for a lipophilic dye-based FRET assay for BoNT/A activity, Neuro-2a cells stably containing a SNAP-$25_{206}$-GFP substrate were grown in 24-well tissue culture dishes and differentiated as described above in Example VI, 1. Differentiated cells were then exposed to 1 nM of BoNT/A for 16 hours. BoNT/A treated cells were then incubated with 0 μM, 0.5 μM, 1.25 μM, 2.5 μM, 5.0 μM or 10 μM of $DiIC_{18}(3)$ and FRET determined using the Typhoon 9140 software with excitation at 488 nm and emission collection at 610 nm+/−30 nm at 2 hours, 4 hours, 6 hours and 8 hours. The greatest difference between BoNT/A-treated Neuro-2A cells and untreated Neuro-2A cells occurred when the cells were incubated with $DiIC_{18}(3)$ at a range of 1.25 μM-2.5 μM for approximately 4 to 6 hours (FIG. 13). A similar procedure will be conducted to optimize conditions using a lipophilic dye as a donor fluorophore and a BoNT/A substrate as an acceptor.

To determine more optimal lipophilic dye conditions for a lipophilic dye-based FRET assay for BoNT/B activity, cells stably containing a BoNT/B VAMP-GFP substrate will be grown in 24-well tissue culture dishes, e.g., as described above in Example V, 2. Media will be replaced with 2 mL of fresh antibiotic-selective, serum-free media and cells will be incubated in a 37° C. incubator under 5% carbon dioxide fro approximately three day to induce differentiation. Differentiated cells will then be exposed to 1 nM of BoNT/B for 16 hours. BoNT/B-treated cells will then be incubated with 0 μM, 0.5 μM, 1.25 μM, 2.5 μM, 5.0 μM or 10 μM of a suitable lipophilic dye, e.g., as identified above in Example VI, 1, and FRET determined using the Typhoon 9140 software with excitation at 488 nm and emission collection at 610 nm+/−30 nm at 2 hours, 4 hours, 6 hours and 8 hours. The greatest difference in the FRET response between BoNT/B-treated cells and untreated cells will identify the appropriate dye concentrations and dye loading times useful to practice aspects of the present invention.

To determine more optimal lipophilic dye conditions for a lipophilic dye-based FRET assay for BoNT/C1 activity, cells stably containing a BoNT/C1 SNAP-GFP substrate will be grown in 24-well tissue culture dishes, e.g., as described above in Example V, 1. Media will be replaced with 2 mL of fresh antibiotic-selective, serum-free media and cells will be incubated in a 37° C. incubator under 5% carbon dioxide fro approximately three day to induce differentiation. Differentiated cells will then be exposed to 1 nM of BoNT/C1 for 16 hours. BoNT/C1-treated cells will then be incubated with 0 μM, 0.5 μM, 1.25 μM, 2.5 μM, 5.0 μM or 10 μM of a suitable lipophilic dye, e.g., as identified above in Example VI, 1, and FRET determined using the Typhoon 9140 software with excitation at 488 nm and emission collection at 610 nm+/−30 nm at 2 hours, 4 hours, 6 hours and 8 hours. The greatest difference in the FRET response between BoNT/C1-treated cells and untreated cells will identify the appropriate dye concentrations and dye loading times useful to practice aspects of the present invention.

To determine more optimal lipophilic dye conditions for a lipophilic dye-based FRET assay for BoNT/D activity, cells stably containing a BoNT/D VAMP-GFP substrate will be grown in 24-well tissue culture dishes, e.g., as described above in Example V, 2. Media will be replaced with 2 mL of fresh antibiotic-selective, serum-free media and cells will be incubated in a 37° C. incubator under 5% carbon dioxide fro approximately three day to induce differentiation. Differentiated cells will then be exposed to 1 nM of BoNT/D for 16 hours. BoNT/D-treated cells will then be incubated with 0 μM, 0.5 μM, 1.25 μM, 2.5 μM, 5.0 μM or 10 μM of a suitable lipophilic dye, e.g., as identified above in Example VI, 1, and FRET determined using the Typhoon 9140 software with excitation at 488 nm and emission collection at 610 nm+/−30 nm at 2 hours, 4 hours, 6 hours and 8 hours. The greatest difference in the FRET response between BoNT/D-treated cells and untreated cells will identify the appropriate dye concentrations and dye loading times useful to practice aspects of the present invention.

Figure 14A:
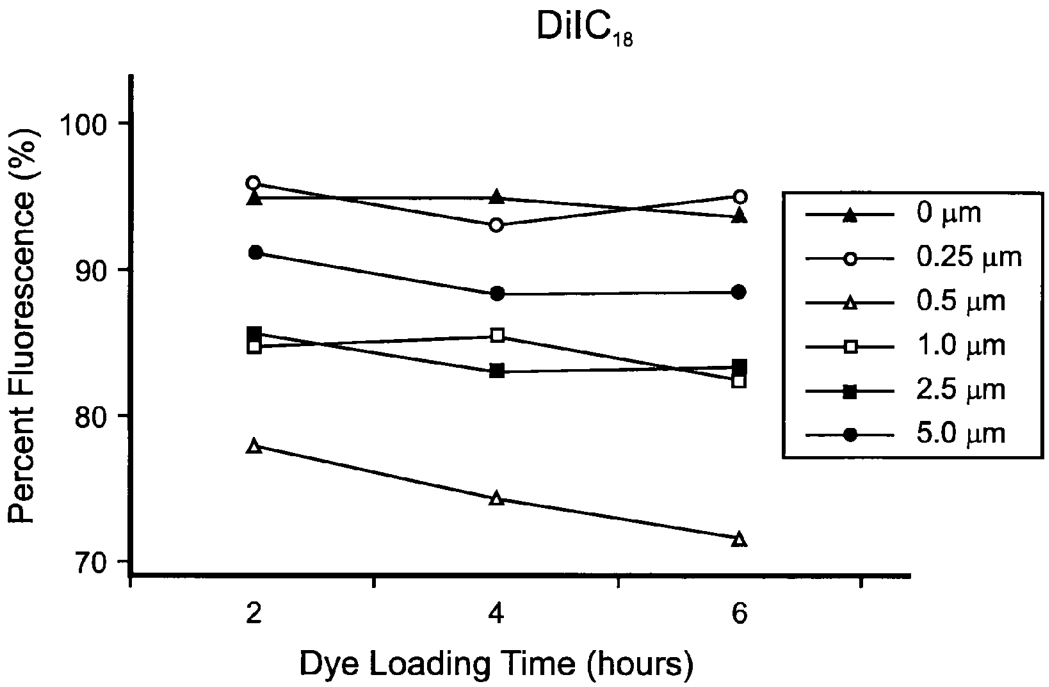
FIG. 14 shows the dose response of SH-SY5Y cells expressing SNAP$25_{206}$-GFP to the lipophilic dye DiI$C_{18}$(3) and the lipophilic cation dye octadecylrhodamine. Control cells and cells expressing SNAP$25_{206}$-GFP were exposed for up to six hours to concentrations of (14a) DiI$C_{18}$(3) or (14b) octadecylrhodamine. Following excitation at 488 nm, fluorescence emission at 610 nm was detected and quantitated using Typhoon 9140 software.
Figure 14B:
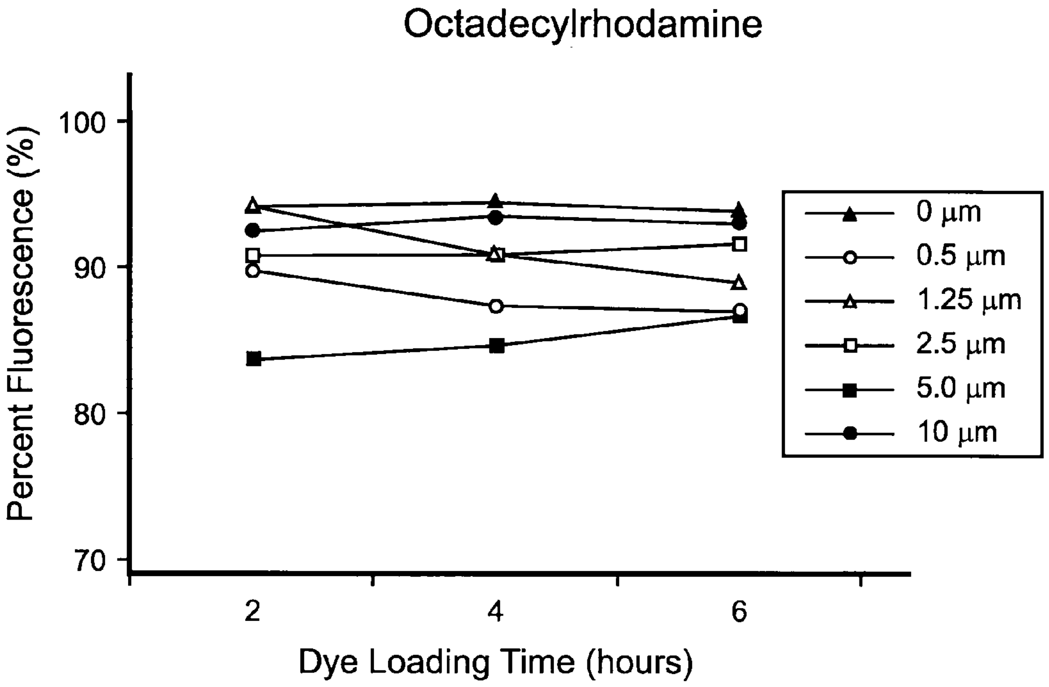

To determine more optimal lipophilic dye conditions for a lipophilic dye-based FRET assay for BoNT/E activity, approximately $2.5\times10^5$ SH-SY5Y cells stably containing a SNAP-$25_{206}$-GFP substrate were plated into each well of a 24-well tissue culture dish containing 2 mL of G418-selective, 1:1 EMEM and Ham's F12 Media (EMEM:F12), supplemented with 10% fetal bovine serum (FBS), 4 mM glutamine (Invitrogen, Inc, Carlsbad, Calif.), 1% sodium pyruvate (Invitrogen, Inc, Carlsbad, Calif.), 1.5 g/L sodium bicarbonate, 1× penicillin/streptomycin solution (Invitrogen, Inc, Carlsbad, Calif.) and 1×MEM non-essential amino acids solution (Invitrogen, Inc, Carlsbad, Calif.), and grown in a 37° C. incubator under 5% carbon dioxide overnight to allow for cell attachment. Media was replaced with 3 mL of fresh G418-selective, serum-free EMEM:F12 and cells were incubated in a 37° C. incubator under 5% carbon dioxide fro approximately three day to induce differentiation. Differentiated cells were then exposed to 100 nM of BoNT/E for approximately 18-24 hours. BoNT/E treated cells were then incubated with 0 μM, 0.25 μM, 0.5 μM, 1.0 μM, 2.5 μM or 5.0 μM of $DiIC_{18}(3)$ or octadecyl rhodamine B and FRET determined using the Typhoon 9140 software with excitation at 488 nm and emission collection at 610 nm+/−30 nm at 2 hours, 4 hours and 6 hours. The greatest difference between BoNT/E-treated SH-SY5Y cells and untreated SH-SY5Y cells occurred when the cells were incubated with 0.5 μM of $DiIC_{18}(3)$ for approximately 4 to 6 hours (FIG. 14*a*).

To determine more optimal lipophilic dye conditions for a lipophilic dye-based FRET assay for BoNT/F activity, cells stably containing a BoNT/F VAMP-GFP substrate will be grown in 24-well tissue culture dishes, e.g., as described above in Example V, 2. Media will be replaced with 2 mL of fresh antibiotic-selective, serum-free media and cells will be incubated in a 37° C. incubator under 5% carbon dioxide fro approximately three day to induce differentiation. Differentiated cells will then be exposed to 1 nM of BoNT/F for 16 hours. BoNT/F-treated cells will then be incubated with 0 μM, 0.5 μM, 1.25 μM, 2.5 μM, 5.0 μM or 10 μM of a suitable lipophilic dye, e.g., as identified above in Example VI, 1, and FRET determined using the Typhoon 9140 software with excitation at 488 nm and emission collection at 610 nm+/−30 nm at 2 hours, 4 hours, 6 hours and 8 hours. The greatest difference in the FRET response between BoNT/F-treated cells and untreated cells will identify the appropriate dye concentrations and dye loading times useful to practice aspects of the present invention.

To determine more optimal lipophilic dye conditions for a lipophilic dye-based FRET assay for BoNT/G activity, cells stably containing a BoNT/G VAMP-GFP substrate will be grown in 24-well tissue culture dishes, e.g., as described above in Example V, 2. Media will be replaced with 2 mL of fresh antibiotic-selective, serum-free media and cells will be incubated in a 37° C. incubator under 5% carbon dioxide fro approximately three day to induce differentiation. Differentiated cells will then be exposed to 1 nM of BoNT/G for 16 hours. BoNT/G-treated cells will then be incubated with 0 μM, 0.5 μM, 1.25 μM, 2.5 μM, 5.0 μM or 10 μM of a suitable lipophilic dye, e.g., as identified above in Example VI, 1, and FRET determined using the Typhoon 9140 software with excitation at 488 nm and emission collection at 610 nm+/−30 nm at 2 hours, 4 hours, 6 hours and 8 hours. The greatest difference in the FRET response between BoNT/G-treated cells and untreated cells will identify the appropriate dye concentrations and dye loading times useful to practice aspects of the present invention.

To determine more optimal lipophilic dye conditions for a lipophilic dye-based FRET assay for BoNT/F activity, cells stably containing a TeNT VAMP-GFP substrate will be grown in 24-well tissue culture dishes, e.g., as described above in Example V, 2. Media will be replaced with 2 mL of fresh antibiotic-selective, serum-free media and cells will be incubated in a 37° C. incubator under 5% carbon dioxide fro approximately three day to induce differentiation. Differentiated cells will then be exposed to 1 nM of TeNT for 16 hours. TeNT-treated cells will then be incubated with 0 μM, 0.5 μM, 1.25 μM, 2.5 μM, 5.0 μM or 10 μM of a suitable lipophilic dye, e.g., as identified above in Example VI, 1, and FRET determined using the Typhoon 9140 software with excitation at 488 nm and emission collection at 610 nm+/−30 nm at 2 hours, 4 hours, 6 hours and 8 hours. The greatest difference in the FRET response between TeNT-treated cells and untreated cells will identify the appropriate dye concentrations and dye loading times useful to practice aspects of the present invention.

The procedures outlined above can be used to more optimize the lipophilic dyes conditions for a lipophilic dye-based FRET assay for Clostridial toxin activity using lipophilic dyes as donor fluorophores in conjunction with fluorescent proteins as acceptors using, e.g., the conditions described above in Example VI, 1.

3. Optimizing Clostridial Toxin Conditions for Lipophilic Dye-Based FRET Assays

Different Clostridial toxin concentrations and different Clostridial toxin treatment times are evaluated in order to determine more optimal FRET conditions for a lipophilic dye-based FRET assay.

Figure 15A:
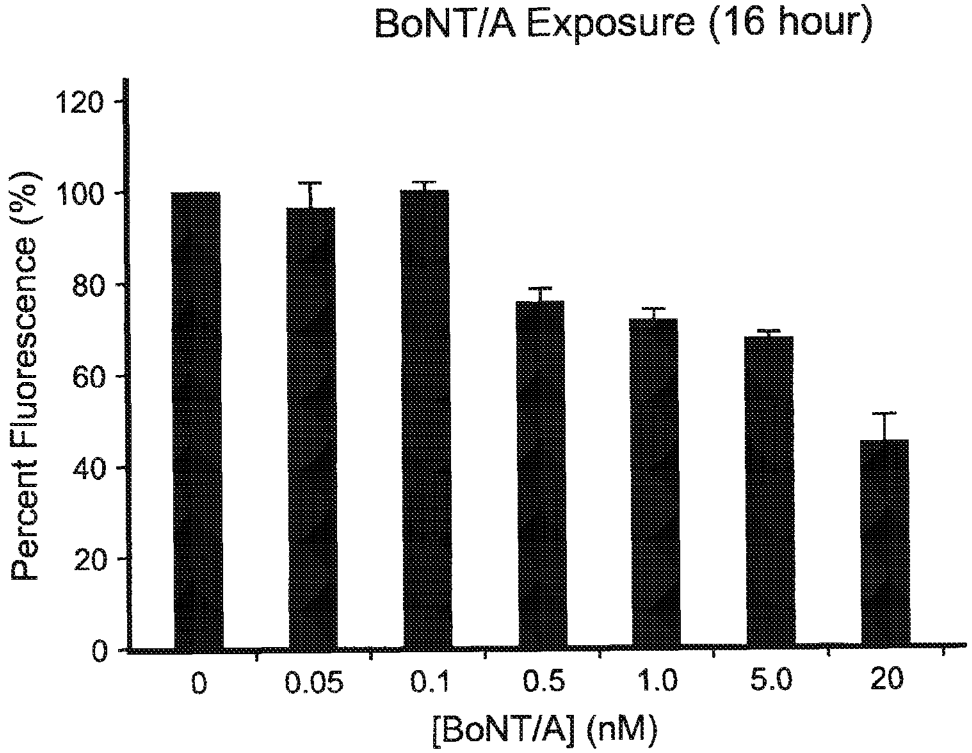
FIG. 15*a* shows the loss of FRET expressed after a 16 hour BoNT/A exposure as percentage of fluorescence measured at 610 nm of non-toxin treated cells stained with DiI$C_{18}$(3).
Figure 15B:
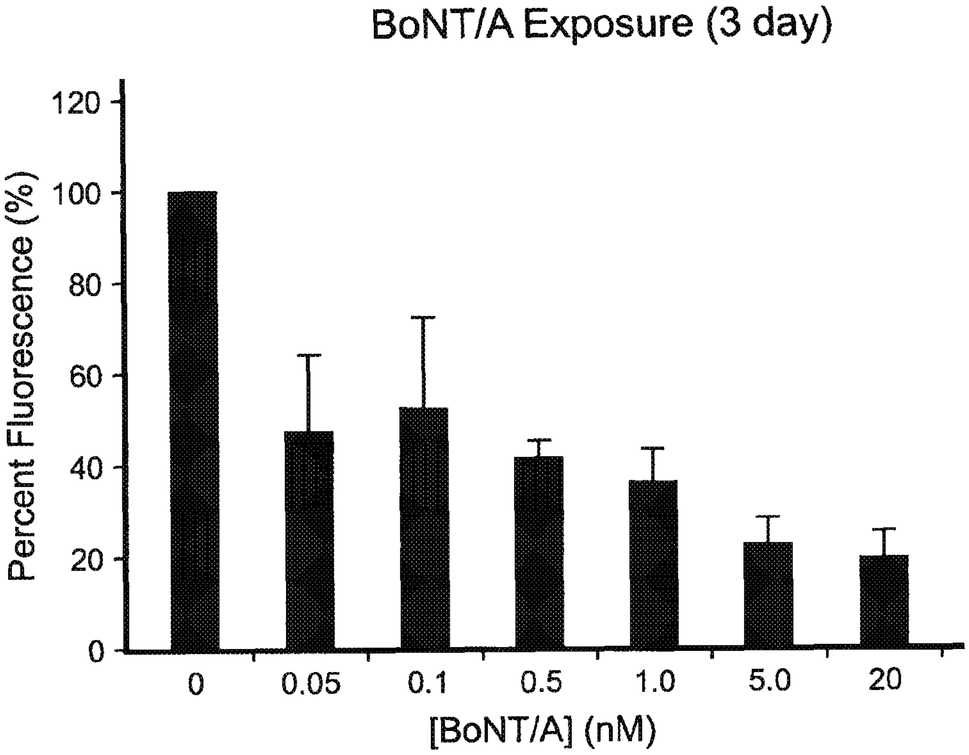
FIG. 15*b* shows the loss of FRET expressed after a 3 day BoNT/A exposure as percentage of fluorescence measured at 610 nm of non-toxin treated cells stained with DiI$C_{18}$(3).

To determine more optimal BoNT/A conditions for a lipophilic dye-based FRET assay, Neuro-2a cells stably containing a SNAP-$25_{206}$-GFP substrate were grown in 24-well tissue culture dishes and differentiated as described above in Example VI, 1. Differentiated cells were then exposed to a range of BoNT/A doses (0 nM, 0.05 nM, 0.1 nM, 0.5 nM, 1.0 nM, 5.0 nM and 20 nM) and incubated for a range of times (15 minutes, 1 hour, 16 hours and 3 days). BoNT/A-treated cells were incubated with 1.25 μM $DiIC_{18}(3)$ for 6 hours and FRET determined using the Typhoon 9140 software with excitation at 488 nm and emission collection at 610 nm+/−30 nm. A dose-response was seen in cells treated for 16 hours and for 3 days. For 16 hour treatments, a positive signal was detected with BoNT/A (150 KDa) concentrations as low as 0.5 nM (FIG. 15*a*). The three day treatments gave positive signals at BoNT/A concentrations as low as 0.05 nM (FIG. 15*b*).

To determine more optimal BoNT/B conditions for a lipophilic dye-based FRET assay, cells stably containing a BoNT/B VAMP-GFP substrate will be grown in 24-well tissue culture dishes and will be differentiated as described above in Example VI, 2. Differentiated cells will then be exposed to a range of BoNT/B doses (0 nM, 0.05 nM, 0.1 nM, 0.5 nM, 1.0 nM, 5.0 nM and 20 nM) and incubated for a range of times (15 minutes, 1 hour, 16 hours and 3 days). BoNT/B-treated cells will be incubated with a suitable lipophilic dye for an appropriate length of time, e.g., as described in Example VI, 2 and FRET will be determined using the Typhoon 9140 software with excitation at 488 nm and emission collection at 610 nm+/−30 nm. A dose-response will be generated and the appropriate BoNT/B concentration and treatment time will be determined.

To determine more optimal BoNT/C1 conditions for a lipophilic dye-based FRET assay, cells stably containing a BoNT/C1 SNAP-GFP substrate will be grown in 24-well tissue culture dishes and will be differentiated as described above in Example VI, 1. Differentiated cells will then be exposed to a range of BoNT/C1 doses (0 nM, 0.05 nM, 0.1 nM, 0.5 nM, 1.0 nM, 5.0 nM and 20 nM) and incubated for a range of times (15 minutes, 1 hour, 16 hours and 3 days). BoNT/C1-treated cells will be incubated with a suitable lipophilic dye for an appropriate length of time, e.g., as described in Example VI, 2 and FRET will be determined using the Typhoon 9140 software with excitation at 488 nm and emission collection at 610 nm+/−30 nm. A dose-response will be generated and the appropriate BoNT/C1 concentration and treatment time will be determined.

To determine more optimal BoNT/D conditions for a lipophilic dye-based FRET assay, cells stably containing a BoNT/D VAMP-GFP substrate will be grown in 24-well tissue culture dishes and will be differentiated as described above in Example VI, 2. Differentiated cells will then be exposed to a range of BoNT/D doses (0 nM, 0.05 nM, 0.1 nM, 0.5 nM, 1.0 nM, 5.0 nM and 20 nM) and incubated for a range of times (15 minutes, 1 hour, 16 hours and 3 days). BoNT/D-treated cells will be incubated with a suitable lipophilic dye for an appropriate length of time, e.g., as described in Example VI, 2 and FRET will be determined using the Typhoon 9140 software with excitation at 488 nm and emission collection at 610 nm+/−30 nm. A dose-response will be generated and the appropriate BoNT/D concentration and treatment time will be determined.

Figure 16:
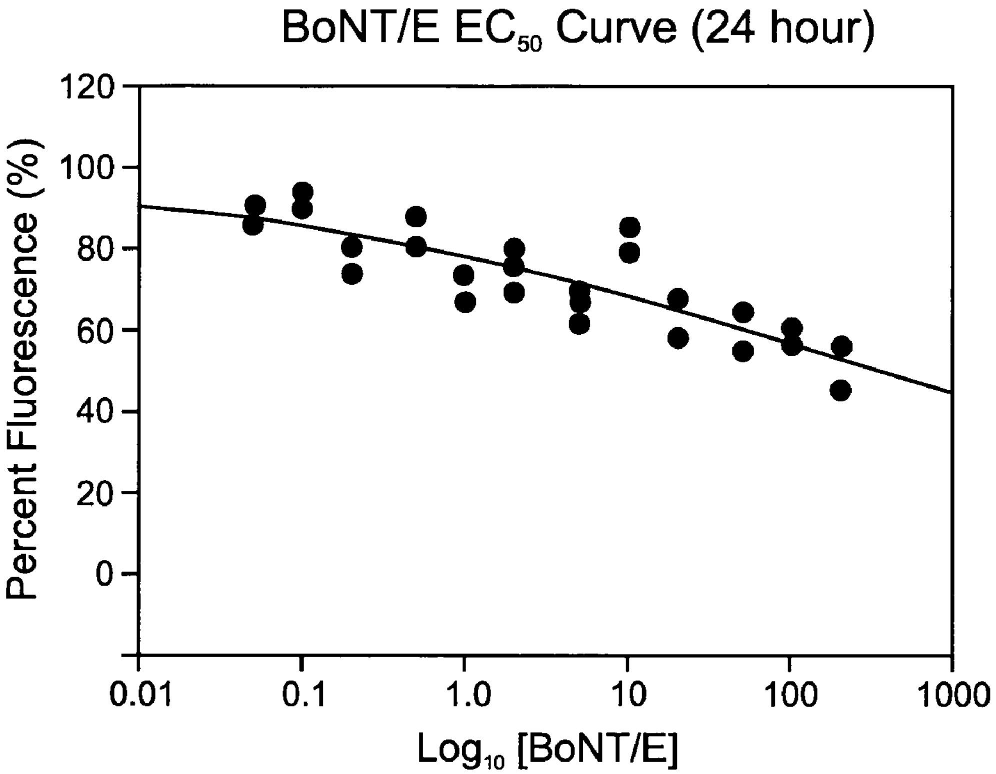
FIG. 16 shows the dose response of differentiated SH-SY5Y cells expressing SNAP$25_{206}$-GFP treated for 24 hours with BoNT/E di-chain at doses ranging from 0.005 nM to 200 nM and measured in the lipophilic dye-based FRET assay. The $EC_{50}$ curve was calculated using SigmaPlot/SigmaStat software.

To determine more optimal BoNT/E conditions for a lipophilic dye-based FRET assay, SH-SY5Y cells stably containing a SNAP-$25_{206}$-GFP substrate were grown in 24-well tissue culture dishes and differentiated as described above in Example VI, 1. Differentiated cells were then exposed to a range of BoNT/E doses (0 nM, 0.05 nM, 0.1 nM, 0.2 nM, 0.5 nM, 1.0 nM, 2.0 nM, 5.0 nM, 10 nM, 20 nM, 50 nM, 100 nM and 200 nM) and incubated for approximately 18-24 hours. BoNT/E-treated cells were incubated with 0.5 μM $DiIC_{18}(3)$ for 6 hours and FRET determined using the Typhoon 9140 software with excitation at 488 nm and emission collection at 610 nm+/−30 nm. A dose-response was seen in cells treated for 24 hours, and a positive signal was detected with BoNT/E (150 KDa) concentrations as low as 0.05 nM (FIG. 16).

To determine more optimal BoNT/F conditions for a lipophilic dye-based FRET assay, cells stably containing a BoNT/F VAMP-GFP substrate will be grown in 24-well tissue culture dishes and will be differentiated as described above in Example VI, 2. Differentiated cells will then be exposed to a range of BoNT/F doses (0 nM, 0.05 nM, 0.1 nM, 0.5 nM, 1.0 nM, 5.0 nM and 20 nM) and incubated for a range of times (15 minutes, 1 hour, 16 hours and 3 days). BoNT/F-treated cells will be incubated with a suitable lipophilic dye for an appropriate length of time, e.g., as described in Example VI, 2 and FRET will be determined using the Typhoon 9140 software with excitation at 488 nm and emission collection at 610 nm+/−30 nm. A dose-response will be generated and the appropriate BoNT/F concentration and treatment time will be determined.

To determine more optimal BoNT/G conditions for a lipophilic dye-based FRET assay, cells stably containing a BoNT/G VAMP-GFP substrate will be grown in 24-well tissue culture dishes and will be differentiated as described above in Example VI, 2. Differentiated cells will then be exposed to a range of BoNT/G doses (0 nM, 0.05 nM, 0.1 nM, 0.5 nM, 1.0 nM, 5.0 nM and 20 nM) and incubated for a range of times (15 minutes, 1 hour, 16 hours and 3 days). BoNT/G-treated cells will be incubated with a suitable lipophilic dye for an appropriate length of time, e.g., as described in Example VI, 2 and FRET will be determined using the Typhoon 9140 software with excitation at 488 nm and emission collection at 610 nm+/−30 nm. A dose-response will be generated and the appropriate BoNT/G concentration and treatment time will be determined.

To determine more optimal TeNT conditions for a lipophilic dye-based FRET assay, cells stably containing a TeNT VAMP-GFP substrate will be grown in 24-well tissue culture dishes and will be differentiated as described above in Example VI, 2. Differentiated cells will then be exposed to a range of TeNT doses (0 nM, 0.05 nM, 0.1 nM, 0.5 nM, 1.0 nM, 5.0 nM and 20 nM) and incubated for a range of times (15 minutes, 1 hour, 16 hours and 3 days). TeNT-treated cells will be incubated with a suitable lipophilic dye for an appropriate length of time, e.g., as described in Example VI, 2 and FRET will be determined using the Typhoon 9140 software with excitation at 488 nm and emission collection at 610 nm+/−30 nm. A dose-response will be generated and the appropriate TeNT concentration and treatment time will be determined.

The procedures outlined above can be used to more optimize the Clostridial toxin conditions for a lipophilic dye-based FRET assay based on lipophilic dyes as donor fluorophores in conjunction with fluorescent proteins as acceptors using, e.g., the conditions described above in Example VI, 1.

4. Optimizing Culture Plate Conditions for Lipophilic Dye-Based FRET Assays

Figure 17A:
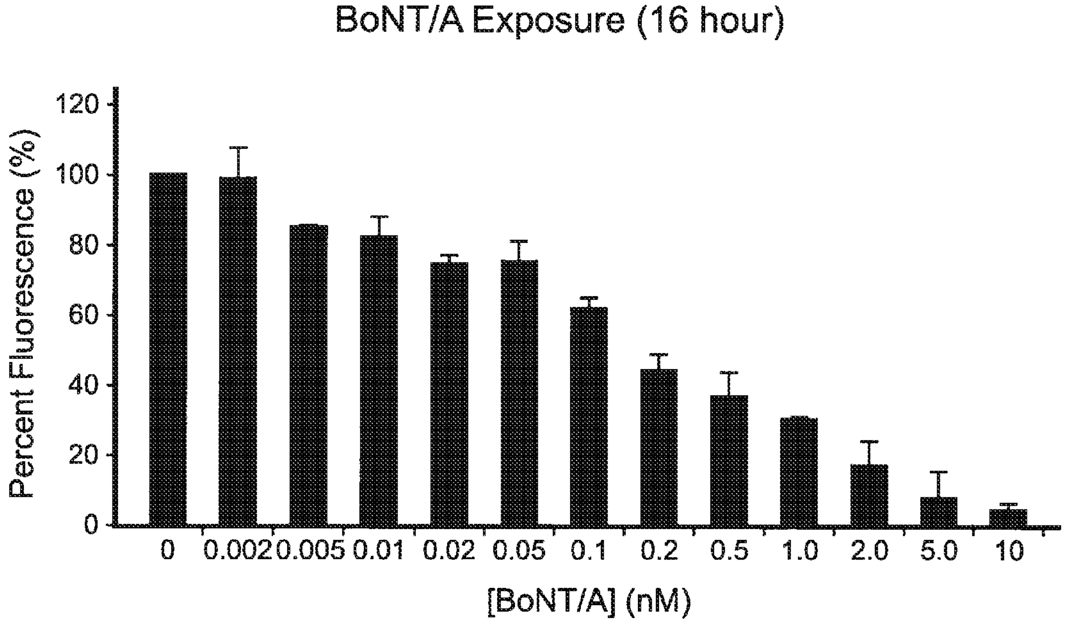
FIG. 17*a* shows the dose response of Neuro-2A cells expressing SNAP$25_{206}$-GFP treated overnight with BoNT/A at doses ranging from 0.002 nM to 10 nM and measured in the lipophilic dye-based FRET assay.
Figure 17B:
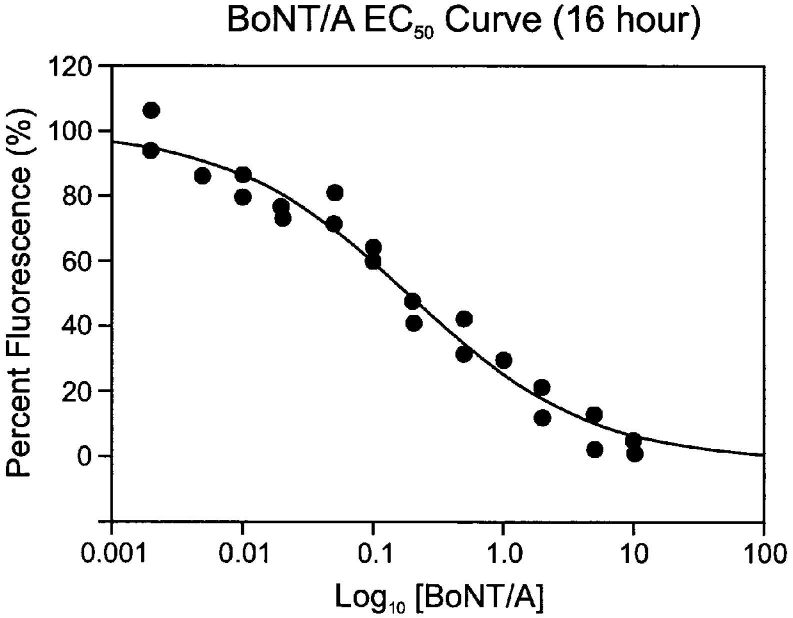
FIG. 17*b* shows an $EC_{50}$ curve calculated with the data from FIG. 17*a* using SigmaPlot/SigmaStat software.
Figure 18A:
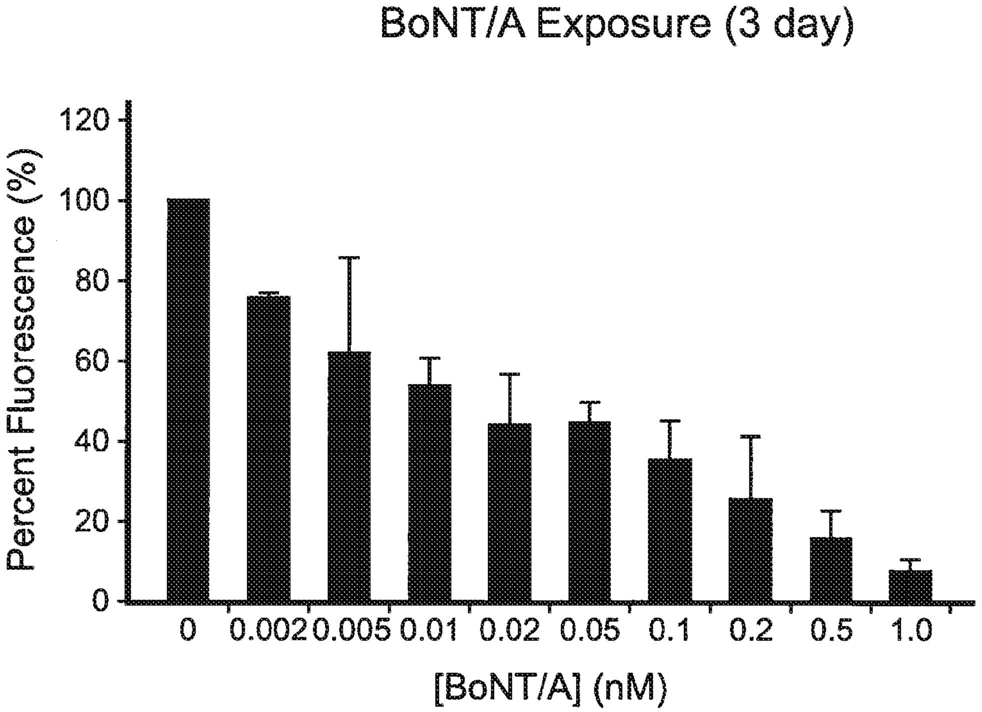
FIG. 18*a* shows the dose response of Neuro-2A cells expressing SNAP$25_{206}$-GFP treated for three days with BoNT/A at doses ranging from 0.002 nM to 10 nM and measured in the lipophilic dye-based FRET assay.
Figure 18B:
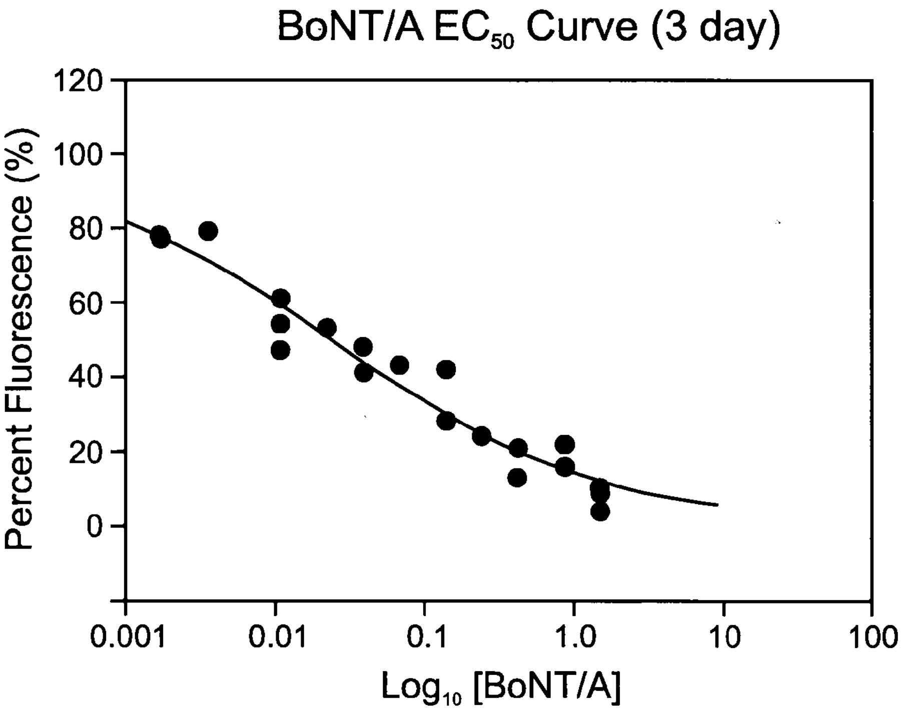
FIG. 18*b* shows an $EC_{50}$ curve calculated with the data from FIG. 18*a* using SigmaPlot/SigmaStat software.

To determine more optimal FRET conditions for a lipophilic dye-based FRET assay, black tissue culture plates with clear bottoms were evaluated. Neuro-2a cells stably containing a SNAP-25206-GFP substrate were grown in 24-well tissue culture dishes and differentiated as described above in Example VI, 1, with the exception that 24-well black tissue culture plates with clear bottoms were used instead of clear plastic 24-well tissue culture plates. Differentiated cells were then exposed to a range of BoNT/A doses (0 nM, 0.002 nM, 0.005 nM, 0.01 nM, 0.02 nM, 0.05 nM, 0.1 nM, 0.2 nM, 0.5 nM, 1.0 nM, 2.0 nM, 5.0 nM and 10 nM) and incubated for either about 16 hours or 3 days. BoNT/A-treated cells were incubated with 1.25 μM $DiIC_{18}(3)$ for 6 hours and FRET determined using the Typhoon 9140 software with excitation at 488 nm and emission collection at 610 nm±30 nm. The use of black tissue culture plates reduced assay to assay variability resulting in a much cleaner. For 16 hour treatments, a positive signal was detected with BoNT/A (150 KDa) concentrations as low as 0.005 nM (see FIG. 17*a*), an increased sensitivity of approximately 100-fold compared to results obtained from clear plastic tissue culture plates (compare FIG. 15*a* with FIG. 17*a*). For 3 day treatments, a positive signal was detected with BoNT/A (150 KDa) concentrations as low as 0.002 nM (FIG. 18*a*), and overall increased sensitivity of the assay was detected at all concentrations used relative to the 16 hour treatment (compare FIG. 17*a* with FIG. 18*a*).

The procedures outlined above can be used to more optimize the FRET conditions for a lipophilic dye-based FRET assay based on lipophilic dyes as donor fluorophores in conjunction with fluorescent proteins as acceptors using, e.g., the conditions described above in Example VI, 1.

Example VII

Lipophilic Dye-Based FRET Assays for Clostridial Activity

1. Lipophilic Dye-Based FRET Assay for BoNT/A Activity

1a. Lipophilic Dye-Based FRET Assay for BoNT/A Activity in a BOTOX® Product

To conduct a lipophilic dye-based FRET assay for BoNT/A activity using a formulated botulinum neurotoxin product such as, e.g., a BOTOX® product, differentiated Neuro-2A cells stably expressing a BoNT/A $SNAP25_{206}$-GFP substrate were grown and differentiated in 24-well black tissue culture plates with clear bottoms as described above in Examples VI, 1d. A standard curve was obtained by treating differentiated Neuro-2A cells with 0.001 nM, 0.002 nM, 0.005 nM, 0.01 nM, 0.02 nM or 0.05 nM of Pure A (BTX-540; Metabiologics, Inc., Madison, Wis.), with each of the concentrations run in triplicates. Simultaneously, separate wells in the same plate were treated with three separate vials of BOTOX® dissolved in 1 ml of complete EMEM media to a final concentration of approximately 5.5 μM. Cells in three replicate wells were treated with the contents of each resuspended BOTOX® vial. BoNT/A-treated cells were incubated with 1.25 μM $DiIC_{18}(3)$ for 6 hours and FRET determined using the Typhoon 9140 software with excitation at 488 nm and emission collection at 610 nm±30 nm. The emissions at each concentration of Pure A and each BOTOX® sample were calculated as a percentage of the untreated control (fluorescence measured at 610 nm±30 nm of non-toxin treated cells). The experimentally-derived BOTOX® concentration for each vial was extrapolated from the Pure A concentration curve using the value calculated from an average of three replicate wells. Calculated average values for the three vials were 6.3 μM, 9.0 μM and 17.7 μM, with the average for each of the three vials of BOTOX® calculated to be 11.0 μM. These results demonstrate that Clostridial toxin activity such as, e.g., BoNT/A activity from formulated products such as BOTOX®, can be detected using a FRET assay in which a lipophilic dye incorporated into a membrane acts as the FRET acceptor.

1b. Lipophilic Dye-Based FRET Assay for BoNT/A Activity in a Food Sample

To conduct a lipophilic dye-based FRET assay for BoNT/A activity using a food sample such as, e.g., a processed food sample, differentiated Neuro-2A cells stably expressing a BoNT/A $SNAP25_{206}$-GFP substrate will be grown and differentiated in 24-well black tissue culture plates with clear bottoms as described above in Examples VI, 1d. A standard curve will be obtained by treating Neuro-2A cells with 0.001, 0.002, 0.005, 0.01, 0.02 or 0.05 nM of Pure A (BTX-540; Metabiologics, Inc., Madison, Wis.), with each of the concentrations run in triplicates. Simultaneously, separate wells in the same plate will be treated with a processed food sample from vials of BOTOX® diluted in 1 ml of complete EMEM media. Cells in three replicate wells will be treated with the contents of each diluted sample. BoNT/A-treated cells will be incubated with 1.25 μM $DiIC_{18}(3)$ for 6 hours and FRET will be determined using the Typhoon 9140 software with excitation at 488 nm and emission collection at 610 nm±30 nm. The emissions at each concentration of Pure A and each processed food sample will be calculated as a percentage of the untreated control (fluorescence measured at 610 nm±30 nm of non-toxin treated cells). The experimentally derived concentration of BoNT/A present in the processed food sample will be extrapolated from the Pure A concentration curve using the value calculated from an average of three replicate wells.

2. Lipophilic Dye-Based FRET Assay for BoNT/B Activity

2a. Lipophilic Dye-Based FRET Assay for BoNT/B Activity in a Formulated BoNT/B Product To conduct a lipophilic dye-based FRET assay for BoNT/B activity using a formulated botulinum neurotoxin product such as, e.g., a formulated BoNT/B product, cells expressing a BoNT/B VAMP-GFP substrate will be grown and differentiated in 24-well black tissue culture plates with clear bottoms using methods known in the art, for example, using one of the methods as described above in Examples IV, 2 and V, 2. A standard curve will be obtained by treating cells with 0.001 nM, 0.002 nM, 0.005 nM, 0.01 nM, 0.02 nM or 0.05 nM of BoNT/B (Metabiologics, Inc., Madison, Wis.), with each of the concentrations run in triplicates. Simultaneously, separate wells in the same plate will be treated with formulated BoNT/B dissolved in 1 ml of complete culture media to a final concentration of approximately 0.0055 nM. Cells in three replicate wells will be treated with the contents of each resuspended formulated BoNT/B vial. BoNT/B-treated cells will be incubated with a suitable lipophilic dye for an appropriate length of time, e.g., as described in Example VI, 2 and FRET will be determined using the Typhoon 9140 software with excitation at 488 nm and emission collection at 610 nm±30 nm. The emissions at each concentration of BoNT/B and each formulated BoNT/B sample will be calculated as a percentage of the untreated control (fluorescence measured at 610 nm±30 nm of non-toxin treated cells). The experimentally-derived concentration of formulated BoNT/B for each vial will be extrapolated from the BoNT/B concentration curve using the value calculated from an average of three replicate wells.

2b. Lipophilic Dye-Based FRET Assay for BoNT/B Activity in a Food Sample

To conduct a lipophilic dye-based FRET assay for BoNT/B activity using a food sample such as, e.g., a processed food sample, cells expressing a BoNT/B VAMP-GFP substrate will be grown and differentiated in 24-well black tissue culture plates with clear bottoms using methods known in the art, for example, using one of the methods as described above in Examples IV, 2 and V, 2. A standard curve will be obtained by treating cells with 0.001, 0.002, 0.005, 0.01, 0.02 or 0.05 nM of BoNT/B (Metabiologics, Inc., Madison, Wis.), with each of the concentrations run in triplicates. Simultaneously, separate wells in the same plate will be treated with a processed food sample from vials of formulated BoNT/B diluted in 1 ml of complete culture media. Cells in three replicate wells will be treated with the contents of each diluted sample. BoNT/B-treated cells will be incubated with a suitable lipophilic dye for an appropriate length of time, e.g., as described in Example VI, 2 and FRET will be determined using the Typhoon 9140 software with excitation at 488 nm and emission collection at 610 nm±30 nm. The emissions at each concentration of BoNT/B and each processed food sample will be calculated as a percentage of the untreated control (fluorescence measured at 610 nm±30 nm of non-toxin treated cells). The experimentally derived concentration of BoNT/B present in the processed food sample will be extrapolated from the BoNT/B concentration curve using the value calculated from an average of three replicate wells.

3. Lipophilic Dye-Based FRET Assay for BoNT/C1 Activity

3a. Lipophilic Dye-Based FRET Assay for BoNT/C1 Activity in a Formulated BoNT/C1 Product To conduct a lipophilic dye-based FRET assay for BoNT/C1 activity using a formulated botulinum neurotoxin product such as, e.g., a formulated BoNT/C1 product, cells expressing a BoNT/C1 SNAP-$25_{206}$-GFP substrate or a BoNT/C1 Syntaxin-GFP substrate will be grown and differentiated in 24-well black tissue culture plates with clear bottoms using methods known in the art, for example, using one of the methods as described above in Examples IV, 3 and V, 3. A standard curve will be obtained by treating cells with 0.001 nM, 0.002 nM, 0.005 nM, 0.01 nM, 0.02 nM or 0.05 nM of BoNT/C1 (Metabiologics, Inc., Madison, Wis.), with each of the concentrations run in triplicates in a 24 well plate. Simultaneously, separate wells in the same plate will be treated with formulated BoNT/C1 dissolved in 1 ml of complete culture media to a final concentration of approximately 0.0055 nM. Cells in three replicate wells will be treated with the contents of each resuspended formulated BoNT/C1 vial. BoNT/C1-treated cells will be incubated with a suitable lipophilic dye for an appropriate length of time, e.g., as described in Example VI, 2 and FRET will be determined using the Typhoon 9140 software with excitation at 488 nm and emission collection at 610 nm+30 nm. The emissions at each concentration of BoNT/C1 and each formulated BoNT/C1 sample will be calculated as a percentage of the untreated control (fluorescence measured at 610 nm+30 nm of non-toxin treated cells). The experimentally-derived concentration of formulated BoNT/C1 for each vial will be extrapolated from the BoNT/C1 concentration curve using the value calculated from an average of three replicate wells.

3b. Lipophilic Dye-Based FRET Assay for BoNT/C1 Activity in a Food Sample

To conduct a lipophilic dye-based FRET assay for BoNT/C1 activity using a food sample such as, e.g., a processed food sample, cells expressing a BoNT/C1 Syntaxin-GFP substrate will be grown and differentiated in 24-well black tissue culture plates with clear bottoms using methods known in the art, for example, using one of the methods as described above in Examples IV, 3 and V, 3. A standard curve will be obtained by treating cells with 0.001, 0.002, 0.005, 0.01, 0.02 or 0.05 nM of BoNT/C1 (Metabiologics, Inc., Madison, Wis.), with each of the concentrations run in triplicates in a 24 well plate. Simultaneously, separate wells in the same plate will be treated with a processed food sample from vials of formulated BoNT/C1 diluted in 1 ml of complete culture media. Cells in three replicate wells will be treated with the contents of each diluted sample. BoNT/C1-treated cells will be incubated with a suitable lipophilic dye for an appropriate length of time, e.g., as described in Example VI, 2 and FRET will be determined using the Typhoon 9140 software with excitation at 488 nm and emission collection at 610 nm±30 nm. The emissions at each concentration of BoNT/C1 and each processed food sample will be calculated as a percentage of the untreated control (fluorescence measured at 610 nm±30 nm of non-toxin treated cells). The experimentally derived concentration of BoNT/C1 present in the processed food sample will be extrapolated from the BoNT/C1 concentration curve using the value calculated from an average of three replicate wells.

4. Lipophilic Dye-Based FRET Assay for BoNT/D Activity

4a. Lipophilic Dye-Based FRET Assay for BoNT/D Activity in a Formulated BoNT/D Product To conduct a lipophilic dye-based FRET assay for BoNT/D activity using a formulated botulinum neurotoxin product such as, e.g., a formulated BoNT/D product, cells expressing a BoNT/D VAMP-GFP substrate will be grown and differentiated in 24-well black tissue culture plates with clear bottoms using methods known in the art, for example, using one of the methods as described above in Examples IV, 4 and V, 4. A standard curve will be obtained by treating cells with 0.001 nM, 0.002 nM, 0.005 nM, 0.01 nM, 0.02 nM or 0.05 nM of BoNT/D (Metabiologics, Inc., Madison, Wis.), with each of the concentrations run in triplicates in a 24 well plate. Simultaneously, separate wells in the same plate will be treated with formulated BoNT/D dissolved in 1 ml of complete culture media to a final concentration of approximately 0.0055 nM. Cells in three replicate wells will be treated with the contents of each resuspended formulated BoNT/D vial. BoNT/D-treated cells will be incubated with a suitable lipophilic dye for an appropriate length of time, e.g., as described in Example VI, 2 and FRET will be determined using the Typhoon 9140 software with excitation at 488 nm and emission collection at 610 nm±30 nm. The emissions at each concentration of BoNT/D and each formulated BoNT/D sample will be calculated as a percentage of the untreated control (fluorescence measured at 610 nm±30 nm of non-toxin treated cells). The experimentally-derived concentration of formulated BoNT/D for each vial will be extrapolated from the BoNT/D concentration curve using the value calculated from an average of three replicate wells.

4b. Lipophilic Dye-Based FRET Assay for BoNT/D Activity in a Food Sample

To conduct a lipophilic dye-based FRET assay for BoNT/D activity using a food sample such as, e.g., a processed food sample, cells expressing a BoNT/D VAMP-GFP substrate will be grown and differentiated in 24-well black tissue culture plates with clear bottoms using methods known in the art, for example, using one of the methods as described above in Examples IV, 4 and V, 4. A standard curve will be obtained by treating cells with 0.001, 0.002, 0.005, 0.01, 0.02 or 0.05 nM of BoNT/D (Metabiologics, Inc., Madison, Wis.), with each of the concentrations run in triplicates in a 24 well plate. Simultaneously, separate wells in the same plate will be treated with a processed food sample from vials of formulated BoNT/D diluted in 1 ml of complete culture media. Cells in three replicate wells will be treated with the contents of each diluted sample. BoNT/D-treated cells will be incubated with a suitable lipophilic dye for an appropriate length of time, e.g., as described in Example VI, 2 and FRET will be determined using the Typhoon 9140 software with excitation at 488 nm and emission collection at 610 nm±30 nm. The emissions at each concentration of BoNT/D and each processed food sample will be calculated as a percentage of the untreated control (fluorescence measured at 610 nm±30 nm of non-toxin treated cells). The experimentally derived concentration of BoNT/D present in the processed food sample will be extrapolated from the BoNT/D concentration curve using the value calculated from an average of three replicate wells.

5. Lipophilic Dye-Based FRET Assay for BoNT/E Activity

5a. Lipophilic Dye-Based FRET Assay for BoNT/E Activity in a Formulated BoNT/E Product To conduct a BoNT/E activity assay using a formulated botulinum neurotoxin product such as, e.g., a formulated BoNT/E product, differentiated SK-N-DZ cells expressing a BoNT/E $SNAP25_{206}$-GFP substrate will be grown and differentiated in 24-well black tissue culture plates with clear bottoms using methods known in the art, for example, using one of the methods as described above in Examples IV, 5 and V, 5. A standard curve will be obtained by treating SK-N-DZ cells with 0.001 nM, 0.002 nM, 0.005 nM, 0.01 nM, 0.02 nM or 0.05 nM of BoNT/E (Metabiologics, Inc., Madison, Wis.), with each of the concentrations run in triplicates in a 24 well plate. Simultaneously, separate wells in the same plate will be treated with formulated BoNT/E dissolved in 1 ml of complete DMEM media to a final concentration of approximately 0.0055 nM. Cells in three replicate wells will be treated with the contents of each resuspended formulated BoNT/E vial. BoNT/E-treated cells will be incubated with a suitable lipophilic dye for an appropriate length of time, e.g., as described in Example VI, 2 and FRET will be determined using the Typhoon 9140 software with excitation at 488 nm and emission collection at 610 nm±30 nm. The emissions at each concentration of BoNT/E and each formulated BoNT/E sample will be calculated as a percentage of the untreated control (fluorescence measured at 610 nm±30 nm of non-toxin treated cells). The experimentally-derived concentration of formulated BoNT/E for each vial will be extrapolated from the BoNT/E concentration curve using the value calculated from an average of three replicate wells.

5b. Lipophilic Dye-Based FRET Assay for BoNT/E Activity in a Food Sample

To conduct a BoNT/E activity assay using a food sample such as, e.g., a processed food sample, differentiated SK-N-DZ cells expressing a BoNT/E $SNAP25_{206}$-GFP substrate will be grown and differentiated in 24-well black tissue culture plates with clear bottoms using methods known in the art, for example, using one of the methods as described above in Examples IV, 5 and V, 5. A standard curve will be obtained by treating SK-N-DZ cells with 0.001, 0.002, 0.005, 0.01, 0.02 or 0.05 nM of BoNT/E (Metabiologics, Inc., Madison, Wis.), with each of the concentrations run in triplicates in a 24 well plate. Simultaneously, separate wells in the same plate will be treated with a processed food sample from vials of formulated BoNT/E diluted in 1 ml of complete DMEM media. Cells in three replicate wells will be treated with the contents of each diluted sample. BoNT/E-treated cells will be incubated with a suitable lipophilic dye for an appropriate length of time, e.g., as described in Example VI, 2 and FRET will be determined using the Typhoon 9140 software with excitation at 488 nm and emission collection at 610 nm±30 nm. The emissions at each concentration of BoNT/E and each processed food sample will be calculated as a percentage of the untreated control (fluorescence measured at 610 nm+30 nm of non-toxin treated cells). The experimentally derived concentration of BoNT/E present in the processed food sample will be extrapolated from the BoNT/E concentration curve using the value calculated from an average of three replicate wells.

6. Lipophilic Dye-Based FRET Assay for BoNT/F Activity

6a. Lipophilic Dye-Based FRET Assay for BoNT/F Activity in a Formulated BoNT/F Product To conduct a BoNT/F activity assay using a formulated botulinum neurotoxin product such as, e.g., a formulated BoNT/F product, cells expressing a BoNT/F VAMP-GFP substrate will be grown and differentiated in 24-well black tissue culture plates with clear bottoms using methods known in the art, for example, using one of the methods as described above in Examples IV, 6 and V, 6. A standard curve will be obtained by treating cells with 0.001 nM, 0.002 nM, 0.005 nM, 0.01 nM, 0.02 nM or 0.05 nM of BoNT/F (Metabiologics, Inc., Madison, Wis.), with each of the concentrations run in triplicates in a 24 well plate. Simultaneously, separate wells in the same plate will be treated with formulated BoNT/F dissolved in 1 ml of complete culture media to a final concentration of approximately 0.0055 nM. Cells in three replicate wells will be treated with the contents of each resuspended formulated BoNT/F vial. BoNT/F-treated cells will be incubated with a suitable lipophilic dye for an appropriate length of time, e.g., as described in Example VI, 2 and FRET will be determined using the Typhoon 9140 software with excitation at 488 nm and emission collection at 610 nm±30 nm. The emissions at each concentration of BoNT/F and each formulated BoNT/F sample will be calculated as a percentage of the untreated control (fluorescence measured at 610 nm±30 nm of non-toxin treated cells). The experimentally-derived concentration of formulated BoNT/F for each vial will be extrapolated from the BoNT/F concentration curve using the value calculated from an average of three replicate wells.

6b. Lipophilic Dye-Based FRET Assay for BoNT/F Activity in a Food Sample

To conduct a BoNT/F activity assay using a food sample such as, e.g., a processed food sample, cells expressing a BoNT/F VAMP-GFP substrate will be grown and differentiated in 24-well black tissue culture plates with clear bottoms using methods known in the art, for example, using one of the methods as described above in Examples IV, 6 and V, 6. A standard curve will be obtained by treating cells with 0.001, 0.002, 0.005, 0.01, 0.02 or 0.05 nM of BoNT/F (Metabiologics, Inc., Madison, Wis.), with each of the concentrations run in triplicates in a 24 well plate. Simultaneously, separate wells in the same plate will be treated with a processed food sample from vials of formulated BoNT/F diluted in 1 ml of complete culture media. Cells in three replicate wells will be treated with the contents of each diluted sample. BoNT/F-treated cells will be incubated with a suitable lipophilic dye for an appropriate length of time, e.g., as described in Example VI, 2 and FRET will be determined using the Typhoon 9140 software with excitation at 488 nm and emission collection at 610 nm±30 nm. The emissions at each concentration of BoNT/F and each processed food sample will be calculated as a percentage of the untreated control (fluorescence measured at 610 nm±30 nm of non-toxin treated cells). The experimentally derived concentration of BoNT/F present in the processed food sample will be extrapolated from the BoNT/F concentration curve using the value calculated from an average of three replicate wells.

7. Lipophilic Dye-Based FRET Assay for BoNT/G Activity

7a. Lipophilic Dye-Based FRET Assay for BoNT/G Activity in a Formulated BoNT/G Product To conduct a BoNT/G activity assay using a formulated botulinum neurotoxin product such as, e.g., a formulated BoNT/G product, cells expressing a BoNT/G VAMP-GFP s substrate will be grown and differentiated in 24-well black tissue culture plates with clear bottoms using methods known in the art, for example, using one of the methods as described above in Examples IV, 7 and V, 7. A standard curve will be obtained by treating cells with 0.001 nM, 0.002 nM, 0.005 nM, 0.01 nM, 0.02 nM or 0.05 nM of BoNT/B (Metabiologics, Inc., Madison, Wis.), with each of the concentrations run in triplicates in a 24 well plate. Simultaneously, separate wells in the same plate will be treated with formulated BoNT/G dissolved in 1 ml of complete culture media to a final concentration of approximately 0.0055 nM. Cells in three replicate wells will be treated with the contents of each resuspended formulated BoNT/G vial. BoNT/G-treated cells will be incubated with a suitable lipophilic dye for an appropriate length of time, e.g., as described in Example VI, 2 and FRET will be determined using the Typhoon 9140 software with excitation at 488 nm and emission collection at 610 nm±30 nm. The emissions at each concentration of BoNT/G and each formulated BoNT/G sample will be calculated as a percentage of the untreated control (fluorescence measured at 610 nm±30 nm of non-toxin treated cells). The experimentally-derived concentration of formulated BoNT/G for each vial will be extrapolated from the BoNT/G concentration curve using the value calculated from an average of three replicate wells.

7b. Lipophilic Dye-Based FRET Assay for BoNT/G Activity in a Food Sample

To conduct a BoNT/G activity assay using a food sample such as, e.g., a processed food sample, cells expressing a BoNT/G VAMP-GFP substrate will be grown and differentiated in 24-well black tissue culture plates with clear bottoms using methods known in the art, for example, using one of the methods as described above in Examples IV, 7 and V, 7. A standard curve will be obtained by treating cells with 0.001, 0.002, 0.005, 0.01, 0.02 or 0.05 nM of BoNT/G (Metabiologics, Inc., Madison, Wis.), with each of the concentrations run in triplicates in a 24 well plate. Simultaneously, separate wells in the same plate will be treated with a processed food sample from vials of formulated BoNT/G diluted in 1 ml of complete culture media. Cells in three replicate wells will be treated with the contents of each diluted sample. BoNT/G-treated cells will be incubated with a suitable lipophilic dye for an appropriate length of time, e.g., as described in Example VI, 2 and FRET will be determined using the Typhoon 9140 software with excitation at 488 nm and emission collection at 610 nm+30 nm. The emissions at each concentration of BoNT/G and each processed food sample will be calculated as a percentage of the untreated control (fluorescence measured at 610 nm+30 nm of non-toxin treated cells). The experimentally derived concentration of BoNT/G present in the processed food sample will be extrapolated from the BoNT/G concentration curve using the value calculated from an average of three replicate wells.

8. Lipophilic Dye-Based FRET Assay for TeNT Activity

8a. Lipophilic Dye-Based FRET Assay for TeNT Activity in a Formulated TeNT Product To conduct a TeNT activity assay using a formulated botulinum neurotoxin product such as, e.g., a formulated TeNT product, cells expressing a TeNT VAMP-GFP substrate will be grown and differentiated in 24-well black tissue culture plates with clear bottoms using methods known in the art, for example, using one of the methods as described above in Examples IV, 8 and V, 8. A standard curve will be obtained by treating cells with 0.001 nM, 0.002 nM, 0.005 nM, 0.01 nM, 0.02 nM or 0.05 nM of TeNT (Metabiologics, Inc., Madison, Wis.), with each of the concentrations run in triplicates in a 24 well plate. Simultaneously, separate wells in the same plate will be treated with formulated TeNT dissolved in 1 ml of complete culture media to a final concentration of approximately 0.0055 nM. Cells in three replicate wells will be treated with the contents of each resuspended formulated TeNT vial. TeNT-treated cells will be incubated with a suitable lipophilic dye for an appropriate length of time, e.g., as described in Example VI, 2 and FRET will be determined using the Typhoon 9140 software with excitation at 488 nm and emission collection at 610 nm±30 nm. The emissions at each concentration of TeNT and each formulated TeNT sample will be calculated as a percentage of the untreated control (fluorescence measured at 610 nm±30 nm of non-toxin treated cells). The experimentally-derived concentration of formulated TeNT for each vial will be extrapolated from the TeNT concentration curve using the value calculated from an average of three replicate wells.

8b. Lipophilic Dye-Based FRET Assay for TeNT Activity in a Food Sample

To conduct a TeNT activity assay using a food sample such as, e.g., a processed food sample, cells expressing a TeNT VAMP-GFP substrate will be grown and differentiated in 24-well black tissue culture plates with clear bottoms using methods known in the art, for example, using one of the methods as described above in Examples IV, 8 and V, 8. A standard curve will be obtained by treating cells with 0.001, 0.002, 0.005, 0.01, 0.02 or 0.05 nM of TeNT (Metabiologics, Inc., Madison, Wis.), with each of the concentrations run in triplicates in a 24 well plate. Simultaneously, separate wells in the same plate will be treated with a processed food sample from vials of formulated TeNT diluted in 1 ml of complete culture media. Cells in three replicate wells will be treated with the contents of each diluted sample. TeNT-treated cells will be incubated with a suitable lipophilic dye for an appropriate length of time, e.g., as described in Example VI, 2 and FRET will be determined using the Typhoon 9140 software with excitation at 488 nm and emission collection at 610 nm±30 nm. The emissions at each concentration of TeNT and each processed food sample will be calculated as a percentage of the untreated control (fluorescence measured at 610 nm±30 nm of non-toxin treated cells). The experimentally derived concentration of TeNT present in the processed food sample will be extrapolated from the TeNT concentration curve using the value calculated from an average of three replicate wells.

9. Lipophilic Dye-Based FRET Assay for Clostridial Toxin Activity Using Lipophilic Dyes as Donor Fluorophores The procedures outlined above in Examples VII, 1-8 can be used to assay formulated Clostridial toxin products and food stuffs using a lipophilic dye-based FRET assay based on lipophilic dyes as donor fluorophores in conjunction with fluorescent proteins as acceptors using, e.g., the conditions described above in Example VI, 1.

9a. Lipophilic Dye-Based FRET Assay for BoNT/A Activity in a BOTOX® Product

To conduct a lipophilic dye-based FRET assay for BoNT/A activity using a formulated botulinum neurotoxin product such as, e.g., a BOTOX® product, differentiated Neuro-2A cells stably expressing a BoNT/A $SNAP25_{206}$-GFP substrate were grown and differentiated in 24-well black tissue culture plates with clear bottoms as described above in Examples VI, 1d. A standard curve was obtained by treating differentiated Neuro-2A cells with 0.001 nM, 0.002 nM, 0.005 nM, 0.01 nM, 0.02 nM or 0.05 nM of Pure A (BTX-540; Metabiologics, Inc., Madison, Wis.), with each of the concentrations run in triplicates. Simultaneously, separate wells in the same plate were treated with three separate vials of BOTOX® dissolved in 1 ml of complete EMEM media to a final concentration of approximately 5.5 μM. Cells in three replicate wells were treated with the contents of each resuspended BOTOX® vial. BoNT/A-treated cells were incubated with 5 μM DPH for 6 hours and FRET determined using the Spectra Max M5 software with excitation at 350 nm and emission collection at 515 nm±30 nm. The emissions at each concentration of Pure A and each BOTOX® sample were calculated as a percentage of the untreated control (fluorescence measured at 515 nm±30 nm of non-toxin treated cells). The experimentally-derived BOTOX® concentration for each vial was extrapolated from the Pure A concentration curve using the value calculated from an average of three replicate wells. Calculated average values for the three vials were 6.3 μM, 9.0 μM and 17.7 μM, with the average for each of the three vials of BOTOX® calculated to be 11.0 μM. These results demonstrate that Clostridial toxin activity such as, e.g., BoNT/A activity from formulated products such as BOTOX®, can be detected using a FRET assay in which a lipophilic dye incorporated into a membrane acts as the FRET acceptor.

1b. Lipophilic Dye-Based FRET Assay for BoNT/A Activity in a Food Sample

To conduct a lipophilic dye-based FRET assay for BoNT/A activity using a food sample such as, e.g., a processed food sample, differentiated Neuro-2A cells stably expressing a BoNT/A $SNAP25_{206}$-GFP substrate will be grown and differentiated in 24-well black tissue culture plates with clear bottoms as described above in Examples VI, 1d. A standard curve will be obtained by treating Neuro-2A cells with 0.001, 0.002, 0.005, 0.01, 0.02 or 0.05 nM of Pure A (BTX-540; Metabiologics, Inc., Madison, Wis.), with each of the concentrations run in triplicates. Simultaneously, separate wells in the same plate will be treated with a processed food sample from vials of BOTOX® diluted in 1 ml of complete EMEM media. Cells in three replicate wells will be treated with the contents of each diluted sample. BoNT/A-treated cells will be incubated with 5 μM DPH for 6 hours and FRET will be determined using the Spectra Max M5 software with excitation at 350 nm and emission collection at 515 nm±30 nm. The emissions at each concentration of Pure A and each processed food sample will be calculated as a percentage of the untreated control (fluorescence measured at 515 nm±30 nm of non-toxin treated cells). The experimentally derived concentration of BoNT/A present in the processed food sample will be extrapolated from the Pure A concentration curve using the value calculated from an average of three replicate wells.

Although the invention has been described with reference to the examples provided above, it should be understood that various modifications can be made without departing from the spirit of the invention. Accordingly, the invention is limited only by the following claims.

What is claimed:

1. A cell comprising:

a) a membrane-associated Clostridial toxin substrate, said substrate comprising i) a first member of a fluorescence resonance energy transfer (FRET) pair;

ii) a Clostridial toxin recognition sequence including a Clostridial toxin cleavage site; and iii) a membrane targeting domain;

b) a membrane-associated second member of a FRET pair; and c) a receptor that binds a Clostridial toxin;

wherein the membrane targeting domain comprises a SNAP-25 or Syntaxin peptide which directs a Clostridial toxin substrate to the cell membrane;

wherein the Clostridial toxin recognition sequence intervenes between the first FRET pair member and the membrane targeting domain;

wherein the cell is capable of Clostridial toxin intoxication;

wherein the FRET pair comprises an acceptor having an absorbance spectrum overlapping the emission spectrum of a donor fluorophore; and wherein under the appropriate conditions, resonance energy transfer is exhibited between the acceptor and the donor fluorophore.

2. The cell of claim 1, wherein the cell transiently contains the Clostridial toxin substrate.

3. The cell of claim 1, wherein the cell stably contains the Clostridial toxin substrate.

4. The cell of claim 1, wherein the Clostridial toxin substrate is expressed from a nucleic acid molecule.

5. The cell of claim 1, wherein the cell is a neuronal cell.

6. The cell of claim 1, wherein the second FRET pair member is a lipophilic dye.

7. The cell of claim 1, wherein the first FRET pair member is the acceptor and the second FRET pair member is the donor fluorophore.

8. The cell of claim 1, wherein the first FRET pair member is the donor fluorophore and the second FRET pair member is the acceptor.

9. The cell according to claim 1, wherein the Clostridial toxin recognition sequence comprises a BoNT/A recognition sequence including a BoNT/A cleavage site, a BoNT/B recognition sequence including a BoNT/B cleavage site, a BoNT/C1 recognition sequence including a BoNT/C1 cleavage site, a BoNT/D recognition sequence including a BoNT/D cleavage site, a BoNT/E recognition sequence including a BoNT/E cleavage site, a BoNT/F recognition sequence including a BoNT/F cleavage site, a BoNT/G recognition sequence including a BoNT/G cleavage site, or a TeNT recognition sequence including a TeNT cleavage site.

10. The cell of claim 1, wherein the Clostridial toxin recognition sequence comprises at least six consecutive residues of SNAP-25, the six consecutive residues comprising Gln-Arg.

11. The cell of claim 1, wherein the receptor is an endogenous Clostridial toxin receptor.

12. The cell of claim 1, wherein the first FRET pair member is a fluorescent protein.

13. A method of determining Clostridial toxin activity in a sample, comprising a) contacting with the sample the cell according to claim 1;

b) exciting said donor fluorophore;

c) detecting fluorescence resonance energy transfer of said cell; and d) comparing the resonance energy transfer detected from the contacted cell with the resonance energy transfer detected from a control cell, wherein the control cell is the cell according to claim 1 but not contacted with said sample and subjected to steps (b)-(c);

wherein a difference in fluorescence resonance energy transfer of the contacted cell as compared to the control cell is indicative of Clostridial toxin activity.

14. The method of claim 13, wherein the sample is a crude cell lysate, a bulk Clostridial toxin, a partially purified Clostridial toxin, a purified Clostridial toxin, an isolated Clostridial toxin light chain, or a formulated Clostridial toxin product.

15. The method of claim 14, wherein the sample is a formulated Clostridial toxin product.

16. The method of claim 15, wherein the formulated Clostridial toxin product is a formulated BoNT/A product.

17. The method of claim 13, wherein the sample is a raw food, a partially cooked or processed food, a cooked or processed food, a beverage, an animal feed, a soil sample, a water sample, or a pond sediments.

* * * * *

UNITED STATES PATENT AND TRADEMARK OFFICE

CERTIFICATE OF CORRECTION

PATENT NO. : 8,124,357 B2
APPLICATION NO. : 11/908438
DATED : February 28, 2012
INVENTOR(S) : Ester Fernandez-Salas et al.

It is certified that error appears in the above-identified patent and that said Letters Patent is hereby corrected as shown below:

On first Page, field (54), in "Title", column 1, line 2, delete "CLOSTRIDAL" and insert -- CLOSTRIDIAL --, therefor.

In column 1, line 2, delete "CLOSTRIDAL" and insert -- CLOSTRIDIAL --, therefor.

In column 1, line 11, delete "GeneBank" and insert -- GenBank --, therefor.

In column 1, line 52, delete "hyperhydrosis" and insert -- hyperhidrosis --, therefor.

Figure 5:
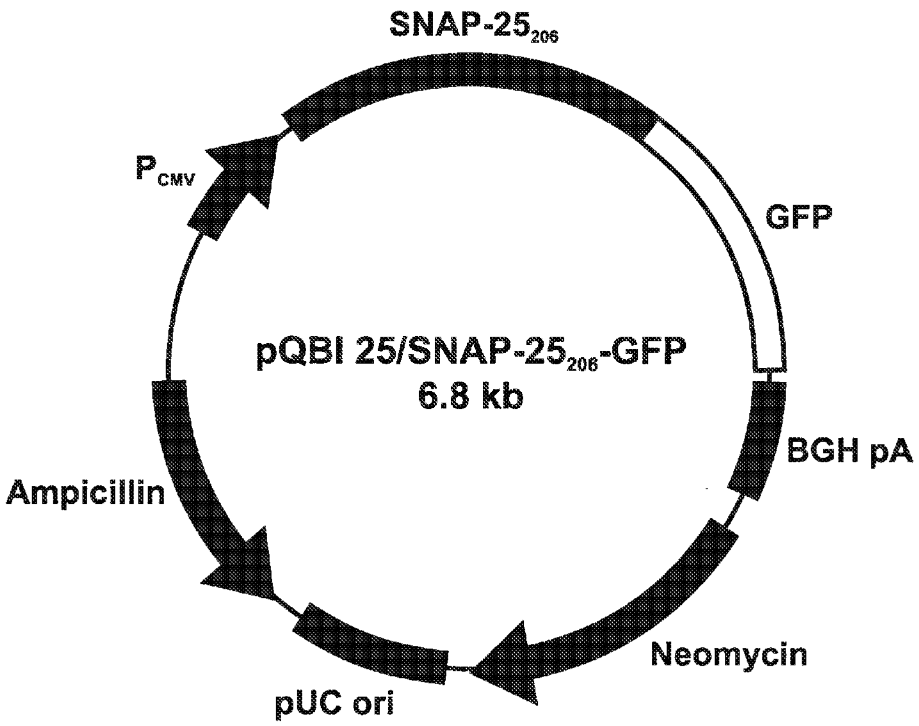
FIG. 5. shows a plasmid map of mammalian expression construct pQBI 25/SNAP-$25_{206}$-GFP encoding a carboxyl-terminal GFP peptide operably-linked to a SNAP-25 peptide of SEQ ID NO: 1. Abbreviations are as follows: $P_{CMV}$, an cytomegalovirus promoter region; $H_C$BoNT/A, the nucleic acid composition encoding the SNAP-25 peptide of SEQ ID NO: 1; GFP, a region encoding a Green Florescence Protein peptide; BGH pA, a bovine growth hormone polyadenylation site; Neomycin, a region encoding an aminophosphotransferase peptide that confers Neomycin resistance; pUC ori, a pUC origin of plasmid replication region; Ampicillin, a region encoding a β-lactamase peptide that confers Ampicillin resistance.

In column 3, line 41, delete "FIG. 5." and insert -- FIG. 5 --, therefor.

In column 4, line 57, delete "(12.5 µM, 25 µM or 50 µM)," and insert -- (12.5 pM, 25 pM or 50 pM), --, therefor.

In column 12, line 31, delete "acid;" and insert -- acid; a --, therefor.

In column 13, line 3, delete "$P_5$'" and insert -- $P_5$', --, therefor.

In column 17, line 56, delete "Poptide" and insert -- Peptide --, therefor.

In column 18, line 3, delete "Poptide" and insert -- Peptide --, therefor.

In column 18, line 21, delete "A98" and insert -- A9B --, therefor.

In column 18, line 26, delete "B" and insert -- B, --, therefor.

In column 18, line 27, delete "X" and insert -- X, --, therefor.

In column 31, line 67, delete "G." and insert -- G, --, therefor.

In column 35, line 23, delete "TABLE 5" and insert -- TABLE 6 --, therefor.

In column 35, line 33, delete "LEDQGEQLN" and insert -- LDEQGEQLN --, therefor.

In column 43, line 58, delete "QPXR1" and insert -- QPXRI --, therefor.

In column 47, lines 31-34, delete "In another aspect of this embodiment, a Clostridial toxin substrate comprises, in part, the membrane targeting domain comprising amino acids IMIMICCIILAIILASTIGGIFA, which corresponds to residues 247-269 of SEQ ID NO: 85." and insert the same on Col. 47, Line 30, after "SEQ ID NO: 85." as a continuation of the same paragraph.

Signed and Sealed this
Twenty-ninth Day of May, 2012

David J. Kappos
*Director of the United States Patent and Trademark Office*

In column 48, line 55, delete "Entacmeae" and insert -- Entacmaea --, therefor.

In column 51, line 14, delete "guernyi" and insert -- gurneyi --, therefor.

In column 54, line 48, delete "striate" and insert -- striata --, therefor.

In column 54, line 67, delete "Entacmeae" and insert -- Entacmaea --, therefor.

In column 55, line 5, delete "Actinaria)," and insert -- Actiniaria), --, therefor.

In column 56, line 37, delete "Nonlimitng" and insert -- Nonlimiting --, therefor.

In column 56, line 47, delete "Covalant" and insert -- Covalent --, therefor.

In column 56, line 61, delete "(Invitrogin" and insert -- (Invitrogen --, therefor.

In column 57, line 42, delete "deriviatives" and insert -- derivatives --, therefor.

In column 57, line 44, delete "deriviatives" and insert -- derivatives --, therefor.

In column 58, line 35, delete "deriviatives" and insert -- derivatives --, therefor.

In column 58, line 38, delete "deriviatives" and insert -- derivatives --, therefor.

In column 60, line 20, delete "$DilCi_6(3)$" and insert -- $DilC_{16}(3)$ --, therefor.

In column 60, line 21, delete "$DilCi_2(3)$" and insert -- $DilC_{12}(3)$ --, therefor.

In column 62, line 23, delete "di bromide" and insert -- dibromide --, therefor.

In column 66, line 50, delete "$R_O$=[8.8×$10^{23}$·$\kappa^2$.$n^{-4}$$QY_D$*$J(\lambda)]^{1/6}A$, where" and insert -- $R_O = [8.8 \times 10^{23} \bullet \kappa^2 \bullet n^{-4} \bullet QY_D \bullet J(\lambda)]^{1/6}$A, where --, therefor.

In column 70, line 4, delete "hemagluttinin" and insert -- hemagglutinin --, therefor.

In column 70, line 55, delete "diethyl-laminoethyl" and insert -- diethyl-aminoethyl --, therefor.

In column 72, line 16, delete "BoNT/E," and insert -- BoNT/E, [$^{125}$I] --, therefor.

In column 74, line 21, delete "Mass.)," and insert -- Mass.). --, therefor.

In column 74, line 36, delete "Mass.)," and insert -- Mass.). --, therefor.

In column 77, line 20, delete "N2," and insert -- N-2, --, therefor.

In column 80, line 40, delete "eurythrocytes," and insert -- erythrocytes, --, therefor.

In column 81, line 29, delete "1," and insert -- I, --, therefor.

In column 82, line 34, delete "1 ." and insert -- I. --, therefor.

In column 84, line 55, delete "Entacmeae" and insert -- Entacmaea --, therefor.

In column 84, line 59, delete "Vitalitye" and insert -- Vitality® --, therefor.

In column 84, line 60, delete "Greene" and insert -- Green® --, therefor.

In column 85, line 3, delete "octadecyl" and insert -- Octadecyl --, therefor.

In column 85, line 11, delete "MBDS" and insert -- MBDS. --, therefor.

In column 85, line 25, delete "Clostridal" and insert -- Clostridial --, therefor.

In column 85, line 29, delete "Clostridal" and insert -- Clostridial --, therefor.

In column 87, line 54, delete "gramacidin S," and insert -- gramicidin S, --, therefor.

In column 88, line 12, delete "diethyl-laminoethyl" and insert -- diethyl-aminoethyl --, therefor.

In column 89, line 31, delete "Adenovirual" and insert -- Adenoviral --, therefor.

In column 89, line 36, delete "AdEaSy™" and insert -- AdEasy™ --, therefor.

In column 89, line 38, delete "AdEaSy™" and insert -- AdEasy™ --, therefor.

In column 90, line 36, delete "Biosciences-Clonetech," and insert -- Biosciences-Clontech, --, therefor.

In column 90, line 38, delete "Clonetech," and insert -- Clontech, --, therefor.

In column 93, line 50, delete "Moiert," and insert -- Moiety, --, therefor.

In column 94, line 30, delete "P3" and insert -- β3 --, therefor.

In column 99, line 18, delete "Entacmeae" and insert -- Entacmaea --, therefor.

In column 99, line 24, delete "Greene" and insert -- Green® --, therefor.

In column 109, line 28, delete "Designd" and insert -- Designs --, therefor.

In column 109, line 32, delete "(Folley" and insert -- (Foley --, therefor.

In column 110, line 49, delete "1 M to 500 μM," and insert -- 1 pM to 500 μM, --, therefor.

In column 110, line 53, delete "10 pM to 10 pM," and insert -- -10 pM to 10 μM, --, therefor.

In column 110, line 56, delete "10 μpM," and insert -- 10 μM, --, therefor.

In column 110, line 58, delete "500 pM" and insert -- 500 pM, --, therefor.

In column 113, line 46, delete "derivitive" and insert -- derivative --, therefor.

In column 113, line 47, delete "derivitive" and insert -- derivative --, therefor.

In column 114, line 48, delete "dye" and insert -- dye. --, therefor.

In column 115, line 60, delete "derivitive" and insert -- derivative --, therefor.

In column 115, line 61, delete "derivitive" and insert -- derivative --, therefor.

In column 116, line 17, delete "8, ," and insert -- 8, --, therefor.

In column 116, line 18, delete "15, ," and insert -- 15, --, therefor.

In column 116, line 27, delete "dye" and insert -- dye. --, therefor.

In column 117, line 31, delete "selcted" and insert -- selected --, therefor.

In column 117, line 36, delete "derivitive" and insert -- derivative --, therefor.

In column 117, line 37, delete "derivitive" and insert -- derivative --, therefor.

In column 117, line 60, delete "8,," and insert -- 8, --, therefor.

In column 117, line 61, delete "15,," and insert -- 15, --, therefor.

In column 118, line 3, delete "dye" and insert -- dye. --, therefor.

In column 119, line 23, delete "teh" and insert -- the --, therefor.

In column 119, line 62, delete "selcted" and insert -- selected --, therefor.

In column 119, line 66, delete "derivitive" and insert -- derivative --, therefor.

In column 119, line 67, delete "derivitive" and insert -- derivative --, therefor.

In column 120, line 36, delete "dye" and insert -- dye. --, therefor.

In column 122, line 35, delete "selcted" and insert -- selected --, therefor.

In column 122, line 39, delete “derivitive” and insert -- derivative --, therefor.

In column 122, line 40, delete “derivitive” and insert -- derivative --, therefor.

In column 122, line 63, delete “8,,” and insert -- 8, --, therefor.

In column 123, line 6, delete “dye” and insert -- dye. --, therefor.

In column 124, line 60, delete “115and” and insert -- -115 and --, therefor.

In column 125, line 4, delete “selcted” and insert -- selected --, therefor.

In column 125, line 8, delete “derivitive” and insert -- derivative --, therefor.

In column 125, line 9, delete “derivitive” and insert -- derivative --, therefor.

In column 125, line 19, delete “732and” and insert -- 732 and --, therefor.

In column 125, line 32, delete “8,,” and insert -- 8, --, therefor.

In column 125, line 57, delete “2-10and” and insert -- 2-10 and --, therefor.

In column 130, line 16, delete “TeNT” and insert -- TeNT. --, therefor.

In column 130, line 57, delete “TeNT” and insert -- TeNT. --, therefor.

In column 131, line 30, delete “TeNT” and insert -- TeNT. --, therefor.

In column 133, line 34, delete “BoNT/C1” and insert -- BoNT/C1. --, therefor.

In column 135, line 44, delete “monolaureate,” and insert -- monolaurate, --, therefor.

In column 135, line 48-49, delete “monolaureate)” and insert -- monolaurate) --, therefor.

In column 169, line 40, delete “monolaureate,” and insert -- monolaurate, --, therefor.

In column 169, line 44-45, delete “monolaureate)” and insert -- monolaurate) --, therefor.

In column 172, line 5, delete “monolaureate,” and insert -- monolaurate, --, therefor.

In column 172, line 9-10, delete “monolaureate)” and insert -- monolaurate) --, therefor.

In column 180, line 65, delete “fro” and insert -- for --, therefor.

In column 181, line 17, delete “fro” and insert -- for --, therefor.

In column 181, line 36, delete “fro” and insert -- for --, therefor.

In column 181, line 64, delete “fro” and insert -- for --, therefor.

In column 182, line 15, delete “fro” and insert -- for --, therefor.

In column 182, line 34, delete “fro” and insert -- for --, therefor.

In column 182, line 53, delete “fro” and insert -- for --, therefor.